(12) United States Patent
Quattropani et al.

(10) Patent No.: US 11,612,599 B2
(45) Date of Patent: *Mar. 28, 2023

(54) GLYCOSIDASE INHIBITORS

(71) Applicant: Asceneuron SA, Lausanne (CH)

(72) Inventors: Anna Quattropani, Rolle (CH);
Santosh S. Kulkarni, Bangalore (IN);
Awadut Gajendra Giri, Bangalore (IN)

(73) Assignee: Asceneuron SA, Lausanne (CH)

( * ) Notice: Subject to any disclaimer, the term of this patent is extended or adjusted under 35 U.S.C. 154(b) by 1136 days.

This patent is subject to a terminal disclaimer.

(21) Appl. No.: 16/078,159

(22) PCT Filed: Feb. 24, 2017

(86) PCT No.: PCT/EP2017/054268
§ 371 (c)(1),
(2) Date: Aug. 21, 2018

(87) PCT Pub. No.: WO2017/144633
PCT Pub. Date: Aug. 31, 2017

(65) Prior Publication Data
US 2021/0186958 A1 Jun. 24, 2021

(30) Foreign Application Priority Data
Feb. 25, 2016 (IN) .............................. 201621006636

(51) Int. Cl.
| | | |
|---|---|---|
| *A61K 31/519* | (2006.01) | |
| *A61K 31/496* | (2006.01) | |
| *A61K 31/454* | (2006.01) | |
| *A61K 31/498* | (2006.01) | |
| *A61K 31/4985* | (2006.01) | |
| *A61K 31/501* | (2006.01) | |
| *A61K 31/506* | (2006.01) | |
| *A61K 31/5383* | (2006.01) | |
| *C07D 401/14* | (2006.01) | |
| *C07D 403/12* | (2006.01) | |
| *C07D 405/12* | (2006.01) | |
| *C07D 405/14* | (2006.01) | |
| *C07D 413/14* | (2006.01) | |
| *C07D 417/12* | (2006.01) | |
| *C07D 417/14* | (2006.01) | |
| *C07D 471/04* | (2006.01) | |
| *C07D 487/04* | (2006.01) | |
| *C07D 491/048* | (2006.01) | |
| *C07D 491/052* | (2006.01) | |
| *C07D 495/04* | (2006.01) | |
| *C07D 498/04* | (2006.01) | |
| *C07D 513/04* | (2006.01) | |
| *C07D 519/00* | (2006.01) | |

(52) U.S. Cl.
CPC .......... *A61K 31/496* (2013.01); *A61K 31/454* (2013.01); *A61K 31/498* (2013.01); *A61K 31/4985* (2013.01); *A61K 31/501* (2013.01); *A61K 31/506* (2013.01); *A61K 31/519* (2013.01); *A61K 31/5383* (2013.01); *C07D 401/14* (2013.01); *C07D 403/12* (2013.01); *C07D 405/12* (2013.01); *C07D 405/14* (2013.01); *C07D 413/14* (2013.01); *C07D 417/12* (2013.01); *C07D 417/14* (2013.01); *C07D 471/04* (2013.01); *C07D 487/04* (2013.01); *C07D 491/048* (2013.01); *C07D 491/052* (2013.01); *C07D 495/04* (2013.01); *C07D 498/04* (2013.01); *C07D 513/04* (2013.01); *C07D 519/00* (2013.01)

(58) Field of Classification Search
CPC .. C07D 471/04; C07D 403/12; C07D 405/14; C07D 401/12; C07D 417/12; C07D 513/04; C07D 401/14; C07D 405/12; C07D 413/14; A61K 31/519
See application file for complete search history.

(56) References Cited

U.S. PATENT DOCUMENTS

| | | |
|---|---|---|
| 3,299,067 A | 1/1967 | Gilbert et al. |
| 3,457,263 A | 7/1969 | Regnier et al. |
| 3,485,757 A | 12/1969 | Shapiro |

(Continued)

FOREIGN PATENT DOCUMENTS

| | | |
|---|---|---|
| CN | 1791594 A | 6/2006 |
| CN | 103435606 | 12/2013 |

(Continued)

OTHER PUBLICATIONS

Hulikal, Deuterium Labeled Compounds in Drug Discovery Process, Abstract (2010).*

(Continued)

*Primary Examiner* — Deepak R Rao
(74) *Attorney, Agent, or Firm* — Cooley LLP

(57) ABSTRACT

Compounds of formula (I), wherein A, R, W, Q, n and m have the meaning according to the claims, can be employed, inter alia, for the treatment of tauopathies and Alzheimer's disease.

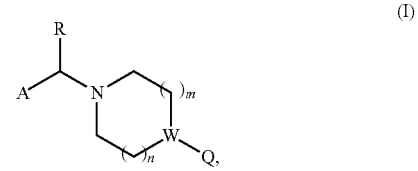

11 Claims, No Drawings

(56) References Cited

U.S. PATENT DOCUMENTS

| | | | |
|---|---|---|---|
| 3,489,757 A | 1/1970 | Koppe et al. | |
| 4,600,025 A | 7/1986 | Grigg et al. | |
| 5,935,974 A | 8/1999 | Rae et al. | |
| 7,582,769 B2 | 9/2009 | Murray et al. | |
| 7,666,875 B2 | 2/2010 | Gallagher, Jr. et al. | |
| 8,008,326 B2 | 8/2011 | Borza et al. | |
| 8,952,166 B2 | 2/2015 | Ding et al. | |
| 9,120,781 B2 | 9/2015 | Li et al. | |
| 10,336,775 B2 | 7/2019 | Quattropani et al. | |
| 10,344,021 B2 | 7/2019 | Quattropani et al. | |
| 10,556,902 B2 | 2/2020 | Quattropani et al. | |
| 10,696,668 B2 | 6/2020 | Quattropani et al. | |
| 10,995,090 B2 | 5/2021 | Quattropani et al. | |
| 11,046,712 B2* | 6/2021 | Quattropani | C07D 403/12 |
| 11,213,525 B2 | 1/2022 | Quattropani et al. | |
| 11,261,183 B2 | 3/2022 | Quattropani et al. | |
| 2004/0106645 A1 | 6/2004 | Blackburn et al. | |
| 2006/0287340 A1 | 12/2006 | Moriya et al. | |
| 2008/0300276 A1 | 12/2008 | Borza et al. | |
| 2009/0012078 A1 | 1/2009 | Andrews et al. | |
| 2009/0163545 A1 | 6/2009 | Goldfarb | |
| 2010/0022517 A1 | 1/2010 | Richards et al. | |
| 2011/0053982 A1 | 3/2011 | Fay et al. | |
| 2011/0060012 A1 | 3/2011 | Meyers et al. | |
| 2011/0060019 A1 | 3/2011 | Murray et al. | |
| 2012/0208808 A1 | 8/2012 | Buchstaller et al. | |
| 2016/0031871 A1 | 2/2016 | Yu et al. | |
| 2017/0298082 A1 | 10/2017 | Quattropani et al. | |
| 2020/0002326 A1 | 1/2020 | Quattropani et al. | |
| 2020/0385375 A1 | 12/2020 | Quattropani et al. | |
| 2021/0077488 A1 | 3/2021 | Quattropani et al. | |
| 2021/0198250 A1 | 7/2021 | Quattropani et al. | |
| 2021/0206766 A1 | 7/2021 | Quattropani et al. | |
| 2021/0213005 A1 | 7/2021 | Quattropani et al. | |
| 2022/0143042 A1 | 4/2022 | Quattropani et al. | |

FOREIGN PATENT DOCUMENTS

| | | |
|---|---|---|
| EP | 2301936 | 3/2011 |
| EP | 2687507 | 1/2014 |
| FR | 1311316 | 12/1962 |
| JP | 2010/270034 | 12/2010 |
| WO | WO1993/021181 | 10/1993 |
| WO | WO1997/043279 | 11/1997 |
| WO | WO1998/046590 | 10/1998 |
| WO | WO99/21850 | 5/1999 |
| WO | WO02/094799 | 11/2002 |
| WO | WO2003/092678 | 11/2003 |
| WO | WO2004/002481 | 1/2004 |
| WO | WO2004/005293 | 1/2004 |
| WO | WO2004/022558 | 3/2004 |
| WO | WO2004/094380 | 11/2004 |
| WO | WO2005/110982 | 11/2005 |
| WO | WO2006/092049 | 9/2006 |
| WO | WO-2007008541 A2 | 1/2007 |
| WO | WO2007/115077 | 10/2007 |
| WO | WO2007/135398 | 11/2007 |
| WO | WO2007/146122 | 12/2007 |
| WO | WO2008/012623 | 1/2008 |
| WO | WO2008/025170 | 3/2008 |
| WO | WO2009/011904 | 1/2009 |
| WO | WO2009/053373 | 4/2009 |
| WO | WO2009/131926 | 10/2009 |
| WO | WO2010/018868 | 2/2010 |
| WO | WO2010/021381 | 2/2010 |
| WO | WO2010/022517 | 3/2010 |
| WO | WO2010/026989 | 3/2010 |
| WO | WO2010/089127 | 8/2010 |
| WO | WO2010/101949 | 9/2010 |
| WO | WO2010/108115 | 9/2010 |
| WO | WO2010/108268 | 9/2010 |
| WO | WO2010/151318 | 12/2010 |
| WO | WO2011/140640 | 11/2011 |
| WO | WO2012/037298 | 3/2012 |
| WO | WO2012/061927 | 5/2012 |
| WO | WO2012/062157 | 5/2012 |
| WO | WO2012/062759 | 5/2012 |
| WO | WO2012/083435 | 6/2012 |
| WO | WO2012/117219 | 9/2012 |
| WO | WO2013/028715 | 2/2013 |
| WO | WO2013/066729 | 5/2013 |
| WO | WO2014/023723 | 2/2014 |
| WO | WO2014/032187 | 3/2014 |
| WO | WO 2014/159234 A1 | 10/2014 |
| WO | WO2015/083028 | 6/2015 |
| WO | WO2015/128333 | 9/2015 |
| WO | WO2015/164508 | 10/2015 |
| WO | WO 2016/030443 A1 | 3/2016 |
| WO | WO2017/001660 | 1/2017 |
| WO | WO2017/076900 | 5/2017 |
| WO | WO2017/087858 | 5/2017 |
| WO | WO2017/087863 | 5/2017 |
| WO | WO2017/091818 | 6/2017 |
| WO | WO2017/106254 | 6/2017 |
| WO | WO2017/144635 | 8/2017 |
| WO | WO2017/144637 | 8/2017 |
| WO | WO2017/144639 | 8/2017 |
| WO | WO 2017/223243 | 12/2017 |
| WO | WO2018/026371 | 2/2018 |
| WO | WO2018/109198 | 6/2018 |
| WO | WO2018/109202 | 6/2018 |
| WO | WO2018/140299 | 8/2018 |
| WO | WO2018/141984 | 8/2018 |
| WO | WO2018/153507 | 8/2018 |
| WO | WO2018/153508 | 8/2018 |
| WO | WO2018/154133 | 8/2018 |
| WO | WO2018/217558 | 11/2018 |

OTHER PUBLICATIONS

Bundgaard, Design of Prodrugs, p. 1, 1985.*
Silverman, Prodrugs and Drug Delivery Systems, The Organic Chemistry of Drug Design and Drug Action, pp. 352-399, 1992.*
Simone, Oncology: Introduction, Cecil Textbook of Medicine, 20th Edition, vol. 1, pp. 1004-1010, 1996.*
Acute Leukemia, Merck Manual (Online Edition) 6 pages, pp. 1-6 (2013).*
Pearce et al., Failure modes in anticancer drug discovery and development, Cancer Drug Design and Discovery Edited by Stephen Neidle, Chapter 18, pp. 424-435 (2008).*
Gura et al., Systems for identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431, 2001.*
Damasio, Alzheimer's Disease and related dementias, Cecil Textbook of Medicine, 20th Edition, vol. 2, pp. 1992-1996, 1996.*
Layzer, Degenerative diseases of the nervous system, Cecil Textbook of Medicine, 20th Edition, vol. 2, pp. 2050-2057, 1996.*
Abdel-Magid, A. F. et al. "Reductive Amination of Aldehydes and Ketones with Sodium Triacetoxyborohydride. Studies on Direct and Indirect Reductive Amination Procedures" J. Org. Chem., (1996), 61, pp. 3849-3862.
Albertson, N. F. "Alkylation with Non-ketonic Mannich Bases. Aminothiazoles and Pyrrole" J. Am. Chem. Soc., 1948, 70(2), 669-670.
Andres, J. I. et al. "Synthesis, Evaluation, and Radiolabeling of New Potent Positive Allosteric Modulators of the Metabotropic Glutamate Receptor 2 as Potential Tracers for Positron Emission Tomography Imaging" J. Med. Chem., (2012), 55, pp. 8685-8699.
Augustine, J. K. et al. "Propylphosphonic anhydride (T3P®): an efficient reagent for the one-pot synthesis of 1,2,4-oxadiazoles, 1,3,4-oxadiazoles, and 1,3,4-thiadiazoles" Tetrahedron, (2009), 65, pp. 9989-9996.
Bastin, R. J. et al. "Salt Selection and Optimisation Procedures for Pharmaceutical New Chemical Entities", Organic Process Research & Development, 2000, 4, 427-435.
Berge, S. M. et al. "Pharmaceutical Salts", Journal of Pharmaceutical Sciences, 1977, 66(1), 1-19.

(56) References Cited

OTHER PUBLICATIONS

Biscoe, M. R. et al. "A New Class of Easily Activated Palladium Precatalysts for Facile C-N Cross-Coupling Reactions and Low Temperature Oxidative Addition of Aryl Chlorides", J. Am. Chem. Soc., 2008, 130, 6686-6687.
Bohnert, T. et al. "Plasma Protein Binding: From Discovery to Development", J. Pharmaceutical Sciences, 2013, 102, 2953-2994.
Bras, N. F. et al. "Glycosidase inhibitors: a patent review (2008-2013)" Expert Opinion on Therapeutic Patents, vol. 24, No. 8, 2014, pp. 857-874.
Bundgaard, H. "Design and Application of Prodrugs", from a Textbook of Drug Design and Development Chapter 5, Harwood Academic Publishers, 1991, 113-191.
Calcagno, A. M. "Comparison of Drug Transporter Levels in Normal Colon, Colon Cancer, and Caco-2 Cells: Impact on Drug Disposition and Discovery", Mol. Pharm., 2006, 3(1), 87-93.
CAS Registry (Online) Nos. 948053-91-6; 540512-02-5; 697229-62-2; 346662-52-0; 345992-64-5 (STN database summary sheets) Sep. 26, 2007.
"Chemical Encyclopedia", vol. 4, pp. 990-993, 1988. (Machine translation attached).
Chen, Y. et al. "Discovery of new acetylcholinesterase and butyrylcholinesterase inhibitors through structurebased virtual screening", RSC Advances, 2017, 7(6), 3429-3438.
Collet, A. "Resolution of Racemates: Did you say 'Classical?'", Angewandte Chemie International Edition, 1998, 37(23), 3239-3241.
Dassanayaka, S. and Jones, S. "O-GlcNAc and the cardiovascular system", Pharmacology & Therapeutics, 2014, 142, 62-71.
Database registry (online) Chemical abstract service, Columbus, Ohio, US; Dec. 6, 2011, "Piperazine, 1-[1-(1,3-benzodioxol-5-yl)ethyl]-4-(5-bromo-6-methoxy-2-pyridinyl)-", Database accession No. 1349611-60-4.
Database Pubchem Compound (Online) NCBI; Jan. 24, 2012, XP002768130, Database accession No. CID 54914491.
Database PubChem Compound (Online) NCBI; May 28, 2009; XP002768131, Database accession No. CID 28798635.
Database PubChem Compound, NCBI; Apr. 9, 2016; XP002768133, Database accession No. CID 118902929.
Database Registry Chemical Abstracts Service, 2016, CID120907609, 10 pages.
Database Registry, Chemical Abstracts Service, Jan. 11, 2017, XP002768132, Database accession No. 2055841-81-9.
Dorfmueller, H. C. et al. "Cell-Penetrant, Nanomolar O-GlcNAcase Inhibitors Selective against Lysosomal Hexosaminidases", Chem. Biol., 2010, 17, 1250-1255.
Dubois, B. et al. "Preclinical Alzheimer's disease: Definition, natural history, and diagnostic criteria", Alzheimers Dement., 2016, 12, 292-323.
Dubois B, et al. "Advancing research diagnostic criteria for Alzheimer's disease: the IWG-2 criteria", Lancet Neurol., 2014, 13, 614-629.
Dyatkin, A.B. et al. "Determination of the Absolute Configuration of a Key Tricyclic Component of a Novel Vasopressin Receptor Antagonist by Use of Vibrational Circular Dichroism", Chirality, 2002, 14, 215-219.
Ellman, J. A et al. "N-tert-Butanesulfinyl mines: Versatile Intermediates for the Asymmetric Synthesis of Amines" Acc. Chem. Res. (2002), 35, pp. 984-995.
Fors, B. P. et al. "A Highly Active Catalyst for Pd-Catalyzed Amination Reactions: Cross-Coupling Reactions Using Aryl Mesylates and the Highly Selective Monoarylation of Primary Amines Using Aryl Chlorides", J. Am. Chem. Soc., 2008, 130, 13552-13554.
Frings, M. et al. "Sulfoximines from a Medicinal Chemist's Perspective: Physicochemical and in vitro Parameters Relevant for Drug Discovery", European Journal of Medicinal Chemistry, 2017, 126, 225-245.

Goho, A. "Tricky Business", Science News, 2004, 166(8), 122-124.
Golub, T. R. et al. "Molecular Classification of Cancer: Class Discovery and Class Prediction by Gene Expression Monitoring", Science, 1999, 286, 531-537.
Gould, P. L. "Salt selection for basic drugs", International Journal of Pharmaceutics, 1986, 33, 201-217.
Graham, D. L. et al. "Increased O-GlcNAcylation reduces pathological tau without affecting its normal phosphorylation in a mouse model of tauopathy", Neuropharmacology, 2014, 79, 307-313.
Gujjar, R. et al. "Lead Optimization of Aryl and Aralkyl Amine-Based Triazolopyrimidine Inhibitors of Plasmodium falciparum Dihydroorotate Dehydrogenase with Antimalarial Activity in Mice", J. Med. Chem., 2011, 54 (11), 3935-3949.
Haleblian, J.; McCrone, W. "Pharmaceutical Applications of Polymorphism", J. Pharm. Sci., 1969, 58(8), 911-929.
Haleblian, J. "Characterization of Habits and Crystalline Modification of Solids and Their Pharmaceutical Applications", J. Pharm. Sci., 1975, 64(8), 1269-1288.
Hemming, K. "Product Class 6: 1,2,4-Oxadizoles" Science of Synthesis, (2004), 13(6), pp. 127-184.
Jakopin Z. et al. "Recent Advances in the Synthesis of 1,2,4- and 1,3,4-Oxadiazoles" Current Organic Chemistry, (2008), 12(10), pp. 850-898.
Kempson, J. "Name Reactions in Heterocyclic Chemistry II" John Wiley & Sons. Eds. Jie Jack Li and E. J. Corey, (2011), pp. 299-308.
Kim, E. J. et al. "Enzymatic characterization of O-GlcNAcase isoforms using a fluorogenic GlcNAc substrate", Carbohydrate Research, 2006, 341(8), 971-982.
Kim, E. J. "Chemical Arsenal for the Study of O-GlcNAc", Molecules, 2011, 16, 1987-2022.
Knapp, S. et al. "An Allosamizoline/ Glucosamine Hybrid NAGase Inhibitor", Synlett, 1997, 5, 435-436.
Lefebvre, T. "Recall sugars, forget Alzheimer's", Nature Chemical Biology, 2012, 8(4), 325-326.
Legros, J. et al. "Applications of Catalytic Asymmetric Sulfide Oxidations to the Syntheses of Biologically Active Sulfoxides", Adv. Synth. Catal., 2005, 347, 19-31.
Liu, X. et al. "Rational Use of Plasma Protein and Tissue Binding Data in Drug Design", J. Med. Chem. 2014, 57, 8238-8248.
Marwaha, A. et al. "Bioisosteric Transformations and Permutations in the Triazolopyrimidine Scaffold to Identify the Minimum Pharmacophore Required for Inhibitory Activity against Plasmodium falciparum Dihydroorotate Dehydrogenase", J. Med. Chem., 2012, 55(17), 7425-7436.
Mariappa, D. et al. "A mutant O-GlcNAcase as a probe to reveal global dynamics of the *Drosophila* O-GlcNAc developmental proteome", Biochem J., 2015, 470(2), 255-262.
Marotta, N. P. et al., "O-GlcNAc modification blocks the aggregation and toxicity of the Parkinson's disease associated protein α-synuclein", Nat. Chem, 2015, 7(11), 913-920.
Masuda, N. et al. "Studies of nonnucleoside HIV-1 reverse transcriptase inhibitors. Part 1: Design and synthesis ofthiazolidenebenzenesulfonamides", Bioorg. Med. Chem., 2004, 12, 6171-6182.
Mittur A. "Piribedil: Antiparkinsonian Properties and Potential Clinical Utility in Dopaminergic Disorders" Current Drug Therapy (2011), 6, pp. 17-34.
Moradi-Afrapoli, F. et al. "In vitro α-glucosidase inhibitory activity of phenolicconstituents from aerial parts of Polygonum hyrcanicum", DARU Journal of Pharmaceutical Sciences, 2012, 20(1), 37, 6 pages.
Nandi, A. et al. "Global Identification of O-GlcNAc-Modified Proteins", Anal. Chem., 2006, 78, 452-458.
Nelson, P. T. et al. "Correlation of Alzheimer Disease Neuropathologic Changes With Cognitive Status: A Review of the Literature", J. Neuropathol. Exp. Neurol., 2012, 71(5), 362-381.
Nettekoven, M. et al. "Synthetic Access to 2-Amido-5-aryl-8-methoxy-triazolopyridine and 2-Amido-5-morpholino-8-methoxy-triazolopyridine Derivatives as Potential Inhibitors of the Adenosine Receptor Subtypes", Synthesis, 2003, 1649-1652.
Obach, R. S. "Prediction of human clearance of twenty-nine drugs from hepatic microsomal intrinsic clearance data: and examination of in vitro half-life approach and nonspecific binding to microsomes", Drug. Metab. Dispos., 1999, 27(11), 1350-1359.

(56) References Cited

OTHER PUBLICATIONS

Okamura, H. et al. "Rhodium-Catalyzed Imination of Sulfoxides and Sulfides: Efficient Preparation of N-Unsubstituted Sulfoximines and Sulfilimines", Organic Letters, 2004, 6, 1305-1307.
O'Mahony, G. E. et al. "Synthesis of enantioenriched sulfoxides" Arkivoc, 2011, 1-110.
Orain, D. et al. "Synthesis of Orthogonally Protected 2,6-Diazaspiro[3.5]nonane and 2,6-Diazaspiro[3,4]octane Analogues as Versatile Building Blocks in Medicinal Chemistry", Synlett, 2015, 26(13), 1815-1818.
Papillon, J. P. N. et al. "Discovery of N-[5-(6-Chloro-3-cyano-1-methyl-1H-indol-2-yl)-pyridin-3-ylmethyl]-ethanesulfonamide, a Cortisol-Sparing CYP11B2 Inhibitor that Lowers Aldosterone in Human Subjects", J. Med. Chem., 2015, 58(23), 9382-9394.
Park, M.-J. et al. "High Glucose-induced O-GlcNAcylated Carbohydrate Response Element-binding Protein (ChREBP) Mediates Mesangial Cell Lipogenesis and Fibrosis", J. Biol. Chem., 2014, 289, 13519-13530.
Rouhi, A. M. et al. "The Right Stuff: From Research and Development to the Clinic, Getting Drug Crystals Right is Full of Pitfalls." Chem. Eng. News. (2003):32-35.
SantaCruz, K. et al. "Tau Suppression in a Neurodegenerative Mouse Model Improves Memory Function", Science, 2005, 309, 476-481.
Serajuddin, A. T. M. "Salt formation to improve drug solubility", Advanced Drug Delivery Reviews, 2007, 59(7), 603-616.
Shan, X. et al. "Reduced protein O-glycosylation in the nervous system of the mutant SOD1 transgenic mouse model of amyotrophic lateral sclerosis", Neuroscience Letters, 2012, 516, 296-301.
Shen, Q. et al. "Hydroxycoumarin Derivatives: Novel and Potent α-Glucosidase Inhibitors", J. Med. Chem., 2010, 53(23), 8252-8259.
Shirude, P. et al. "Lead Optimization of 1,4-Azaindoles as Antimycobacterial Agents", J. Med. Chem., 2014, 57(13), 5728-5737.
Sippy, K. B. et al. "Preparation and characterization of N-(3-pyridinyl) spirocyclic diamines as ligands for nicotinic acetylcholine receptors", Bioorganic & Med. Chemistry Letters, 2009, 19(6), 1682-1685.
Skedelj, V. et al. "Discovery of the first inhibitors of bacterial enzyme D-aspartate ligase from Enterococcus faecium (Asl$_{fm}$)", Eur. J. Med. Chem., 2013, 67, 208-220.
Song, S. et al. "Efficient and Practical Oxidative Bromination and Iodination of Arenes and Heteroarenes with DMSO and Hydrogen Halide: A Mild Protocol for Late-Stage Functionalization", Org. Lett., 2015, 17(12), 2886-2889.
Sperling, R. A. et al. "Toward defining the preclinical stages of Alzheimer's disease: Recommendations from the National Institute on Aging-Alzheimer's Association workgroups on diagnostic guidelines for Alzheimer's disease", Alzheimers Dement., 2011, 7, 280-292.
Spillantini, M. G.; Goedert, M. "Tau pathology and neurodegeneration", Lancet Neurol., 2013, 12, 609-622.
Tamura, B. K. et al. "Weight Loss in Patients with Alzheimer's Disease" J. Nutrition for the Elderly (2008), 26(3-4), pp. 21-38.
Tan, H. et al. "Rational Screening Approach for Classical Chiral Resolution under Thermodynamic Equilibrium: A Case Study of Diphenyl-Substituted N-Methyl-Piperazine", Organic Process Research and Development, 2011, 15(1), 53-63.
Tanuwidjaja, J. et al. "One-Pot Asymmetric Synthesis of Either Diastereomer of tert-Butanesulfinyl-protected Amines from Ketones", J. Org. Chem. 2007, 72, 626-629.
The U. S. Pharmacopeia 38—National Formulary 35 Chapter 941, Characterization of crystalline and partially crystalline solids by X-ray powder diffraction (XRPD) Official May 1, 2015, 427-431.
Thiel, O. R. et al. "Practical Synthesis of a Vanilloid Receptor-1 Antagonist" J. Org. Chem., (2008), 73(9), pp. 3508-3515.
Trapannone, R. et al. "O-GlcNAc transferase inhibitors: current tools and future challenges", Biochemical Society Transactions, 2016, 44(1), 88-93.
Vasudevan, A. et al. "Identification of aminopiperidine benzamides as MCHr1 antagonists", Bioorganic & Medicinal Chemistry Letters, 2005, 15(14), 3412-3416.
Volpe, D. A. " Application of Method Suitability for Drug Permeability Classification", The AAPS Journal, 2010, 12(4), 670-678.
Wall, G. M. "Pharmaceutical Applications of Drug Crystal Studies", Pharm. Manuf., 1986, 3, 32-42.
Wang, Z. et al. "Enrichment and Site Mapping of O-Linked N-Acetylglucosamine by a Combination of Chemical/Enzymatic Tagging, Photochemical Cleavage, and Electron Transfer Dissociation Mass Spectrometry", Mol. Cell Proteomics, 2010, 9(1), 153-160.
Waterman, K. C. "Improved Protocol and Data Analysis for Accelerated Shelf-Life Estimation of Solid Dosage Forms", Pharm. Res., 2007, 24(4), 780-790.
Weinberg, K. et al. "Synthesis and differential functionalisation of pyrrolidine and piperidine based spirodiamine scaffolds", Tetrahedron, 2013, 69(23), 4694-4707.
Wermuth, C. G. et al. "Designing Prodrugs and Bioprecursors I: Carrier Prodrugs", The Practice of Medicinal Chemistry: Chapter 31, Academic Press, 1996, 671-696.
Wiessner et al. "A novel non-carbohydrate o-linked beta-n-acetylglucosaminidase inhibitor increases tau o-glcnacylation In vivo", Abstracts of the Annual Meeting of the Society for Neuroscience, Society for Neuroscience, 2013, 43, 2 pages.
Williams, D. R. et al. "Pathological tau burden and distribution distinguishes progressive supranuclear palsy-parkinsonism from Richardson's syndrome", Brain, 2007, 130, 1566-1576.
Yoshida, M. et al. "Study of biodegradable copoly(L-lactic acid/glycolic acid) formulations with controlled release of Z-100 for application in radiation therapy", Int. J. Pharm., 1995, 115, 61-67.
Yuzwa, S. A. et al. "Mapping O-GlcNAc modification sites on tau and generation of a site-specific O-GlcNAc tau antibody", Amino Acids, 2011, 40, 857-868.
Yuzwa, S. A. et al. "A potent mechanism-inspired O-GlcNAcase inhibitor that blocks phosphorylation of tau in vivo", Nat. Chem. Biol., 2008, 4(8), 483-490.
Yuzwa, S. A. et al. "Increasing O-GlcNAc slows neurodegeneration and stabilizes tau against aggregation", Nat. Chem. Biol., 2012, 8(4), 393-399.
Zenzola, M. et al. "Transfer of Electrophilic NH Using Convenient Sources of Ammonia: Direct Synthesis of NH Sulfoximines from Sulfoxides", Angew. Chem. Int. Ed., 2016, 55, 7203-7207.
Aitipamula, S. et al. "Polymorphs, Salts, and Cocrystals: What's in a Name?", Crystal Growth & Design, 2012, vol. 12, No. 5, p. 2147-2152.
Apsunde, T.D. et al. "Microwave-Assisted Iridium-Catalyzed Synthesis of Nicotine and Anabasine Derivatives", Synthesis, vol. 45, No. 15, 2013, p. 2120-2124.
Aube, J. et al. "Intramolecular Schmidt reaction of alkyl azides", J. Am. Chem. Soc. 1991, vol. 113, No. 23, p. 8965-8966.
Chen, W. et al. "Redox-Neutral α-Arylation of Amines", Organic Letters, vol. 16, No. 3, 2014, p. 730-732.
Chrovian, C. C. et al. "A Dipolar Cycloaddition Reaction to Access 6-Methyl-4,5,6,7-tetrahydro-1H-[1,2,3]triazolo[4,5-c]pyridines Enables the Discovery Synthesis and Preclinical Profiling of a P2X7 Antagonist Clinical Candidate", J. Med. Chem. 2018, vol. 61, No. 1, p. 207-223.
Dai, W. et al. "Highly Chemoselective and Enantioselective Catalytic Oxidation of Heteroaromatic Sulfides via High-Valent Manganese(IV)—Oxo Cation Radical Oxidizing Intermediates", ACS Catalysis, 2017, vol. 7, p. 4890-4895.
Fleury-Bregeot et al. "Suzuki-Miyaura Cross-Coupling of Potassium Alkoxyethyltri-fluoroborates: Access to Aryl/Heteroarylethyloxy Motifs", J. Org. Chem. 2012, vol. 77, No. 22, p. 10399-10408.
Frehel, D. et al. "New synthesis of 5,6,7,8-tetrahydro-4H-thieno[2,3-d]azepine", Journal of Heterocyclic Chemistry, 1985, vol. 22, p. 1011-1016.
Kim et al. "Discovery of β-Arrestin Biased Ligands of 5-HT$_7$R", Journal of Medicinal Chemistry, 2019, vol. 61, p. 7218-7233.
Merchant, R. R. et al. "Regioselective Preparation of Saturated Spirocyclic and Ring-Expanded Fused Pyrazoles", J. Org. Chem. 2014, vol. 79, No. 18, p. 8800-8811.

(56) References Cited

OTHER PUBLICATIONS

Micksch, M. et al. "Synthesis of 1,2-Diaryl- and 1-Aryl-2-alkylimidazoles with Sterically Demanding Substituents", Eur. J. Org. Chem. 2013, Issue 27, p. 6137-6145.

Miller III et al. "Design of e-pharmacophore models using compound fragments for the trans-sialidase of Trypanosoma cruzi: screening for novel inhibitor scaffolds", Journal of Molecular Graphics and Modelling, vol. 45, 2013, p. 84-97.

Motiwala, H.F. et al. "Remodeling and Enhancing Schmidt Reaction Pathways in Hexafluoroisopropanol", J. Org. Chem. 2016, vol. 81, No. 8, p. 1593-1609.

Reddy et al. "Synthesis of Chiral Benzimidazole-Pyrrolidine Derivatives and their Application in Organocatalytic Aldol and Michael Addition Reactions", Synthetic Communications, vol. 37, No. 24, 2007, pp. 4289-4299.

Xu, D. et al. "The synthesis of chiral tridentate ligands from L-proline and their application in the copper(II)-catalyzed enantioselective Henry reaction", Tetrahedron Asymmetry, vol. 28, No. 7, 2017, pp. 954-963.

Youngdale et al. "Synthesis and pharmacological activity of 3-(2-pyrrolidinyl)indoles", Journal of Medicinal Chemistry, vol. 7, 1964, pp. 415-427.

Yu, Y. et al. "One-Pot Synthesis of Spirocyclic or Fused Pyrazoles from Cyclic Ketones: Calcium Carbide as the Carbon Source in Ring Expansion", J. Org. Chem. 2017, vol. 82, No. 18, pp. 9479-9486.

Zhang, Chen et al. "Nontraditional Reactions of Azomethine Ylides: Decarboxylative Three-Component Couplings of $\alpha$-Amino Acids", Journal of the American Chemical Society, vol. 132, No. 6, 2010, pp. 1798-1799.

U.S. Appl. No. 16/078,155, filed Aug. 21, 2018.
U.S. Appl. No. 16/078,715, filed Aug. 22, 2018.
U.S. Appl. No. 16/079,162, filed Aug. 23, 2018.

Hiroshi Yamanaka, Hiroshi Miyazaki and Naomi chi Murakami, Chemical Abstract, "Separation of optical isomers", Japan, Gakkai Shopping Santa, 1989, No. 6, pp. 8, 9, 124, 212, and 213 (21 pages).

Ansari et al. "The Role of Insulin Resistance and Protein O-GlcNAcylation in Neurodegeneration", Frontiers in Neuroscience, 2019, vol. 13, Article 473, 9 pages.

Gong et al. "O-GlcNAcylation: A regulator of tau pathology and neurodegeneration", Alzheimer's & Dementia, 2016, vol. 12, p. 1078-1089.

Ryan et al. "The O-GlcNAc modification protects against protein misfolding and aggregation in neurodegenerative disease", ACS Chemical Neuroscience, 2019, 17 pages.

Yuzwa et al. "O-GlcNAc and neurodegeneration: biochemical mechanisms and potential roles in Alzheimer's disease and beyond", Chem. Soc. Review, 2014, 20 pages.

Smith, P.W. et al. "New spiropiperidines as potent and selective non-peptide tachykinin $NK_2$ receptor antagonists", J. Med. Chem., vol. 38, pp. 3772-3779, 1995.

\* cited by examiner

GLYCOSIDASE INHIBITORS

RELATED APPLICATIONS

This application is a U.S. National Phase application, filed under 35 U.S.C. § 371(c), of International Application No. PCT/EP2017/054268, filed Feb. 24, 2017, which claims priority to, and the benefit of, Indian Patent Application No. 201621006636, filed Feb. 25, 2016. The contents of each of which is incorporated by reference herein in its entirety for all purposes.

The present invention relates to a medicament comprising a compound of formula (I)

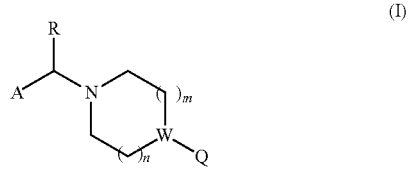

wherein A, R, W, Q, n and m have the meaning according to the claims, and/or physiologically acceptable salts, tautomers, solvates, stereoisomers and derivatives thereof. The compounds of formula (I) can be used as glycosidase inhibitors. Objects of the invention are also pharmaceutical compositions comprising the compounds of formula (I), and the use of the compounds of formula (I) for the treatment of one or more tauopathies and Alzheimer's disease.

A wide range of cellular proteins, both nuclear and cytoplasmic, are post-translationally modified by the addition of the monosaccharide 2-acetamido-2-deoxy-β-D-glucopyranoside (β-N-acetyl glucosamine) which is attached via an O-glycosidic linkage. This modification is generally referred to as O-linked N-acetylglucosamine or O-GlcNAc. The enzyme responsible for post-translationally linking β-N-acetylglucosamine (GlcNAc) to specific serine and threonine residues of numerous nucleocytoplasmic proteins is O-GlcNAc transferase (OGTase). A second enzyme, known as O-GlcNAcase, removes this post-translational modification to liberate proteins making the O-GlcNAc-modification a dynamic cycle occurring several times during the lifetime of a protein.

O-GlcNAc-modified proteins regulate a wide range of vital cellular functions including, for example, transcription, proteasomal degradation and cellular signaling. O-GlcNAc is also found on many structural proteins. For example, it has been found on a number of cytoskeletal proteins, including neurofilament proteins, synapsins, synapsin-specific clathrin assembly protein AP-3 and Ankyrin-G. O-GlcNAc modification has been found to be abundant in the brain. It has also been found on proteins clearly implicated in the etiology of several diseases including tauopathies, Alzheimer's disease (AD), synucleinopathies, Parkinson's disease, amyotrophic lateral sclerosis, and cancer.

For example, it is well established that AD and a number of related tauopathies including Down's Syndrome, progressive supranuclear palsy (PSP), Pick's disease, corticobasal degeneration (CBD), argyrophilic grain disease (AGD), globular glial tauopathy (GGT), frontotemporal dementia and parkinsonism linked to chromosome-17 (FTLD-17, Niemann-Pick Type C disease are characterized, in part, by the development of neurofibrillary tangles (NFTs). NFTs are also a histopathological hallmark of chronic traumatic encephalopathy that is a consequence of traumatic brain injury. These NFTs are aggregates of paired helical filaments (PHFs) and are composed of an abnormal form of the cytoskeletal protein "tau". Normally, tau stabilizes a key cellular network of microtubules that is essential for distributing proteins and nutrients within neurons. In AD patients, however, tau becomes hyperphosphorylated, disrupting its normal function, forming PHFs and ultimately aggregating to form NFTs. Six isoforms of tau are found in the human brain. In AD patients, all six isoforms of tau are found in NFTs, and all are markedly hyperphosphorylated. Tau in healthy brain tissue bears only 2 or 3 phosphate groups, whereas those found in the brains of AD patients bear, on average, 8 phosphate groups. A clear parallel between NFT levels in the brains of AD patients and the severity of dementia strongly supports a key role for tau dysfunction in AD. The precise causes of this hyperphosphorylation of tau remain elusive. Accordingly, considerable effort has been dedicated toward: a) elucidating the molecular physiological basis of tau hyperphosphorylation; and b) identifying strategies that could limit tau hyperphosphorylation in the hope that these might halt, or even reverse, the progression of tauopathies and Alzheimer's disease. Several lines of evidence suggest that up-regulation of a number of kinases may be involved in hyperphosphorylation of tau, although very recently, an alternative basis for this hyperphosphorylation has been advanced.

In particular, it has recently emerged that phosphate levels of tau are regulated by the levels of O-GlcNAc on tau. The presence of O-GlcNAc on tau has stimulated studies that correlate O-GlcNAc levels with tau phosphorylation levels. The recent interest in this field stems from the observation that O-GlcNAc modification has been found to occur on many proteins at amino acid residues that are also known to be phosphorylated. Consistent with this observation, it has been found that increases in phosphorylation levels result in decreased O-GlcNAc levels and conversely, increased O-GlcNAc levels correlate with decreased phosphorylation levels. This reciprocal relationship between O-GlcNAc and phosphorylation has been termed the "Yin-Yang hypothesis" and has gained strong biochemical support by the recent discovery that the enzyme OGTase forms a functional complex with phosphatases that act to remove phosphate groups from proteins. Like phosphorylation, O-GlcNAc is a dynamic modification that can be removed and reinstalled several times during the lifespan of a protein. Suggestively, the gene encoding O-GlcNAcase has been mapped to a chromosomal locus that is linked to AD. Hyperphosphorylated tau in human AD brains has markedly lower levels of O-GlcNAc than are found in healthy human brains. Very recently, it has been shown that O-GlcNAc levels of soluble tau protein from human brains affected with AD are markedly lower than those from healthy brain. Furthermore, PHF from diseased brain was suggested to lack completely any O-GlcNAc modification whatsoever. The molecular basis of this hypoglycosylation of tau is not known, although it may stem from increased activity of kinases and/or dysfunction of one of the enzymes involved in processing O-GlcNAc. Supporting this latter view, in both PC-12 neuronal cells and in brain tissue sections from mice, a nonselective N-acetylglucosaminidase inhibitor was used to increase tau O-GlcNAc levels, whereupon it was observed that phosphorylation levels decreased. Moreover, it has been described that the O-GlcNAc modification of tau directly inhibits its aggregation without perturbing the conformational properties of tau monomers. The implication of these collective results is that by maintaining healthy O-GlcNAc levels in AD patients, such as by inhibiting the action of O-GlcNAcase (OGA), one should be able to block hyperphosphorylation of tau and all of the associated effects of tau hyperphosphorylation, including the formation of NFTs and downstream effects. However, because the proper functioning of the lysosomal β-hexosaminidases is critical, any potential therapeutic intervention for the treatment of AD that blocks the action of O-GlcNAcase would have to avoid the concomitant inhibition of both lysosomal hexosaminidases A and B.

Consistent with the known properties of the hexosamine biosynthetic pathway, the enzymatic properties of O-GlcNAc transferase (OGTase), and the reciprocal relationship between O-GlcNAc and phosphorylation, it has been shown that decreased glucose availability in brain leads to tau hyperphosphorylation. The gradual impairment of glucose transport and metabolism leads to decreased O-GlcNAc and hyperphosphorylation of tau (and other proteins). Accordingly, the inhibition of O-GlcNAcase should compensate for the age-related impairment of glucose metabolism within the brains of health individuals as well as patients suffering from AD or related neurodegenerative diseases.

These results suggest that a malfunction in the mechanisms regulating tau O-GlcNAc levels may be vitally important in the formation of NFTs and associated neurodegeneration. Good support for blocking tau hyperphosphorylation as a therapeutically useful intervention comes from studies showing that when transgenic mice harboring human tau are treated with kinase inhibitors, they do not develop typical motor defects and, in another case, show a decreased level of insoluble tau. These studies provide a clear link between lowering tau phosphorylation levels and alleviating AD-like behavioral symptoms in a murine model of this disease.

There is evidence indicating that the modification with O-GlcNAc may have a general function in preventing harmful protein aggregation. This has been directly demonstrated for the tau protein and also for the protein alpha-synuclein that is a toxic aggregating protein associated with synucleinopathies, including Parkinson's disease. Two other aggregating proteins that are associated with amyotrophic lateraly sclerosis (Tar DNA binding protein-43 (TDP-43) and superoxide-dismutase I (SOD-I)) and frontotemporal lobar degeneration (TDP-43) are known to carry the O-GlcNAc modification. These results indicate that increasing O-GlcNAcylation with OGA inhibitors could be in general beneficial in diseases associated with protein aggregation.

There is also a large body of evidence indicating that increased levels of O-GlcNAc protein modification provides protection against pathogenic effects of stress in cardiac tissue, including stress caused by ischemia, hemorrhage, hypervolemic shock, and calcium paradox. For example, activation of the hexosamine biosynthetic pathway (HBP) by administration of glucosamine has been demonstrated to exert a protective effect in animal models of ischemia/reperfusion, trauma hemorrhage, hypervolemic shock and calcium paradox. Moreover, strong evidence indicates that these cardioprotective effects are mediated by elevated levels of protein O-GlcNAc modification. There is also evidence that the O-GlcNAc modification plays a role in a variety of neurodegenerative diseases, including Parkinson's disease and related synucleinopathies, and Huntington's disease.

Humans have three genes encoding enzymes that cleave terminal β-N-acetyl-glucosamine residues from glycoconjugates. The first of these encodes the enzyme O-glycoprotein-2-acetamido-2-deoxy-β-D-glucopyranosidase (O-GlcNAcase). O-GlcNAcase is a member of family 84 of glycoside hydrolases. O-GlcNAcase acts to hydrolyze O-GlcNAc off of serine and threonine residues of post-translationally modified proteins. Consistent with the presence of O-GlcNAc on many intracellular proteins, the enzyme O-GlcNAcase appears to have a role in the etiology of several diseases including type II diabetes, AD and cancer. Although O-GlcNAcase was likely isolated earlier on, about 20 years elapsed before its biochemical role in acting to cleave O-GlcNAc from serine and threonine residues of proteins was understood. More recently O-GlcNAcase has been cloned, partially characterized, and suggested to have additional activity as a histone acetyltransferase.

However, a major challenge in developing inhibitors for blocking the function of mammalian glycosidases, including O-GlcNAcase, is the large number of functionally related enzymes present in tissues of higher eukaryotes. Accordingly, the use of non-selective inhibitors in studying the cellular and organismal physiological role of one particular enzyme is complicated because complex phenotypes arise from the concomitant inhibition of such functionally related enzymes. In the case of β-N-acetylglucosaminidases, existing compounds that act to block O-GlcNAcase function are non-specific and act potently to inhibit the lysosomal β-hexosaminidases.

Low molecular weight OGA inhibitors are e.g. disclosed in the international applications WO 2008/025170 and WO 2014/032187. However, no OGA inhibitor has reached the market yet. Thus, there is still a need for low molecular weight molecules that selectively inhibit OGA.

U.S. Pat. No. 3,489,757. mentions i.a. the following compounds:

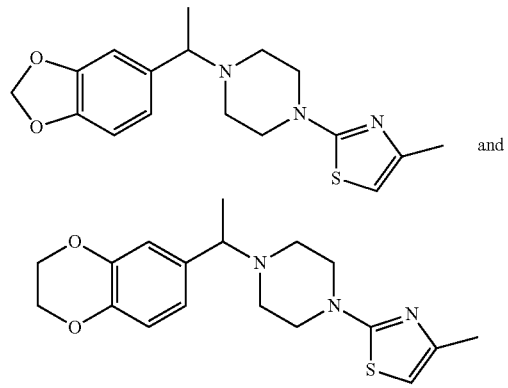

and (1-[1-(1,3-benzodioxol-5-yl)ethyl]-4-(4-methyl-2-thiazolyl)-piperazine and 2-(4-(1-(2,3-dihydrobenzo[b][1,4]dioxin-6-yl)ethyl)piperazin-1-yl)-4-methylthiazole).

U.S. Pat. No. 3,485,757 teaches the respective compounds for the treatment of hypertension and does not relate to the use in the treatment neurodegenerative diseases, diabetes, cancer, cardiovascular diseases and stroke or to OGA inhibitor activity.

U.S. Pat. No. 3,299,067 discloses compounds as medicaments, in particular as peripheral vasodilators, analgesics and anti-inflammatory agents. U.S. Pat. No. 3,299,067 does not disclose any OGA inhibitor activity. The compounds of U.S. Pat. No. 3,299,067 bear a methylene group in the bridging position. U.S. Pat. No. 3,299,067 does not refer to any OGA inhibitor activity.

WO 99/21850 discloses compounds that bind to the dopamine D4 receptor subtype and are said to be useful in treatment of various neuropsychological disorders. However, the compounds are not active as OGA inhibitors. For example, compound 5 of WO 99/21850 shows the following data, when measured according to Example B01 of the present application (Human O-GlcNAcase enzyme inhibition assay):

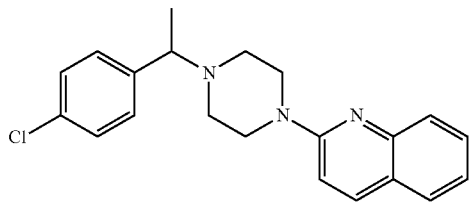

OGA IC$_{50}$ > 30000 nM

Compounds that modulate MCH binding to MCH receptors are presented in WO 2005/110982. The compounds are said to be useful in the treatment of eating disorders, sexual disorders, diabetes, heart disease, and stroke, which are unrelated to the indications of the present invention. The compounds are not active as OGA inhibitors. For instance, the compound of example 72 of WO 2005/110982 provides the following data, when measured according to Example B01 of the present application:

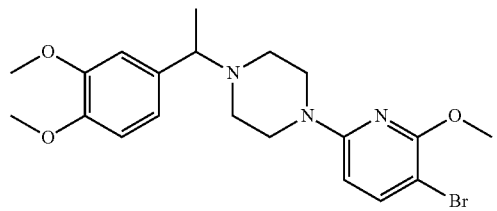

OGA IC$_{50}$ > 30000 nM

WO 2009/053373 discloses molecules for the treatment of PARP-mediated disorders, such as neurodegenerative diseases. The molecules of WO 2009/053373 are not useful as OGA inhibitors. For instance, the compound of example 56 of WO 99/21850 shows the following data, when measured according to Example B01 of the present application:

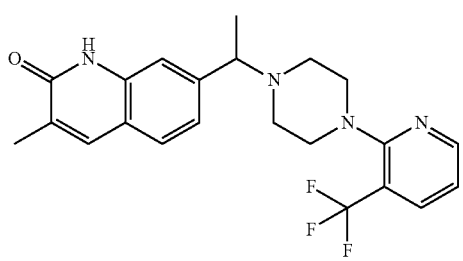

OGA IC$_{50}$ > 30000 nM

The present invention has the object of finding novel compounds having valuable properties, in particular those which can be used for the preparation of medicaments.

It has been surprisingly found that the compounds according to the invention and salts thereof have very valuable pharmacological properties. In particular, they act as glycosidase inhibitors. The invention relates to compounds of formula (I)

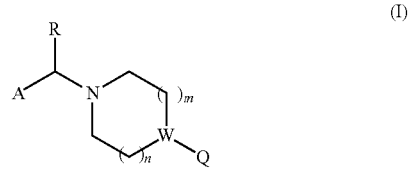

wherein

R is straight chain or branched alkyl having 1 to 6 carbon atoms, wherein 1 to 5 hydrogen atoms may be replaced by Hal or OH. Preferably R is methyl, CH$_2$OH, CF$_3$, CHF$_2$, CH$_2$F;

W is CH or N, preferably N;

A denotes one of the following groups:

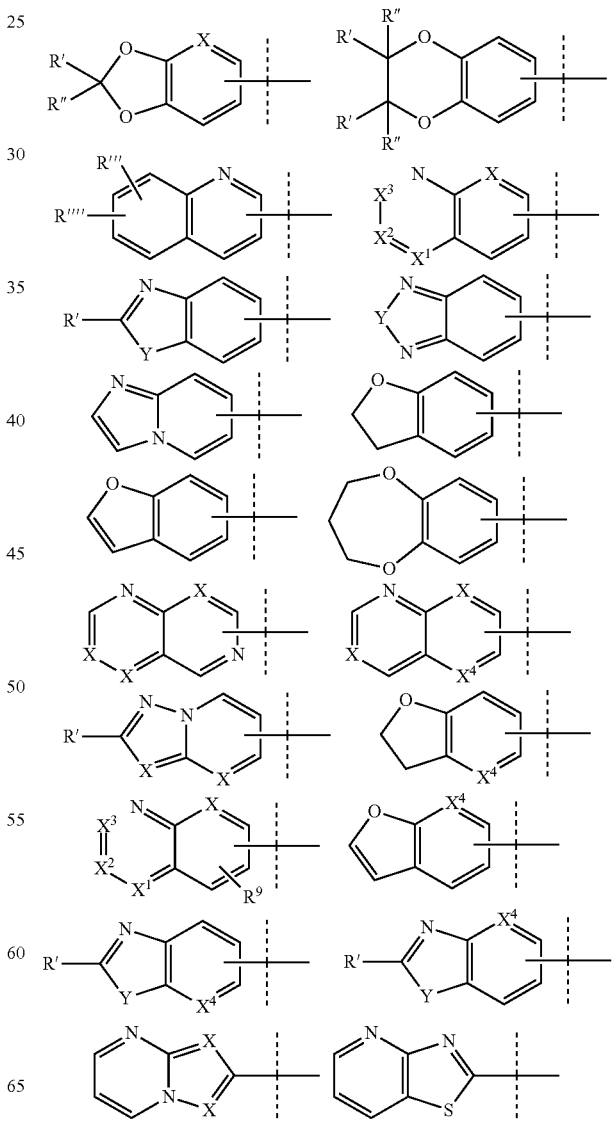

-continued

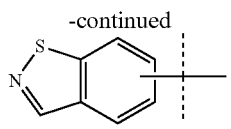

X is N or CR'''. Preferably all or one or two of X in a group are CH;

$X^1$, $X^2$ is N or CR''';

$X^3$ is N or CR'''';

$X^4$ is N or $CR^9$;

$R^9$ denotes Hal, $NR^3R^4$, $CHR^3R^4$, $OR^3$, CN, straight chain or branched alkyl having 1 to 12 carbon atoms, wherein 1 to 3 $CH_2$-groups may be replaced by a group selected from O, $NR^3$, S, SO, $SO_2$, S(O)(NH), CO, COO, OCO, $CONR^3$, $NR^3CO$ and wherein 1 to 5 hydrogen atoms may be replaced by Hal, $NR^3R^4$ or $NO_2$;

Y is O, S, SO or $SO_2$. Preferably Y is O or S;

R', R" denote each independently H, Hal or straight chain or branched alkyl having 1 to 12 carbon atoms. Preferably both are either H, F or methyl;

R''', R'''' independently denote H, Hal, $NR^3R^4$, $CHR^3R^4$, $OR^3$, CN, straight chain or branched alkyl having 1 to 12 carbon atoms, wherein 1 to 3 $CH_2$-groups may be replaced by a group selected from O, $NR^3$, S, SO, $SO_2$, S(O)(NH), CO, COO, OCO, $CONR^3$, $NR^3CO$ and wherein 1 to 5 hydrogen atoms may be replaced by Hal, $NR^3R^4$ or $NO_2$. Preferably both R''' and/or R'''' are H, Hal, $NR^3R^4$, $CHR^3R^4$, $OR^3$, CN or alkyl;

R'''' denotes H, Hal, $NR^3R^4$, $CHR^3R^4$, CN, straight chain or branched alkyl having 1 to 12 carbon atoms, wherein 1 to 3 $CH_2$-groups may be replaced by a group selected from O, $NR^3$, S, SO, $SO_2$, S(O)(NH), CO, COO, OCO, $CONR^3$, $NR^3CO$ and wherein 1 to 5 hydrogen atoms may be replaced by Hal, $NR^3R^4$ or $NO_2$. Preferably, R is H, Hal or alkyl;

$R^3$, $R^4$ denote each independently H or a straight chain or branched alkyl group having 1 to 12 carbon atoms, preferably H, methyl or ethyl;

Q denotes one of the following groups:

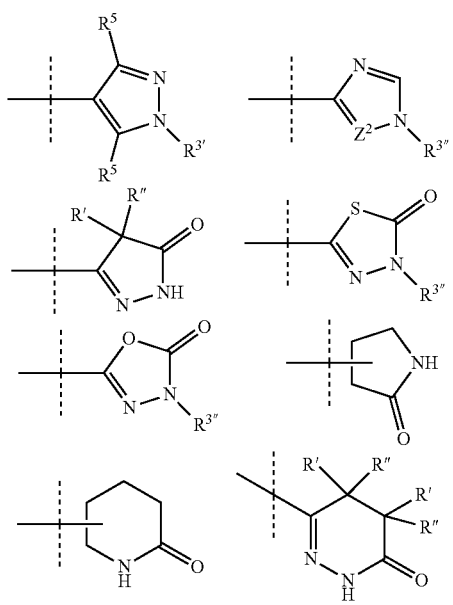

-continued

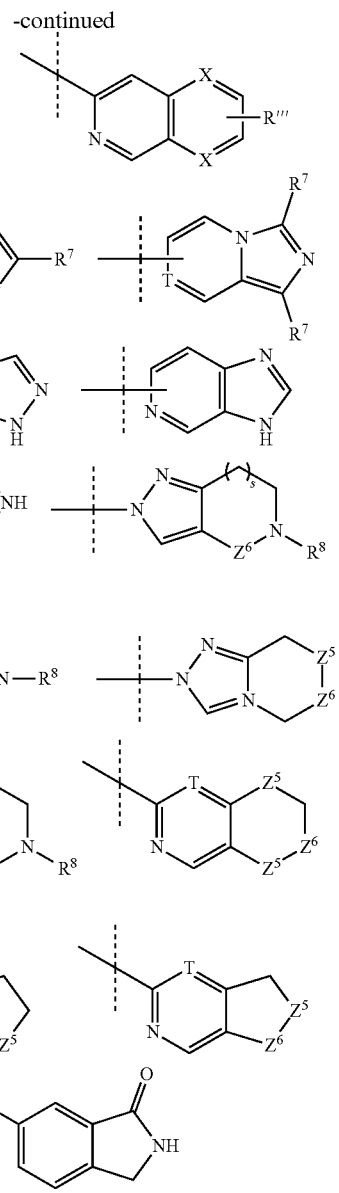

$Z^2$, denotes $CR^5$, $CR^6$ or N;

$Z^4$ is N, CH, CON, COCH;

$Z^5$ is S, O, $NR^8$, $SO_2$, $CHR^5$, preferably NH, $NCH_3$, $NCOCH_3$, $NSO_2CH_3$, $CHSO_2CH_3$ or $CHNHSO_2CH_3$;

$Z^{5'}$ is S, O, $NR^8$, $SO_2$;

$Z^6$ is $CH_2$, CO;

s denotes 0 or 1;

T is N, CH or $CR^7$;

$R^{3'}$ denotes H or a straight chain or branched alkyl group having 1 to 12 carbon atoms, wherein 1 to 3 $CH_2$-groups may be replaced by a group selected from $SO_2$, CO, O and wherein 1 to 5 hydrogen atoms may be replaced by Hal;

$R^{3''}$ denotes a straight chain or branched alkyl group having 1 to 12 carbon atoms, wherein 1 to 3 $CH_2$-groups are replaced by a group selected from $SO_2$, CO, O and wherein 1 to 5 hydrogen atoms may be replaced by Hal;

$R^5$, $R^6$, $R^7$ independently denote H, Hal, $NR^3R^4$, $NO_2$, straight chain or branched alkyl having 1 to 12 carbon atoms, wherein 1 to 3 $CH_2$-groups may be replaced by a group selected from O, $NR^3$, S, SO, $SO_2$, S(O)(NH), CO, COO, OCO, CONR$^3$, NR$^3$CO and wherein 1 to 5 hydrogen atoms may be replaced by Hal, NR$^3$R$^4$, NO$_2$, OR$^3$, Het, Ar, Cyc, or denote Ar, Het or Cyc, R$^5$, R$^6$, R$^7$ independently also denote preferably OH;

R$^8$ denotes H, methyl or straight chain or branched alkyl having 2 to 12 carbon atoms, wherein 1 to 3 CH$_2$-groups may be replaced by a group selected from O, NR$^3$, S, SO, SO$_2$, CO, COO, OCO, CONR$^3$, NR$^3$CO and wherein 1 to 5 hydrogen atoms may be replaced by Hal, NR$^3$R$^4$ or NO$_2$;

Hal denotes F, Cl, Br or I, preferably F, Cl or Br;

Het denotes a saturated, unsaturated or aromatic ring, being monocyclic or bicyclic or fused-bicyclic and having 3- to 8-members and containing 1 to 4 heteroatoms selected from N, O and S, which may be substituted by 1 to 3 substituents selected from R$^5$, Hal and OR$^3$;

Ar denotes a 6-membered carbocyclic aromatic ring or a fused or non-fused bicyclic aromatic ring system, which is optionally substituted by 1 to 3 substituents independently selected from R$^5$, OR$^3$ and Hal;

Cyc denotes a saturated or an unsaturated carbocyclic ring having from 3 to 8 carbon atoms which is optionally substituted by 1 to 3 substituents independently selected from R$^5$ or Hal or OH;

m and n denote independently from one another 0, 1, 2 or 3 and pharmaceutically usable derivatives, solvates, salts, prodrugs, tautomers, enantiomers, racemates and stereoisomers thereof, including mixtures thereof in all ratios and compounds of formula I, wherein one or more H atoms are replaced by D (deuterium).

Specifically, formula (I) includes the following two enantiomers of formula Ia and Ib:

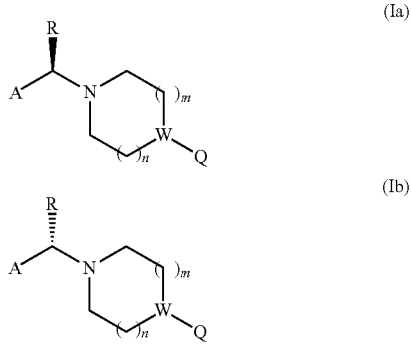

wherein A, R, W, Q, n and m have the meaning given above.

The invention also relates to a mixture of, i.e. a composition comprising, compounds Ia and Ib as set out above, having identical groups A, R, W, Q, n and m, in equal or unequal amounts.

Throughout the specification, R in formula I, Ia and Ib is preferably methyl. The indices m and n in formula I, Ia and Ib are preferably simultaneously 1.

Most preferably, compounds of formula I are the compounds of formula A and B:

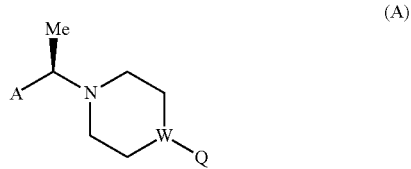

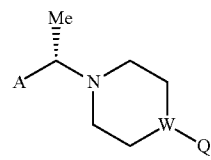

If individual groups, such as T, occurs more than once in a compound of formula I, it can have the same or different meanings according to the respective definition of that group.

Preferred compounds of the present invention are preferably used in their non-racemic form, i.e. as enantiomerically pure compounds or their enaniomerically enriched mixtures of the enantiomers. If R is an unsubstituted straight chain or branched alkyl having 1 to 6 carbon atoms, such as methyl, ethyl, n-propyl or iso-butyl, the S-entantiomers of compounds of formula I are preferred. Very preferred are formulae Ib and B.

In general, compounds of formula I are preferred that contain one ore more preferred groups such as R' to R'''' or R$^3$ to R$^7$ or indices such as m or n. Compounds of formula I are the more preferred, the more preferred groups or indices they contain.

If substituents, such as the group R$^8$, are connected to the remainder of the molecule through a heteroatom, the connecting atom in the respective group is preferably a carbon atom or the respective group is H.

The invention also relates to the use of compounds of formula (I) as a medicament.

In the meaning of the present invention, the compound is defined to include pharmaceutically usable derivatives, solvates, prodrugs, tautomers, enantiomers, racemates and stereoisomers thereof, including mixtures thereof in all ratios.

The term "pharmaceutically usable derivatives" is taken to mean, for example, the salts of the compounds according to the invention and also so-called prodrug compounds. The term "solvates" of the compounds is taken to mean adductions of inert solvent molecules onto the compounds, which are formed owing to their mutual attractive force. Solvates are, for example, mono- or dihydrates or alkoxides. The invention also comprises solvates of salts of the compounds according to the invention. The term "prodrug" is taken to mean compounds according to the invention which have been modified by means of, for example, alkyl or acyl groups, sugars or oligopeptides and which are rapidly cleaved in the organism to form the effective compounds according to the invention. These also include biodegradable polymer derivatives of the compounds according to the invention. It is likewise possible for the compounds of the invention to be in the form of any desired prodrugs such as, for example, esters, carbonates, carbamates, ureas, amides or phosphates, in which cases the actually biologically active form is released only through metabolism. Any compound that can be converted in-vivo to provide the bioactive agent (i.e. compounds of the invention) is a prodrug within the scope and spirit of the invention. Various forms of prodrugs are well known in the art. It is further known that chemical substances are converted in the body into metabolites which may where appropriate likewise elicit the desired biological effect—in some circumstances even in more pronounced form. Any biologically active compound that was converted in-vivo by metabolism from any of the compounds of the invention is a metabolite within the scope and spirit of the invention.

The compounds of the invention may be present in the form of their double bond isomers as pure E or Z isomers, or in the form of mixtures of these double bond isomers. Where possible, the compounds of the invention may be in the form of the tautomers, such as keto-enol tautomers. All stereoisomers of the compounds of the invention are contemplated, either in a mixture or in pure or substantially pure form. The compounds of the invention can have asymmetric centers at any of the carbon atoms. Consequently, they can exist in the form of their racemates, in the form of the pure enantiomers and/or diastereomers or in the form of mixtures of these enantiomers and/or diastereomers. The mixtures may have any desired mixing ratio of the stereoisomers. Thus, for example, the compounds of the invention which have one or more centers of chirality and which occur as racemates or as diastereomer mixtures can be fractionated by methods known per se into their optical pure isomers, i.e. enantiomers or diastereomers. The separation of the compounds of the invention can take place by column separation on chiral or non-chiral phases or by re-crystallization from an optionally optically active solvent or with use of an optically active acid or base or by derivatization with an optically active reagent such as, for example, an optically active alcohol, and subsequent elimination of the radical.

The invention also relates to the use of mixtures of the compounds according to the invention, for example mixtures of two diastereomers, for example in the ratio 1:1, 1:2, 1:3, 1:4, 1:5, 1:10, 1:100 or 1:1000. These are particularly preferably mixtures of stereoisomeric compounds.

An enantiomerically enriched mixture denotes a compound of Formula (I) or related formula having an enantiomeric excess, as measured by methods well known by one skilled in the art, of 10% or more, preferably 50% or more, and more preferably more than 95%. Most preferably an enantiomerically enriched mixture denotes a compound of Formula (I) or related Formulae having an enantiomeric excess of more than 98%.

The nomenclature as used herein for defining compounds, especially the compounds according to the invention, is in general based on the rules of the IUPAC-organization for chemical compounds and especially organic compounds. The compounds of invention have been named according to the standards used in the program AutoNom 2000 or ACD Lab Version 12.01. The determination of the stereochemistry (S) or (R) is performed using standard rules of the nomenclature well known by one skilled in the art. The terms indicated for explanation of the above compounds of the invention always, unless indicated otherwise in the description or in the claims, have the following meanings:

The term "unsubstituted" means that the corresponding radical, group or moiety has no substituents. The term "substituted" means that the corresponding radical, group or moiety has one or more substituents. Where a radical has a plurality of substituents, and a selection of various substituents is specified, the substituents are selected independently of one another and do not need to be identical. Even though a radical has a plurality of a specific-designated substituent the expression of such substituent may differ from each other (e.g. methyl and ethyl). It shall be understood accordingly that a multiple substitution by any radical of the invention may involve identical or different radicals. Hence, if individual radicals occur several times within a compound, the radicals adopt the meanings indicated, independently of one another.

The term "alkyl" or "alkyl group" refers to acyclic saturated or unsaturated hydrocarbon radicals, which may be branched or straight-chain and preferably have 1, 2, 3, 4, 5, 6, 7, 8, 9 or 10 carbon atoms, i.e. $C_1$-$C_{10}$-alkanyls. Examples of suitable alkyl radicals are methyl, ethyl, n-propyl, isopropyl, 1,1-, 1,2- or 2,2-dimethylpropyl, 1-ethylpropyl, 1-ethyl-1-methylpropyl, 1-ethyl-2-methylpropyl, 1,1,2- or 1,2,2-trimethylpropyl, n-butyl, isobutyl, sec-butyl, tert-butyl, 1-, 2- or 3-methylbutyl, 1,1-, 1,2-, 1,3-, 2,2-, 2,3- or 3,3-dimethylbutyl, 1- or 2-ethylbutyl, n-pentyl, iso-pentyl, neo-pentyl, tert-pentyl, 1-, 2-, 3- or -methyl-pentyl, n-hexyl, 2-hexyl, isohexyl, n-heptyl, n-octyl, n-nonyl, n-decyl, n-undecyl, n-dodecyl, n-tetradecyl, n-hexadecyl, n-octadecyl, n-icosanyl, n-docosanyl.

In an embodiment of the invention, alkyl denotes unbranched or branched alkyl having 1-10 C atoms, in which 1-7H atoms may be replaced independently from one another by Hal. A preferred embodiment of alkyl denotes unbranched or branched alkyl having 1-6 C atoms, in which 1-4 atoms may be replaced independently from one another by Hal. In a more preferred embodiment of the invention, alkyl denotes unbranched or branched alkyl having 1-4 C atoms, in which 1-3H atoms can be replaced independently from one another by Hal, particularly by F and/or Cl. It is most preferred that alkyl denotes unbranched or branched alkyl having 1-6 C atoms. Highly preferred is $C_{1-4}$-alkyl. A $C_{1-4}$-alkyl radical is for example a methyl, ethyl, propyl, isopropyl, butyl, isobutyl, tert-butyl, sec-butyl, tert-butyl, fluoromethyl, difluoromethyl, trifluoromethyl, pentafluoroethyl, 1,1,1-trifluoroethyl or bromomethyl, especially methyl, ethyl, propyl or trifluoromethyl. It shall be understood that the respective denotation of alkyl is independently of one another in any radical of the invention.

The terms "cycloalkyl" or "Cyc" for the purposes of this invention refers to saturated and partially unsaturated non-aromatic cyclic hydrocarbon groups/radicals, having 1 to 3 rings, that contain 3 to 20, preferably 3 to 12, more preferably 3 to 9 carbon atoms. The cycloalkyl radical may also be part of a bi- or polycyclic system, where, for example, the cycloalkyl radical is fused to an aryl, heteroaryl or heterocyclyl radical as defined herein by any possible and desired ring member(s). The bonding to the compounds of the general formula (I) can be effected via any possible ring member of the cycloalkyl radical. Examples of suitable cycloalkyl radicals are cyclopropyl, cyclobutyl, cyclopentyl, cyclohexyl, cycloheptyl, cyclooctyl, cyclodecyl, cyclohexenyl, cyclopentenyl and cyclooctadienyl.

In an embodiment of the invention, Cyc denotes cycloalkyl having 3-7 C atoms, in which 1-4H atoms may be replaced independently of one another by Hal. Preferred is $C_3$-$C_7$-cycloalkyl. More preferred is $C_4$-$C_7$-cycloalkyl. Most preferred is $C_5$-$C_7$-cycloalkyl, i.e. cyclopentyl, cyclohexyl or cycloheptyl, highly preferably cyclohexyl. It shall be understood that the respective denotation of Cyc is independently of one another in any radical of the invention.

The term "Ar", "aryl" or "carboaryl" for the purposes of this invention refers to a mono- or polycyclic aromatic hydrocarbon systems having 3 to 14, preferably 3-12, more preferably 4 to 12, most preferably 5 to 10, highly preferably 6 to 8 carbon atoms, which can be optionally substituted. The term "Ar" or "aryl" also includes systems in which the aromatic cycle is part of a bi- or polycyclic saturated, partially unsaturated and/or aromatic system, such as where the aromatic cycle is fused to an aryl, cycloalkyl, heteroaryl or heterocyclyl group as defined herein via any desired and possible ring member of the aryl radical. The bonding to the compounds of the general formula (I) can be effected via any possible ring member of the aryl radical. Examples of suited aryl radicals are phenyl, biphenyl, naphthyl, 1-naphthyl, 2-naphthyl and anthracenyl, but likewise indanyl, indenyl or 1,2,3,4-tetrahydronaphthyl. Preferred carboaryls of the invention are optionally substituted phenyl, naphthyl and biphenyl, more preferably optionally substituted monocylic carboaryl having 6-8 C atoms, most preferably optionally substituted phenyl.

Ar and aryl are preferably selected from the following group: phenyl, o-, m- or p-tolyl, o-, m- or p-ethylphenyl, o-, m- or p-propylphenyl, o-, m- or p-isopropylphenyl, o-, m- or p-tert.-butylphenyl, o-, m- or p-hydroxyphenyl, o-, m- or p-methoxyphenyl, o-, m- or p-ethoxyphenyl, o-, m- or p-fluoro-phenyl, o-, m- or p-bromophenyl, o-, m- or p-chlorophenyl, o-, m- or p-sulfonamidophenyl, o-, m- or p-(N-methyl-sulfonamido)phenyl, o-, m- or p-(N,N-dimethyl-sulfonamido)-phenyl, o-, m- or p-(N-ethyl-N-methyl-sulfonamido)phenyl, o-, m- or p-(N,N-diethyl-sulfonamido)-phenyl, particularly 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl or 2,5-dimethyl-4-chlorophenyl.

Irrespective of further substitutions, Het denotes preferably 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazoM-, -4- or -5-yl, 1,2,4-triazo-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-iso-5indolyl, indazolyl, 1-, 2-, 4- or 5-benzimidazolyl, 1-, 3-, 4-, 5-, 6- or 7-benzo-pyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4-, -5-yl or 2,1,3-benzoxadiazol-5-yl, azabicyclo-[3.2.1]octyl or dibenzofuranyl.

The heterocyclic radicals may also be partially or fully hydrogenated.

Irrespective of further substitutions, Het can thus also denote, preferably, 2,3-dihydro-2-, -3-, -4- or -5-furyl, 2,5-dihydro-2-, -3-, -4- or 5-furyl, tetra-hydro-2- or -3-furyl, 1,3-dioxolan-4-yl, tetrahydro-2- or -3-thienyl, 2,3-di-hydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-(-2-, -3-, -4-, -5-, -6-, -7- or -8-quinolyl, 1,2,3,4-tetra-hydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydro-benzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl, 2,3-dihydro-2-oxo-furanyl, 3,4-dihydro-2-oxo-1H-quinazolinyl, 2,3-dihydrobenzoxazolyl, 2-oxo-2,3-dihydrobenzoxazolyl, 2,3-dihydrobenzimidazolyl, 1,3-dihydroindole, 2-oxo-1,3-dihydroindole or 2-oxo-2, 3-dihydrobenzimidazolyl.

Het preferably denotes piperidinyl, 4-hydroxypiperidinyl, piperazinyl, 4-methylpiperazinyl, pyrrolidinyl, morpholinyl, dihydro-pyrazolyl, dihydro-pyridyl, dihydropyranyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, quinolyl, isoquinolyl, benzimidazolyl, benzotriazolyl, indolyl, benzo-1,3-dioxolyl, 2,3-dihydro-benzo[1,4]dioxinyl, indazolyl or benzothiadiazolyl, each of which is unsubstituted or mono-, di- or trisubstituted.

The term "halogen", "halogen atom", "halogen substituent" or "Hal" for the purposes of this invention refers to one or, where appropriate, a plurality of fluorine (F, fluoro), bromine (Br, bromo), chlorine (Cl, chloro) or iodine (I, iodo) atoms. The designations "dihalogen", "trihalogen" and "perhalogen" refer respectively to two, three and four substituents, where each substituent can be selected independently from the group consisting of fluorine, chlorine, bromine and iodine. Halogen preferably means a fluorine, chlorine or bromine atom. Fluorine and chlorine are more preferred, particularly when the halogens are substituted on an alkyl (haloalkyl) or alkoxy group (e.g. $CF_3$ and $CF_3O$). It shall be understood that the respective denotation of Hal is independently of one another in any radical of the invention.

R is preferably straight chain alkyl having 1 to 4 carbon atoms, wherein 1 to 5 hydrogen atoms may be replaced by Hal or OH. More preferably R is methyl or ethyl, and most preferably methyl.

W is preferably N.

A preferably denotes one of the following groups:

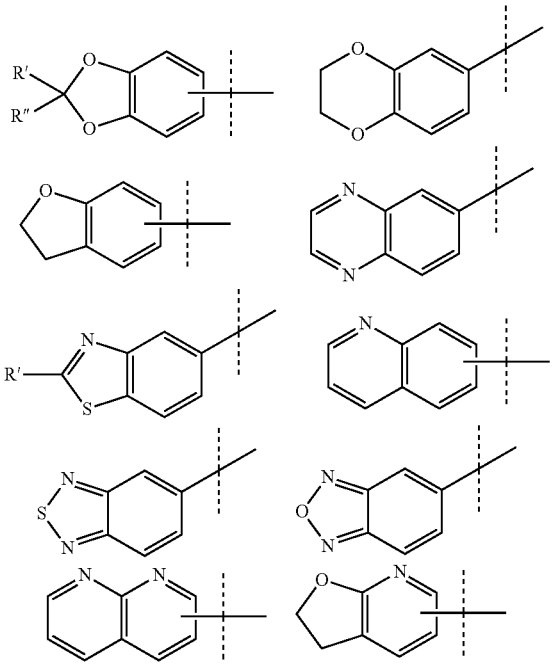

-continued
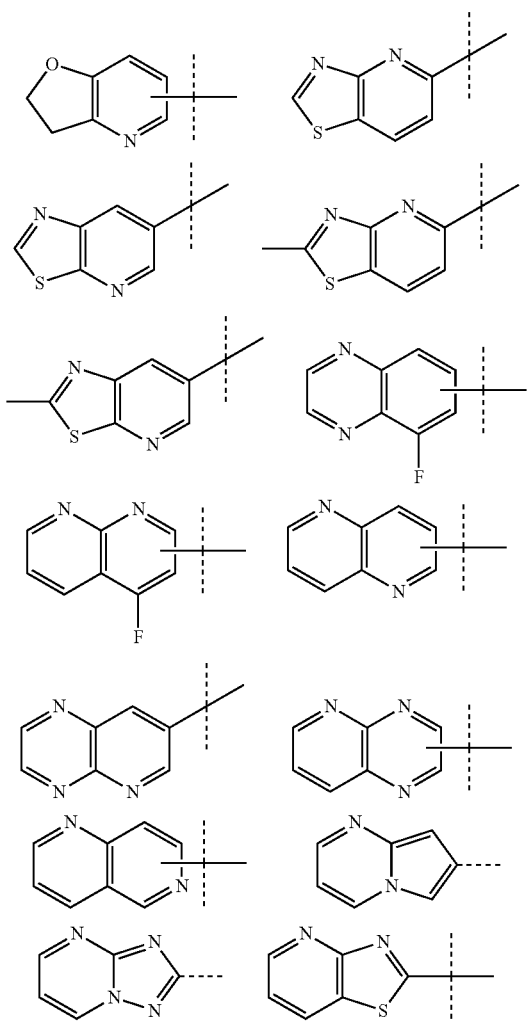
A is especially preferred one of the following groups:
Q is preferably
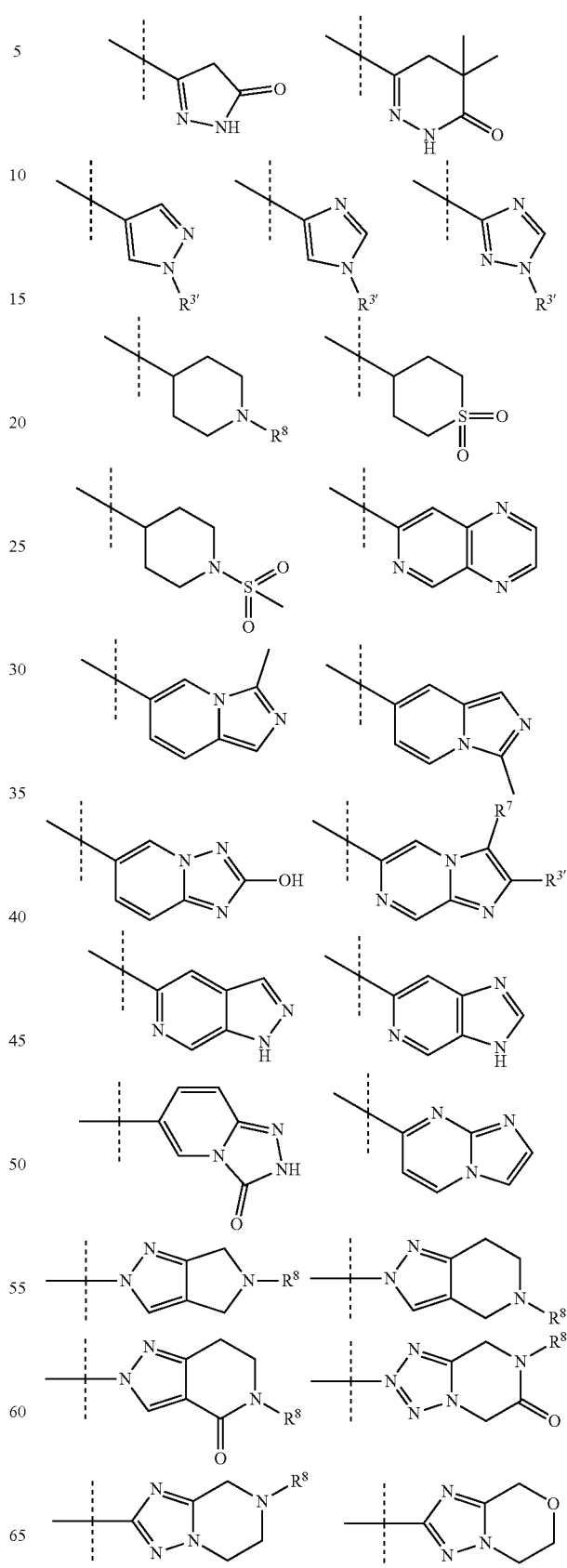

-continued

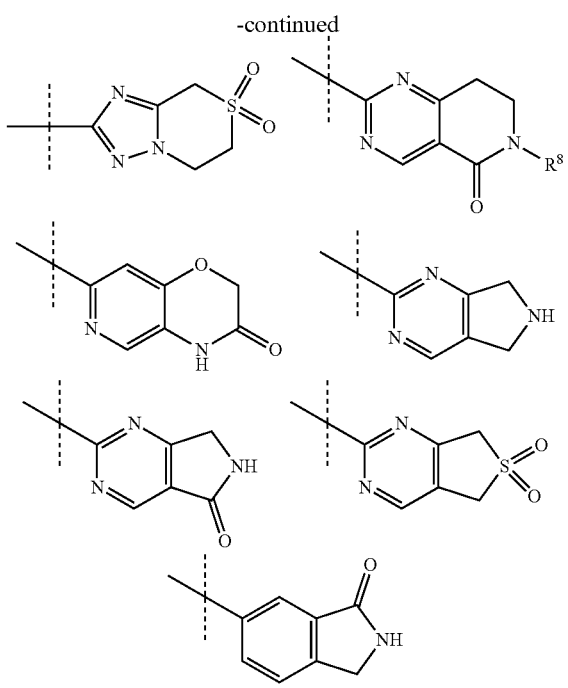

Wherein R³', R⁷ and R⁸ have the meaning given above.

R⁵, R⁵', R⁶ are preferably independently H, Hal, NR³R⁴, NO₂, phenyl, 2-,3- or 4-hydroxy or methoxyphenyl, alkyl, preferably methyl, ethyl, isopropyl, isobutyl, tert-butyl, CF₃, alkoxy (Oalkyl), preferably methoxy or ethoxy, hydroxyalkylen, preferably CH₂OH, alkoxyalkylen preferably CH₂OCH₃, COOH, COOalkyl, preferably COOCH₃, COOCH₂CH₃, CONHalkyl, preferably CONHCH₃, CONHCH₂CH₃, CONHisopropyl, CONHcyclohexyl, CONH₂, CON(CH₃)₂, NHCOalkyl, preferably NHCOCH₃, NHCOCH₂CH₃, NHCOPropyl, NHCOisopropyl, NHCOcyclopropyl, NHCO-4-Chloro-phenyl, NHCH₂CH₃, NHCH₂CH₂CH₃, NHCOCH₂CH₂OH, CO—N-morpholinyl, CON(CH₃)CH₂CH₂N(CH₃)₂, CO-1-piperidinyl, CO-4-hydroxy-1-piperidinyl, CO-1-piperazinyl, CO-4-methyl-1-piperazinyl, CH₂—N-morpholinyl, CH₂N(H)COCH₃, CH₂N(CH₃)COCH₃, CH₂NH₂, NH₂, CH(OH)CH₃, CH(OR³)CH₃

Most preferably, one of R⁵, R⁶ is H.

R⁷ has preferably the meaning of R⁵ and R⁶. More preferably, R⁷ is H, OCH₃, CH₃, CH₂CH₃, CF₃, Hal, preferably Cl, I, F, NH₂, NO₂, CONHalkyl, preferably CONHCH₃, CON(CH₃)₂, NHCOalkyl such as NHCOCH₃, NHalkyl, such as NHCH₂CH₂CH₃, COOalkyl, preferably COOCH₂CH₃, hydroxyalkylen, preferably CH₂OH, CH(CH₃)OH, C(CH₃)₂OH, cyclohexyl, cyclopentyl, morpholinyl, tetrahydrofuranyl. Preferably cyclohexyl, cyclopentyl, morpholinyl, tetrahydrofuranyl are substituted by OH. Most preferred are:

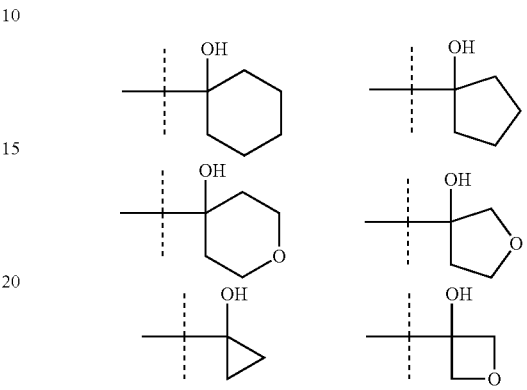

R⁸ is preferably H, COalkyl or alkyl. More preferably, R⁸ is H, COmethyl or methyl.

Most preferably, m and n simultaneously denote 1.

Accordingly, the subject-matter of the invention relates to compounds of formula (I) as medicament, in which at least one of the aforementioned radicals has any meaning, particularly realize any preferred embodiment, as described above. Radicals, which are not explicitly specified in the context of any embodiment of formula (I), sub-formulae thereof or other radicals thereto, shall be construed to represent any respective denotations according to formula (I) as disclosed hereunder for solving the problem of the invention. That means that the aforementioned radicals may adopt all designated meanings as each described in the prior or following course of the present specification, irrespective of the context to be found, including, but not limited to, any preferred embodiments. It shall be particularly understood that any embodiment of a certain radical can be combined with any embodiment of one or more other radicals.

Particularly highly preferred embodiments are those compounds of formula (I) listed in Table 1 and/or physiologically acceptable salts thereof.

TABLE 1

Compounds of formulae (I). OGA enzyme inhibition assay:

| No | Structure | Configuration specification | OGA IC50 (M) |
|---|---|---|---|
| 1 | 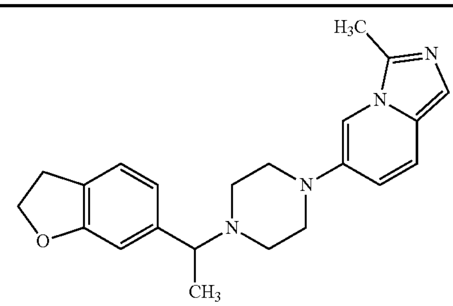 | racemic | ++++ |

TABLE 1-continued

Compounds of formulae (I). OGA enzyme inhibition assay:

| No | Structure | Configuration specification | OGA IC50 (M) |
|---|---|---|---|
| 2 | 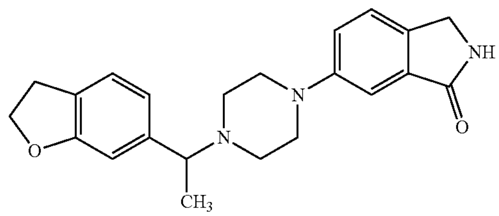 [SMILES: CC(c1ccc2c(c1)OCC2)N1CCN(c2ccc3c(c2)C(=O)NC3)CC1] | racemic | ++++ |
| 3 | 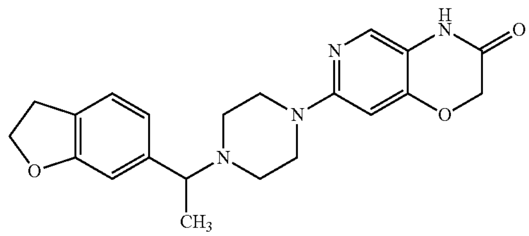 [SMILES: CC(c1ccc2c(c1)OCC2)N1CCN(c2cc3c(cn2)NC(=O)CO3)CC1] | racemic | ++++ |
| 4 | 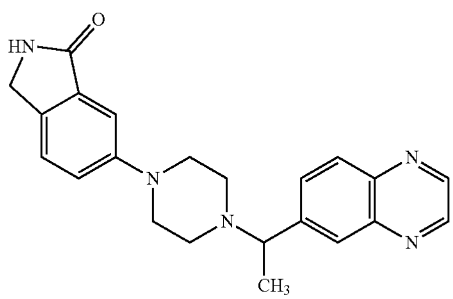 [SMILES: CC(c1ccc2nccnc2c1)N1CCN(c2ccc3c(c2)C(=O)NC3)CC1] | racemic | +++ |
| 5 | 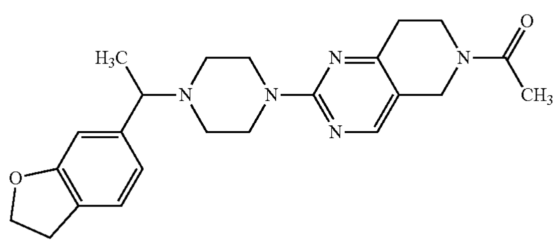 [SMILES: CC(=O)N1CCc2nc(N3CCN(C(C)c4ccc5c(c4)OCC5)CC3)ncc2C1] | racemic | ++++ |
| 6 | 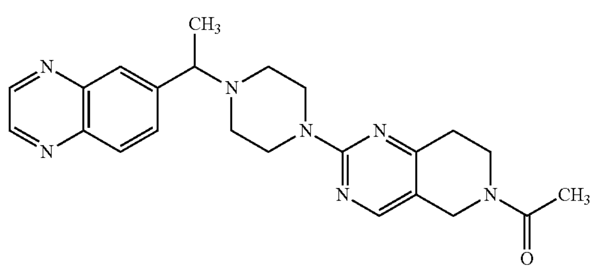 [SMILES: CC(=O)N1CCc2nc(N3CCN(C(C)c4ccc5nccnc5c4)CC3)ncc2C1] | racemic | +++ |
| 7 | 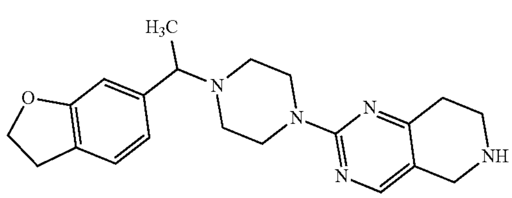 [SMILES: CC(c1ccc2c(c1)OCC2)N1CCN(c2ncc3c(n2)CCNC3)CC1] | racemic | ++++ |

TABLE 1-continued

Compounds of formulae (I). OGA enzyme inhibition assay:

| No | Structure | Configuration specification | OGA IC50 (M) |
|----|-----------|-----------------------------|--------------|
| 8  | 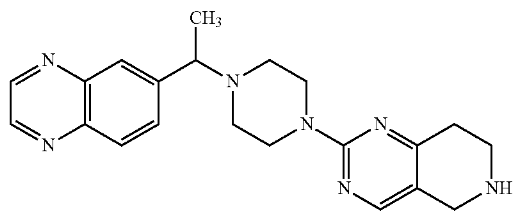 [SMILES: CC(c1ccc2nccnc2c1)N1CCN(c2ncc3c(n2)CCNC3)CC1]          | racemic                     | ++++         |
| 9  | 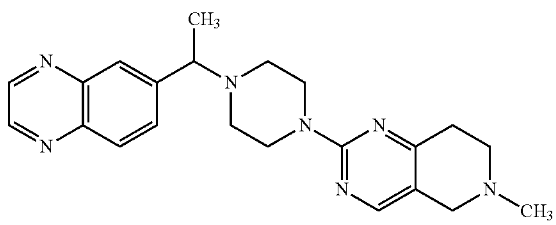 [SMILES: CC(c1ccc2nccnc2c1)N1CCN(c2ncc3c(n2)CCN(C)C3)CC1]          | racemic                     | ++++         |
| 10 | 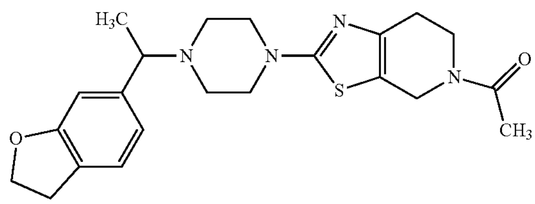 [SMILES: CC(=O)N1CCc2nc(N3CCN(C(C)c4ccc5c(c4)OCC5)CC3)sc2C1]          | racemic                     | ++++         |
| 11 | 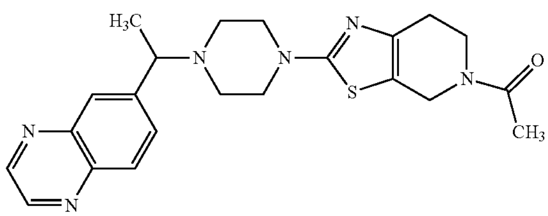 [SMILES: CC(=O)N1CCc2nc(N3CCN(C(C)c4ccc5nccnc5c4)CC3)sc2C1]          | racemic                     | +++          |
| 12 | 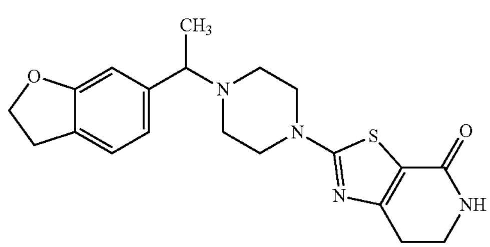          | racemic                     | ++++         |
| 13 | 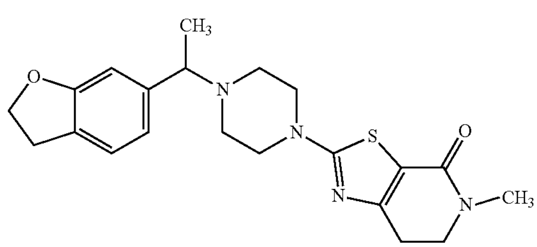 [SMILES: CC(c1ccc2c(c1)OCC2)N1CCN(c2nc3c(s2)C(=O)N(C)CC3)CC1]          | racemic                     | ++++         |

TABLE 1-continued

Compounds of formulae (I). OGA enzyme inhibition assay:

| No | Structure | Configuration specification | OGA IC50 (M) |
|---|---|---|---|
| 14 | 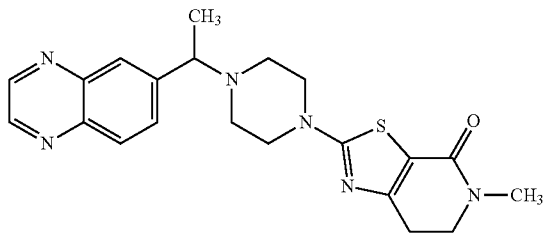 [SMILES: CC(c1ccc2nccnc2c1)N1CCN(c2nc3c(s2)C(=O)N(C)CC3)CC1] | racemic | ++ |
| 15 | 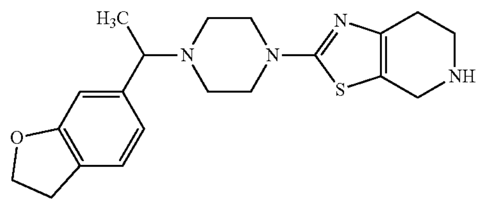 [SMILES: CC(c1ccc2c(c1)OCC2)N1CCN(c2nc3c(s2)CNCC3)CC1] | racemic | ++++ |
| 16 | 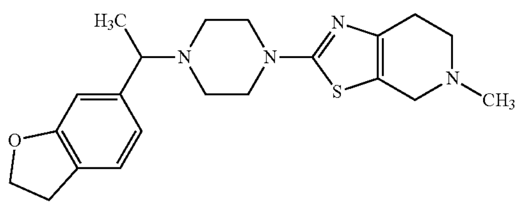 [SMILES: CC(c1ccc2c(c1)OCC2)N1CCN(c2nc3c(s2)CN(C)CC3)CC1] | racemic | ++++ |
| 17 | 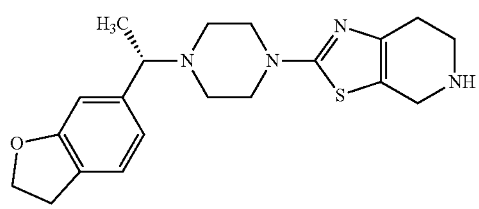 | Chiral HPLC Method P: 1st eluting compound | ++++ |
| 18 | 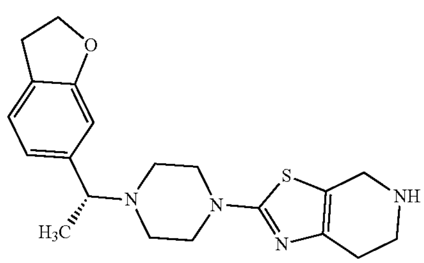 [SMILES: C[C@H](c1ccc2c(c1)OCC2)N1CCN(c2nc3c(s2)CNCC3)CC1] | Chiral HPLC Method P: 2nd eluting compound | + |
| 19 | 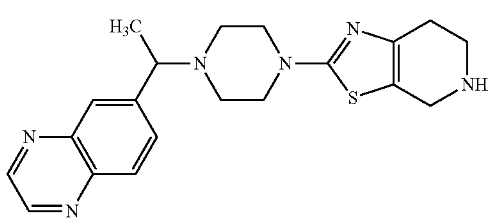 [SMILES: CC(c1ccc2nccnc2c1)N1CCN(c2nc3c(s2)CNCC3)CC1] | racemic | +++ |

TABLE 1-continued

Compounds of formulae (I). OGA enzyme inhibition assay:

| No | Structure | Configuration specification | OGA IC50 (M) |
|---|---|---|---|
| 20 | 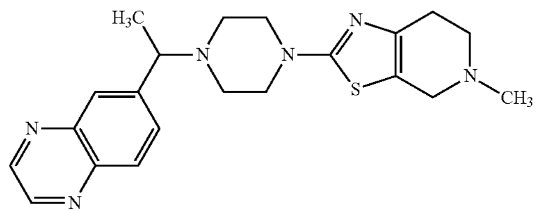 [SMILES: CC(c1ccc2nccnc2c1)N1CCN(c2nc3c(s2)CN(C)CC3)CC1] | racemic | +++ |
| 21 | 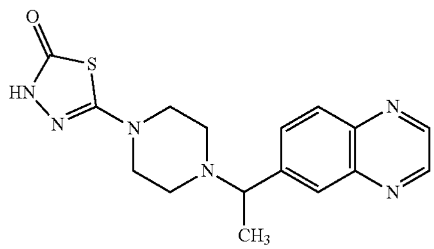 [SMILES: CC(c1ccc2nccnc2c1)N1CCN(c2n[nH]c(=O)s2)CC1] | racemic | +++ |
| 22 | 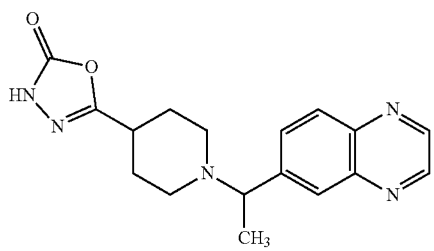 | racemic | ++ |
| 23 | 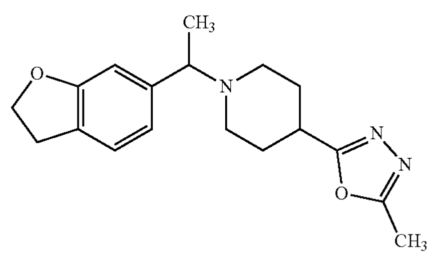 [SMILES: Cc1nnc(C2CCN(C(C)c3ccc4c(c3)OCC4)CC2)o1] | racemic | ++++ |
| 24 | 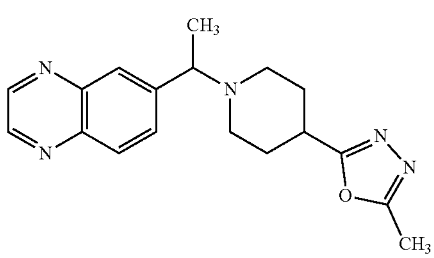 [SMILES: Cc1nnc(C2CCN(C(C)c3ccc4nccnc4c3)CC2)o1] | racemic | ++ |
| 25 | 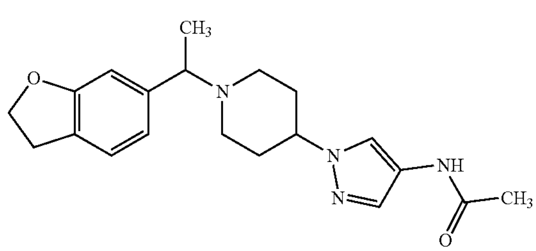 [SMILES: CC(=O)Nc1cnn(C2CCN(C(C)c3ccc4c(c3)OCC4)CC2)c1] | racemic | +++ |

TABLE 1-continued

Compounds of formulae (I). OGA enzyme inhibition assay:

| No | Structure | Configuration specification | OGA IC50 (M) |
|---|---|---|---|
| 26 | 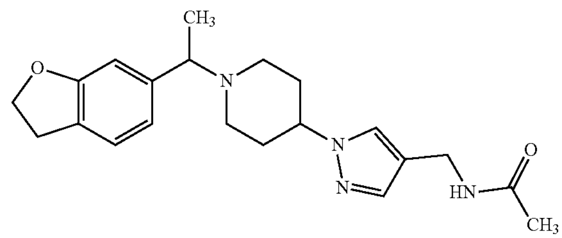 [SMILES: CC(=O)NCc1cnn(C2CCN(C(C)c3ccc4c(c3)OCC4)CC2)c1] | racemic | ++ |
| 27 | 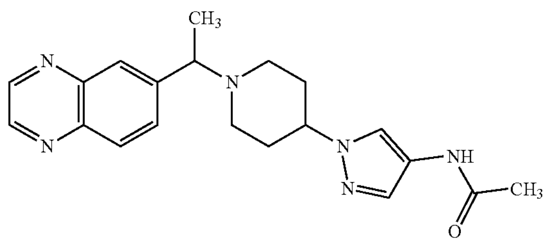 [SMILES: CC(=O)Nc1cnn(C2CCN(C(C)c3ccc4nccnc4c3)CC2)c1] | racemic | + |
| 28 | 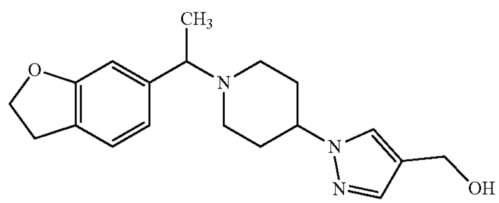 [SMILES: CC(c1ccc2c(c1)OCC2)N1CCC(n2cc(CO)cn2)CC1] | racemic | ++ |
| 29 | 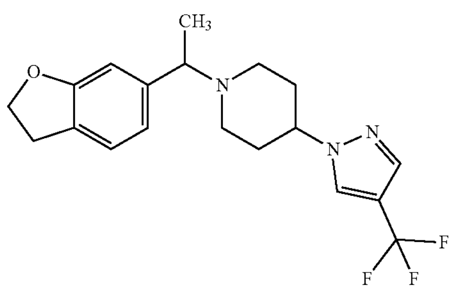 [SMILES: CC(c1ccc2c(c1)OCC2)N1CCC(n2cc(C(F)(F)F)cn2)CC1] | racemic | ++ |
| 30 | 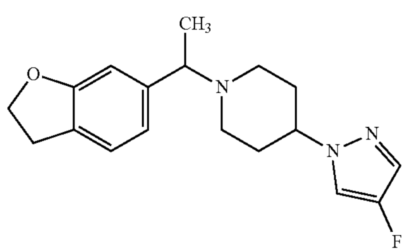 [SMILES: CC(c1ccc2c(c1)OCC2)N1CCC(n2cc(F)cn2)CC1] | racemic | ++ |
| 31 | 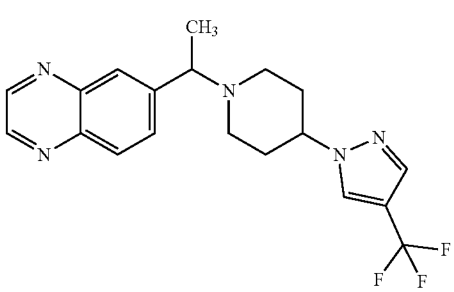 [SMILES: CC(c1ccc2nccnc2c1)N1CCC(n2cc(C(F)(F)F)cn2)CC1] | racemic | + |

TABLE 1-continued

Compounds of formulae (I). OGA enzyme inhibition assay:

| No | Structure | Configuration specification | OGA IC50 (M) |
|---|---|---|---|
| 32 | 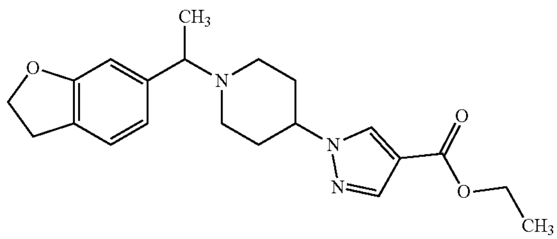 [SMILES: CCOC(=O)c1cnn(C2CCN(C(C)c3ccc4c(c3)OCC4)CC2)c1] | racemic | +++ |
| 33 | 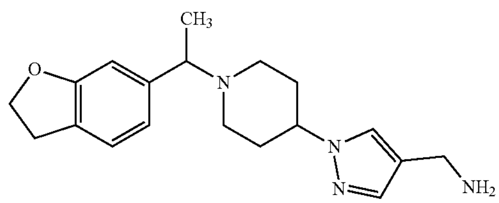 [SMILES: CC(c1ccc2c(c1)OCC2)N1CCC(n2cc(CN)cn2)CC1] | racemic | ++ |
| 34 | 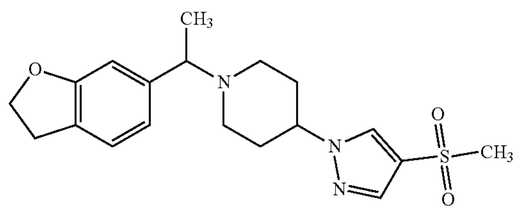 [SMILES: CC(c1ccc2c(c1)OCC2)N1CCC(n2cc(S(C)(=O)=O)cn2)CC1] | racemic | ++ |
| 35 | 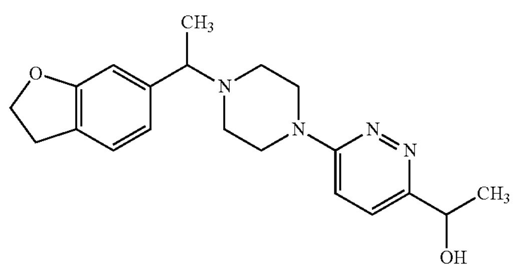 [SMILES: CC(O)c1ccc(N2CCN(C(C)c3ccc4c(c3)OCC4)CC2)nn1] | racemic | ++++ |
| 36 | 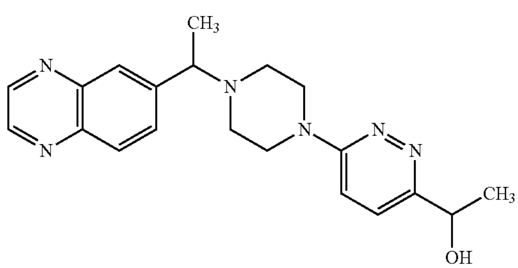 [SMILES: CC(O)c1ccc(N2CCN(C(C)c3ccc4nccnc4c3)CC2)nn1] | racemic | ++ |
| 37 | 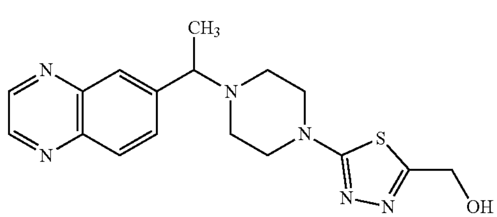 [SMILES: CC(c1ccc2nccnc2c1)N1CCN(c2nnc(CO)s2)CC1] | racemic | ++ |

TABLE 1-continued

Compounds of formulae (I). OGA enzyme inhibition assay:

| No | Structure | Configuration specification | OGA IC50 (M) |
|---|---|---|---|
| 38 | 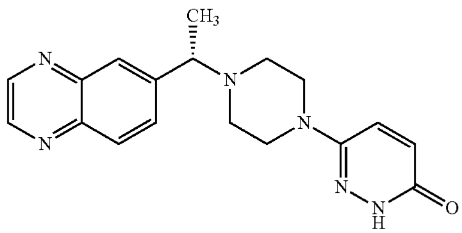 [SMILES: C[C@@H](c1ccc2nccnc2c1)N1CCN(c2ccc(=O)[nH]n2)CC1] | Chiral HPLC Method P: 1st eluting compound | +++ |
| 39 | 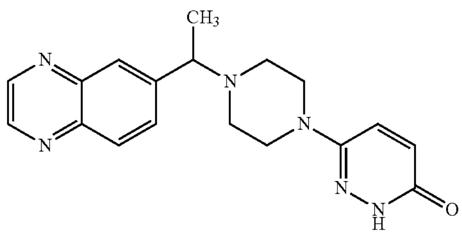 | racemic | +++ |
| 40 | 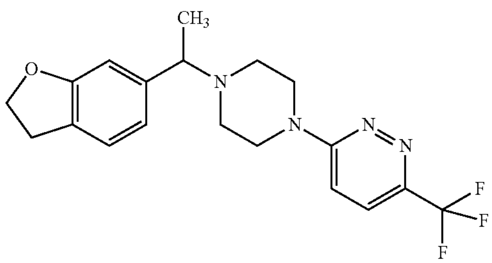 [SMILES: CC(c1ccc2c(c1)OCC2)N1CCN(c2ccc(C(F)(F)F)nn2)CC1] | racemic | ++++ |
| 41 | 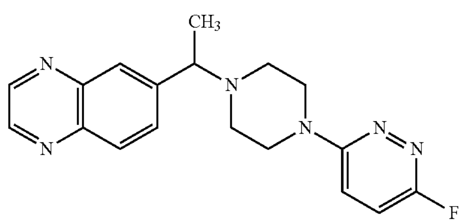 [SMILES: CC(c1ccc2nccnc2c1)N1CCN(c2ccc(F)nn2)CC1] | racemic | ++ |
| 42 | 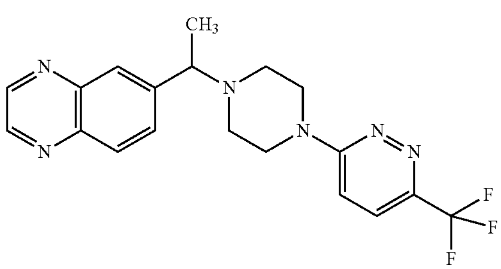 [SMILES: CC(c1ccc2nccnc2c1)N1CCN(c2ccc(C(F)(F)F)nn2)CC1] | racemic | ++ |
| 43 | 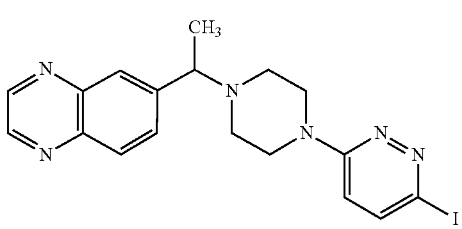 [SMILES: CC(c1ccc2nccnc2c1)N1CCN(c2ccc(I)nn2)CC1] | racemic | ++ |

TABLE 1-continued

Compounds of formulae (I). OGA enzyme inhibition assay:

| No | Structure | Configuration specification | OGA IC50 (M) |
|----|-----------|----------------------------|--------------|
| 44 | (quinoxalin-6-yl)-CH(CH₃)-piperazine-N-(6-methylpyridazin-3-yl) | racemic | ++ |
| 45 | (2,3-dihydrobenzofuran-6-yl)-CH(CH₃)-piperazine-N-(6-methylsulfonylpyridazin-3-yl) | racemic | ++++ |
| 46 | N-acetamido-pyridine-piperazine-CH(CH₃)-quinoxaline | racemic | +++ |
| 47 | (2,3-dihydrobenzofuran-6-yl)-CH(CH₃)-piperazine-N-pyridine-CH(OH)CH₃ | racemic | ++++ |
| 48 | (2,3-dihydrobenzofuran-6-yl)-CH(CH₃)-piperazine-N-pyridine-C(CH₃)₂OH | racemic | ++++ |

TABLE 1-continued
Compounds of formulae (I). OGA enzyme inhibition assay:
| No | Structure | Configuration specification | OGA IC50 (M) |
|---|---|---|---|
| 49 | 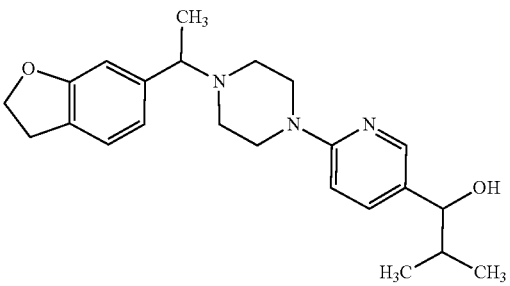 [SMILES: CC(C)C(O)c1ccc(N2CCN(C(C)c3ccc4c(c3)OCC4)CC2)nc1] | racemic | ++++ |
| 50 | 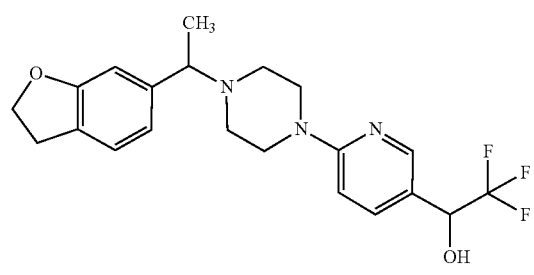 [SMILES: CC(c1ccc2c(c1)OCC2)N1CCN(c2ccc(C(O)C(F)(F)F)cn2)CC1] | racemic | ++++ |
| 51 | 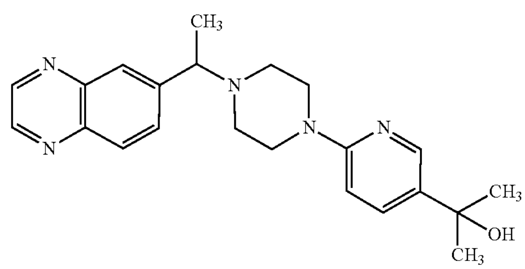 [SMILES: CC(c1ccc2nccnc2c1)N1CCN(c2ccc(C(C)(C)O)cn2)CC1] | racemic | +++ |
| 52 | 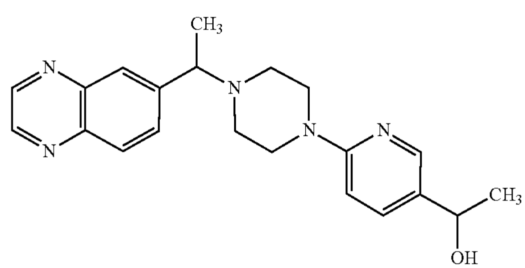 [SMILES: CC(O)c1ccc(N2CCN(C(C)c3ccc4nccnc4c3)CC2)nc1] | racemic | ++ |
| 53 | 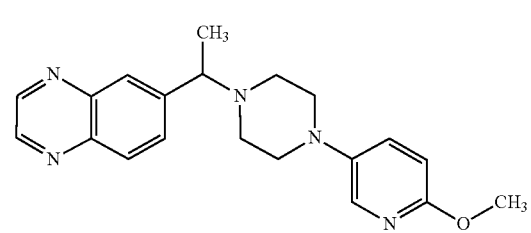 [SMILES: COc1ccc(N2CCN(C(C)c3ccc4nccnc4c3)CC2)cn1] | racemic | ++ |

TABLE 1-continued

Compounds of formulae (I). OGA enzyme inhibition assay:

| No | Structure | Configuration specification | OGA IC50 (M) |
|----|-----------|----------------------------|--------------|
| 54 | 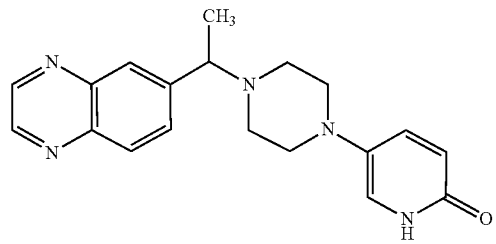 [SMILES: CC(c1ccc2nccnc2c1)N1CCN(c2ccc(=O)[nH]c2)CC1] | racemic | ++ |
| 55 | 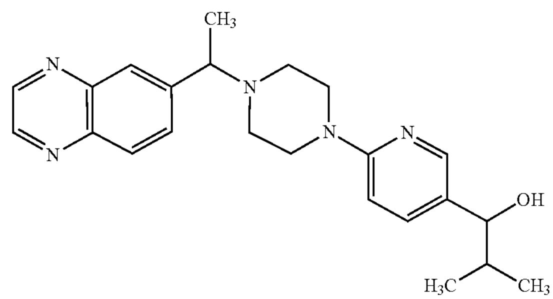 [SMILES: CC(C)C(O)c1ccc(N2CCN(C(C)c3ccc4nccnc4c3)CC2)nc1] | racemic | ++ |
| 56 | 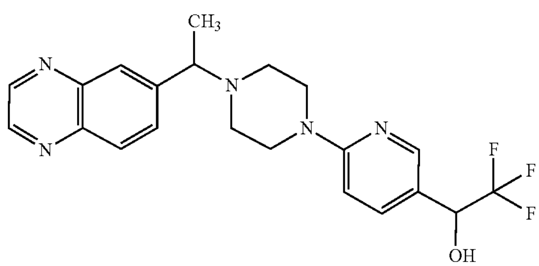 [SMILES: CC(c1ccc2nccnc2c1)N1CCN(c2ccc(C(O)C(F)(F)F)cn2)CC1] | racemic | +++ |
| 57 | 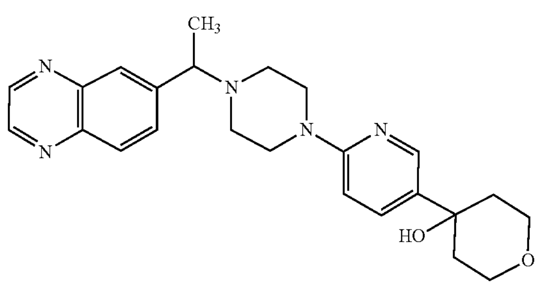 [SMILES: CC(c1ccc2nccnc2c1)N1CCN(c2ccc(C3(O)CCOCC3)cn2)CC1] | racemic | +++ |
| 58 | 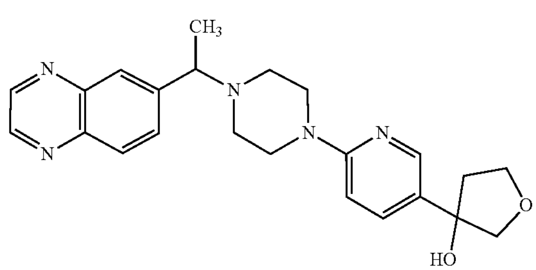 [SMILES: CC(c1ccc2nccnc2c1)N1CCN(c2ccc(C3(O)CCOC3)cn2)CC1] | racemic | +++ |

TABLE 1-continued

Compounds of formulae (I). OGA enzyme inhibition assay:

| No | Structure | Configuration specification | OGA IC50 (M) |
|---|---|---|---|
| 59 | 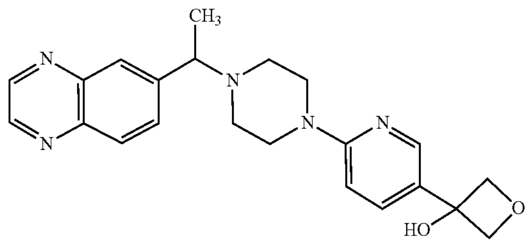 [SMILES: CC(c1ccc2nccnc2c1)N1CCN(c2ccc(C3(O)COC3)cn2)CC1] | racemic | +++ |
| 60 | 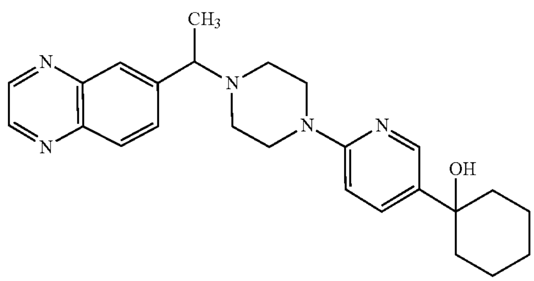 [SMILES: CC(c1ccc2nccnc2c1)N1CCN(c2ccc(C3(O)CCCCC3)cn2)CC1] | racemic | ++ |
| 61 | 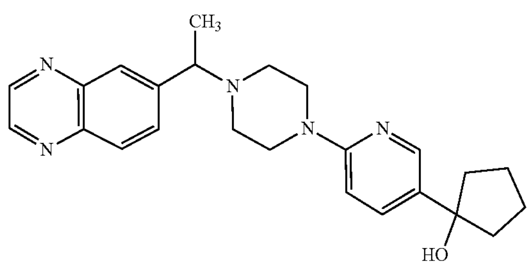 [SMILES: CC(c1ccc2nccnc2c1)N1CCN(c2ccc(C3(O)CCCC3)cn2)CC1] | racemic | +++ |
| 62 | 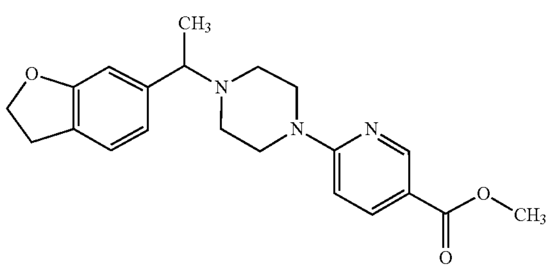 [SMILES: COC(=O)c1ccc(N2CCN(C(C)c3ccc4c(c3)OCC4)CC2)nc1] | racemic | ++++ |
| 63 | 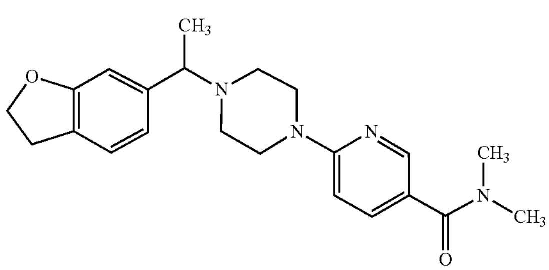 [SMILES: CC(c1ccc2c(c1)OCC2)N1CCN(c2ccc(C(=O)N(C)C)cn2)CC1] | racemic | ++++ |

TABLE 1-continued

Compounds of formulae (I). OGA enzyme inhibition assay:

| No | Structure | Configuration specification | OGA IC50 (M) |
|---|---|---|---|
| 64 | 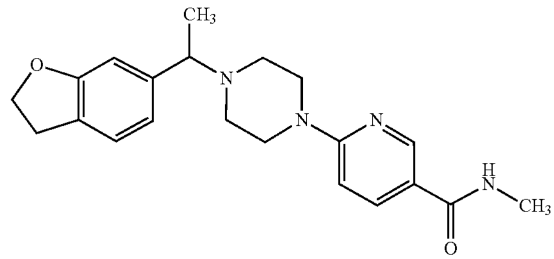 [SMILES: CNC(=O)c1ccc(N2CCN(C(C)c3ccc4c(c3)OCC4)CC2)nc1] | racemic | ++++ |
| 65 | 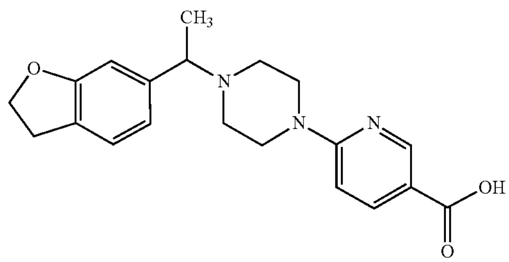 [SMILES: CC(c1ccc2c(c1)OCC2)N1CCN(c2ccc(C(=O)O)cn2)CC1] | racemic | ++++ |
| 66 | 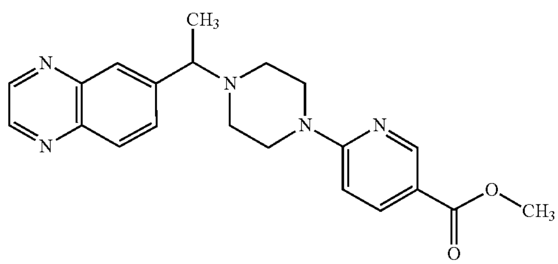 [SMILES: COC(=O)c1ccc(N2CCN(C(C)c3ccc4nccnc4c3)CC2)nc1] | racemic | +++ |
| 67 | 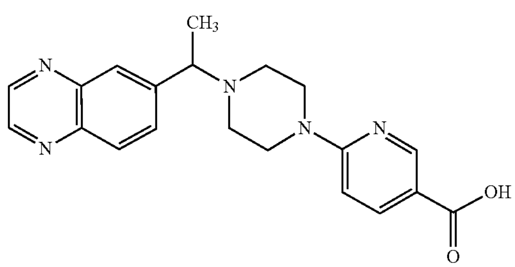 [SMILES: CC(c1ccc2nccnc2c1)N1CCN(c2ccc(C(=O)O)cn2)CC1] | racemic | +++ |
| 68 | 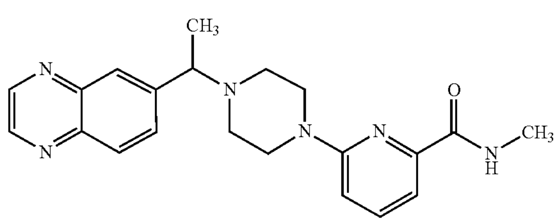 [SMILES: CNC(=O)c1cccc(N2CCN(C(C)c3ccc4nccnc4c3)CC2)n1] | racemic | +++ |
| 69 | 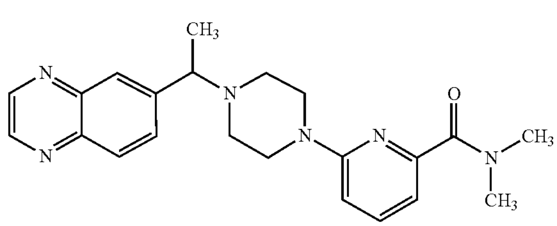 [SMILES: CC(c1ccc2nccnc2c1)N1CCN(c2cccc(C(=O)N(C)C)n2)CC1] | racemic | ++ |

TABLE 1-continued

Compounds of formulae (I). OGA enzyme inhibition assay:

| No | Structure | Configuration specification | OGA IC50 (M) |
|----|-----------|----------------------------|--------------|
| 70 | 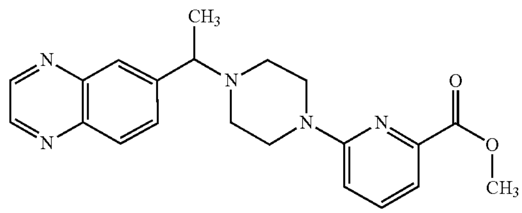 [SMILES: COC(=O)c1cccc(N2CCN(C(C)c3ccc4nccnc4c3)CC2)n1] | racemic | ++ |
| 71 | 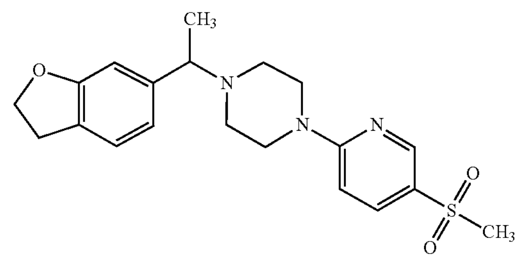 [SMILES: CC(c1ccc2c(c1)OCC2)N1CCN(c2ccc(S(C)(=O)=O)cn2)CC1] | racemic | ++++ |
| 72 | 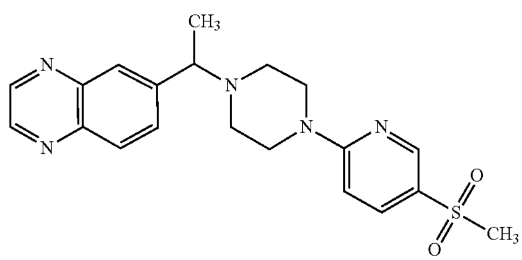 [SMILES: CC(c1ccc2nccnc2c1)N1CCN(c2ccc(S(C)(=O)=O)cn2)CC1] | racemic | +++ |
| 73 | 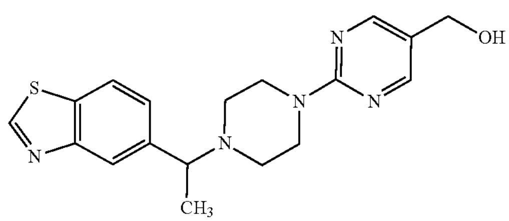 [SMILES: CC(c1ccc2scnc2c1)N1CCN(c2ncc(CO)cn2)CC1] | racemic | ++++ |
| 74 | 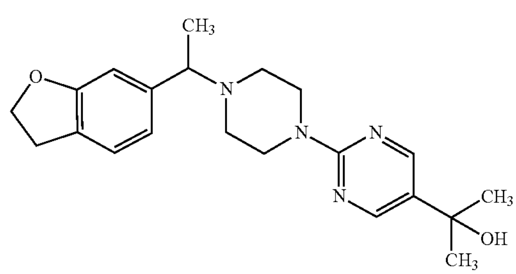 | racemic | ++++ |
| 75 | 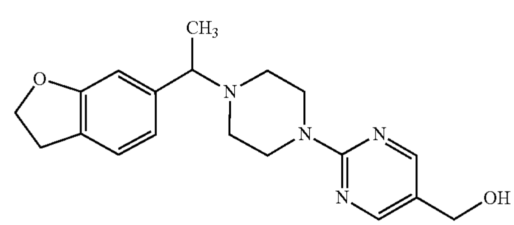 [SMILES: CC(c1ccc2c(c1)OCC2)N1CCN(c2ncc(CO)cn2)CC1] | racemic | ++++ |

TABLE 1-continued
Compounds of formulae (I). OGA enzyme inhibition assay:
| No | Structure | Configuration specification | OGA IC50 (M) |
|---|---|---|---|
| 76 | 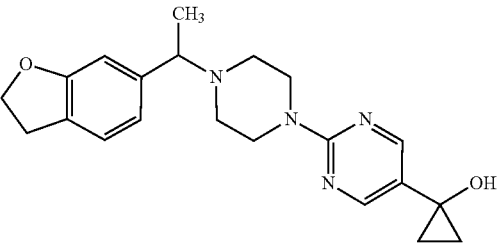 [SMILES: CC(c1ccc2c(c1)OCC2)N1CCN(c2ncc(C3(O)CC3)cn2)CC1] | racemic | ++++ |
| 77 | 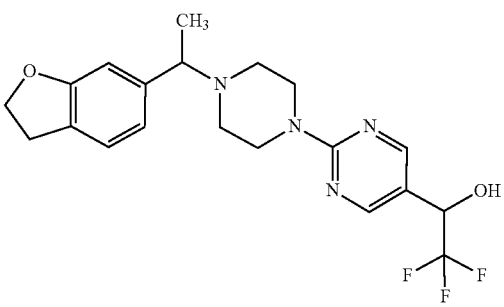 [SMILES: CC(c1ccc2c(c1)OCC2)N1CCN(c2ncc(C(O)C(F)(F)F)cn2)CC1] | racemic | ++++ |
| 78 | 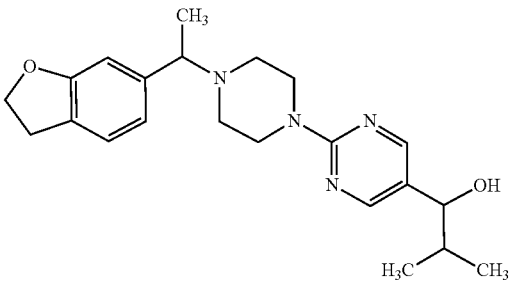 [SMILES: CC(C)C(O)c1cnc(N2CCN(C(C)c3ccc4c(c3)OCC4)CC2)nc1] | racemic | ++++ |
| 79 | 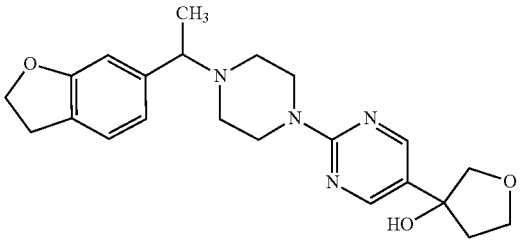 [SMILES: CC(c1ccc2c(c1)OCC2)N1CCN(c2ncc(C3(O)CCOC3)cn2)CC1] | racemic | ++++ |
| 80 | 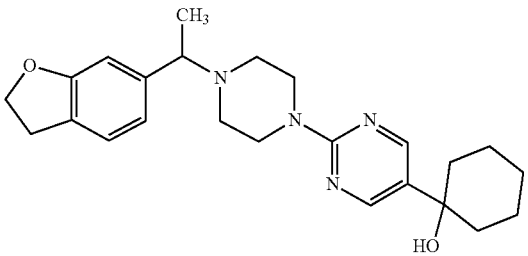 [SMILES: CC(c1ccc2c(c1)OCC2)N1CCN(c2ncc(C3(O)CCCCC3)cn2)CC1] | racemic | ++++ |

TABLE 1-continued

Compounds of formulae (I). OGA enzyme inhibition assay:

| No | Structure | Configuration specification | OGA IC50 (M) |
|---|---|---|---|
| 81 | 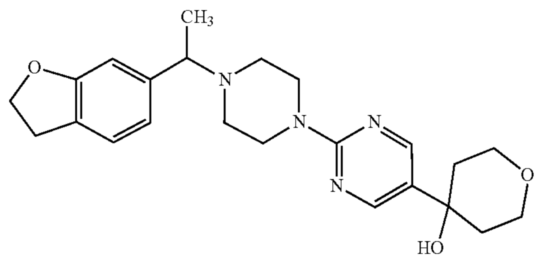 [SMILES: CC(c1ccc2c(c1)OCC2)N1CCN(c2ncc(C3(O)CCOCC3)cn2)CC1] | racemic | ++++ |
| 82 | 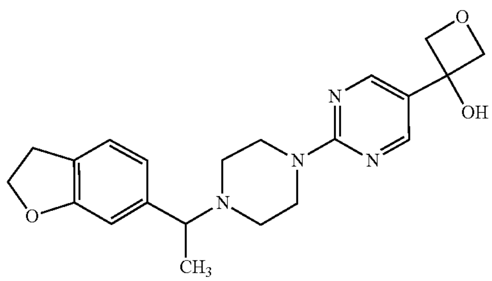 [SMILES: CC(c1ccc2c(c1)OCC2)N1CCN(c2ncc(C3(O)COC3)cn2)CC1] | racemic | ++++ |
| 83 | 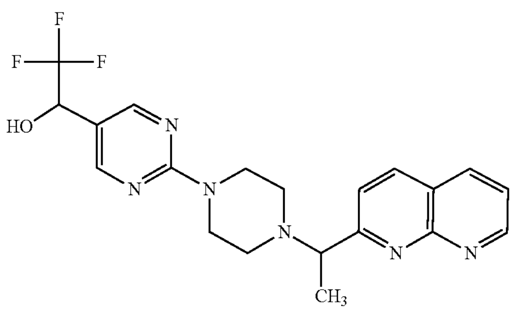 [SMILES: CC(c1ccc2cccnc2n1)N1CCN(c2ncc(C(O)C(F)(F)F)cn2)CC1] | racemic | ++++ |
| 84 | 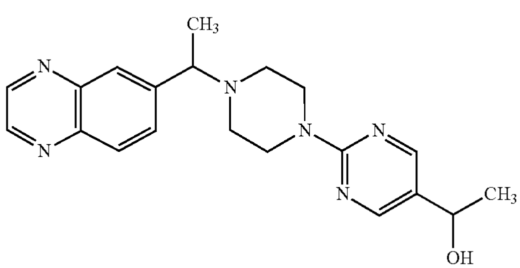 [SMILES: CC(O)c1cnc(N2CCN(C(C)c3ccc4nccnc4c3)CC2)nc1] | racemic | +++ |
| 85 | 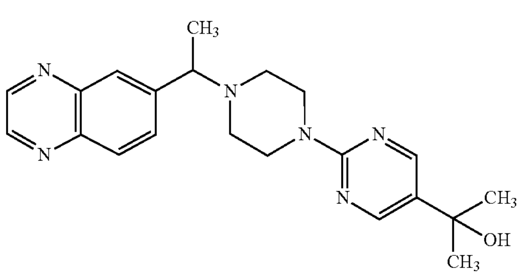 [SMILES: CC(c1ccc2nccnc2c1)N1CCN(c2ncc(C(C)(C)O)cn2)CC1] | racemic | +++ |

TABLE 1-continued

Compounds of formulae (I). OGA enzyme inhibition assay:

| No | Structure | Configuration specification | OGA IC50 (M) |
|---|---|---|---|
| 86 | 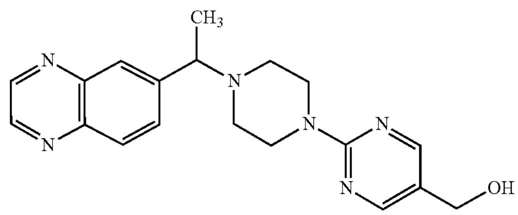 [SMILES: CC(c1ccc2nccnc2c1)N1CCN(c2ncc(CO)cn2)CC1] | racemic | +++ |
| 87 | 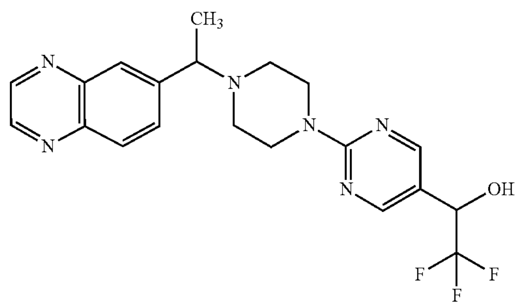 [SMILES: CC(c1ccc2nccnc2c1)N1CCN(c2ncc(C(O)C(F)(F)F)cn2)CC1] | racemic | +++ |
| 88 | 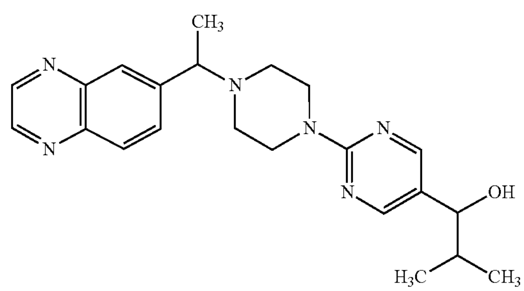 [SMILES: CC(C)C(O)c1cnc(N2CCN(C(C)c3ccc4nccnc4c3)CC2)nc1] | racemic | +++ |
| 89 | 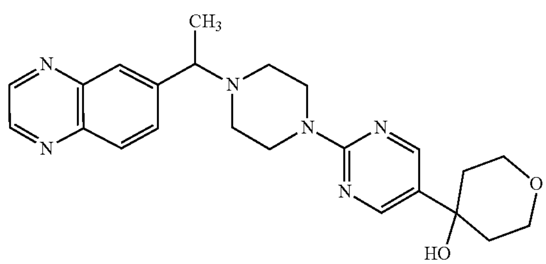 [SMILES: CC(c1ccc2nccnc2c1)N1CCN(c2ncc(C3(O)CCOCC3)cn2)CC1] | racemic | +++ |
| 90 | 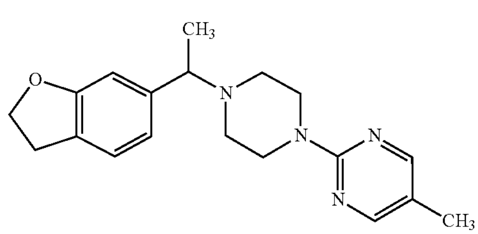 [SMILES: Cc1cnc(N2CCN(C(C)c3ccc4c(c3)OCC4)CC2)nc1] | racemic | ++++ |

TABLE 1-continued

Compounds of formulae (I). OGA enzyme inhibition assay:

| No | Structure | Configuration specification | OGA IC50 (M) |
|---|---|---|---|
| 91 | 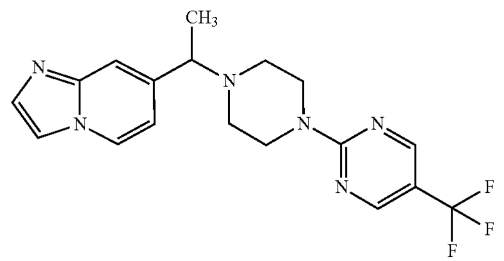 [SMILES: CC(c1ccn2ccnc2c1)N1CCN(c2ncc(C(F)(F)F)cn2)CC1] | racemic | + |
| 92 | 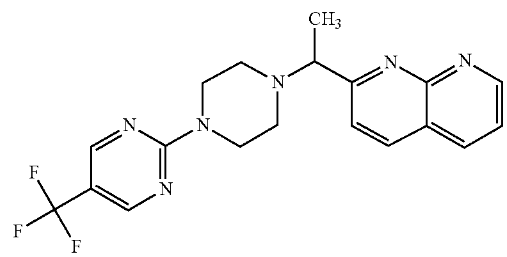 [SMILES: CC(c1ccc2cccnc2n1)N1CCN(c2ncc(C(F)(F)F)cn2)CC1] | racemic | +++ |
| 94 | 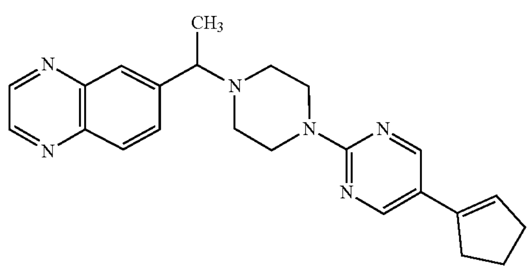 [SMILES: CC(c1ccc2nccnc2c1)N1CCN(c2ncc(C3=CCCC3)cn2)CC1] | racemic | ++ |
| 95 | 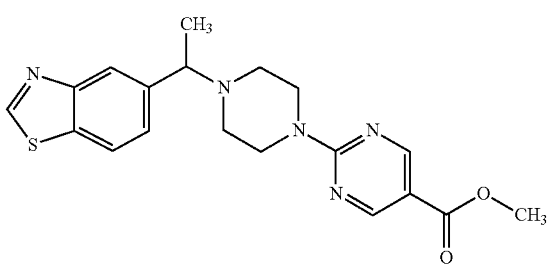 [SMILES: COC(=O)c1cnc(N2CCN(C(C)c3ccc4scnc4c3)CC2)nc1] | racemic | ++++ |
| 96 | 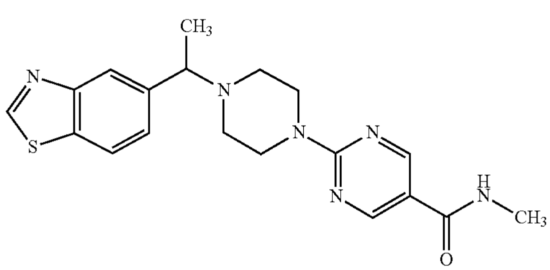 [SMILES: CNC(=O)c1cnc(N2CCN(C(C)c3ccc4c(c3)OCC4)CC2)nc1] | racemic | ++++ |

TABLE 1-continued

Compounds of formulae (I). OGA enzyme inhibition assay:

| No | Structure | Configuration specification | OGA IC50 (M) |
|----|-----------|------------------------------|--------------|
| 97 | benzothiazole-CH(CH₃)-piperazine-pyrimidine-C(O)N(CH₃)₂ | racemic | ++++ |
| 98 | 2,3-dihydrobenzofuran-CH(CH₃)-piperazine-pyrimidine-C(O)OCH₃ | racemic | ++++ |
| 99 | 2,3-dihydrobenzofuran-CH(CH₃)-piperazine-pyrimidine-C(O)NHCH₃ | racemic | ++++ |
| 100 | 2,3-dihydrobenzofuran-CH(CH₃)-piperazine-pyrimidine-C(O)N(CH₃)₂ | racemic | ++++ |
| 101 | 2,3-dihydrobenzofuran-CH(CH₃)-piperazine-pyrimidine(4-C(O)N(CH₃)₂) | racemic | ++++ |
| 102 | 2,3-dihydrobenzofuran-CH(CH₃)-piperazine-pyrimidine(4-C(O)OMe) | racemic | ++++ |

TABLE 1-continued

Compounds of formulae (I). OGA enzyme inhibition assay:

| No | Structure | Configuration specification | OGA IC50 (M) |
|---|---|---|---|
| 103 | 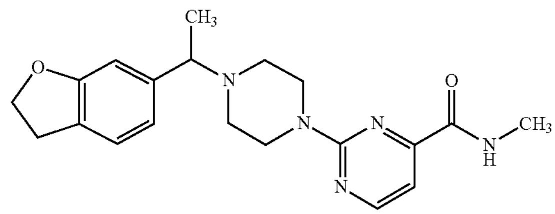 [SMILES: CNC(=O)c1ccnc(N2CCN(C(C)c3ccc4c(c3)OCC4)CC2)n1] | racemic | ++++ |
| 104 | 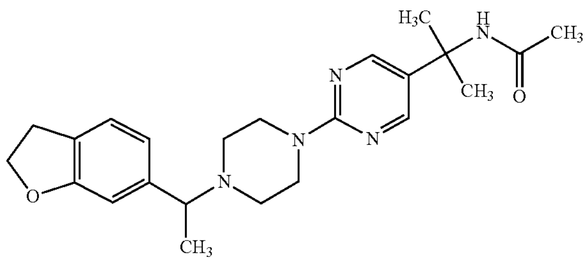 [SMILES: CC(=O)NC(C)(C)c1cnc(N2CCN(C(C)c3ccc4c(c3)OCC4)CC2)nc1] | racemic | ++++ |
| 105 | 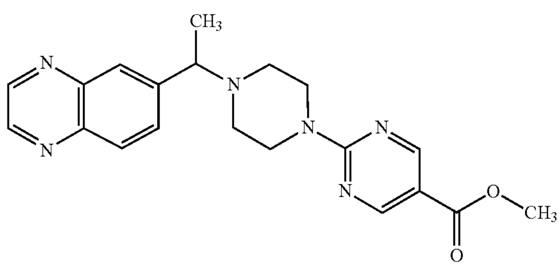 [SMILES: COC(=O)c1cnc(N2CCN(C(C)c3ccc4nccnc4c3)CC2)nc1] | racemic | +++ |
| 106 | 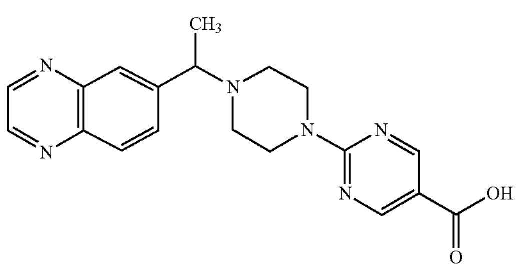 [SMILES: CC(c1ccc2nccnc2c1)N1CCN(c2ncc(C(=O)O)cn2)CC1] | racemic | +++ |
| 107 | 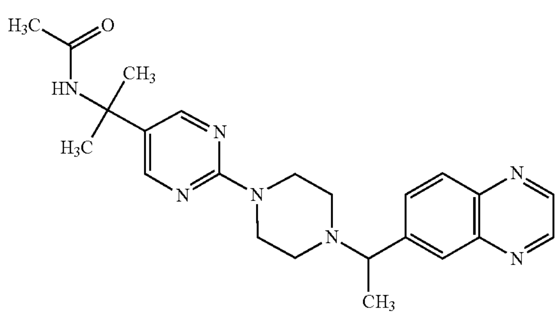 [SMILES: CC(=O)NC(C)(C)c1cnc(N2CCN(C(C)c3ccc4nccnc4c3)CC2)nc1] | racemic | ++ |

TABLE 1-continued

Compounds of formulae (I). OGA enzyme inhibition assay:

| No | Structure | Configuration specification | OGA IC50 (M) |
|---|---|---|---|
| 108 | 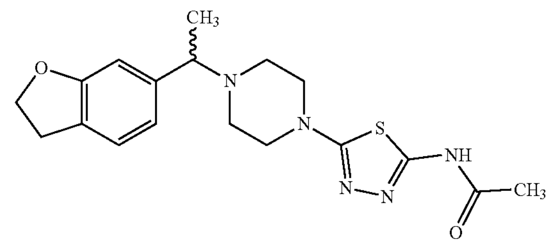 [SMILES: CC(=O)Nc1nnc(N2CCN(C(C)c3ccc4c(c3)OCC4)CC2)s1] | Chiral HPLC SFC Method AA: 1st eluting compound | + |
| 109 | 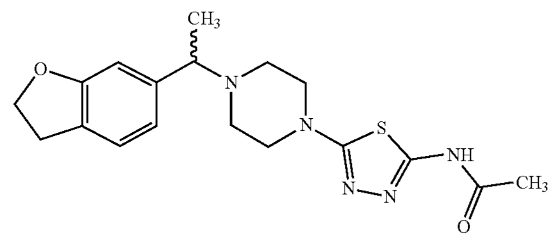 [SMILES: CC(=O)Nc1nnc(N2CCN(C(C)c3ccc4c(c3)OCC4)CC2)s1] | Chiral HPLC SFC Method AA: 2nd eluting compound | ++++ |
| 110 | 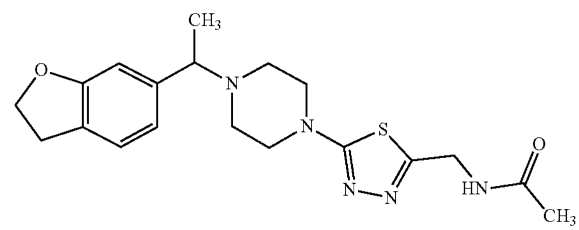 [SMILES: CC(=O)NCc1nnc(N2CCN(C(C)c3ccc4c(c3)OCC4)CC2)s1] | racemic | ++++ |
| 112 | 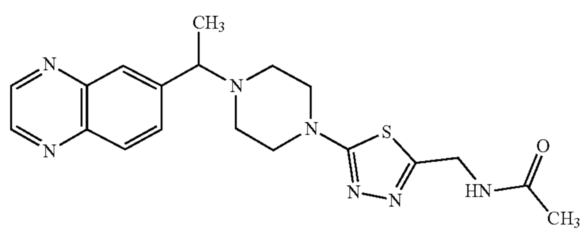 [SMILES: CC(=O)NCc1nnc(N2CCN(C(C)c3ccc4nccnc4c3)CC2)s1] | racemic | +++ |
| 113 | 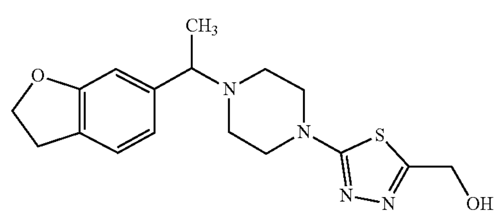 [SMILES: CC(c1ccc2c(c1)OCC2)N1CCN(c2nnc(CO)s2)CC1] | racemic | ++++ |
| 114 | 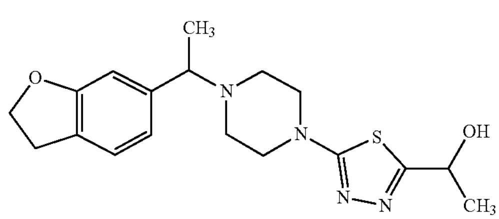 [SMILES: CC(O)c1nnc(N2CCN(C(C)c3ccc4c(c3)OCC4)CC2)s1] | racemic | ++++ |

TABLE 1-continued

Compounds of formulae (I). OGA enzyme inhibition assay:

| No | Structure | Configuration specification | OGA IC50 (M) |
|---|---|---|---|
| 115 | 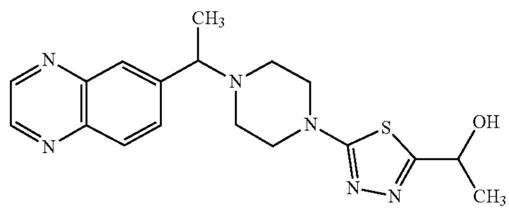 [SMILES: CC(O)c1nnc(N2CCN(C(C)c3ccc4nccnc4c3)CC2)s1] | racemic | ++ |
| 116 | 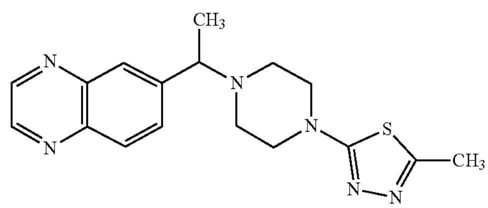 [SMILES: Cc1nnc(N2CCN(C(C)c3ccc4nccnc4c3)CC2)s1] | racemic | ++ |
| 117 | 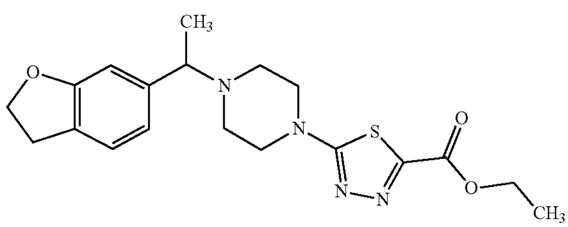 [SMILES: CCOC(=O)c1nnc(N2CCN(C(C)c3ccc4c(c3)OCC4)CC2)s1] | racemic | +++ |
| 118 | 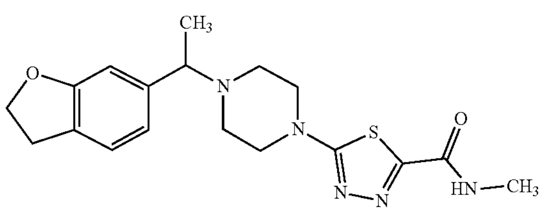 [SMILES: CNC(=O)c1nnc(N2CCN(C(C)c3ccc4c(c3)OCC4)CC2)s1] | racemic | ++++ |
| 119 | 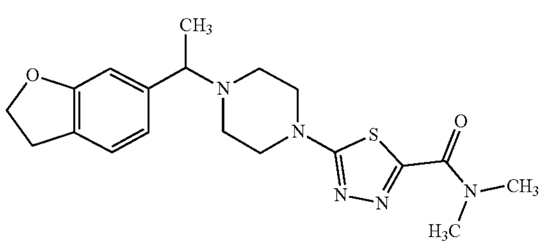 [SMILES: CC(c1ccc2c(c1)OCC2)N1CCN(c2nnc(C(=O)N(C)C)s2)CC1] | racemic | ++++ |
| 120 | 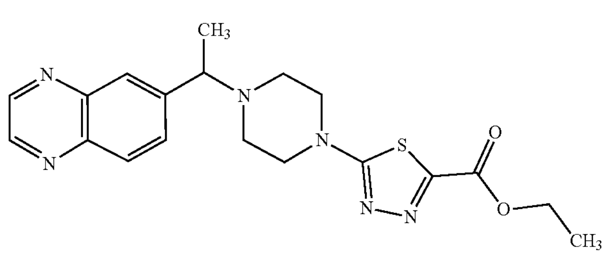 [SMILES: CCOC(=O)c1nnc(N2CCN(C(C)c3ccc4nccnc4c3)CC2)s1] | racemic | + |

TABLE 1-continued

Compounds of formulae (I). OGA enzyme inhibition assay:

| No | Structure | Configuration specification | OGA IC50 (M) |
|---|---|---|---|
| 121 | quinoxaline-CH(CH₃)-piperazine-1,3,4-thiadiazole-C(O)NH-CH₃ | racemic | ++ |
| 122 | quinoxaline-CH(CH₃)-piperazine-1,3,4-thiadiazole-C(O)N(CH₃)₂ | racemic | ++ |
| 123 | 2,3-dihydrobenzofuran-CH(CH₃)-piperazine-1,3,4-thiadiazole-CH₂N(CH₃)₂ | racemic | ++++ |
| 124 | 2,3-dihydrobenzofuran-CH(CH₃)-piperazine-1,3,4-thiadiazole-CH₂NH₂ | racemic | ++++ |
| 125 | quinoxaline-CH(CH₃)-piperazine-1,3,4-thiadiazole-CH₂N(CH₃)₂ | racemic | ++ |
| 126 | quinoxaline-CH(CH₃)-piperazine-1,3,4-thiadiazole-CH₂NH₂ | racemic | ++ |

US 11,612,599 B2
TABLE 1-continued
Compounds of formulae (I). OGA enzyme inhibition assay:
| No | Structure | Configuration specification | OGA IC50 (M) |
|---|---|---|---|
| 135 | 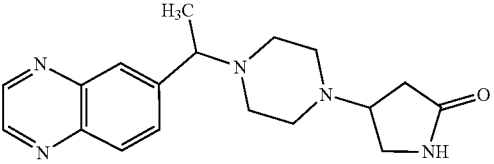 [SMILES: CC(c1ccc2nccnc2c1)N1CCN(C2CNC(=O)C2)CC1] | | |
| 136 | 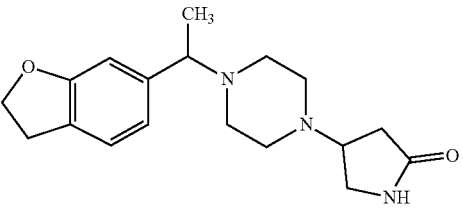 [SMILES: CC(c1ccc2c(c1)OCC2)N1CCN(C2CNC(=O)C2)CC1] | | |
| 137 | 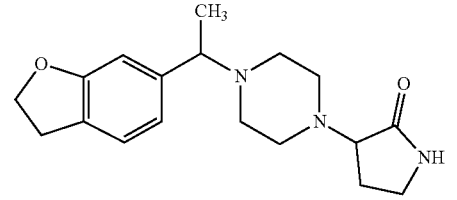 [SMILES: CC(c1ccc2c(c1)OCC2)N1CCN(C2CCNC2=O)CC1] | | |
| 138 | 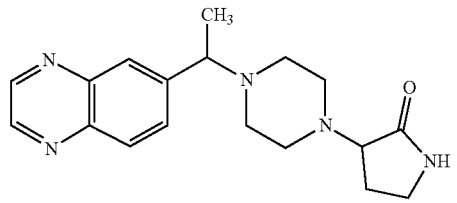 [SMILES: CC(c1ccc2nccnc2c1)N1CCN(C2CCNC2=O)CC1] | | |
| 139 | 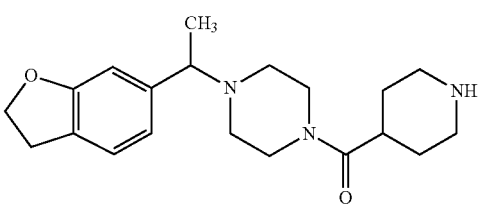 [SMILES: CC(c1ccc2c(c1)OCC2)N1CCN(C(=O)C2CCNCC2)CC1] | | |
| 140 | 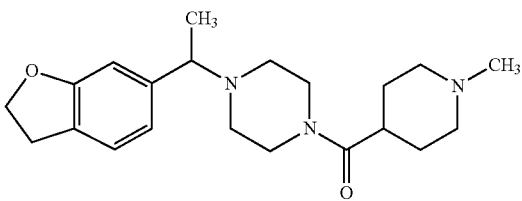 [SMILES: CC(c1ccc2c(c1)OCC2)N1CCN(C(=O)C2CCN(C)CC2)CC1] | | |
| 141 | 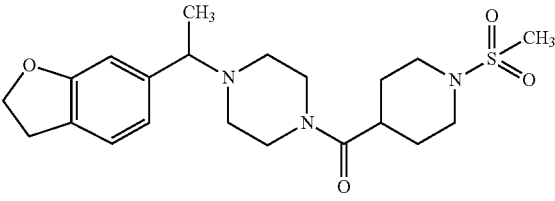 [SMILES: CC(c1ccc2c(c1)OCC2)N1CCN(C(=O)C2CCN(S(C)(=O)=O)CC2)CC1] | | |

TABLE 1-continued
Compounds of formulae (I). OGA enzyme inhibition assay:
| No | Structure | Configuration specification | OGA IC50 (M) |
|---|---|---|---|
| 142 | 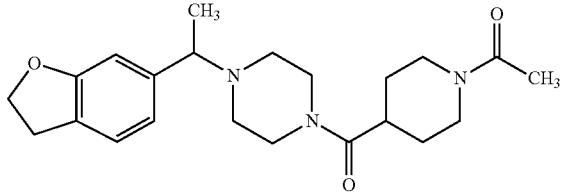 [SMILES: CC(=O)N1CCC(C(=O)N2CCN(C(C)c3ccc4c(c3)OCC4)CC2)CC1] | | |
| 143 | 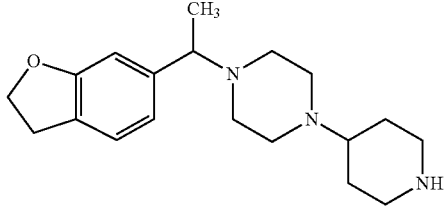 [SMILES: CC(c1ccc2c(c1)OCC2)N1CCN(C2CCNCC2)CC1] | | |
| 144 | 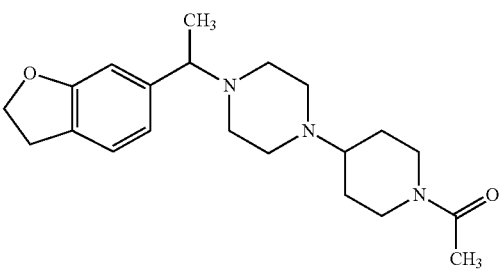 [SMILES: CC(=O)N1CCC(N2CCN(C(C)c3ccc4c(c3)OCC4)CC2)CC1] | | |
| 145 | 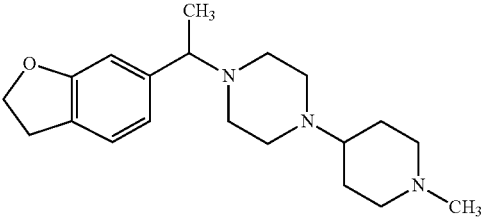 [SMILES: CC(c1ccc2c(c1)OCC2)N1CCN(C2CCN(C)CC2)CC1] | | |
| 146 | 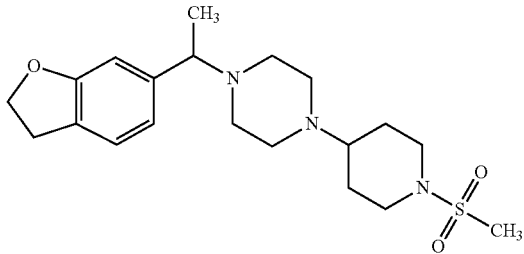 [SMILES: CC(c1ccc2c(c1)OCC2)N1CCN(C2CCN(S(C)(=O)=O)CC2)CC1] | | |
| 147 | 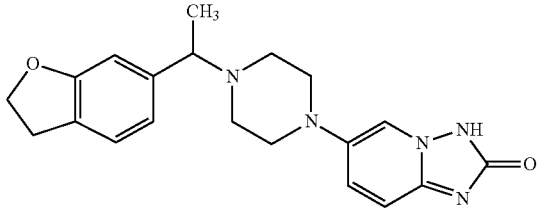 [SMILES: CC(c1ccc2c(c1)OCC2)N1CCN(c2ccc3nc(=O)[nH]n3c2)CC1] | | |

TABLE 1-continued

Compounds of formulae (I). OGA enzyme inhibition assay:

| No | Structure | Configuration specification | OGA IC50 (M) |
|---|---|---|---|
| 148 | 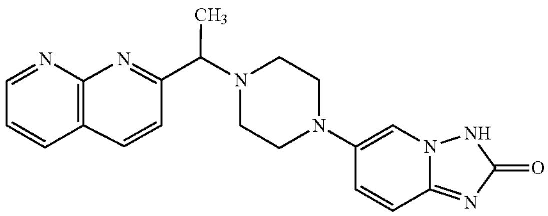 [SMILES: CC(c1ccc2cccnc2n1)N1CCN(c2ccc3nc(=O)[nH]n3c2)CC1] | | |
| 149 | 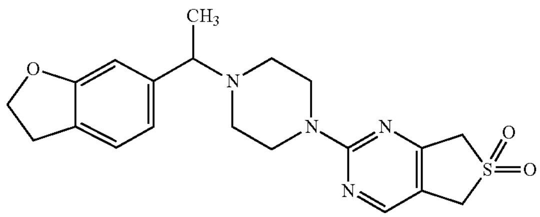 [SMILES: CC(c1ccc2c(c1)OCC2)N1CCN(c2ncc3c(n2)CS(=O)(=O)C3)CC1] | | |
| 150 | 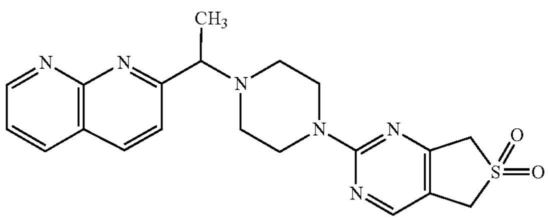 [SMILES: CC(c1ccc2cccnc2n1)N1CCN(c2ncc3c(n2)CS(=O)(=O)C3)CC1] | | |
| 151 | 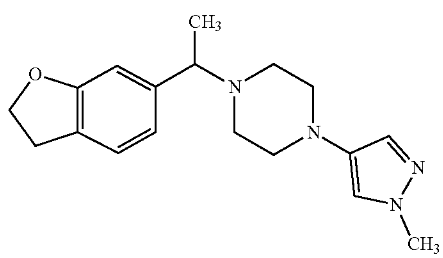 [SMILES: CC(c1ccc2c(c1)OCC2)N1CCN(c2cnn(C)c2)CC1] | | |
| 152 | 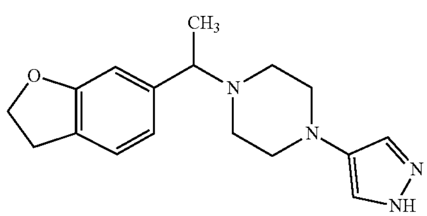 [SMILES: CC(c1ccc2c(c1)OCC2)N1CCN(c2cn[nH]c2)CC1] | | |
| 153 | 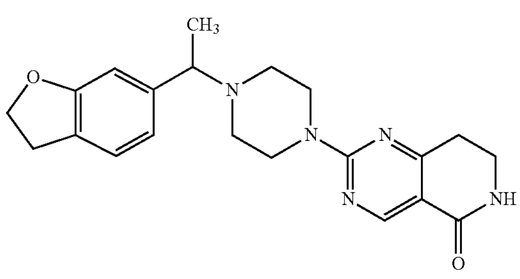 [SMILES: CC(c1ccc2c(c1)OCC2)N1CCN(c2ncc3c(n2)CCNC3=O)CC1] | | |

TABLE 1-continued

Compounds of formulae (I). OGA enzyme inhibition assay:

| No | Structure | Configuration specification | OGA IC50 (M) |
|----|-----------|-----------------------------|--------------|
| 154 | 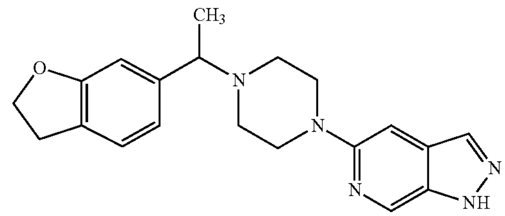 [SMILES: CC(c1ccc2c(c1)OCC2)N1CCN(c2cc3cn[nH]c3cn2)CC1] | | |
| 155 | 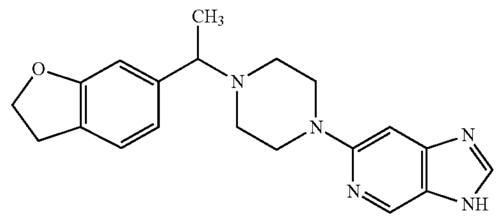 [SMILES: CC(c1ccc2c(c1)OCC2)N1CCN(c2cc3nc[nH]c3cn2)CC1] | | |
| 156 | 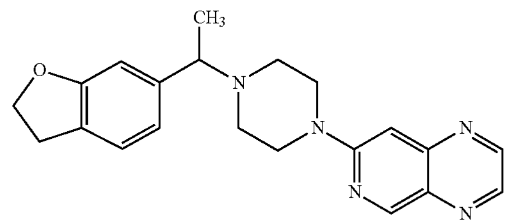 [SMILES: CC(c1ccc2c(c1)OCC2)N1CCN(c2cc3nccnc3cn2)CC1] | | |
| 157 | 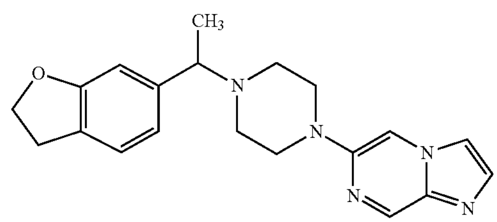 [SMILES: CC(c1ccc2c(c1)OCC2)N1CCN(c2cn3ccnc3cn2)CC1] | | |
| 158 | 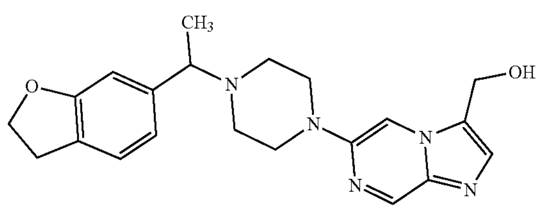 [SMILES: CC(c1ccc2c(c1)OCC2)N1CCN(c2cn3c(CO)cnc3cn2)CC1] | | |
| 159 | 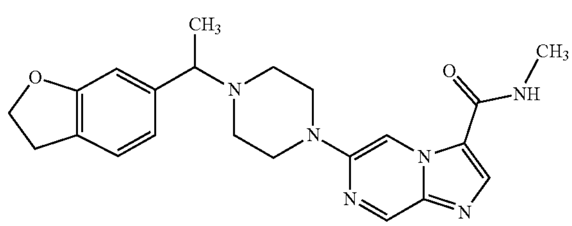 [SMILES: CNC(=O)c1cnc2cnc(N3CCN(C(C)c4ccc5c(c4)OCC5)CC3)cn12] | | |
| 160 | 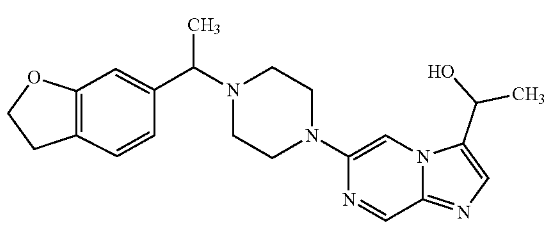 [SMILES: CC(O)c1cnc2cnc(N3CCN(C(C)c4ccc5c(c4)OCC5)CC3)cn12] | | |

TABLE 1-continued

Compounds of formulae (I). OGA enzyme inhibition assay:

| No | Structure | Configuration specification | OGA IC50 (M) |
|----|-----------|------------------------------|--------------|
| 161 | 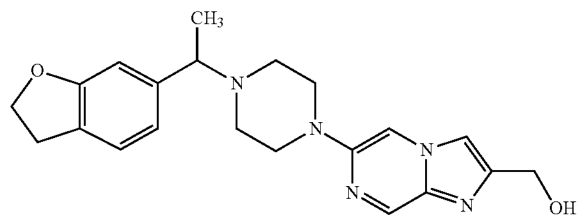 [SMILES: CC(c1ccc2c(c1)OCC2)N1CCN(c2cn3cc(CO)nc3cn2)CC1] | | |
| 162 | 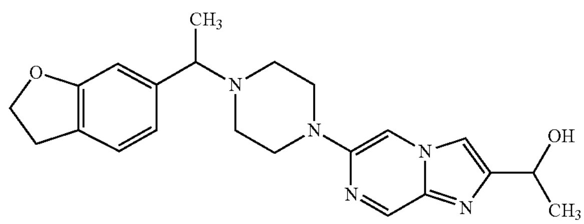 [SMILES: CC(O)c1cn2cc(N3CCN(C(C)c4ccc5c(c4)OCC5)CC3)ncc2n1] | | |
| 163 | 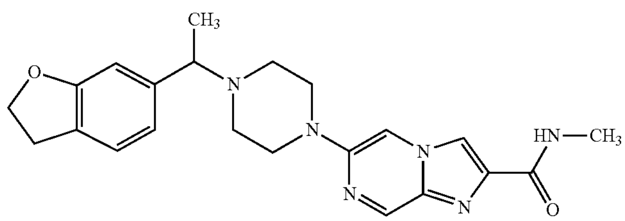 [SMILES: CNC(=O)c1cn2cc(N3CCN(C(C)c4ccc5c(c4)OCC5)CC3)ncc2n1] | | |
| 164 | 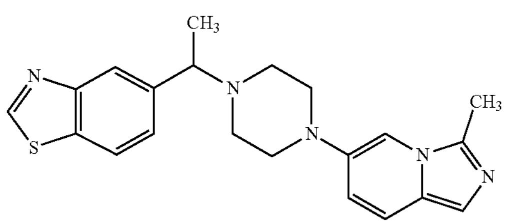 [SMILES: Cc1ncc2ccc(N3CCN(C(C)c4ccc5scnc5c4)CC3)cn12] | | |
| 165 | 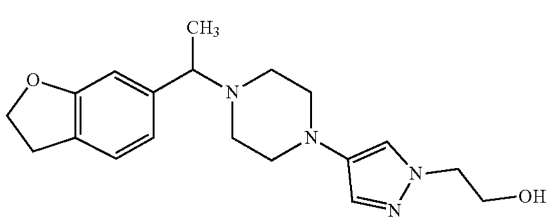 [SMILES: CC(c1ccc2c(c1)OCC2)N1CCN(c2cnn(CCO)c2)CC1] | | |
| 166 | 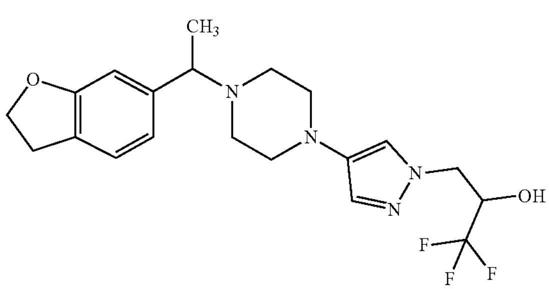 [SMILES: CC(c1ccc2c(c1)OCC2)N1CCN(c2cnn(CC(O)C(F)(F)F)c2)CC1] | | |

TABLE 1-continued

Compounds of formulae (I). OGA enzyme inhibition assay:

| No | Structure | Configuration specification | OGA IC50 (M) |
|---|---|---|---|
| 167 | 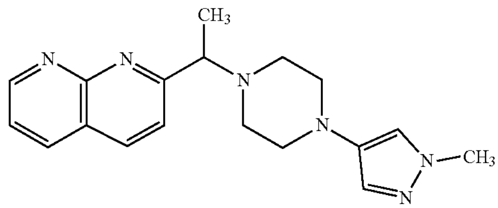 [SMILES: CC(c1ccc2cccnc2n1)N1CCN(c2cnn(C)c2)CC1] | | |
| 168 | 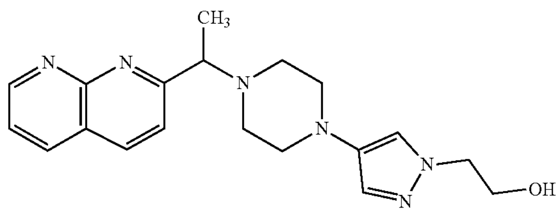 [SMILES: CC(c1ccc2cccnc2n1)N1CCN(c2cnn(CCO)c2)CC1] | | |
| 169 | 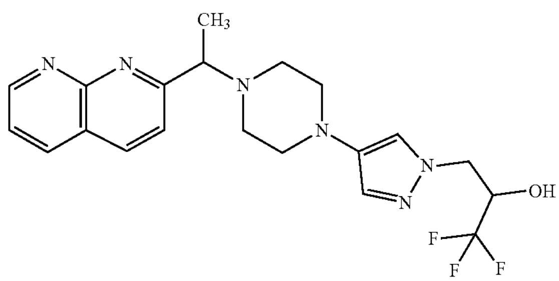 [SMILES: CC(c1ccc2cccnc2n1)N1CCN(c2cnn(CC(O)C(F)(F)F)c2)CC1] | | |
| 170 | 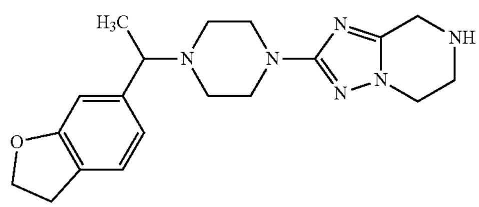 [SMILES: CC(c1ccc2c(c1)OCC2)N1CCN(c2nc3n(n2)CCNC3)CC1] | | |
| 171 | 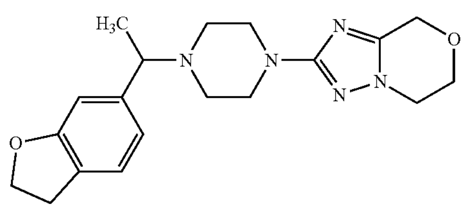 [SMILES: CC(c1ccc2c(c1)OCC2)N1CCN(c2nc3n(n2)CCOC3)CC1] | | |
| 172 | 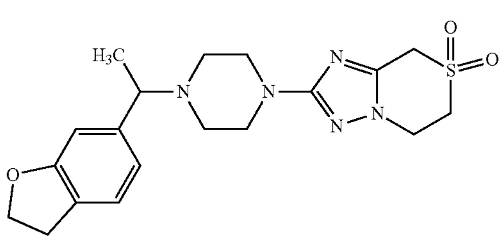 [SMILES: CC(c1ccc2c(c1)OCC2)N1CCN(c2nc3n(n2)CCS(=O)(=O)C3)CC1] | | |

TABLE 1-continued

Compounds of formulae (I). OGA enzyme inhibition assay:

| No | Structure | Configuration specification | OGA IC50 (M) |
|---|---|---|---|
| 173 | 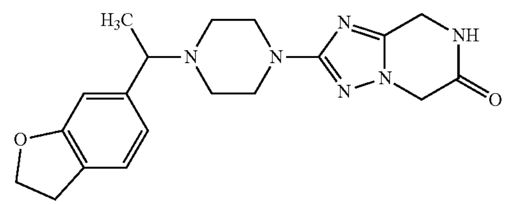 [SMILES: CC(c1ccc2c(c1)OCC2)N1CCN(c2nc3n(n2)CC(=O)NC3)CC1] | | |
| 174 | 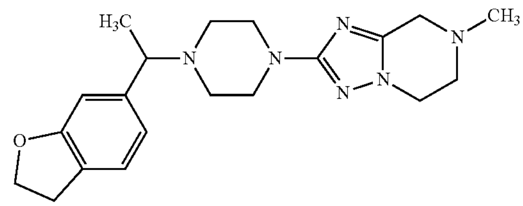 | | |
| 175 | 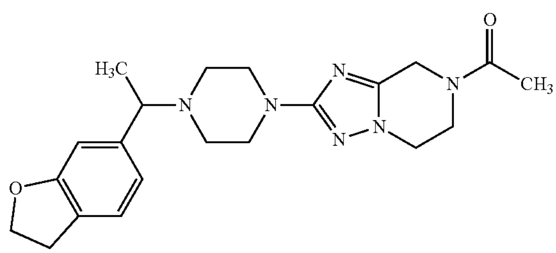 [SMILES: CC(=O)N1CCn2nc(N3CCN(C(C)c4ccc5c(c4)OCC5)CC3)nc2C1] | | |
| 176 | 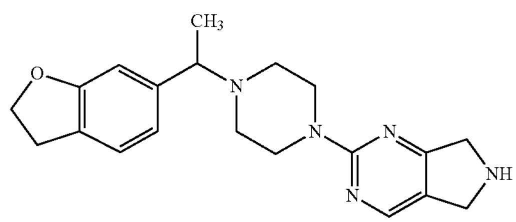 [SMILES: CC(c1ccc2c(c1)OCC2)N1CCN(c2ncc3c(n2)CNC3)CC1] | | |
| 177 | 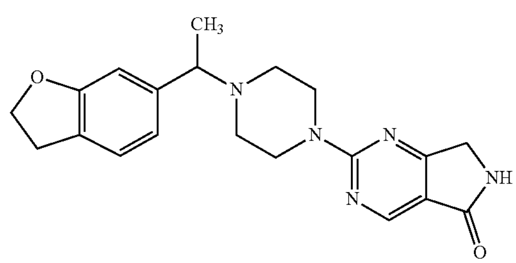 [SMILES: CC(c1ccc2c(c1)OCC2)N1CCN(c2ncc3c(n2)CNC3=O)CC1] | | |
| 178 | 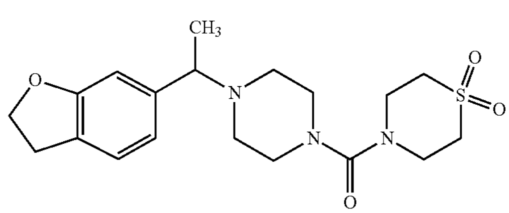 [SMILES: CC(c1ccc2c(c1)OCC2)N1CCN(C(=O)N2CCS(=O)(=O)CC2)CC1] | | |

TABLE 1-continued

Compounds of formulae (I). OGA enzyme inhibition assay:

| No | Structure | Configuration specification | OGA IC50 (M) |
|---|---|---|---|
| 179 | 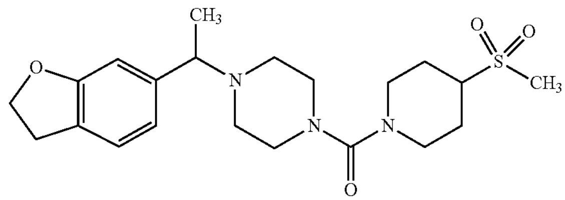 [SMILES: CC(c1ccc2c(c1)OCC2)N1CCN(C(=O)N2CCC(S(C)(=O)=O)CC2)CC1] | | |
| 180 | 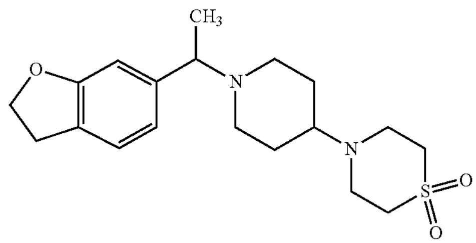 [SMILES: CC(c1ccc2c(c1)OCC2)N1CCC(N2CCS(=O)(=O)CC2)CC1] | | |
| 181 | 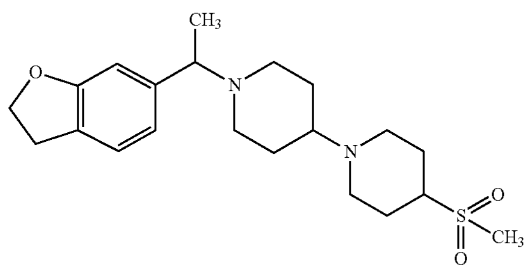 [SMILES: CC(c1ccc2c(c1)OCC2)N1CCC(N2CCC(S(C)(=O)=O)CC2)CC1] | | |
| 182 | 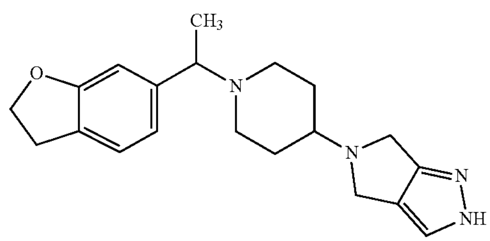 [SMILES: CC(c1ccc2c(c1)OCC2)N1CCC(N2Cc3c[nH]nc3C2)CC1] | | |
| 183 | 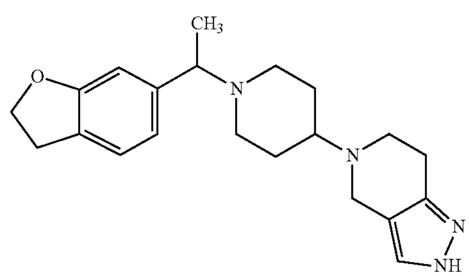 [SMILES: CC(c1ccc2c(c1)OCC2)N1CCC(N2CCc3n[nH]cc3C2)CC1] | | |
| 184 | 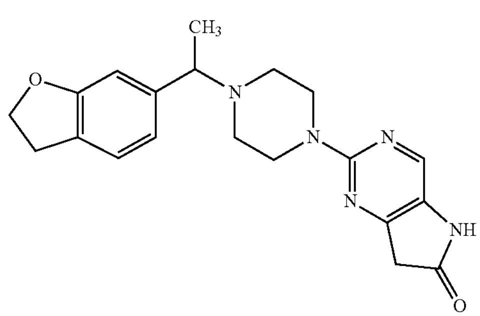 [SMILES: CC(c1ccc2c(c1)OCC2)N1CCN(c2ncc3c(n2)CC(=O)N3)CC1] | | |

TABLE 1-continued

Compounds of formulae (I). OGA enzyme inhibition assay:

| No | Structure | Configuration specification | OGA IC50 (M) |
|---|---|---|---|
| 185 | 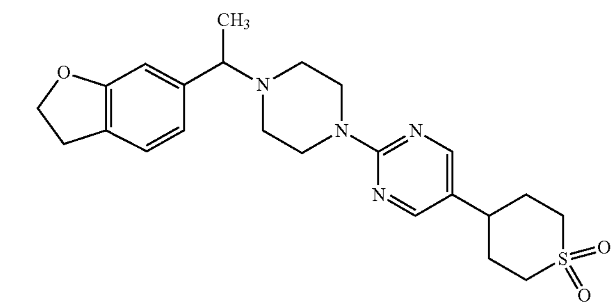 [SMILES: CC(c1ccc2c(c1)OCC2)N1CCN(c2ncc(C3CCS(=O)(=O)CC3)cn2)CC1] | | |
| 186 | 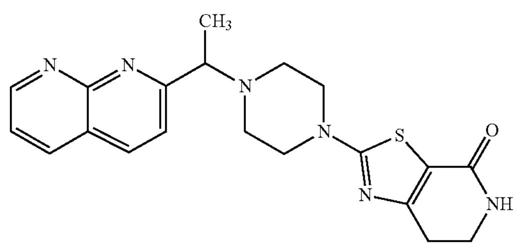 [SMILES: CC(c1ccc2cccnc2n1)N1CCN(c2nc3c(s2)C(=O)NCC3)CC1] | | |
| 187 | 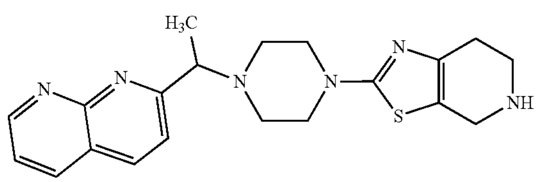 [SMILES: CC(c1ccc2cccnc2n1)N1CCN(c2nc3c(s2)CNCC3)CC1] | | |
| 188 | 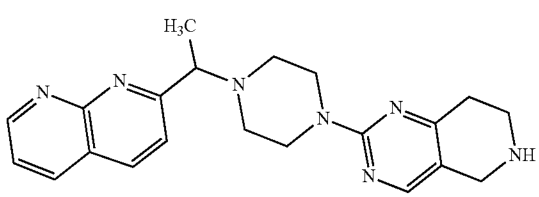 [SMILES: CC(c1ccc2cccnc2n1)N1CCN(c2ncc3c(n2)CCNC3)CC1] | | |
| 189 | 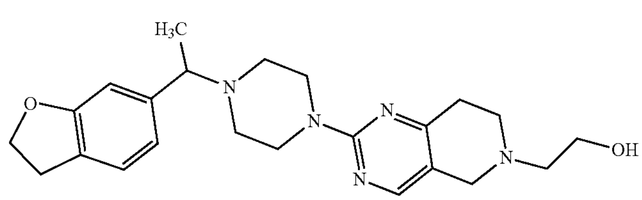 [SMILES: CC(c1ccc2c(c1)OCC2)N1CCN(c2ncc3c(n2)CCN(CCO)C3)CC1] | | |
| 190 | 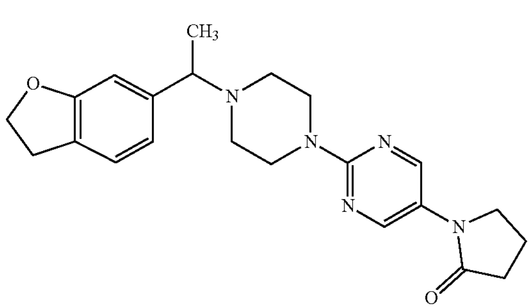 [SMILES: CC(c1ccc2c(c1)OCC2)N1CCN(c2ncc(N3CCCC3=O)cn2)CC1] | | |

US 11,612,599 B2
TABLE 1-continued
Compounds of formulae (I). OGA enzyme inhibition assay:
| No | Structure | Configuration specification | OGA IC50 (M) |
|---|---|---|---|
| 191 | 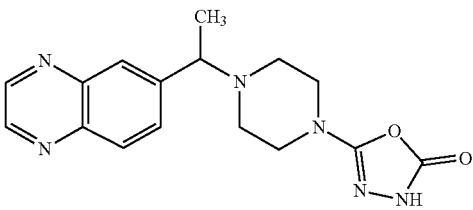 [SMILES: CC(c1ccc2nccnc2c1)N1CCN(c2n[nH]c(=O)o2)CC1] | | |
| 192 | 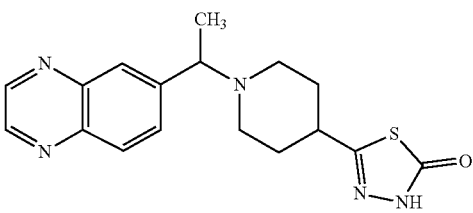 [SMILES: CC(c1ccc2nccnc2c1)N1CCC(c2n[nH]c(=O)s2)CC1] | | |
| 193 | 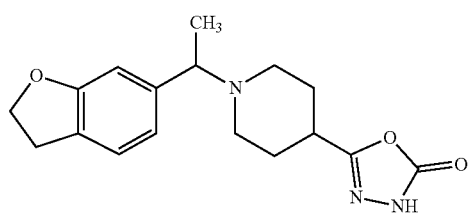 [SMILES: CC(c1ccc2c(c1)OCC2)N1CCC(c2n[nH]c(=O)o2)CC1] | | |
| 194 | 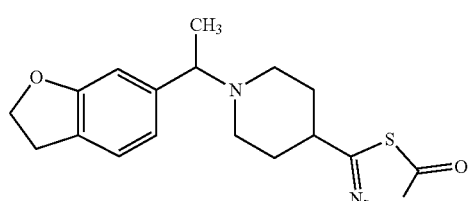 | | |
| 195 | 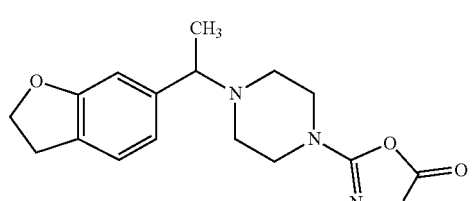 | | |
| 196 | 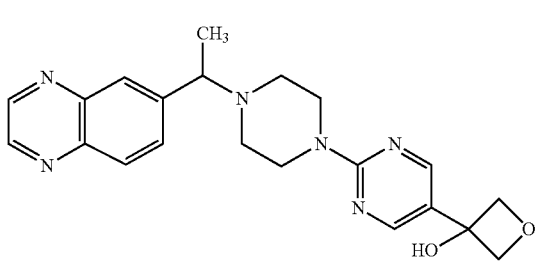 [SMILES: CC(c1ccc2nccnc2c1)N1CCN(c2ncc(C3(O)COC3)cn2)CC1] | | |
| 197 | 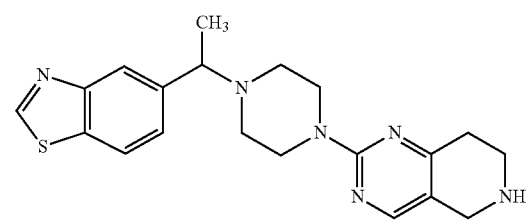 [SMILES: CC(c1ccc2scnc2c1)N1CCN(c2ncc3c(n2)CCNC3)CC1] | | |

TABLE 1-continued

Compounds of formulae (I). OGA enzyme inhibition assay:

| No | Structure | Configuration specification | OGA IC50 (M) |
|---|---|---|---|
| 198 | 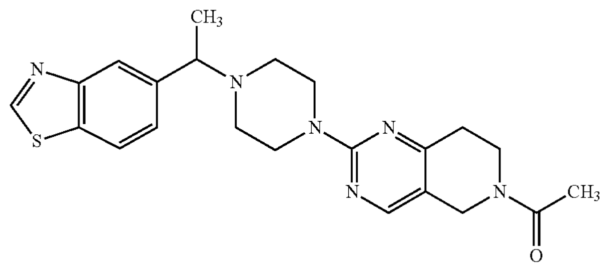 [SMILES: CC(=O)N1CCc2nc(N3CCN(C(C)c4ccc5scnc5c4)CC3)ncc2C1] | | |
| 199 | 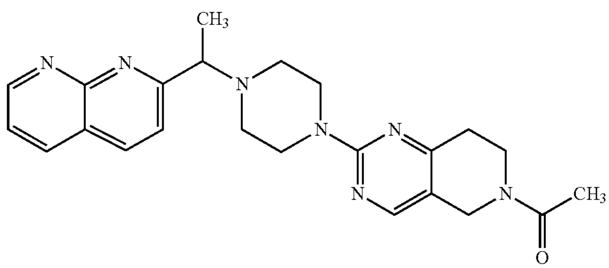 [SMILES: CC(=O)N1CCc2nc(N3CCN(C(C)c4ccc5cccnc5n4)CC3)ncc2C1] | | |
| 200 | 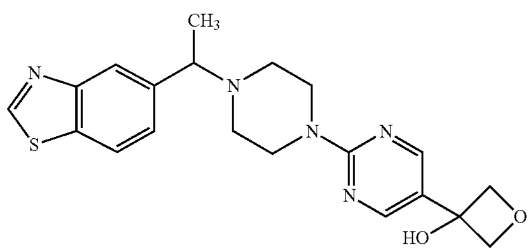 [SMILES: CC(c1ccc2scnc2c1)N1CCN(c2ncc(C3(O)COC3)cn2)CC1] | | |
| 201 | 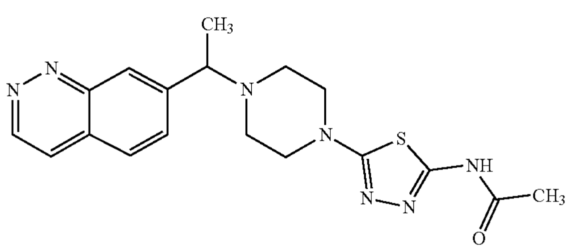 [SMILES: CC(=O)Nc1nnc(N2CCN(C(C)c3ccc4ccnnc4c3)CC2)s1] | | |
| 202 | 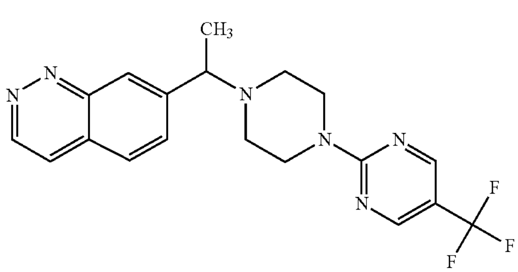 [SMILES: CC(c1ccc2ccnnc2c1)N1CCN(c2ncc(C(F)(F)F)cn2)CC1] | | |

US 11,612,599 B2
85                                                                      86
TABLE 1-continued
Compounds of formulae (I). OGA enzyme inhibition assay:
| No | Structure | Configuration specification | OGA IC50 (M) |
|---|---|---|---|
| 203 | 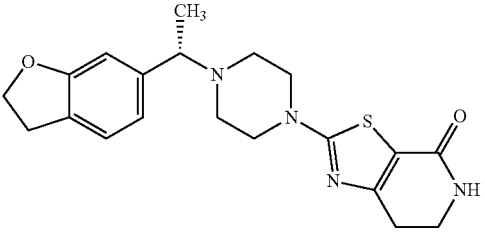 [SMILES: C[C@@H](c1ccc2c(c1)OCC2)N1CCN(c2nc3c(s2)C(=O)NCC3)CC1] | | |
| 204 | 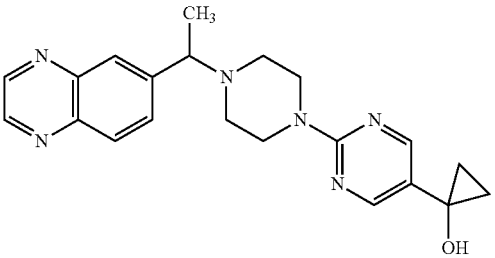 [SMILES: CC(c1ccc2nccnc2c1)N1CCN(c2ncc(C3(O)CC3)cn2)CC1] | | |
| 205 | 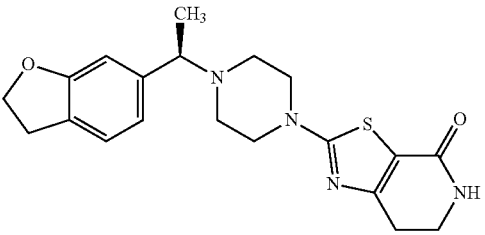 [SMILES: C[C@H](c1ccc2c(c1)OCC2)N1CCN(c2nc3c(s2)C(=O)NCC3)CC1] | | |
| 206 | 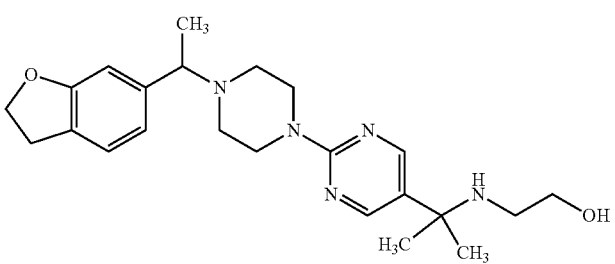 [SMILES: CC(c1ccc2c(c1)OCC2)N1CCN(c2ncc(C(C)(C)NCCO)cn2)CC1] | | |
| 207 | 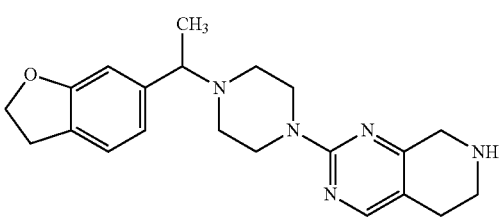 [SMILES: CC(c1ccc2c(c1)OCC2)N1CCN(c2ncc3c(n2)CNCC3)CC1] | | |
| 208 | 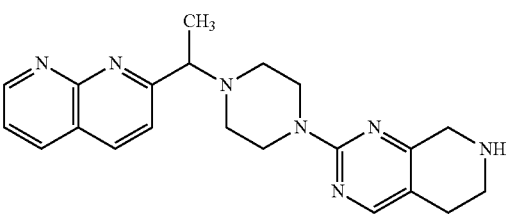 [SMILES: CC(c1ccc2cccnc2n1)N1CCN(c2ncc3c(n2)CNCC3)CC1] | | |

TABLE 1-continued

Compounds of formulae (I). OGA enzyme inhibition assay:

| No | Structure | Configuration specification | OGA IC50 (M) |
|----|-----------|-----------------------------|--------------|
| 209 | 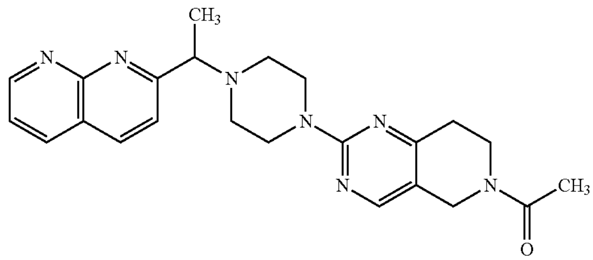 [SMILES: CC(=O)N1CCc2nc(N3CCN(C(C)c4ccc5cccnc5n4)CC3)ncc2C1] | | |
| 210 | 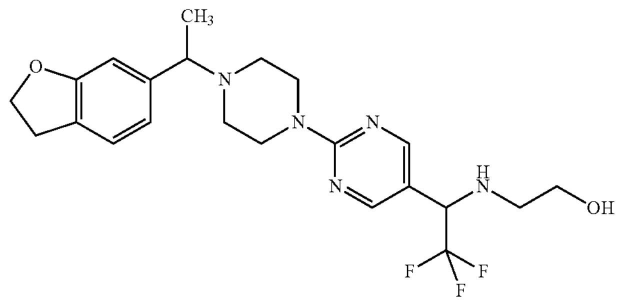 [SMILES: CC(c1ccc2c(c1)OCC2)N1CCN(c2ncc(C(NCCO)C(F)(F)F)cn2)CC1] | | |
| 211 | 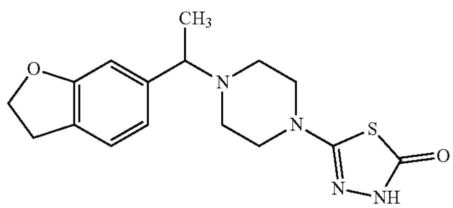 [SMILES: CC(c1ccc2c(c1)OCC2)N1CCN(c2n[nH]c(=O)s2)CC1] | | |
| 212 | 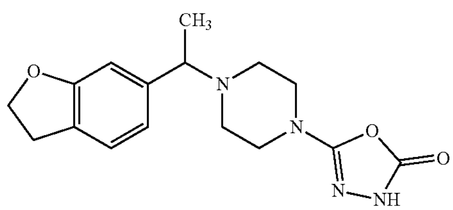 [SMILES: CC(c1ccc2c(c1)OCC2)N1CCN(c2n[nH]c(=O)o2)CC1] | | |
| 213 | 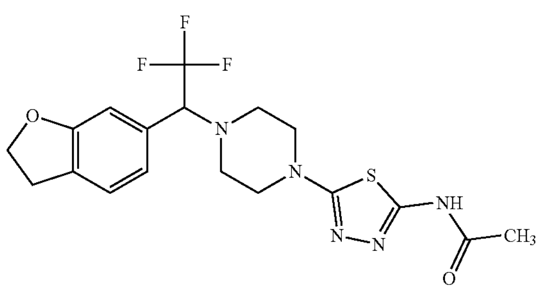 [SMILES: CC(=O)Nc1nnc(N2CCN(C(c3ccc4c(c3)OCC4)C(F)(F)F)CC2)s1] | | |
| 214 | 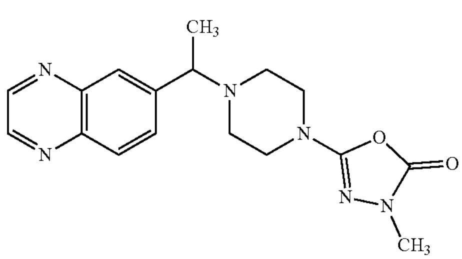 [SMILES: CC(c1ccc2nccnc2c1)N1CCN(c2nn(C)c(=O)o2)CC1] | | |

TABLE 1-continued

Compounds of formulae (I). OGA enzyme inhibition assay:

| No | Structure | Configuration specification | OGA IC50 (M) |
|---|---|---|---|
| 215 | 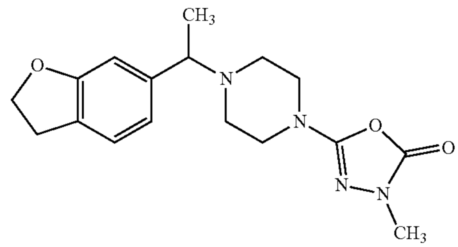 [SMILES: CC(c1ccc2c(c1)OCC2)N1CCN(c2nn(C)c(=O)o2)CC1] | | |
| 216 | 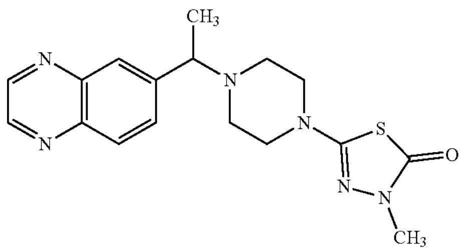 | | |
| 217 | 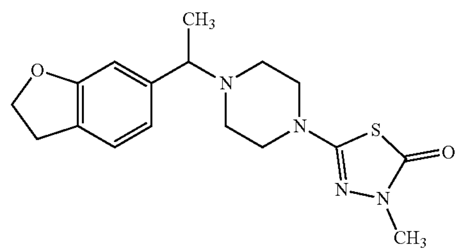 | | |
| 218 | 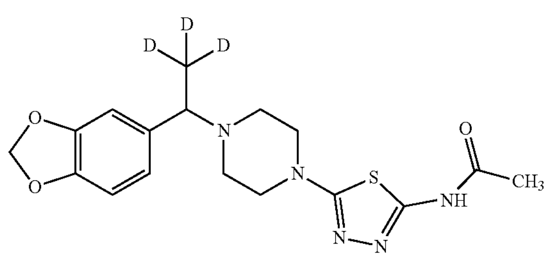 [SMILES: [2H]C([2H])([2H])C(c1ccc2c(c1)OCO2)N1CCN(c2nnc(NC(C)=O)s2)CC1] | | |
| 219 | 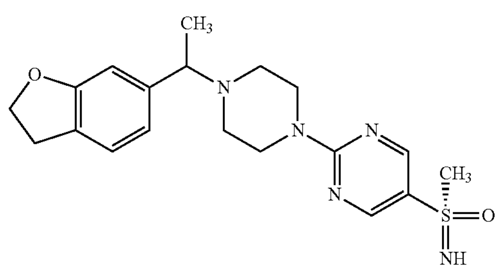 [SMILES: CC(c1ccc2c(c1)OCC2)N1CCN(c2ncc([S@](C)(=N)=O)cn2)CC1] | | |
| 220 | 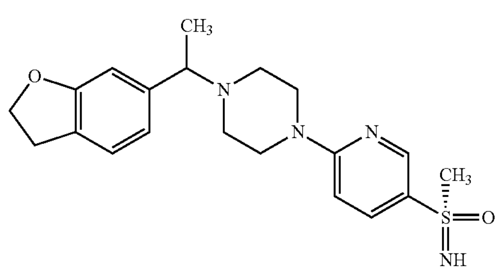 [SMILES: CC(c1ccc2c(c1)OCC2)N1CCN(c2ccc([S@](C)(=N)=O)cn2)CC1] | | |

TABLE 1-continued

Compounds of formulae (I). OGA enzyme inhibition assay:

| No | Structure | Configuration specification | OGA IC50 (M) |
|----|-----------|-----------------------------|--------------|
| 231 | 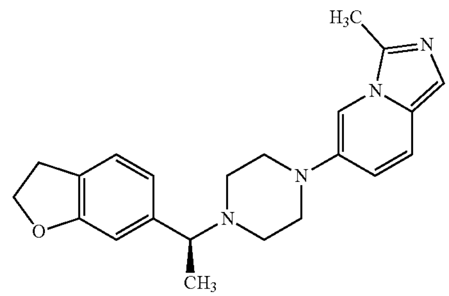 [SMILES: Cc1ncc2ccc(N3CCN([C@@H](C)c4ccc5c(c4)OCC5)CC3)cn12] | S-enantiomer | |
| 232 | 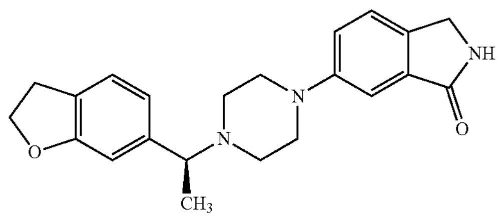 | S-enantiomer | |
| 233 | 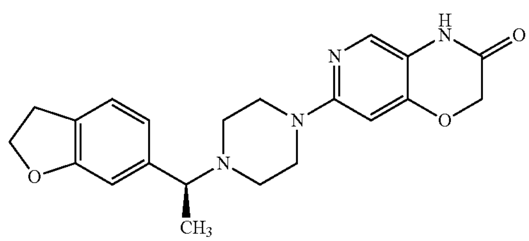 [SMILES: C[C@@H](c1ccc2c(c1)OCC2)N1CCN(c2cc3c(cn2)NC(=O)CO3)CC1] | S-enantiomer | |
| 234 | 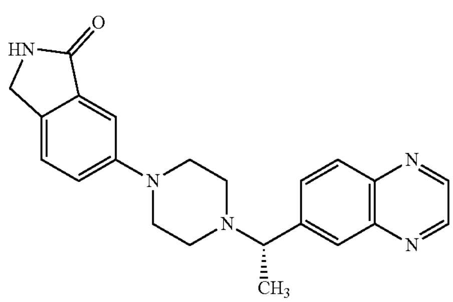 | S-enantiomer | |
| 235 | 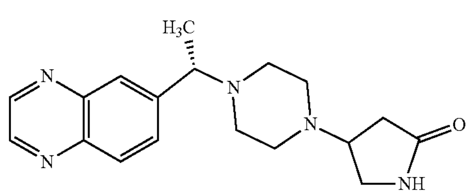 [SMILES: C[C@@H](c1ccc2nccnc2c1)N1CCN(C2CNC(=O)C2)CC1] | S-enantiomer | |
| 236 | 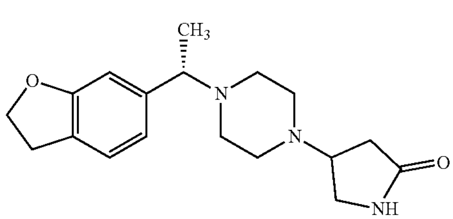 [SMILES: C[C@@H](c1ccc2c(c1)OCC2)N1CCN(C2CNC(=O)C2)CC1] | S-enantiomer | |

TABLE 1-continued

Compounds of formulae (I). OGA enzyme inhibition assay:

| No | Structure | Configuration specification | OGA IC50 (M) |
|---|---|---|---|
| 237 | 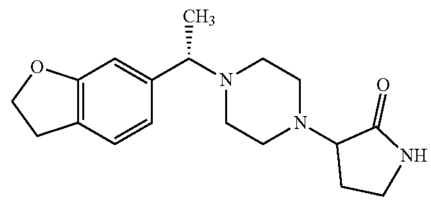 [SMILES: C[C@@H](c1ccc2c(c1)OCC2)N1CCN(C2CCNC2=O)CC1] | S-enantiomer | |
| 238 | 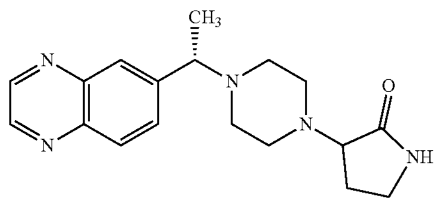 [SMILES: C[C@@H](c1ccc2nccnc2c1)N1CCN(C2CCNC2=O)CC1] | S-enantiomer | |
| 239 | 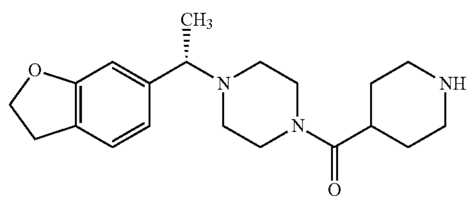 [SMILES: C[C@@H](c1ccc2c(c1)OCC2)N1CCN(C(=O)C2CCNCC2)CC1] | S-enantiomer | |
| 240 | 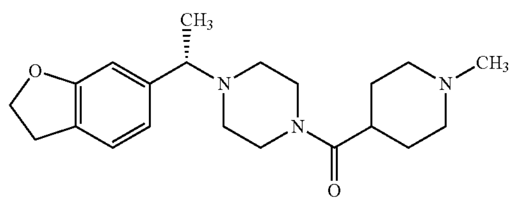 [SMILES: C[C@@H](c1ccc2c(c1)OCC2)N1CCN(C(=O)C2CCN(C)CC2)CC1] | S-enantiomer | |
| 241 | 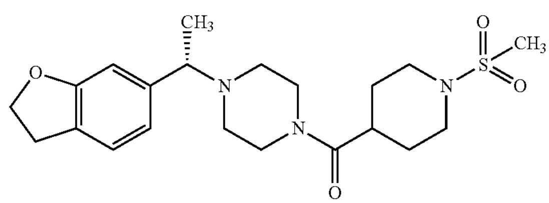 [SMILES: C[C@@H](c1ccc2c(c1)OCC2)N1CCN(C(=O)C2CCN(S(C)(=O)=O)CC2)CC1] | S-enantiomer | |
| 242 | 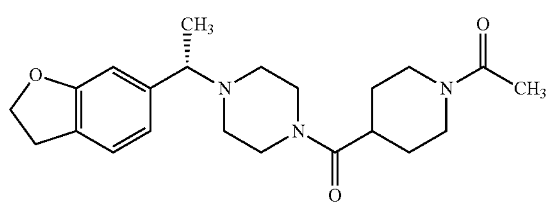 [SMILES: CC(=O)N1CCC(C(=O)N2CCN([C@@H](C)c3ccc4c(c3)OCC4)CC2)CC1] | S-enantiomer | |
| 243 | 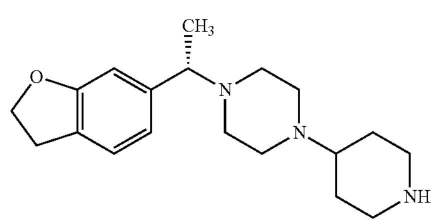 [SMILES: C[C@@H](c1ccc2c(c1)OCC2)N1CCN(C2CCNCC2)CC1] | S-enantiomer | |

TABLE 1-continued

Compounds of formulae (I). OGA enzyme inhibition assay:

| No | Structure | Configuration specification | OGA IC50 (M) |
|---|---|---|---|
| 244 | 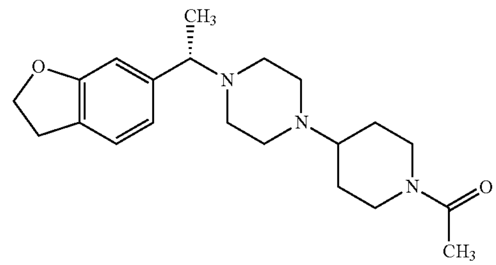 | S-enantiomer | |
| 245 | 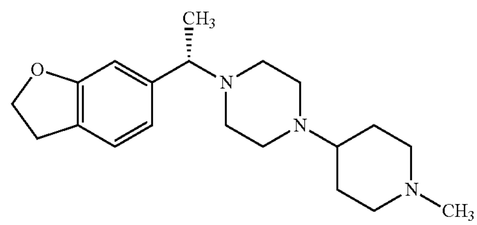 | S-enantiomer | |
| 246 | 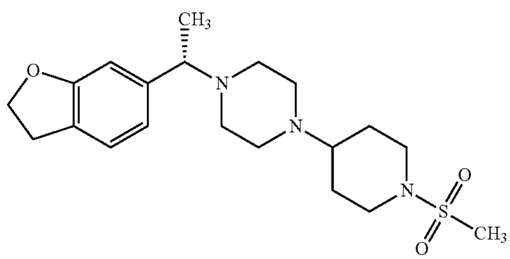 [SMILES: C[C@@H](c1ccc2c(c1)OCC2)N1CCN(C2CCN(S(C)(=O)=O)CC2)CC1] | S-enantiomer | |
| 247 | 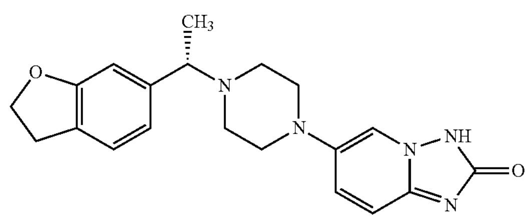 | S-enantiomer | |
| 248 | 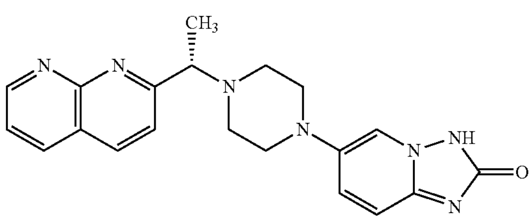 [SMILES: C[C@@H](c1ccc2cccnc2n1)N1CCN(c2ccc3nc(=O)[nH]n3c2)CC1] | S-enantiomer | |
| 249 | 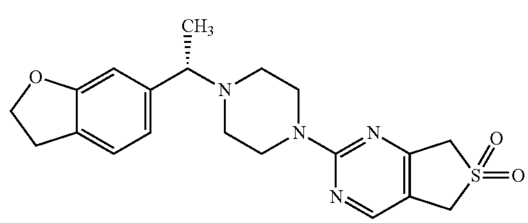 [SMILES: C[C@@H](c1ccc2c(c1)OCC2)N1CCN(c2ncc3c(n2)CS(=O)(=O)C3)CC1] | S-enantiomer | |

TABLE 1-continued

Compounds of formulae (I). OGA enzyme inhibition assay:

| No | Structure | Configuration specification | OGA IC50 (M) |
|---|---|---|---|
| 250 | 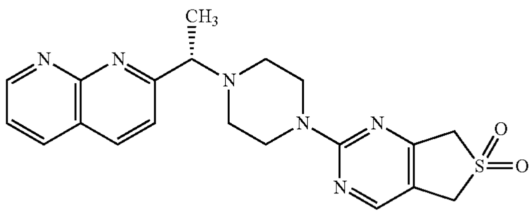 [SMILES: C[C@@H](c1ccc2cccnc2n1)N1CCN(c2ncc3c(n2)CS(=O)(=O)C3)CC1] | S-enantiomer | |
| 251 | 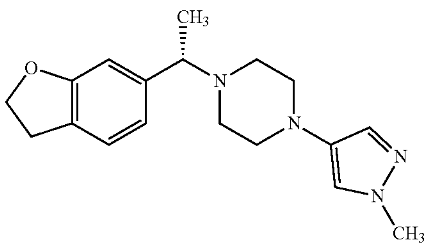 [SMILES: C[C@@H](c1ccc2c(c1)OCC2)N1CCN(c2cnn(C)c2)CC1] | S-enantiomer | |
| 252 | 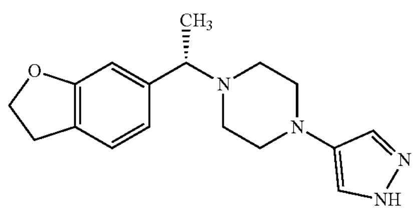 [SMILES: C[C@@H](c1ccc2c(c1)OCC2)N1CCN(c2cn[nH]c2)CC1] | S-enantiomer | |
| 253 | 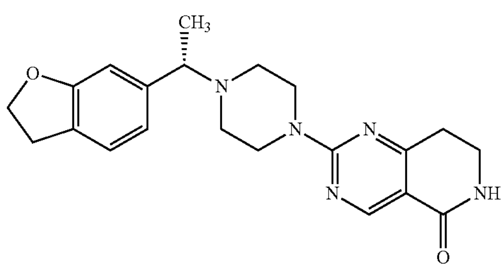 | S-enantiomer | |
| 254 | 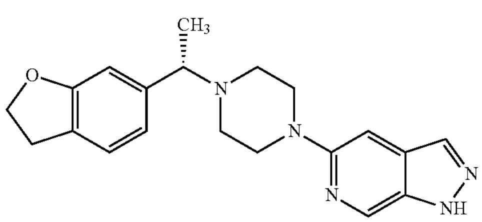 [SMILES: C[C@@H](c1ccc2c(c1)OCC2)N1CCN(c2cc3cn[nH]c3cn2)CC1] | S-enantiomer | |
| 255 | 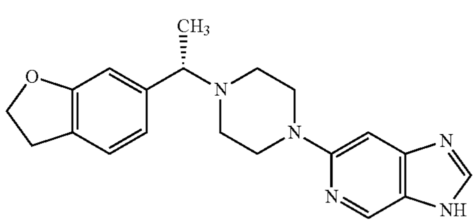 | S-enantiomer | |

TABLE 1-continued

Compounds of formulae (I). OGA enzyme inhibition assay:

| No | Structure | Configuration specification | OGA IC50 (M) |
|---|---|---|---|
| 256 | 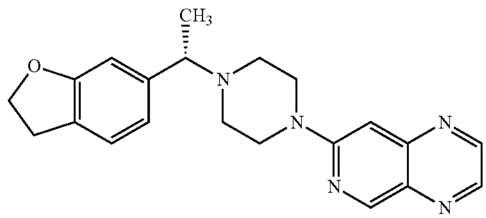 [SMILES: C[C@@H](c1ccc2c(c1)OCC2)N1CCN(c2cc3nccnc3cn2)CC1] | S-enantiomer | |
| 257 | 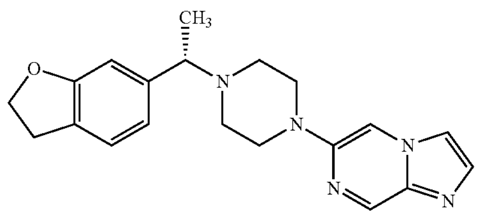 [SMILES: C[C@@H](c1ccc2c(c1)OCC2)N1CCN(c2cn3ccnc3cn2)CC1] | S-enantiomer | |
| 258 | 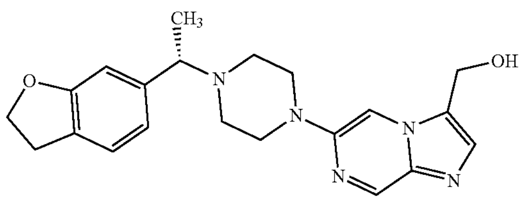 [SMILES: C[C@@H](c1ccc2c(c1)OCC2)N1CCN(c2cn3c(CO)cnc3cn2)CC1] | S-enantiomer | |
| 259 | 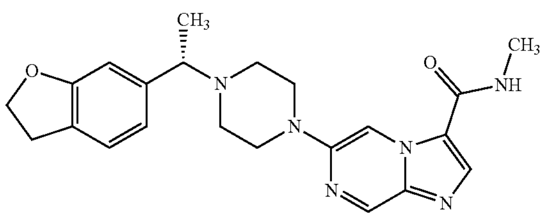 [SMILES: CNC(=O)c1cnc2cnc(N3CCN([C@@H](C)c4ccc5c(c4)OCC5)CC3)cn12] | S-enantiomer | |
| 260 | 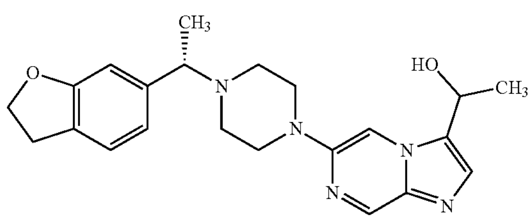 [SMILES: CC(O)c1cnc2cnc(N3CCN([C@@H](C)c4ccc5c(c4)OCC5)CC3)cn12] | S-enantiomer | |
| 261 | 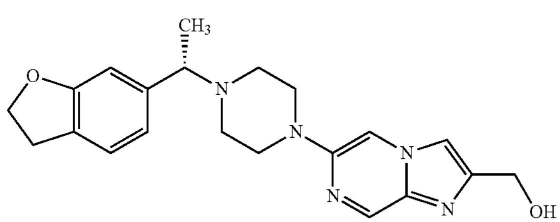 [SMILES: C[C@@H](c1ccc2c(c1)OCC2)N1CCN(c2cn3cc(CO)nc3cn2)CC1] | S-enantiomer | |
| 262 | 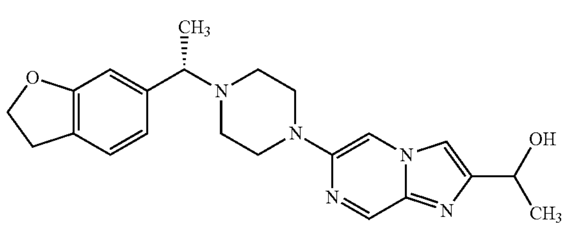 | S-enantiomer | |

TABLE 1-continued
Compounds of formulae (I). OGA enzyme inhibition assay:
| No | Structure | Configuration specification | OGA IC50 (M) |
|---|---|---|---|
| 263 | 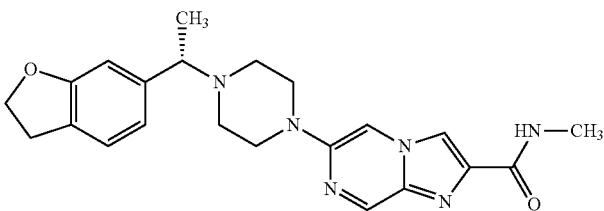 [SMILES: CNC(=O)c1cn2cc(N3CCN([C@@H](C)c4ccc5c(c4)OCC5)CC3)ncc2n1] | S-enantiomer | |
| 264 | 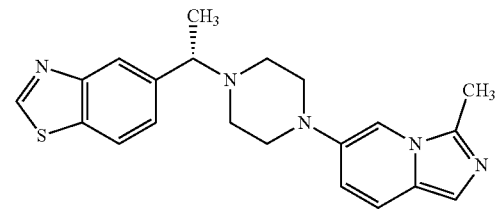 [SMILES: Cc1ncc2ccc(N3CCN([C@@H](C)c4ccc5scnc5c4)CC3)cn12] | S-enantiomer | |
| 265 | 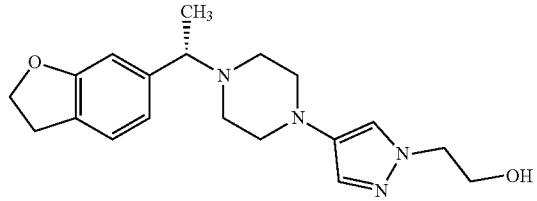 [SMILES: C[C@@H](c1ccc2c(c1)OCC2)N1CCN(c2cnn(CCO)c2)CC1] | S-enantiomer | |
| 266 | 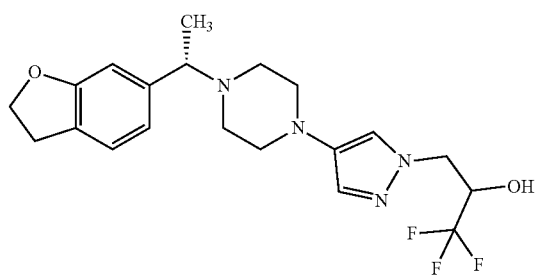 [SMILES: C[C@@H](c1ccc2c(c1)OCC2)N1CCN(c2cnn(CC(O)C(F)(F)F)c2)CC1] | S-enantiomer | |
| 267 | 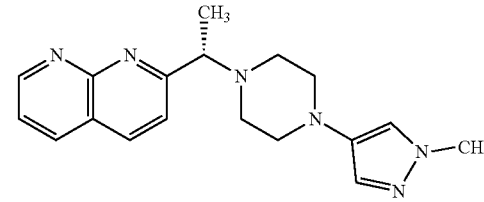 | S-enantiomer | |
| 268 | 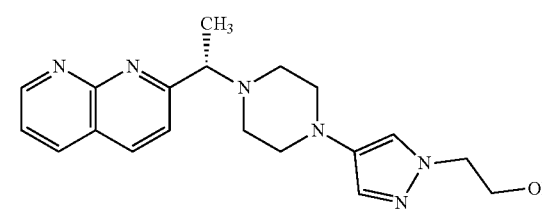 | S-enantiomer | |

TABLE 1-continued

Compounds of formulae (I). OGA enzyme inhibition assay:

| No | Structure | Configuration specification | OGA IC50 (M) |
|---|---|---|---|
| 269 | 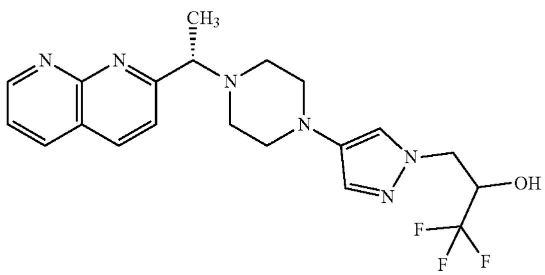 [SMILES: C[C@@H](c1ccc2cccnc2n1)N1CCN(c2cnn(CC(O)C(F)(F)F)c2)CC1] | S-enantiomer | |
| 270 | 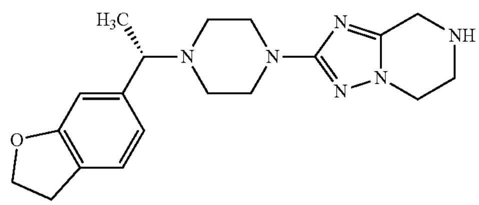 | S-enantiomer | |
| 271 | 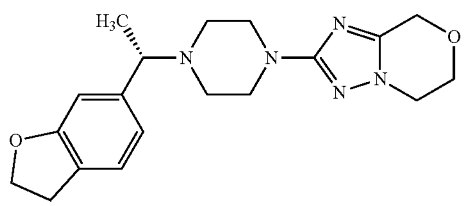 [SMILES: C[C@@H](c1ccc2c(c1)OCC2)N1CCN(c2nc3n(n2)CCOC3)CC1] | S-enantiomer | |
| 272 | 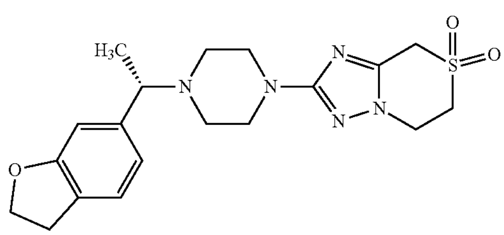 [SMILES: C[C@@H](c1ccc2c(c1)OCC2)N1CCN(c2nc3n(n2)CCS(=O)(=O)C3)CC1] | S-enantiomer | |
| 273 | 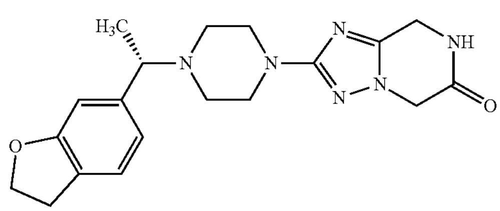 | S-enantiomer | |
| 274 | 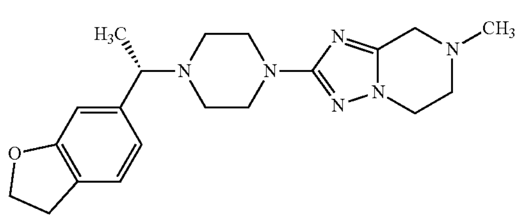 | S-enantiomer | |

TABLE 1-continued
Compounds of formulae (I). OGA enzyme inhibition assay:
| No | Structure | Configuration specification | OGA IC50 (M) |
|---|---|---|---|
| 275 | 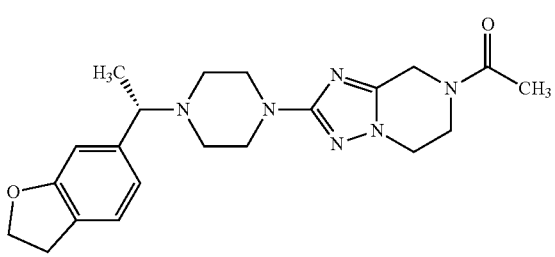 [SMILES: CC(=O)N1CCn2nc(N3CCN([C@@H](C)c4ccc5c(c4)OCC5)CC3)nc2C1] | S-enantiomer | |
| 276 | 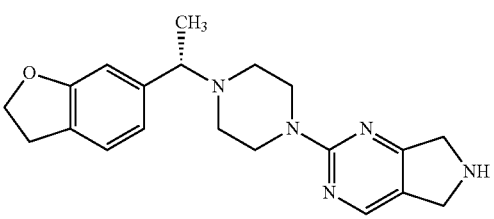 | S-enantiomer | |
| 277 | 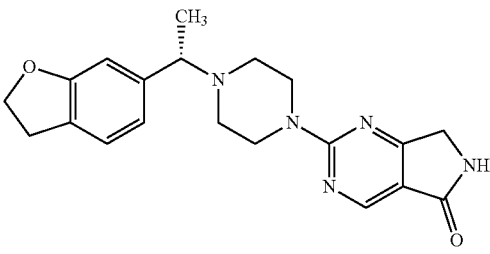 [SMILES: C[C@@H](c1ccc2c(c1)OCC2)N1CCN(c2ncc3c(n2)CNC3=O)CC1] | S-enantiomer | |
| 278 | 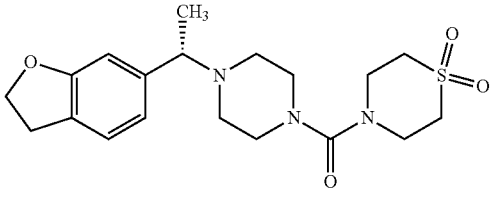 [SMILES: C[C@@H](c1ccc2c(c1)OCC2)N1CCN(C(=O)N2CCS(=O)(=O)CC2)CC1] | S-enantiomer | |
| 279 | 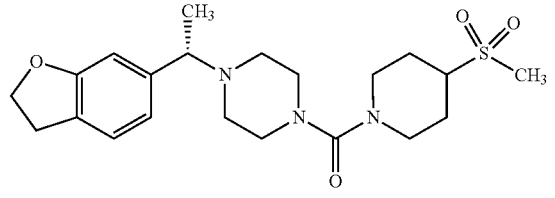 [SMILES: C[C@@H](c1ccc2c(c1)OCC2)N1CCN(C(=O)N2CCC(S(C)(=O)=O)CC2)CC1] | S-enantiomer | |
| 280 | 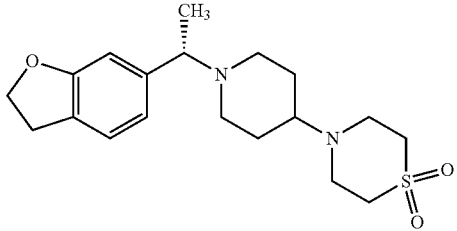 [SMILES: C[C@@H](c1ccc2c(c1)OCC2)N1CCC(N2CCS(=O)(=O)CC2)CC1] | S-enantiomer | |

TABLE 1-continued
Compounds of formulae (I). OGA enzyme inhibition assay:
| No | Structure | Configuration specification | OGA IC50 (M) |
|---|---|---|---|
| 281 | 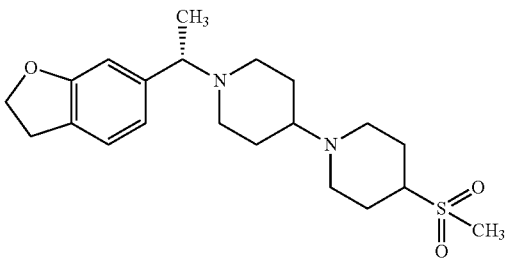 | S-enantiomer | |
| 282 | 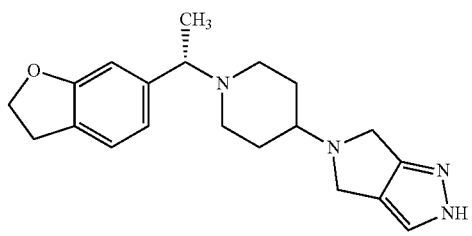 [SMILES: C[C@@H](c1ccc2c(c1)OCC2)N1CCC(N2Cc3c[nH]nc3C2)CC1] | S-enantiomer | |
| 283 | 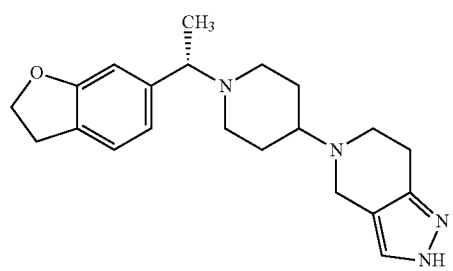 [SMILES: C[C@@H](c1ccc2c(c1)OCC2)N1CCC(N2CCc3n[nH]cc3C2)CC1] | S-enantiomer | |
| 284 | 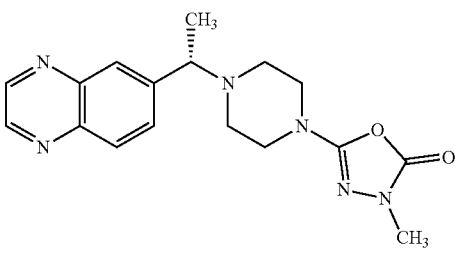 [SMILES: C[C@@H](c1ccc2nccnc2c1)N1CCN(c2nn(C)c(=O)o2)CC1] | S-enantiomer | |
| 285 | 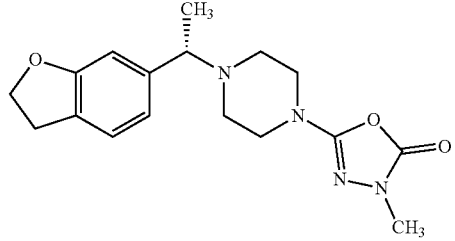 [SMILES: C[C@@H](c1ccc2c(c1)OCC2)N1CCN(c2nn(C)c(=O)o2)CC1] | S-enantiomer | |
| 286 | 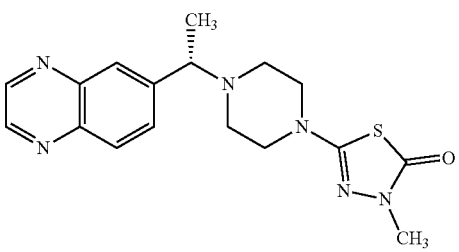 | S-enantiomer | |

TABLE 1-continued

Compounds of formulae (I). OGA enzyme inhibition assay:

| No | Structure | Configuration specification | OGA IC50 (M) |
|----|-----------|----------------------------|--------------|
| 287 | 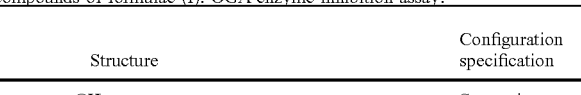 | S-enantiomer | |

Activity range of the compounds of Formula (I) is the following:
+ 1 to 10 µM
++ 0.2 to 1 µM
+++ 0.2 to 0.05 µM
++++ below 0.05 µM Preferred compounds of the present invention demonstrate adequate properties for use as a drug. In particular such preferred compounds show a high solid state stability, high stability in the presence of liver microsome, high oxidation stability and suitable permeability. Further preferred compounds of the present invention demonstrate their suitability as drugs by potent biological activity, such as the level of O-GlcNAcylation of total proteins measured in brain extracts. Relevant tests for determining such parameters are known by the person skilled in the art, e.g. solid state stability (Waterman K. C. (2007) Pharm Res 24(4); 780-790), stability in the presence of liver microsome (Obach R. S. (1999) Drug Metab Dispos 27(11); 1350-135) and the permeability (e.g. Caco-2 permeability assay, Calcagno A. M. (2006) Mol Pharm 3(1); 87-93); alternatively, they are described in Examples below, such as Example B02 describing the determination of O-GlcNAcylation level of total proteins measured in brain extracts. Compounds of the present invention that show a high potency in OGA inhibition assays and one or more of the above properties are especially suitable as a drug for the indications mentioned in the present specification.

The compounds according to formula (I) and the starting materials for its preparation, respectively, are produced by methods known per se, as described in the literature, i.e. under reaction conditions that are known and suitable for said reactions.

Use can also be made of variants that are known per se, but are not mentioned in greater detail herein. If desired, the starting materials can also be formed in-situ by leaving them in the un-isolated status in the crude reaction mixture, but immediately converting them further into the compound according to the invention. On the other hand, it is possible to carry out the reaction stepwise.

The following abbreviations refer respectively to the definitions below: Ac (acetyl), aq (aqueous), h (hour), g (gram), L (liter), mg (milligram), MHz (Megahertz), µM (micromolar), min (minute), mm (millimeter), mmol (millimole), mM (millimolar), m.p. (melting point), equiv (equivalent), mL (milliliter), µL (microliter), ACN (acetonitrile), AcOH (acetic acid), BINAP (2,2'-bis(disphenylphosphino)-1,1'-binaphthalene, BOC (tert-butoxy-carbonyl), CBZ (carbobenzoxy), CDCl$_3$ (deuterated chloroform), CD$_3$OD (deuterated methanol), CH$_3$CN (acetonitrile), c-hex (cyclohexane), DCC (dicyclohexyl carbodiimide), DCM (dichloromethane), dppf (1,1'-bis(diphenylphosphino)ferrocene), DIC (diisopropyl carbodiimide), DIEA (diisopropylethylamine), DMF (dimethylformamide), DMSO (dimethylsulfoxide), DMSO-d$_6$ (deuterated dimethylsulfoxide), EDC (1-(3-dimethyl-amino-propyl)-3-ethylcarbodiimide), ESI (Electro-spray ionization), EtOAc (Ethyl acetate), Et$_2$O (diethyl ether), EtOH (ethanol), FMOC (fluorenylmethyloxycarbonyl), HATU (dimethylamino-([1,2,3]triazolo[4,5-b]pyridin-3-yloxy)-methylene]-dimethyl-ammonium hexafluorophosphate), HPLC (High Performance Liquid Chromatography), i-PrOH (2-propanol), K$_2$CO$_3$ (potassium carbonate), LC (Liquid Chromatography), MD Autoprep (Mass directed Autoprep), MeOH (methanol), MgSO$_4$ (magnesium sulfate), MS (mass spectrometry), MTBE (Methyl tert-butyl ether), Mtr. (4-Methoxy-2, 3, 6-trimethylbenzensulfonyl), MW (microwave), NBS (N-bromo succinimide), NaHCO$_3$ (sodium bicarbonate), NaBH$_4$ (sodium borohydride), NMM (N-methyl morpholine), NMR (Nuclear Magnetic Resonance), POA (phenoxyacetate), Py (pyridine), PyBOP® (benzotriazole-1-yl-oxy-tris-pyrrolidino-phosphonium hexafluorophosphate), RT (room temperature), Rt (retention time), SFC (supercritical fluid chromatography), SPE (solid phase extraction), T3P (propylphosphonic anhydride), TBAF (tetra-n-butylammonium fluoride), TBTU (2-(1-H-benzotriazole-1-yl)-1,1,3,3-tetramethyluromium tetrafluoro borate), TEA (triethylamine), TFA (trifluoroacetic acid), THF (tetrahydrofurane), TLC (Thin Layer Chromatography), UV (Ultraviolet).

In general, the compounds according to Formula (I) and related formulae of this invention may be prepared from readily available starting materials. If such starting materials are not commercially available, they may be prepared by standard synthetic techniques. In general, the synthesis pathways for any individual compound of Formula (I) and related formulae will depend on the specific substituents of each molecule, such factors being appreciated by those having ordinary skill in the art. The following general methods and procedures described hereinafter in the examples may be employed to prepare compounds of Formula (I) and related formulae. Reaction conditions depicted in the following schemes, such as temperatures, solvents, or co-reagents, are given as examples only and are not restrictive. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by a person skilled in the art, using routine optimisation procedures. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3$^{rd}$ Edition 1999.

A "leaving group" LG denotes a chemical moiety which can be removed or replaced by another chemical group. Throughout the specification, the term leaving group preferably denotes Cl, Br, I or a reactively modified OH group, such as, for example, an activated ester, an imidazolide or alkylsulfonyloxy having 1 to 6 carbon atoms (preferably methylsulfonyloxy or trifluoromethylsulfonyloxy) or arylsulfonyloxy having 6 to 10 carbon atoms (preferably phenyl- or p-tolylsulfonyloxy). When a leaving group LG is attached to an aromatic or heteroaromatic ring, LG can denote in addition $SO_2$-alkyl or F. Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart). Activated esters are advantageously formed in situ, for example through addition of HOBt, N-hydroxysuccinimide or HATU.

Depending on the nature of A, R, W, Q, m and n, different synthetic strategies may be selected for the synthesis of compounds of Formula (I). In the process illustrated in the following schemes, A, R, W, Q, m and n are as above-defined in the description unless otherwise mentioned.

Compounds of Formula (I), wherein A, R, W, Q, m and n are defined as above, can be prepared from alternative compounds of Formula (I), using suitable interconversion procedures such as those described hereinafter in the examples, or conventional interconversion procedures well known by one skilled in the art.

Compound of formula (I) can be separated into compounds of formula (Ia) and (Ib) by chiral chromatography or by chiral resolution, re-crystallization with use of an optically active acid, using methods known by one skilled in the art and as described below in the examples (Scheme 1).

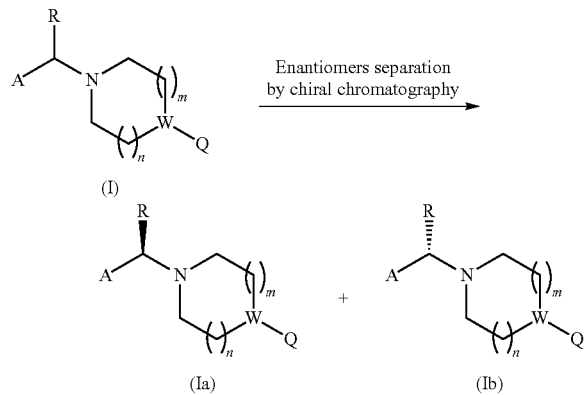

Compounds of formula (Ic), wherein A, R, Q, m and n are defined as above and W=N, can be prepared by the addition of an amine of formula (II) to a heterocycle of formula (III), where LG is a leaving group as defined above. This addition can be performed under thermic conditions, heating both compounds at a temperature between 50° C. and 200° C., using regular heating or microwave irradiation, in the presence of a base, such as but not limited to TEA, DIEA, $K_2CO_3$ or $Cs_2CO_3$, in a polar solvent, e.g. DMF, DMA or NMP. Alternatively, this addition can be catalysed by a metal complex, such as but not limited to $PdCl_2$, $Pd(OAc)_2$, $Pd_2(dba)_3$ in the presence of a ligand, e.g. BINAP, o-Tol$_3$P, X-Phos, and a base, e.g. NaOtBu, $Cs_2CO_3$ or $K_2CO_3$, in a suitable solvent or solvent mixture, for example dioxane, Toluene/MeOH, at a temperature between RT to 150° C., preferably at RT, for a few hours, e.g. one hour to 24 h (Scheme 2). Amine of formula (II) is obtained after deprotection of compound (IVa). PG is a suitable protecting group, which is compatible with the chemistry described below, such as but not limited to BOC. It can be removed under acidic conditions, such as but not limited to HCl in MeOH or dioxane or TFA in DCM, yielding isolation of amine (II).

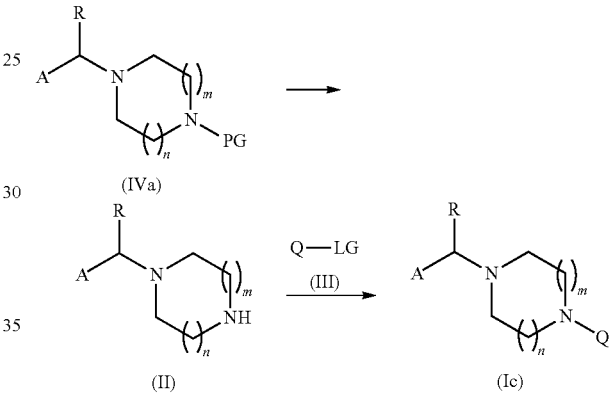

Compounds of formula (Id), wherein A, R, Q, m and n are defined as above and W=CH, can be prepared from an ester (IVb) using method known by a person killed in the art and as described in the examples below. Different heterocycles Q can be prepared from ester functionality, such as but not limited to oxadiazole, thiadiazole and thiazole, (Jakopin, Z. et al. Curr. Org. Chem. 2008, 12, 850-898. Hemming, K. Science of Synthesis, 2004, 13, 127-184. Augustine, J. K. et al. Tetrahedron, 2009, 65, 9989-9996. 37. Kempson, J. Name Reactions in Heterocyclic Chemistry II (2011), 299-308). Depending on the nature of Q, compound of formula (Id) can be obtained from compound (IVc) by displacement of the leaving group LG, as defined above, in the presence of a base such as but not limited to $Cs_2CO_3$ in a polar solvent, e.g. DMF, DMSO or NMP (Scheme 3). Alternatively compound of formula (Id) can be prepared by metal catalysed cross coupling reaction with a suitable boronic acid (Va) or ester (Vb) and an heterocycle of formula (III), using conditions known by a person skilled in the art, such as but not limited to $Pd(PPh_3)_4$ as catalyst, $K_2CO_3$ as base, dioxane as solvent at temperature ranging from RT to 180° C. (Scheme 3). Hydrogenation of the resulting coupling product in the presence of a catalyst such as $Pd(OH)_2$, would yield compound of formula (Id) (e.g. Andres, J.-I. et al. J. Med. Chem. 2012, 55, 8685-8699) (Scheme 3).

Scheme 3

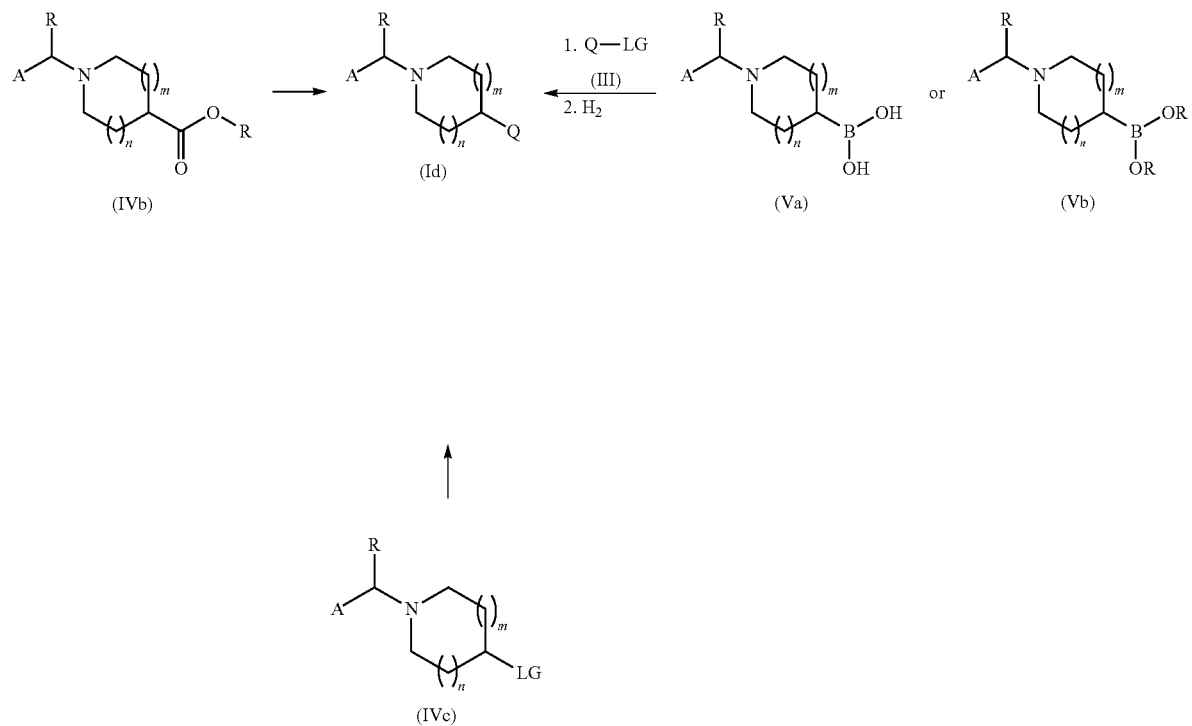

Compound of formula (IV), wherein A, R, W, Q, m and n are defined as above and $Y^1$ is a protecting group PG when W=N or an ester when W=CH, can be prepared from the corresponding ketone (IX) by reductive amination with amine (VI), using conditions known to the one skilled in the art, such as but not limited to the use of NaBH(OAc)$_3$ as reducing agent, in the presence of one equivalent of AcOH in DCE. Alternatively, reductive amination can be performed in two steps, with first imine formation, that can be catalysed by Ti(OiPr)$_4$, followed by reduction with suitable reducing agent, such as but not limited to NaBH$_4$ in MeOH (Abdel-Magid, A. F. at al. *J. Org. Chem.* 1996, 61, 3849-3862). Alternatively, ketone (IX) can be reduced into the corresponding alcohol (VIII) using usual reductive agents such as NaBH$_4$ in an alcoholic solvent, such as MeOH. Alcohol functionality can be then transformed into a suitable leaving group, such as but not limited to Cl or OMs, using conditions known to a person skilled in the art. The addition of amine (VI) to intermediate (VII) would yield the formation of compound (IV).

Scheme 4

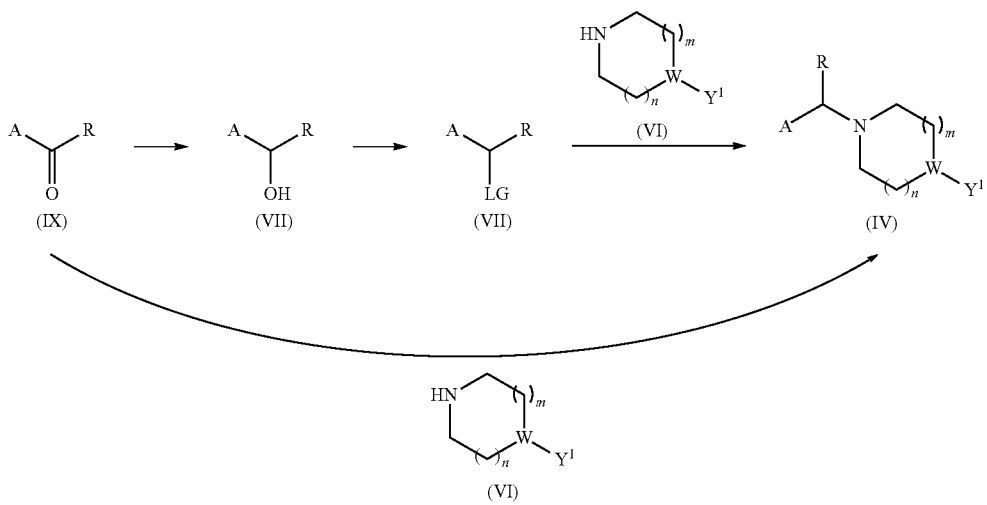

Alternatively, compound of formula (X), wherein W, Q, m and n are defined as above and PG is a suitable protecting group, such as but not limited to BOC, can be prepared from amine (XI), from compounds (XII), wherein m, n and PG are defined as above and $Y^2$ is an ester or a leaving group, or from compounds (XIIIa) or (XIIIb) (Scheme 5).

When W is N, compound of formula (X) can be prepared by the addition of an amine of formula (XI) to a heterocycle of formula (III), where LG is a leaving group as defined above. This addition can be performed under thermic conditions or can be catalysed by a metal complex, using conditions known by a person skilled in the art and as described below in the examples.

When W is CH, compound of formula (X) can be prepared from an ester (XII), wherein $Y^2$=COOR and W=CH, using method known by a person skilled in the art and as described in the examples below. Different heterocycles Q can be prepared from ester functionality, such as but not limited to oxadiazole, thiadiazole and thiazole, (Jakopin, Z. et al. *Curr. Org. Chem.* 2008, 12, 850-898. Hemming, K. *Science of Synthesis*, 2004, 13, 127-184. Augustine, J. K. et al. *Tetrahedron*, 2009, 65, 9989-9996. 37. Kempson, J. Name *Reactions in Heterocyclic Chemistry II* (2011), 299-308). Depending on the nature of Q, compound of formula (X) can be obtained from compound (XII), wherein W is CH and $Y^2$=LG as defined above, by displacement of the leaving group LG in the presence of a base such as but not limited to $Cs_2CO_3$ in a polar solvent, e.g. DMF, DMSO or NMP.

Compound of formula (X), wherein Q is a thiazole, can be obtained from compound (XII), wherein $Y^2$ is an aminomethanecarbothioyl group, and a suitable alpha-bromo ketone, using conditions know by a person skilled in the art.

Alternatively, compound of formula (X) can be prepared by metal catalysed cross coupling reaction with a suitable boronic acid (XIIIa) or ester (XIIIb), and a heterocycle of formula (III), using conditions known by a person skilled in the art, such as but not limited to $Pd(PPh_3)_4$ as catalyst, $K_2CO_3$ as base, dioxane as solvent at temperature ranging from RT to 180° C. (Scheme 5). Hydrogenation of the resulting coupling product in the presence of a catalyst such as $Pd(OH)_2$, would yield compound of formula (X) (e.g. Andres, J.-I. et al. *J. Med. Chem.* 2012, 55, 8685-8699) (Scheme 5).

PG is a suitable protecting group, which is compatible with the chemistry described above, such as but not limited to BOC. It can be removed under acidic conditions, such as but not limited to HCl in MeOH or dioxane or TFA in DCM, yielding isolation of amine (XIV). It can be further transformed into compound of formula (I) by reductive alkylation with ketone of formula (IX), following conditions well known by a person skilled in the art, as described in the examples (Abdel-Magid, A. F. at al. *J. Org. Chem.* 1996, 61, 3849-3862). Alternatively, amine (XIV) addition to compound (VII), prepared as described above and in the examples, would yield the formation of compound of formula (I).

Scheme 5

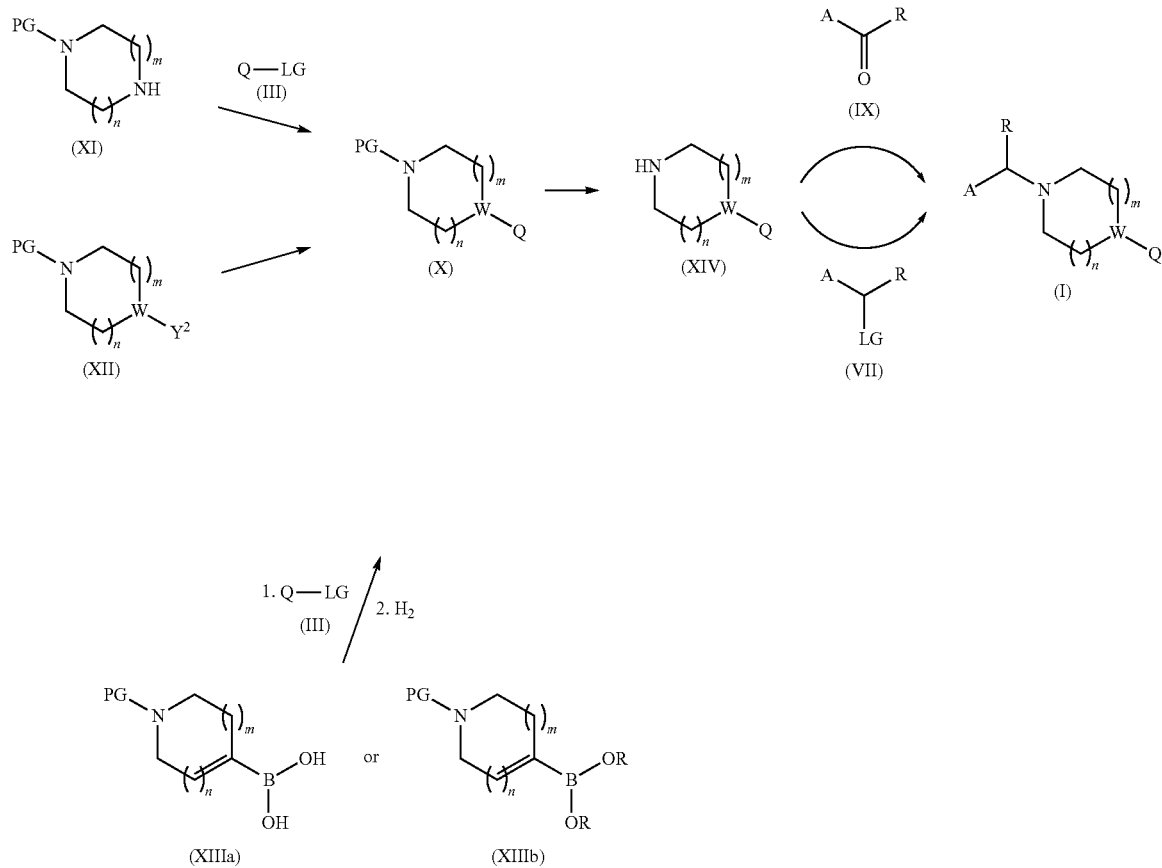

Amine of formula (II) can be separated into amines of formula (IIa) and (IIb) by chiral chromatography or chiral resolution by re-crystallization with an optically active acid, using methods known by one skilled in the art and as described below in the examples (Scheme 6).

Scheme 6

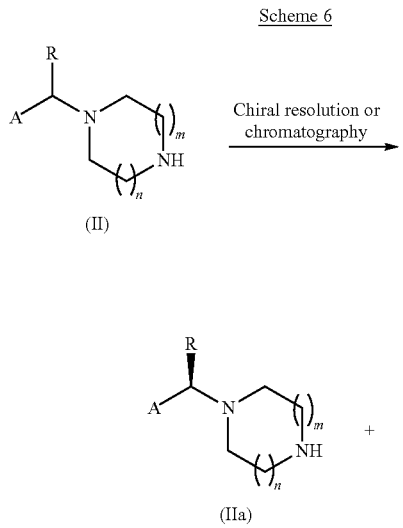

Alternatively, amines of formula (IIa) and (IIb) can be synthesized from chiral amines (XVIa) and (XVIb) respectively. Addition of amines (XVIa) and (XVIb) to reagent (XV), wherein PG is a protecting group, e.g. BOC or SO$_2$Tol and LG is a leaving group, e.g. Cl, would yield the formation of protected amines (IVe) and (IVf) respectively (Thiel, O. R. et al. *J. Org. Chem.* 2008, 73, 3508-3515). Deprotection conditions need to be selected based on the nature of the PG, such as HCl in dioxane or MeOH or TFA in DCM for BOC protecting group. Alternatively a mixture of HBr, AcOH and 4-hydroxybenzoic acid or a mixture of H$_2$SO$_4$ and trifluoroacetic acid at temperatures ranging from RT to 100° C. would be used to cleave a sulfonamide protecting group, such as para-toluene sulfonamide Scheme 7

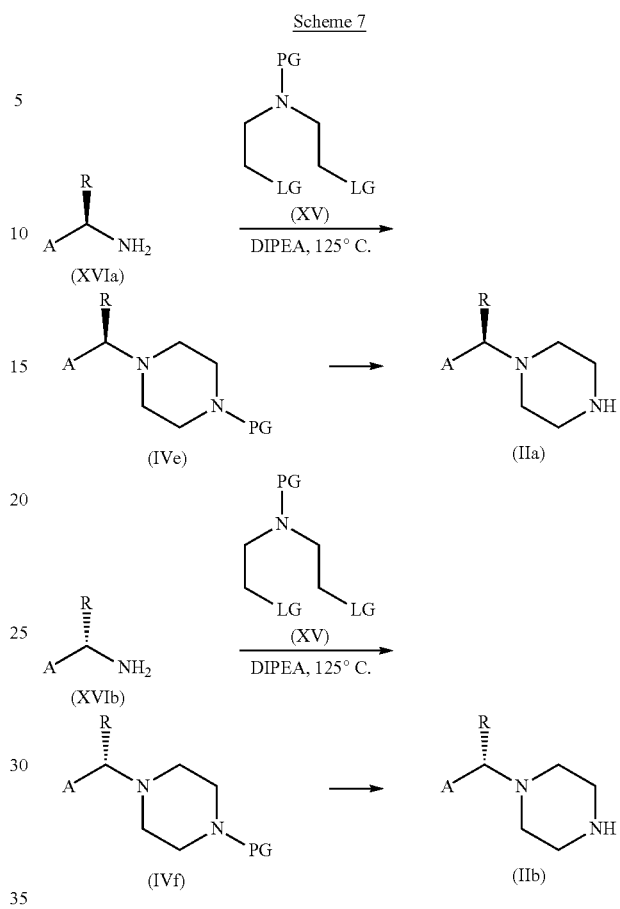

For the preparation of amines of formula (XVIa) and (XVIb), ketone of formula (IX) can be transformed into chiral imine (XVIII), reacting with a chiral auxiliary, such as but not limited to tert-butanesulfinamide group in the presence of titanium ethoxide (Ellman J. A. et al. *Acc. Chem. Res.* 2002, 35, 984-995). It can be further transformed into sulfinamide (XVIIa) or (XVIIb), depending on the conditions used for the reduction step, as described in the reference from Ellman J. A. et al. *J. Org. Chem.* 2007, 72, 626-629.

Scheme 8

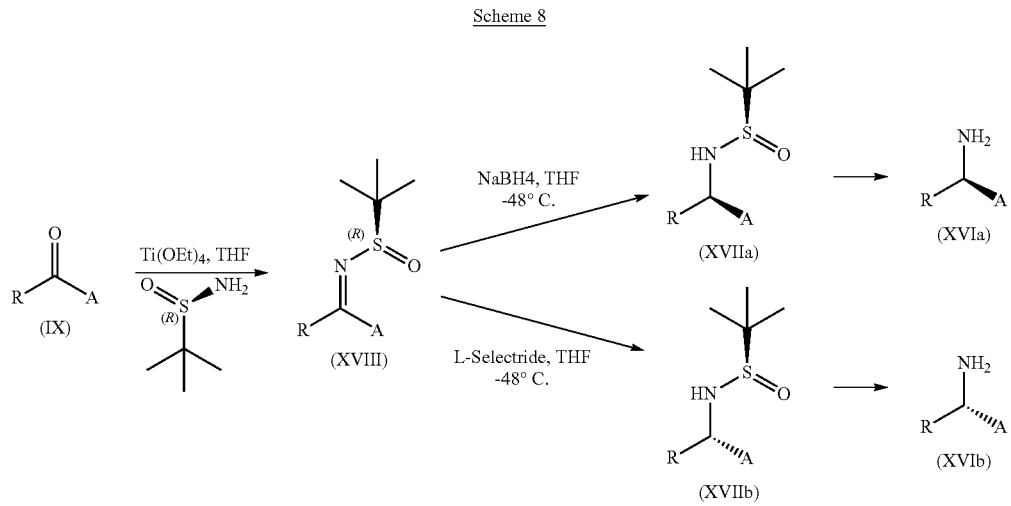

Alternatively aldehyde of formula (XIX) can be transformed into alcohol of formula (VIII) with addition of a suitable nucleophile, such as but not limited to a Grignard reagent (Scheme 9). In another process, ketone of formula (IXa) can be obtained by Stille cross coupling reaction between aryl halide (XX) and tributyl(1-ethoxyvinyl)tin in the presence of a catalyst, such as but not limited to Pd(PPh$_3$)$_2$Cl$_2$ in toluene at temperatures ranging from RT to 110° C. (Scheme 10).

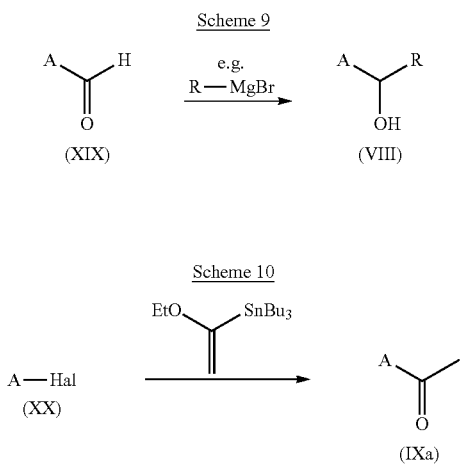

When a reaction is preferably performed under basic conditions, a suitable base might be selected from metal oxides, e.g. aluminum oxide, alkaline metal hydroxide (potassium hydroxide, sodium hydroxide and lithium hydroxide, inter alia), alkaline earth metal hydroxide (barium hydroxide and calcium hydroxide, inter alia), alkaline metal alcoholates (potassium ethanolate and sodium propanolate, inter alia), alkaline metal carbonates (e.g., sodium bicarbonate) and several organic bases (e.g., N,N-diisopropylethylamine, piperidine or diethanolamine, inter alia).

The reaction is generally carried out in an inert solvent. Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid, acetic acid or trifluoroacetic acid (TFA); nitro compounds, such as nitromethane or nitrobenzene; esters, such as ethyl acetate, or mixtures of the said solvents. Particular preference is given to TFA, DMF, dichloromethane, THF, H$_2$O, methanol, tert. butanol, tert. amylalcohol, triethylamine or dioxane.

Depending on the conditions used, the reaction time is between a few minutes and 14 days, the reaction temperature is between about −80° C. and 140° C., normally between −50° C. and 120° C., preferably between −20° C. and 100° C.

The compounds of formula (I) and sub-formulae thereof are accessible via the routes above. The starting materials, are usually known to the skilled artisan, or they can be easily prepared by known methods.

The compounds of formula (I) can be modified, like hydrogenated or metal-reduced, to remove the chlorine, or put into a substitution reaction, and/or to be transformed with an acid or base into a salt, preferably with a strong acid. Numerous papers and methods are available and useful for the one skilled in the art in respect for organic chemistry, chemical strategies and tactics, synthetic routes, protection of intermediates, cleavage and purification procedure, isolation and characterization. General chemical modifications are known to the one skilled in the art. Halogenation of aryls or hydroxy substitution by halogens of acids, alcohols, phenols, and their tautomeric structures can be preferably carried out by use of POCl$_3$, or SOCl$_2$, PCl$_5$, SO$_2$Cl$_2$. In some instances oxalyl chloride is also useful. Temperatures can vary from 0° C. to reflux depending on the task to halogenate a pyridone structure or a carboxylic acid or a sulfonic acid. Time will also be adjusted from minutes to several hours or even over night. Similarly, alkylation, ether formation, ester formation, amide formation are known to the one skilled in the art. Arylation with aryl boronic acids can be performed in presence of a Pd catalyst, appropriate ligand and base, preferably a carbonate, phosphate, borate salt of sodium, potassium or cesium. Organic bases, like Et$_3$N, DIPEA or the more basic DBU can also be used. Solvents can vary too, from toluene, dioxane, THF, diglyme, monoglyme, alcohols, DMF, DMA, NMP, acetonitrile, in some cases even water, and others. Commonly used catalysts like Pd (PPh$_3$)$_4$, or Pd(OAc)$_2$, PdCl$_2$ type precursors of PdO catalysts have advanced to more complex ones with more efficient ligands. In C—C arylations, instead of boronic acids and esters, aryl-trifluoroborate potassium salts (Suzuki-Miyaura coupling), organo silanes (Hiyama coupling), Grignard reagents (Kumada), organozinc compounds (Negishi coupling) and stannanes (Stifle coupling) may be useful. This experience can be transferred to N- and O-arylations. Numerous papers and methods are available and useful for the one skilled in the art in respect of N-arylation and even of electron deficient anilines, and with aryl chlorides and anilines as well as for O-arylation by using Cu catalysis and Pd catalysis.

In the final step of the processes above, a salt of the compounds, preferably those of formula (I), is optionally provided. The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds according to the invention are for the most part prepared by conventional methods. If the compound according to the invention contains a carboxyl group, one of its suitable salts can be formed by the reaction of the compound with a suitable base to give the corresponding base-addition salt. Such bases are, for example, alkali metal hydroxides, including potassium hydroxide, sodium hydroxide and lithium hydroxide; alkaline earth metal hydroxides, such as magnesium hydroxide, calcium hydroxide and barium hydroxide; alkali metal alkoxides, for example potassium ethoxide and sodium propoxide; and various organic bases, such as piperidine, diethanolamine and N-methyl-glucamine (meglumine), benzathine, choline, diethanolamine, ethylenediamine, benethamine, diethylamine, piperazine, lysine, L-arginine, ammonia, triethanolamine, betaine, ethanolamine, morpholine and tromethamine. The aluminum salts of the compounds according to the invention are likewise included. In the case of certain compounds of the formula I, which contain a basic center, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as methanesulfonate, ethanesulfonate, toluenesulfonate and benzenesulfonate, and other organic acids and corresponding salts thereof, such as carbonate, acetate, trifluoroacetate, tartrate, maleate, succinate, citrate, benzoate, salicylate, ascorbate and the like. Accordingly, pharmaceutically acceptable acid-addition salts of the compounds according to the invention include the following: acetate, adipate, alginate, arginate, aspartate, benzoate, benzenesulfonate (besylate), bisulfate, bisulfite, bromide, butyrate, camphorate, camphorsulfonate, caprate, caprylate, chloride, chlorobenzoate, citrate, cyclamate, cinnamate, cyclopentanepropionate, digluconate, dihydrogenphosphate, dinitrobenzoate, dodecylsulfate, ethanesulfonate, formate, glycolate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Both types of salts may be formed or interconverted preferably using ion-exchange resin techniques.

With regard to that stated above, it can be seen that the expressions "pharmaceutically acceptable salt" and "physiologically acceptable salt", which are used interchangeable herein, in the present connection are taken to mean an active ingredient which comprises a compound according to the invention in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, me-glumine, nitrate, oleate, phosphonate, pivalate, sodium phosphate, stearate, sulfate, sulfosalicylate, tartrate, thiomalate, tosylate and tro-meth-amine, but this is not intended to represent a restriction.

The acid-addition salts of basic compounds of the formula (I) are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts other-wise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanol-amine, ethylenediamine, N-methyl-D-glucamine and procaine. This is not intended to represent a restriction.

The base-addition salts of acidic compounds of the formula I are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts other-wise correspond to the respective free acid forms thereof.

If a compound of the formula (I) contains more than one group which is capable of forming pharmaceutically acceptable salts of this type, the formula I also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expressions "pharmaceutically acceptable salt" and "physiologically acceptable salt", which are used interchangeable herein, in the present connection are taken to mean an active ingredient which comprises a compound according to the invention in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Owing to their molecular structure, the compounds of the formula (I) can be chiral and can accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the Intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the (R) and (S) forms of tartaric acid, diacetyltartaric acid, dibenzoyltartaric acid, di-O-p-toluoyl-tartaric acid, mandelic acid, malic acid, lactic acid, suitable N-protected amino acids (for example N-benzoylproline or N-benzenesulfonylproline), or the various optically active camphorsulfonic acids. The suitably formed salt with optically active acid is crystallized using various combinations of solvents, such as but not limited to methanol, ethanol, isopropanol, THF, water, diethyl ether, acetone, methyl tert-butyl ethers and other solvents known to the person skilled in the art. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

When discovering and developing therapeutic agents, the person skilled in the art attempts to optimize pharmacokinetic parameters while retaining desirable in-vitro properties. It is reasonable to assume that many compounds with poor pharmacokinetic profiles are susceptible to oxidative metabolism. In-vitro liver microsomal assays currently available provide valuable information on the course of oxidative metabolism of this type, which in turn permits the rational design of deuterated compounds of the formula (I) with improved stability through resistance to such oxidative metabolism. Significant improvements in the pharmacokinetic profiles of compounds of the formula (I) are thereby obtained, and can be expressed quantitatively in terms of increases in the in vivo half-life (t/2), concentration at maximum therapeutic effect ($C_{max}$), area under the dose response curve (AUC), and F; and in terms of reduced clearance, dose and materials costs.

A further aspect of the invention relates to the use of compounds according to formula (I) and/or physiologically acceptable salts thereof for inhibiting a glycosidase. Such use may be therapeutic or non-therapeutic in character. The term "inhibition" denotes any reduction in glycosidase activity, which is based on the action of the specific inventive compounds capable to interact with the target glycosidase in such a manner that makes recognition, binding and blocking possible. It shall be understood that the compounds of the invention finally interact with the target to unfold the effect. The compounds are characterized by such an appreciable affinity to at least one glycoside hydrolase which ensures a reliable binding and preferably a complete blocking of glycosidase activity. More preferably, the substances are mono-specific in order to guarantee an exclusive and directed recognition with the chosen single glycosidase target. In the context of the present invention, the term "recognition"—without being limited thereto—relates to any type of interaction between the specific compounds and the target, particularly covalent or non-covalent binding or association, such as a covalent bond, hydrophobic/hydrophilic interactions, van der Waals forces, ion pairs, hydrogen bonds, ligand-receptor interactions, and the like. Such association may also encompass the presence of other molecules such as peptides, proteins or nucleotide sequences. The present receptor/ligand-interaction is preferably characterized by high affinity, high selectivity and minimal or even lacking cross-reactivity to other target molecules to exclude unhealthy and harmful impacts to the treated subject.

In a preferred embodiment of the present invention, the glycosidase comprises glycoside hydrolases, more preferably family 84 glycoside hydrolases, most preferably O-glycoprotein-2-acetamido-2deoxy-β-D-glucopyranosidase (OGA), highly preferably a mammalian O-GlcNAcase. It is particularly preferred that the compounds of formula (I) according to the invention selectively bind an O-GlcNAcase, e.g. thereby selectively inhibiting the cleavage of 2-acetamido-2-deoxy-3-D-glucopyranoside (O-GlcNAc) while they do not substantially inhibit a lysosomal β-hexosaminidase.

The compounds according to the invention preferably exhibit an advantageous biological activity, which is easily demonstrated in enzyme activity assays as described herein or known from prior art. In such in-vitro assays, the compounds preferably exhibit and cause an inhibitory effect. $IC_{50}$ is the concentration of a compound that produces 50% of the maximal inhibition for that compound. The glycosidase target is especially half inhibited by the compounds described herein if the concentration of the compounds amounts to less than 100 µM, preferably less than 10 µM, more preferably less than 1 µM, most preferably less than 0.2 µM. Most preferably, compounds of Formula (I) exhibit an $IC_{50}$ less than 0.02 µM.

A further aspect of the present invention relates to a method for inhibiting a glycosidase, wherein a system capable of expressing the glycosidase, particularly expressing said glycosidase, is contacted with at least one compound of formula (I) according to the invention and/or physiologically acceptable salts thereof, under conditions such that said glycosidase is inhibited. In a preferred embodiment of the method, the glycosidase is contacted with a compound selectively inhibiting O-GlcNAcase and more preferably having an $IC_{50}$ of less than 0.2 µM. It is also preferred that the method is performed in-vitro and/or that the method is not practiced on the human body. A cellular system is preferred in the scope of the method. The cellular system is defined to be any subject provided that the subject comprises cells. The cell refers to any type of primary cells or genetically engineered cells, whether in the isolated status, in culture, as cell line, assembled in tissue, organs or intact laboratory mammals, provided that they are capable of expressing the glycosidase. It shall also be understood that the cell expresses the glycosidase as inherent pre-condition to put the methods of inhibition into practice. Although it is particularly preferred that the cells are capable of expressing or do express the glycosidase, it shall not be excluded that glycosidase-deficient cells can be used and the glycosidase is artificially added to the cellular system. The assay of the invention can be even completely performed in-vitro such that the cell is waived but a glycosidase is contacted with at least one compound of formula (I) according to the invention and/or physiologically acceptable salts thereof. Hence, an amount of isolated glycosidase is provided in crude or purified form for this purpose.

As discussed herein, the glycosidase-signaling pathways are relevant for various diseases, preferably neurodegenerative diseases, diabetes, cancer, cardiovascular diseases and stroke. Accordingly, the compounds according to the invention are useful in the prophylaxis and/or treatment of diseases that are dependent on the said signaling pathways by interaction with one or more of them. The present invention therefore relates to the therapeutic and non-therapeutic use of compounds according to the invention as inhibitors of the signaling pathways described herein, preferably of the OGA-mediated signaling.

The method of the invention can be performed either in-vitro or in-vivo. The susceptibility of a particular cell to treatment with the compounds according to the invention can be particularly determined by in-vitro tests, whether in the course of research or clinical application. Typically, a culture of the cell is combined with a compound according to the invention at various concentrations for a period of time which is sufficient to allow the active agents to modulate glycosidase activity, usually between about one hour and one week. In-vitro treatment can be carried out using cultivated cells from any sample or cell line.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

For identification of a signal transduction pathway and for detection of interactions between various signal transduction pathways, various scientists have developed suitable models or model systems, for example cell culture models and models of transgenic animals. For the determination of certain stages in the signal transduction cascade, interacting compounds can be utilized in order to modulate the signal. The compounds according to the invention can also be used as reagents for testing OGA-dependent signal transduction pathways in animals and/or cell culture models or in the clinical diseases mentioned in this application.

The use according to the previous paragraphs of the specification may be either performed in-vitro or in-vivo models. The inhibition can be monitored by the techniques described in the course of the present specification. The in-vitro use is preferably applied to samples of humans suffering from neurodegenerative diseases, diabetes, cancer, cardiovascular diseases and stroke. Testing of several specific compounds and/or derivatives thereof makes the selection of that active ingredient possible that is best suited for the treatment of the human subject. The in-vivo dose rate of the chosen derivative is advantageously pre-adjusted to the glycosidase susceptibility and/or severity of disease of the respective subject with regard to the in-vitro data. Therefore, the therapeutic efficacy is remarkably enhanced. Moreover, the subsequent teaching of the present specification concerning the use of the compounds according to formula (I) and its derivatives for the production of a medicament for the prophylactic or therapeutic treatment and/or monitoring is considered as valid and applicable without restrictions to the use of the compound for the inhibition of glycosidase activity, preferably OGA activity, if expedient.

A further aspect of the invention relates to a medicament comprising at least one compound according to the invention and/or pharmaceutically usable derivatives, salts, solvates and stereoisomers thereof, including mixtures thereof in all ratios. A "medicament" in the meaning of the invention is any agent in the field of medicine, which comprises one or more compounds of formula (I) or preparations thereof (e.g. a pharmaceutical composition or pharmaceutical formulation) and can be used in prophylaxis, therapy, follow-up or aftercare of patients who suffer from diseases, which are associated with OGA activity, in such a way that a pathogenic modification of their overall condition or of the condition of particular regions of the organism could establish at least temporarily.

Consequently, the invention also relates to a pharmaceutical composition comprising as active ingredient an effective amount of at least one compound of formula (I) according to the invention and/or physiologically acceptable salts thereof together with pharmaceutically tolerable adjuvants and/or excipients.

In the meaning of the invention, an "adjuvant" denotes every substance that enables, intensifies or modifies a specific response against the active ingredient of the invention if administered simultaneously, contemporarily or sequentially. Known adjuvants for injection solutions are, for example, aluminum compositions, such as aluminum hydroxide or aluminum phosphate, saponins, such as QS21, muramyldipeptide or muramyltripeptide, proteins, such as gamma-interferon or TNF, M59, squalen or polyols.

Furthermore, the active ingredient may be administered alone or in combination with other treatments. A synergistic effect may be achieved by using more than one compound in the pharmaceutical composition, i.e. the compound of formula (I) is combined with at least another agent as active ingredient, which is either another compound of formula (I) or a compound of different structural scaffold. The active ingredients can be used either simultaneously or sequentially. The present compounds are suitable for combination with agents known to those of skill in the art (e.g., WO 2008/025170) and are useful with the compounds of the invention.

In some embodiments, a compound according to the invention, or for use according to the invention, may be provided in combination with any other active agents or pharmaceutical compositions where such combined therapy may be useful to modulate O-GlcNAcase activity, for example to treat neurodegenerative, inflammatory, cardiovascular, or immunoregulatory diseases or any condition described herein. In some embodiments, a compound according to the invention, or for use according to the invention, may be provided in combination with one or more agents useful in the prevention or treatment of tauopathies and Alzheimer's disease. Examples of such agents may include, without limitation,

- Acetylcholine esterase inhibitors (AChEIs) such as Aricept® (Donepezil), Exelon® (Rivastigmine), Razadyne® (Razadyne ER®, Reminyl®, Nivalin®, Galantamine), Cognex® (Tacrine), NMDA antagonists such as memantine (Axura®, Ebixa®), Huperzine A, Phenserine, Debio-9902 SR (ZT-1 SR), Zanapezil (TAK0147), ganstigmine, NP7557, α7 nicotinic acetylcholine receptor agonists, 5-HT6 receptor antagonists, M1 muscarinic acetylcholine receptor agonists and positive allosteric modulators, etc
- Tau aggregation inhibitors such as methylene blue, etc
- Agents blocking tau aggregation seeding and propagation such as tau antibodies and tau vaccines, etc
- Microtubule stabilizers such as AL-108, AL-208, paclitaxel, etc
- Amyloid-β (A β) peptide lowering agents such as β-secretase (BACE-1) inhibitors, senile plaque-clearing biologics such as Aβ antibodies and Aβ vaccines The invention also relates to a set (kit) consisting of separate packs of an effective amount of a compound according to the invention and/or pharmaceutically acceptable salts, derivatives, solvates and stereoisomers thereof, including mixtures thereof in all ratios, and an effective amount of a further medicament active ingredient. The set comprises suitable containers, such as boxes, individual bottles, bags or ampoules. The set may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further medicament active ingredient in dissolved or lyophilized form.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intra-dermal) methods. Such formulations can be prepared using processes known in the pharmaceutical art by, e.g., combining the active ingredient with the excipient(s) or adjuvant(s).

The pharmaceutical composition of the invention is produced in a known way using common solid or liquid carriers, diluents and/or additives and usual adjuvants for pharmaceutical engineering and with an appropriate dosage. The amount of excipient material that is combined with the active ingredient to produce a single dosage form varies depending upon the host treated and the particular mode of administration. Suitable excipients include organic or inorganic substances that are suitable for the different routes of administration, such as enteral (e.g. oral), parenteral or topical application, and which do not react with compounds of formula (I) or salts thereof. Examples of suitable excipients are water, vegetable oils, benzyl alcohols, alkylene glycols, polyethylene glycols, glycerol triacetate, gelatin, carbohydrates, e.g. lactose or starch, magnesium stearate, talc and petroleum jelly.

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilized) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavors.

In a preferred embodiment of the present invention, the pharmaceutical composition is adapted for oral administration. The preparations can be sterilized and/or can comprise auxiliaries, such as carrier proteins (e.g. serum albumin), lubricants, preservatives, stabilizers, fillers, chelating agents, antioxidants, solvents, bonding agents, suspending agents, wetting agents, emulsifiers, salts (for influencing the osmotic pressure), buffer substances, colorants, flavorings and one or more further active substances, for example one or more vitamins. Additives are well known in the art, and they are used in a variety of formulations.

Accordingly, the invention also relates to a pharmaceutical composition comprising as active ingredient an effective amount of at least one compound of formula (I) according to the invention and/or physiologically acceptable salts thereof together with pharmaceutically tolerable adjuvants for oral administration, optionally in combination with at least another active pharmaceutical ingredient. The prior teaching of the present specification concerning administration route and combination product, respectively, is valid and applicable without restrictions to the combination of both features if expedient.

The terms "effective amount" or "effective dose" or "dose" are interchangeably used herein and denote an amount of the pharmaceutical compound having a prophylactically or therapeutically relevant effect on a disease or pathological conditions, i.e. which causes in a tissue, system, animal or human a biological or medical response which is sought or desired, for example, by a researcher or physician. A "prophylactic effect" reduces the likelihood of developing a disease or even prevents the onset of a disease. A "therapeutically relevant effect" relieves to some extent one or more symptoms of a disease or returns to normality either partially or completely one or more physiological or biochemical parameters associated with or causative of the disease or pathological conditions. In addition, the expression "therapeutically effective amount" denotes an amount which, compared with a corresponding subject who has not received this amount, has the following consequence: improved treatment, healing, prevention or elimination of a disease, syndrome, condition, complaint, disorder or side-effects or also the reduction in the advance of a disease, complaint or disorder. The expression "therapeutically effective amount" also encompasses the amounts which are effective for increasing normal physiological function.

The respective dose or dosage range for administering the pharmaceutical composition according to the invention is sufficiently high in order to achieve the desired prophylactic or therapeutic effect of reducing symptoms of the aforementioned diseases. It will be understood that the specific dose level, frequency and period of administration to any particular human will depend upon a variety of factors including the activity of the specific compound employed, the age, body weight, general state of health, gender, diet, time and route of administration, rate of excretion, drug combination and the severity of the particular disease to which the specific therapy is applied. Using well-known means and methods, the exact dose can be determined by one of skill in the art as a matter of routine experimentation. The prior teaching of the present specification is valid and applicable without restrictions to the pharmaceutical composition comprising the compounds of formula (I) if expedient.

Pharmaceutical formulations can be administered in the form of dosage units which comprise a predetermined amount of active ingredient per dosage unit. The concentration of the prophylactically or therapeutically active ingredient in the formulation may vary from about 0.1 to 100 wt %. Preferably, the compound of formula (I) or the pharmaceutically acceptable salts thereof are administered in doses of approximately 0.5 to 1000 mg, more preferably between 1 and 700 mg, most preferably 5 and 100 mg per dose unit. Generally, such a dose range is appropriate for total daily incorporation. In other terms, the daily dose is preferably between approximately 0.02 and 100 mg/kg of body weight. The specific dose for each patient depends, however, on a wide variety of factors as already described in the present specification (e.g. depending on the condition treated, the method of administration and the age, weight and condition of the patient). Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Although a therapeutically effective amount of a compound according to the invention has to be ultimately determined by the treating doctor or vet by considering a number of factors (e.g. the age and weight of the animal, the precise condition that requires treatment, severity of condition, the nature of the formulation and the method of administration), an effective amount of a compound according to the invention for the treatment of neurodegenerative diseases, for example tauopathies and Alzheimer's disease, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The pharmaceutical composition of the invention can be employed as medicament in human and veterinary medicine. According to the invention, the compounds of formula (I) and/or physiologically salts thereof are suited for the prophylactic or therapeutic treatment and/or monitoring of diseases that are caused, mediated and/or propagated by OGA activity. It is particularly preferred that the diseases are neurodegenerative diseases, diabetes, cancer, cardiovascular diseases and stroke, more preferably neurodegenerative diseases, most preferably one or more tauopathies, highly preferably Alzheimer's disease and dementia. It shall be understood that the host of the compound is included in the present scope of protection according to the present invention.

Another aspect of the present invention relates to compounds of formula (I) according to the invention and/or physiologically acceptable salts thereof for use in the prophylactic or therapeutic treatment and/or monitoring of diseases that are caused, mediated and/or propagated by OGA activity. Another aspect of the invention concerns compounds of formula (I) according to the invention and/or physiologically acceptable salts thereof for use in the prophylactic or therapeutic treatment and/or monitoring of neurodegenerative diseases, diabetes, cancer, cardiovascular diseases and stroke. The prior teaching of the present specification concerning the compounds of formula (I), including any preferred embodiment thereof, is valid and applicable without restrictions to the compounds according to formula (I) and their salts for use in the prophylactic or therapeutic treatment and/or monitoring of neurodegenerative diseases, diabetes, cancer, cardiovascular diseases and stroke.

Another aspect of the invention relates to a method for treating a disease that is caused, mediated and/or propagated by OGA activity, wherein an effective amount of at least one compound of formula (I) according to the invention and/or physiologically acceptable salts thereof is administered to a mammal in need of such treatment. Another aspect of the invention relates to a method for treating neurodegenerative diseases, diabetes, cancer, cardiovascular diseases and stroke, preferably a tauopathy, wherein an effective amount of at least one compound of formula (I) according to the invention and/or physiologically acceptable salts thereof is administered to a mammal in need of such treatment. The preferred treatment is an oral administration. The prior teaching of the invention and its embodiments is valid and applicable without restrictions to the methods of treatment if expedient.

The neurodegenerative disease or condition is more preferably selected from the group of one or more tauopathies and Alzheimer's disease, Amyotrophic lateral sclerosis (ALS), Amyotrophic lateral sclerosis with cognitive impairment (ALSci), Argyrophilic grain disease, Behavior variant frontotemporal dementia (bvFTD), Bluit disease, Bluit disease, Corticobasal degeneration (CBP), Dementia pugilistica, Dementia with Lewy Bodies, Diffuse neurofibrillary tangles with calcification, Down's syndrome, Familial British dementia, Familial Danish dementia, Frontotemporal dementia with parkinsonism linked to chromosome 17 (FTDP-17), Frontotemporal Lobar Degeneration (FTLD), Ganglioglioma, Gangliocytoma, Gerstmann-Straussler-Scheinker disease, Globular glial tauopathy, Guadeloupean parkinsonism, Hallevorden-Spatz disease (neurodegeneration with brain iron accumulation type 1), Lead encephalopathy, Lipofuscinosis, Meningioangiomatosis, Multiple system atrophy, Myotonic dystrophy, Niemann-Pick disease (type C), Pallido-ponto-nigral degeneration, Parkinson's disease, Parkinson's disease dementia (PDD), Parkinsonism-dementia complex of Guam, Pick's disease (PiD), Postencephalitic parkinsonism (PEP), Primary progressive aphasia, Prion diseases (including Creutzfeldt-Jakob Disease (GJD), Variant Creutzfeldt-Jakob Disease (vCJD), Fatal Familial Insomnia, Kuru, Progressive supercortical gliosis, Progressive supranuclear palsy (PSP), Pure Autonomic Failure, Richardson's syndrome, Subacute sclerosing panencephalitis, Tangle-only dementia, Tuberous Sclerosis, Huntington's disease. Most preferred are one ore more tauopathies and Alzheimer's disease.

The invention also relates to the use of compounds according to formula (I) and/or physiologically acceptable salts thereof for the prophylactic or therapeutic treatment and/or monitoring of diseases that are caused, mediated and/or propagated by OGA activity. Furthermore, the invention relates to the use of compounds according to formula (I) and/or physiologically acceptable salts thereof for the production of a medicament for the prophylactic or therapeutic treatment and/or monitoring of diseases that are caused, mediated and/or propagated by OGA activity. Compounds of formula (I) and/or a physiologically acceptable salt thereof can furthermore be employed as intermediate for the preparation of further medicament active ingredients. The medicament is preferably prepared in a non-chemical manner, e.g. by combining the active ingredient with at least one solid, fluid and/or semi-fluid carrier or excipient, and optionally in conjunction with a single or more other active substances in an appropriate dosage form.

The compounds of formula (I) according to the invention can be administered before or following an onset of disease once or several times acting as therapy. The aforementioned compounds and medical products of the inventive use are particularly used for the therapeutic treatment. A therapeutically relevant effect relieves to some extent one or more symptoms of a disorder, or returns to normality, either partially or completely, one or more physiological or biochemical parameters associated with or causative of a disease or pathological condition. Monitoring is considered as a kind of treatment provided that the compounds are administered in distinct intervals, e.g. in order to booster the response and eradicate the pathogens and/or symptoms of the disease completely. Either the identical compound or different compounds can be applied. The medicament can also be used to reducing the likelihood of developing a disorder or even prevent the initiation of disorders associated with OGA activity in advance or to treat the arising and continuing symptoms. The disorders as concerned by the invention are preferably neurodegenerative diseases, diabetes, cancer, cardiovascular diseases and stroke.

In the meaning of the invention, prophylactic treatment is advisable if the subject possesses any preconditions for the aforementioned physiological or pathological conditions, such as a familial disposition, a genetic defect, or a previously passed disease.

In the scope of the present invention, compounds of formula (I) are provided for the first time. The low molecular weight compounds of the invention are strong and selective glycosidase inhibitors with improved passive permeability. The compounds of formula (I) have been shown to be competitive with PUGNAc, a known OGA inhibitor that binds in the substrate pocket. The endogenous substrate is an O-GlcNAcylated protein. O-GlcNAcylation of nuclear and cytoplasmic proteins is one of the most common post-translational modifications in animals and plants. O-GlcNAc cycling modulates a number of cellular processes, and evidence is mounting that dysregulation of O-GlcNAcylation plays a role in the etiology of several diseases, including tauopathies and Alzheimer's disease. O-GlcNAc transferase (OGT) and O-GlcNAcase (OGA) are the two enzymes that regulate O-GlcNAc cycling. Emerging data suggest that inhibitors that block OGA may help maintain healthy O-GlcNAc levels in tauopathies and Alzheimer's disease patients and thereby inhibit the formation of neurofibrillary tangles. Hence, the current invention comprises the use of compounds of formula (I) in the regulation, modulation and/or inhibition of the glycosidase signal cascade, which can be advantageously applied as research tool, for diagnosis and/or in treatment of any disorders that are responsive to OGA signaling and inhibition.

The low molecular weight inhibitors can be applied either themselves and/or in combination with physical measurements for diagnostics of treatment effectiveness. Medicaments and pharmaceutical compositions containing said compounds and the use of said compounds to treat glycosidase-mediated conditions is a promising, novel approach for a broad spectrum of therapies causing a direct and immediate improvement in the state of health, whether in man and animal. The impact is of special benefit to efficiently combat tauopathies and Alzheimer's disease, either alone or in combination with other neurodegenerative treatments.

Due to the surprisingly appreciable inhibitory activity on OGA, along with passive permeability, the compounds of the invention can be advantageously administered at lower doses compared to other less potent or selective inhibitors of prior art while still achieving equivalent or even superior desired biological effects. In addition, such a dose reduction advantageously leads to less or even no medicinal adverse effects.

The compounds of formula (I), their salts, isomers, tautomers, enantiomeric forms, diastereomers, racemates, derivatives, prodrugs and/or metabolites are characterized by a high specificity and stability, low manufacturing costs and convenient handling. These features form the basis for a reproducible action, wherein the lack of cross-reactivity is included, and for a reliable and safe interaction with the target structure.

All the references cited herein are incorporated by reference in the disclosure of the invention hereby.

The techniques that are essential according to the invention are described in detail in the specification. Other techniques which are not described in detail correspond to known standard methods that are well known to a person skilled in the art, or the techniques are described in more detail in cited references, patent applications or standard literature. Although methods and materials similar or equivalent to those described herein can be used in the practice or testing of the present invention, suitable examples are described below. The following examples are provided by way of illustration and not by way of limitation. Within the examples, standard reagents and buffers that are free from contaminating activities (whenever practical) are used. The examples are particularly to be construed such that they are not limited to the explicitly demonstrated combinations of features, but the exemplified features may be unrestrictedly combined again provided that the technical problem of the invention is solved. Similarly, the features of any claim can be combined with the features of one or more other claims.

EXPERIMENTAL PART

The compounds according to Formula (I) can be prepared from readily available starting materials by several synthetic approaches, using both solution-phase and solid-phase chemistry protocols or mixed solution and solid phase protocols. Examples of synthetic pathways are described below in the examples. All reported yields are non optimized yields. Unless otherwise stated, compounds of Formula (I) and related formulae obtained as a racemic mixture can be separated to provide an enantiomerically enriched mixture or a pure enantiomer.

The commercially available starting materials used in the following experimental description were purchased from Aldrich, Sigma, ACROS, ABCR, Combi-Blocks, Matrix, Apollo scientific, Alfa Aesar, etc. unless otherwise reported.

The HPLC, MS and NMR data provided in the examples described below are obtained as followed:

$^1$H NMR analyses were carried out using BRUKER NMR, model AV-II and AV-III 400 MHz FT-NMR. Residual signal of deuterated solvent was used as internal reference. Chemical shifts ($\delta$) are reported in ppm in relative to the residual solvent signal ($\delta$=2.50 for $^1$H NMR in DMSO-$d_6$, and 7.26 in CDCl$_3$). s (singlet), d (doublet), t (triplet), q (quadruplet), br (broad), quint (quintuplet).

The MS data provided in the examples described below were obtained as followed: Mass spectrum: LC/MS Agilent (ESI/APCI), Chemstration, 1200 Series.

LCMS Methods:
LCMS Method A
Method: A—0.1% TFA in H$_2$O, B—0.1% TFA in ACN: Flow—2.0 mL/min.
Column: XBridge C8 (50×4.6 mm, 3.5 μm+ve mode
LCMS Method B
Method: A—10 mM NH$_4$HCO$_3$ in H$_2$O, B—ACN: Flow—1.0 mL/min.
Column: XBridge C8 (50×4.6 mm, 3.5 μm), −ve mode
LCMS Method C
Method: A—10 mM NH$_4$HCO$_3$ in H$_2$O, B—ACN: Flow—1.0 mL/min.
Column: XBridge C8 (50×4.6 mm, 3.5 μm), −ve mode
HPLC analyses were obtained using Agilent 1200 Series instruments as followed using % with UV detection (maxplot).
HPLC Method A
Method: A—0.1% TFA in H$_2$O, B—0.1% TFA in ACN: Flow—2.0 mL/min.
Column: XBridge C8 (50×4.6 mm, 3.5 μm).

HPLC Method B
Method: A—10 mM NH$_4$HCO$_3$ in H$_2$O, B—ACN: Flow—1.0 mL/min.
Column: XBridge C8 (50×4.6 mm, 3.5 μm).

The chiral HPLC methods described below may preferably be performed on an Agilent 1260 DAD instrument.

Chiral HPLC (Method A):
Mobile Phase: 0.1% DEA in n-HEXANE:IPA: 60:40; COLUMN: CHIRALPAK AD-H (250×4.6) mm, 5 μm, FLOW: 1.0 mL/min Chiral HPLC (Method B):
Mobile Phase: n-HEXANE:EtOH: 90:10; COLUMN: CHIRALPAK IC (250×4.6) mm, 5 μm; FLOW: 1.0 mL\min;

Chiral HPLC (Method C):
Mobile Phase: 0.1% TFA in n-HEXANE:IPA: 60:40; COLUMN: CHIRALcell OD-H (250×4.6) mm, 5 μm, FLOW: 1.0 mL/min Chiral HPLC (Method D):
Mobile Phase: 0.1% DEA in Hexane:EtOH: 80:20; COLUMN: Chiralcell OJ-H column (250×4.6) mm, 5 μm; FLOW: 1.0 mL\min Chiral HPLC (Method P):
Mobile Phase: 0.1% TFA in n-Hexane:EtOH: 60:40; COLUMN: CHIRALPAK AD-H (250×4.6) mm, 5 μm; FLOW: 1.0 mL\min Chiral HPLC (Method R):
Mobile Phase: 0.1% DEA in Hexane:IPA: 80:20; COLUMN: Chiralcell OJ-H column (250×4.6) mm, 5 μm; FLOW: 12.0 mL\min MD Autoprep HPLC Conditions
The mass directed preparative HPLC purifications were performed with a mass directed autopurification Fractionlynx from Waters.

MD Autoprep HPLC Method A
0.1% HCOOH in H$_2$O, B-MeOH or ACN, Column: Symmetry C8 (300 mm×19 mm), 7 μm MD Autoprep HPLC Method B
0.1% TFA in H$_2$O, B-MeOH or ACN, Column: Symmetry C8 (300 mm×19 mm), 7 μm MD Autoprep HPLC Method C
10 mM NH$_4$HCO$_3$ in H$_2$O, B-MeOH or ACN, Column: Symmetry C8 (300 mm×19 mm), 7 μm MD Autoprep HPLC Method D
10 mM NH$_4$OAc in H$_2$O, B-MeOH or ACN, Column: Symmetry C8 (300 mm×19 mm), 7 μm Prep-HPLC Conditions
Mobile phase: A—10 mM NH$_4$HCO$_3$ in H$_2$O, B-MeOH or ACN, Column: Sunfire C8 (19 mm×250 mm) 5 μm or Sunfire C18 (30 mm×250 mm) 10 μm.

The chiral HPLC SFC analysis may preferably be performed on a THAR SFC AMDS Instrument.

Chiral HPLC SFC Method A
COLUMN: YMC Cellulose SB (250×4.6) mm, 5 μm; CO-SOLVENTS: 0.5% DEA in Methanol; FLOW: 10 mL/min Chiral HPLC SFC Method B:
COLUMN: Lux C2 (250×4.6) mm, 5 μm; CO-SOLVENTS: 20 mM Ammonia in Methanol FLOW: 10 mL/min Chiral HPLC SFC Method C:
COLUMN: YMC Cellulose C (250×4.6) mm, 5 μm; CO-SOLVENTS: 20 mM Ammonia in Methanol; FLOW: 10 mL/min Chiral HPLC SFC Method D:
COLUMN: YMC Amylose SA (250×4.6) mm, 5 μm; CO-SOLVENTS: 20 mM Ammonia in IPA; FLOW: 10 mL/min Chiral HPLC SFC Method E:
COLUMN: YMC Amylose SA (250×4.6) mm, 5 μm; CO-SOLVENTS: 20 mM Ammonia in MeOH; FLOW: 3 mL/min Chiral HPLC SFC Method F:
COLUMN: Lux C3 (250×4.6) mm, 5 μm; CO-SOLVENTS: 20 mM Ammonia in Methanol; FLOW: 4 mL/min;

Chiral HPLC SFC Method G:
COLUMN: YMC Cellulose SB (250×4.6) mm, 5 μm; CO-SOLVENTS: 20 mM Ammonia in MeOH; FLOW: 4 mL/min Chiral HPLC SFC Method H:
COLUMN: Chiralpak ADH (250×4.6) mm, 5 μm; CO-SOLVENTS: 20 mM Ammonia in IPA; FLOW: 4 mL/min Chiral HPLC SFC Method I:
COLUMN: Lux A1 (250×4.6) mm, 5 μm; CO-SOLVENTS: 20 mM Ammonia in IPA; FLOW: 4 mL/min;

Chiral HPLC SFC Method J:
COLUMN: YMC Cellulose SB (250×4.6) mm 5 μm; CO-SOLVENTS: 0.5% DEA in Methanol FLOW: 5 mL/min Chiral HPLC SFC Method K:
COLUMN: YMC Cellulose SB (250×4.6) mm, 5 μm; CO-SOLVENTS: 0.5% DEA in Methanol 40%; FLOW: 4 mL/min;

The SFC purifications were performed with a Prep SFC, THAR-SFC 80 and THAR-SFC 200.

SFC Preparative Chiral Method PA:
COLUMN: YMC Cellulose SB (250×30) mm, 5 μm; CO-SOLVENTS: 0.5% DEA in Methanol 40%; FLOW: 60 mL/min;

The microwave chemistry was performed on a single mode microwave reactor Initiator™ Sixty from Biotage.

General flash chromatography conditions used for the purification of intermediates or compounds of Formula I: silica gel 230-400 mesh; gradients used as eluent: 10 to 80% EtOAc in petroleum ether or 1 to 15% MeOH in DCM Intermediate 1: 6-(1-chloroethyl)quinoxaline

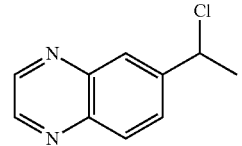

Step 1: 1-(quinoxalin-6-yl)ethan-1-one

6-Bromo quinoxaline (2.0 g, 9.5 mmol) in toluene (20 mL) was degassed for 30 min. To this solution, 1-ethoxy vinyl tributyltin (3.8 g, 10.5 mmol) and bis(triphenylphosphine)palladium dichloride (0.67 g, 0.95 mmol) were added at rt and stirred for 16 hours at 90° C. The reaction mixture was cooled to rt and filtered through celite. After evaporation of the solvent, 6 N HCl solution in water (20 mL) was added and the mixture was stirred for 1 hour at rt. It was concentrated and neutralized with sat. NaHCO$_3$. The desired product was extracted with DCM (100 mL), dried over Na$_2$SO$_4$ and concentrated. The crude product was purified by column chromatography to afford the title compound (brown solid).
$^1$H NMR (400 MHz, DMSO-d$_6$): δ 9.06-9.04 (m, 2H), 8.70 (d, J=2.4 Hz, 1H), 8.28 (t, J=2.8 Hz, 1H), 8.16 (d, J=11.6 Hz, 1H), 2.97 (s, 3H). LCMS: (Method A) 173 (M+H), Rt. 2.25 min, 99.06% (Max).

Step 2: 1-(quinoxalin-6-yl)ethan-1-ol

To a stirred solution of 1-(quinoxalin-6-yl)ethan-1-one (0.8 g, 4.65 mmol) in dry MeOH (20 mL), sodium borohydride (0.36 g, 9.3 mmol) was added portion wise at 0° C. and the resulting mixture was stirred for 1 h. It was then concentrated, diluted with DCM (80 mL), washed with water (20 mL), dried over $Na_2SO_4$ and concentrated. The crude product was taken for next step without further purification. Yield: 75% (600 mg, dark brown liquid). $^1$H NMR (400 MHz, DMSO-$d_6$): δ 8.91-8.89 (m, 2H), 8.03 (t, J=11.6 Hz, 2H), 7.87-7.86 (m, 1H), 5.49 (d, J=5.9 Hz, 1H), 4.97 (t, J=6.2 Hz, 1H), 1.42 (d, J=8.6 Hz, 3H). LCMS: (Method A) 175.0 (M+H), Rt. 1.89 min, 95.0% (Max).

Step 3: 6-(1-chloroethyl)quinoxaline

To a stirred solution of 1-(quinoxalin-6-yl)ethan-1-ol (0.6 g, 3.46 mmol) in dry DCM (10 mL), thionyl chloride (0.5 mL, 6.93 mmol) was added dropwise at 0° C. and stirred at rt for 1 hour. The reaction mixture was evaporated to dryness and was used without further purification. Yield: 97% (650 mg, off white solid). $^1$H NMR (400 MHz, DMSO-$d_6$): δ 8.74 (s, 2H), 7.93 (s, 1H), 7.70-7.68 (m, 2H), 4.46-4.23 (m, 1H), 1.87 (s, 3H). LCMS: (Method A) 193 (M+H), Rt. 3.41 min, 71.4% (Max).

Intermediate 2: 6-(1-(piperazin-1-yl)ethyl)quinoxaline hydrochloride

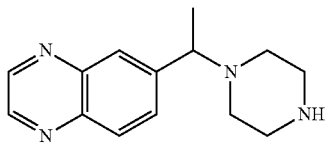 [SMILES: CC(c1ccc2nccnc2c1)N1CCNCC1]

Step 1: tert-butyl 4-(1-(quinoxalin-6-yl) ethyl) piperazine-1-carboxylate

To a stirred solution of 1-boc piperazine (3.8 g, 20.83 mmol) in dry DMF (40 mL), TEA (8.7 mL, 62.4 mmol) and Intermediate 6 (4 g, 20.83 mmol) were added at rt and the reaction mixture was stirred overnight at 90° C. The reaction mixture was cooled to rt and concentrated under vacuum. To this crude mixture, water (50 mL) was added and the product was extracted with DCM (150 mL). Organic layer was dried over anhydrous $Na_2SO_4$ and concentrated to get the crude product. The crude product was purified by column chromatography to afford the title compound (brown solid). LCMS: (Method A) 343.2 (M+H), Rt. 2.59 min, 75.3% (Max).

Step 2: 6-(1-(piperazin-1-yl) ethyl) quinoxaline hydrochloride

To a solution of tert-butyl 4-(1-(quinoxalin-6-yl) ethyl) piperazine-1-carboxylate (3.5 g, 10.23 mmol) in methanol (5 mL), dioxane HCl (35 mL, 10 V) was added at rt and the reaction mixture was stirred at for 2 h. The reaction mixture was concentrated under reduced pressure and then triturated with diethyl ether (15 mL) to afford the title compound. Yield: 87% (2.1 g, brown solid). $^1$H NMR (400 MHz, DMSO-$d_6$): 8.94 (d, J=6.0 Hz, 2H), 8.09 (d, J=8.8 Hz, 1H), 8.01 (s, 1H), 7.88 (d, J=8.8 Hz, 1H), 3.85 (d, J=6.8 Hz, 1H), 3.54 (t, J=5.2 Hz, 2H), 3.16 (d, J=3.6 Hz, 2H), 3.06-2.96 (m, 1H), 2.92-3.02 (m, 1H), 2.67 (s, 2H), 2.55-2.58 (m, 2H), 1.42 (d, J=6.8 Hz, 3H). LCMS: (Method A) 243.3 (M+H), Rt. 1.36 min, 95.02% (Max).

Intermediate 3: 5-(1-chloroethyl)benzo[d]thiazole

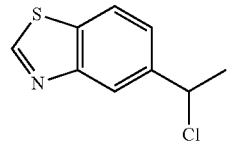

Step 1: 1-(benzo[d]thiazol-5-yl)ethan-1-one

The title compound was prepared according to the procedure described for Intermediate 6, Step 1, using 5-bromobenzo[d]thiazole (3 g, 14 mmol) as starting material. The crude product was purified by column chromatography to give the title compound. Yield: 64.5% (1.6 g, pale yellow solid). LCMS: (Method A) 178.0 (M+H), Rt. 2.61 min, 81.8% (Max).

Step 2: 1-(benzo[d]thiazol-5-yl)ethan-1-ol

To a stirred solution of 1-(benzo[d]thiazol-5-yl)ethan-1-one (1.6 g, 9.0 mmol) in methanol (20 mL), sodium borohydride (683 mg, 18 mmol) was added slowly at 0° C. and stirred 1.5 h. The completion of the reaction was monitored by TLC and the solvents were evaporated at 45° C. under vacuum. The residue was diluted with EtOAc (50 mL) and washed with water (50 mL), brine solution (50 mL) and dried over $Na_2SO_4$. The organic layer was evaporated at 40° C. to give the title compound. Yield: 91.9% (1.49 g, pale brown solid). LCMS: (Method A) 180.0 (M+H), Rt. 2.35 min, 92.8% (Max).

Step 3: 5-(1-chloroethyl)benzo[d]thiazole

The title was synthesized from 1-(benzo[d]thiazol-5-yl)ethan-1-ol (1.49 g, 8.3 mmol), according the general procedure B. The crude product was used in the next step without further purification. Yield: quantitative (1.64 g, pale yellow solid). $^1$H NMR (400 MHz, DMSO-$d_6$): δ 9.43 (s, 1H), 8.19-8.17 (m, 2H), 7.63-7.61 (m, 1H), 5.57-5.52 (m, 1H), 1.87 (d, J=6.7 Hz, 3H). LCMS: (Method A) 198.0 (M+H), Rt. 3.98 min, 62.0% (Max).

Intermediate 4: 6-(1-chloroethyl)-2,3-dihydrobenzofuran

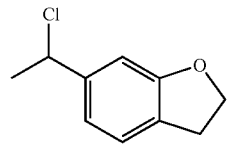

Step 1: 2-(2,5-dibromophenoxy)ethan-1-ol

To a stirred solution of 1,4-dibromo-2-fluorobenzene (100 g, 395.2 mmol) in ethylene glycol (510 mL), NMP (50 mL)

was added at rt under $N_2$ atmosphere. Then tBuOK (155.2 g, 1383.0 mmol) was added slowly over 10 min at 10° C. The reaction mixture was heated at 100° C. for 12 h. The completion of the reaction was monitored by TLC. The reaction mixture was cooled to rt and diluted with water (200 mL) and stirred for 15 min at rt. The resulting solid was filtered and washed with ethylene glycol (2×30 mL). Water (2200 mL) was added to the filtrate, the solution was cooled to 15° C. and stirred for 1 h. The resulting precipitate was filtered and washed with water (2×100 mL), pet ether (2×100 mL) and dried. It was further dried with the addition of toluene and its evaporation (3×200 mL). It was then use in the next step without further purification. Yield: 77.5% (90 g, pale brown solid). $^1$H NMR (400 MHz, $CDCl_3$): δ 7.41 (d, J=8.4 Hz, 1H), 7.06 (d, J=2.0 Hz, 1H), 7.02 (dd, J=8.4, 2.4 Hz, 1H), 4.14 (t, J=4.4 Hz, 2H), 4.03-4.00 (m, 2H), 2.36 (t, J=6.4 Hz, 1H).

Step 2: 1, 4-dibromo-2-(2-bromoethoxy)benzene

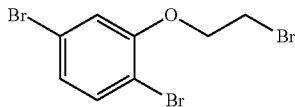 [SMILES: BrCCOc1cc(Br)ccc1Br]

To a stirred solution of 2-(2,5-dibromophenoxy)ethan-1-ol (45 g, 152 mmol) in toluene (315 mL) under inert atmosphere, $PBr_3$ (18.47 g, 68.0 mmol) was added slowly at 0° C. The resulting mixture was heated at 90° C. for 2 h. It was cooled to 0° C. and $PBr_3$ (8.2 g, 30.0 mmol) and water (0.9 mL) were added slowly and the heating was continued at 90° C. for 8 h. Completion of the reaction was monitored by TLC. The reaction mixture was cooled to 10° C. and quenched with 1N NaOH solution (270 mL). The organic phase was separated and was washed with water (150 mL), brine (150 mL), dried over $Na_2SO_4$ and evaporated at 45° C. under vacuum to give the title compound. Yield: 90.8% (99 g, off white solid). $^1$H NMR (400 MHz, $CDCl_3$): δ 7.43 (d, J=8.8 Hz, 1H), 7.05-7.02 (m, 2H), 4.34 (t, J=6.4 Hz, 2H), 3.70 (t, J=6.4 Hz, 2H).

Step 3: 2, 3-dihydrobenzofuran-6-carbaldehyde

To a stirred solution of 1,4-dibromo-2-(2-bromoethoxy) benzene (99 g, 275.9 mmol) in dry THF (990 mL) under inert atmosphere and cooled down to −78° C., n-butyl lithium (189 mL, 303.5 mmol, 1.6 M in hexane) was added slowly over 30 min. After 1 h, the same amount of n-butyl lithium (189 mL, 303.5 mmol, 1.6 M in hexane) was added slowly over 30 min at −78° C. The reaction mixture was stirred 1 h at −78° C. DMF (40.3 g, 551.8 mmol) was then added slowly and the temperature was maintained 45 min at −78° C. Reaction mixture was then warmed to 10° C. and quenched with a saturated solution of $NH_4Cl$ (450 mL). The reaction mixture was extracted with EtOAc (2×200 mL). The combined organic layer was washed with water (200 mL), brine solution (200 mL), dried over $Na_2SO_4$ and evaporated at 40° C. under reduced pressure to give the title compound. Yield: crude (40.8 g, Pale brown solid). $^1$H NMR (400 MHz, $CDCl_3$): δ 9.93 (s, 1H), 7.41-7.39 (m, 2H), 7.28-7.27 (m, 1H), 4.66 (t, J=8.8 Hz, 2H), 3.30 (t, J=8.8 Hz, 2H).

Step 4: 1-(2,3-dihydrobenzofuran-6-yl)ethan-1-ol

To a stirred solution 2,3-dihydrobenzofuran-6-carbaldehyde (30 g, 202 mmol) in dry THF (300 mL) under inert atmosphere, methyl magnesium chloride solution (135 mL, 404 mmol, 3 M in THF) was added slowly over 30 min at 0° C. The reaction mixture was stirred for 2 h at the same temperature. Completion of the reaction was monitored by TLC. Reaction mixture was quenched by using a saturated solution of $NH_4Cl$ (250 mL) and extracted with EtOAc (2×100 mL). The combined organic layer was washed with water (100 mL), brine (100 mL), dried over $Na_2SO_4$ and evaporated at 40° C. under reduced pressure. The resulting crude product was purified by flash chromatography (22% EtOAc in pet ether) to give the title compound. Yield: 58.6% (19.5 g, Pale Yellow liquid). $^1$H NMR (300 MHz, $CDCl_3$): δ 7.18 (d, J=7.5 Hz, 1H), 6.87 (dd, J=9.4, 1.2 Hz, 2H), 4.89-4.83 (m, 1H), 4.59 (t, J=8.7 Hz, 2H), 3.21 (t, J=8.7 Hz, 2H), 1.51-1.50 (m, 3H). LCMS: (Method A) 147.2 (M+H-$H_2O$), Rt. 2.63 min, 94.7% (Max). HPLC: (Method A) Rt 2.61 min, 96.5% (Max).

Step 5: 6-(1-chloroethyl)-2, 3-dihydrobenzofuran

To a stirred solution of 1-(2,3-dihydrobenzofuran-6-yl) ethan-1-ol (9 g, 54.0 mmol) in DCM (180 mL), $SOCl_2$ (19.4 g, 165 mmol) was added at 0° C. The reaction mixture was stirred at rt for 1 h. Completion of the reaction was monitored by TLC. The reaction mixture was concentrated under reduced pressure at 40° C. The resulting crude mixture was dissolved in DCM and evaporated two times (2×100 mL) and dried at 40° C. under reduced pressure to give the title compound. Yield: crude (100%) (9.98 g, dark brown liquid). $^1$H NMR (400 MHz, $CDCl_3$): δ 7.16 (d, J=7.6 Hz, 1H), 6.92-6.88 (m, 2H), 5.06 (q, J=6.8 Hz, 1H), 4.59 (t, J=8.8 Hz, 2H), 3.21 (t, J=8.8 Hz, 2H), 1.84 (d, J=6.8 Hz, 3H).

Intermediate 5: N-(5-(piperazin-1-yl)-1,3,4-thiadiazol-2-yl)acetamide hydrochloride

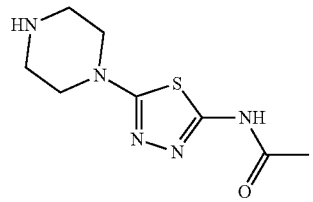

Step 1: tert-Butyl 4-(5-amino-1,3,4-thiadiazol-2-yl) piperazine-1-carboxylate

To a stirred solution of 2-amino 5-bromo-1, 3, 4-thiadiazole (10.0 g, 55.5 mmol) in dry DMF (100 mL), $K_2CO_3$ (15.3 g, 111.1 mmol) and 1-boc piperazine (12.4 g, 66.65 mmol) were added at 0° C. The reaction mixture was stirred overnight at 80° C. The reaction mixture was concentrated under vacuum. To the resulting crude solids, DCM (200 mL) was added. The DCM layer was washed with water (100 mL), brine (100 mL) and, dried over anhydrous $Na_2SO_4$ and concentrated. The crude product was purified by silica gel column chromatography to afford the title compound. Yield: 76% (12 g, pale brown solid). $^1$H NMR (400 MHz, DMSO-$d_6$): δ 6.51 (s, 2H), 3.39 (d, J=6.9 Hz, 4H), 3.19 (d, J=7.7 Hz, 4H), 1.39 (s, 9H). LCMS: (Method A) 286.1 (M+H), Rt. 2.71 min, 97.6% (Max).

Step 2: tert-Butyl 4-(5-acetamido-1,3,4-thiadiazol-2-yl)piperazine-1-carboxylate To a stirred solution of tert-butyl 4-(5-amino-1,3,4-thiadiazol-2-yl)piperazine-1-carboxylate (12.0 g, 42.09 mmol) in pyridine (120 mL), acetic anhydride (5.1 g, 50.5 mmol) was added at 0° C. The reaction mixture was stirred overnight at 50° C. The reaction mixture was concentrated under vacuum and triturated with diethyl ether (100 mL). The solid obtained was filtered, washed with diethyl ether (20 mL), dried and taken for next step without any further purification. Yield: 87% (12 g, off white solid). $^1$H NMR (400 MHz, DMSO-$d_6$): δ 12.07 (br.s, 1H), 3.45-3.34 (m, 8H), 2.11 (s, 3H), 1.42 (s, 9H). LCMS: (Method A) 328.0 (M+H), Rt. 3.11 min, 86.3% (Max).

Step 3: N-(5-(Piperazin-1-yl)-1,3,4-thiadiazol-2-yl)acetamide hydrochloride

To a stirred solution of tert-butyl 4-(5-acetamido-1,3,4-thiadiazol-2-yl)piperazine-1-carboxylate (12.0 g) in dry dioxane (100 mL), HCl in dioxane (100 mL, 4 N) was added and the reaction mixture was stirred at rt for 3 h. The reaction mixture was concentrated under vacuum and the resulting crude product was suspended diethyl ether (50 mL). The title compound was obtained after evaporation of the solvent. Yield: 93% (9 g, white solid). $^1$H NMR (400 MHz, DMSO-$d_6$): δ 12.07 (br. s, 1H), 3.67 (s, 4H), 3.21 (s, 4H), 2.13 (s, 3H). LCMS: (Method A) 228.0 (M+H), Rt. 0.71 min, 85.3% (Max).

Intermediate 6: 2-(piperazin-1-yl)-6,7-dihydrothiazolo[5,4-c]pyridin-4(5H)-one dihydrochloride

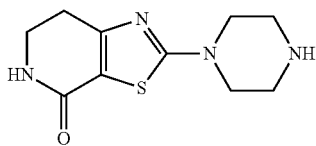 [SMILES: O=C1NCCc2nc(N3CCNCC3)sc21]

Step 1: tert-butyl 3-bromo-2,4-dioxopiperidine-1-carboxylate

To a stirred solution of tert-butyl 2,4-dioxopiperidine-1-carboxylate (1 g, 4.69 mmol) in dry CCl$_4$ (10 mL), N-bromosuccinimide (0.83 g, 4.69 mmol) was added at 10° C. The reaction mixture was stirred at 10-15° C. for 2 h. It was then evaporated under reduced pressure. Water (10 mL) was added and the desired product was extracted with EtOAc (2×30 mL). The combined organic layer was dried over Na$_2$SO$_4$ and concentrated. The resulting crude product was purified by column chromatography, affording the title product. Yield: 99% (1.4 g, off white solid). $^1$H NMR (400 MHz, DMSO-$d_6$): δ 5.50 (s, 1H), 3.74-3.71 (m, 2H), 2.69-2.66 (m, 2H), 1.46 (s, 9H). LCMS: (Method A) 193.8 (M-Boc+H), Rt. 2.93 min, 81.51% (Max).

Step 2: tert-butyl-2-(4-(tert-butoxycarbonyl)piperazin-1-yl)-4-oxo-6,7-dihydrothiazolo[5,4-c]pyridine-5(4H)-carboxylate To a stirred solution of tert-butyl 4-carbamothioylpiperazine-1-carboxylate (synthesized according to Example 5, Step 1, 1.31 g, 5.36 mmol) in isopropanol (15 mL), tert-butyl 3-bromo-2,4-dioxopiperidine-1-carboxylate obtained in the first step (1.3 g, 4.46 mmol) was added at rt. The reaction mixture was stirred overnight at 90° C. It was cooled down to rt and evaporated under reduced pressure. Water (10 mL) was added and the desired product was extracted with diethyl ether (2×30 mL), dried over Na$_2$SO$_4$ and concentrated, affording the title product. Yield: 74% (1.42 g, yellow solid). LCMS: (Method A) 239.0 (M-Boc+H), Rt. 0.70 min, 48.39% (Max).

Step 3: 2-(piperazin-1-yl)-6,7-dihydrothiazolo[5,4-c]pyridin-4(5H)-one dihydrochloride To a stirred solution of tert-butyl-2-(4-(tert-butoxycarbonyl)piperazin-1-yl)-4-oxo-6,7-dihydrothiazolo[5,4-c]pyridine-5(4H)-carboxylate obtained in previous step (1.3 g, 2.96 mmol) in 1,4-dioxane (10 mL), HCl in dioxane (4 M solution, 13 mL, 10 V) was added at 0° C. The reaction mixture was stirred for 2 h at rt. It was evaporated and the resulting solid was triturated with EtOAc (3×20 mL) to afford titled compound which was used without further purification. Yield: 99% (crude) (2.25 g, white solid). LCMS: (Method A) 239.0 (M+H), Rt. 0.663 min, 82.012% (Max).

Intermediate 7: 7-(1-chloroethyl) imidazo [1,2-a]pyridine

Step 1: 7-bromoimidazo [1, 2-a] pyridine

To a stirred solution of 4-bromopyridin-2-amine (5 g, 28.9 mmol, Molekula Biokem Ltd) in EtOH (50 mL), added sodium bicarbonate (7.28 g, 86.7 mmol) and chloroacetaldehyde (5 mL, 115 mmol) and refluxed for 16 h. The reaction mixture was evaporated under vacuum and water (25 mL) was added to the crude mixture. The resulting solution was extracted with EtOAc (2×50 mL). The organic layer was dried over anhydrous Na$_2$SO$_4$ and concentrated. The resulting crude product was purified by flash chromatography. Yield: 63% (3.6 g, brown solid). LCMS: (Method B) 199.0 (M+H), Rt. 3.92 min, 94.50% (Max).

Step 2: 1-(imidazo [1, 2-a] pyridin-7-yl)ethan-1-one

To a stirred solution of 7-bromoimidazo [1, 2-a] pyridine (3.6 g, 18.7 mmol) in toluene (35 mL), 1-ethoxy vinyl tributyltin (7.3 mL, 20.1 mmol) and bis(triphenylphosphine) palladium chloride (0.64 g, 0.90 mmol) were added under inert atmosphere. The reaction mixture was refluxed at 90° C. for 16 h. It was evaporated under vacuum and 6 N HCl solution (20 mL) was added. The resulting mixture was stirred at rt for 1 h and concentrated under vacuum. It was neutralized with saturated solution of NaHCO$_3$ (20 mL) and was extracted with EtOAc (2×50 mL). The organic layer was dried over anhydrous Na$_2$SO$_4$ and concentrated. The crude product was purified by flash chromatography. Yield: 73% (2.1 g, yellow solid). $^1$H NMR (400 MHz, DMSO-d$_6$): δ 8.62-8.61 (m, 1H), 8.34 (d, J=0.8 Hz, 1H), 8.14 (d, J=0.8 Hz, 1H), 7.81 (s, 1H), 7.32-7.31 (m, 1H), 2.65 (s, 3H). LCMS: (Method B) 161.0 (M+H), Rt. 3.140 min, 95.59% (Max).

Step 3: 1-(imidazo [1, 2-a] pyridin-7-yl) ethan-1-ol

To a stirred solution of 1-(imidazo [1, 2-a] pyridin-7-yl) ethan-1-one (2.1 g, 13.1 mmol) in MeOH (20 mL), sodium borohydride (0.65 g, 17.0 mmol) was added at 0° C. and the mixture was stirred at rt for 1 h. It was evaporated under vacuum and water (10 mL) was added. The product was extracted with DCM (2×50 mL) and the organic layer was washed with brine (10 mL) and dried over anhydrous Na$_2$SO$_4$. Solvent was evaporated, affording the titled product. Yield: 98% (2 g, brown liquid). $^1$H NMR (400 MHz, DMSO-d6): δ 8.46-8.44 (m, 1H), 7.85 (s, 1H), 7.49 (d, J=1.5 Hz, 1H), 7.41 (d, J=1.0 Hz, 1H), 6.86-6.85 (m, 1H), 5.34 (d, J=5.9 Hz, 1H), 4.73-4.71 (m, 1H), 1.33 (d, J=8.6 Hz, 3H). LCMS: (Method B) 163.2 (M+H), Rt. 2.83 min, 96.00% (Max).

Step 4: 7-(1-chloroethyl) imidazo [1, 2-a] pyridine

To a stirred solution of 1-(imidazo [1, 2-a] pyridin-7-yl) ethan-1-ol (1.1 g, 6.78 mmol) in DCM (10 mL), thionyl chloride was added at 0° C. and the mixture was stirred at rt for 1 h. Volatiles were evaporated under vacuum and the crude product was dissolved in DCM (10 mL). This process was repeated twice to remove any excess of thionyl chloride. Yield: 93% (1.12 g, brown solid). $^1$H NMR (400 MHz, DMSO-d$_6$): δ 8.93 (d, J=9.4 Hz, 1H), 8.36 (d, J=2.5 Hz, 1H), 8.21 (d, J=2.7 Hz, 1H), 8.03 (s, 1H), 7.65-7.63 (m, 1H), 5.63-5.61 (m, 1H), 1.82 (d, J=9.0 Hz, 3H). LCMS: (Method A) 181.0 (M+H), Rt. 1.72 min, 97.41% (Max).

Intermediate 8: 7-(1-(Piperazin-1-yl)ethyl)imidazo [1,2-a]pyridine hydrochloride

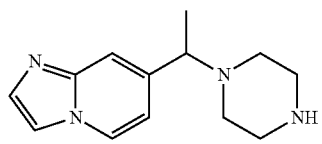 [SMILES: CC(c1ccn2ccnc2c1)N1CCNCC1]

Step 1: tert-butyl4-(1-(imidazo [1, 2-a] pyridin-7-yl) ethyl) piperazine-1-carboxylate To a stirred solution of 1-Boc piperazine (1.1 g, 6.11 mmol) in DMF was added TEA (2.3 mL, 16.6 mmol) and Intermediate 7 (1.0 g, 5.55 mmol) and stirred at 80° C. for 16 h. The reaction mixture was evaporated under vacuum and water (5 mL) was added. The product was extracted with EtOAc (2×25 mL) and the organic layer was dried over anhydrous Na$_2$SO$_4$ and concentrated. The resulting crude product was purified by flash chromatography, affording the title compound (off white solid). $^1$H NMR (400 MHz, CDCl$_3$): δ 8.13 (d, J=7.0 Hz, 1H), 7.66 (s, 1H), 7.60-7.58 (m, 2H), 7.06 (d, J=6.5 Hz, 1H), 3.53-3.51 (m, 5H), 2.54-2.44 (m, 4H), 1.46-1.42 (m, 12H). LCMS: (Method A) 331.2 (M+H), Rt. 1.71 min, 75.51% (Max).

Step 2: 7-(1-(Piperazin-1-yl)ethyl)imidazo[1,2-a] pyridine hydrochloride

To a stirred solution of tert-butyl 4-(1-(imidazo[1,2-a] pyridin-7-yl)ethyl)piperazine-1-carboxylate (0.7 g, 2.12 mmol) in dry dioxane (100 mL), HCl in dioxane (100 mL, 4 N) was added and the reaction mixture was stirred at rt for 3 h. The reaction mixture was concentrated under vacuum and the resulting crude product was suspended in diethyl ether (50 mL). The title compound was obtained after evaporation of the solvent. Yield: 99% (0.47 g, off white solid). LCMS: (Method A) 231.3 (M+H), Rt. 0.49 min, 86.4% (Max).

Intermediate 9: Methyl 6-(piperazin-1-yl) nicotinate hydrochloride

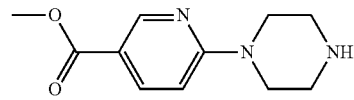 [SMILES: COC(=O)c1ccc(N2CCNCC2)nc1]

Step 1: Tert-butyl 4-(5-(methoxycarbonyl) pyridin-2-yl) piperazine-1-carboxylate A stirred solution of 1-Boc piperazine (9.5 g, 51.28 mmol, Symax fine chemicals) in dry DMF (80 mL), TEA (12.9 mL, 93.24 mmol) and methyl 6-chloronicotinate (8 g, 46.62 mmol, combi block chemicals) were added. The reaction mixture was stirred at 80° C. for 14 h. The resulting reaction mixture was cooled to rt and poured in to water (100 mL). The formed precipitate was filtered to afford the title product. Yield: 96.7% (14.5 g, off white solid). $^1$H NMR (400 MHz, DMSO-d$_6$): δ 8.66 (d, J=2.2 Hz, 1H), 7.97 (dd, J=9.1, 2.4 Hz, 1H), 6.88 (d, J=9.1 Hz, 1H), 3.79 (s, 3H), 3.66 (t, J=4.7 Hz, 4H), 3.43 (t, J=5.2 Hz, 4H), 1.43 (s, 9H). LCMS: (Method A) 322.3 (M+H), Rt. 2.42 min, 99.42% (Max).

Step 2: Methyl 6-(piperazin-1-yl) nicotinate hydrochloride

A stirred solution of tert-butyl 4-(5-(methoxycarbonyl) pyridin-2-yl) piperazine-1-carboxylate (14.5 g, 45.11 mmol) in 1, 4-dioxane (50 mL), HCl in dioxane (4N in dioxane, 145 mL, 10V) was added at rt and the resulting mixture was stirred for 3 h. The white precipitate formed was filtered and washed with diethyl ether (25 mL) and EtOAc (2×20 mL) and dried over Na$_2$SO$_4$ to afford the title product. Yield: 94.6% (11 g, pale brown solid). $^1$H NMR (400 MHz, DMSO-d$_6$): δ 9.29 (br s, 2H), 8.69 (d, J=2.0 Hz, 1H), 8.04 (dd, J=8.8, 2.0 Hz, 1H), 6.99 (d, J=8.8 Hz, 1H), 3.90 (t, J=4.8 Hz, 4H), 3.81 (s, 3H), 3.18 (br s, 4H). LCMS: (Method A) 222.1 (M-35), Rt. 1.40 min, 98.40% (Max).

Intermediate 10: Ethyl 1-(piperidin-4-yl)-1H-pyrazole-4-carboxylate hydrochloride

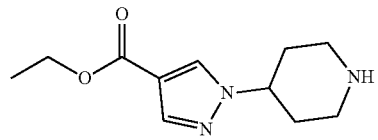 [SMILES: CCOC(=O)c1cnn(C2CCNCC2)c1]

Step 1: Tert-butyl 4-((methylsulfonyl)-oxy) piperidine-1-carboxylate

To a stirred solution of 4-hydroxy N-Boc-piperidine (8.0 g, 39.7 mmol) and TEA (14 mL, 99.3 mmol) in DCM (80 mL), methane sulfonyl chloride (3.6 mL, 47.6 mmol) was added dropwise at 0° C. and the mixture was stirred for 2 h at rt. The completion of the reaction was monitored by TLC. The reaction mixture was quenched with water. The organic layer was washed with water (50 mL) and brine (50 mL), dried over $Na_2SO_4$ and concentrated. The resulting title product was taken for the next step without any further purification. Yield: 85% (9.9 g, pale brown oil). $^1$H NMR (400 MHz, DMSO-$d_6$): δ 4.85-4.81 (m, 1H), 3.64-3.60 (m, 2H), 3.20 (s, 3H), 3.18-3.16 (m, 2H), 1.94-1.89 (m, 2H), 1.64-1.50 (m, 2H), 1.40 (s, 9H). LCMS: (Method A) 180.0 (M-boc), Rt. 2.63 min, 99.8% (ELSD).

Step 2: Tert-butyl 4-(4-(ethoxycarbonyl)-1H-pyrazol-1-yl) piperidine-1-carboxylate

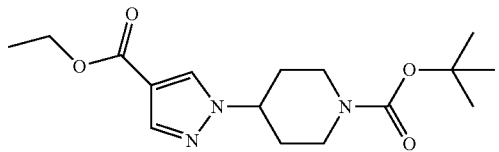 [SMILES: CCOC(=O)c1cnn(C2CCN(C(=O)OC(C)(C)C)CC2)c1]

To a stirred solution of ethyl-1-H pyrazole carboxylate (5.0 g, 3.7 mmol) in DMF (50 mL), $Cs_2CO_3$ (23 g, 71.35 mmol) and tert-butyl 4-((methylsulfonyl)-oxy) piperidine-1-carboxylate (9.9 g, 35.6 mmol) were added at 5° C. and reaction mixture was stirred at 90° C. overnight. The completion of the reaction was confirmed by TLC. The reaction mixture was poured into ice cold water. The resulting solid was filtered, washed with water (50 mL) and dried under reduced pressure. It was used in the next step without any further purification. Yield:

87% (10 g, off white solid). $^1$H NMR (400 MHz, DMSO-$d_6$): δ 8.39 (s, 1H), 7.87 (s, 1H), 4.45-4.39 (m, 1H), 4.21 (q, J=7.2 Hz, 2H), 4.05-4.02 (m, 2H), 2.01-1.98 (m, 2H), 1.85-1.78 (m, 2H), 1.42 (s, 9H), 1.26 (t, J=7.2 Hz, 3H). LCMS: (Method A) 222.0 (M-Boc), Rt. 2.77 min, 92.86% (Max).

Step 3: Ethyl 1-(piperidin-4-yl)-1H-pyrazole-4-carboxylate hydrochloride

A stirred solution of tert-butyl 4-(4-(ethoxycarbonyl)-1H-pyrazol-1-yl) piperidine-1-carboxylate (10 g, 30.92 mmol) in 1,4-dioxane (50 mL), HCl in dioxane (4 M, 100 mL, 10V) was added and the resulting mixture was stirred at rt for 2 h. The white precipitate formed was filtered and washed with diethyl ether (25 mL) and EtOAc (2×20 mL) to afford the title product. Yield: 92% (7.4 g, off white solid). $^1$H NMR (400 MHz, DMSO-d6): δ 9.12 (br s, 1H), 8.92 (br s, 1H), 8.35 (s, 1H), 7.91 (s, 1H), 4.57-4.52 (m, 1H), 4.21 (q, J=7.2 Hz, 2H), 3.04-2.88 (m, 4H), 2.19-2.13 (m, 4H), 1.25 (t, J=7.2 Hz, 3H).

LCMS: (Method A) 224.2 (M-35), Rt. 1.88 min, 95.2% (Max).

Intermediate 11: N-(1-(piperidin-4-yl)-1H-pyrazol-4-yl)acetamide hydrochloride

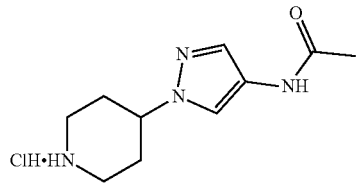

Step 1: tert-butyl 4-(4-nitro-1H-pyrazol-1-yl)piperidine-1-carboxylate

To a stirred solution of 4-nitro-1H-pyrazole (2.0 g, 17.7 mmol, combi block) in dry MeCN (20 mL), potassium carbonate (7.3 g, 53.4 mmol) and tert-butyl 4-((methylsulfonyl)-oxy) piperidine-1-carboxylate (obtained as described in Step 1 of Intermediate 10, 4.9 g, 17.6 mmol) were added at 0° C. The reaction mixture was stirred overnight at 80° C. The reaction mixture was concentrated under vacuum and DCM (200 mL) was added to the resulting crude solid. The solution was washed with water (100 mL), brine (100 mL), dried over anhydrous $Na_2SO_4$ and concentrated. The resulting crude product was purified by flash chromatography to get the titled compound. Yield: 58% (3 g, pale brown solid). $^1$H NMR (400 MHz, DMSO-$d_6$): δ 8.95 (s, 1H), 8.28 (s, 1H), 4.48-4.43 (m, 1H), 4.05-4.02 (m, 2H), 2.89-2.86 (m, 2H), 2.04-2.01 (m, 2H), 1.85-1.75 (m, 2H), 1.41 (s, 9H).

Step 2: tert-butyl 4-(4-amino-1H-pyrazol-1-yl)piperidine-1-carboxylate

To a stirred solution of tert-butyl 4-(4-nitro-1H-pyrazol-1-yl)piperidine-1-carboxylate (2.5 g, 6.7 mmol) in dry MeOH (30 mL), was added 10% palladium on charcoal (250 mg) under nitrogen atmosphere. The reaction was stirred at rt for 3 h under hydrogen atmosphere. The reaction progress was monitored by TLC. After completion of reaction, the reaction mixture was filtered through celite and washed with MeOH. The filtrate was concentrated to get the title compound. Yield: 70% (2 g, brown solid). $^1$H NMR (400 MHz, DMSO-$d_6$): δ 7.06 (s, 1H), 6.91 (s, 1H), 4.16-4.08 (m, 1H), 4.01-3.98 (m, 2H), 3.77 (br s, 2H), 3.21-2.87 (m, 2H), 1.92-1.89 (m, 2H), 1.72-1.41 (m, 2H), 1.40 (s, 9H). LCMS: (Method A) 267.3 (M+H), Rt. 1.98 min, 93.97% (Max).

Step 3: tert-Butyl 4-(4-acetamido-1H-pyrazol-1-yl) piperidine-1-carboxylate

To a stirred solution of tert-butyl 4-(4-amino-1H-pyrazol-1-yl)piperidine-1-carboxylate (1.6 g, 6.0 mmol) in DCM, N-methyl morpholin (0.72 mL, 6.6 mmol) and acetic anhydride (0.56 mL, 6.0 mmol) were added at 0° C. The reaction mixture was stirred at rt for 2 h. The reaction mixture was concentrated under vacuum and triturated with diethyl ether (10 mL). The resulting solid was filtered, washed with hexane (20 mL), dried and taken for next step without any further purification. Yield: 91.7% (1.7 g, brown solid). $^1$H NMR (400 MHz, DMSO-$d_6$): δ 9.90 (s, 1H), 7.87 (s, 1H), 7.40 (s, 1H), 4.32-4.27 (m, 1H), 4.03-4.00 (m, 2H), 3.21-2.87 (m, 2H), 1.96 (s, 3H), 1.95-1.91 (m, 2H), 1.75-1.71 (m, 2H), 1.42 (s, 9H). LCMS: (Method A) 309.2 (M+H), Rt. 3.01 min, 96.36% (Max).

Step 4: N-(1-(piperidin-4-yl)-1H-pyrazol-4-yl)acetamide hydrochloride

To a stirred solution of tert-butyl 4-(4-acetamido-1H-pyrazol-1-yl)piperidine-1-carboxylate (1.7 g) in dry dioxane (10 mL), HCl in dioxane (17 mL, 4 N) was added and the reaction mixture was stirred at rt for 3 h. The reaction mixture was concentrated under vacuum and the resulting crude product was triturated in diethyl ether (20 mL) and dried under vacuum, affording the title product. Yield: 94.2% (1.2 g, off white solid). $^1$H NMR (400 MHz, DMSO-d$_6$): δ 10.10 (s, 1H), 9.32 (br s, 1H), 7.88 (s, 1H), 7.43 (s, 1H), 4.46-4.42 (m, 1H), 3.36-3.32 (m, 2H), 3.05-3.01 (m, 2H), 2.15-2.10 (m, 4H), 1.97 (s, 3H). LCMS: (Method B) 209.2 (M+H), Rt. 1.33 min, 98.71% (Max).

Intermediate 12: Methyl 2-(piperazin-1-yl)pyrimidine-5-carboxylate hydrochloride

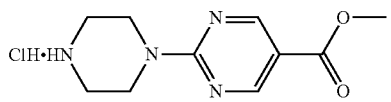

Step 1: 5-(4-(1-(imidazo[1,2-a]pyridin-7-yl)ethyl)piperazin-1-yl)-1,3,4-thiadiazol-2-amine To a stirred solution of methyl 2-chloropyrimidine-5-carboxylate (5 g, 28.97 mmol) in dry DMF (60 mL), TEA (12.09 mL, 86.92 mmol) and tert-butyl piperazine-1-carboxylate (5.93 g, 31.87 mmol) were added at 0° C. The reaction mixture was heated at 100° C. overnight. It was concentrated to half of the volume and filtered. The resulting solid was dissolved in DCM (35 mL) and washed with water (20 mL), dried over Na$_2$SO$_4$ and concentrated affording the title product. Yield: 70% (7 g, off white solid). $^1$H NMR (400 MHz, DMSO-d$_6$): δ 8.81 (s, 2H), 3.84 (t, J=4.8 Hz, 4H), 8.80 (s, 3H), 3.48-3.38 (m, 4H), 1.42 (s, 9H). LCMS: (Method A) 323.3 (M+H), Rt. 4.31 min, 99.89% (Max).

Step 2: Methyl 2-(piperazin-1-yl)pyrimidine-5-carboxylate hydrochloride

To a stirred solution of 5-(4-(1-(imidazo[1,2-a]pyridin-7-yl)ethyl)piperazin-1-yl)-1,3,4-thiadiazol-2-amine (6.9 g, 21.42 mmol) in dry dioxane (30 mL), HCl in dioxane (50 mL, 4 N) was added and the reaction mixture was stirred at rt for 3 h. The reaction mixture was concentrated under vacuum and the resulting crude product was suspended diethyl ether (50 mL). The title compound was obtained after evaporation of the solvent. Yield: 98% (4.7 g, off white solid). LCMS: (Method A) 223.3 (M-Boc), Rt. 1.62 min, 99.83% (Max).

Intermediate 13: 1-(1-(2,3-dihydrobenzofuran-6-yl)ethyl)piperazine dihydrochloride

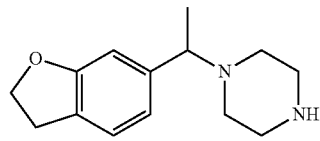 [SMILES: CC(c1ccc2c(c1)OCC2)N1CCNCC1]

Step 1: tert-butyl 4-(1-(2,3-dihydrobenzofuran-6-yl)ethyl)piperazine-1-carboxylate To a stirred solution of N-boc piperazine (5.5 g, 29.5 mmol), TEA (11.9 g, 11.8 mmol) in DMF (55 mL), Intermediate 4 (7.5 g, 41.3 mmol) was added at rt and the resulting mixture was heated at 70° C. overnight. Completion of the reaction was monitored by TLC. The reaction mixture was concentrated under reduced pressure and the resulting crude mixture was dissolved in EtOAc (100 mL). The organic layer was washed with water (50 mL), brine (50 mL), dried over Na$_2$SO$_4$ and concentrated. The crude product was purified by flash chromatography (12% EtOAc in pet ether as eluent) to give the title compound. Yield: 52% (58% purity) (5.1 g, brown thick oil). $^1$H NMR (400 MHz, CDCl$_3$): δ 7.19-7.12 (m, 1H), 6.88-6.77 (m, 2H), 4.62-4.59 (m, 2H), 3.42-3.39 (m, 4H), 3.36-3.31 (m, 1H), 3.23-3.18 (m, 2H), 2.44-2.34 (m, 4H), 1.46 (s, 9H), 1.35 (d, J=6.4 Hz, 3H). LCMS: (Method A) 333.3 (M+H), Rt. 3.12 min, 58.09% (Max).

Step 2: 1-(1-(2,3-dihydrobenzofuran-6-yl)ethyl)piperazine dihydrochloride

To a stirred solution of tert-butyl 4-(1-(2,3-dihydrobenzofuran-6-yl)ethyl)piperazine-1-carboxylate (5.1 g, 15.3 mmol) in 1,4 dioxane (25 mL), HCl solution in dioxane (4 M, 10 V) was added at 0° C. The resulting mixture was stirred at rt for 2 h. Completion of the reaction was monitored by TLC. The reaction mixture was evaporated at 40° C. under reduced pressure. The resulting product was triturated with n-hexanes (2×100 mL) and decanted two times. It was then dried at 40° C. under reduced pressure to give the title compound. Yield: 66.2% (3.1 g, Off white solid). $^1$H NMR (400 MHz, DMSO-d6): δ 7.15 (d, J=7.2 Hz, 1H), 6.76-6.71 (m, 2H), 4.36-4.30 (m, 2H), 3.55-3.53 (m, 4H), 3.43-3.41 (m, 1H), 3.15-3.11 (m, 2H), 2.53-2.43 (m, 4H), 1.31-1.29 (m, 3H). LCMS: (Method A) 233.2 (M+H), Rt. 1.67 min, 90.31% (Max).

Intermediate 14: 5-bromo-2-(piperazin-1-yl)pyrimidine hydrochloride

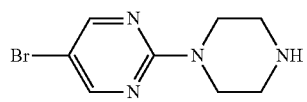 [SMILES: Brc1cnc(N2CCNCC2)nc1]

Step 1: Tert-butyl-4-(5-bromopyrimidin-2-yl) piperazine-1-carboxylate

To a stirred solution of 1-boc piperazine (10.42 g, 56.86 mmol, Symax fine chemicals) in dry DMF (100 mL), TEA (14.43 mL, 103.39 mmol) and 5-bromo-2-chloropyrimidine (10 g, 51.69 mmol, Oakwood chemicals) were added at rt and the reaction mixture was stirred at 80° C. for 14 h. The reaction mixture was cooled to rt and poured into water (100 mL). The formed precipitate was filtered and washed with diethyl ether (50 mL) to afford the title product. Yield: 84.5% (15 g, off white solid). $^1$H NMR (400 MHz, DMSO-d$_6$): δ 8.49 (s, 2H), 3.69 (t, J=5.2 Hz, 4H), 3.40 (t, J=5.1 Hz, 4H), 1.42 (s, 9H). LCMS: (Method A) 345.23 (M+2), Rt. 4.92 min, 99.6% (Max).

Step 2: 5-bromo-2-(piperazin-1-yl)pyrimidine hydrochloride

To a stirred solution of tert-butyl-4-(5-bromopyrimidin-2-yl) piperazine-1-carboxylate (15.0 g, 43.7 mmol) in 1,4-dioxane (50 mL), HCl in dioxane (150 mL, 10V, 4N) was added at 0° C. and stirred at rt for 4 h. The resulting white precipitate was filtered and was washed with Et$_2$O (25 mL), EtOAc (2×20 mL) to afford the title product. Yield: 98.2% (12.0 g, off white solid). $^1$H NMR (400 MHz, DMSO-d$_6$): δ 9.40 (br s, 2H), 8.54 (s, 2H), 3.93 (t, J=4.8 Hz, 4H), 3.13 (br s, 4H). LCMS: (Method A) 244.9 (M-35), Rt. 1.71 min, 99.8% (Max).

Intermediate 15: 2-(Piperazin-1-yl)-5-trityl-4,5,6,7-tetrahydrothiazolo[5,4-c]pyridine

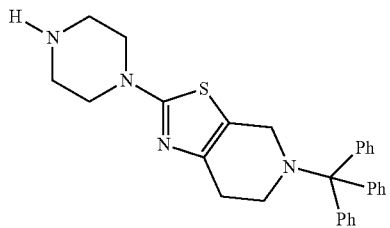 [SMILES: c1ccc(C(c2ccccc2)(c2ccccc2)N2CCc3nc(N4CCNCC4)sc3C2)cc1]

Step 1: Benzyl 4-carbamothioylpiperazine-1-carboxylate

To a stirred solution of 1-Z-piperazine (8.5 g, 38.5 mmol) in dry THF (100 mL), 1,1-thiocarbonyldimidazole (12.37 g, 69.4 mmol) was added and the mixture was stirred at 60° C. for 5 h. It was concentrated under vacuum and NH$_3$ in EtOH (2 N, 300 mL) was added at 0° C. The resulting mixture was stirred at 55° C. for 8 h in an autoclave. It was diluted with water (100 mL) and extracted with DCM (2×100 mL). The DCM layer was washed with water (100 mL), dried over in anhydrous Na$_2$SO$_4$ and concentrated. The resulting crude product was purified by flash chromatography to afford the title product. Yield: 87% (7 g, white solid). $^1$H NMR (400 MHz, DMSO-d$_6$): δ 7.51 (s, 2H), 7.38-7.31 (m, 5H), 5.1 (s, 2H), 3.78 (m, 4H), 3.43-3.33 (m, 4H). LCMS: (Method A) 280.2 (M+H), Rt. 2.33 min, 95.4% (Max).

Step 2: tert-butyl 2-(4-((benzyloxy)carbonyl)piperazin-1-yl)-6,7-dihydrothiazolo[5,4-c]pyridine-5(4H)-carboxylate To a stirred solution of benzyl 4-carbamothioylpiperazine-1-carboxylate (7.0 g, 20.43 mmol) in dry THF (50 mL), triethylamine (5.2 mL, 37.5 mmol) and 3-bromo-4-oxo-piperidine-1-carboxylic acid tert-butyl ester (8.3 g, 30.0 mmol) were added at 0° C. and the mixture was stirred for 8 h at 90° C. The reaction mixture was concentrated under vacuum. DCM (200 mL) was added and the resulting solution was washed with water (100 mL), brine (100 mL), dried over anhydrous Na$_2$SO$_4$ and concentrated. The crude product was purified by flash chromatography to give the title product. Yield: 70% (8 g, White solid). $^1$H NMR (400 MHz, DMSO-d$_6$): δ 7.37-7.31 (m, 5H), 5.1 (s, 2H), 4.37 (s, 2H), 3.59-3.51 (m, 6H), 3.37-3.30 (m, 4H), 1.4 (s, 9H). LCMS: (Method A) 459.2.2 (M+H), Rt. 2.65 min, 97.3% (Max).

Step 3: Benzyl 4-(4,5,6,7-tetrahydrothiazolo[5,4-c]pyridin-2-yl)piperazine-1-carboxylate To a stirred solution of tert-butyl 2-(4-((benzyloxy)carbonyl)piperazin-1-yl)-6,7-dihydrothiazolo[5,4-c]pyridine-5(4H)-carboxylate (3.5 g, 7.6 mmol) in DCM, TFA (20% in DCM, 50 mL) was added at 0° C. and the mixture was stirred for 4 h at rt. Completion of the reaction was monitored by TLC. It was concentrated and DCM (200 mL) was added. The resulting solution was washed with NaHCO$_3$ (100 mL), brine (100 mL), dried over anhydrous Na$_2$SO$_4$ and concentrated. The resulting crude product was used in the next step without further purification. Yield: 96% (2.6 g, brown solid). LCMS: (Method B) 359.2 (M+H), Rt. 2.0, 98.7% (Max). $^1$H NMR (400 MHz, DMSO-d$_6$): δ 7.37-7.31 (m, 5H), 5.1 (s, 2H), 3.7 (s, 2H), 3.6-3.59 (m, 4H), 3.35-3.32 (m, 4H), 2.93 (t, J=5.6 Hz, 2H), 2.49-2.48 (m, 2H).

Step 4: Benzyl 4-(5-trityl-4,5,6,7-tetrahydrothiazolo[5,4-c]pyridin-2-yl)piperazine-1-carboxylate To a stirred solution of benzyl 4-(4,5,6,7-tetrahydrothiazolo[5,4-c]pyridin-2-yl)piperazine-1-carboxylate (2.9 g, 8.1 mmol) in dry DCM (50 mL), triethylamine (3 mL, 20.2 mmol) and trityl chloride (2.92 g, 10.0 mmol) were added at 0° C. The reaction mixture was stirred at rt for 2 h. It was quenched with iced water. The phases were separated and the organic phase was washed with water (100 mL), brine (100 mL), dried over anhydrous Na$_2$SO$_4$ and concentrated. The resulting crude product was used in the next step without further purification. Yield: 58% (3 g, White solid). $^1$H NMR (400 MHz, DMSO-d$_6$): δ 7.45-7.05 (m, 20H), 5.1 (s, 2H), 3.55-3.1 (m, 4H), 3.33-3.27 (m, 4H), 3.22 (m, 2H), 2.8-2.7 (m, 2H), 2.49-2.48 (m, 2H). LCMS: (Method A) 600.8 (M+H), Rt. 8.4.min, 47.70% (Max).

Step 5: 2-(Piperazin-1-yl)-5-trityl-4,5,6,7-tetrahydrothiazolo[5,4-c]pyridine To a stirred solution of benzyl 4-(5-trityl-4,5,6,7-tetrahydrothiazolo[5,4-c]pyridin-2-yl)piperazine-1-carboxylate (3.0 g, 5 mmol) in dry ethanol (50 mL), 6N NaOH (15 mL) was added at 0° C. The reaction mixture was stirred at 85° C. for 8 h. Completion of the reaction was monitored by TLC. The reaction mixture was concentrated and DCM (200 mL) was added. The resulting solution was washed with water (100 mL), brine (100 mL), dried over anhydrous Na$_2$SO$_4$. After evaporation of the solvents, the crude product was purified by flash chromatography affording the title product. Yield: 78% (1.5 g, off-white solid). $^1$H NMR (400 MHz, DMSO-d$_6$): δ 7.44 (d, J=7.0 Hz, 6H), 7.32 (t, J=7.4 Hz, 6H), 7.20 (t, J=7.0 Hz, 3H), 3.21-3.15 (m, 6H), 2.80-

2.72 (m, 4H), 2.68-2.65 (m, 2H), 2.50-2.42 (m, 3H). LCMS: (Method A) 467.0 (M+H), Rt. 7.26.min, 99.4% (Max).

Intermediate 16: 1-(5-bromopyridin-2-yl)piperazine hydrochloride

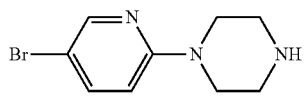 [SMILES: Brc1ccc(N2CCNCC2)nc1]

Step 1: Tert-butyl 4-(5-bromopyridin-2-yl)piperazine-1-carboxylate

To a stirred solution of 1-Boc piperazine (10.6 g, 57.29 mmol, Symax fine chemicals) in dry DMF (100 mL), TEA (14.43 mL, 103.39 mmol) and 5-bromo-2-chloropyrimidine (10 g, 52.08 mmol, Oakwood chemicals) were added and the reaction mixture was stirred at 80° C. for 14 h. It was cooled down to rt and poured on iced water (100 mL). The resulting precipitate was filtered and washed with hexane (50 mL) to afford the title compound. Yield: 58.8% (10 g, off white solid). $^1$H NMR (400 MHz, DMSO-d$_6$): δ 8.60 (s, 1H), 8.13 (dd, J=8.6, 2.4 Hz, 1H), 7.54 (dd, J=8.4, 0.4 Hz, 1H), 3.22-3.20 (m, 4H), 2.61-2.59 (m, 4H), 1.42 (s, 9H). LCMS: (Method A) 343.9 (M+2H), Rt. 5.58 min, 98.9% (Max).

Step 2: 1-(5-bromopyridin-2-yl)piperazine hydrochloride

To a stirred solution of tert-butyl 4-(5-bromopyridin-2-yl)piperazine-1-carboxylate (10 g, 29.21 mmol) in 1,4-dioxane (50 mL), 4N HCl solution in dioxane (100 mL, 10V) was added and the mixture was stirred 4 h at rt. The white precipitate formed was filtered and residue was washed with diethyl ether (25 mL) to afford the title compound. Yield: 95.2% (9 g, off white solid). $^1$H NMR (400 MHz, DMSO-d$_6$): δ 10.05 (br s, 2H), 8.21 (d, J=2.4 Hz, 1H), 7.82 (dd, J=9.2, 2.4 Hz, 1H), 6.99 (d, J=9.2 Hz, 1H), 3.80-3.77 (m, 4H), 3.33-3.13 (m, 4H). LCMS: (Method A) 243.9 (M+2H), Rt. 1.69 min, 99.3% (Max).

Intermediate 17: Tert-butyl 2-chloro-7, 8-dihydropyrido [4, 3-d] pyrimidine-6(5H)-carboxylate

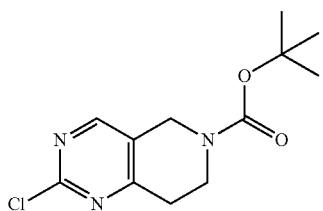 [SMILES: CC(C)(C)OC(=O)N1CCc2nc(Cl)ncc2C1]

Step 1: 6-benzyl-5, 6, 7, 8-tetrahydropyrido [4, 3-d] pyrimidine-2, 4(1H, 3H)-dione A stirred solution of ethyl-1-benzyl-4-oxo-3-piperidine carboxylate, hydrochloride (15 g, 50.4 mmol, combi blocks) and urea (6.36 g, 105 mmol) in dry MeOH (110 mL), sodium methoxide (16.4 mL, 75.14 mmol, and 25% wt. in methanol) was added drop wise at rt and the mixture was refluxed for 40 h. It was cooled to 0° C. and filtered. The residue was stirred with water (40 mL) for 30 min at rt and again cooled to 0° C. and filtered. The residue was washed with diethyl ether (2×20 mL) and dried, affording the title compound. Yield: 60% (7.2 g, Off white solid). $^1$H NMR (400 MHz, DMSO-d6): δ 9.03 (s, 2H), 7.33-7.32 (m, 4H), 7.26-7.25 (m, 1H), 3.56 (s, 2H), 2.68 (s, 2H), 2.55 (t, J=5.2 Hz, 2H), 2.26 (t, J=5.2 Hz, 2H). LCMS: (Method A) 258.2 (M+2), Rt. 1.31 min, 99.60% (Max).

Step 2: 6-benzyl-2, 4-dichloro-5, 6, 7, 8-tetrahydropyrido [4, 3-d] pyrimidine

To 6-benzyl-5, 6, 7, 8-tetrahydropyrido [4, 3-d] pyrimidine-2, 4(1H, 3H)-dione (7.2 g, 27.9 mmol), POCl$_3$ (45 mL, 6V) was added slowly at 0° C. and refluxed for 4 h. The reaction mixture was evaporated under vacuum. EtOAc (200 mL) was added and the solution was poured over cold 3M NaOH solution. The resulting organic layer was separated and washed with brine (30 mL), dried over anhydrous Na$_2$SO$_4$ and evaporated, affording the title compound. Yield: 79% (6.5 g, brown solid). $^1$H NMR (400 MHz, DMSO-d6): δ 7.33-7.32 (m, 5H), 3.77 (s, 2H), 3.56 (s, 2H), 2.94 (t, J=7.2 Hz, 2H), 2.80 (t, J=6.8 Hz, 2H). LCMS: (Method A) 296.3 (M+2), Rt. 2.50 min, 97.94% (Max).

Step 3: 6-benzyl-2-chloro-5, 6, 7, 8-tetrahydropyrido [4, 3-d] pyrimidine

To the stirred solution of 6-benzyl-2, 4-dichloro-5, 6, 7, 8-tetrahydropyrido [4, 3-d] pyrimidine (6 g, 20.4 mmol) in EtOH (120 mL), zinc powder (10.65 g, 163 mmol) and ammonium hydroxide (14.2 mL, 102 mmol) were added at rt and the mixture was stirred at 78° C. for 15 h. It was cooled to rt and filtered through celite. Resulting filtrate was evaporated under vacuum. The resulting crude mixture was diluted with EtOAc (150 mL) and washed with water (15 mL). The organic layer was dried over anhydrous anhydrous Na$_2$SO$_4$ and evaporated under vacuum. The resulting crude product was purified by flash chromatography. Yield: 52% (2.7 g, off white solid). $^1$H NMR (400 MHz, DMSO-d$_6$): δ 8.48 (s, 1H), 7.32-7.31 (m, 5H), 3.71 (s, 2H), 3.57 (s, 2H), 2.89 (t, J=7.6 Hz, 2H), 2.79 (t, J=7.2 Hz, 2H). LCMS: (Method A) 260.2 (M+2), Rt. 1.86 min, 97.15% (Max).

Step 4: 2-chloro-5, 6, 7, 8-tetrahydropyrido [4, 3-d] pyrimidine hydrochloride

To the stirred solution of 6-benzyl-2-chloro-5, 6, 7, 8-tetrahydropyrido [4, 3-d] pyrimidine (2.7 g, 10.4 mmol) in dry DCM (60 mL), 1-chloroethyl chloroformate (1.47 mL, 13.5 mmol) was added at 0° C. The reaction mixture was stirred at 0° C. for 15 min and then refluxed for 2 h. The reaction mixture was evaporated under vacuum and resulting crude mixture was refluxed with MeOH (30 mL) for 1 h. Then the reaction mixture was cooled to rt and evaporated under vacuum to give title compound. Yield: 70% (crude) (1.5 g, brown thick oil). $^1$H NMR (400 MHz, DMSO-d$_6$): δ 8.45 (s, 1H), 3.84 (d, J=5.6 Hz, 2H), 3.01 (t, J=8.0 Hz, 2H), 2.76 (t, J=8.0 Hz, 2H). LCMS: (Method B) 170.0 (M+2), Rt. 2.16 min, 81.936% (Max).

Step 5: tert-butyl 2-chloro-7, 8-dihydropyrido [4, 3-d] pyrimidine-6(5H)-carboxylate To the stirred solution of 2-chloro-5, 6, 7, 8-tetrahydropyrido [4, 3-d] pyrimidine hydrochloride (1.8 g, 8.73 mmol)

Intermediate 18: 2-methyl-1-(6-(piperazin-1-yl)pyridin-3-yl)propan-1-ol hydrochloride

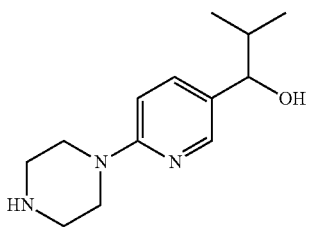 [SMILES: CC(C)C(O)c1ccc(N2CCNCC2)nc1]

Step 1: tert-butyl 4-(5-(1-hydroxy-2-methylpropyl)pyridin-2-yl)piperazine-1-carboxylate To a solution of tert-butyl 4-(5-formylpyridin-2-yl)piperazine-1-carboxylate (1.4 g, 4.81 mmol) in dry THF (14 mL), isopropyl magnesium chloride (2M in Et₂O) (2.9 mL, 5.77 mmol) was added at −10° C. and the reaction mixture was stirred at 0° C. for 2 h. Upon completion (monitored by TLC), the reaction mixture was quenched with saturated ammonium chloride solution (10 mL) and the layers were separated. The organic layer was diluted with ethylacetate (15 mL), washed with brine (15 mL), dried over anhydrous Na₂SO₄, filtered and concentrated. The crude product was purified by flash column chromatography to afford the titled compound. Yield: 69% (1.1 g, off white solid). ¹H NMR (400 MHz, DMSO-d₆): δ 8.00 (d, J=2.8 Hz, 1H), 7.49-7.45 (m, 1H), 6.79-6.82 (m, 1H), 5.00 (d, J=6.0 Hz, 1H), 4.13 (t, J=8.4 Hz, 1H), 3.43-3.33 (m, 8H), 1.78-1.74 (m, 1H), 1.42 (s, 9H), 0.87 (d, J=8.80 Hz, 3H), 0.70 (d, J=8.80 Hz, 3H). LCMS: (Method A) 336.2 (M+H), Rt. 2.97 min, 96.7% (Max).

Step 2: 2-methyl-1-(6-(piperazin-1-yl)pyridin-3-yl)propan-1-ol hydrochloride

To a 0° C. solution of tert-butyl 4-(5-(1-hydroxy-2-methylpropyl)pyridin-2-yl)piperazine-1-carboxylate (1.1 g, 3.28 mmol) in dry 1,4-dioxane (11 mL), 4 M HCl in dioxane (4 mL) was added and the reaction mixture was stirred at rt for 3 h. Upon completion (monitored by TLC), the reaction mixture was concentrated and triturated with diethylether (15 mL). The solid was filtered affording the titled compound. Yield: 99% (0.9 g, off white solid). LCMS: (Method A) 236.2 (M+H), Rt. 1.32 min, 96.6% (Max).

in dry THF (20 mL), TEA (6.1 mL, 43.6 mmol) and Boc anhydride (3.8 mL, 17.4 mmol) were added at 0° C. The reaction mixture was stirred at rt overnight. It was diluted with EtOAc (30 mL) and washed with water (10 mL). The organic layer was dried over anhydrous Na₂SO₄ and evaporated under vacuum. The resulting crude product was purified by flash chromatography to give the title compound. Yield: 60% (0.9 g, off white solid). ¹H NMR (400 MHz, DMSO-d6): δ 8.45 (s, 1H), 4.56 (s, 2H), 3.66 (t, J=8.0 Hz, 2H), 2.88 (t, J=8.0 Hz, 2H), 1.50 (s, 9H). LCMS: (Method A) 270.2 (M+2), Rt. 3.68 min, 76.45% (Max).

Intermediate 19: 6-bromo-3-methylimidazo[1,5-a]pyridine

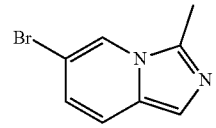

Step 1: (5-bromopyridin-2-yl)methanamine

To a solution of 5-bromopicolinonitrile (5 g, 27.32 mmol) in THF, BH₃.THF (1M solution) (163.92 mL, 163.92 mmol) was added at rt and the mixture was heated to reflux for 2 h. It was then cooled to 0° C. and MeOH (20 mL) and 1N HCl solution were added. The mixture was further refluxed for 7 h. It was quenched with 10% K₂CO₃ solution (500 mL) and extracted with DCM (6×100 mL). The combined organic layer was dried over Na₂SO₄ and concentrated under vacuum affording the title product. It was taken for next step without any further purification (Yellow solid). LCMS: (Method A) 187.3 (M+H), Rt. 1.33 min, 77.38% (Max).

Step 2: N-((5-bromopyridin-2-yl)methyl)acetamide

To a stirred solution of (5-bromopyridin-2-yl)methanamine (2 g, 10.69 mmol) in DCM, Et₃N (2.23 mL, 16.03 mmol) followed by acetyl chloride (0.91 mL, 12.83 mmol) were added at 0° C. The reaction mixture was stirred at rt for 3 h. It was then diluted with water (15 mL) and extracted with DCM (2×20 mL). The combined organic layer was dried over Na₂SO₄ and concentrated under vacuum to give crude product which was taken for next step without further purification. Yield: 54% (1.3 g, Yellow solid). LCMS: (Method A) 229.3 (M+H), Rt. 1.61 min, 69.56% (Max).

Step 3: 6-bromo-3-methylimidazo[1,5-a]pyridine

To a stirred solution of N-((5-bromopyridin-2-yl)methyl)acetamide (1.3 g, 5.67 mmol) in toluene (20 mL) at 0° C., POCl₃ (1.05 mL, 11.34 mmol) was added dropwise over 5 min and the mixture was refluxed at 110° C. for 6 h. It was then quenched with water (15 mL) and concentrated under reduced pressure. A saturated NaHCO₃ solution (15 mL) was added and was extracted with DCM (2×20 mL). The combined organic layer was dried over Na₂SO₄ and concentrated under vacuum. The crude product was purified by flash chromatography (eluent: 2-3% MeOH in DCM), to give the title product (yellow solid). ¹H NMR (400 MHz, DMSO-d₆): δ 8.42 (s, 1H), 7.50 (t, J=12.8 Hz, 1H), 7.32 (s, 1H), 6.78 (dd, J=12.4, 7.2 Hz, 1H), 2.58 (s, 3H). LCMS: (Method A) 213.0 (M+H), Rt. 1.54 min, 99.10% (Max).

Intermediate 20: 2-methyl-1-(2-(piperazin-1-yl)pyrimidin-5-yl)propan-1-ol dihydrochloride

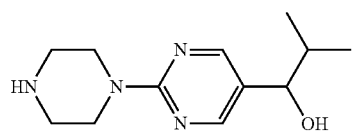

The title compound was synthesized according to the procedure described for Intermediate 18, starting from methyl 2-chloropyrimidine-5-carboxylate. Yield: 100% (crude) (200 mg, pale yellow solid). $^1$H NMR (400 MHz, DMSO-d$_6$): δ 9.28 (s, 2H), 8.32 (s, 2H), 4.19-4.18 (m, 1H), 3.95-3.92 (m, 4H), 3.14-3.13 (m, 4H), 1.83-1.81 (m, 1H), 0.85 (d, J=6.4 Hz, 3H), 0.73 (d, J=6.8 Hz, 3H). LCMS: (Method A) 237.3 (M+H-2HCl), Rt. 1.81 min, 58.32% (Max). HPLC: (Method A) Rt 1.79 min, 89.12% (Max).

Intermediate 21:
4-(4-(methylsulfonyl)-1H-pyrazol-1-yl)piperidine hydrochloride

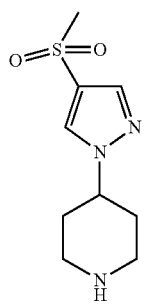

The title compound was synthesized according to the procedure described for Intermediate 10, starting from 4-(methylsulfonyl)-1H-pyrazole. Yield: 92% (0.9 g, white solid). LCMS: (Method A) 230.0 (M+H), Rt. 1.89 min, 90.68% (Max).

Intermediate 22:
1-(2-chloropyrimidin-5-yl)cyclohexan-1-ol

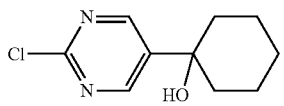

To a stirred solution of 5-bromo-2-chloropyrimidine (1 g, 5.2 mmol) in Et$_2$O cooled to −100° C. was added n-BuLi (1.6 M) (3.88 mL, 6.2 mmol) over a period of 20 min. The mixture was stirred for 45 min at −100° C. Cyclohexanone (1.014 g, 10.34 mmol) was added dropwise at −100° C. and the mixture was stirred 1 h at the same temperature. It was quenched with a saturated solution of NH$_4$Cl (10 mL) and extracted with EtOAc (2×20 mL). Combined organic layer was washed with brine (10 mL) and dried over Na$_2$SO$_4$. After evaporation of the solvent, the crude product was purified by flash chromatography (eluent: 30% EtOAc in petroleum ether) affording the title compound (yellow thick oil). LCMS: (Method A) 213.3 (M+H), Rt. 2.908 min, 98.455% (Max).

Intermediate 23:
4-(2-chloropyrimidin-5-yl)tetrahydro-2H-pyran-4-ol

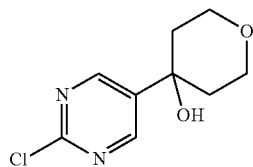 [SMILES: OC1(c2cnc(Cl)nc2)CCOCC1]

The title compound was synthesized according to the procedure described for Intermediate 22, with the addition of tetrahydro pyran-4-one as ketone (yellow solid). LCMS: (Method A) 214.9 (M+2H), Rt. 1.47 min, 72.0% (Max).

Intermediate 24:
4-(6-chloropyridin-3-yl)tetrahydro-2H-pyran-4-ol

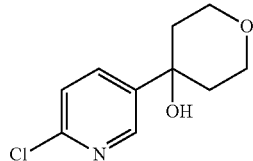 [SMILES: OC1(c2ccc(Cl)nc2)CCOCC1]

The title compound was synthesized according to the procedure described for Intermediate 22, starting with 5-bromo-2-chloropyridine and the addition of tetrahydro pyran-4-one as ketone (off white solid). $^1$H NMR (400 MHz, DMSO-d$_6$): δ 8.78-8.52 (m, 1H), 7.96-7.92 (m, 1H), 7.49-7.46 (m, 1H), 5.35 (s, 1H), 3.78-3.72 (m, 4H), 2.04-1.94 (m, 2H), 1.57-1.53 (m, 2H). LCMS: (Method A) 214.0 (M+H), Rt. 2.08 min, 76.24% (Max).

Intermediate 25:
3-(6-chloropyridin-3-yl)tetrahydrofuran-3-ol

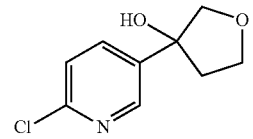 [SMILES: OC1(c2ccc(Cl)nc2)CCOC1]

The title compound was synthesized according to the procedure described for Intermediate 22, starting with 5-bromo-2-chloropyridine and the addition of tetrahydro-furan-3-one as ketone. Yield: 62% (440 mg, Colourless liquid). LCMS: (Method A) 200.0 (M+H), Rt. 1.91 min, 99.02% (Max).

Intermediate 26: 3-(6-chloropyridin-3-yl)oxetan-3-ol

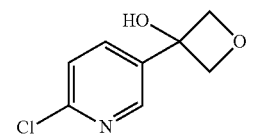 [SMILES: OC1(c2ccc(Cl)nc2)COC1]

The title compound was synthesized according to the procedure described for Intermediate 22, starting with 5-bromo-2-chloropyridine and the addition of oxetan-3-one as ketone (colourless liquid). ¹H NMR (400 MHz, DMSO-d₆): δ 8.61 (d, J=2.8 Hz, 1H), 8.03 (q, J=8.4 Hz, 1H), 7.55 (d, J=8.4 Hz, 1H), 6.66 (s, 1H), 4.78 (d, J=7.2 Hz, 2H), 4.69 (d, J=7.2 Hz, 2H). LCMS: (Method A) 185.9 (M+H), Rt. 1.61 min, 99.20% (Max).

Intermediate 27:
1-(6-chloropyridin-3-yl)cyclohexan-1-ol

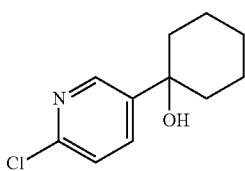 [SMILES: OC1(c2ccc(Cl)nc2)CCCCC1]

The title compound was synthesized according to the procedure described for Intermediate 22, starting with 5-bromo-2-chloropyridine and the addition of cyclohexanone as ketone (white solid). ¹HNMR (400 MHz, DMSO-d₆): δ 8.51 (s, 1H), 7.91 (dd, J=2.8, 8.2 Hz, 1H), 7.44 (d, J=8.4 Hz, 1H), 5.01 (s, 1H), 1.75-1.61 (m, 8H), 1.50 (t, J=4.4 Hz, 2H). LCMS: (Method A) 212.0 (M+H), Rt. 2.44 min, 96.05% (Max).

Intermediate 28:
3-(2-chloropyrimidin-5-yl)tetrahydrofuran-3-ol

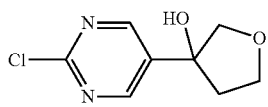

The title compound was synthesized according to the procedure described for Intermediate 22, with the addition of dihydrofuran-3(2H)-one as ketone (yellow thick oil). LCMS: (Method A) 201.2 (M+H), Rt. 1.421 min, 96.024% (Max).

Intermediate 29:
2-(1-chloroethyl)-1,8-naphthyridine

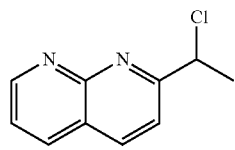

Step 1: 2-methyl-1,8-naphthyridine

To a stirred solution of 2-amino-3-formyl pyridine (7 g, 57 mmol) in acetone (70 mL), a saturated solution of KOH in methanol (0.5 mL) was added and the mixture was stirred at 55° C. for 6 h. Completion of the reaction was monitored by TLC. The mixture was concentrated and the resulting crude product was purified by flash chromatography (Elutant: 65-85% EtOAc in pet ether) to give the title compound. Yield: 88.3% (7.3 g, pale brown solid). ¹H NMR (400 MHz, CDCl₃): δ 9.10-9.09 (m, 1H), 8.18-8.15 (m, 1H), 8.09 (d, J=8.4 Hz, 1H), 7.47-7.39 (m, 1H), 7.29-7.28 (m, 1H), 2.84 (s, 3H). LCMS: (Method B) 145.0 (M+H), Rt. 3.06 min, 97.85% (Max). HPLC: (Method B) Rt 2.98 min, 98.09% (Max).

Step 2: 1,8-naphthyridine-2-carbaldehyde

A solution of selenium dioxide (8.61 g, 77.56 mmol) in 1,4 dioxane (140 mL) with 0.5 mL of water was stirred at 100° C. for 5 min. The mixture was cooled down to 0° C. and 2-Methyl-1,8-naphthyridine (7 g, 48.5 mmol) was added dropwise. The mixture was heated again at 100° C. for 5 h. Completion of the reaction was monitored by TLC. The reaction mixture was filtered through celite bed, washed with EtOAc (50 mL) and concentrated. The resulting crude mixture was dissolved in EtOAc (150 mL) and washed with water (3×60 mL), brine (30 mL), dried over Na₂SO₄ and concentrated to give the title compound (brown solid). ¹H NMR (300 MHz, DMSO-d₆): δ 10.18 (s, 1H), 9.28-9.27 (m, 1H), 8.74 (d, J=8.1 Hz, 1H), 8.63 (d, J=8.1 Hz, 1H), 8.11 (dd, J=8.4, 1.2 Hz, 1H), 7.83-7.79 (m, 1H). LCMS: (Method B) 159.0 (M+H), Rt. 2.44 min, 91.59% (Max). HPLC: (Method B) Rt 2.41 min, 87.86% (Max).

Step 3: 1-(1,8-naphthyridin-2-yl)ethan-1-ol

To a stirred solution of 1,8-naphthyridine-2-carbaldehyde (3.3 g, 20.8 mmol) in dry THF (100 mL), methyl magnesium chloride in THF (14 mL, 41.7 mmol, 3M) was added at 0° C. and stirred 2 h at rt. Completion of the reaction was monitored by TLC. The reaction mixture was quenched with saturated NH₄Cl solution (20 mL) and extracted with EtOAc. The EtOAc layer was washed with water (2×25 mL), brine (25 mL), dried over Na₂SO₄ and concentrated. The resulting crude product was purified by flash chromatography (Elutant: 65-80% EtOAc in pet ether) to give the title compound. Yield: 60.6% (2.2 g, brown thick oil). ¹H NMR (300 MHz, CDCl₃): δ 9.16-9.13 (m, 1H), 8.27-8.23 (m, 2H), 7.57-7.53 (m, 2H), 5.17-5.10 (m, 1H), 1.68-1.48 (m, 3H). LCMS: (Method B) 175.0 (M+H), Rt. 2.86 min, 51.51% (Max). HPLC: (Method A) Rt 0.73 min, 63.62% (Max).

Step 4: 2-(1-chloroethyl)-1,8-naphthyridine

To a stirred solution of 1-(1,8-naphthyridin-2-yl)ethan-1-ol (500 mg, 2.87 mmol) in DCM (10 mL), thionyl chloride was added at 0° C. and stirred 1.5 h at rt. Completion of the reaction was monitored by TLC. The reaction mixture was concentrated under vacuum. DCM (20 mL) was added and evaporated. This process was repeated twice, affording the title product. Yield: 100% (550 mg, brown thick oil). ¹H NMR (300 MHz, DMSO-d₆): δ 9.29-9.27 (m, 1H), 8.89 (dd, J=8.1, 1.8 Hz, 1H), 8.76 (d, J=8.4 Hz, 1H), 8.04 (d, J=8.4 Hz, 1H), 7.96-7.92 (m, 1H), 5.63-5.61 (m, 1H), 1.96 (d, J=6.6 Hz, 3H). LCMS: (Method A) 193.0 (M+H), Rt. 1.99 min, 75.76% (Max).

Intermediate 30: 1-(6-chloropyridin-3-yl)cyclopentan-1-ol

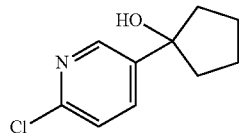 [SMILES: OC1(c2ccc(Cl)nc2)CCCC1]

The title compound was synthesized according to the procedure described for Intermediate 22, starting with 5-bromo-2-chloropyridine and the addition of cyclopentanone as ketone (white solid). $^1$H NMR (400 MHz, CDCl$_3$): δ 8.52 (s, 1H), 7.80 (dd, J=2.4, 8.2 Hz, 1H), 7.31 (dd, J=0.4, 8.0 Hz, 1H), 2.04-1.99 (m, 6H), 1.92-1.89 (m, 2H). LCMS: (Method A) 198.2 (M+H), Rt. 2.29 min, 89.7% (Max).

Intermediate 31: 1-(1-(2,3-dihydrobenzofuran-6-yl)ethyl)piperidin-4-yl methanesulfonate

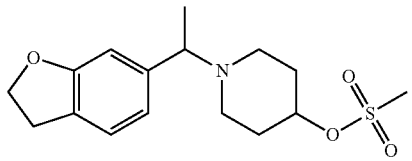 [SMILES: CC(c1ccc2c(c1)OCC2)N1CCC(OS(C)(=O)=O)CC1]

Step 1: 1-(1-(2,3-dihydrobenzofuran-6-yl)ethyl) piperidin-4-ol

To a stirred solution of 4-Hydroxy piperidine (2.5 g, 24.7 mmol) in dry acetonitrile (10 mL), were added TEA (10.3 mL, 74.1 mmol) and 6-(1-chloroethyl)-2,3-dihydrobenzofuran, (4.5 g, 24.7 mmol) at rt and the mixture was stirred overnight. The reaction mixture was concentrated under vacuum. To the resulting crude mixture, DCM (50 mL) was added and was washed with water (20 mL), brine (20 mL), dried over anhydrous Na$_2$SO$_4$ and concentrated. The crude product was purified by silica gel column chromatography to afford the titled compound (off white solid). $^1$H NMR (400 MHz, CDCl$_3$): δ 7.15 (s, 1H), 6.74-6.73 (m, 2H), 4.54-4.48 (m, 4H), 3.14 (t, J=11.6 Hz, 2H), 1.96 (d, J=9.6 Hz, 2H), 1.80-1.61 (m, 3H), 1.41-1.20 (m, 6H). LCMS: (Method A) 248.1 (M+H), Rt. 1.67 min, 97.8% (Max).

Step 2: 1-(1-(2,3-dihydrobenzofuran-6-yl)ethyl) piperidin-4-yl methanesulfonate To a stirred solution of step 1:1-(1-(2,3-dihydrobenzofuran-6-yl)ethyl)piperidin-4-ol (0.2 g, 0.8 mmol) in dry DCM (4 mL) were added TEA (0.33 mL, 2.4 mmol) and methane sulphonyl chloride (0.12 mL, 1.6 mmol, Spectro chem) at 0° C. The reaction mixture was stirred at rt for 4 h. The reaction progress was monitored by TLC. After the completion of reaction, the reaction mixture was diluted with DCM (30 mL) and washed with 10% NaHCO$_3$ (30 mL) solution. The organic layer was washed with water (30 mL), brine (30 mL) and dried over Na$_2$SO$_4$. After evaporation of the solvent, the title compound was obtained and was used without further purification. Yield: 80.2% (0.2 g, brown thick oil). LCMS: (Method A) 326.3 (M+H), Rt. 2.72 min, 55.05% (Max).

Intermediate 33: N-(2-(2-chloropyrimidin-5-yl)propan-2-yl)acetamide

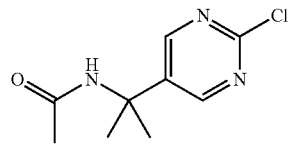

Step 1: 2-(2-chloropyrimidin-5-yl) propan-2-ol

To the reaction mixture of methyl 2-chloropyrimidine-5-carboxylate (2.5 g, 14.487 mmol) in THF (10 mL), methyl magnesium chloride (14.487 mL, 43.463 mmol) was added drop wise at 0° C. and the mixture was stirred at rt for 30 min. After completion of reaction the reaction mixture was poured into 50 mL of 1N HCl and extracted with ether. The ether layer was washed with water, dried over anhydrous Na$_2$SO$_4$ and concentrated. The resulting crude product was purified by flash chromatography (Elutant: 55-60% EtOAc in pet ether) to afford title compound (pale yellow solid). $^1$H NMR (400 MHz, DMSO-d$_6$): δ 1.48 (s, 6H), 5.51 (s, 1H), 8.84 (s, 2H). LCMS: (Method A) 173.0 (M+H), Rt. 1.659 min, 98.64% (Max).

Step 2: N-(2-(2-chloropyrimidin-5-yl)propan-2-yl) acetamide

To a solution of 2-(2-chloropyrimidin-5-yl) propan-2-ol (1.1 g, 6.376 mmol) in MeCN, conc. H$_2$SO$_4$ (2.37 mL, 44.637 mmol) was added dropwise at 0° C. and the mixture was stirred at rt for 24 h. After completion of reaction, the reaction mixture was cooled to 0° C. and diluted with NH$_4$OH solution slowly. Then the reaction mixture was extracted with ether. The ether layer was washed with water, dried over Na$_2$SO$_4$ and concentrated. The resulting crude product was purified by flash chromatography to afford title compound (off white). LCMS: (Method A) 214.2 (M+H), Rt. 1.662 min, 98.72% (Max).

Intermediate 34: 3-(2-chloropyrimidin-5-yl)oxetan-3-ol

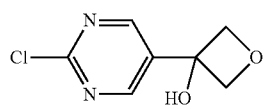 [SMILES: OC1(c2cnc(Cl)nc2)COC1]

The title compound was synthesized according to the procedure described for Intermediate 22, using oxetan-3-one as ketone (off white crystals). $^1$H NMR (300 MHz, DMSO-d$_6$): δ 8.95 (s, 2H), 6.85 (s, 1H), 4.78 (s, 4H). LCMS: (Method A) 187.0 (M+H), Rt. 1.321 min, 84.213% (Max).

Intermediate 35: 6-(piperazin-1-yl)isoindolin-1-one, hydrochloride

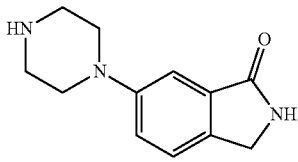

Step 1: tert-butyl 4-(3-oxoisoindolin-5-yl)piperazine-1-carboxylate

To a degassed solution of 6-bromoisoindolin-1-one (0.7 g, 3.3 mmol), 1-Boc piperazine (0.921 g, 4.9 mmol) and sodium tert butoxide (0.95 g, 2.5 mmol) in toluene (10 mL), $Pd_2(dba)_3$ (0.151 g, 0.165 mmol) and BINAP (0.205 g, 0.33 mmol) were added at rt and heated to 80° C. overnight in sealed tube. Then the reaction mixture was filtered through celite and concentrated. Water (4 mL) was added and was extracted with EtOAc (2×10 mL). The combined organic layer was dried over $Na_2SO_4$ and concentrated under vacuum. The resulting crude product was purified by flash chromatography (Eluent: 5-6% MeOH in DCM). After evaporation, the resulting solid was triturated in $Et_2O$ and filtered, affording the title product (white solid). $^1H$ NMR (400 MHz, $CDCl_3$): δ 8.72-8.70 (m, 1H), 7.79 (d, J=1.6 Hz, 1H), 7.56 (d, J=8.4 Hz, 1H), 7.26-7.23 (m, 1H), 4.26 (s, 2H), 3.49-3.46 (m, 4H), 3.18-3.13 (m, 4H), 1.43 (s, 9H). LCMS: (Method A) 318.0 (M+H), Rt. 2.26 min, 39.9% (Max).

Step 2: 6-(piperazin-1-yl)isoindolin-1-one, hydrochloride

To a stirred solution of tert-butyl 4-(5-acetamido-1,3,4-thiadiazol-2-yl)piperazine-1-carboxylate (0.35 g 0.9 mmol) in dry dioxane (4 mL), HCl in dioxane (5 mL, 4 N) was added at rt and the reaction mixture was stirred at rt for 2 h. The reaction mixture was concentrated under vacuum and the resulting crude product was triturated with $Et_2O$ (20 mL) to get the title compound. Yield: 50% (120 mg, Yellow solid). $^1H$ NMR (400 MHz, DMSO-$d_6$): δ 8.95 (s, 2H), 7.47-7.44 (m, 1H), 7.06-7.02 (m, 1H), 6.76 (s, 1H), 4.35-4.28 (m, 2H), 3.41-3.39 (m, 4H), 3.30-3.20 (m, 4H). LCMS: (Method A) 218.2 (M+H), Rt. 1.05 min, 65.4% (Max).

Intermediate 36: 5-(piperazin-1-yl)-1,3,4-thiadiazol-2(3H)-one hydrochloride

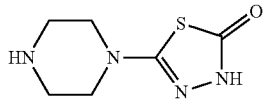

Step 1: tert-butyl 4-(hydrazinocarbonothioyl)piperazine-1-carboxylate

To the stirred solution of tert-butyl piperazine-1-carboxylate (5.0 g, 26.845 mmol) in THF (50 mL), triethylamine (22.6 mL, 161.072 mmol) and thiocarbonyldiimidazole (9.568 g, 53.690 mmol) were added and stirred for 2 h at rt. Hydrazine hydrate (2.68 mL, 53.690 mmol) was added and the reaction mixture was further stirred for 2 h at room temperature. The reaction the reaction mixture was poured into 50 mL of brine solution and extracted with EtOAc. The EtOAc layer was dried over $Na_2SO_4$ and concentrated under reduced pressure to get crude compound. The resulting crude product was purified by flash chromatography (Elutant: 1-2% MeOH in DCM) to afford title compound (off white solid). $^1H$ NMR (400 MHz, DMSO-$d_6$): δ 7.10 (s, 1H), 4.43 (s, 2H), 3.84-0.00 (m, 4H), 3.57-3.50 (m, 4H), 1.49 (s, 9H). LCMS: (Method A) 262.0 (M+H), Rt. 1.659 min, 92.71% (Max).

Step 2: tert-butyl 4-(5-oxo-4,5-dihydro-1,3,4-thiadiazol-2-yl)piperazine-1-carboxylate To the tert-butyl 4-(hydrazinocarbonothioyl)piperazine-1-carboxylate (2.0 g, 7.692 mmol) in DCM (20 mL), triethylamine (3.2 mL, 23.076 mmol) and carbonyldiimidazole (3.74 g, 23.076 mmol) were added at rt and stirred for 4 h at rt. After completion of reaction, the reaction mixture was poured into 50 mL of brine solution and extracted with EtOAc. The EtOAc layer was dried over $Na_2SO_4$ and concentrated. The resulting crude product was purified by flash chromatography (Elutant: 1-2% MeOH in DCM) to afford title compound. Yield: 52.2% (1.1 g, off white). $^1H$ NMR: (400 MHz, DMSO-$d_6$): δ 3.54-3.50 (m, 4H), 3.28-3.25 (m, 4H), 1.49 (s, 9H). LCMS: (Method A) 287.0 (M+H), Rt. 2.406 min, 99.95% (Max).

Step 3: 5-(piperazin-1-yl)-1,3,4-thiadiazol-2(3H)-one hydrochloride

The stirred solution of tert-butyl 4-(hydrazinocarbonothioyl)piperazine-1-carboxylate (1.0 g, mmol) in 1,4 dioxane (10 mL), hydrochloric acid in dioxane (4 M, 10 mL) was added at 0° C. and the mixture was stirred for 4 h at rt. After completion of the reaction, the reaction mixture was concentrated under reduced pressure to get tittle compound. Yield: 87.0% (550 mg, off white). $^1H$ NMR: (400 MHz, DMSO-$d_6$): δ 11.96 (s, 1H), 9.57 (s, 2H), 3.47-3.45 (m, 4H), 3.44-3.15 (m, 4H). LCMS: (Method A) 186.9 (M+H), Rt. 0.549 min, 98.72% (Max).

Intermediate 37: 5-(piperidin-4-yl)-1,3,4-oxadiazol-2(3H)-one hydrochloride

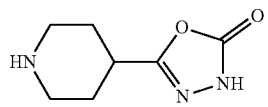

Step 1: tert-butyl 4-(5-oxo-4,5-dihydro-1,3,4-oxadiazol-2-yl)piperidine-1-carboxylate To tert-butyl 4-(hydrazinocarbonyl)piperidine-1-carboxylate (1.0 g, 4.112 mmol) in DCM (10 mL), triethylamine (1.7 mL, 12.337 mmol) and carbonyldiimidazole (2.0 g, 12.337 mmol) were added and the mixture was stirred for 4 h at rt. After completion of reaction, the reaction mixture was poured into 50 mL of brine solution and extracted with EtOAc. The EtOAc layer was dried over $Na_2SO_4$ and concentrated under reduced pressure to get crude compound.

The resulting crude was purified by flash chromatography (Elutant: 1-2% MeOH in DCM) to afford title compound. Yield: 55.4% (610 mg, off white). $^1$H NMR: (400 MHz, DMSO-$d_6$) δ 12.10 (br, 1H), 3.84-3.92 (m, 2H), 2.80-2.95 (m, 3H), 1.83-1.91 (m, 2H), 1.38-1.50 (m, 2H), 1.39 (5, 9H). LCMS: (Method A) 170.2 (M+H), Rt. 2.382 min, 94.3% (Max).

Step 2: 5-(piperidin-4-yl)-1, 3,4-oxadiazol-2(3H)-one hydrochloride

To the tert-butyl 4-(5-oxo-4,5-dihydro-1,3,4-oxadiazol-2-yl)piperidine-1-carboxylate (520 mg, 2.512 mmol) in 1,4 dioxane (5 mL), 4M hydrochloric acid in dioxane (5 mL) was added at 0° C. The reaction mixture was stirred for 4 h at rt. After completion of reaction, the reaction mixture was concentrated to get tittle compound. Yield: 95.0% (311 mg, off white). LCMS: (Method A) 170.2 (M+H), Rt. 0.610 min, 77.0% (Max).

Intermediate 38: 7-(piperazin-1-yl)-2H-pyrido[4,3-b][1,4]oxazin-3(4H)-one

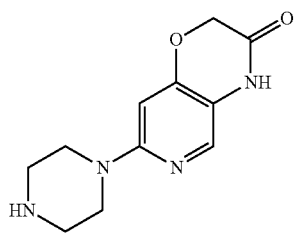 [SMILES: O=C1COc2cc(N3CCNCC3)ncc2N1]

Step 1: Methyl 2-(2-chloro-5-nitropyridin-4-yl)oxy)acetate

To a stirred solution of 2,4-dichloro-5-nitropyridine (26 mmol, 5 g) and methyl glycolate (31.2 mmol, 2.41 mL) in DMF at 0° C., sodium hydride was added (60% in mineral oil, 31.2 mmol, 1.25 g) and the mixture was stirred at rt overnight. The reaction mixture was quenched with ammonium chloride solution (30 mL) and extracted with EtOAc (3×50 mL). The combined organic layer was dried over $Na_2SO_4$ and concentrated under vacuum. The resulting crude product was purified by column chromatography affording the title product (yellow solid). $^1$H NMR (400 MHz, DMSO-$d_6$): δ 8.93 (s, 1H), 7.71 (s, 1H), 5.23 (s, 2H), 3.74 (s, 3H). LCMS: (Method A) 247.0 (M+H), Rt. 2.436 min, 83.5% (Max).

Step 2: 7-chloro-2H-pyrido[4,3-b][1,4]oxazin-3(4H)-one

To a stirred suspension of methyl 2-((2-chloro-5-nitropyridin-4-yl)oxy)acetate (10 mmol, 2.5 g) in ethanol (25 mL), acetic acid (10 mL) and iron powder (50 mmol, 2.8 g) were added at rt and the mixture was heated to 80° C. for 20 h. The reaction mixture was filtered through celite and concentrated. The resulting product was purified by flash chromatography, affording the title product. Yield: 77% (1.4 g, pale brown solid). $^1$H NMR (400 MHz, DMSO-$d_6$): δ 11.03 (s, 1H), 7.84 (s, 1H), 7.15 (s, 1H), 4.75 (s, 2H). LCMS: (Method B) 185 (M+H), Rt. 2.078 min, 98.29% (Max).

Step 3: 7-(piperazin-1-yl)-2H-pyrido[4,3-b][1,4]oxazin-3(4H)-one

To a stirred solution of methyl 2-((2-chloro-5-nitropyridin-4-yl)oxy)acetate (1.0 g 5.43 mmol) in NMP (4 mL) was added piperazine (27 mmol, 2.3 g mmol) at rt and the mixture was heated at 150° C. overnight. The completion of the reaction was confirmed by TLC. The reaction mixture was evaporated under reduced pressure. The resulting crude mixture was suspended in water (2 mL) and extracted with EtOAc (2×10 mL). The organic layer was dried over $Na_2SO_4$ and concentrated. The resulting product was purified by column chromatography (yellow solid). LCMS: (Method A) 235.3 (M+H), Rt. 0.516 min, 54.4% (Max).

Intermediate 39: (S)-1-(1-(benzo[d][1,3]dioxol-5-yl)ethyl)piperazine hydrochloride

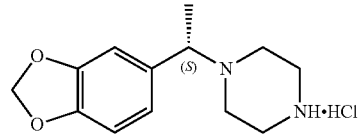

Step 1: (R)—N-(1-(benzo[d][1,3]dioxol-5-yl)ethylidene)-2-methylpropane-2-sulfinamide To a mixture of 1-(benzo[d][1,3]dioxol-5-yl)ethan-1-one (105.7 g, 644.6 mmol), (R)-(+)-2-methyl-2-propanesulfinamide (85.79 g, 709 mmol) in THF (1.0 L), titanium(IV) ethoxide (294.06 g, 1289.2 mmol) was added at rt over 30 min and refluxed for 35 h. The reaction was monitored by HPLC. The reaction mixture was cooled to rt and slowly quenched with water (500 mL). The precipitate observed was filtered through celite bed (100 g) and washed with EtOAc (2.0 L). The organic layer was washed with water (500 mL), brine solution (300 mL) and dried over $Na_2SO_4$. (100 g) and evaporated under vacuum at 50° C. The resulting crude product was codistilled with toluene (2×500 mL) and used as such for next step without any further purification (164 g, brown liquid). LCMS: (Method A) 268.0 (M+H), Rt. 3.87 min, 83.05% (Max).

HPLC: (Method A) Rt. 3.81 min, 57.62% (Max).

Step 2: (R)—N—((S)-1-(benzo[d][1,3]dioxol-5-yl)ethyl)-2-methylpropane-2-sulfinamide To a stirred solution of (R)—N-(1-(benzo[d][1,3]dioxol-5-yl)ethylidene)-2-methylpropane-2-sulfinamide (96 g, 359 mmol) in THF (960 mL), L-Selectride (539 mL, 539 mmol, 1 M solution in THF) was added under nitrogen atmosphere at −50° C. over 30 min and stirred for 1 h. The completion of the reaction was confirmed by TLC. The reaction mixture was quenched with methanol (150 mL), water (750 mL) and stirred overnight at rt. The aqueous layer was extracted with EtOAc (2×300 mL). The combined organic layer was washed with sat. $NH_4Cl$ (2×250 mL), brine (250 mL), dried over $Na_2SO_4$ and evaporated under vacuum at 50° C. The resulting crude product (as light brown thick oil) was diluted with pet ether (250 mL) and stirred at −20° C. for 30 min. The resulting precipitate was filtered and washed with pet ether (2×100 mL). It was dried under vacuum to give the title compound. Yield: 70.2% (68 g, Off white solid). $^1$H NMR (400 MHz, DMSO-$d_6$): δ 6.89 (s, 1H), 6.83-6.77 (m, 2H), 5.99-5.95 (m, 2H), 5.25 (d, J=5.2 Hz, 1H), 4.30 (q, J=6.0 Hz, 1H), 1.39 (d, J=1.6 Hz, 3H), 1.11-1.06 (m, 9H). LCMS: (Method A) 270.0 (M+H), Rt. 3.66 min, 99.65% (Max). HPLC: (Method A) Rt. 3.62 min, 99.69% (Max). Chiral HPLC: (Method C) Rt. 9.71 min, 100%.

Step 3: (S)-1-(benzo[d][1,3]dioxol-5-yl)ethan-1-amine

To a stirred solution of $(R_S)$—N—((S)-1-(benzo[d][1,3]dioxol-5-yl)ethyl)-2-methylpropane-2-sulfinamide (68 g, 252 mmol) in MeOH (680 mL), thionyl chloride (74.3 g, 630 mmol) was added at 0° C. over 15 min and the resulting mixture was stirred at rt for 1 h. The completion of the reaction was confirmed by TLC. The reaction mixture was concentrated under vacuum at 50° C. The resulting residue was suspended in EtOAc (300 mL), filtered and washed with EtOAc (150 mL). The product was basified with 30% aqueous ammonia solution (300 mL) and extracted with EtOAc (2×250 mL). The combined organic layer was washed with brine solution (1×150 mL) and dried over $Na_2SO_4$. The solvent was evaporated at under vacuum to give the title compound. Yield: 92.84% (38.3 g, brown liquid). $^1$H NMR (400 MHz, DMSO-$d_6$): δ 6.95 (s, 1H), 6.81-6.77 (m, 2H), 5.95 (s, 2H), 3.90 (q, J=6.56 Hz, 1H), 1.85 (s, 2H), 1.19 (m, J=6.56 Hz, 3H). LCMS: (Method A) 149.0 (M-16), Rt. 1.65 min, 99.56% (Max). HPLC: (Method A) Rt. 1.60 min, 99.61% (Max). Chiral HPLC: (Method B) Rt 11.11 min, 100%.

Step 4: (S)-1-(1-(benzo[d][1,3]dioxol-5-yl)ethyl)-4-tosylpiperazine

To a stirred solution of (S)-1-(benzo[d][1,3]dioxol-5-yl)ethan-1-amine (41 g, 248 mmol) in DIPEA (86.6 mL, 496 mmol), N,N-bis(2-chloroethyl)-p-toluene sulfonamide (80.74 g, 273 mmol) was added at rt and the resulting mixture was heated at 105° C. overnight. The completion of the reaction was confirmed by TLC and the reaction mixture was diluted with water (1000 mL) and extracted with EtOAc (2×500 mL). The combined organic layer was washed with water (200 mL), brine solution (200 mL) and dried over $Na_2SO_4$. After evaporation of the solvent, the resulting crude solid was suspended in pet ether (350 mL) and stirred for 10 min at rt. The suspension was filtered and was washed with $Et_2O$ (2×200 mL) and dried under vacuum to give the title compound. Yield: 63.2% (61 g, Off white solid). $^1$H NMR (400 MHz, DMSO-$d_6$): δ 7.59 (d, J=8.2 Hz, 2H), 7.45 (d, J=8.2 Hz, 2H), 6.81-6.77 (m, 1H), 6.69 (d, J=7.4 Hz, 1H), 5.96 (s, 2H), 3.32 (q, J=7.76 Hz, 1H), 2.81-2.80 (m, 4H), 2.42 (s, 3H), 2.36-2.32 (m, 4H), 1.18 (d, J=6.4 Hz, 3H). LCMS: (Method A) 389.2 (M+H), Rt. 3.40 min, 98.09% (Max). HPLC: (Method A) Rt. 3.30 min, 98.69% (Max). Chiral HPLC: (Method D) Rt. 15.79 min, 100.00%

Step 5: (S)-1-(1-(benzo[d][1,3]dioxol-5-yl)ethyl)piperazine hydrochloride

To a mixture of (S)-1-(1-(benzo[d][1,3]dioxol-5-yl)ethyl)-4-tosylpiperazine (61 g, 157 mmol) and 4-hydroxy benzoic acid (65.01 g, 471 mmol), HBr in acetic acid (244 mL) was added at 0° C. and the reaction mixture was stirred at rt overnight. The completion of the reaction was confirmed by TLC. The reaction mixture was diluted with water (400 mL). The precipitate was filtered through celite bed and washed with water (200 mL). The aqueous filtrate was washed with EtOAc (4×300 mL) and basified up to pH 11 with NaOH pellet (30 g) at 0° C. (during basification the colour of aqeuous was converted to light back). The product was extracted with EtOAc (4×300 mL). The combined organic layer was dried over $Na_2SO_4$ and evaporated under vacuum. The resulting light black oil was diluted in 1,4 Dioxane (50 mL) and cooled to 0° C. and 4.5 N HCl solution in dioxane (100 mL) was added and stirred for 15 min at rt. The solvent was evaporated at 45° C. under reduced pressure to get the title compound (pale brown solid). $^1$H NMR (400 MHz, DMSO-$d_6$): δ 12.11 (s, 1H), 7.32 (s, 1H), 7.06-6.99 (m, 2H), 6.07 (s, 2H), 4.55-4.52 (m, 1H), 3.80-3.61 (m, 2H), 3.05-2.95 (m, 2H), 2.51-2.50 (m 4H), 1.68 (s, 3H). LCMS: (Method A) 235.3 (M+H), Rt. 1.53 min, 95.85% (Max). HPLC: (Method A) Rt. 1.52 min, 95.06% (Max). Chiral HPLC: (Method A) Rt. 8.11 min, 100%.

Intermediate 40: (S)-1-(1-(benzo[d][1,3]dioxol-5-yl)ethyl)piperazine

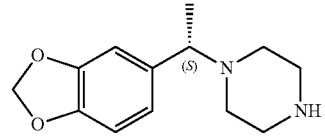

The hydrochloride salt of 1-(1-(benzo[d][1,3]dioxol-5-yl)ethyl)piperazine (20 g) was suspended in NaOH solution (1 M, 150 mL) and extracted with EtOAc (150 mL). The water layer was further extracted two times with EtOAc (50 mL). The combined organic layers were dried over $MgSO_4$ and filtered off. After evaporation of the solvent, the title compound was isolated as an oil (10 g). The aqueous layer was further basified to pH 12 (pH after the extraction was around 7-8) by addition of 2 M NaOH solution and further extracted with EtOAc. A second batch of the title compound (5 g) was isolated.

Example 1: 6-(4-(1-(2,3-dihydrobenzofuran-6-yl)ethyl)piperazin-1-yl)-3-methylimidazo[1,5-a]pyridine

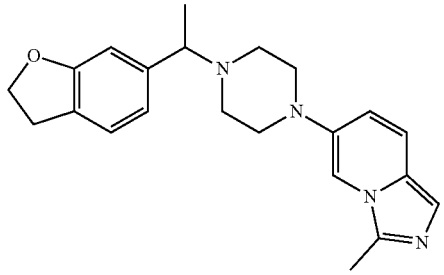 [SMILES: Cc1ncc2ccc(N3CCN(C(C)c4ccc5c(c4)OCC5)CC3)cn12]

To a degassed solution of Intermediate 13 (178 mg, 0.77 mmol), Intermediate 19 (125 mg, 0.59 mmol) and sodium tert-butoxide (170 mg, 1.77 mmol) in 1,4 dioxane (4 mL), $Pd_2(dba)_3$ (27 mg, 0.03 mmol) and Xphos (28 mg, 0.05 mmol) were added at rt and the mixture was heated in sealed tube at 100° C. overnight. The reaction mixture was filtered through celite and concentrated. The crude mixture was diluted with water (4 mL) and extracted with DCM (2×10 mL). The combined organic layer was dried over Na$_2$SO$_4$ and concentrated. The crude product was purified by flash chromatography, followed by preparative HPLC, affording the title product (yellow solid). $^1$H NMR (400 MHz, DMSO-d$_6$): δ 7.37 (d, J=10.0 Hz, 1H), 7.16 (q, J=14.4 Hz, 3H), 6.79-6.70 (m, 3H), 4.51 (t, J=8.4 Hz, 2H), 3.49-3.35 (m, 1H), 3.14 (t, J=8.4 Hz, 2H), 3.11-2.83 (m, 4H), 2.67-2.51 (m, 4H), 2.50-2.33 (m, 3H), 1.31 (d, J=6.4 Hz, 3H). LCMS: (Method A) 363.3 (M+H), Rt. 2.15 min, 97.41% (Max). HPLC: (Method A) Rt 2.32 min, 96.88% (Max).

Example 2: 6-(4-(1-(2,3-dihydrobenzofuran-6-yl)ethyl)piperazin-1-yl)isoindolin-1-one

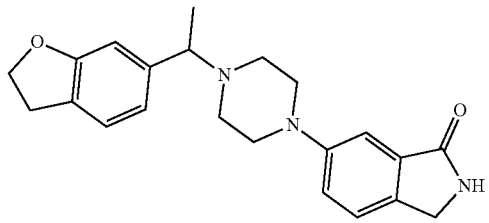 [SMILES: CC(c1ccc2c(c1)OCC2)N1CCN(c2ccc3c(c2)C(=O)NC3)CC1]

The title compound was synthesized according to the procedure described for Example 12, starting from Intermediate 4 and Intermediate 35 (brown solid). $^1$H NMR (400 MHz, DMSO-d$_6$): δ 8.42 (s, 1H), 7.38 (d, J=8.4 Hz, 1H), 7.20-7.16 (m, 2H), 7.07 (s, 1H), 6.78 (d, J=7.6 Hz, 1H), 6.73 (s, 1H), 6.54 (s, 1H), 4.51 (t, J=8.8 Hz, 2H), 4.24 (s, 2H), 3.19-3.10 (m, 6H), 2.62-2.55 (m, 2H), 2.49-2.42 (m, 2H), 1.30 (d, J=6.80 Hz, 3H). LCMS: (Method A) 364.2 (M+H), Rt. 2.50 min, 93.23% (Max). HPLC: (Method A) Rt 2.56 min, 91.88% (Max).

Example 3: 7-(4-(1-(2,3-dihydrobenzofuran-6-yl)ethyl)piperazin-1-yl)-2H-pyrido[4,3-b][1,4]oxazin-3(4H)-one

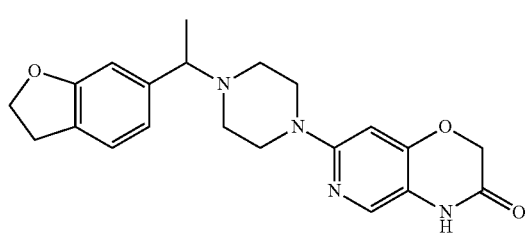 [SMILES: CC(c1ccc2c(c1)OCC2)N1CCN(c2cc3c(cn2)NC(=O)CO3)CC1]

The title compound was synthesized according to the procedure described for Example 12, starting from Intermediate 4 and Intermediate 38 (off white solid). $^1$H NMR (400 MHz, DMSO-d$_6$): δ 10.58 (s, 1H), 7.65 (s, 1H), 7.15 (d, J=7.2 Hz, 1H), 6.74 (t, J=7.6 Hz, 2H), 6.39 (s, 1H), 4.60-4.53 (m, 2H), 3.34-3.32 (m, 2H), 2.68 (s, 7H), 2.48-2.46 (m, 2H), 1.27 (d, J=6.8 Hz, 3H). LCMS: (Method A) 381.2 (M+H), Rt. 2.013 min, 99.2% (Max). HPLC: (Method A) Rt 2.04 min, 99.5% (Max).

Example 4: 6-(4-(1-(quinoxalin-6-yl)ethyl)piperazin-1-yl)isoindolin-1-one

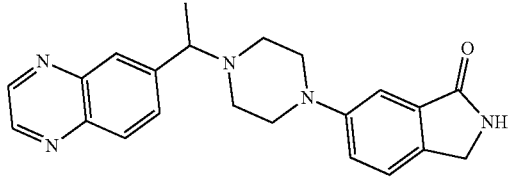 [SMILES: CC(c1ccc2nccnc2c1)N1CCN(c2ccc3c(c2)C(=O)NC3)CC1]

The title compound was synthesized according to the procedure described for Example 12, starting from Intermediate 1 and Intermediate 35 (white solid). $^1$H NMR (400 MHz, DMSO-d$_6$): δ 8.93 (dd, J=1.6, -7.4 Hz, 2H), 8.41 (s, 1H), 8.09 (d, J=8.8 Hz, 1H), 8.01 (d, J=1.2 Hz, 1H), 7.92 (dd, J=1.6, 8.6 Hz, 1H), 7.37 (d, J=8.4 Hz, 1H), 7.19 (dd, J=2.0, 8.4 Hz, 1H), 7.07 (d, J=2.0 Hz, 1H), 4.23 (s, 2H), 3.77-3.75 (m, 1H), 3.19-3.16 (m, 4H), 2.67-2.65 (m, 4H), 1.44 (d, J=6.40 Hz, 3H). LCMS: (Method A) 374.2 (M+H), Rt. 1.93 min, 99.2% (Max). HPLC: (Method A) Rt 2.01 min, 99.35% (Max).

Example 5: 1-(2-(4-(1-(2,3-dihydrobenzofuran-5-yl)ethyl) piperazin-1-yl)-7,8-dihydropyrido[4,3-d]pyrimidin-6(5H)-yl)ethan-1-one

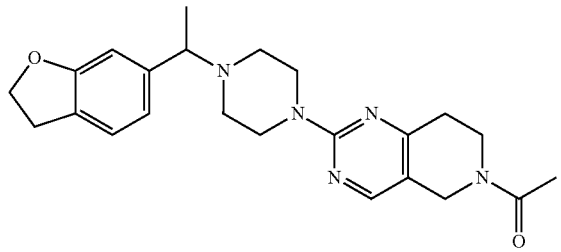 [SMILES: CC(=O)N1CCc2nc(N3CCN(C(C)c4ccc5c(c4)OCC5)CC3)ncc2C1]

The title compound was synthesized according to the procedure described for Example 10, starting from Example 7. The resulting crude was purified by flash chromatography to give the title compound (yellow solid). $^1$H NMR (400 MHz, DMSO-d6): δ 8.18 (s, 1H), 7.14 (d, J=7.6 Hz, 1H), 6.75 (d, J=7.2 Hz, 1H), 6.71 (s, 1H), 4.50 (t, J=8.8 Hz, 2H), 4.43 (s, 2H), 4.43-3.66 (m, 7H), 3.13 (t, J=8.4 Hz, 2H), 2.73 (t, J=6.0 Hz, 2H), 2.61-2.59 (m, 2H), 2.34-2.31 (m, 2H), 2.08 (s, 3H), 1.27 (d, J=6.40 Hz, 3H). LCMS: (Method A) 408.2 (M+H), Rt. 2.56 min, 97.96% (Max). HPLC: (Method A) Rt. 2.49 min, 97.69% (Max).

Example 6: 1-(2-(4-(1-(quinoxalin-6-yl) ethyl) piperazin-1-yl)-7, 8-dihydropyrido[4,3-d]pyrimidin-6(5H)-yl)ethan-1-one

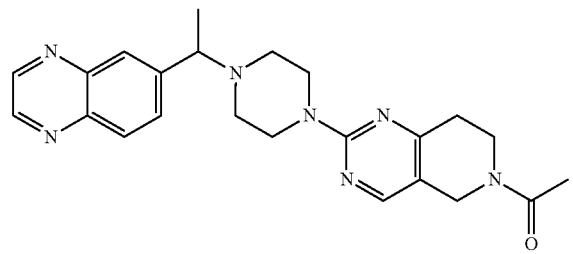 [SMILES: CC(=O)N1CCc2nc(N3CCN(C(C)c4ccc5nccnc5c4)CC3)ncc2C1]

The title compound was synthesized according to the procedure described for Example 10, starting from Example 8. The final product was purified by flash chromatography (off white solid). ¹H NMR (400 MHz, DMSO-d₆): δ 8.94-8.92 (dd, J=7.2, 2.0 Hz, 2H), 8.18 (s, 1H), 8.09 (d, J=8.8 Hz, 1H), 8.00 (s, 1H), 7.92 (dd, J=8.8, 1.6 Hz, 1H), 4.48-4.43 (m, 2H), 3.77-3.75 (m, 1H), 3.70-3.69 (m, 6H), 2.73 (t, J=6.0 Hz, 2H), 2.51 (t, J=1.6 Hz, 2H), 2.41 (t, J=4.80 Hz, 2H), 2.07 (s, 3H), 1.43 (d, J=6.80 Hz, 3H). LCMS: (Method A) 418.2 (M+H), Rt. 1.94 min, 99.44% (Max). HPLC: (Method A) Rt. 1.99 min, 99.23% (Max).

Example 7: 2-(4-(1-(2,3-dihydrobenzofuran-5-yl) ethyl)piperazin-1-yl)-5,6,7,8-tetrahydropyrido[4,3-d] pyrimidine

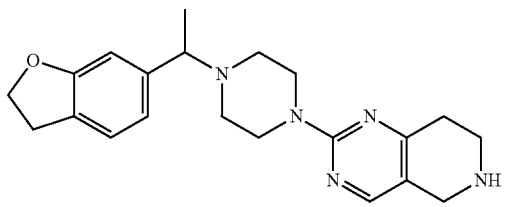 [SMILES: CC(c1ccc2c(c1)OCC2)N1CCN(c2ncc3c(n2)CCNC3)CC1]

The title compound was synthesized according to the procedure described for Example 8, starting from Intermediate 13 and Intermediate 17. Yield: 65% (0.095 g, pale yellow solid). ¹H NMR (400 MHz, DMSO-d₆): δ 8.05 (s, 1H), 7.13 (d, J=7.6 Hz, 1H), 6.74 (d, J=8.0 Hz, 1H), 6.70 (s, 1H), 4.49 (t, J=8.8 Hz, 2H), 3.75 (s, 2H), 3.63-3.63 (m, 5H), 3.12 (t, J=8.8 Hz, 2H), 3.04 (t, J=6.0 Hz, 2H), 2.60 (t, J=5.6 Hz, 2H), 2.45-2.41 (m, 4H), 1.26 (d, J=6.8 Hz, 3H). LCMS: (Method A) 366.3 (M+H), Rt. 1.98 min, 95.91% (Max). HPLC: (Method A) Rt. 2.021 min, 95.60% (Max).

Example 8: 2-(4-(1-(quinoxalin-6-yl) ethyl) piperazin-1-yl)-5, 6, 7, 8-tetrahydropyrido [4,3-d]pyrimidine

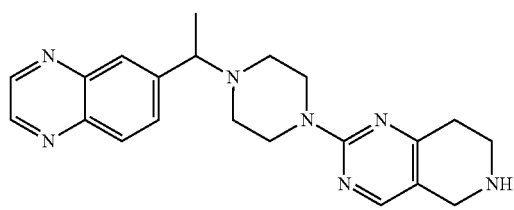 [SMILES: CC(c1ccc2nccnc2c1)N1CCN(c2ncc3c(n2)CCNC3)CC1]

Step 1: Tert-butyl 2-(4-(1-(quinoxalin-6-yl) ethyl) piperazin-1-yl)-7, 8-dihydropyrido [4, 3-d] pyrimidine-6(5H)-carboxylate To the stirred solution of Intermediate 2 (1.7 g, 6.28 mmol) in dry DMF (15 mL), TEA (2.67 mL, 19.33 mmol) and Intermediate 17 (1.3 g, 4.83 mmol) were added at rt and stirred at 80° C. overnight. The reaction mixture was evaporated under vacuum. The resulting crude mixture was diluted with EtOAc (30 mL) and washed with water (10 mL), dried over anhydrous Na₂SO₄ and evaporated under vacuum. The resulting crude product was purified by flash chromatography to give title compound. Yield: 36% (0.6 g, Brown thick oil). ¹H NMR (400 MHz, DMSO-d₆): δ 8.94 (d, J=2.4 Hz, 2H), 8.17 (s, 1H), 7.93-7.90 (m, 3H), 4.34 (s, 2H), 3.76-3.74 (m, 5H), 3.57 (t, J=7.6 Hz, 2H), 2.89-2.89 (m, 2H), 2.43-2.41 (m, 4H), 1.45 (s, 9H), 1.43 (d, J=11.2 Hz, 3H). LCMS: (Method A) 476.2 (M+2), Rt. 3.44 min, 87.38% (Max).

Step 2: 2-(4-(1-(quinoxalin-6-yl) ethyl) piperazin-1-yl)-5, 6, 7, 8-tetrahydropyrido [4, 3-d] pyrimidine To the stirred solution of tert-butyl 2-(4-(1-(quinoxalin-6-yl) ethyl) piperazin-1-yl)-7, 8-dihydropyrido [4, 3-d] pyrimidine-6(5H)-carboxylate (0.6 g, 1.26 mmol) in 1,4-dioxane (2 mL), 4M HCl in dioxane (5 mL) was added and the mixture was stirred at rt for 2 h. It was evaporated under vacuum. To the resulting crude mixture MeOH (10 mL) was added and the solution was basified with 10% NaOH solution (2 mL). It was concentrated and the resulting crude mixture was purified by flash chromatography to give title compound. Yield: 78% (0.37 g, brown solid). ¹H NMR (400 MHz, DMSO-d6): δ 8.94-8.92 (m, 2H), 8.10 (s, 1H), 8.01 (d, J=9.6 Hz, 2H), 7.93-7.91 (m, 1H), 3.72-3.72 (m, 1H), 3.67-3.65 (m, 6H), 3.33 (s, 1H), 2.94 (t, J=6.0 Hz, 2H), 2.68 (t, J=1.6 Hz, 2H), 2.55 (t, J=5.6 Hz, 2H), 2.34 (t, J=1.60 Hz, 2H), 1.43 (d, J=6.40 Hz, 3H). LCMS: (Method A) 376.3 (M+2), Rt. 1.53 min, 97.74% (Max). HPLC: (Method A) Rt. 1.54 min, 99.50% (Max).

Example 9: 6-methyl-2-(4-(1-(quinoxalin-6-yl)ethyl) piperazin-1-yl)-5,6,7,8-tetrahydropyrido[4,3-d]pyrimidine

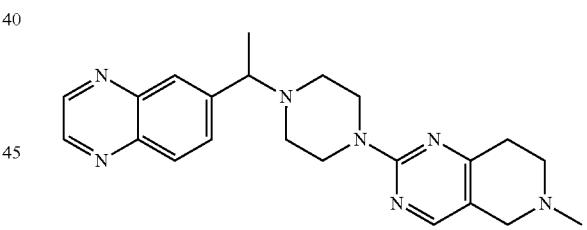

To the stirred solution of Example 8 (0.15 g, 0.40 mmol) in 1,2-dichloroethane (3 mL), p-formaldehyde (0.024 g, 0.80 mmol) was added at rt and the mixture was stirred at rt. After 2 h, sodium triacetoxy borohydride (0.25 g, 1.20 mmol) was added and the mixture was stirred at rt overnight. The reaction mixture was diluted with DCM (10 mL) and washed with water (2 mL), dried over anhydrous Na₂SO₄ and evaporated under vacuum. The resulting crude product was purified by flash chromatography affording the title compound (brown solid). ¹H NMR (400 MHz, DMSO-d₆): δ 8.94-8.92 (m, 2H), 8.09 (d, J=8.4 Hz, 1H), 8.05 (s, 1H), 8.00 (s, 1H), 7.92 (d, J=6.8 Hz, 1H), 3.88-3.85 (m, 1H), 3.75 (t, J=6.8 Hz, 4H), 3.32 (t, J=5.2 Hz, 2H), 2.68-2.66 (m, 2H), 2.63 (t, J=12.8 Hz, 2H), 2.54-2.51 (m, 2H), 2.42-2.41 (m, 2H), 2.33 (s, 3H), 1.43 (d, J=6.8 Hz, 3H). LCMS: (Method A) 390.2 (M+2), Rt. 1.51 min, 97.08% (Max). HPLC: (Method A) Rt. 1.55 min, 96.75% (Max).

Example 10: 1-(2-(4-(1-(2,3-dihydrobenzofuran-6-yl)ethyl)piperazin-1-yl)-6,7-dihydrothiazolo[5,4-c]pyridin-5(4H)-yl)ethan-1-one

SGN020616-01

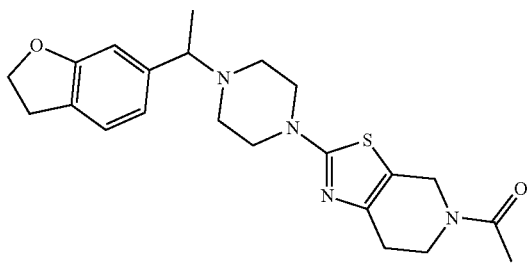 [SMILES: CC(=O)N1CCc2nc(N3CCN(C(C)c4ccc5c(c4)OCC5)CC3)sc2C1]

To a stirred solution of Example 15 (150 mg, 0.4 mmol) in DCM, TEA (0.11 mL, 0.81 mmol) and acetyl chloride (0.038 mg, 0.48 mmol) were added at 0° C. and the mixture was stirred for 2 h at rt. It was quenched with iced water and the two phases were separated. The organic phase was washed with NaHCO$_3$ (10 mL), brine (10 mL) and dried over anhydrous Na$_2$SO$_4$. After evaporation of the solvent, the crude product was purified by MD Autoprep HPLC (Method C), affording the title product (white solid). $^1$H NMR (400 MHz, DMSO-d$_6$): δ 7.15 (d, J=7.6 Hz, 1H), 6.75 (d, J=7.6 Hz, 1H), 6.71 (s, 1H), 4.53-4.46 (m, 4H), 3.71-3.65 (m, 2H), 3.39-3.37 (m, 1H), 3.33-3.30 (m, 4H), 3.13 (t, J=8.4 Hz, 2H), 2.51-2.50 (m, 5H), 2.08 (s, 3H), 1.27 (d, J=6.40 Hz, 3H). LCMS: (Method A) 413.3 (M+H), Rt. 2.2 min, 97.8% (Max). HPLC: (Method A) Rt 2.3 min, 98.9% (Max).

Example 11: 1-(2-(4-(1-(quinoxalin-6-yl)ethyl)piperazin-1-yl)-6,7-dihydrothiazolo[5,4-c]pyridin-5(4H)-yl)ethan-1-one

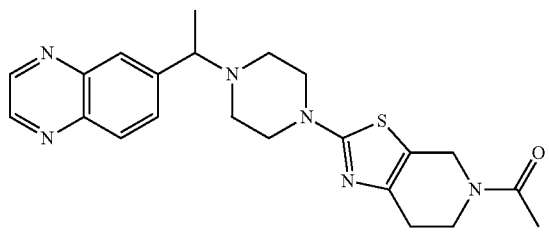 [SMILES: CC(=O)N1CCc2nc(N3CCN(C(C)c4ccc5nccnc5c4)CC3)sc2C1]

The title compound was synthesized according to the procedure described for Example 10, starting from Example 19 (yellow solid). $^1$H NMR (400 MHz, DMSO-d$_6$): δ 8.94 (dd, J=2.0, 7.0 Hz, 2H), 8.09 (d, J=8.8 Hz, 1H), 8.00 (s, 1H), 7.91 (dd, J=2.0, 8.6 Hz, 1H), 4.48 (d, J=14.8 Hz, 2H), 3.81-3.79 (m, 1H), 3.70-3.65 (m, 2H), 3.40-3.33 (m, 4H), 2.61-2.58 (m, 2H), 2.51-2.50 (m, 4H), 2.08 (s, 3H), 1.44 (d, J=6.80 Hz, 3H). LCMS: (Method A) 423.3 (M+H), Rt. 1.81 min, 99.2% (Max). HPLC: (Method A) Rt 1.85 min, 98.9% (Max).

Example 12: 2-(4-(1-(2,3-dihydrobenzofuran-6-yl)ethyl)piperazin-1-yl)-6,7-dihydrothiazolo[5,4-c]pyridin-4(5H)-one

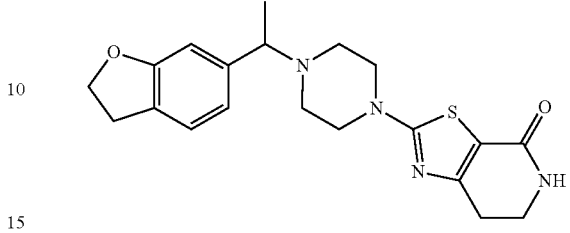

To a stirred solution of Intermediates 6 (0.5 g, 1.61 mmol) in DMF (5 mL, 10V), TEA (0.89 mL, 6.4 mmol) and Intermediate 4 (0.44 g, 2.41 mmol) were added at rt and the mixture was stirred at 80° C. for 12 h. It was concentrated under vacuum and resulting crude mixture was purified by MD Autoprep HPLC (Method C) to afford titled compound (off white solid). $^1$H NMR (400 MHz, DMSO-d6): δ 7.29 (s, 1H), 7.16 (d, J=7.2 Hz, 1H), 6.76 (d, J=7.6 Hz, 1H), 6.72 (s, 1H), 4.51 (t, J=8.8 Hz, 2H), 3.46-3.42 (m, 4H), 3.38-3.36 (m, 4H), 3.14 (t, J=8.8 Hz, 2H), 2.69 (t, J=7.2 Hz, 2H), 2.44-2.43 (m, 2H), 1.28 (d, J=6.80 Hz, 3H). LCMS: (Method A) 358.0 (M+H), Rt. 2.324 min, 97.963% (Max). HPLC: (Method A) Rt. 2.279 min, 99.224% (Max).

Example 13: 2-(4-(1-(2,3-dihydrobenzofuran-6-yl)ethyl)piperazin-1-yl)-5-methyl-6,7-dihydrothiazolo[5,4-c]pyridin-4(5H)-one

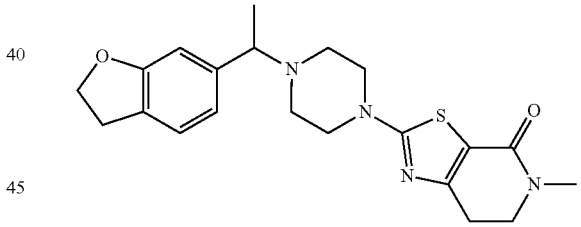

To a stirred solution of Example 12 (0.3 g, 0.78 mmol) in THF (3 mL, 10V), NaH (0.125 g, 3.12 mmol) was added at 0° C. and the mixture was stirred for 1 h. Then MeI (0.22 g, 1.56 mmol) was added at same temperature and the stirring was continued for 12 h. The reaction mixture was quenched with iced water (3 mL) and extracted with EtOAc (2×10 mL). The combined organic layer was washed with brine, dried over Na$_2$SO$_4$ and concentrated under vacuum. After flash chromatograghy, the resulting product was further purified by MD Autoprep HPLC (Method C) to afford titled compound (dark yellow thick oil). $^1$H NMR (400 MHz, DMSO-d$_6$): δ 7.15 (d, J=7.6 Hz, 1H), 6.75 (d, J=7.6 Hz, 1H), 6.71 (s, 1H), 4.50 (t, J=8.4 Hz, 2H), 3.49-3.44 (m, 7H), 3.18-3.11 (m, 2H), 2.87 (s, 3H), 2.80-2.78 (m, 2H), 2.41-2.39 (m, 4H), 1.27 (d, J=6.8 Hz, 3H). LCMS: (Method A) 399.2 (M+H), Rt. 2.857 min, 97.21% (Max). HPLC: (Method A) Rt. 2.512 min, 98.36% (Max).

Example 14: 5-methyl-2-(4-(1-(quinoxalin-6-yl)ethyl)piperazin-1-yl)-6,7-dihydrothiazolo[5,4-c]pyridin-4(5H)-one

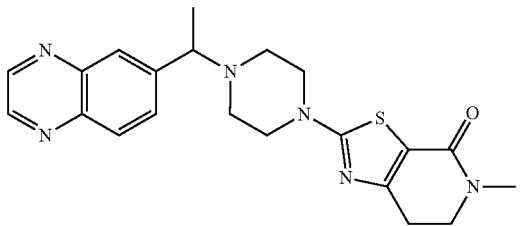 [SMILES: CC(c1ccc2nccnc2c1)N1CCN(c2nc3c(s2)C(=O)N(C)CC3)CC1]

The title compound was synthesized according to the procedure described for Example 13, starting from Intermediates 1 and 6 (dark yellow thick oil). $^1$H NMR (400 MHz, DMSO-d6): δ 8.94 (d, J=6.8 Hz, 2H), 8.10 (d, J=8.4 Hz, 1H), 8.01 (s, 1H), 7.92 (d, J=8.8 Hz, 1H), 3.83 (d, J=6.8 Hz, 1H), 3.49-3.48 (m, 6H), 2.87 (s, 3H), 2.79 (t, J=7.2 Hz, 2H), 2.62-2.61 (m, 4H), 1.44 (d, J=6.4 Hz, 3H). LCMS: (Method A) 409.2 (M+H), Rt. 1.956 min, 99.033% (Max). HPLC: (Method A) Rt. 2.003 min, 99.291% (Max).

Example 15: 2-(4-(1-(2,3-dihydrobenzofuran-6-yl)ethyl)piperazin-1-yl)-4,5,6,7-tetrahydrothiazolo[5,4-c]pyridine

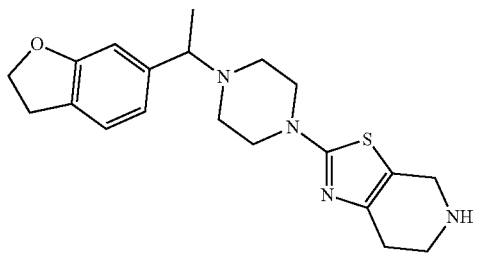 [SMILES: CC(c1ccc2c(c1)OCC2)N1CCN(c2nc3c(s2)CNCC3)CC1]

Step 1: 2-(4-(1-(2,3-Dihydrobenzofuran-7-yl)ethyl)piperazin-1-yl)-5-trityl-4,5,6,7-tetrahydrothiazolo[5,4-c]pyridine To a stirred solution of Intermediate 15 (1.5 g, 3.2 mmol) in DMF (10 mL), TEA (1.3 mL, 9.6 mmol) and Intermediate 4 (0.878 g, 4.8 mmol), were added at 0-5° C. and the mixture was stirred at 100° C. overnight. It was concentrated and EtOAc (30 mL) was added. The resulting solution was washed with water (20 mL), brine (20 mL) and dried over Na$_2$SO$_4$. After evaporation of the solvents, the crude product was purified by flash chromatography affording the title product (yellow solid). LCMS: (Method A) 612.8 (M+H), Rt. 8.6.min, 35.4% (Max).

Step 2: 2-(4-(1-(2,3-dihydrobenzofuran-6-yl)ethyl)piperazin-1-yl)-4,5,6,7-tetrahydrothiazolo[5,4-c]pyridine To a stirred solution of 2-(4-(1-(2,3-dihydrobenzofuran-7-yl)ethyl)piperazin-1-yl)-5-trityl-4,5,6,7-tetrahydrothiazolo[5,4-c]pyridine (0.2 g, 0.32 mmol) in DCM, TFA (20% in DCM, 8 mL) was added at 0° C. and the mixture was stirred for 2 h at rt. The reaction mixture was concentrated and DCM (200 mL) was added. The resulting solution was washed with NaHCO$_3$ (10 mL), brine (10 mL), dried over anhydrous Na$_2$SO$_4$ and concentrated. The crude product was purified by MD Autoprep HPLC (Method C). Yield: 62% (70 mg, Yellow solid). $^1$H NMR (400 MHz, DMSO-d$_6$): δ 7.15 (d, J=7.6 Hz, 1H), 6.75 (d, J=7.6 Hz, 1H), 6.71 (s, 1H), 4.51 (t, J=8.8 Hz, 2H), 3.67 (s, 2H), 3.39-3.37 (m, 1H), 3.34-3.29 (m, 4H), 3.14 (t, J=8.4 Hz, 2H), 2.90 (t, J=5.6 Hz, 2H), 2.47-2.46 (m, 2H), 2.40-2.30 (m, 4H), 1.27 (d, J=6.80 Hz, 3H). LCMS: (Method A) 371.2 (M+H), Rt. 2.0 min, 96.4% (Max). HPLC: (Method A) Rt 1.97 min, 97.8% (Max).

Example 16: 2-(4-(1-(2,3-dihydrobenzofuran-6-yl)ethyl)piperazin-1-yl)-5-methyl-4,5,6,7-tetrahydrothiazolo[5,4-c]pyridine

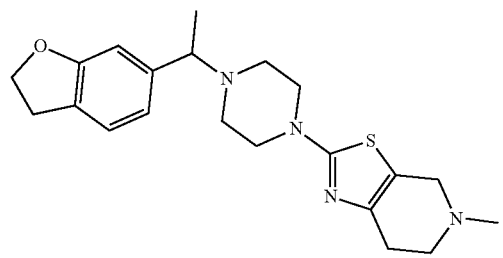 [SMILES: CC(c1ccc2c(c1)OCC2)N1CCN(c2nc3c(s2)CN(C)CC3)CC1]

To a stirred solution of Example 15 (0.15 g, 0.4 mmol) in MeOH, para formaldehyde (0.36 mg, 1.2 mmol) and sodium cyanoborohydride (0.038 mg, 0.6 mmol) were added at 0° C. and the mixture was stirred for 2 h at rt. It was concentrated and DCM was added. The resulting solution was washed with water (10 mL), brine (10 mL), dried over anhydrous Na$_2$SO$_4$. After evaporation of the solvents, the crude product was purified by MD Autoprep HPLC (Method C), affording the title product (pale brown). $^1$H NMR (400 MHz, DMSO-d$_6$): δ 7.15 (d, J=7.6 Hz, 1H), 6.75 (d, J=7.6 Hz, 1H), 6.71 (s, 1H), 4.51 (t, J=8.8 Hz, 2H), 3.39-3.37 (m, 4H), 3.34-3.29 (m, 4H), 3.14 (t, J=8.4 Hz, 2H), 2.62 (t, J=5.6 Hz, 2H), 2.56 (t, J=1.6 Hz, 2H), 2.51-2.50 (m, 2H), 2.33 (s, 3H), 1.27 (d, J=6.80 Hz, 3H). LCMS: (Method A) 385.2 (M+H), Rt. 1.96 min, 96.9% (Max). HPLC: (Method A) Rt 1.99 min, 96.5% (Max).

Example 17 and 18: (S)-2-(4-(1-(2,3-dihydrobenzofuran-6-yl)ethyl)piperazin-1-yl)-4,5,6,7-tetrahydrothiazolo[5,4-c]pyridine and (R)-2-(4-(1-(2,3-dihydrobenzofuran-6-yl)ethyl)piperazin-1-yl)-4,5,6,7-tetrahydrothiazolo[5,4-c]pyridine

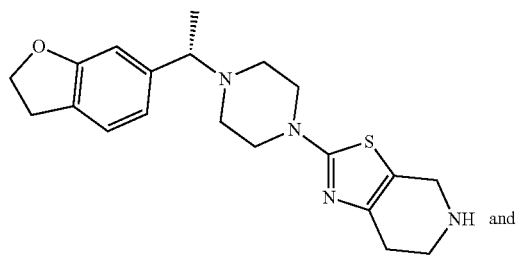

and

-continued

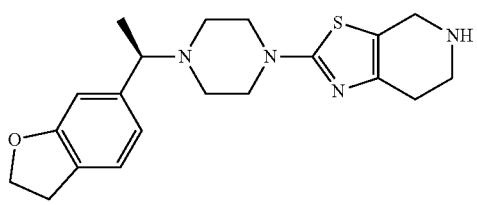

The racemic mixture of Example 15 was separated by chiral preparative HPLC, using the chiral preparative HPLC (Method X).

The first eluting compound correspond to Example 17 (yellow solid). $^1$H NMR (400 MHz, DMSO-$d_6$): δ 7.15 (d, J=7.6 Hz, 1H), 6.75 (d, J=7.6 Hz, 1H), 6.71 (s, 1H), 4.50 (t, J=8.8 Hz, 2H), 3.66 (s, 2H), 3.38-3.37 (m, 1H), 3.30-3.27 (m, 4H), 3.13 (t, J=8.8 Hz, 2H), 2.89 (t, J=5.6 Hz, 2H), 2.47-2.45 (m, 2H), 2.40-2.37 (m, 4H), 1.27 (d, J=6.40 Hz, 3H). LCMS: (Method A) 371.2 (M+H), Rt. 1.95 min, 97.9% (Max). HPLC: (Method A) Rt 1.98 min, 98.8% (Max). CHIRAL HPLC: (Method P) Rt. 7.15 min, 100% (Max).

The second eluting compound correspond to Example 18 (yellow solid). $^1$H NMR (400 MHz, DMSO-$d_6$): δ 7.15 (d, J=7.6 Hz, 1H), 6.75 (d, J=7.6 Hz, 1H), 6.71 (s, 1H), 4.50 (t, J=8.8 Hz, 2H), 3.66 (s, 2H), 3.38-3.37 (m, 1H), 3.30-3.27 (m, 4H), 3.13 (t, J=8.8 Hz, 2H), 2.89 (t, J=6.0 Hz, 2H), 2.47-2.45 (m, 2H), 2.40-2.37 (m, 4H), 1.27 (d, J=6.40 Hz, 3H). LCMS: (Method A) 371.2 (M+H), Rt. 1.95 min, 99.5% (Max). HPLC: (Method A) Rt 1.99 min, 99.4% (Max). CHIRAL HPLC: (Method P) Rt. 20.9 min, 100% (Max).

Example 19: 2-(4-(1-(quinoxalin-6-yl)ethyl)piperazin-1-yl)-4,5,6,7-tetrahydrothiazolo[5,4-c]pyridine

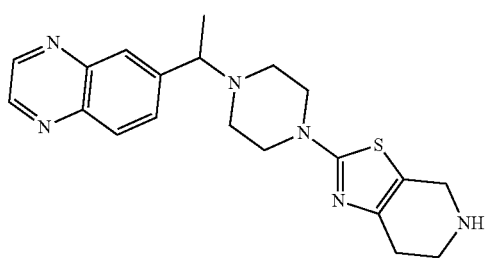 [SMILES: CC(c1ccc2nccnc2c1)N1CCN(c2nc3c(s2)CNCC3)CC1]

The title compound was synthesized according to the procedure described for Example 15, starting from Intermediate 1 and Intermediate 15 (brown solid). $^1$H NMR (400 MHz, DMSO-$d_6$): δ 8.93 (dd, J=2.0, 5.2 Hz, 2H), 8.08 (dd, J=2.0, 8.8 Hz, 1H), 7.99 (s, 1H), 7.90 (d, J=8.8 Hz, 1H), 3.79-3.77 (m, 1H), 3.66 (s, 2H), 3.37-3.30 (m, 4H), 2.91 (t, J=5.6 Hz, 2H), 2.59-2.56 (m, 2H), 2.56-2.40 (m, 5H), 1.42 (d, J=6.40 Hz, 3H). LCMS: (Method A) 381.2 (M+H), Rt. 1.47 min, 99.5% (Max). HPLC: (Method A) Rt 1.52 min, 99.04% (Max).

Example 20: 5-Methyl-2-(4-(1-(quinoxalin-6-yl)ethyl)piperazin-1-yl)-4,5,6,7-tetrahydrothiazolo[5,4-c]pyridine

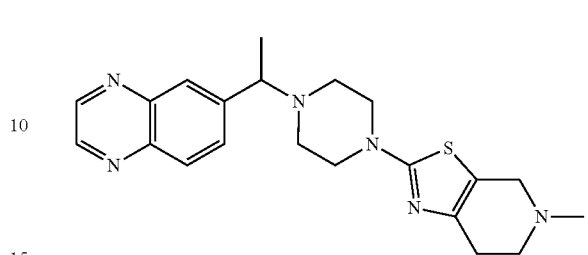

The title compound was synthesized according to the procedure described for Example 16, starting from Example 19 (white solid). $^1$H NMR (400 MHz, DMSO-$d_6$): δ 8.94 (dd, J=2.0, 7.0 Hz, 2H), 8.08 (d, J=8.4 Hz, 1H), 7.99 (s, 1H), 7.90 (d, J=8.4 Hz, 1H), 3.79-3.78 (m, 1H), 3.39 (s, 2H), 3.36-3.30 (m, 4H), 2.66-2.64 (m, 4H), 2.45-2.44 (m, 4H), 2.34 (s, 3H), 1.42 (s, 3H). LCMS: (Method A) 395.2 (M+H), Rt. 1.5 min, 98.9% (Max). HPLC: (Method A) Rt 1.52 min, 99.1% (Max).

Example 21: 5-(4-(1-(quinoxalin-6-yl)ethyl)piperazin-1-yl)-1,3,4-thiadiazol-2(3H)-one

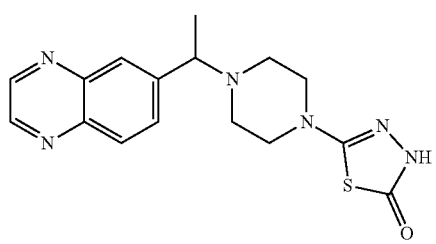 [SMILES: CC(c1ccc2nccnc2c1)N1CCN(c2n[nH]c(=O)s2)CC1]

The title compound was synthesized according to the procedure described for Example 12, starting from Intermediate 1 and Intermediate 36 (pale brown solid). $^1$H NMR (400 MHz, DMSO-$d_6$): δ 8.87 (s, 2H), 8.51 (s, 1H), 8.12 (d, J=8.4 Hz, 1H), 8.03 (s, 1H), 7.89 (d, J=8.8 Hz, 1H), 3.74 (d, J=6.0 Hz, 1H), 3.38-3.21 (m, 4H), 2.68-2.66 (m, 2H), 2.56-2.54 (m, 2H), 1.50 (d, J=6.0 Hz, 3H). LCMS: (Method A) 343.2 (M+H), Rt. 1.63 min, 98.23% (Max). HPLC: (Method A) Rt. 1.69 min, 98.3% (Max).

Example 22: 5-(1-(1-(quinoxalin-6-yl)ethylpiperidin-4-yl)-1,3,4-oxadiazol-2(3H)-one

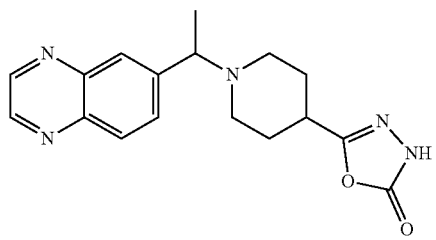 [SMILES: CC(c1ccc2nccnc2c1)N1CCC(c2n[nH]c(=O)o2)CC1]

The title compound was synthesized according to the procedure described for Example 12, starting from Intermediate 1 and Intermediate 37 (dark brown solid). $^1$H NMR (400 MHz, DMSO-$d_6$): δ 12.06 (s, 1H), 8.93 (s, 2H), 8.07-7.89 (m, 3H), 3.81 (s, 1H), 2.98 (s, 1H), 2.81 (s, 1H), 2.11-0.00 (m, 2H), 1.91-1.83 (m, 2H), 1.61-0.00 (m, 2H), 1.42-0.00 (m, 3H). LCMS: (Method A) 326.3 (M+H), Rt. 1.55 min, 96.75% (Max). HPLC: (Method A) Rt. 3.48 min, 96.9%.

Example 23: 2-(1-(1-(2,3-dihydrobenzofuran-6-yl)ethyl)piperazin-4-yl)-5-methyl-1,3,4-oxadiazole

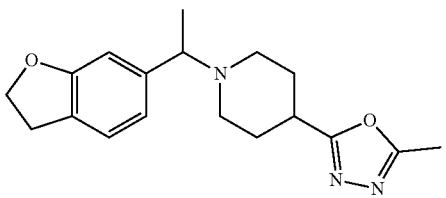 [SMILES: Cc1nnc(C2CCN(C(C)c3ccc4c(c3)OCC4)CC2)o1]

The title compound was synthesized according to the procedure described for Example 24, starting from Intermediate 4 (dark yellow solid). $^1$H NMR (400 MHz, DMSO-$d_6$): δ 7.13 (d, J=7.2 Hz, 1H), 6.73 (d, J=7.6 Hz, 1H), 6.69 (s, 1H), 4.49 (t, J=8.8 Hz, 2H), 3.40-3.37 (m, 1H), 3.12 (t, J=8.8 Hz, 2H), 2.93-2.90 (m, 1H), 2.80-2.74 (m, 2H), 2.43 (s, 3H), 2.04-1.88 (m, 4H), 1.69-1.59 (m, 2H), 1.25 (d, J=6.80 Hz, 3H). LCMS: (Method A) 314.2 (M+1) Rt. 2.263 min, 95.868% (Max). HPLC: (Method A) Rt. 2.220 min, 94.865% (Max).

Example 24: 2-methyl-5-(1-(1-(quinoxalin-6-yl)ethylpiperidin-4-yl)-1,3,4-oxadiazole

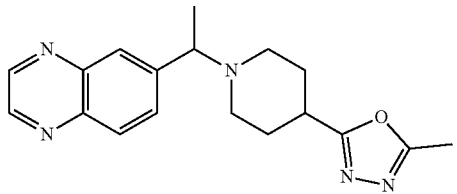 [SMILES: Cc1nnc(C2CCN(C(C)c3ccc4nccnc4c3)CC2)o1]

To a stirred solution of 2-methyl-5-(piperidin-4-yl)-1,3,4-oxadiazole hydrochloride (0.3 g, 1.47 mmol, ABCR) in DMF (3 mL, 10V), cooled to 0° C., TEA (0.82 mL, 5.89 mmol) followed by Intermediate 1 (0.57 g, 2.94 mmol) were added and the mixture was stirred at 80° C. for 12 h. It was then concentrated. Water (3 mL) was added and was extracted with EtOAc (2×10 mL). The combined organic layer was washed with brine (5 mL) and dried over Na$_2$SO$_4$. After evaporation of the solvents, the resulting crude product was purified by flash chromatography to afford titled compound (dark yellow solid). $^1$H NMR (400 MHz, DMSO-$d_6$): δ 8.94 (d, J=1.6 Hz, 1H), 8.92 (d, J=2.0 Hz, 1H), 8.08 (d, J=8.8 Hz, 1H), 7.98 (s, 1H), 7.91 (d, J=8.8 Hz, 1H), 3.82-3.81 (m, 1H), 3.00-2.97 (m, 1H), 2.86-2.84 (m, 2H), 2.44 (s, 3H), 2.18-2.16 (m, 2H), 2.00-1.97 (m, 2H), 1.78-1.74 (m, 2H), 1.43 (d, J=6.80 Hz, 3H). LCMS: (Method A) 324.2 (M+1) Rt. 1.624 min, 97.172% (Max). HPLC: (Method A) Rt. 1.665 min, 97.713% (Max).

Example 25: N-(1-(1-(1-(2,3-dihydrobenzofuran-6-yl)ethyl)piperazin-4-yl)-1H-pyrazol-4-yl)acetamide

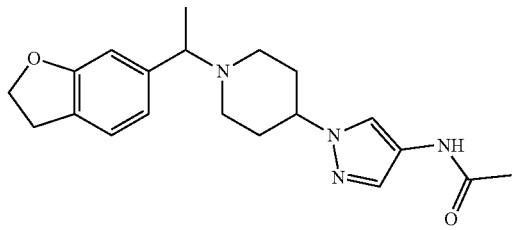 [SMILES: CC(=O)Nc1cnn(C2CCN(C(C)c3ccc4c(c3)OCC4)CC2)c1]

To a stirred solution of Intermediate 11 (0.25 g, 1.2 mmol) in DMF (10 mL), TEA (0.5 mL, 3.6 mmol) and Intermediate 4 (0.22 g, 1.2 mmol) were added at 0-5° C. The reaction mixture was stirred at 100° C. overnight. The completion of the reaction was confirmed by TLC. The reaction mixture was evaporated at 50° C. under reduced pressure and the resulting crude mixture was diluted with EtOAc (30 mL). The organic layer was washed with water (10 mL), brine (10 mL) and dried over Na$_2$SO$_4$. After evaporation of the solvents, the crude product was purified by flash chromatography (5-8% MeOH in DCM) to give the title compound (yellow solid). $^1$H NMR (400 MHz, DMSO-$d_6$): δ 9.88 (s, 1H), 7.83 (s, 1H), 7.38 (s, 1H), 7.16-6.71 (m, 3H), 4.55-4.49 (m, 2H), 4.12-3.99 (m, 1H), 3.43-3.41 (m, 1H), 3.16-3.12 (m, 2H), 3.11-3.01 (m, 1H), 2.84-2.82 (m, 1H), 2.33-1.80 (m, 9H), 1.26 (d, J=5.20 Hz, 3H). LCMS: (Method A) 355.2 (M+H), Rt. 2.22 min, 97.98% (Max). HPLC: (Method A), Rt. 2.26 min, 96.08% (Max).

Example 26: N-((1-(1-(1-(2,3-dihydrobenzofuran-5-yl)ethyl)piperidin-4-yl)-1H-pyrazol-4-yl)methyl)acetamide

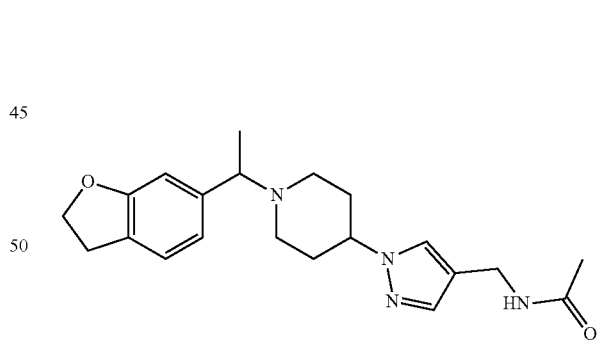

The title compound was synthesized according to the procedure described for Example 112, starting from Example 33. Yield: 62.08% (35 mg, colorless solid thick oil). $^1$H NMR (400 MHz, DMSO-$d_6$): δ 8.06 (d, J=4.4 Hz, 1H), 7.62 (s, 1H), 7.31 (s, 1H), 7.15 (d, J=7.2 Hz, 1H), 6.76 (d, J=7.6 Hz, 1H), 6.72 (s, 1H), 4.51 (t, J=8.8 Hz, 2H), 4.06-4.04 (m, 3H), 3.43-3.41 (m, 1H), 3.16-3.12 (m, 2H), 3.03 (d, J=10.80 Hz, 1H), 2.84 (d, J=9.60 Hz, 1H), 2.08-2.02 (m, 1H), 1.97-1.87 (m, 5H), 1.80 (s, 3H), 1.3 (t, J=6.8 Hz, 3H). LCMS: (Method A) 369.2 (M+H), Rt. 2.161 min, 99.71% (Max). HPLC: (Method A), Rt. 2.204 min, 98.24% (Max).

Example 27: N-(1-(1-(1-(quinoxalin-6-yl)ethyl)piperidin-4-yl)-1H-pyrazol-4-yl)acetamide

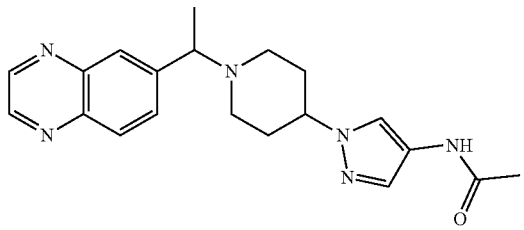 [SMILES: CC(=O)Nc1cnn(C2CCN(C(C)c3ccc4nccnc4c3)CC2)c1]

To a stirred solution of Intermediate 11 (0.5 g, 2.4 mmol) in DMF (10 mL), TEA (1.0 mL, 7.2 mmol) and Intermediate 1 (0.46 g, 2.4 mmol) were added at 0-5° C. The reaction mixture was stirred at 100° C. overnight. The completion of the reaction was confirmed by TLC. The reaction mixture was evaporated at 50° C. under reduced pressure and diluted with EtOAc (30 mL). The organic layer was washed with water (10 mL), brine (10 mL) and dried over $Na_2SO_4$. After evaporation of the solvents, the crude product was purified by flash chromatography (5-8% MeOH in DCM) to give the title compound (yellow solid). $^1$H NMR (400 MHz, DMSO-$d_6$): δ 9.88 (s, 1H), 8.93 (dd, J=7.2, 1.6 Hz, 2H), 8.08 (d, J=8.8 Hz, 1H), 8.00 (s, 1H), 7.93 (dd, J=8.8, 1.6 Hz, 1H), 7.84 (s, 1H), 7.38 (s, 1H), 4.12-4.04 (m, 1H), 3.84-3.83 (m, 1H), 3.09-3.06 (m, 1H), 2.90-2.87 (m, 1H), 2.14-2.12 (m, 2H), 1.95 (s, 3H), 1.90-1.88 (m, 4H), 1.44 (d, J=6.80 Hz, 3H). LCMS: (Method A) 365.2 (M+H), Rt. 1.73 min, 97.63% (Max). HPLC: (Method A), Rt. 1.74 min, 97.46% (Max).

Example 28: (1-(1-(1-(2,3-dihydrobenzofuran-6-yl)ethyl) piperidin-4-yl)-1H-pyrazol-4-yl) methanol

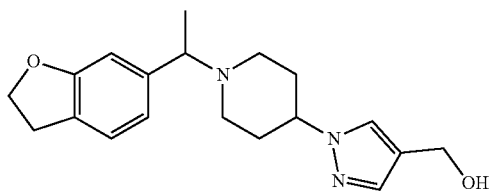 [SMILES: CC(c1ccc2c(c1)OCC2)N1CCC(n2cc(CO)cn2)CC1]

To a stirred solution of Example 32 (0.4 g, 1.08 mmol) in dry THF: MeOH mixture (4:1, 10 mL), lithium borohydride (0.81 mL, 1.62 mmol, 2M in THF) was added at 0° C. and reaction was stirred at rt for 10 h. The reaction mixture was quenched with ice cooled water (10 mL) and extracted with EtOAc (25 mL). The organic layer was washed with brine (4 mL), dried over anhydrous $Na_2SO_4$ and concentrated. The resulting crude product was purified by flash chromatography to afford the title compound. Yield: 56.4% (0.2 g, off white solid). $^1$H NMR (400 MHz, DMSO-d6): δ 7.62 (s, 1H), 7.33 (s, 1H), 7.15 (d, J=7.6 Hz, 1H), 6.76 (d, J=7.2 Hz, 1H), 6.72 (s, 1H), 4.76 (t, J=5.2 Hz, 1H), 4.51 (t, J=8.4 Hz, 2H), 4.32 (d, J=5.6 Hz, 2H), 3.99 (q, J=6.8 Hz, 1H), 3.42 (d, J=6.4 Hz, 1H), 3.14 (t, J=8.4 Hz, 2H), 3.03 (d, J=10.80 Hz, 1H), 2.84 (t, J=10.0 Hz, 1H), 2.08-2.02 (m, 1H), 1.97-1.81 (m, 5H), 1.3 (d, J=6.8 Hz, 3H). LCMS: (Method A) 328.3 (M+H), Rt. 2.14 min, 96.83% (Max). HPLC: (Method A) Rt. 2.14 min, 98.26% (Max).

Example 29: 1-(1-(2,3-Dihydrobenzofuran-6-yl)ethyl)-4-(4-(trifluoromethyl)-1H-pyrazol-1-yl) piperidine

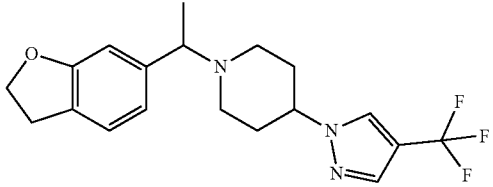 [SMILES: CC(c1ccc2c(c1)OCC2)N1CCC(n2cc(C(F)(F)F)cn2)CC1]

To a stirred solution of 4-(4-(trifluoromethyl)-1H-pyrazol-1-yl)piperidine hydrochloride (0.25 g, 0.98 mmol, Anichem) in dry MeCN (5 mL), TEA (0.4 mL, 2.94 mmol) and Intermediate 31 (0.27 g, 1.47 mmol) were added at rt. The reaction mixture was stirred at 60° C. for 14 h. Then the reaction mixture was cooled to rt and partitioned between water (5 mL) and EtOAc (60 mL). The organic layer was dried over anhydrous Na2SO4 and concentrated. The resulting crude product was purified by MD Autoprep HPLC (Method C) (yellow thick oil). $^1$H NMR (400 MHz, MeOD): δ 8.15 (s, 1H), 7.77 (s, 1H), 7.22 (d, J=7.2 Hz, 1H), 6.86 (d, J=7.2 Hz, 1H), 6.81 (s, 1H), 4.57 (t, J=8.4 Hz, 2H), 4.31-4.30 (m, 1H), 3.81-3.80 (m, 1H), 3.44-3.43 (m, 1H), 3.21 (t, J=8.8 Hz, 2H), 3.21-3.19 (m, 1H), 2.50-2.49 (m, 2H), 2.22-2.13 (m, 4H), 1.53 (d, J=6.0 Hz, 3H).

LCMS: (Method A) 366.3 (M+H), Rt. 3.36 min, 97.15% (Max). HPLC: (Method A) Rt. 3.31 min, 95.61% (Max).

Example 30: 1-(1-(2,3-dihydrobenzofuran-6-yl)ethyl)-4-(4-fluoro-1H-pyrazol-1-yl)piperidine

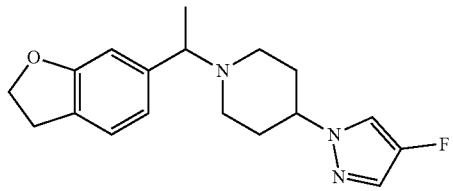 [SMILES: CC(c1ccc2c(c1)OCC2)N1CCC(n2cc(F)cn2)CC1]

The title compound was synthesized according to the procedure described for Example 29, starting from Intermediate 31 and 4-fluoro-1H-pyrazole. The crude product was purified by MD auto prep (Method B) to get the title compound (brown thick oil). $^1$H NMR (400 MHz, DMSO-$d_6$): δ 7.92 (d, J=4.4 Hz, 1H), 7.42 (d, J=4.0 Hz, 1H), 7.14 (d, J=7.2 Hz, 1H), 6.76-6.71 (m, 2H), 4.50 (t, J=8.4 Hz, 2H), 3.95 (s, 1H), 3.42-3.40 (m, 1H), 3.16-3.11 (m, 2H), 3.04-3.02 (m, 1H), 2.84-2.81 (m, 1H), 2.04 (t, J=9.60 Hz, 1H), 1.94-1.83 (m, 4H), 1.80-1.77 (m, 1H), 1.27 (d, J=6.40 Hz, 3H). LCMS: (Method A) 316.2 (M+H), Rt. 2.79 min, 98.82% (Max). HPLC: (Method A), Rt. 2.77 min, 98.59% (Max).

Example 31: 6-(1-(4-(4-(Trifluoromethyl)-1H-pyrazol-1-yl)piperazin-1-yl)ethyl)quinoxaline

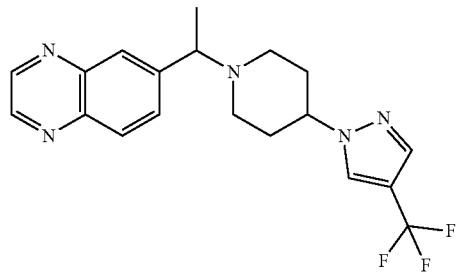 [SMILES: CC(c1ccc2nccnc2c1)N1CCC(n2cc(C(F)(F)F)cn2)CC1]

Step 1: tert-Butyl 4-(4-(trifluoromethyl)-1H-pyrazol-1-yl)piperidine-1-carboxylate To a stirred suspension of 4-(trifluoromethyl)-1H-pyrazole (0.4 g, 2.93 mmol) in dry DMF (8 mL), $Cs_2CO_3$ (1.91 g, 5.87 mmol) and tert-butyl 4-((methylsulfonyl)-oxy) piperidine-1-carboxylate (obtained as described in Step 1 of Intermediate 10, 1.23 g, 5.87 mmol) were added at 0° C. The reaction mixture was stirred at 80° C. overnight, and the reaction mixture was diluted with water (10 mL). The product was extracted with EtOAc (2×10 mL). The combined organic layer was dried over anhydrous $Na_2SO_4$ and concentrated under vacuum. The crude product was purified by flash chromatography on silica gel (230-400 mesh) to afford the title compound. Yield: 73% (0.69 g, pale brown solid). $^1$H NMR (400 MHz, DMSO-$d_6$): δ 8.71 (s, 1H), 7.90 (s, 1H), 4.44 (q, J=7.6 Hz, 1H), 4.04-4.06 (m, 2H), 3.10-2.69 (m, 2H), 2.02-2.08 (d, 2H), 1.84-1.75 (m, 2H), 1.42 (s, 9H). LCMS: (Method A) 264.2 (M-56), Rt. 4.82 min, 91.18% (Max).

Step 2: 4-(4-(trifluoromethyl)-1H-pyrazol-1-yl)piperidine hydrochloride

To a stirred solution of tert-butyl 4-(4-(trifluoromethyl)-1H-pyrazol-1-yl) piperidine-1-carboxylate (0.68 g, 2.12 mmol) in dry dioxane (2 mL), HCl in dioxane (5 mL, 4 N) was added and the reaction mixture was stirred at rt for 3 h. The reaction mixture was concentrated under vacuum and the resulting crude product was suspended in diethyl ether (15 mL) and filtered, affording the title compound. Yield: 94% (0.51 g, off white solid). LCMS: (Method A) 220.2 (M+H), Rt. 2.29 min, 87.95% (Max).

Step 3: 6-(1-(4-(4-(Trifluoromethyl)-1H-pyrazol-1-yl)piperazin-1-yl)ethyl)quinoxaline To a stirred solution of 4-(4-(trifluoromethyl)-1H-pyrazol-1-yl)piperidine hydrochloride (0.3 g, 1.17 mmol) in DMF (6 mL), TEA (0.5 mL, 3.52 mmol) and Intermediate 1 (0.27 g, 1.41 mmol) were added at 0° C. The reaction mixture was stirred at 80° C. for 16 h. The completion of the reaction was monitored by TLC. The reaction mixture was evaporated under reduced pressure and diluted with EtOAc (10 mL). The organic layer was washed with water (5 mL), brine solution (5 mL) and dried over $Na_2SO_4$. After evaporation of the solvents, the crude product was purified by flash chromatography on silica gel (230-400 mesh) using 55-60% EtOAc in pet ether as eluent, affording the title compound (off white solid). $^1$H NMR (400 MHz, DMSO-$d_6$): δ 9.01-8.82 (m, 2H), 8.44 (s, 1H), 8.09 (d, J=8.8 Hz, 1H), 8.01 (s, 1H), 7.92 (d, J=8.8 Hz, 1H), 7.88 (s, 1H), 4.31-4.07 (m, 1H), 3.86 (d, J=6.4 Hz, 1H), 3.10-3.12 (m, 1H), 2.92-2.94 (m, 1H), 2.16-2.18 (m, 2H), 2.03-1.99 (m, 4H), 1.45 (d, J=6.40 Hz, 3H). LCMS: (Method A) 376.3 (M+H), Rt. 2.79 min, 98.0% (Max). HPLC: (Method A) Rt 2.86 min, 97.1% (Max).

Example 32: Ethyl 1-(1-(1-(2, 3-dihydrobenzofuran-6-yl) ethyl) piperidin-4-yl)-1H-pyrazole-4-carboxylate

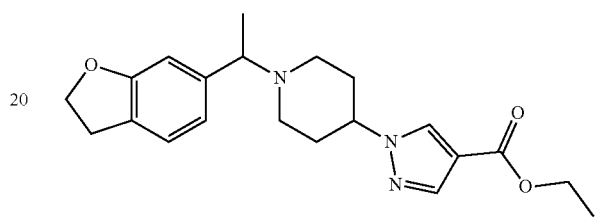

To a stirred solution of Intermediate 10 (2 g, 7.70 mmol) in dry DMF (20 mL), TEA (3.2 mL, 23.10 mmol) and Intermediate 4 (1.54 g, 8.47 mmol) were added. The reaction mixture was stirred at 60° C. overnight. After cooling down the mixture at rt, the solvent was evaporated. Resulting crude mixture was diluted with EtOAc (50 mL) and washed with water (20 mL). The organic layer was dried over anhydrous $Na_2SO_4$ and concentrated. The crude product was purified by flash chromatography affording the title compound (off white solid). $^1$H NMR (400 MHz, DMSO-$d_6$): δ 8.33 (s, 1H), 7.85 (s, 1H), 7.15 (d, J=7.2 Hz, 1H), 6.76 (d, J=7.6 Hz, 1H), 6.72 (s, 1H), 4.51 (t, J=8.8 Hz, 2H), 4.20 (q, J=7.2 Hz, 2H), 4.14-4.10 (m, 1H), 3.46 (q, J=6.8 Hz, 1H), 3.14 (t, J=8.4 Hz, 2H), 3.03-3.06 (m, 1H), 2.85-2.87 (m, 1H), 2.08-2.02 (m, 1H), 1.98-1.77 (m, 5H), 1.36-1.24 (m, 6H). LCMS: (Method A) 370.2 (M+H), Rt. 2.95 min, 97.6% (Max). HPLC: (Method A), Rt. 3.05 min, 97.08% (Max).

Example 33: (1-(1-(1-(2,3-dihydrobenzofuran-5-yl) ethyl)piperidine-4-yl)-1H-pyrazol-4-yl) methanamine

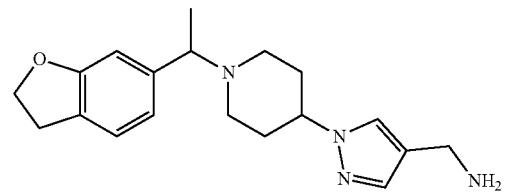 [SMILES: CC(c1ccc2c(c1)OCC2)N1CCC(n2cc(CN)cn2)CC1]

The title compound was synthesized according to the procedure described for Example 126, starting from Example 28 (colorless solid). $^1$H NMR (400 MHz, DMSO-d6): δ 7.57 (s, 1H), 7.30 (s, 1H), 7.14 (d, J=7.2 Hz, 1H), 6.75 (dd, J=7.6, 1.2 Hz, 1H), 6.71 (s, 1H), 4.50 (t, J=8.8 Hz, 2H), 3.96 (br s, 1H), 3.53 (s, 2H), 3.13 (t, J=8.8 Hz, 2H), 3.03-3.00 (m, 1H), 2.82-2.81 (m, 1H), 2.04-2.03 (m, 1H), 1.96-1.77 (m, 6H), 1.26 (d, J=6.80 Hz, 3H). LCMS: (Method A) 327.0 (M+H), Rt. 4.26 min, 96.2% (Max).

Example 34: 1-(1-(2,3-dihydrobenzofuran-6-yl)ethyl)-4-(4-(methylsulfonyl)-1H-pyrazol-1-yl)piperidine

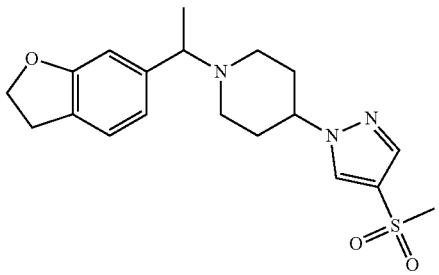 [SMILES: CC(c1ccc2c(c1)OCC2)N1CCC(n2cc(S(C)(=O)=O)cn2)CC1]

The title compound was synthesized according to the procedure described for Example 12, starting from Intermediate 4 and Intermediate 21 (pale yellow thick oil). ¹H NMR (400 MHz, DMSO-d₆): δ 8.43 (s, 1H), 7.90 (s, 1H), 7.14 (d, J=7.6 Hz, 1H), 6.76-6.71 (m, 2H), 4.50-4.48 (m, 2H), 4.16 (t, J=10.8 Hz, 1H), 3.46-3.43 (m, 1H), 3.17-3.11 (m, 5H), 3.02 (d, J=10.8 Hz, 1H), 2.85 (d, J=11.2 Hz, 1H), 2.08-1.83 (m, 6H), 1.27 (d, J=6.80 Hz, 3H). LCMS: (Method A) 376.2 (M+H), Rt. 2.40 min, 97.18% (Max). HPLC: (Method A) Rt. 2.40 min, 97.83% (Max).

Example 35: 1-(6-(4-(1-(2,3-dihydrobenzofuran-6-yl)ethyl)piperazin-1-yl)pyridazin-3-yl)ethan-1-ol

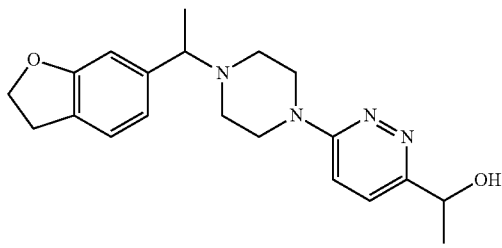 [SMILES: CC(O)c1ccc(N2CCN(C(C)c3ccc4c(c3)OCC4)CC2)nn1]

Step 1: 3-(4-(1-(2,3-dihydrobenzofuran-6-yl)ethyl)piperazin-1-yl)-6-iodopyridazine To a stirred solution of Intermediate 13 (700 mg, 2.3 mmol) in DMF (10 mL), TEA (929 mg, 9.2 mmol) and 3-chloro-6-iodopyridazine (826 mg, 3.4 mmol) were added at rt and the resulting mixture was heated at 60° C. overnight. Completion of the reaction was monitored by TLC. Reaction mixture was evaporated. The resulting crude product was triturated with DCM (15 mL) and filtered. The solid was dried under reduced pressure, affording the title compound (off white solid). LCMS: (Method A) 437.3 (M+H), Rt. 2.71 min, 79.38% (Max).

Step 2: 1-(6-(4-(1-(2,3-dihydrobenzofuran-6-yl)ethyl)piperazin-1-yl)pyridazin-3-yl)ethan-1-one The title compound was prepared according to the procedure described for Example 36, step 1, starting from 3-(4-(1-(2,3-dihydrobenzofuran-6-yl)ethyl)piperazin-1-yl)-6-iodopyridazine. The crude product was purified by flash chromatography (eluent: 50% EtOAc in pet ether), affording the title compound that was directly used in the next step. (pale brown oil). LCMS: (Method A) 353.2 (M+H), Rt. 2.51 min, 23.74% (Max).

Step 3: 1-(6-(4-(1-(2,3-dihydrobenzofuran-6-yl)ethyl)piperazin-1-yl)pyridazin-3-yl)ethan-1-ol The title compound was prepared according to the procedure described for Example 36, step 2, starting from 1-(6-(4-(1-(2,3-dihydrobenzofuran-6-yl)ethyl)piperazin-1-yl)pyridazin-3-yl)ethan-1-one. The crude was purified by flash chromatography (elutant: 6% MeOH in DCM), affording the title product (beige solid). ¹H NMR (400 MHz, DMSO-d₆): δ 7.42 (d, J=9.6 Hz, 1H), 7.22 (d, J=9.6 Hz, 1H), 7.14 (d, J=7.6 Hz, 1H), 6.77-6.71 (m, 2H), 5.32 (d, J=4.8 Hz, 1H), 4.81-4.78 (m, 1H), 4.49 (t, J=8.8 Hz, 2H), 3.51-3.35 (m, 5H), 3.12 (t, J=8.4 Hz, 2H), 2.66-2.32 (m, 4H), 1.34-1.23 (m, 6H). LCMS: (Method A) 355.2 (M+H), Rt. 1.93 min, 96.62% (Max). HPLC: (Method A) Rt 1.93 min, 97.83% (Max).

Example 36: 1-(6-(4-(1-(quinoxalin-6-yl)ethyl)piperazin-1-yl)pyridazin-3-yl)ethan-1-ol

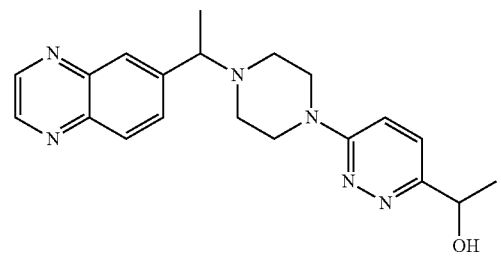 [SMILES: CC(O)c1ccc(N2CCN(C(C)c3ccc4nccnc4c3)CC2)nn1]

Step 1: 1-(6-(4-(1-(quinoxalin-6-yl)ethyl)piperazin-1-yl)pyridazin-3-yl)ethan-1-one A stirred solution of Example 43 (500 mg, 1.12 mmol) in dry toluene was degassed for 15 min with nitrogen. 1-ethoxy vinyl tributyltin (450 mg, 1.23 mmol) and bis(triphenylphosphine)palladium(II) dichloride (80 mg, 0.12 mmol) were added at rt. The reaction mixture was stirred for overnight at 90° C. It was cooled to rt and filtered through celite. The filtrate was concentrated under vacuum and HCl solution (50 mL, 6N) was added. The mixture was stirred 1 h at rt and was neutralized with a saturated solution of NaHCO₃. It was extracted with DCM (100 mL), the organic layer was dried over anhydrous Na₂SO₄ and concentrated. The crude product was purified by flash chromatography to afford the title compound (pale brown solid). LCMS: (Method A) 173.0 (M+H), Rt. 2.20 min, 95.3% (Max).

Step 2: 1-(6-(4-(1-(quinoxalin-6-yl)ethyl)piperazin-1-yl)pyridazin-3-yl)ethan-1-ol To a stirred solution of 1-(6-(4-(1-(quinoxalin-6-yl)piperazin-1-yl)pyridazin-3-yl)ethan-1-one (100 mg, 0.21 mmol) in dry MeOH (2 mL), sodium borohydride (15 mg, 0.41 mmol, spectrochem) was added portion wise at 0° C. and the resulting mixture was stirred for 1 h. It was concentrated under vacuum. The resulting residue was dissolved in DCM (20 mL), washed with brine (5 mL), dried over Na₂SO₄ and concentrated. The crude product was purified by MD Autoprep HPLC (Method D) to afford the titled compound (brown thick oil). ¹H NMR (400 MHz, DMSO-d₆): δ 8.94 (dd, J=7.2, 1.6 Hz, 2H), 8.10 (d, J=8.4 Hz, 1H), 8.02 (s, 1H), 7.93 (d, J=8.8 Hz, 1H), 7.44 (d, J=9.6 Hz, 1H), 7.25 (d, J=9.2 Hz, 1H), 5.34 (d, J=4.8 Hz, 1H), 4.80 (t, J=4.8 Hz, 1H), 3.78 (d, J=6.4 Hz, 1H), 3.55-3.51 (m, 4H), 2.64-2.61 (m, 2H), 2.51-2.33 (m, 2H), 1.45 (d, J=6.80 Hz, 3H), 1.35 (d, J=6.8 Hz, 3H). LCMS: (Method A) 365.2 (M+H), Rt. 1.43 min, 99.32% (Max). HPLC: (Method A) Rt. 1.46 min, 98.77% (Max).

Example 37: (5-(4-(1-(quinoxalin-6-yl)ethyl)piperazin-1-yl)-1,3,4-thiadiazol-2-yl)methanol

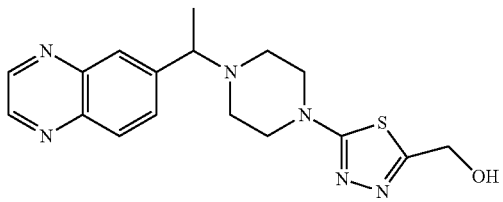 [SMILES: CC(c1ccc2nccnc2c1)N1CCN(c2nnc(CO)s2)CC1]

The title compound was synthesized according to the procedure described for Example 113, starting from Example 120 (brown solid). ¹H NMR (400 MHz, DMSO-d₆): δ 8.93 (d, J=6.4 Hz, 2H), 8.08 (d, J=8.8 Hz, 1H), 8.00 (s, 1H), 7.90 (d, J=8.8 Hz, 1H), 4.56 (d, J=38.4 Hz, 2H), 3.89-3.75 (m, 1H), 3.50-3.38 (m, 4H), 2.70-2.65 (m, 2H), 2.49-2.42 (m, 2H), 1.43 (d, J=6.4 Hz, 3H). LCMS: (Method A) 357.2 (M+H), Rt. 1.50 min, 99.4% (Max). HPLC: (Method A) Rt 1.52 min, 99.30% (Max).

Example 38: (S)-6-(4-(1-(quinoxalin-6-yl)ethyl)piperazin-1-yl)pyridazin-3(2H)-one or (R)-6-(4-(1-(quinoxalin-6-yl)ethyl)piperazin-1-yl)pyridazin-3(2H)-one

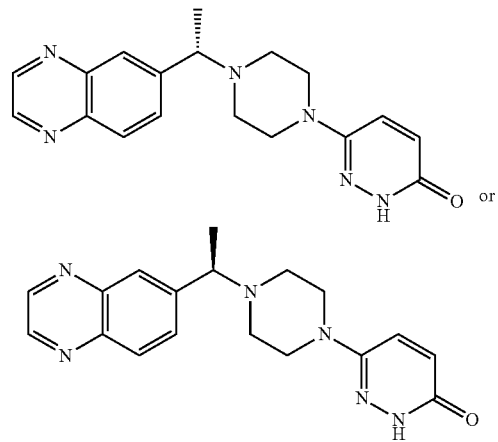

The racemic mixture of Example 39 was separated by chiral preparative HPLC, using the chiral preparative HPLC (Method Q).

The first eluting compound correspond to Example 38. Yield: 28% (14.32 mg, off white solid). ¹H NMR (400 MHz, DMSO-d₆): δ 12.06 (s, 1H), 8.93 (d, J=6.8 Hz, 2H), 8.08 (d, J=8.8 Hz, 1H), 7.99 (s, 1H), 7.89 (d, J=8.8 Hz, 1H), 7.45 (d, J=10.4 Hz, 1H), 6.74 (d, J=10.0 Hz, 1H), 3.79-3.71 (m, 1H), 3.18-3.16 (m, 4H), 2.61-2.59 (m, 4H), 1.43 (d, J=6.40 Hz, 3H). LCMS: (Method A) 337.2 (M+H), Rt. 1.463 min, 99.315% (Max). HPLC: (Method A) Rt. 1.549 min, 98.517% (Max). CHIRAL HPLC: (Method P) Rt. 11.173 min, 99.708% (Max).

Second eluting compound: Yield: 28% (14.17 mg, off white solid). ¹H NMR (400 MHz, DMSO-d₆): δ 12.06 (s, 1H), 8.93 (d, J=5.6 Hz, 2H), 8.08 (d, J=8.4 Hz, 1H), 7.99 (s, 1H), 7.90 (d, J=7.6 Hz, 1H), 7.45 (d, J=10.4 Hz, 1H), 6.74 (d, J=11.2 Hz, 1H), 3.76-3.74 (m, 1H), 3.19-3.16 (m, 4H), 2.60-2.57 (m, 4H), 1.43 (d, J=7.20 Hz, 3H). LCMS: (Method A) 337.2 (M+H), Rt. 1.462 min, 99.692% (Max). HPLC: (Method A) Rt. 1.554 min, 99.192% (Max). CHIRAL HPLC: (Method P) Rt. 17.953 min, 99.333% (Max).

Example 39: 2-amino-1-(4-(1-(quinoxalin-6-yl)ethyl)piperazin-1-yl)ethan-1-one

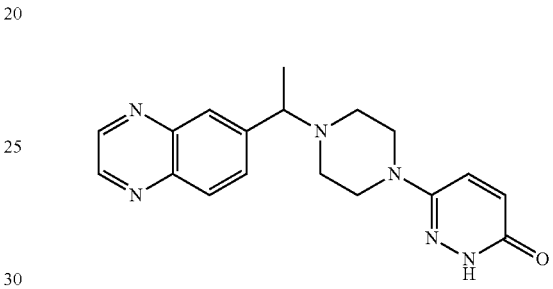

Step 1: 6-(1-(4-(6-chloropyridazin-3-yl)piperazin-1-yl)ethyl)quinoxaline

To a stirred solution of Intermediate 2 (0.4 g, 1.43 mmol, IS00537-008) in THF (8 mL, 20 V), TEA (0.598 mL, 4.3 mmol) and 3,6-dichloropyridazine (0.427 g, 2.86 mmol) were added at rt and the mixture was stirred at 70° C. for 12 h. It was evaporated under vacuum. Water (5 mL) was added to the resulting crude mixture and was extracted with EtOAc (2×15 mL). The combined EtOAc layer was washed with brine and dried over Na₂SO₄ concentrated under vacuum. The crude product was purified by flash chromatography to afford title compound (yellow thick oil). ¹H NMR (400 MHz, DMSO-d6): δ 300 MHz, DMSO-d6: δ 8.94 (d, J=3.6 Hz, 2H), 8.11-8.08 (m, 3H), 7.52 (dd, J=2.7, 9.6 Hz, 1H), 7.35 (d, J=9.6 Hz, 1H), 3.80-3.78 (m, 1H), 3.58-3.44 (m, 4H), 2.73-2.59 (m, 4H), 1.45 (d, J=6.6 Hz, 3H). LCMS: (Method A) 355.2 (M+H), Rt. 1.989 min, 93.235% (Max).

Step 2: 2-amino-1-(4-(1-(quinoxalin-6-yl)ethyl)piperazin-1-yl)ethan-1-one

To a stirred solution of 6-(1-(4-(6-chloropyridazin-3-yl)piperazin-1-yl)ethyl)quinoxaline in AcOH (2.3 mL), NaOAc (0.106 g, 1.29 mmol) was added and the mixture was stirred at 200° C. in microwave reactor for 10 min. Reaction mixture was concentrated under vacuum. 10% MeOH in THF (3 mL) and KOH (0.072 g, 1.29 mmol) were added and the mixture was refluxed for 1 h. After evaporation of the solvents, the crude product was purified by flash chromatography to afford the title product (brown thick oil). ¹H NMR (400 MHz, DMSO-d₆): δ 12.06 (s, 1H), 8.94 (q, J=1.6 Hz, 2H), 8.09 (d, J=8.8 Hz, 1H), 8.00 (d, J=1.6 Hz, 1H), 7.91 (q, J=2.0 Hz, 1H), 7.46 (d, J=10.0 Hz, 1H), 6.76 (d, J=10.0 Hz, 1H), 3.77-3.76 (m, 1H), 3.19 (t, J=5.2 Hz, 4H), 2.56-

2.55 (m, 4H), 1.44 (d, J=6.40 Hz, 3H). LCMS: (Method A) 337.0 (M+H), Rt. 1.540 min, 96.804% (Max). HPLC: (Method A) Rt 1.509 min, 99.272% (Max).

Example 40: 3-(4-(1-(2,3-dihydrobenzofuran-6-yl)ethyl)piperazin-1-yl)-6-(trifluoromethyl)pyridazine

SGN020581-01-00501-018N01:

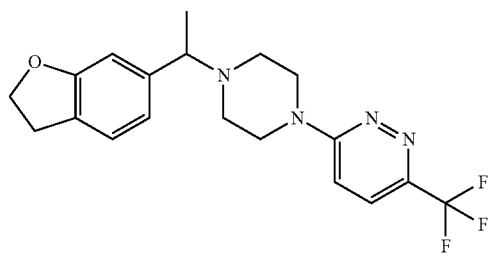 [SMILES: CC(c1ccc2c(c1)OCC2)N1CCN(c2ccc(C(F)(F)F)nn2)CC1]

To a stirred solution of Intermediate 13 (250 mg, 0.81 mmol), in DMF (3 mL), TEA (330 mg, 3.26 mmol) and 3-chloro-6-(trifluoromethyl)pyridazine (224 mg, 1.2 mmol) were added at rt. The resulting mixture was heated at 85° C. overnight. Completion of the reaction was monitored by TLC. Reaction mixture was evaporated. Water (10 mL) was added and extracted with EtOAc (2×30 mL). The combined organic layer was washed with water (10 mL), brine (10 mL), dried over Na$_2$SO$_4$ and evaporated. The crude product was purified by flash chromatography (elutant: 2-3% MeOH in DCM) to afford the title product (off white solid). $^1$H NMR (400 MHz, DMSO-d$_6$): δ 7.77 (d, J=9.6 Hz, 1H), 7.35 (d, J=9.6 Hz, 1H), 7.15 (d, J=7.6 Hz, 1H), 6.77-6.73 (m, 2H), 4.50 (t, J=8.4 Hz, 2H), 3.68 (t, J=5.2 Hz, 4H), 3.39-3.32 (m, 1H), 3.13 (t, J=8.4 Hz, 2H), 2.44-2.39 (m, 4H), 1.29 (d, J=6.8 Hz, 3H). LCMS: (Method A) 379.2 (M+H), Rt. 3.06 min, 95.18% (Max). HPLC: (Method A) Rt. 3.12 min, 98.21% (Max).

Example 41: 6-(1-(4-(6-Fluoropyridazin-3-yl)piperazin-1-yl)ethyl)quinoxaline

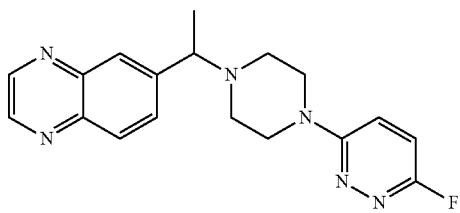 [SMILES: CC(c1ccc2nccnc2c1)N1CCN(c2ccc(F)nn2)CC1]

To a stirred solution of Intermediate 2 (0.2 g, 0.8 mmol) in dry DMF (5 mL), TEA (0.36 ml, 2.85 mmol) and 3,6-difluropyridazine (0.19 g, 1.90 mmol) were added at rt and the reaction mixture was stirred at 90° C. overnight. The resulting reaction mixture was cooled to rt and DMF was evaporated under reduced pressure. To the resulting crude product, water (20 mL) was added and product was extracted with EtOAc (2×30 mL). The organic layer was dried over Na$_2$SO$_4$ and concentrated. The crude product was purified by flash chromatography to afford the title compound (pale brown thick oil). $^1$H NMR (400 MHz, CDCl$_3$) δ 8.12 (d, J=8.8 Hz, 1H), 8.05 (d, J=1.6 Hz, 1H), 7.92 (dd, J=8.6, 1.6 Hz, 1H), 7.06 (dd, J=9.6, 6.0 Hz, 1H), 7.00 (dd, J=7.4, 3.2 Hz, 1H), 3.75-3.68 (m, 1H), 3.67-3.56 (m, 4H), 2.76-2.70 (m, 2H), 2.62-2.57 (m, 2H), 1.52 (d, J=6.8 Hz, 3H). LCMS: (Method A) 339.2 (M+H), Rt. 1.77 min, 98.68% (Max). HPLC: (Method A) Rt 1.80 min, 97.59% (Max).

Example 42: 6-(1-(4-(6-(trifluoromethyl)pyridazin-3-yl)piperazin-1-yl)ethyl)quinoxaline

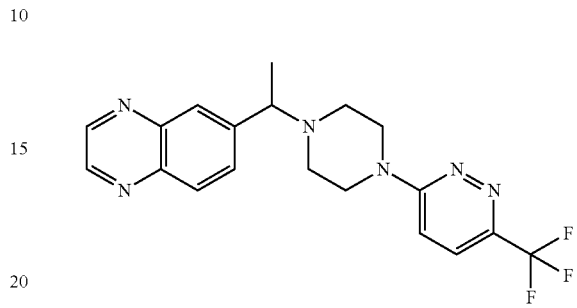

To a stirred solution of Intermediate 2 (0.2 g, 0.8 mmol) in dry DMF (5 mL), TEA (0.36 ml, 2.85 mmol) and 2-chloro-5(trifluoromethyl) pyridazine (0.19 g, 1.90 mmol) were added at rt and the reaction mixture was stirred at 90° C. overnight. The resulting reaction mixture was cooled to rt and DMF was evaporated under reduced pressure. To the resulting crude product, water (20 mL) was added and the product was extracted with EtOAc (2×30 mL). The organic layer was dried over Na$_2$SO$_4$ and concentrated. This product was purified by flash chromatography to afford the title compound (off white solid). $^1$H NMR (400 MHz, CDCl$_3$): δ 8.87 (s, 2H), 8.14 (d, J=8.8 Hz, 1H), 8.06 (s, 1H), 7.94 (s, 1H), 7.47 (d, J=9.6 Hz, 1H), 6.90 (d, J=9.6 Hz, 1H), 3.80-3.82 (m, 5H), 2.68-2.70 (m, 1H), 1.54-1.52 (br s, 6.8 Hz, 3H). LCMS: (Method A) 389.2 (M+H), Rt. 2.50 min, 99.68% (Max). HPLC: (Method A) Rt. 2.53 min, 98.79% (Max).

Example 43: 6-(1-(4-(6-(trifluoromethyl)pyridazin-3-yl)piperazin-1-yl)ethyl)quinoxaline

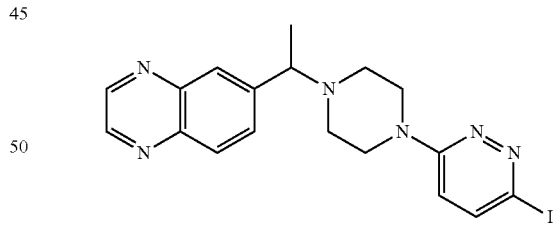

To a stirred solution of Intermediate 2 (0.25 g, 0.8 mmol) in dry DMF (5 mL), TEA (0.36 ml, 2.85 mmol) and 3-chloro-6-iodopyridazine (0.123 g, 0.99 mmol) were added at rt and the reaction mixture was stirred at 90° C. overnight. The resulting reaction mixture was cooled to rt and DMF was evaporated under reduced pressure. To the resulting crude mixture, water (20 mL) was added and the product was extracted with EtOAc (2×30 mL). The resulting organic layer was dried over Na$_2$SO$_4$ and concentrated. This crude product was purified by flash column chromatography to afford the title compound (off white solid). $^1$H NMR (400 MHz, CDCl$_3$): δ 8.86-8.84 (m, 2H), 8.11 (d, J=8.8 Hz, 1H), 8.03 (d, J=2.0 Hz, 1H), 7.90 (dd, J=8.8, 2.0 Hz, 1H), 7.45 (d, J=9.6 Hz, 1H), 6.60 (d, J=9.6 Hz, 1H), 3.65-3.58 (m, 5H), 2.73-2.67 (m, 2H), 2.59-2.54 (m, 2H), 1.51 (d, J=6.8 Hz, 3H). LCMS: (Method A) 447.0 (M+H), Rt. 2.13 min, 99.59% (Max). HPLC: (Method A) Rt. 2.16 min, 98.99% (Max).

Example 44: 6-(1-(4-(6-Methylpyridazin-3-yl)piperazin-1-yl)ethyl)quinoxaline

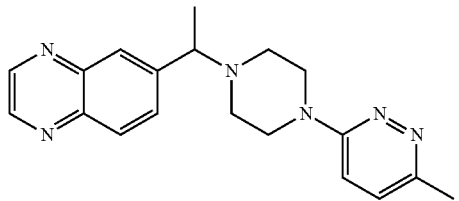 [SMILES: Cc1ccc(N2CCN(C(C)c3ccc4nccnc4c3)CC2)nn1]

The stirred solution of Example 43 (100 mg, 0.22 mmol) in dry toluene was degassed for 15 min with nitrogen. Tetramethyl tin (79.0 mg, 0.44 mmol) and bis(triphenylphosphine)palladium dichloride (14 mg, 0.02 mmol) were added at rt and the resulting mixture was stirred overnight at 90° C. The reaction mixture was cooled to rt and filtered through celite. This filtrate was concentrated and an aqueous solution of HCl (6 N, 50 mL) was added. The resulting mixture was stirred for 1 h at rt and was neutralized with a saturated solution of NaHCO$_3$. It was extracted with DCM (100 mL). The organic layer was dried over anhydrous Na$_2$SO$_4$ and concentrated. The crude was purified by flash chromatography to afford the title compound (brown thick oil). $^1$H NMR (400 MHz, DMSO-d$_6$): δ 8.94 (d, J=5.2 Hz, 2H), 8.10 (d, J=8.8 Hz, 1H), 8.02 (s, 1H), 7.92 (t, J=6.8 Hz, 1H), 7.26 (d, J=9.2 Hz, 1H), 7.17 (d, J=9.6 Hz, 1H), 3.88 (d, J=15.8 Hz, 1H), 3.50 (br s, 4H), 2.60 (br s, 4H), 2.41 (s, 3H), 1.45 (d, J=5.60 Hz, 3H). LCMS: (Method A) 335.2 (M+H), Rt. 1.43 min, 96.15% (Max). HPLC: (Method A) Rt. 1.42 min, 96.07% (Max).

Example 45: 3-(4-(1-(2,3-dihydrobenzofuran-6-yl)ethyl)piperazin-1-yl)-6-(methylsulfonyl)pyridazine

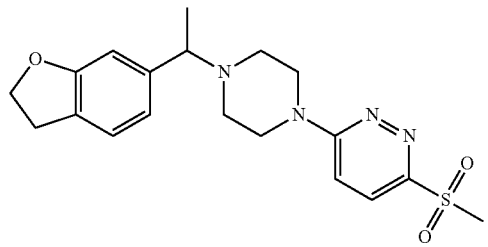 [SMILES: CC(c1ccc2c(c1)OCC2)N1CCN(c2ccc(S(C)(=O)=O)nn2)CC1]

To a stirred solution of Intermediate 13 (150 mg, 0.49 mmol), TEA (198 mg, 1.96 mmol) in MeCN (5 mL), 3-chloro-6-(methylsulfonyl)pyridazine (142 mg, 0.73 mmol) was added at rt and the resulting mixture was stirred overnight at rt. Completion of the reaction was monitored by TLC. Reaction mass was evaporated. Water (10 mL) was added and was extracted with EtOAc (2×30 mL). The combined organic layer was washed with water (10 mL), brine solution (10 mL), dried over Na$_2$SO$_4$ and evaporated. The crude product was purified by flash chromatography (elutant: 75% EtOAc in pet ether) and further purified by MD Autoprep HPLC (Method C) to afford the title product (off white solid). $^1$H NMR (400 MHz, DMSO-d6): δ 7.81 (d, J=9.6 Hz, 1H), 7.36 (d, J=9.6 Hz, 1H), 7.15 (d, J=7.2 Hz, 1H), 6.76 (d, J=7.6 Hz, 1H), 6.72 (s, 1H), 4.50 (t, J=8.4 Hz, 2H), 3.72-3.70 (m, 4H), 3.39-3.38 (m, 1H), 3.28 (s, 3H), 3.13 (t, J=9.2 Hz, 2H), 2.44-2.32 (m, 4H), 1.29 (d, J=6.80 Hz, 3H). LCMS: (Method A) 389.2 (M+H), Rt. 2.35 min, 97.79% (Max). HPLC: (Method A) Rt. 2.37 min, 97.46% (Max).

Example 46: N-(6-(4-(1-(quinoxalin-6-yl)ethyl)piperazin-1-yl)pyridin-3-yl)acetamide

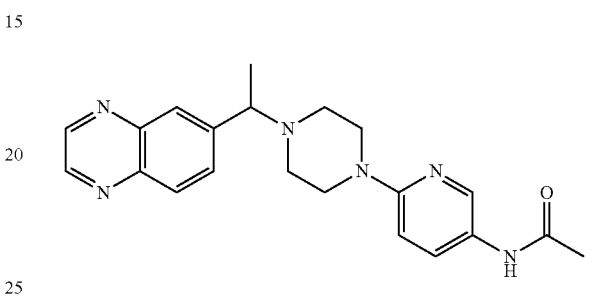

The title compound was synthesized according to the procedure described for Example 40, starting from Intermediate 2 and N-(6-bromopyridin-2-yl)acetamide (off white solid). $^1$H NMR (400 MHz, DMSO-d$_6$): δ 9.89 (s, 1H), 8.94 (d, J=2.0 Hz, 1H), 8.93 (d, J=1.6 Hz, 1H), 8.09 (d, J=8.8 Hz, 1H), 8.01 (s, 1H), 7.93 (d, J=8.8 Hz, 1H), 7.47 (d, J=8.0 Hz, 1H), 7.32 (s, 1H), 6.44 (d, J=8.0 Hz, 1H), 3.77-3.72 (m, 1H), 3.51-3.45 (m, 4H), 2.58-2.53 (m, 2H), 2.49-2.44 (m, 2H), 2.04 (s, 3H), 1.44 (d, J=6.80 Hz, 3H). LCMS: (Method A) 377.2 (M+H), Rt. 1.998 min, 95.756% (Max).
HPLC: (Method A) Rt. 2.057 min, 95.464% (Max).

Example 47: 1-(6-(4-(1-(2,3-dihydrobenzofuran-6-yl)ethyl)piperazin-1-yl)pyridin-3-yl)ethan-1-ol

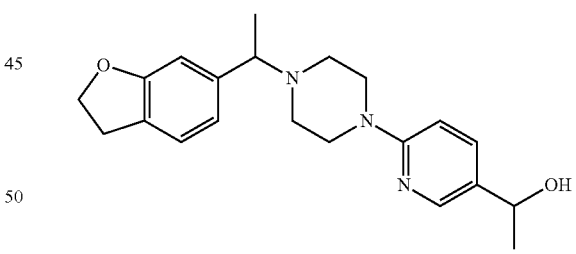

Step 1: 1-(5-bromopyridin-2-yl)-4-(1-(2,3-dihydrobenzofuran-6-yl)ethyl)piperazine To a stirred solution of 2-chloro-5-bromopyridine (5.4 g, 19.7 mmol) in dry DMF (25 mL), TEA (11.6 mL, 77.5 mmol) and Intermediate 13 (3 g, 16.4 mmol) were added at rt and the mixture was stirred at 80° C. overnight. The reaction mixture was evaporated under vacuum and the resulting crude mixture was dissolved in EtOAc (100 mL), washed with water (20 mL), dried over anhydrous Na$_2$SO$_4$ and concentrated. The crude product was purified by flash chromatography to afford the title compound (yellow solid). $^1$H NMR (400 MHz, DMSO-d$_6$): δ 8.13 (d, J=2.4 Hz, 1H), 7.64 (dd, J=9.2, 2.4 Hz, 1H), 7.15-7.11 (m, 1H), 6.78-6.71 (m, 3H), 4.52-4.48 (m, 3H), 3.43-3.41 (m, 4H), 3.17-3.11 (m, 2H), 2.46-2.43 (m, 2H), 2.38-2.32 (m, 2H), 1.28-1.25 (m, 3H). LCMS: (Method A) 388.0 (M+H), Rt. 2.34 min, 90.08% (Max).

Step 2: 1-(6-(4-(1-(2,3-dihydrobenzofuran-6-yl)ethyl)piperazin-1-yl)pyridin-3-yl)ethan-1-one The title compound was synthesized according to the procedure described for Example 36, step 1, starting with 1-(5-bromopyridin-2-yl)-4-(1-(2,3-dihydrobenzofuran-6-yl)ethyl)piperazine (0.8 g, 2.00 mmol). The resulting crude product was purified by flash chromatography, affording the title compound. Yield: 53% (0.5 g, yellow solid). $^1$H NMR (400 MHz, DMSO-d$_6$): δ 8.69 (s, 1H), 7.94 (d, J=9.2 Hz, 1H), 7.15 (d, J=7.6 Hz, 1H), 6.83 (d, J=8.8 Hz, 1H), 6.76 (d, J=7.2 Hz, 1H), 6.72 (s, 1H), 4.53-4.48 (m, 3H), 3.65-3.64 (m, 4H), 3.16-3.11 (m, 2H), 2.51-2.50 (m, 4H), 2.40 (s, 3H), 1.31 (d, J=9.20 Hz, 3H). LCMS: (Method A) 352.0 (M+H), Rt. 2.00 min, 98.60% (Max).

Step 3: 1-(6-(4-(1-(2,3-dihydrobenzofuran-6-yl)ethyl)piperazin-1-yl)pyridin-3-yl)ethan-1-ol The title compound was synthesized according to the procedure described for Example 36, step 2, starting with 1-(6-(4-(1-(2,3-dihydrobenzofuran-6-yl)ethyl)piperazin-1-yl)pyridin-3-yl)ethan-1-one (0.1 g, 0.27 mmol) in dry MeOH (5 mL). The crude was purified by MD Autoprep HPLC (Method C) to get the title compound (off white solid). $^1$H NMR (400 MHz, DMSO-d$_6$): δ 8.02 (s, 1H), 7.48 (d, J=8.0 Hz, 1H), 7.14 (d, J=8.0 Hz, 1H), 6.76-6.71 (m, 3H), 4.99 (d, J=3.6 Hz, 1H), 4.52-4.47 (m, 3H), 3.40-3.38 (m, 5H), 3.15-3.11 (m, 2H), 2.37-2.36 (m, 4H), 1.27 (dd, J=6.2, 2.8 Hz, 6H). LCMS: (Method B) 354.0 (M+H), Rt. 5.06 min, 97.55% (Max). HPLC: (Method A) Rt. 1.98 min, 98.32% (Max).

Example 48: 2-(6-(4-(1-(2,3-dihydrobenzofuran-6-yl)ethyl)piperazin-1-yl)pyridin-3-yl)propan-2-ol

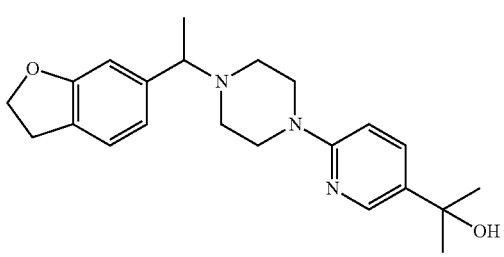 [SMILES: CC(c1ccc2c(c1)OCC2)N1CCN(c2ccc(C(C)(C)O)cn2)CC1]

The title compound was synthesized according to the procedure described for Example 85, starting from Example 62 (0.3 g, 0.39 mmol). The crude product was purified by flash chromatography to get the title compound (off white solid). $^1$H NMR (400 MHz, DMSO-d$_6$): δ 8.17 (s, 1H), 7.58 (d, J=8.8 Hz, 1H), 7.15 (d, J=6.8 Hz, 1H), 6.78-6.70 (m, 3H), 4.92 (s, 1H), 4.51 (t, J=8.0 Hz, 2H), 3.39-3.34 (m, 5H), 3.14 (t, J=8.4 Hz, 2H), 2.39-2.38 (m, 4H), 1.39 (s, 6H), 1.28 (d, J=5.60 Hz, 3H). LCMS: (Method B) 368.0 (M+H), Rt. 5.28 min, 98.92% (Max). HPLC: (Method A) Rt. 2.07 min, 98.89% (Max).

Example 49: 1-(6-(4-(1-(2,3-dihydrobenzofuran-6-yl)ethyl)piperazin-1-yl)pyridin-3-yl)-2-methylpropan-1-ol

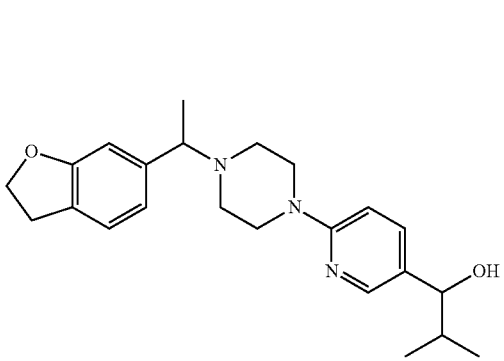 [SMILES: CC(C)C(O)c1ccc(N2CCN(C(C)c3ccc4c(c3)OCC4)CC2)nc1]

The title compound was synthesized according to the procedure described for Example 12, starting from Intermediate 4 and Intermediate 18 (pale brown solid). $^1$H NMR (400 MHz, DMSO-d$_6$): δ 7.96 (s, 1H), 7.43 (dd, J=8.80, 2.00 Hz, 1H), 7.15 (d, J=7.60 Hz, 1H), 6.78-6.72 (m, 3H), 4.96 (d, J=4.00 Hz, 1H), 4.51 (t, J=8.80 Hz, 2H), 4.10 (t, J=4.40 Hz, 1H), 3.49-3.36 (m, 4H), 3.14 (t, J=8.80 Hz, 2H), 2.47-2.46 (m, 2H), 2.39-2.34 (m, 2H), 1.79-1.74 (m, 1H), 1.28 (d, J=6.80 Hz, 3H), 0.87 (d, J=6.80 Hz, 3H), 0.70 (d, J=6.80 Hz, 3H). LCMS: (Method A) 382.3 (M+H), Rt. 2.33 min, 98.4% (Max). HPLC: (Method A) Rt 2.38 min, 99.4% (Max).

Example 50: 1-(6-(4-(1-(2,3-dihydrobenzofuran-6-yl)ethyl)piperazin-1-yl)pyridin-3-yl)-2,2,2-trifluoroethan-1-ol

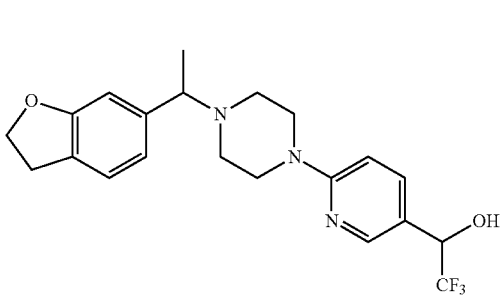 [SMILES: CC(c1ccc2c(c1)OCC2)N1CCN(c2ccc(C(O)C(F)(F)F)cn2)CC1]

The title compound was synthesized according to the procedure described for Example 87, starting from Example 62 (pale brown solid). $^1$H NMR (400 MHz, DMSO-d$_6$): δ 8.13 (s, 1H), 7.57 (d, J=8.80 Hz, 1H), 7.14 (d, J=7.60 Hz, 1H), 6.81-6.74 (m, 2H), 6.71-6.67 (m, 2H), 5.02 (s, 1H), 4.49 (t, J=8.80 Hz, 2H), 3.52-3.40 (m, 5H), 3.13 (t, J=8.40 Hz, 2H), 2.46-2.33 (m, 4H), 1.27 (d, J=6.40 Hz, 3H). LCMS: (Method A) 408.0 (M+H), Rt. 2.73 min, 94.3% (Max). HPLC: (Method A) Rt 2.67 min, 97.8% (Max).

Example 51: 2-(6-(4-(1-(quinoxalin-6-yl) ethyl) piperazin-1-yl) pyridin-3-yl) propan-2-ol

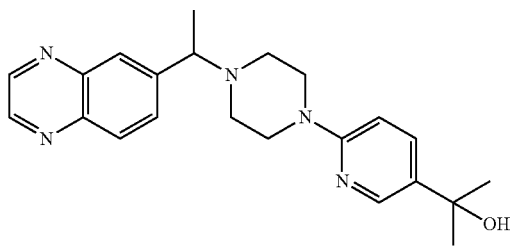 [SMILES: CC(c1ccc2nccnc2c1)N1CCN(c2ccc(C(C)(C)O)cn2)CC1]

The title compound was synthesized according to the procedure described for Example 85, starting from Example 66 (off white solid). ¹H NMR (400 MHz, DMSO-d₆): δ 8.93 (d, J=5.2 Hz, 2H), 8.16 (s, 1H), 8.08 (d, J=8.8 Hz, 1H), 8.00 (s, 1H), 7.92 (d, J=8.4 Hz, 1H), 7.57 (t, J=6.8 Hz, 1H), 6.71 (d, J=9.2 Hz, 1H), 4.89 (d, J=6.0 Hz, 1H), 3.74 (d, J=6.8 Hz, 1H), 3.42 (br s, 4H), 2.50 (br s, 4H), 1.43 (d, J=6.4 Hz, 3H), 1.37 (s, 6H). LCMS: (Method A) 378.3 (M+H), Rt. 1.651 min, 98.83% (Max). HPLC: (Method A), Rt. 1.644 min, 98.54% (Max).

Example 52: 1-(6-(4-(1-(quinoxalin-6-yl)ethyl)piperazin-1-yl)pyridin-3-yl)ethan-1-ol

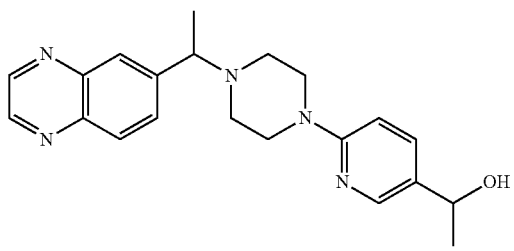 [SMILES: CC(O)c1ccc(N2CCN(C(C)c3ccc4nccnc4c3)CC2)nc1]

The title compound was synthesized according to the procedure described for Example 84, starting from Intermediate 1 and Intermediate 16 (brown solid). ¹H NMR (400 MHz, DMSO-d₆): δ 8.94-8.93 (m, 2H), 8.08 (d, J=8.8 Hz, 1H), 8.01 (d, J=9.6 Hz, 2H), 7.91 (d, J=8.8 Hz, 1H), 7.48 (d, J=8.4 Hz, 1H), 6.74 (d, J=8.8 Hz, 1H), 4.99 (d, J=4.0 Hz, 1H), 4.62-4.59 (m, 1H), 3.75-3.73 (m, 1H), 3.43-3.39 (m, 4H), 2.60-2.57 (m, 2H), 2.45-2.44 (m, 2H), 1.43 (d, J=6.40 Hz, 3H), 1.28 (d, J=6.40 Hz, 3H). LCMS: (Method B) 364.0 (M+H), Rt. 4.16 min, 98.12% (Max). HPLC: (Method A) Rt. 1.54 min, 99.11% (Max).

Example 53: 6-(1-(4-(6-methoxypyridin-3-yl)piperazin-1-yl)ethyl)quinoxaline

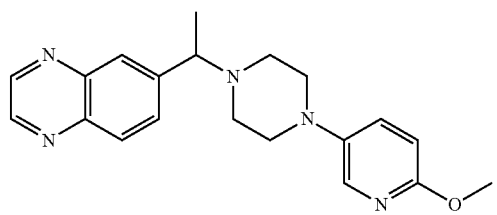 [SMILES: COc1ccc(N2CCN(C(C)c3ccc4nccnc4c3)CC2)cn1]

The title compound was synthesized according to the procedure described for Example 12, starting from Intermediate 1 and 1-(5-methoxy-2-pyridinyl)piperazine (brown solid). 1H NMR (400 MHz, DMSO-d₆): δ 8.93 (q, J=1.6 Hz, 2H), 8.08 (d, J=8.8 Hz, 1H), 8.00 (s, 1H), 7.91 (q, J=1.6 Hz, 1H), 7.74 (d, J=3.2 Hz, 1H), 7.40 (q, J=2.8 Hz, 1H), 6.68 (d, J=8.8 Hz, 1H), 3.75 (s, 4H), 3.08-3.03 (m, 4H), 2.66-2.61 (m, 4H), 1.44 (d, J=6.40 Hz, 3H). LCMS: (Method A) 350.0 (M+H), Rt. 1.908 min, 97.686% (Max). HPLC: (Method A) Rt. 1.856 min, 98.999% (Max).

Example 54: 5-(4-(1-(quinoxalin-6-yl)ethyl)piperazin-1-yl)pyridin-2(1H)-one

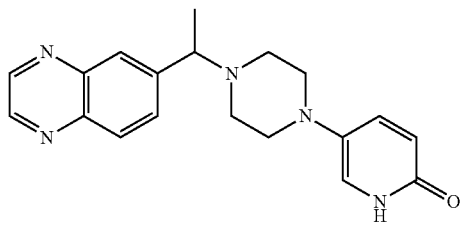

To a stirred solution of Example 53 (0.04 g, 0.114 mmol) in DCM (0.4 mL) cooled to 0° C. was added BBr₃ in DCM (1M) (0.24 mL, 0.228 mmol) and the mixture was stirred at rt for 18 h. Reaction mixture was cooled to 0° C. and quenched with a saturated solution of NaHCO₃ (1 mL) and extracted with DCM (2×10 mL), washed with brine (2 mL) and dried over Na₂SO₄. The resulting crude product was purified by flash chromatography (eluent: 10% MeOH in DCM), to afford the title product (dark fluffy solid). ¹H NMR (400 MHz, DMSO-d₆): δ 11.16 (s, 1H), 8.93 (d, J=6.8 Hz, 2H), 8.08 (d, J=8.4 Hz, 1H), 7.99 (s, 1H), 7.89 (d, J=8.4 Hz, 1H), 7.38 (q, J=3.2 Hz, 1H), 6.70 (s, 1H), 6.27 (d, J=9.6 Hz, 1H), 3.75-3.73 (m, 1H), 2.88-2.81 (m, 4H), 2.62-2.56 (m, 4H), 1.42 (d, J=6.80 Hz, 3H). LCMS: (Method A) 336.2 (M+H), Rt. 1.555 min, 97.205% (Max). HPLC: (Method A) Rt. 1.523 min, 99.129% (Max).

Example 55: 2-methyl-1-(6-(4-(1-(quinoxalin-6-yl)ethyl)piperazin-1-yl)pyridin-3-yl)propan-1-ol

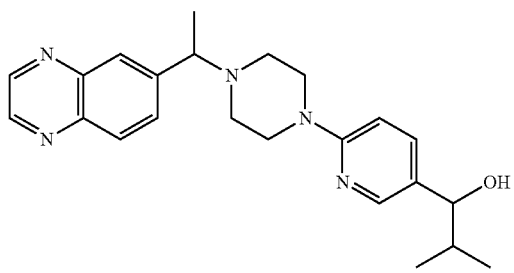 [SMILES: CC(C)C(O)c1ccc(N2CCN(C(C)c3ccc4nccnc4c3)CC2)nc1]

The title compound was synthesized according to the procedure described for Example 12, starting from Intermediate 1 and Intermediate 18 (pale brown solid). ¹H NMR (400 MHz, DMSO-d₆): δ 8.94 (dd, J=7.20, 2.00 Hz, 2H), 8.09 (d, J=8.40 Hz, 1H), 8.01 (d, J=1.20 Hz, 1H), 7.93 (d, J=2.00 Hz, 1H), 7.91 (d, J=1.60 Hz, 1H), 7.43 (dd, J=8.80, 2.40 Hz, 1H), 6.75 (d, J=8.80 Hz, 1H), 4.96 (d, J=4.40 Hz, 1H), 4.11-4.09 (m, 1H), 3.76-3.74 (m, 1H), 3.52-3.38 (m, 4H), 2.59-2.57 (m, 2H), 2.48-2.45 (m, 2H), 1.78-1.73 (m, 1H), 1.44 (d, J=6.80 Hz, 3H), 0.86 (d, J=6.80 Hz, 3H), 0.69 (d, J=6.80 Hz, 3H). LCMS: (Method A) 392.3 (M+H), Rt. 1.93 min, 99.2% (Max). HPLC: (Method A) Rt 1.97 min, 99.6% (Max).

Example 56: 2,2,2-trifluoro-1-(6-(4-(1-(quinoxalin-6-yl)ethyl)piperazin-1-yl)pyridin-3-yl)ethan-1-ol

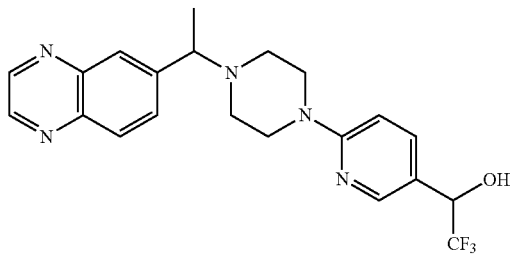 [SMILES: CC(c1ccc2nccnc2c1)N1CCN(c2ccc(C(O)C(F)(F)F)cn2)CC1]

The title compound was synthesized according to the procedure described for Example 87, starting from Example 66 (pale brown solid). ¹H NMR (400 MHz, DMSO-d₆): δ 8.94-8.93 (m, 2H), 8.14 (s, 1H), 8.09 (d, J=8.40 Hz, 1H), 8.01 (s, 1H), 7.93 (d, J=8.80 Hz, 1H), 7.58 (d, J=8.80 Hz, 1H), 6.82 (d, J=8.80 Hz, 1H), 6.69 (d, J=5.60 Hz, 1H), 5.03 (t, J=6.40 Hz, 1H), 3.77-3.75 (m, 1H), 3.54-3.45 (m, 4H), 2.60-2.59 (m, 4H), 1.44 (d, J=6.80 Hz, 3H). LCMS: (Method A) 418.2 (M+H), Rt. 2.12 min, 99.3% (Max). HPLC: (Method A) Rt 2.16 min, 99.3% (Max).

Example 57: 4-(6-(4-(1-(quinoxalin-6-yl)ethyl)piperazin-1-yl)pyridin-3-yl)tetrahydro-2H-pyran-4-ol

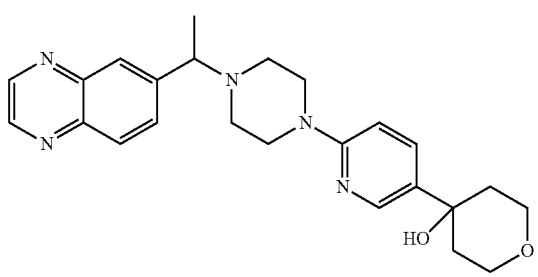 [SMILES: CC(c1ccc2nccnc2c1)N1CCN(c2ccc(C3(O)CCOCC3)cn2)CC1]

To a degassed solution of Intermediate 24 (125 mg, 0.58 mmol), Intermediate 2 (212 mg, 0.76 mmol) and sodium tert butoxide (432 mg, 1.46 mmol) in 1,4 dioxane (4 mL) at rt, Pd₂(dba)₃ (27 mg, 0.03 mmol) and BINAP (36 mg, 0.05 mmol) were added. The reaction mixture was sealed and heated to 100° C. overnight. It was then filtered through celite and concentrated. Water (4 mL) was added and was extracted with EtOAc (2×10 mL). The combined organic layer was dried over Na₂SO₄ and concentrated. The crude product was purified by flash chromatography (eluent: 5-6% MeOH in DCM). After trituration in Et₂O and filtration, the title product was isolated (brown solid). ¹H NMR (400 MHz, DMSO-d₆): δ 8.93 (d, J=5.2 Hz, 2H), 8.18 (s, 1H), 8.08 (d, J=8.8 Hz, 1H), 8.00 (s, 1H), 7.91 (d, J=8.8 Hz, 1H), 7.62-7.50 (m, 1H), 6.74 (d, J=9.2 Hz, 1H), 4.92 (s, 1H), 3.77-3.71 (m, 3H), 3.70-3.65 (m, 2H), 3.50-3.39 (m, 4H), 2.63-2.52 (m, 4H), 1.91-1.87 (m, 2H), 1.53-1.50 (m, 2H), 1.43 (d, J=6.40 Hz, 3H). LCMS: (Method A) 420.2 (M+H), Rt. 1.62 min, 95.40% (Max). HPLC: (Method A) Rt 1.59 min, 98.75% (Max).

Example 58: 3-(6-(4-(1-(quinoxalin-6-yl)ethyl)piperazin-1-yl)pyridin-3-yl)tetrahydrofuran-3-ol

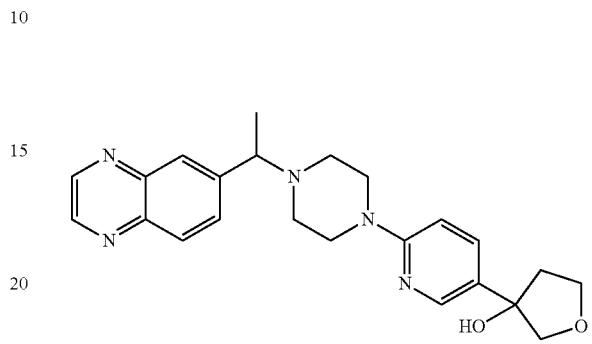

The title compound was synthesized according to the procedure described for Example 57, starting from Intermediate 2 and Intermediate 25 (brown solid). ¹H NMR (400 MHz, DMSO-d₆): δ 8.93 (dd, J=6.4, 2.6 Hz, 2H), 8.18 (d, J=2.0 Hz, 1H), 8.08 (d, J=8.4 Hz, 1H), 8.00 (s, 1H), 7.91 (d, J=8.4 Hz, 1H), 7.56 (dd, J=8.8, 5.6 Hz, 1H), 6.75 (d, J=8.8 Hz, 1H), 3.98-3.92 (m, 2H), 3.80-3.71 (m, 2H), 3.64 (d, J=8.8 Hz, 1H), 3.50-3.37 (m, 4H), 2.59-2.55 (m, 2H), 2.47-2.39 (m, 3H), 2.19-2.13 (m, 1H), 2.08-2.04 (m, 1H), 1.4 (d, J=6.8 Hz, 3H). LCMS: (Method A) 406.2 (M+H), Rt. 1.55 min, 99.00% (Max). HPLC: (Method A) Rt 1.53 min, 99.39% (Max).

Example 59: 3-(6-(4-(1-(quinoxalin-6-yl)ethyl)piperazin-1-yl)pyridin-3-yl)oxetan-3-ol

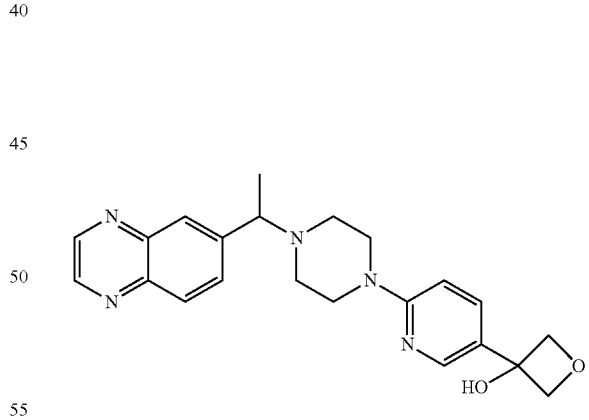

The title compound was synthesized according to the procedure described for Example 57, starting from Intermediate 2 and Intermediate 26 (pale brown solid). ¹H NMR (400 MHz, DMSO-d₆): δ 8.94-8.82 (m, 2H), 8.26 (d, J=2.4 Hz, 1H), 8.08 (d, J=8.4 Hz, 1H), 8.00 (s, 1H), 7.92 (d, J=8.4 Hz, 1H), 7.68-7.65 (m, 1H), 6.81 (d, J=9.2 Hz, 1H), 6.22 (d, J=2.0 Hz, 1H), 4.70-4.64 (m, 4H), 3.80-3.70 (m, 1H), 3.58-3.40 (m, 4H), 2.64-2.57 (m, 2H), 2.49-2.43 (m, 2H), 1.43 (d, J=6.80 Hz, 3H). LCMS: (Method A) 392.2 (M+H), Rt. 1.51 min, 98.29% (Max). HPLC: (Method A) Rt 1.49 min, 98.37% (Max).

Example 60: 1-(6-(4-(1-(quinoxalin-6-yl)ethyl)piperazin-1-yl)pyridin-3-yl)cyclohexan-1-ol

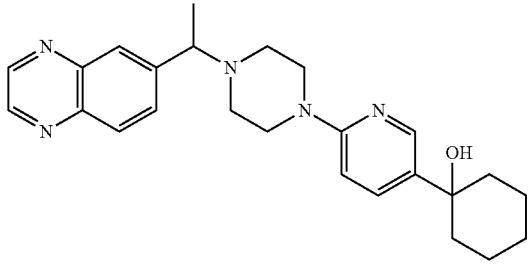 [SMILES: CC(c1ccc2nccnc2c1)N1CCN(c2ccc(C3(O)CCCCC3)cn2)CC1]

The title compound was synthesized according to the procedure described for Example 57, starting from Intermediate 2 and Intermediate 27 (off white solid). $^1$H NMR (400 MHz, DMSO-d$_6$): δ 8.93 (dd, J=7.2, 1.6 Hz, 2H), 8.18 (d, J=2.4 Hz, 1H), 8.09 (d, J=8.4 Hz, 1H), 8.01 (s, 1H), 7.93-7.91 (m, 1H), 7.58 (d, J=2.4, 8.8 Hz, 1H), 6.72 (d, J=8.8 Hz, 1H), 4.59 (s, 1H), 3.76-3.74 (m, 1H), 3.48-3.43 (m, 4H), 2.60-2.56 (m, 2H), 2.46-2.43 (m, 2H), 1.69-1.66 (m, 3H), 1.63-1.60 (m, 4H), 1.45-1.43 (m, 5H), 1.30-1.20 (m, 1H). LCMS: (Method A) 418.2 (M+H), Rt. 2.18 min, 98.2% (Max). HPLC: (Method A) Rt 2.16 min, 98.9% (Max).

Example 61: 1-(6-(4-(1-(quinoxalin-6-yl)ethyl)piperazin-1-yl)pyridin-3-yl)cyclopentan-1-ol

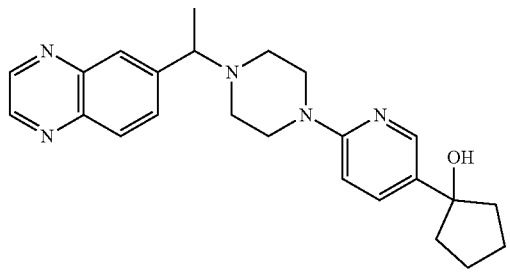 [SMILES: CC(c1ccc2nccnc2c1)N1CCN(c2ccc(C3(O)CCCC3)cn2)CC1]

The title compound was synthesized according to the procedure described for Example 57, starting from Intermediate 2 and Intermediate 30 (yellow solid). $^1$H NMR (400 MHz, DMSO-d$_6$): δ 8.94 (dd, J=1.6, 7.0 Hz, 2H), 8.18 (d, J=2.0 Hz, 1H), 8.09 (d, J=8.4 Hz, 1H), 8.01 (s, 1H), 7.92 (dd, J=1.6, 8.4 Hz, 1H), 7.57 (dd, J=2.8, 8.8 Hz, 1H), 6.73 (d, J=8.8 Hz, 1H), 4.68 (s, 1H), 3.76-3.74 (m, 1H), 3.45-3.44 (m, 4H), 2.61-2.58 (m, 2H), 2.45-2.43 (m, 2H), 1.83-1.80 (m, 6H), 1.77-1.68 (m, 2H), 1.44 (d, J=6.40 Hz, 3H). LCMS: (Method A) 404.2 (M+H), Rt. 1.9 min, 98.6% (Max). HPLC: (Method A) Rt 1.8 min, 99.44% (Max).

Example 62: Methyl 6-(4-(1-(2,3-dihydrobenzofuran-6-yl)ethyl)piperazin-1-yl)nicotinate

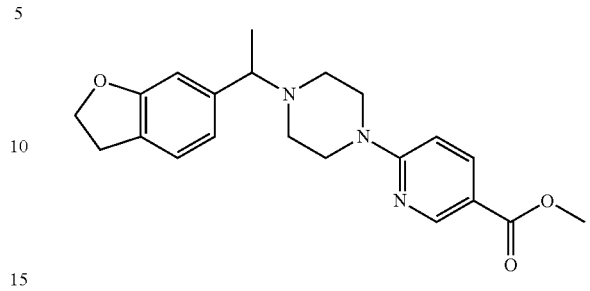

The title compound was synthesized according to the procedure described for Example 66, replacing Intermediate 1 with Intermediate 4 (off white solid). $^1$H NMR (400 MHz, DMSO-d$_6$): δ 8.61 (d, J=2.4 Hz, 1H), 7.91 (dd, J=9.2, 2.4 Hz, 1H), 7.14 (d, J=7.6 Hz, 1H), 6.82 (d, J=9.2 Hz, 1H), 6.76-6.71 (m, 2H), 4.49 (t, J=8.8 Hz, 2H), 3.77 (s, 3H), 3.62-3.61 (m, 4H), 3.37-3.32 (m, 1H), 3.12 (t, J=8.8 Hz, 2H), 2.46-2.33 (m, 4H), 1.27 (d, J=6.80 Hz, 3H). LCMS: (Method A) 368.3 (M+H), Rt. 2.83 min, 99.73% (Max). HPLC: (Method A) Rt 2.89 min, 99.60% (Max).

Example 63: 6-(4-(1-(2,3-dihydrobenzofuran-6-yl)ethyl)piperazin-1-yl)-N,N-dimethylnicotinamide

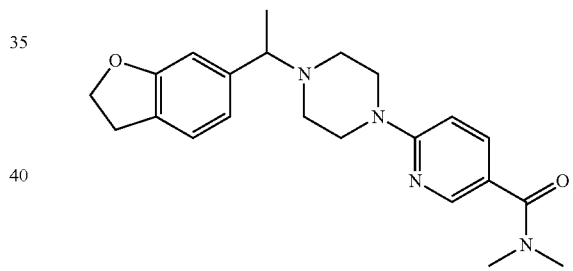

To a stirred solution of Example 65 (250 mg, 0.7 mmol) in DMF (3 mL), HATU (322 mg, 0.84 mmol) was added at rt. The mixture was cooled to 0° C. and a solution of dimethylamine in THF (1.75 mL, 3.5 mmol, 2M) and DIPEA (271 mg, 2.1 mmol) were added. The resulting mixture was stirred at rt overnight. Completion of the reaction was monitored by TLC. Reaction mixture was evaporated. The resulting crude mixture was dissolved in EtOAc (40 mL), washed with water (5 mL), a solution of 10% NaHCO$_3$ (5 mL), dried over Na$_2$SO$_4$ and evaporated. The crude product was purified by flash chromatography (3-4% MeOH in DCM as eluent) and further purified by MD Autoprep HPLC (Method C) to afford the title product (beige thick oil). $^1$H NMR (400 MHz, DMSO-d$_6$): δ 8.20-8.17 (m, 1H), 7.57 (dd, J=8.8, 2.4 Hz, 1H), 7.14 (d, J=7.2 Hz, 1H), 6.78-6.71 (m, 3H), 4.49 (t, J=8.8 Hz, 2H), 3.52-3.51 (m, 4H), 3.16-3.10 (m, 3H), 2.95 (s, 6H), 2.39-2.32 (m, 4H), 1.27 (d, J=6.8 Hz, 3H). LCMS: (Method A) 381.2 (M+H), Rt. 2.24 min, 97.05% (Max). HPLC: (Method A) Rt. 2.28 min, 99.83% (Max).

Example 64: 6-(4-(1-(2,3-dihydrobenzofuran-6-yl)ethyl)piperazin-1-yl)-N-methylnicotinamide

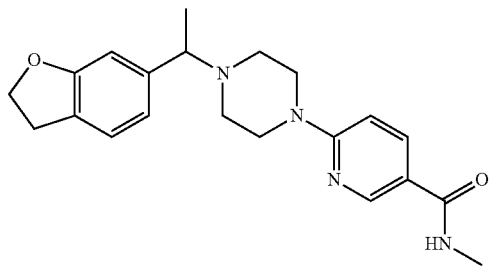 [SMILES: CNC(=O)c1ccc(N2CCN(C(C)c3ccc4c(c3)OCC4)CC2)nc1]

Example 64 was synthesized according to the protocol followed for Example 63, replacing the dimethylamine with a methylamine solution in THF (1.75 mL, 3.5 mmol, 2M). The crude product was purified by flash chromatography (2% MeOH in DCM as eluent) to afford the title product (pale brown solid). $^1$H NMR (400 MHz, DMSO-d6): δ 8.54 (d, J=2.4 Hz, 1H), 8.17 (d, J=4.4 Hz, 1H), 7.89 (dd, J=9.0, 2.0 Hz, 1H), 7.14 (d, J=7.6 Hz, 1H), 6.79-6.71 (m, 3H), 4.50 (t, J=8.4 Hz, 2H), 3.55-3.35 (m, 4H), 3.13 (t, J=8.8 Hz, 2H), 2.73 (d, J=4.4 Hz, 3H), 2.55-2.34 (m, 4H), 1.28 (d, J=6.40 Hz, 3H). LCMS: (Method A) 367.3 (M+H), Rt. 2.14 min, 98.04% (Max). HPLC: (Method A) Rt. 2.16 min, 96.78% (Max).

Example 65: 6-(4-(1-(2,3-Dihydrobenzofuran-6-yl)ethyl)piperazin-1-yl)nicotinic acid

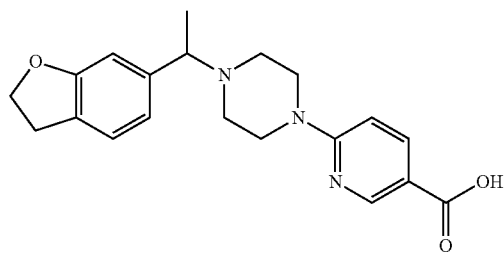 [SMILES: CC(c1ccc2c(c1)OCC2)N1CCN(c2ccc(C(=O)O)cn2)CC1]

To a stirred solution of Example 62 (750 mg, 2.0 mmol) in THF:H$_2$O mixture (9:1, 5 mL), LiOH (128 mg, 3.06 mmol) was added at rt and the resulting mixture was heated to 55° C. overnight. Completion of the reaction was monitored by TLC. Reaction mixture was neutralized with citric acid and evaporated at 45° C. under reduced pressure. The residue was dissolved in 10% MeOH in DCM (50 mL), filtrated and evaporated under reduced pressure. The resulting crude product was purified by MD Autoprep HPLC (Method B) to afford the title product. Yield: 83% (600 mg, pale brown solid). $^1$H NMR (400 MHz, DMSO-d$_6$): δ 8.50 (s, 1H), 7.86 (d, J=8.4 Hz, 1H), 7.14 (d, J=7.6 Hz, 1H), 6.77-6.71 (m, 2H), 6.60 (d, J=8.4 Hz, 1H), 4.49 (t, J=8.4 Hz, 2H), 3.43-3.37 (m, 4H), 3.32-3.31 (m, 1H), 3.13 (t, J=8.4 Hz, 2H), 2.45-2.33 (m, 4H), 1.27 (d, J=6.80 Hz, 3H). LCMS: (Method A) 354.2 (M+H), Rt. 2.30 min, 99.16% (Max). HPLC: (Method A) Rt. 2.33 min, 99.61% (Max).

Example 66: Methyl-6-(4-(1-(quinoxalin-6-yl)ethyl) piperazin-1-yl) nicotinate

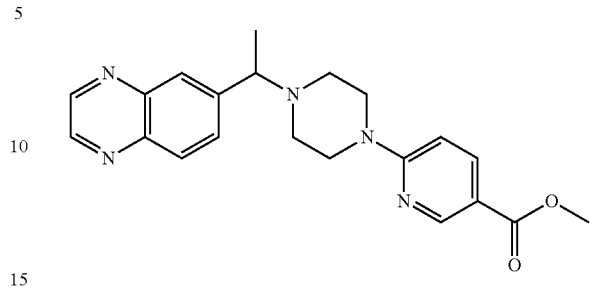

To a stirred solution of Intermediate 9 (5.35 g, 20.76 mmol) in dry DMF (55 mL), TEA (14.46 mL, 103.81 mmol) and Intermediate 1 (4 g, 20.76 mmol) were added. The reaction mixture was stirred at 80° C. overnight. Resulting reaction mixture was cooled to rt and solvent was evaporated under vacuum. The crude product was dissolved in EtOAc (200 mL) and washed with water (40 mL). The organic layer was dried over anhydrous Na$_2$SO$_4$ and concentrated. The product was purified by flash chromatography to afford the title compound (off white solid). $^1$H NMR (400 MHz, DMSO-d$_6$): δ 8.94 (dd, J=6.8, 1.6 Hz, 2H), 8.62 (s, 1H), 8.10 (d, J=8.8 Hz, 1H), 8.01 (s, 1H), 7.92 (d, J=11.6 Hz, 2H), 6.84 (d, J=8.8 Hz, 1H), 3.79 (br s, 1H), 3.78 (s, 3H), 3.65 (br s, 4H), 2.61-2.56 (m, 2H), 2.51-2.43 (m, 2H), 1.45 (d, J=6.40 Hz, 3H). LCMS: (Method A) 378.3 (M+H), Rt. 2.24 min, 99.68% (Max). HPLC: (Method A), Rt. 2.30 min, 99.34% (Max).

Example 67: 6-(4-(1-(quinoxalin-6-yl) ethyl) piperazin-1-yl) nicotinic acid

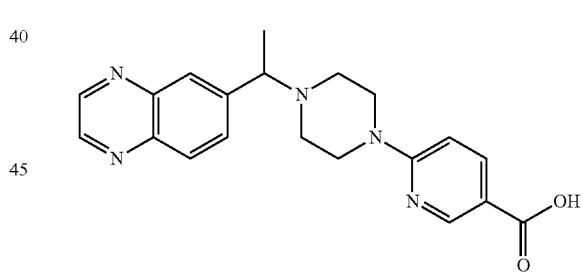

To a stirred solution of Example 66 (1.2 g, 3.179 mmol) in THF (12 mL), MeOH (6 mL) and water (2 mL), LiOH—H$_2$O (0.2 g, 4.768 mmol) was added at rt and the resulting mixture was stirred for 14 h at same temperature. The reaction mixture was evaporated under vacuum and the resulting crude mixture was acidified to pH=4 with 1.5 N HCl solution. It was extracted with 10% methanol in DCM (30 mL). The organic layer was dried over anhydrous Na$_2$SO$_4$ and concentrated. The resulting crude product was purified by flash chromatography to give title compound. Yield: 51% (600 mg, off white solid). $^1$H NMR (400 MHz, MEOD): δ 8.98 (s, 2H), 8.75 (d, J=2.0 Hz, 1H), 8.31-8.27 (m, 2H), 8.11 (dd, J=9.0, 2.4 Hz, 1H), 8.02 (dd, J=2.0, 9.0 Hz, 1H), 6.90 (d, J=8.8 Hz, 1H), 4.80 (q, J=6.8 Hz, 1H), 4.57-0.00 (m, 8H), 1.94 (d, J=6.8 Hz, 3H). LCMS: (Method A) 364.2 (M+H), Rt. 1.74 min, 99.73% (Max). HPLC: (Method A), Rt. 1.75 min, 99.87% (Max).

Example 68: N-methyl-6-(4-(1-(quinoxalin-6-yl) ethyl piperazin-1-yl) picolinamide

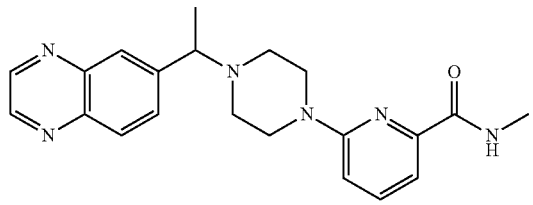 [SMILES: CNC(=O)c1cccc(N2CCN(C(C)c3ccc4nccnc4c3)CC2)n1]

A stirred solution of Intermediate 2 (0.6 g, 1.91 mmol) in dry 1,4-dioxane (10 mL), was added cesium carbonate (1.9 g, 5.88 mmol) followed by 6-chloro-N-methylpicolinamide (0.25 g, 1.47 mmol, ABCR). Nitrogen was flushed into the solution for 20 min and Pd(OAc)$_2$ (0.016 g, 0.07 mmol) and 2-2'-bis (diphenylphosphino)-1-1'-binaphthyl (0.091 g, 0.14 mmol) were added. The reaction mixture was stirred at 100° C. for 12 h. The resulting reaction mixture was filtered through celite and evaporated under vacuum. Water (5 mL) was added and the mixture was extracted with EtOAc (50 mL). The organic layer was dried over anhydrous Na$_2$SO$_4$ and evaporated. The resulting crude product was purified by column chromatography (brown solid). $^1$H NMR (400 MHz, DMSO-d$_6$): δ 8.94-8.92 (m, 2H), 8.41 (d, J=4.0 Hz, 1H), 8.09 (d, J=8.8 Hz, 1H), 8.01 (s, 1H), 7.94-7.94 (m, 1H), 7.63 (t, J=8.4 Hz, 1H), 7.25-7.23 (m, 1H), 6.94 (d, J=8.4 Hz, 1H), 3.79-3.77 (m, 1H), 3.58-3.58 (m, 4H), 2.77 (d, J=4.80 Hz, 3H), 2.59-2.58 (m, 2H), 2.49-2.45 (m, 2H), 1.45 (d, J=6.80 Hz, 3H). LCMS: (Method A) 377.2 (M+H), Rt. 2.14 min, 95.23% (Max). HPLC: (Method A) Rt. 2.07 min, 96.75% (Max).

Example 69: N, N-dimethyl-6-(4-(1-(quinoxalin-6-yl) ethyl) piperazin-1-yl) picolinamide

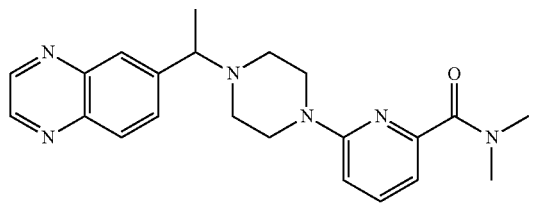 [SMILES: CC(c1ccc2nccnc2c1)N1CCN(c2cccc(C(=O)N(C)C)n2)CC1]

The title compound was synthesized according to the procedure described for Example 68, starting from Intermediate 2 and 6-chloro-N,N-dimethylpicolinamide. The resulting crude product was purified by MD Autoprep HPLC (Method C). (yellow solid). $^1$H NMR (400 MHz, DMSO-d$_6$): δ 8.94 (d, J=5.2 Hz, 2H), 8.09 (d, J=8.8 Hz, 1H), 8.01 (s, 1H), 7.93 (d, J=8.8 Hz, 1H), 7.60 (t, J=8.0 Hz, 1H), 6.84 (d, J=8.4 Hz, 1H), 6.75 (d, J=7.2 Hz, 1H), 3.78-3.76 (m, 1H), 3.50-3.49 (m, 4H), 2.95-2.92 (m, 6H), 2.60 (t, J=5.20 Hz, 2H), 2.46-2.45 (m, 2H), 1.45 (d, J=6.40 Hz, 3H), LCMS: (Method A) 391.2 (M+H), Rt. 99.57 min, 98.20% (Max). HPLC: (Method A) Rt. 2.06 min, 99.57% (Max).

Example 70: Methyl 6-(4-(1-(quinoxalin-6-yl)ethyl) piperazin-1-yl)picolinate

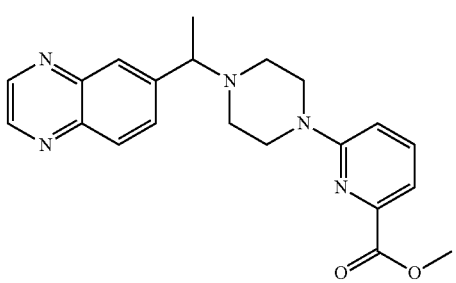 [SMILES: COC(=O)c1cccc(N2CCN(C(C)c3ccc4nccnc4c3)CC2)n1]

The title compound was synthesized according to the procedure described for Example 40, starting from Intermediate 2 and methyl 6-chloropicolinate The crude product was purified by flash chromatography (Eluent: 2.3% MeOH in DCM), to afford the title compound (off white solid). $^1$H NMR (400 MHz, DMSO-d$_6$): δ 8.94 (d, J=5.2 Hz, 2H), 8.10 (d, J=8.4 Hz, 1H), 8.02 (s, 1H), 7.93 (d, 8.2 Hz, 1H), 7.66 (t, J=8.4 Hz, 1H), 7.29 (d, J=7.2 Hz, 1H), 7.04 (d, J=8.8 Hz, 1H), 3.81-3.75 (m, 4H), 3.60-3.40 (m, 4H), 2.68-2.51 (m, 2H), 2.39-2.33 (m, 2H), 1.45 (d, J=6.80 Hz, 3H). LCMS: (Method A) 378.2 (M+H), Rt. 2.46 min, 97.78% (Max). HPLC: (Method A) Rt. 2.38 min, 97.32% (Max).

Example 71: 1-(5-(methylsulfonyl)pyridin-2-yl)-4-(1-(2,3,3a,7a-tetrahydrobenzofuran-6-yl)ethyl)piperazine

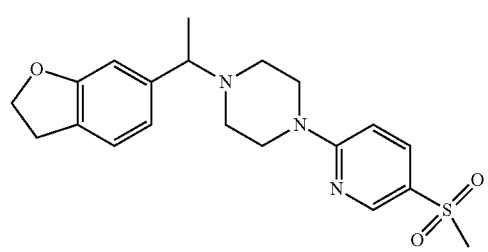 [SMILES: CC(c1ccc2c(c1)OCC2)N1CCN(c2ccc(S(C)(=O)=O)cn2)CC1]

The title compound was synthesized according to the procedure described for Example 40, starting from Intermediate 13 and 2-chloro-5-(methylsulfonyl)-pyridine (off white solid). $^1$H NMR (400 MHz, DMSO-d$_6$): δ 8.47 (d, J=2.4 Hz, 1H), 7.86 (dd, J=9.2, 2.4 Hz, 1H), 7.15 (d, J=7.6 Hz, 1H), 6.91 (d, J=9.2 Hz, 1H), 6.77-6.72 (m, 2H), 4.51 (t, J=8.8 Hz, 2H), 3.64 (t, J=4.8 Hz, 4H), 3.38 (d, J=6.8 Hz, 1H), 3.18-3.11 (m, 5H), 2.47-2.35 (m, 4H), 1.29 (d, J=6.80 Hz, 3H). LCMS: (Method A) 388.0 (M+H), Rt. 2.63 min, 97.77% (Max). HPLC: (Method A) Rt 2.61 min, 99.72% (Max).

Example 72: 6-(1-(4-(5-(methylsulfonyl)pyridin-2-yl)piperazin-1-yl)ethyl)quinoxaline

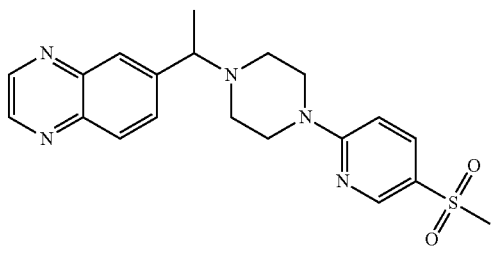 [SMILES: CC(c1ccc2nccnc2c1)N1CCN(c2ccc(S(C)(=O)=O)cn2)CC1]

The title compound was synthesized according to the procedure described for Example 40, starting from Intermediate 2 and 2-chloro-5-(methylsulfonyl)-pyridine (off white solid). $^1$H NMR (400 MHz, DMSO-$d_6$): δ 8.93 (dd, J=6.8, 1.6 Hz, 2H), 8.46 (d, J=2.8 Hz, 1H), 8.09 (d, J=8.8 Hz, 1H), 8.00 (s, 1H), 7.91 (dd, J=8.6, 2.0 Hz, 1H), 7.85 (dd, J=9.2, 2.8 Hz, 1H), 3.78 (d, J=6.8 Hz, 1H), 3.67 (s, 4H), 3.13 (s, 3H), 2.67-2.55 (m, 2H), 2.46-2.32 (m, 2H), 1.44 (d, J=6.40 Hz, 3H). LCMS: (Method A) 398.0 (M+H), Rt. 2.04 min, 98.07% (Max). HPLC: (Method A) Rt 2.01 min, 99.13% (Max).

Example 73: (2-(4-(1-(benzo[d]thiazol-5-yl)ethyl)piperazin-1-yl)pyrimidin-5-yl)methanol

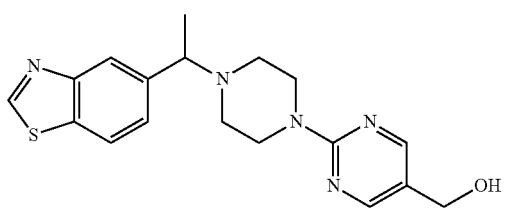 [SMILES: CC(c1ccc2scnc2c1)N1CCN(c2ncc(CO)cn2)CC1]

The title compound was synthesized according to the procedure described for Examples 98 and 75, starting from Intermediate 3 and Intermediate 12 (brown thick oil). $^1$H NMR (400 MHz, DMSO-$d_6$): δ 9.37 (s, 1H), 8.26 (s, 2H), 8.11 (d, J=8.40 Hz, 1H), 8.01 (s, 1H), 7.49 (d, J=8.40 Hz, 1H), 5.03 (t, J=5.20 Hz, 1H), 4.29 (d, J=5.60 Hz, 2H), 3.71-3.68 (m, 4H), 3.66-3.63 (m, 1H), 2.46-2.38 (m, 4H), 1.39 (d, J=6.40 Hz, 3H). LCMS: (Method A) 356.3 (M+1), Rt. 1.97 min, 97.5% (Max). HPLC: (Method A) Rt 2.07 min, 98.2% (Max).

Example 74: 2-(2-(4-(1-(2, 3-dihydrobenzofuran-6-yl) ethyl) piperazin-1-yl) pyrimidin-5-yl) propan-2-ol

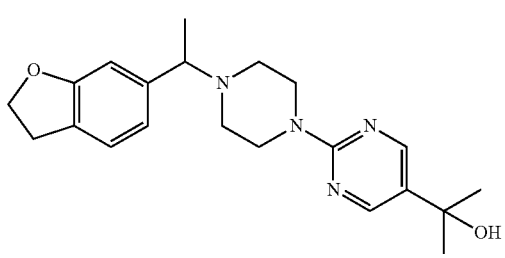 [SMILES: CC(c1ccc2c(c1)OCC2)N1CCN(c2ncc(C(C)(C)O)cn2)CC1]

The title compound was synthesized according to the procedure described for Example 85, starting from Example 98 (0.2 g, 0.54 mmol). The crude product was purified by flash chromatography to get the title compound (pale yellow solid). $^1$H NMR (400 MHz, DMSO-$d_6$): δ 8.38 (s, 2H), 7.13 (d, J=7.2 Hz, 1H), 6.75 (d, J=7.6 Hz, 1H), 6.70 (s, 1H), 5.04 (s, 1H), 4.49 (t, J=8.8 Hz, 2H), 3.64-3.63 (m, 5H), 3.12 (t, J=8.8 Hz, 2H), 2.44-2.42 (m, 4H), 1.38 (s, 6H), 1.25 (d, J=6.4 Hz, 3H). LCMS: (Method A) 369.2 (M+H), Rt. 2.52 min, 98.68% (Max). HPLC: (Method A) Rt. 2.59 min, 99.01% (Max).

Example 75: (2-(4-(1-(2,3-Dihydrobenzofuran-6-yl)ethyl)piperazin-1-yl) pyrimidin-5-yl) methanol

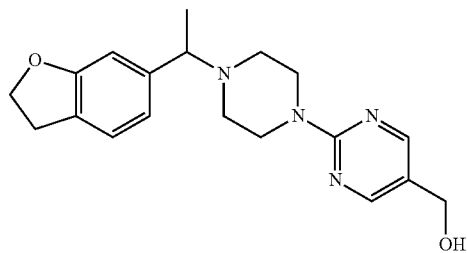 [SMILES: CC(c1ccc2c(c1)OCC2)N1CCN(c2ncc(CO)cn2)CC1]

To a stirred solution of Example 98 (0.1 g, 0.27 mmol) in dry THF (4 mL) cooled at −10° C., lithium aluminium hydride (0.17 mL, 0.35 mmol, 2M in THF, Symax Fine Chemicals) was added drop wise and the reaction mixture was stirred at same temperature for 10 min. The resulting reaction mixture was quenched with a saturated solution of NH$_4$Cl (3 mL) and extracted with EtOAc (20 mL). The organic layer was washed with brine (4 mL), dried over anhydrous Na$_2$SO$_4$ and concentrated. The resulting crude product was purified by flash chromatography (off white solid). $^1$H NMR (400 MHz, DMSO-$d_6$): δ 8.26 (s, 2H), 7.13 (d, J=7.6 Hz, 1H), 6.73 (d, J=7.2 Hz, 1H), 6.70 (s, 1H), 5.02 (s, 1H), 4.49 (t, J=8.8 Hz, 2H), 4.27 (d, J=5.2 Hz, 2H), 3.66 (t, J=4.4 Hz, 4H), 3.12 (t, J=8.8 Hz, 2H), 2.44-2.43 (m, 4H), 1.26 (d, J=6.4 Hz, 3H). LCMS: (Method A) 341.1 (M+H), Rt. 2.22 min, 99.42% (Max). HPLC: (Method A) Rt. 2.24 min, 99.45% (Max).

Example 76: 1-(2-(4-(1-(2,3-dihydrobenzofuran-6-yl)ethyl)piperazin-1-yl)pyrimidin-5-yl)cyclopropan-1-ol

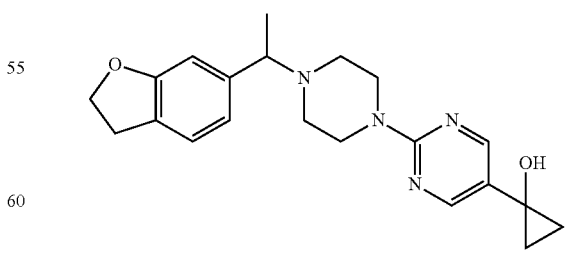

To a stirred solution of Example 98 (200 mg, 0.5 mmol) in THF (3 mL), titanium iso propoxide (78 mg, 0.27 mmol) was added. Then ethyl magnesium bromide in diethyl ether (0.54 mL, 1.6 mmol, 3M) was added slowly at 20° C. for 1 h and the mixture was stirred 3 h at the same temperature. Completion of the reaction was monitored by TLC. The reaction mixture was quenched with saturated ammonium chloride solution (10 mL), the product was extracted with EtOAc (2×20 mL). Combined organic layer was dried over Na₂SO₄ and concentrated. The resulting crude product was purified by flash chromatography (Eluant: 3-5% MeOH in DCM) and further purified by preparative HPLC (Method B) to afford the title product (pale yellow solid).

¹H NMR (400 MHz, DMSO-d6): δ 8.24 (s, 2H), 7.15 (d, J=7.2 Hz, 1H), 6.76 (dd, J=7.6, 1.2 Hz, 1H), 6.72 (s, 1H), 5.91 (s, 1H), 4.50 (t, J=8.8 Hz, 2H), 3.67-3.65 (m, 4H), 3.35-3.34 (m, 1H), 3.13 (t, J=8.8 Hz, 2H), 2.45-2.32 (m, 4H), 1.28 (d, J=6.4 Hz, 3H), 0.99-0.96 (m, 2H), 0.87-0.84 (m, 2H). LCMS: (Method A) 367.3 (M+H), Rt. 2.55 min, 99.03% (Max). HPLC: (Method A) Rt 2.60 min, 98.90% (Max).

Example 77: 1-(2-(4-(1-(2,3-dihydrobenzofuran-6-yl)ethyl)piperazin-1-yl)pyrimidin-5-yl)-2,2,2-trifluoroethan-1-ol

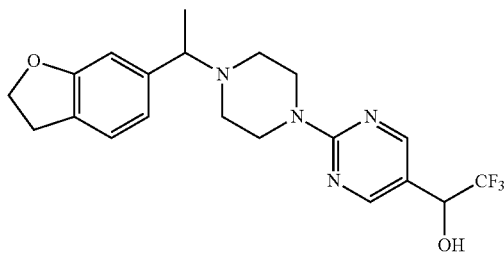 [SMILES: CC(c1ccc2c(c1)OCC2)N1CCN(c2ncc(C(O)C(F)(F)F)cn2)CC1]

The title compound was synthesized according to the procedure described for Example 87, starting from Example 75 (pale green solid). ¹H NMR (400 MHz, DMSO-d6): δ 8.37 (s, 2H), 7.14 (d, J=7.6 Hz, 1H), 6.84 (d, J=5.6 Hz, 1H), 6.76-6.71 (m, 2H), 5.07 (t, J=6.8 Hz, 1H), 4.50 (t, J=8.8 Hz, 2H), 3.71-3.69 (m, 4H), 3.37-3.31 (m, 1H), 3.13 (t, J=8.8 Hz, 2H), 2.44-2.32 (m, 4H), 1.27 (d, J=6.40 Hz, 3H). LCMS: (Method A) 409.2 (M+H), Rt. 3.04 min, 97.18% (Max). HPLC: (Method A) Rt 3.15 min, 99.10% (Max).

Example 78: 1-(2-(4-(1-(2,3-dihydrobenzofuran-6-yl)ethyl)piperazin-1-yl)pyrimidin-5-yl)-2-methylpropan-1-ol

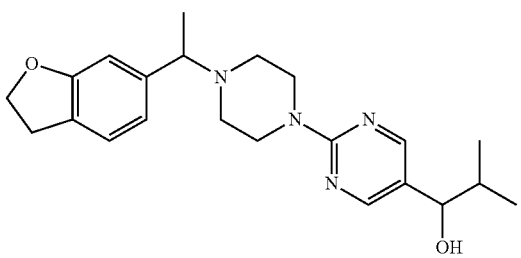 [SMILES: CC(C)C(O)c1cnc(N2CCN(C(C)c3ccc4c(c3)OCC4)CC2)nc1]

The title compound was synthesized according to the procedure described for Example 12, starting from Intermediate 4 and Intermediate 20 (pale yellow solid). ¹H NMR (400 MHz, DMSO-d₆): δ 8.22 (s, 2H), 7.14 (d, J=7.6 Hz, 1H), 6.76-6.71 (m, 2H), 5.08 (d, J=4.4 Hz, 1H), 4.49 (t, J=8.4 Hz, 2H), 4.12-4.09 (m, 1H), 3.67-3.65 (m, 4H), 3.32-3.31 (m, 1H), 3.12 (t, J=8.8 Hz, 2H), 2.45-2.32 (m, 4H), 1.80-1.78 (m, 1H), 1.27 (d, J=6.40 Hz, 3H), 0.85 (d, J=6.40 Hz, 3H), 0.71 (d, J=6.40 Hz, 3H). LCMS: (Method A) 383.3 (M+H), Rt. 2.93 min, 99.74% (Max). HPLC: (Method A) Rt 3.01 min, 99.32% (Max).

Example 79: 3-(2-(4-(1-(2,3-dihydrobenzofuran-6-yl)ethyl)piperazin-1-yl)pyrimidin-5-yl)tetrahydrofuran-3-ol

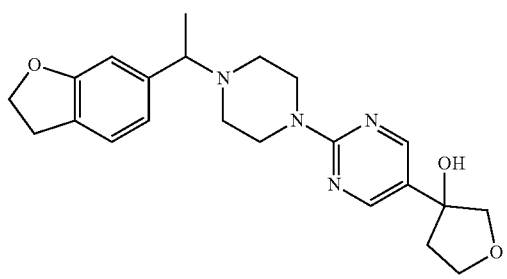 [SMILES: CC(c1ccc2c(c1)OCC2)N1CCN(c2ncc(C3(O)CCOC3)cn2)CC1]

The title compound was synthesized according to the procedure described for Example 40, starting from Intermediate 13 and Intermediate 28 (brown solid). ¹H NMR (400 MHz, DMSO-d₆): δ 8.40 (s, 2H), 7.14 (d, J=7.6 Hz, 1H), 6.75 (d, J=7.6 Hz, 1H), 6.71 (s, 1H), 5.39 (s, 1H), 4.49 (t, J=8.8 Hz, 2H), 3.95-3.94 (m, 2H), 3.77-3.75 (m, 1H), 3.68-3.67 (m, 4H), 3.16-3.15 (m, 2H), 2.44-2.43 (m, 2H), 2.34-2.33 (m, 2H), 2.21-2.01 (m, 4H), 1.27 (d, J=6.80 Hz, 2H). LCMS: (Method A) 397.2 (M+H), Rt. 2.331 min, 97.394% (Max). HPLC: (Method A) Rt. 2.375 min, 96.579% (Max).

Example 80: 1-(2-(4-(1-(2,3-dihydrobenzofuran-6-yl)ethyl)piperazin-1-yl)pyrimidin-5-yl)cyclohexan-1-ol

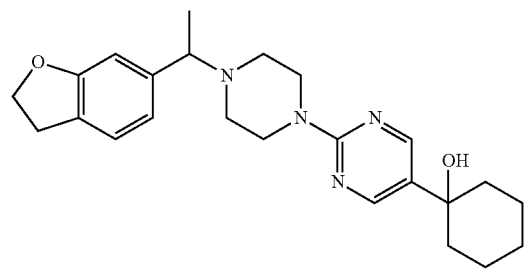 [SMILES: CC(c1ccc2c(c1)OCC2)N1CCN(c2ncc(C3(O)CCCCC3)cn2)CC1]

The title compound was synthesized according to the procedure described for Example 40, starting from Intermediate 13 and Intermediate 22 (brown thick oil). ¹H NMR (400 MHz, DMSO-d₆): δ 8.40 (s, 2H), 7.15 (d, J=7.6 Hz, 1H), 6.76 (d, J=7.2 Hz, 1H), 6.72 (s, 1H), 4.74 (s, 1H), 4.50 (t, J=8.8 Hz, 2H), 3.66 (t, J=4.8 Hz, 4H), 3.34 (s, 1H), 3.13 (t, J=8.8 Hz, 2H), 2.44-2.43 (m, 2H), 2.34 (q, J=4.80 Hz, 2H), 1.67-1.64 (m, 7H), 1.46-1.43 (m, 2H), 1.28 (d, J=6.40 Hz, 3H). LCMS: (Method A) 409.2 (M+H), Rt. 3.185 min, 99.358% (Max). HPLC: (Method A) Rt. 3.253 min, 99.334% (Max).

Example 81: 4-(2-(4-(1-(2,3-dihydrobenzofuran-6-yl)ethyl)piperazin-1-yl)pyrimidin-5-yl)tetrahydro-2H-pyran-4-ol

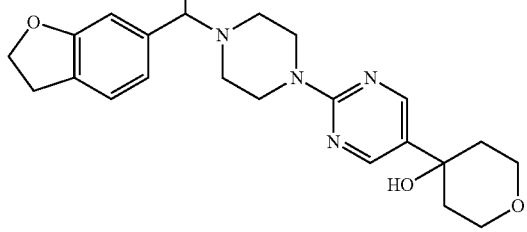

The title compound was synthesized according to the procedure described for Example 40, starting from Intermediate 13 and Intermediate 23. The crude product was purified by MD Autoprep HPLC (Method B) to get the title compound (yellow solid). $^1$H NMR (400 MHz, DMSO-d$_6$): δ 8.40 (d, J=6.4 Hz, 2H), 7.14 (d, J=7.6 Hz, 1H), 6.76-6.71 (m, 2H), 5.06 (s, 1H), 4.49 (t, J=8.8 Hz, 2H), 3.74-3.65 (m, 8H), 3.34-3.31 (m, 1H), 3.12 (t, J=8.8 Hz, 2H), 2.43-2.39 (m, 2H), 2.34-2.31 (m, 2H), 1.90-1.89 (m, 2H), 1.56-1.53 (m, 2H), 1.27 (d, J=6.80 Hz, 3H). LCMS: (Method A) 411.2 (M+H), Rt. 2.38 min, 98.92% (Max). HPLC: (Method A) Rt. 2.43 min, 98.50% (Max).

Example 82: 3-(2-(4-(1-(2,3-dihydrobenzofuran-6-yl)ethyl)piperazin-1-yl)pyrimidin-5-yl)oxetan-3-ol

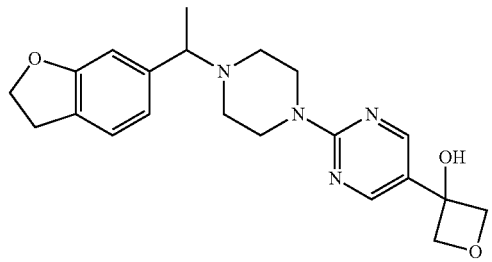 [SMILES: CC(c1ccc2c(c1)OCC2)N1CCN(c2ncc(C3(O)COC3)cn2)CC1]

The title compound was synthesized according to the procedure described for Example 40, starting from Intermediate 13 and Intermediate 34. The resulting crude product was purified by column chromatography (eluent: 3% MeOH in DCM) to afford the title compound (off white solid). $^1$H NMR (400 MHz, DMSO-d$_6$): δ 8.49 (s, 2H), 7.15 (d, J=7.6 Hz, 1H), 6.76 (d, J=7.6 Hz, 1H), 6.72 (s, 1H), 6.35 (s, 1H), 4.70 (s, 4H), 4.50 (t, J=8.8 Hz, 2H), 3.70 (t, J=4.8 Hz, 4H), 3.36-0.00 (m, 1H), 3.13 (t, J=8.4 Hz, 2H), 2.45-2.44 (m, 2H), 2.37-2.36 (m, 2H), 1.28 (d, J=6.80 Hz, 3H). LCMS: (Method A) 383.3 (M+H), Rt. 2.317 min, 98.76% (Max). HPLC: (Method A) Rt. 2.334 min, 99.04% (Max).

Example 83: 1-(2-(4-(1-(1,8-naphthyridin-2-yl)ethyl)piperazin-1-yl)pyrimidin-5-yl)-2,2,2-trifluoro-ethan-1-ol

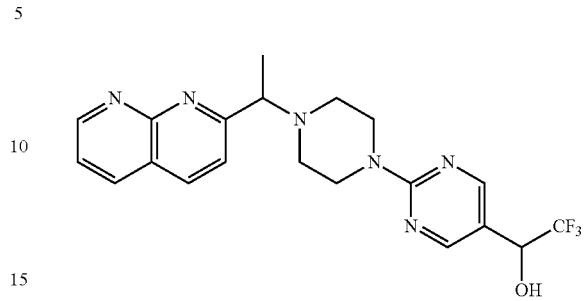

The title compound was synthesized according to the procedure described for Example 87, starting from Intermediate 29 (pale brown solid). $^1$H NMR (400 MHz, DMSO-d$_6$): δ 9.05-9.04 (m, 1H), 8.44 (d, J=8.8 Hz, 2H), 8.38 (s, 2H), 7.80 (d, J=8.4 Hz, 1H), 7.62-7.59 (m, 1H), 6.84 (d, J=6.0 Hz, 1H), 5.09-5.06 (m, 1H), 3.89-3.87 (m, 1H), 3.75-3.74 (m, 4H), 2.67-2.57 (m, 2H), 2.50-2.32 (m, 2H), 1.43 (d, J=6.80 Hz, 3H). LCMS: (Method A) 419.2 (M+H), Rt. 2.25 min, 96.08% (Max). HPLC: (Method A) Rt 2.27 min, 97.02% (Max).

Example 84: 1-(2-(4-(1-(quinoxalin-6-yl) ethyl) piperazin-1-yl) pyrimidin-5-yl) ethan-1-ol

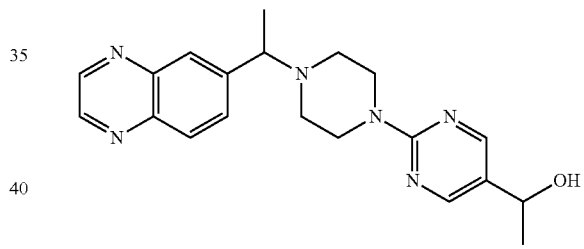

Step 1: 6-(1-(4-(5-bromopyrimidin-2-yl) piperazin-1-yl) ethyl) quinoxaline

To a stirred solution of Intermediate 14 (2.5 g, 8.99 mmol) in dry DMF (25 mL), TEA (4.9 mL, 35.9 mmol) and Intermediate 1 (2.6 g, 13.4 mmol) were added at rt. The resulting mixture was heated at 80° C. overnight. It was concentrated under vacuum and the resulting crude mixture was dissolved in EtOAc (100 mL), washed with water (20 mL), dried over anhydrous Na$_2$SO$_4$ and concentrated. The crude product was purified by flash chromatography, affording the title compound (yellow solid). $^1$H NMR (400 MHz, DMSO-d$_6$): δ 8.92 (d, J=5.6 Hz, 2H), 8.30 (s, 2H), 8.19 (d, J=8.4 Hz, 1H), 7.99 (s, 1H), 7.91 (d, J=8.4 Hz, 1H), 3.69-3.67 (m, 5H), 2.77-2.75 (m, 4H), 1.42 (d, J=6.8 Hz, 3H). LCMS: (Method A) 401.2 (M+H), Rt. 2.60 min, 70.09% (Max).

Step 2: 1-(2-(4-(1-(quinoxalin-6-yl) ethyl) piperazin-1-yl) pyrimidin-5-yl) ethan-1-one The title compound was synthesized according to the procedure described for Example 36, step 1, starting with 6-(1-(4-(5-bromopyrimidin-2-yl) piperazin-1-yl) ethyl) quinoxaline (0.8 g, 2.00 mmol). The resulting crude product was purified by flash chromatography, affording the title compound (yellow solid). $^1$H NMR (400 MHz, DMSO-$d_6$): δ 8.93 (d, J=5.2 Hz, 2H), 8.83 (s, 2H), 8.09 (d, J=8.8 Hz, 1H), 8.00 (s, 1H), 7.92 (d, J=8.8 Hz, 1H), 3.88-3.86 (m, 5H), 2.57-2.56 (m, 2H), 2.50-2.49 (m, 5H), 1.44 (d, J=6.8 Hz, 3H). LCMS: (Method A) 363.3 (M+H), Rt. 2.02 min, 90.62% (Max).

Step 3: 1-(2-(4-(1-(quinoxalin-6-yl) ethyl) piperazin-1-yl) pyrimidin-5-yl) ethan-1-ol The title compound was synthesized according to the procedure described for Example 36, step 2, starting with 1-(2-(4-(1-(quinoxalin-6-yl) ethyl) piperazin-1-yl) pyrimidin-5-yl) ethan-1-one (0.1 g, 0.27 mmol) in dry THF: MeOH (1:1, 5 mL). The crude was purified by flash chromatography to give the title product. Yield: 67% (0.067 g, off white solid). $^1$H NMR (400 MHz, DMSO-$d_6$): δ 8.92 (dd, J=5.6 Hz, 2H), 8.28 (s, 2H), 8.08 (d, J=8.8 Hz, 1H), 7.99 (s, 1H), 7.91 (d, J=8.8 Hz, 1H), 5.05 (d, J=4.4 Hz, 1H), 4.61-4.58 (m, 1H), 3.74-3.69 (m, 5H), 2.59-2.57 (m, 2H), 2.42-2.40 (m, 2H), 1.42 (d, J=6.8 Hz, 3H), 1.39 (d, J=6.4 Hz, 3H). LCMS: (Method A) 365.2 (M+H), Rt. 1.87 min, 99.74% (Max). HPLC: (Method A) Rt. 1.89 min, 99.44% (Max).

Example 85: 2-(2-(4-(1-(quinoxalin-6-yl) ethyl) piperazin-1-yl) pyrimidin-5-yl) propen-2-ol

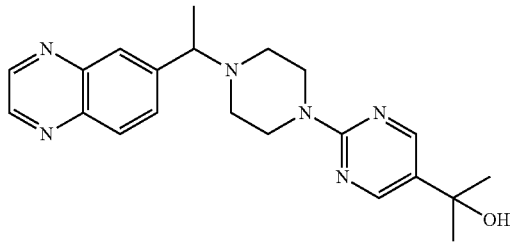 [SMILES: CC(c1ccc2nccnc2c1)N1CCN(c2ncc(C(C)(C)O)cn2)CC1]

To a stirred solution of Example 105 (0.15 g, 0.39 mmol) in dry THF (5 mL), methyl magnesium chloride (0.4 mL, 1.19 mmol, 3M in THF, Symax Fine Chemicals) was added drop wise at −40° C. and the resulting mixture was stirred at rt for 2 h. It was quenched with a saturated solution of NH$_4$Cl (3 mL) and was extracted with EtOAc (20 mL). The organic phase was washed with brine (5 mL), dried over anhydrous Na$_2$SO$_4$ and concentrated. The resulting crude product was purified by flash chromatography followed by MD Autoprep HPLC (Method C), affording the title compound (off white solid). $^1$H NMR (400 MHz, DMSO-$d_6$): δ 8.93-8.91 (m, 2H), 8.38 (s, 2H), 8.08 (d, J=8.8 Hz, 1H), 7.99 (s, 1H), 7.90 (d, J=8.8 Hz, 1H), 5.04 (s, 1H), 3.74-3.72 (m, 5H), 2.55-2.53 (m, 2H), 2.41-2.40 (m, 2H), 1.42 (d, J=6.8 Hz, 3H), 1.38 (s, 6H). LCMS: (Method A) 379.0 (M+H), Rt. 2.10 min, 99.26% (Max). HPLC: (Method A) Rt. 2.04 min, 99.15% (Max).

Example 86: (2-(4-(1-(Quinoxalin-6-yl)ethyl)piperazin-1-yl)pyrimidin-5-yl) methanol

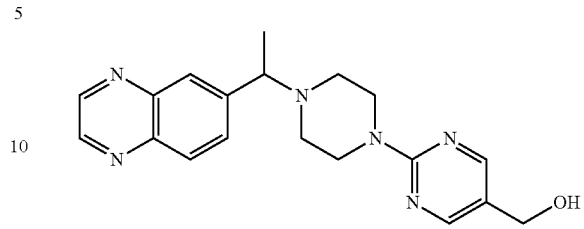

The title product was prepared according to the protocol described for Example 75, starting from Example 105. The resulting crude product was purified by flash chromatography (brown thick oil). $^1$H NMR (400 MHz, DMSO-$d_6$): δ 8.92 (d, J=5.6 Hz, 2H), 8.76 (s, 2H), 8.08 (d, J=12.0 Hz, 1H), 7.99 (s, 1H), 7.91 (d, J=8.8 Hz, 1H), 5.04 (t, J=5.6 Hz, 1H), 4.27 (d, J=5.2 Hz, 2H), 3.73 (t, J=6.8 Hz, 5H), 2.40 (t, J=5.2 Hz, 4H), 1.42 (d, J=6.4 Hz, 3H). LCMS: (Method A) 351.2 (M+H), Rt. 1.689 min, 97.79% (Max). HPLC: (Method A) Rt. 1.72 min, 99.19% (Max).

Example 87: 2, 2, 2-trifluoro-1-(2-(4-(1-(quinoxalin-6-yl) ethyl) piperazin-1-yl)pyrimidin-5-yl)ethan-1-ol

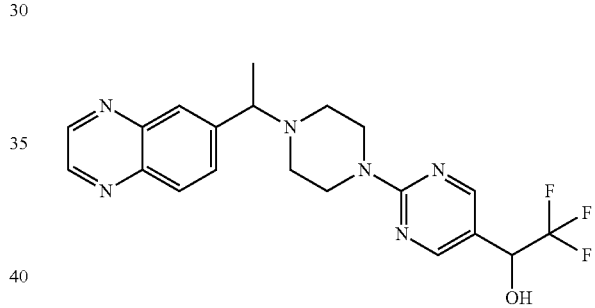

Step 1: 2-(4-(1-(quinoxalin-6-yl) ethyl) piperazin-1-yl) pyrimidine-5-carbaldehyde A stirred solution of Example 86 (0.65 g, 1.85 mmol) in dry DCM (110 mL), Desmartin periodinane (1.58 g, 3.71 mmol) was added at 0° C. and the mixture was stirred for 1 h at the same temperature. The reaction mixture was diluted with DCM (30 mL) and washed with a saturated solution of NaHCO$_3$ (2×5 mL). The resulting DCM layer was dried over anhydrous Na$_2$SO$_4$ and evaporated under vacuum. The crude product was purified by flash chromatography, affording the title compound. Yield: 50% (0.33 g, yellow thick oil). $^1$H NMR (400 MHz, DMSO-d6: δ 9.79 (s, 1H), 8.94 (d, J=4.8 Hz, 2H), 8.84 (s, 1H), 8.77-8.77 (m, 2H), 8.12-8.09 (m, 2H), 4.23-4.18 (m, 5H), 3.97-3.91 (m, 4H), 1.45 (d, J=19.6 Hz, 3H). LCMS: (Method A) 349.0 (M+2), Rt. 1.98 min, 64.53% (Max).

Step 2: 2, 2, 2-trifluoro-1-(2-(4-(1-(quinoxalin-6-yl) ethyl) piperazin-1-yl)pyrimidin-5-yl)ethan-1-ol A stirred solution of 2-(4-(1-(quinoxalin-6-yl) ethyl) piperazin-1-yl) pyrimidine-5-carbaldehyde (0.15 g, 0.43 mmol) in dry DMF (2 mL), K$_2$CO$_3$ (0.118 g, 0.86 mmol) and (trifluoromethyl) trimethylsilane (0.122 g, 0.86 mmol) were added at 10° C. and the mixture was stirred at rt for 1 h. It was quenched with water (2 mL) and extracted with EtOAc (15 mL). The EtOAc layer was dried over anhydrous Na$_2$SO$_4$ and evaporated under vacuum. The resulting crude was purified by flash chromatography followed by MD Autoprep HPLC (Method C) (off white solid). $^1$H NMR (400 MHz, DMSO-d6): δ 8.93 (dd, J=1.6, 2H), 8.39 (s, 2H), 8.09 (d, J=8.8 Hz, 1H), 8.01 (d, J=1.6 Hz, 1H), 7.94-7.94 (m, 1H), 6.83 (d, J=6.0 Hz, 1H), 5.09 (t, J=6.8 Hz, 1H), 3.78-3.77 (m, 5H), 2.52-2.51 (m, 2H), 2.50-2.50 (m, 2H), 1.44 (d, J=6.40 Hz, 3H). LCMS: (Method A) 419.2 (M+2), Rt. 2.46 min, 99.11% (Max). HPLC: (Method A) Rt. 2.53 min, 99.48% (Max).

Example 88: 2-methyl-1-(2-(4-(1-(quinoxalin-6-yl) ethyl) piperazin-1-yl) pyrimidin-5-yl) propan-1-ol

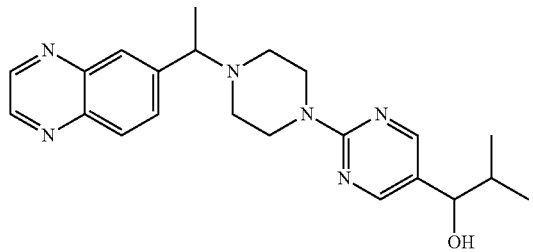 [SMILES: CC(C)C(O)c1cnc(N2CCN(C(C)c3ccc4nccnc4c3)CC2)nc1]

The title compound was synthesized according to the procedure described for Example 12, starting from Intermediate 1 and Intermediate 20 (off white solid). $^1$H NMR (400 MHz, DMSO-d$_6$): δ 8.94 (dd, J=7.2, 1.6 Hz, 2H), 8.23 (s, 2H), 8.09 (d, J=8.8 Hz, 1H), 8.01 (s, 1H), 7.93 (dd, J=8.8, 1.6 Hz, 1H), 5.09 (d, J=4.4 Hz, 1H), 4.13-4.12 (m, 1H), 3.77-3.75 (m, 1H), 3.71 (t, J=4.4 Hz, 4H), 2.44-2.43 (m, 4H), 1.80-1.79 (m, 1H), 1.44 (d, J=6.80 Hz, 3H), 0.86 (d, J=6.80 Hz, 3H), 0.72 (d, J=6.80 Hz, 3H). LCMS: (Method A) 393.2 (M+H), Rt. 2.37 min, 96.65% (Max). HPLC: (Method A) Rt. 2.43 min, 99.62% (Max).

Example 89: 4-(2-(4-(1-(quinoxalin-6-yl)ethyl)piperazin-1-yl)pyrimidin-5-yl)tetrahydro-2H-pyran-4-ol

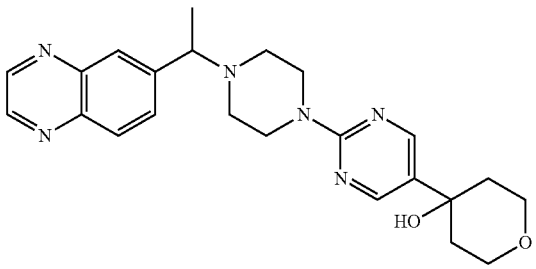 [SMILES: CC(c1ccc2nccnc2c1)N1CCN(c2ncc(C3(O)CCOCC3)cn2)CC1]

The title compound was synthesized according to the procedure described for Example 40, starting from Intermediate 2 and Intermediate 23 (44 mg, pale brown solid). $^1$H NMR (400 MHz, DMSO-d$_6$): δ 8.93-8.92 (m, 2H), 8.41 (s, 2H), 8.08 (d, J=8.4 Hz, 1H), 7.99 (s, 1H), 7.91 (d, J=8.4 Hz, 1H), 5.06 (s, 1H), 3.76-3.66 (m, 9H), 2.42-2.40 (m, 4H), 1.92-1.89 (m, 2H), 1.55-1.52 (m, 2H), 1.43 (d, J=6.00 Hz, 3H). LCMS: (Method A) 421.2 (M+2H), Rt. 1.96 min, 98.37% (Max). HPLC: (Method A) Rt. 1.92 min, 99.41% (Max).

Example 90: 2-(4-(1-(2, 3-dihydrobenzofuran-6-yl) ethyl) piperazin-1-yl)-5-methylpyrimidine

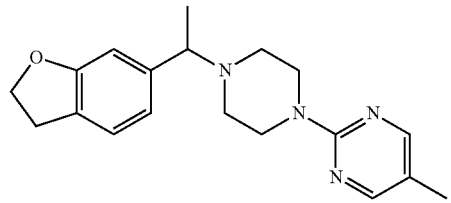 [SMILES: Cc1cnc(N2CCN(C(C)c3ccc4c(c3)OCC4)CC2)nc1]

To a stirred solution of Example 98 (0.3 g, 0.82 mmol) in dry THF (6 mL), lithium aluminium hydride solution (0.17 mL, 0.35 mmol, 2M in THF, Symax Fine Chemicals) was added drop wise at 0° C. and the resulting mixture was stirred at rt for 1 h. It was quenched with a saturated solution of NH$_4$Cl (10 mL) and extracted with EtOAc (35 mL). The organic layer was washed with brine, dried over anhydrous Na$_2$SO$_4$ and concentrated. The resulting crude product was purified by flash chromatography, affording the title compound (off white solid). $^1$H NMR (400 MHz, DMSO-d$_6$): 8.19 (s, 2H), 7.14 (d, J=7.6 Hz, 1H), 6.75 (d, J=8.4 Hz, 1H), 6.71 (s, 1H), 4.49 (t, J=8.4 Hz, 2H), 3.63-3.61 (m, 5H), 3.12 (t, J=8.8 Hz, 2H), 2.51-2.49 (m, 2H), 2.40-2.39 (m, 2H), 2.05 (s, 3H), 1.26 (d, J=6.4 Hz, 3H). LCMS: (Method A) 325.2 (M+H), Rt. 2.75 min, 98.02% (Max). HPLC: (Method A) Rt. 2.77 min, 98.513% (Max).

Example 91: 7-(1-(4-(5-(trifluoromethyl)pyrimidin-2-yl)piperazin-1-yl)ethyl)imidazo[1,2-a]pyridine

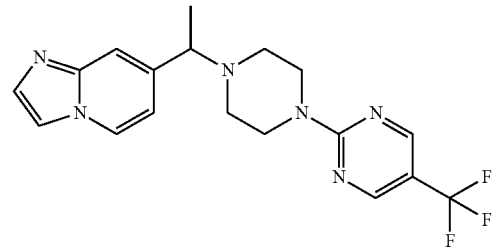 [SMILES: CC(c1ccn2ccnc2c1)N1CCN(c2ncc(C(F)(F)F)cn2)CC1]

To a stirred solution of 2-chloro-5-(trifluoromethyl)pyrimidine (0.15 g, 0.83 mmol) in dry DMF (7 mL), TEA (0.43 mL, 3.12 mmol) and Intermediate 8 (0.24 g, 1.04 mmol) were added at 0° C. The reaction mixture was stirred at 100° C. for 12 h. The reaction mixture was concentrated under vacuum to give a crude product, which was purified by flash column chromatography using 2-3% MeOH in DCM as eluent. The title compound was isolated after evaporation of the solvents (dark brown thick oil). $^1$H NMR (400 MHz, DMSO-d$_6$): δ 8.66 (s, 2H), 8.48 (d, J=7.2 Hz, 1H), 7.88 (s, 1H), 7.52 (s, 1H), 7.43 (s, 1H), 6.93 (d, J=6.8 Hz, 1H), 3.82 (t, J=4.4 Hz, 4H), 3.60-3.50 (m, 1H), 2.59-2.51 (m, 2H), 2.49-2.38 (m, 2H), 1.34 (d, J=6.8 Hz, 3H). LCMS: (Method A) 377.2 (M+H), Rt. 2.29 min, 99.4% (Max). HPLC: (Method A) Rt 2.33 min, 99.18% (Max).

Example 92: 2-(1-(4-(5-(trifluoromethyl)pyrimidin-2-yl)piperazin-1-yl)ethyl)-1,8-naphthyridine

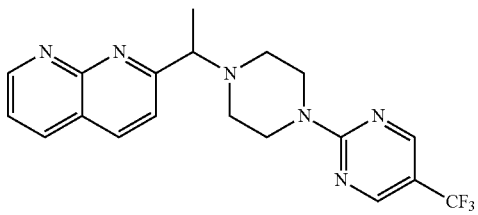 [SMILES: CC(c1ccc2cccnc2n1)N1CCN(c2ncc(C(F)(F)F)cn2)CC1]

The title compound was synthesized according to the procedure described for Example 12, using Intermediate 29 and 2-(1-piperazinyl)-5-(trifluoromethyl)-pyrimidine (brown thick oil). $^1$H NMR (400 MHz, DMSO-d$_6$): δ 9.06-9.04 (m, 1H), 8.67 (s, 2H), 8.46 (d, J=8.4 Hz, 2H), 7.81 (d, J=8.4 Hz, 1H), 7.63-7.60 (m, 1H), 3.92-3.90 (m, 1H), 3.85-3.84 (m, 4H), 2.64-2.60 (m, 2H), 2.47-2.43 (m, 2H), 1.45 (d, J=6.8 Hz, 3H). LCMS: (Method A) 389.2 (M+H), Rt. 2.72 min, 98.07% (Max). HPLC: (Method A) Rt. 2.76 min, 98.46% (Max).

Example 94: 6-(1-(4-(5-(cyclopent-1-en-1-yl)pyrimidin-2-yl)piperazin-1-yl)ethyl)quinoxaline

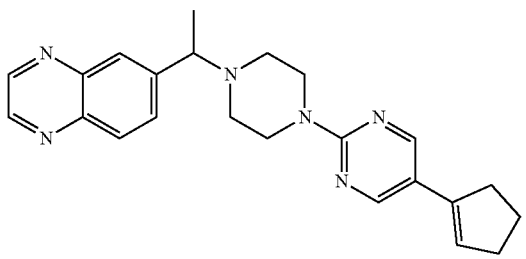 [SMILES: CC(c1ccc2nccnc2c1)N1CCN(c2ncc(C3=CCCC3)cn2)CC1]

Step 1: tert-butyl 4-(5-(1-hydroxycyclopentyl)pyrimidin-2-yl)piperazine-1-carboxylate A solution of the tert-butyl 4-(5-bromopyrimidin-2-yl)piperazine-1-carboxylate (1.5 g, 4.37 mmol) in dry diethyl ether was cooled to −80° C. and kept under inert atmosphere. n-BuLi (1.6 mL, 5.24 mmol, 2.5 m in Hexane) was added dropwise. The solution was allowed stand at −80° C. for 1 h and cyclopentanone (1.2 equiv) was added slowly to reaction mixture at same temperature. After 15 min, the temperature was increased to rt and the mixture was stirred for 1 h at rt. It was quenched with a saturated solution of NH$_4$Cl (3 mL) and extracted with EtOAc (3×50 mL). The organic phase was washed with brine (5 mL), dried over anhydrous Na$_2$SO$_4$ and concentrated. The crude product was purified by flash chromatography to afford the title compound. $^1$H NMR 400 MHz, DMSO-d$_6$): δ 8.48 (s, 2H), 3.83 (t, J=5.2 Hz, 4H), 3.52 (t, J=5.2 Hz, 4H), 2.02-1.94 (m, 6H), 1.85-1.84 (m, 2H). LCMS: (Method A) 349.0 (M+H), Rt. 2.39 min, 98.13% (Max).

Step 2: 5-(cyclopent-1-en-1-yl)-2-(piperazin-1-yl)pyrimidine hydrochloride

To a stirred solution of tert-butyl 4-(5-(1-hydroxycyclopentyl)pyrimidin-2-yl)piperazine-1-carboxylate (250 mg, 0.71 mmol) in 1,4-dioxane (5 mL), HCl in 1,4-dioxane (2.5 mL, 4.0 M in dioxane) was added slowly at rt, and the reaction mixture was stirred at rt for 2 h. The reaction mixture was concentrated under vacuum. The resulting crude product was triturated with diethyl ether (15 mL) to afford the title compound. Yield: 88% (150 mg, white solid). $^1$H NMR (400 MHz, DMSO-d$_6$): δ 8.55 (s, 2H), 6.25 (br s, 1H), 3.19-3.16 (m, 4H), 2.66-2.55 (m, 4H), 2.50-2.46 (m, 4H), 1.97-1.92 (m, 2H). LCMS: (Method A) 231.0 (M+H), Rt. 2.07 min, 95.97% (Max).

Step 3: 6-(1-(4-(5-(cyclopent-1-en-1-yl)pyrimidin-2-yl)piperazin-1-yl)ethyl)quinoxaline The title compound was synthesized according to the procedure described for Example 12, starting from Intermediate 1 and 5-(cyclopent-1-en-1-yl)-2-(piperazin-1-yl)pyrimidine hydrochloride (white solid). $^1$H NMR (400 MHz, DMSO-d$_6$): δ 8.92 (dd, J=2.0, −7.2 Hz, 2H), 8.45 (s, 2H), 8.08 (d, J=8.8 Hz, 1H), 8.00 (d, J=1.6 Hz, 1H), 7.91 (dd, J=8.8, 2.0 Hz, 1H), 6.15 (s, 1H), 3.77-3.72 (m, 4H), 2.67-2.49 (m, 4H), 2.45-2.32 (m, 4H), 1.91 (t, J=7.2 Hz, 2H), 1.43 (d, J=6.80 Hz, 3H). LCMS: (Method B) 387.0 (M+H), Rt. 6.36 min, 98.06% (Max). HPLC: (Method A) Rt. 3.36 min, 98.14% (Max).

Example 95: Methyl 2-(4-(1-(benzo[d]thiazol-5-yl)ethyl)piperazin-1-yl)pyrimidine-5-carboxylate

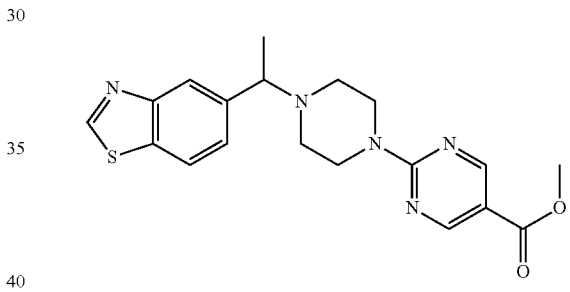

The title compound was synthesized according to the procedure described for Example 12, starting from Intermediate 3 and Intermediate 12 (white solid). $^1$H NMR (400 MHz, DMSO-d$_6$): δ 9.39 (s, 1H), 8.76 (s, 2H), 8.12 (d, J=8.00 Hz, 1H), 8.03 (s, 1H), 7.50 (d, J=8.40 Hz, 1H), 3.85 (t, J=4.80 Hz, 4H), 3.79 (s, 3H), 3.70-3.65 (m, 1H), 2.53-2.51 (m, 2H), 2.45-2.41 (m, 2H), 1.41 (d, J=6.80 Hz, 3H). LCMS: (Method A) 384.0 (M+1), Rt. 2.71 min, 97.0% (Max). HPLC: (Method A) Rt 2.66 min, 97.8% (Max).

Example 96: 2-(4-(1-(benzo[d]thiazol-5-yl)ethyl)piperazin-1-yl)-N-methylpyrimidine-5-carboxamide

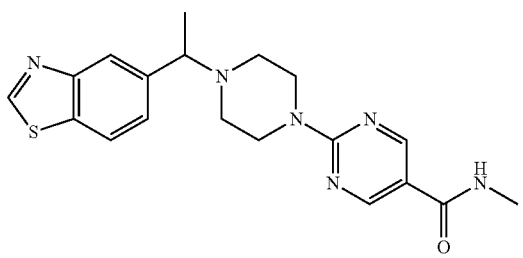 [SMILES: CNC(=O)c1cnc(N2CCN(C(C)c3ccc4scnc4c3)CC2)nc1]

The title compound was synthesized according to the procedure described for Examples 65 and 64, starting from Example 95 (white solid). $^1$H NMR (400 MHz, DMSO-$d_6$: δ 9.38 (s, 1H), 8.70 (s, 2H), 8.27 (d, J=4.40 Hz, 1H), 8.11 (d, J=8.00 Hz, 1H), 8.02 (s, 1H), 7.49 (d, J=8.00 Hz, 1H), 3.81-3.78 (m, 4H), 3.67-3.64 (m, 1H), 2.73 (d, J=4.40 Hz, 3H), 2.45-2.32 (m, 4H), 1.40 (d, J=6.80 Hz, 3H). LCMS: (Method A) 383.0 (M+H), Rt. 2.16 min, 99.2% (Max). HPLC: (Method A) Rt 2.11 min, 97.8% (Max).

Example 97: 2-(4-(1-(benzo[d]thiazol-5-yl)ethyl)piperazin-1-yl)-N,N-dimethylpyrimidine-5-carboxamide

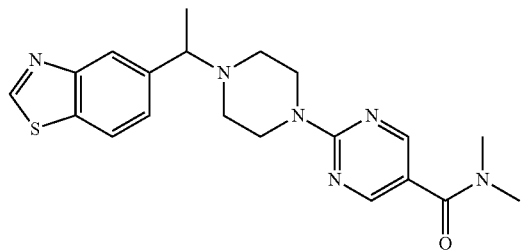 [SMILES: CC(c1ccc2scnc2c1)N1CCN(c2ncc(C(=O)N(C)C)cn2)CC1]

The title compound was synthesized according to the procedure described for Examples 65 and 63, starting from Example 95 (white solid). $^1$H NMR (400 MHz, DMSO-$d_6$: δ 9.38 (d, J=1.20 Hz, 1H), 8.44 (d, J=1.20 Hz, 2H), 8.11 (d, J=8.40 Hz, 1H), 8.02 (s, 1H), 7.50 (d, J=8.00 Hz, 1H), 3.79-3.75 (m, 4H), 3.73-3.66 (m, 1H), 2.96 (s, 6H), 2.45-2.39 (m, 4H), 1.40 (d, J=6.40 Hz, 3H). LCMS: (Method A) 397.2 (M+H), Rt. 2.29 min, 99.3% (Max). HPLC: (Method A) Rt 2.23 min, 99.3% (Max).

Example 98: Methyl 2-(4-(1-(2,3-dihydrobenzofuran-6-yl)ethyl)piperazin-1-yl)pyrimidine-5-carboxylate

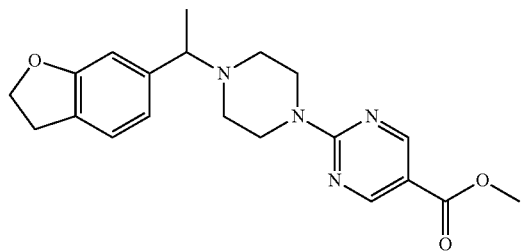 [SMILES: COC(=O)c1cnc(N2CCN(C(C)c3ccc4c(c3)OCC4)CC2)nc1]

To a stirred solution of Intermediate 12 (1 g, 3.87 mmol) in dry DMF (10 mL), TEA (1.94 mL, 13.95 mmol) and Intermediate 4 (0.24 g, 1.04 mmol) were added at 0° C. The reaction mixture was heated at 100° C. for 12 h. Then the reaction mixture was concentrated under vacuum. The resulting crude product was purified by column chromatography (2-3% MeOH in DCM as eluent) to afford the title compound (off white solid). $^1$H NMR (400 MHz, DMSO-$d_6$): δ 8.76 (s, 2H), 7.15 (d, J=7.2 Hz, 1H), 6.76 (d, J=7.6 Hz, 1H), 6.72 (s, 1H), 4.50 (t, J=8.8 Hz, 2H), 3.82 (t, J=4.8 Hz, 4H), 3.79 (s, 3H), 3.50-3.42 (m, 1H), 3.13 (t, J=8.8 Hz, 2H), 2.49-2.44 (m, 2H), 2.42-2.33 (m, 2H), 1.28 (d, J=6.80 Hz, 3H). LCMS: (Method A) 369.2 (M+H), Rt. 2.96 min, 98.9% (Max). HPLC: (Method A) Rt. 2.95 min, 98.8% (Max).

Example 99: 2-(4-(1-(2,3-dihydrobenzofuran-6-yl)ethyl)piperazin-1-yl)-N-methylpyrimidine-5-carboxamide

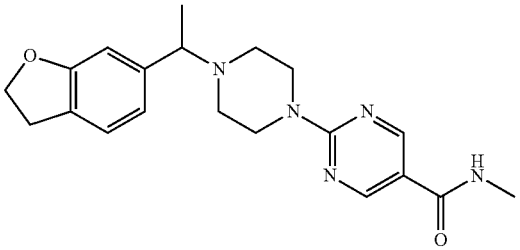 [SMILES: CNC(=O)c1cnc(N2CCN(C(C)c3ccc4c(c3)OCC4)CC2)nc1]

Step 1: 2-(4-(1-(2,3-dihydrobenzofuran-6-yl)ethyl)piperazin-1-yl)pyrimidine-5-carboxylic acid To a stirred solution of Example 98 (0.840 g, 2.28 mmol) in dioxane (2 mL), LiOH (10 M, 1.14 mL, 1.14 mmol) was added at rt and the resulting mixture was stirred for 4 h. The completion of reaction was monitored by TLC. Solvent was evaporated and the product was further dried by azeotropic evaporation of toluene (3×2 mL). The resulting product was used in the next step without any further purification. Yield: 99.1% (0.90 g, off white solid). LCMS: (Method A) 355 (M+H), Rt. 2.421 min 90.06% (Max).

Step 2: 2-(4-(1-(2,3-dihydrobenzofuran-6-yl)ethyl)piperazin-1-yl)-N-methylpyrimidine-5-carboxamide Example 99 was synthesized according to the protocol described for Example 63, starting with 2-(4-(1-(2,3-dihydrobenzofuran-6-yl)ethyl)piperazin-1-yl)pyrimidine-5-carboxylic acid and replacing the dimethylamine with a methylamine solution in THF (3.175 ml, 6.35 mmol). The crude product was purified by flash chromatography (2% MeOH in DCM as eluent) to afford the title product (off white solid). LCMS: (Method A) 368 (M+H), Rt 2.413 min 94.23% (Max). HPLC: (Method A), Rt 2.344 min, 96.76% (Max). $^1$H NMR (400 MHz, DMSO-$d_6$): δ 8.70 (s, 2H), 8.27 (d, J=4.4 Hz, 1H), 7.14 (d, J=7.6 Hz, 1H), 6.76-6.74 (m, 2H), 4.49 (t, J=8.8 Hz, 2H), 3.78-3.76 (m, 4H), 3.32 (s, 1H), 3.14 (t, J=8.8 Hz, 2H), 2.74-2.73 (m, 3H), 2.42-2.36 (m, 4H), 1.27 (d, J=6.80 Hz, 3H).

Example 100: 2-(4-(1-(2,3-dihydrobenzofuran-6-yl)ethyl)piperazin-1-yl)-N,N-dimethylpyrimidine-5-carboxamide

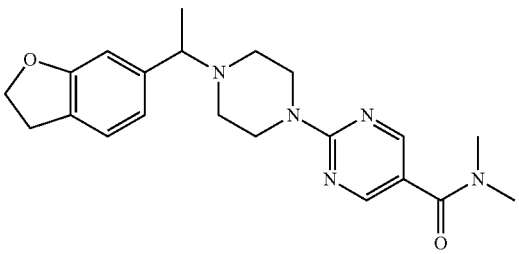 [SMILES: CC(c1ccc2c(c1)OCC2)N1CCN(c2ncc(C(=O)N(C)C)cn2)CC1]

Example 100 was synthesized according to the protocol described for Example 63, starting with 2-(4-(1-(2, 3-dihydrobenzofuran-6-yl)ethyl)piperazin-1-yl)pyrimidine-5-carboxylic acid (example 99, step 1). The crude product was purified by flash chromatography (2% MeOH in DCM as eluent) to afford the title product (brown solid). LCMS: (Method A) 382 (M+H), Rt. 2.436 min 98.34% (Max). HPLC: (Method A), Rt. 2.473 min, 97.0% (Max). $^1$H NMR: (400 MHz, DMSO-$d_6$): δ 8.45 (s, 2H), 7.15 (d, J=7.2 Hz, 1H), 6.75 (t, J=7.2 Hz, 1H), 4.50 (t, J=8.8 Hz, 2H), 3.77-3.76 (m, 4H), 3.13 (t, J=8.8 Hz, 2H), 3.11-2.97 (m, 7H), 1.29-1.27 (m, 3H).

Example 101: 2-(4-(1-(2,3-dihydrobenzofuran-6-yl)ethyl)piperazin-1-yl)-N,N-dimethylpyrimidine-4-carboxamide

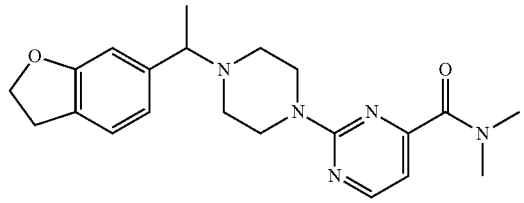 [SMILES: CC(c1ccc2c(c1)OCC2)N1CCN(c2nccc(C(=O)N(C)C)n2)CC1]

Example 101 was synthesized according to the protocol described for Example 100, starting with Example 102. Yield: 62% (321 mg, off white solid). $^1$H NMR (400 MHz, DMSO-d6): δ 8.43 (d, J=5.2 Hz, 1H), 7.14 (d, J=7.2 Hz, 1H), 6.75 (d, J=7.6 Hz, 1H), 6.71 (s, 1H), 6.63-6.62 (m, 1H), 4.49 (t, J=8.8 Hz, 2H), 3.68-3.67 (m, 4H), 3.36-3.32 (m, 1H), 3.12 (t, J=8.8 Hz, 2H), 2.94 (s, 3H), 2.89 (s, 3H), 2.45-2.33 (m, 4H), 1.27 (d, J=6.40 Hz, 3H). LCMS: (Method A) 382.2 (M+H), Rt. 2.60 min, 97.9% (Max). HPLC: (Method A) Rt 2.55 min, 99.26% (Max).

Example 102: Methyl 2-(4-(1-(2,3-dihydrobenzofuran-6-yl)ethyl)piperazin-1-yl)pyrimidine-4-carboxylate

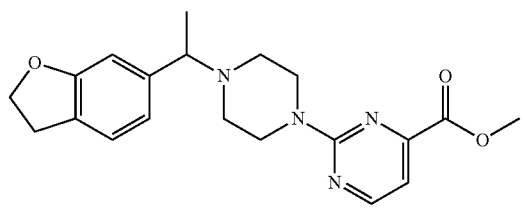 [SMILES: COC(=O)c1ccnc(N2CCN(C(C)c3ccc4c(c3)OCC4)CC2)n1]

The title compound was synthesized according to the procedure described for Example 40, starting from Intermediate 13 and methyl 2-chloropyrimidine-4-carboxylate. The crude product was purified by flash chromatography (Elutant: 55-75% EtOAc in pet ether), affording the title product. Yield: 68.1% (574 mg, pale yellow thick oil). $^1$H NMR (400 MHz, DMSO-$d_6$): δ 8.56-8.55 (m, 1H), 7.14 (d, J=7.6 Hz, 1H), 7.07-7.05 (m, 1H), 6.75 (d, J=7.6 Hz, 1H), 6.71 (s, 1H), 4.49 (t, J=8.8 Hz, 2H), 3.84 (s, 3H), 3.73-3.72 (m, 4H), 3.37-3.32 (m, 1H), 3.12 (t, J=8.8 Hz, 2H), 2.38-2.32 (m, 4H), 1.28 (d, J=6.80 Hz, 3H). LCMS: (Method A) 369.2 (M+H), Rt. 2.83 min, 98.25% (Max). HPLC: (Method A) Rt 2.88 min, 98.43% (Max).

Example 103: 2-(4-(1-(2,3-dihydrobenzofuran-6-yl)ethyl)piperazin-1-yl)-N-methylpyrimidine-4-carboxamide

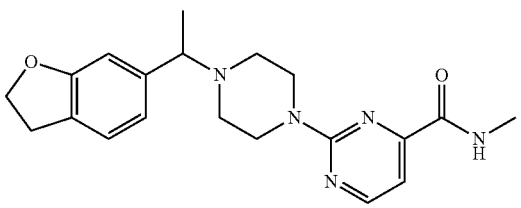 [SMILES: CNC(=O)c1ccnc(N2CCN(C(C)c3ccc4c(c3)OCC4)CC2)n1]

Example 103 was synthesized according to the protocol described for Example 99, starting with Example 102. The crude product was purified by flash chromatography (Elutant: 90% EtOAc in pet ether) to afford the title compound (pale yellow solid). $^1$H NMR (400 MHz, DMSO-$d_6$): δ 8.69 (d, J=4.4 Hz, 1H), 8.52 (d, J=4.8 Hz, 1H), 7.15 (d, J=7.2 Hz, 1H), 7.06 (d, J=4.8 Hz, 1H), 6.77 (dd, J=7.6, 1.2 Hz, 1H), 6.73 (s, 1H), 4.51 (t, J=8.4 Hz, 2H), 3.80-3.79 (m, 4H), 3.40-3.38 (m, 1H), 3.14 (t, J=8.8 Hz, 2H), 2.79 (d, J=4.80 Hz, 3H), 2.45-2.33 (m, 4H), 1.30 (d, J=6.80 Hz, 3H). LCMS: (Method A) 368.2 (M+H), Rt. 2.62 min, 97.33% (Max). HPLC: (Method A) Rt 2.58 min, 99.41% (Max).

Example 104: N-(2-(2-(1-(4-(quinoxalin-6-yl)piperazin-1-yl)ethyl)pyrimidin-5-yl)propan-2-yl)acetamide

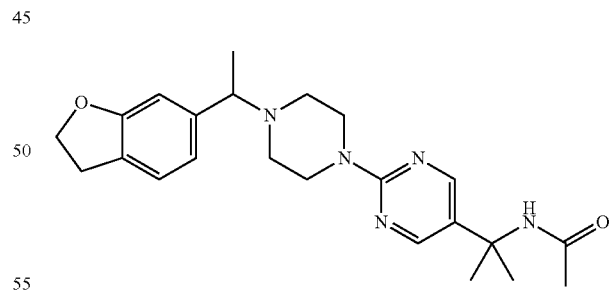

The title compound was synthesized according to the procedure described for Example 40, starting from Intermediate 13 and Intermediate 33 (off-White solid). $^1$H NMR (400 MHz, DMSO-$d_6$): δ 8.26 (s, 1H), 8.04 (s, 1H), 7.15 (d, J=7.6 Hz, 3H), 6.72-6.76 (m, 2H), 4.51 (t, J=8.4 Hz, 2H), 3.64-3.65 (m, 4H), 3.14 (t, J=8.4 Hz, 2H), 2.42-2.44 (m, 2H), 2.31-2.33 (m, 2H), 1.79 (s, 3H), 1.49 (s, 6H), 1.28 (t, J=6.4 Hz, 3H). LCMS: (Method A) 410.5 (M+H), Rt. 2.58 min, 98.25% (Max). HPLC: (Method A) Rt. 2.61 min, 99.51% (Max).

Example 105: Methyl 2-(4-(1-(quinoxalin-6-yl)ethyl)piperazin-1-yl)pyrimidine-5-carboxylate

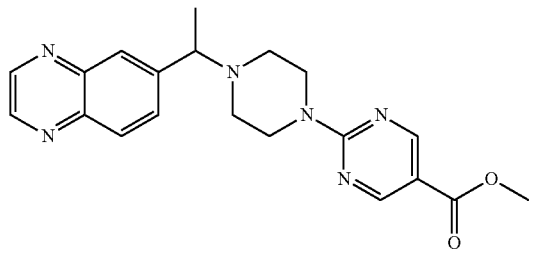 [SMILES: COC(=O)c1cnc(N2CCN(C(C)c3ccc4nccnc4c3)CC2)nc1]

To a stirred solution of Intermediate 1 (0.1 g, 0.51 mmol) in dry DMF (5.0 mL), TEA (0.21 mL, 1.5 mmol) and Intermediate 12 (0.115 g, 0.5 mmol) were added at rt and the reaction mixture was stirred at 90° C. overnight. The reaction mixture was cooled to rt and concentrated under vacuum. To this resulting crude mixture, water (50 mL) was added and product was extracted with DCM (150 mL). Organic layer was dried over anhydrous $Na_2SO_4$ and concentrated. The crude product was purified by flash chromatography to afford the title compound (pale yellow solid). $^1$H NMR (400 MHz, DMSO-$d_6$): δ 8.94 (d, J=5.6 Hz, 2H), 8.77 (s, 2H), 8.10 (d, J=8.8 Hz, 1H), 8.01 (s, 1H), 7.93 (d, J=8.8 Hz, 1H), 3.89-3.86 (m, 4H), 3.82-3.78 (m, 1H), 3.79 (s, 3H), 2.56-2.57 (m, 2H), 2.46-2.44 (m, 2H), 1.44 (d, J=6.4 Hz, 3H). LCMS: (Method A) 379.2 (M+H), Rt. 2.27 min, 99.84% (Max). HPLC: (Method A) Rt. 2.33 min, 98.75% (Max).

Example 106: 2-(4-(1-(quinoxalin-6-yl)ethyl)piperazin-1-yl)pyrimidine-5-carboxylic acid

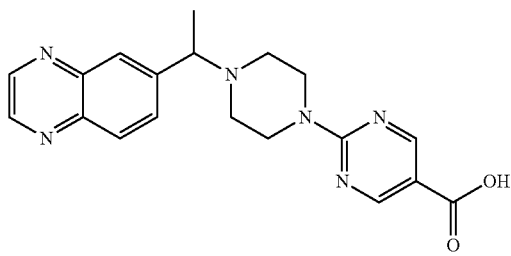 [SMILES: CC(c1ccc2nccnc2c1)N1CCN(c2ncc(C(=O)O)cn2)CC1]

To a stirred solution of Example 105 (1.5 g, 5.96 mmol) in THF (15.0 mL), methanol (4.5 mL) and water (4.5 mL), LiOH (330 mg; 7.92 mmol) was added at the resulting mixture was stirred for 12 h at rt. After completion of the reaction, the reaction mixture was acidified to pH 4 with a 1N HCl solution. The resulting precipitate was filtered and dissolved in DCM (100 mL). The DCM solution was washed with water (1.0 mL), dried over $Na_2SO_4$ and concentrated to afford the titled compound (yellow solid). $^1$H NMR (400 MHz, DMSO-$d_6$): δ 12.84 (s, 1H), 8.93 (dd, J=2.0, 7.2 Hz, 2H), 8.73 (s, 2H), 8.09 (d, J=8.8 Hz, 1H), 8.01 (d, J=1.6 Hz, 1H), 7.93 (dd, J=2.0, 8.6 Hz, 1H), 3.85 (t, J=5.2 Hz, 4H), 3.79 (d, J=6.8 Hz, 1H), 2.60-2.55 (m, 2H), 2.50-2.43 (m, 2H), 1.44 (d, J=6.80 Hz, 3H). LCMS: (Method A) 365.2 (M+H), Rt. 1.84 min, 99.36% (Max). HPLC: (Method A) Rt. 1.88 min, 98.35% (Max).

Example 107: N-(2-(2-(4-(1-(quinoxalin-6-yl)ethyl)piperazin-1-yl)pyrimidin-5-yl)propan-2-yl)acetamide

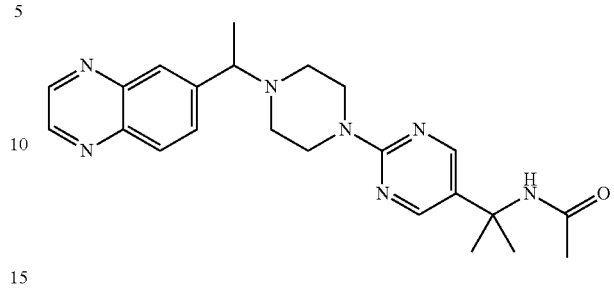

The title compound was synthesized according to the procedure described for Example 40, starting from Intermediate 2 and Intermediate 33 (pale Brown solid). $^1$H NMR (400 MHz, DMSO-$d_6$): δ 8.95 (d, J=1.6 Hz, 1H), 8.93 (d, J=1.6 Hz, 1H), 8.26 (s, 2H), 8.10-8.01 (m, 3H), 7.93 (dd, J=1.6, 8.8 Hz, 1H), 3.76-3.69 (m, 5H), 2.57-2.54 (m, 2H), 2.43-2.40 (m, 2H), 1.79 (s, 3H), 1.49-1.43 (m, 9H). LCMS: (Method A) 420.2 (M+H), Rt. 2.05 min, 97.13% (Max). HPLC: (Method A) Rt. 2.09 min, 98.84% (Max).

Examples 108 and 109: (R)—N-(5-(4-(1-(2,3-dihydrobenzofuran-6-yl)ethyl)piperazin-1-yl)-1,3,4-thiadiazol-2-yl)acetamide and (S)—N-(5-(4-(1-(2,3-dihydrobenzofuran-6-yl)ethyl)piperazin-1-yl)-1,3,4-thiadiazol-2-yl)acetamide

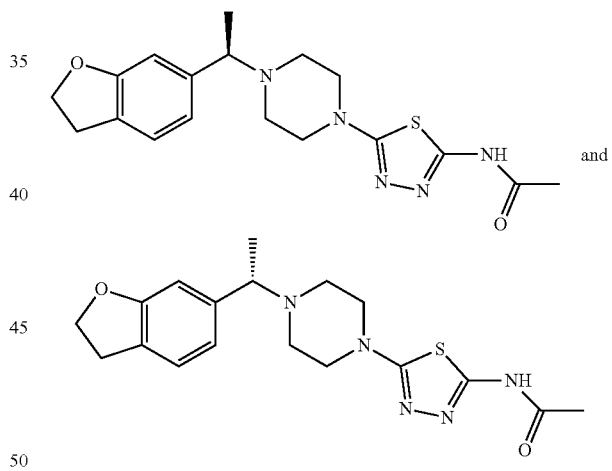

The title compound was synthesized according to the procedure described for Example 105, starting from Intermediate 4 and Intermediate 5. The crude product was purified by flash chromatography to give the racemic mixture of the title compound.

Both enantiomers were further separated by SFC using the preparative chiral method PA.

The first eluting compound correspond to Example 108 (off white solid). $^1$H NMR (400 MHz, DMSO-$d_6$): δ 11.99 (s, 1H), 7.14 (d, J=7.6 Hz, 1H), 6.75 (d, J=7.2 Hz, 1H), 6.71 (s, 1H), 4.50 (t, J=8.8 Hz, 2H), 3.38-3.36 (m, 1H), 3.35-3.33 (m, 4H), 3.13 (t, J=8.4 Hz, 2H), 2.42-2.38 (m, 4H), 2.07 (s, 3H), 1.27 (d, J=6.80 Hz, 3H). LCMS: (Method A) 374.2 (M+H), Rt. 2.31 min, 99.4% (Max). HPLC: (Method A) Rt 2.34 min, 99.7% (Max). CHIRAL HPLC: (SFC Method K) Rt. 2.81 min, 100% (Max).

The second eluting compound corresponds to Example 109 (white solid). $^1$H NMR (400 MHz, DMSO-d$_6$): δ 12.05 (s, 1H), 7.14 (d, J=7.6 Hz, 1H), 6.75 (d, J=7.6 Hz, 1H), 6.70 (s, 1H), 4.49 (t, J=8.8 Hz, 2H), 3.37-3.36 (m, 1H), 3.32-3.31 (m, 4H), 3.13 (t, J=8.8 Hz, 2H), 2.41-2.38 (m, 4H), 2.08 (s, 3H), 1.27 (d, J=6.40 Hz, 3H). LCMS: (Method A) 374.2 (M+H), Rt. 2.31 min, 99.37% (Max). HPLC: (Method A) Rt 2.35 min, 99.59% (Max). CHIRAL HPLC: (SFC Method K) Rt. 3.45 min, 99.42% (Max).

Example 110: (N-((5-(4-(1-(2,3-dihydrobenzofuran-6-yl)ethyl)piperazin-1-yl)-1,3,4-thiadiazol-2-yl)methyl)acetamide

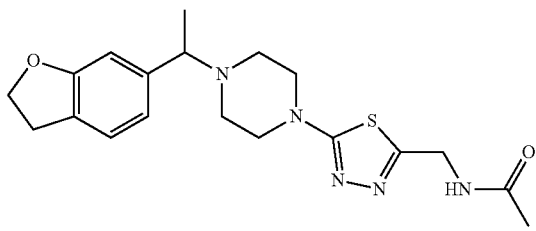 [SMILES: CC(=O)NCc1nnc(N2CCN(C(C)c3ccc4c(c3)OCC4)CC2)s1]

The title compound was synthesized according to the procedure described for Example 112, starting from Example 124 (brown thick oil). $^1$H NMR (400 MHz, DMSO-d$_6$): δ 8.70-8.59 (m, 1H), 7.15 (d, J=7.60 Hz, 1H), 6.75 (d, J=7.60 Hz, 1H), 6.71 (s, 1H), 4.50 (t, J=8.80 Hz, 2H), 4.37 (d, J=6.00 Hz, 2H), 3.39-3.36 (m, 5H), 3.17-3.11 (m, 2H), 2.42-2.38 (m, 4H), 1.83 (s, 3H), 1.27 (d, J=6.80 Hz, 3H). LCMS: (Method A) 388.3 (M+H), Rt. 2.07 min, 96.1% (Max). HPLC: (Method A) Rt 2.09 min, 95.8% (Max).

Example 112: N-((5-(4-(1-(quinoxalin-6-yl)ethyl)piperazin-1-yl)-1,3,4-thiadiazol-2-yl)methyl)acetamide

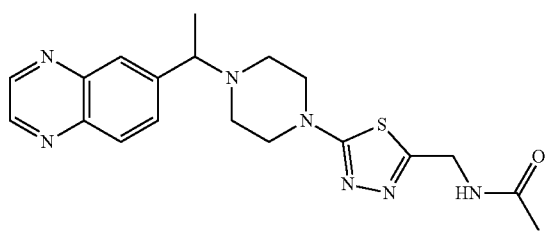 [SMILES: CC(=O)NCc1nnc(N2CCN(C(C)c3ccc4nccnc4c3)CC2)s1]

To a stirred solution of Example 126 (150 mg, 0.42 mmol) in DCM (2 mL) at 0° C., pyridine (0.07 mL) followed by acetic anhydride (0.06 mL, 0.63 mmol) were added. The reaction mixture was stirred at rt overnight. It was quenched with water (3 mL) and extracted with DCM (2×5 mL). The combined organic layer was dried over anhydrous Na$_2$SO$_4$. After evaporation of the solvents, the crude product was purified by flash chromatography (eluent: 6-7% MeOH in DCM) affording the title product (yellow solid). $^1$H NMR (400 MHz, DMSO-d$_6$): δ 8.93 (dd, J=6.8, 2.4 Hz, 2H), 8.64 (t, J=6.0 Hz, 1H), 8.08 (d, J=8.4 Hz, 1H), 8.00 (d, J=1.2 Hz, 1H), 7.91-7.89 (m, 1H), 4.37 (d, J=6.0 Hz, 2H), 3.80 (q, J=6.8 Hz, 1H), 3.40 (t, J=4.8 Hz, 4H), 2.62-2.58 (m, 4H), 1.83 (s, 3H), 1.42 (d, J=6.80 Hz, 3H). LCMS: (Method A) 398.3 (M+H), Rt. 1.55 min, 98.91% (Max). HPLC: (Method A) Rt 1.58 min, 98.72% (Max).

Example 113: (5-(4-(1-(2,3-dihydrobenzofuran-6-yl)ethyl)piperazin-1-yl)-1,3,4-thiadiazol-2-yl)methanol

SGN020621-01-00536-031N01:

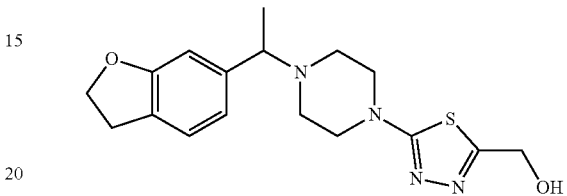

To a stirred solution of Example 117 (0.21 g, 5.40 mmol) in methanol (4 mL), sodium borohydride (62 mg, 1.62 mmol) was added at 0° C. and the mixture was stirred at rt for 2 h. It was concentrated under vacuum. EtOAc (10 mL) was added and was washed with water (10 mL), brine (10 mL), dried over anhydrous Na$_2$SO$_4$ and concentrated. The crude product was purified by flash chromatography affording the title compound (off white solid). $^1$H NMR (400 MHz, DMSO-d$_6$): δ 7.15 (d, J=7.6 Hz, 1H), 6.75 (d, J=7.6 Hz, 1H), 6.71 (s, 1H), 5.86 (t, J=5.6 Hz, 1H), 4.60 (d, J=6.0 Hz, 2H), 4.50 (t, J=8.4 Hz, 2H), 3.39-3.37 (m, 5H), 3.13 (t, J=8.8 Hz, 2H), 2.43-2.39 (m, 4H), 1.27 (d, J=6.8 Hz, 3H). LCMS: (Method A) 347.2 (M+H), Rt. 2.08 min, 96.5% (Max). HPLC: (Method A) Rt 2.04 min, 96.3% (Max).

Example 114: 1-(5-(4-(1-(2,3-dihydrobenzofuran-6-yl)ethyl)piperazin-1-yl)-1,3,4-thiadiazol-2-yl)ethan-1-ol

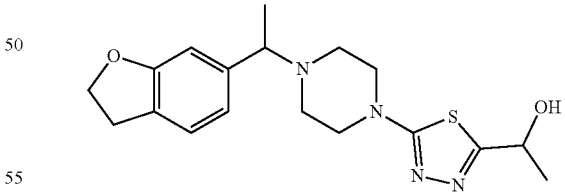

The title compound was synthesized according to the procedure described for Example 115, starting from Example 113 (white solid). $^1$H NMR (400 MHz, DMSO-d$_6$): δ 7.14 (d, J=7.60 Hz, 1H), 6.75 (d, J=7.60 Hz, 1H), 6.70 (s, 1H), 6.00 (d, J=4.80 Hz, 1H), 4.86-4.83 (m, 1H), 4.49 (t, J=8.80 Hz, 2H), 3.38-3.35 (m, 5H), 3.12 (t, J=8.40 Hz, 2H), 2.41-2.38 (m, 4H), 1.39 (d, J=6.40 Hz, 3H), 1.27 (d, J=6.80 Hz, 3H). LCMS: (Method A) 361.2 (M+H), Rt. 2.20 min, 97.8% (Max). HPLC: (Method A) Rt 2.17 min, 98.5% (Max).

Example 115: 1-(5-(4-(1-(quinoxalin-6-yl)ethyl)piperazin-1-yl)-1,3,4-thiadiazol-2-yl)ethan-1-ol

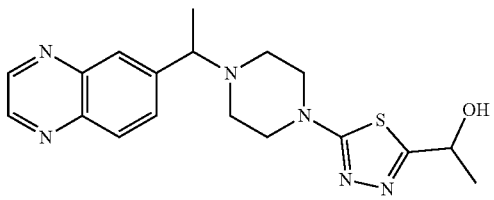 [SMILES: CC(O)c1nnc(N2CCN(C(C)c3ccc4nccnc4c3)CC2)s1]

Step 1: (5-(4-(1-(quinoxalin-6-yl)ethyl)piperazin-1-yl)-1,3,4-thiadiazol-2-yl)methanol The title compound was obtained following the same procedure as described for Example 113, starting from Example 120. The crude product was purified by flash chromatography (eluent: 4-5% MeOH in DCM) affording the title compound (brown solid). $^1$H NMR (400 MHz, DMSO-$d_6$): δ 8.95-8.96 (m, 2H), 8.10 (d, J=8.8 Hz, 1H), 8.01 (s, 1H), 7.91 (dd, J=8.8, 5.2 Hz, 1H), 5.88 (t, J=6.0 Hz, 1H), 4.61 (d, J=6.0 Hz, 2H), 3.82 (q, J=13.6 Hz, 1H), 3.43 (t, J=4.8 Hz, 4H), 2.65-2.60 (m, 2H), 2.60-2.51 (m, 2H), 1.44 (d, J=6.80 Hz, 3H). LCMS: (Method A) 357.2 (M+H), Rt. 1.48 min, 99.13% (Max).

Step 2: 5-(4-(1-(quinoxalin-6-yl)ethyl)piperazin-1-yl)-1,3,4-thiadiazole-2-carbaldehyde To a stirred solution of (5-(4-(1-(quinoxalin-6-yl)ethyl)piperazin-1-yl)-1,3,4-thiadiazol-2-yl)methanol (0.4 g, 1.12 mmol) in dry DCM (8 mL), Dess-Martin periodinane (571 mg, 1.34 mmol) was added at 0° C. and the resulting mixture was stirred at rt for 6 h. After completion of the reaction, the reaction mixture was quenched with saturated NaHCO$_3$ solution (10 mL) and extracted with DCM (3×10 mL). The combined organic layer was dried over Na$_2$SO$_4$ and concentrated. The resulting crude product was purified by flash chromatography (3-4% MeOH in DCM), affording the title compound. Yield: 93% (350 mg, brown solid). LCMS: (Method A) 355.0 (M+H), Rt. 4.44 min, 89% (Max).

Step 3: 1-(5-(4-(1-(quinoxalin-6-yl)ethyl)piperazin-1-yl)-1,3,4-thiadiazol-2-yl)ethan-1-ol To a stirred solution of 5-(4-(1-(quinoxalin-6-yl)ethyl)piperazin-1-yl)-1,3,4-thiadiazole-2-carbaldehyde (100 mg, 1.55 mmol) in dry THF (12 mL) cooled down to −10° C., methyl magnesium chloride (3M in Et$_2$O, 0.5 mL, 1.41 mmol) was added and the mixture was stirred at rt for 3 h. After completion of the reaction, the reaction mixture was quenched with water (2 mL) and concentrated under vacuum. The crude product was dissolved in DCM (10 mL), washed with saturated NH$_4$Cl solution (4 mL) and dried over Na$_2$SO$_4$. After evaporation of the solvent, the crude product was purified by flash chromatography (eluent: 5-6% MeOH in DCM), affording the title compound (brown solid). $^1$H NMR (400 MHz, DMSO-$d_6$): δ 8.94-8.93 (m, 2H), 8.09 (d, J=8.8 Hz, 1H), 8.01 (s, 1H), 7.91 (d, J=8.8 Hz, 1H), 6.02 (d, J=4.8 Hz, 1H), 4.86 (t, J=5.2 Hz, 1H), 3.81 (t, J=6.4 Hz, 1H), 3.42 (s, 4H), 2.68-2.58 (m, 2H), 2.49-2.43 (m, 2H), 1.45-1.40 (m, 6H). LCMS: (Method A) 371.0 (M+H), Rt. 1.71 min, 96.06% (Max). HPLC: (Method A) Rt 1.68 min, 97.89% (Max).

Example 116: 2-methyl-5-(4-(1-(quinoxalin-6-yl)ethyl)piperazin-1-yl)-1,3,4-thiadiazolequinoxaline

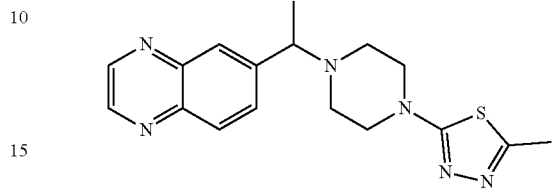

To a stirred solution of Intermediate 2 (0.1 g, 0.4 mmol) in dry DMF (5 mL), TEA (0.15 mL, 1.03 mmol) and 2-chloro-5-methyl-1,3,4-thiadiazole (0.066 g, 0.4 mmol) was added at rt and the reaction mixture was stirred at 90° C. overnight. The resulting reaction mixture was cooled to rt and DMF was evaporated under reduced pressure. To the resulting crude mixture, EtOAc (60 mL) was added and washed with water. The organic layer was dried over Na$_2$SO$_4$ and concentrated. The crude product was purified by flash chromatography to afford the title compound (pale brown solid). $^1$H NMR (400 MHz, DMSO-$d_6$): δ 8.94 (dd, J=6.9, 2.0 Hz, 2H), 8.09 (d, J=8.8 Hz, 1H), 8.01 (s, 1H), 7.91 (d, J=8.8 Hz, 1H), 3.82 (q, J=6.4 Hz, 1H), 3.41-3.40 (m, 4H), 2.62-2.60 (m, 4H), 2.51 (s, 3H), 1.44 (d, J=6.8 Hz, 3H). LCMS: (Method A) 341.2 (M+H), Rt. 1.69 min, 99.6% (Max). HPLC: (Method A) Rt 1.74 min, 98.6% (Max).

Example 117: Ethyl 5-(4-(1-(2,3-dihydrobenzofuran-6-yl)ethyl)piperazin-1-yl)-1,3,4-thiadiazole-2-carboxylate

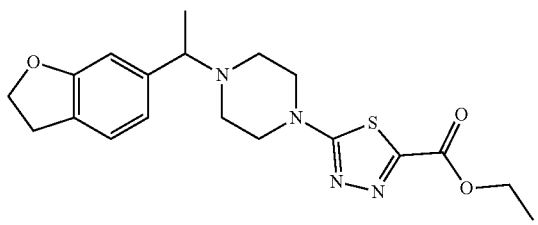 [SMILES: CCOC(=O)c1nnc(N2CCN(C(C)c3ccc4c(c3)OCC4)CC2)s1]

To a stirred solution of ethyl 5-chloro-1,3,4-thiadiazole-2-carboxylate (0.25 g, 1.29 mmol) in dry DMF (2.5 mL), K$_2$CO$_3$ (0.54 g, 3.89 mmol) and Intermediate 13 (0.59 g, 1.93 mmol) were added at rt. The reaction mixture was stirred overnight at 80° C. It was then concentrated under vacuum. EtOAc (10 mL) was added and the resulting solution was washed with water (10 mL), brine (10 mL), dried over anhydrous Na$_2$SO$_4$ and concentrated. The crude product was purified by flash chromatography to afford the title compound. Yield: 51% (0.26 g, off white solid). $^1$H NMR (400 MHz, DMSO-$d_6$): δ 7.15 (d, J=7.60 Hz, 1H), 6.75 (d, J=7.60 Hz, 1H), 6.71 (s, 1H), 4.50 (t, J=8.80 Hz, 2H), 4.33 (q, J=6.80 Hz, 2H), 3.54 (t, J=5.20 Hz, 4H), 3.43-3.41 (m, 1H), 3.13 (t, J=8.40 Hz, 2H), 2.45-2.32 (m, 4H), 1.31-1.27 (m, 6H). LCMS: (Method A) 389.2 (M+H), Rt. 2.88 min, 95.7% (Max). HPLC: (Method A) Rt 2.81 min, 96.5% (Max).

Example 118: 5-(4-(1-(2,3-dihydrobenzofuran-6-yl)ethyl)piperazin-1-yl)-N-methyl-1,3,4-thiadiazole-2-carboxamide

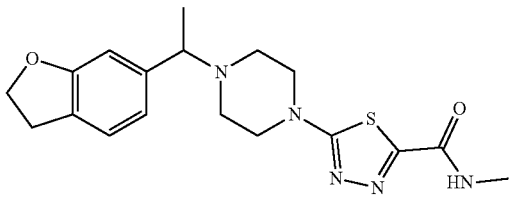 [SMILES: CNC(=O)c1nnc(N2CCN(C(C)c3ccc4c(c3)OCC4)CC2)s1]

The title compound was synthesized according to the procedure described for Example 121, starting from Example 117 (brown thick oil). $^1$H NMR (400 MHz, DMSO-$d_6$): δ 8.74 (q, J=4.8 Hz, 1H), 7.16 (d, J=7.2 Hz, 1H), 6.76 (d, J=1.2 Hz, 1H), 6.72 (s, 1H), 4.51 (t, J=8.40 Hz, 2H), 3.49 (t, J=4.80 Hz, 4H), 3.43-3.41 (m, 1H), 3.14 (t, J=8.80 Hz, 2H), 2.75 (d, J=4.8 Hz, 3H), 2.53-2.51 (m, 2H), 2.46-2.42 (m, 2H), 1.28 (d, J=6.8 Hz, 3H). LCMS: (Method A) 374.0 (M+H), Rt. 2.35 min, 96.4% (Max).
HPLC: (Method A) Rt 2.30 min, 98.2% (Max).

Example 119: 5-(4-(1-(2,3-dihydrobenzofuran-6-yl)ethyl)piperazin-1-yl)-N,N-dimethyl-1,3,4-thiadiazole-2-carboxamide

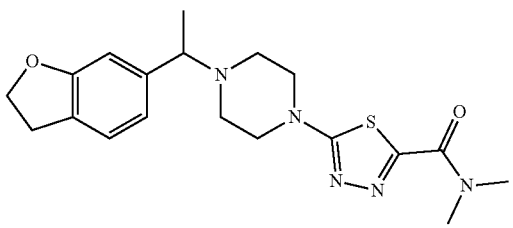 [SMILES: CC(c1ccc2c(c1)OCC2)N1CCN(c2nnc(C(=O)N(C)C)s2)CC1]

The title compound was synthesized according to the procedure described for Example 122, starting from Example 117 (pale yellow solid). $^1$H NMR (400 MHz, DMSO-$d_6$): δ 7.15 (d, J=8.0 Hz, 1H), 6.75 (d, J=8.0 Hz, 1H), 6.71 (s, 1H), 4.50 (t, J=8.4 Hz, 2H), 3.48 (t, J=4.80 Hz, 4H), 3.39-3.98 (m, 4H), 3.13 (t, J=9.20 Hz, 2H), 2.99 (s, 3H), 2.63-2.58 (m, 2H), 2.42-2.41 (m, 2H), 1.27 (d, J=6.80 Hz, 3H). LCMS: (Method A) 388.0 (M+H), Rt. 2.53 min, 99.3% (Max). HPLC: (Method A) Rt 2.48 min, 98.9% (Max).

Example 120: Ethyl 5-(4-(1-(quinoxalin-6-yl)ethyl)piperazin-1-yl)-1,3,4-thiadiazole-2-carboxylate

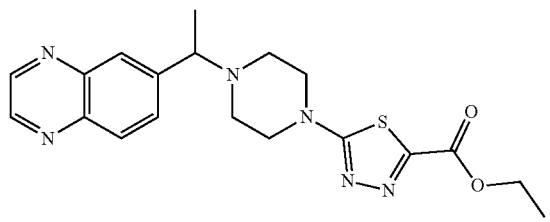 [SMILES: CCOC(=O)c1nnc(N2CCN(C(C)c3ccc4nccnc4c3)CC2)s1]

To a stirred solution of Intermediate 2 (2.62 g, 9.40 mmol) in dry DMF (25 mL), TEA (2.8 mL, 20.15 mmol) and ethyl 5-chloro-1,3,4-thiadiazole-2-carboxylate (1.2 g, 6.71 mmol) were added at 0° C. The reaction mixture was stirred at 100° C. overnight. The reaction mixture was concentrated under vacuum. The resulting crude mixture was dissolved in DCM (35 mL), washed with water (20 mL) and dried over Na$_2$SO$_4$. After evaporation of the solvent, the resulting product was triturated in Et$_2$O (2×4 mL), affording the title compound. Yield: 50% (1.3 g, off white solid). $^1$H NMR (400 MHz, DMSO-$d_6$): δ 8.93 (d, J=6.0 Hz, 2H), 8.09 (d, J=8.8 Hz, 1H), 8.01 (s, 1H), 7.91 (d, J=8.8 Hz, 1H), 4.33 (q, J=7.2 Hz, 2H), 3.85 (t, J=6.0 Hz, 1H), 3.58 (s, 4H), 2.70-2.58 (m, 2H), 2.58-2.50 (m, 2H), 1.44 (d, J=6.4 Hz, 3H), 1.29 (t, J=6.80 Hz, 3H). LCMS: (Method A) 399.2 (M+H), Rt. 2.22 min, 96.96% (Max). HPLC: (Method A) Rt 2.27 min, 96.97% (Max).

Example 121: N-methyl-5-(4-(1-(quinoxalin-6-yl)ethyl)piperazin-1-yl)-1,3,4-thiadiazole-2-carboxamide

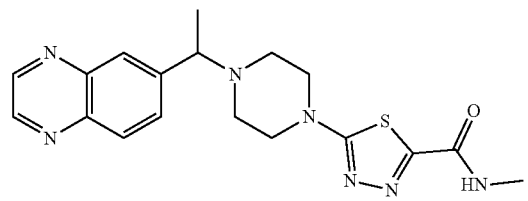 [SMILES: CNC(=O)c1nnc(N2CCN(C(C)c3ccc4nccnc4c3)CC2)s1]

To a solution of Example 120 (0.22 g, 0.55 mmol) and methyl amine (2M in THF, 0.94 mL, 1.83 mmol) in dry toluene (3 mL), bis-trimethyl aluminium 1,4 diazabicylco[2,2,2,] octane adduct (241 mg, 0.94 mmol) was added at 0° C. and the resulting mixture was heated at 100° C. overnight in a sealed tube. After completion of the reaction, solvents are evaporated. Water was added and was extracted with EtOAc (2×8 mL). The combined organic layer was dried over Na2SO4 and concentrated. The resulting residue was purified by MD Autoprep HPLC (Method ?), affording the title compound (off white solid). $^1$H NMR (400 MHz, DMSO-$d_6$): δ 8.95 (dd, J=7.2, 2.6 Hz, 2H), 8.74 (d, J=4.8 Hz, 1H), 8.10 (d, J=8.8 Hz, 1H), 8.01 (s, 1H), 7.91 (dd, J=8.4, 5.2 Hz, 1H), 3.84 (q, J=13.2 Hz, 1H), 3.53 (t, J=4.8 Hz, 4H), 2.75 (d, J=4.4 Hz, 3H), 2.68-2.61 (m, 2H), 2.57-2.51 (m, 2H), 1.44 (d, J=6.40 Hz, 3H). LCMS: (Method A) 384.2 (M+H), Rt. 1.74 min, 99.16% (Max). HPLC: (Method A) Rt 1.77 min, 99.41% (Max).

Example 122: N,N-dimethyl-5-(4-(1-(quinoxalin-6-yl)ethyl)piperazin-1-yl)-1,3,4-thiadiazole-2 carboxamide

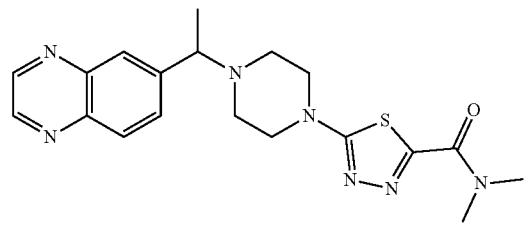 [SMILES: CC(c1ccc2nccnc2c1)N1CCN(c2nnc(C(=O)N(C)C)s2)CC1]

Example 122 was synthesized according to the protocol described for Example 121, replacing the methyl amine solution with a dimethyl amine solution in THF (2M, 3 mL, 6.27 mmol). The crude product was purified by flash chromatography (eluent: 3-4% MeOH in DCM), affording the title compound (off white solid). $^1$H NMR (400 MHz, DMSO-$d_6$): δ 8.94 (d, J=5.2 Hz, 2H), 8.10 (d, J=8.8 Hz, 1H), 8.01 (s, 1H), 7.93-7.83 (m, 1H), 3.93-3.76 (m, 1H), 3.54 (t, J=4.8 Hz, 4H), 3.42 (s, 3H), 3.00 (s, 3H), 2.65-2.61 (m, 4H), 1.45 (d, J=6.8 Hz, 3H). LCMS: (Method A) 398.0 (M+H), Rt. 1.99 min, 96.23% (Max). HPLC: (Method A) Rt 1.95 min, 96.55% (Max).

Example 123: 1-(5-(4-(1-(2,3-dihydrobenzofuran-6-yl)ethyl)piperazin-1-yl)-1,3,4-thiadiazol-2-yl)-N,N-dimethylmethanamine

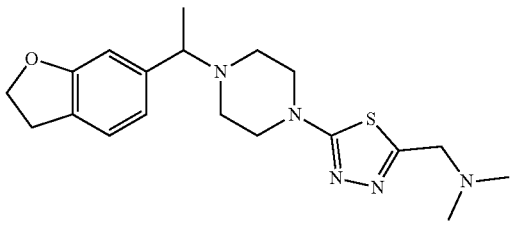 [SMILES: CC(c1ccc2c(c1)OCC2)N1CCN(c2nnc(CN(C)C)s2)CC1]

Step 1: (5-(4-(1-(2,3-dihydrobenzofuran-6-yl)ethyl)piperazin-1-yl)-1,3,4-thiadiazol-2-yl)methyl methanesulfonate To a solution of Example 113 (0.1 g, 0.29 mmol) in dry DCM (2 mL), DIPEA (0.15 mL, 0.86 mmol) and methanesulphonyl chloride (0.027 mL, 0.34 mmol) were added at 0° C. and the reaction mixture was stirred at rt for 2 h. Upon completion of reaction, 10% solution of NaHCO$_3$ (2 mL) was added and the mixture was stirred for 5 minutes. Two layers were separated and the organic layer was washed with brine (2 mL) and dried over Na$_2$SO$_4$. The evaporation of the solvent afforded the title compound that was used directly in the following step. Yield: 85% (0.12 g, brown thick oil). LCMS: (Method A) 365.0 (M+H), Rt. 2.66 min, 87.5% (Max).

Step 2: 1-(5-(4-(1-(2,3-dihydrobenzofuran-6-yl)ethyl)piperazin-1-yl)-1,3,4-thiadiazol-2-yl)-N,N-dimethylmethanamine To a stirred solution of (5-(4-(1-(2,3-dihydrobenzofuran-6-yl)ethyl)piperazin-1-yl)-1,3,4-thiadiazol-2-yl)methyl methanesulfonate (0.1 g, 0.24 mmol) in dry THF (1 mL), N,N-dimethylamine solution (2M in THF, 0.12 mL, 1.22 mmol) was added at rt and the reaction mixture was heated to 80° C. for 6 h in sealed tube. The reaction mixture was cooled to rt and concentrated under vacuum. The resulting residue was dissolved in DCM (5 ml) and washed with brine (5 mL) and dried over anhydrous Na$_2$SO$_4$. After evaporation, the crude product was purified by flash chromatography to get the title compound (brown thick oil). $^1$H NMR (400 MHz, DMSO-$d_6$): δ 7.16 (d, J=7.60 Hz, 1H), 6.76 (d, J=7.60 Hz, 1H), 6.72 (s, 1H), 4.51 (t, J=8.40 Hz, 2H), 3.62 (s, 2H), 3.45-3.36 (m, 5H), 3.14 (t, J=8.40 Hz, 2H), 2.61-2.56 (m, 2H), 2.47-2.39 (m, 2H), 2.20 (s, 6H), 1.28 (d, J=6.80 Hz, 3H). LCMS: (Method A) 374.2 (M+H), Rt. 1.86 min, 97.0% (Max). HPLC: (Method A) Rt 1.89 min, 97.2% (Max).

Example 124: (5-(4-(1-(2,3-dihydrobenzofuran-6-yl)ethyl)piperazin-1-yl)-1,3,4-thiadiazol-2-yl)methanamine

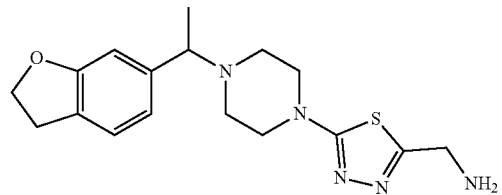 [SMILES: CC(c1ccc2c(c1)OCC2)N1CCN(c2nnc(CN)s2)CC1]

The title compound was synthesized according to the procedure described for Example 123, starting from Example 113, replacing N,N-dimethylamine solution with NaN$_3$ in DMF. The resulting azidomethyl analogue was reduced with Pd/C (10% wt/wt) under H$_2$ atmosphere (yellow solid). $^1$H NMR (400 MHz, DMSO-$d_6$): δ 7.14 (d, J=7.60 Hz, 1H), 6.75 (d, J=7.60 Hz, 1H), 6.70 (s, 1H), 4.49 (t, J=8.80 Hz, 2H), 3.86 (s, 2H), 3.41-3.34 (m, 5H), 3.13 (t, J=8.40 Hz, 2H), 2.42-2.37 (m, 4H), 1.27 (d, J=6.40 Hz, 3H). LCMS: (Method A) 346.3 (M+H), Rt. 1.84 min, 97.7% (Max). HPLC: (Method A) Rt 1.82 min, 97.9% (Max).

Example 125: N,N-dimethyl-1-(5-(4-(1-(quinoxalin-6-yl)ethyl)piperazin-1-yl)-1,3,4-thiadiazol-2-yl)methanamine

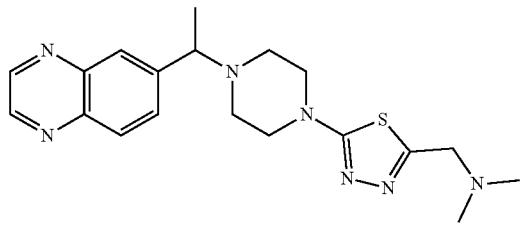 [SMILES: CC(c1ccc2nccnc2c1)N1CCN(c2nnc(CN(C)C)s2)CC1]

The title compound was synthesized according to the procedure described for Example 123, starting from Example 115, step 1 product (37 mg, brown solid). $^1$H NMR (400 MHz, DMSO-$d_6$): δ 8.95 (dd, J=6.8, 2.6 Hz, 2H), 8.10 (dd, J=8.4, Hz, 1H), 8.01 (s, 1H), 7.91 (dd, J=8.8, 5.2 Hz, 1H), 3.88-3.72 (m, 1H), 3.62 (s, 2H), 3.42 (t, J=4.8 Hz, 5H), 2.63-2.61 (m, 3H), 2.19 (s, 6H), 1.44 (d, J=6.8 Hz, 3H). LCMS: (Method A) 384.0 (M+H), Rt. 1.44 min, 96.27% (Max). HPLC: (Method A) Rt 1.43 min, 98.70% (Max).

Example 126: (5-(4-(1-(quinoxalin-6-yl)ethyl)piperazin-1-yl)-1,3,4-thiadiazol-2-yl)methanamine

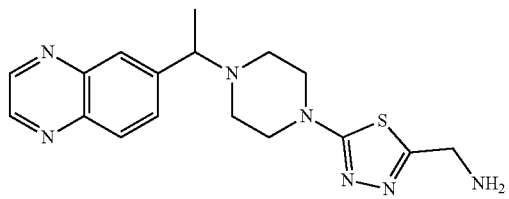 [SMILES: CC(c1ccc2nccnc2c1)N1CCN(c2nnc(CN)s2)CC1]

The title compound was synthesized according to the procedure described for Example 123, starting from Example 115, step 1 product, replacing N,N-dimethylamine solution with $NaN_3$ in DMF. The resulting azidomethyl analogue was reduced with Pd/C (10% wt/wt) under $H_2$ atmosphere. Yield: 83% (190 mg, off white solid). $^1$H NMR (400 MHz, DMSO-$d_6$): δ 8.93 (d, J=5.2 Hz, 2H), 8.08 (d, J=8.8 Hz, 1H), 8.00 (s, 1H), 7.90 (d, J=8.2 Hz, 1H), 3.89-3.72 (m, 3H), 3.39 (t, J=4.8 Hz, 4H), 2.65-2.52 (m, 4H), 1.43 (d, J=6.4 Hz, 3H). LCMS: (Method A) 356.3 (M+H), Rt. 1.35 min, 97.28% (Max). HPLC: (Method A) Rt 1.37 min, 97.78% (Max).

The examples below were synthesized according to procedures described in the previous examples. These compounds and their tautomers, enantiomers, and salts are further preferred embodiments of the present invention.

TABLE 2

| Ex | Structure | Configuration specification | 1H NMR |
|----|-----------|-----------------------------|--------|
| 288 | 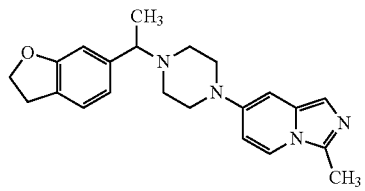 [SMILES: Cc1ncc2cc(N3CCN(C(C)c4ccc5c(c4)OCC5)CC3)ccn12] | Racemic | $^1$H NMR (400 MHz, DMSO-$d_6$): δ 7.90 (d, J = 7.6 Hz, 1H), 7.16 (d, J = 7.6 Hz, 1H), 6.87 (s, 1H), 6.79-6.73 (m, 2H), 6.59 (d, J = 8.0 Hz, 1H), 6.50 (s, 1H), 4.51 (t, J = 8.4 Hz, 2H), 3.40-3.30 (m, 4H), 3.15 (t, J = 8.4 Hz, 2H), 3.15-2.99 (m, 4H), 2.52 (s, 3H), 2.52-2.49 (m, 4H), 1.29 (d, J = 6.40 Hz, 3H). |
| 289 | 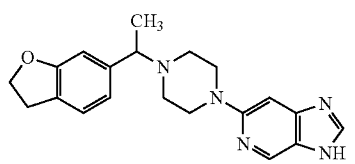 [SMILES: CC(c1ccc2c(c1)OCC2)N1CCN(c2cc3nc[nH]c3cn2)CC1] | Racemic | $^1$H NMR (400 MHz, DMSO-$d_6$): δ 12.26 (s, 1H), 8.51 (s, 1H), 8.06 (s, 1H), 7.15 (d, J = 7.6 Hz, 1H), 6.77 (d, J = 8.4 Hz, 1H), 6.76-6.68 (m, 2H), 4.50 (t, J = 8.4 Hz, 2H), 3.37-3.32 (m, 5H), 3.13 (t, J = 8.4 Hz, 2H), 2.43-2.39 (m, 4H), 1.29-1.28 (m, 3H). |
| 290 | 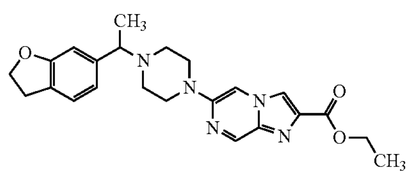 [SMILES: CCOC(=O)c1cn2cc(N3CCN(C(C)c4ccc5c(c4)OCC5)CC3)ncc2n1] | Racemic | $^1$H NMR (400 MHz, DMSO-$d_6$): δ 9.04 (d, J = 1.2 Hz, 1H), 8.38 (s, 1H), 8.28 (s, 1H), 7.17 (d, J = 7.6 Hz, 1H), 6.79 (d, J = 7.2 Hz, 1H), 6.75 (s, 1H), 4.54-4.49 (m, 2H), 4.40-4.35 (m, 2H), 3.39-3.29 (m, 5H), 3.15 (t, J = 8.4 Hz, 2H), 2.61-2.60 (m, 2H), 2.58-2.48 (m, 2H), 1.37-1.30 (m, 6H). |
| 291 | 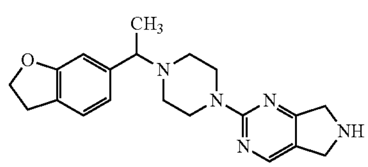 [SMILES: CC(c1ccc2c(c1)OCC2)N1CCN(c2ncc3c(n2)CNC3)CC1] | Racemic | $^1$H NMR (400 MHz, DMSO-$d_6$): δ 8.21 (s, 1H), 7.14 (d, J = 7.2 Hz, 1H), 7.25 (d, J = 7.6 Hz, 1H), 6.71 (s, 1H), 4.50 (t, J = 8.8 Hz, 2H), 3.97 (s, 2H), 3.87 (s, 2H), 3.75-3.60 (m, 4H), 3.29-3.27 (m, 1H), 3.13 (t, J = 8.8 Hz, 2H), 2.44-2.40 (m, 2H), 2.36-2.33 (m, 2H), 1.27 (d, J = 6.40 Hz, 3H). |
| 292 | 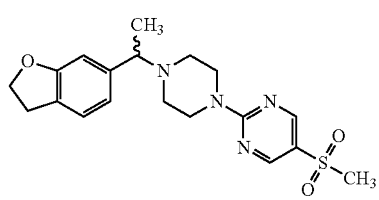 [SMILES: CC(c1ccc2c(c1)OCC2)N1CCN(c2ncc(S(C)(=O)=O)cn2)CC1] | Chiral HPLC SFC Method D: 1st eluting compound | $^1$H NMR (400 MHz, DMSO-$d_6$): δ 8.68 (s, 2H), 7.15 (d, J = 8.2 Hz, 1H), 6.77-6.73 (m, 2H), 4.50 (t, J = 8.8 Hz, 2H), 3.85-3.83 (m, 4H), 3.40-3.37 (m, 1H), 3.21 (s, 3H), 3.13 (t, J = 8.7 Hz, 2H), 2.40-2.33 (m, 4H), 1.28 (d, J = 6.8 Hz, 3H). |
| 293 | 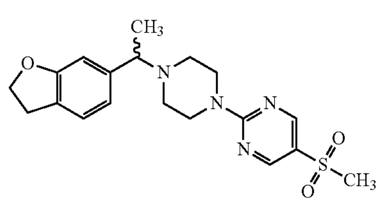 [SMILES: CC(c1ccc2c(c1)OCC2)N1CCN(c2ncc(S(C)(=O)=O)cn2)CC1] | Chiral HPLC SFC Method D: 2nd eluting compound | $^1$H NMR (400 MHz, DMSO-$d_6$): δ 8.68 (s, 2H), 7.15 (d, J = 8.2 Hz, 1H), 6.77-6.73 (m, 2H), 4.50 (t, J = 8.8 Hz, 2H), 3.85-3.83 (m, 4H), 3.40-3.37 (m, 1H), 3.21 (s, 3H), 3.13 (t, J = 8.7 Hz, 2H), 2.40-2.33 (m, 4H), 1.28 (d, J = 6.8 Hz, 3H). |

TABLE 2-continued

| Ex | Structure | Configuration specification | 1H NMR |
|---|---|---|---|
| 294 | 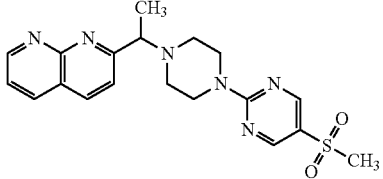 [SMILES: CC(c1ccc2cccnc2n1)N1CCN(c2ncc(S(C)(=O)=O)cn2)CC1] | Racemic | ¹H NMR (400 MHz, DMSO-d₆): δ 9.05-9.04 (m, 1H), 8.68 (s, 2H), 8.43-8.41 (m, 2H), 7.80 (d, J = 8.4 Hz, 1H), 7.63-7.60 (m, 1H), 3.92-3.88 (m, 5H), 3.20 (s, 3H), 2.65-2.50 (m, 4H), 1.44 (d, J = 6.8 Hz, 3H) |
| 295 | 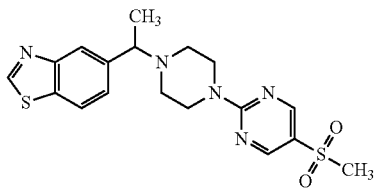 | Racemic | ¹H NMR (400 MHz, DMSO-d₆): δ 9.38 (s, 1H), 8.67 (s, 2H), 8.12 (d, J = 8.4 Hz, 1H), 8.02 (s, 1H), 7.50 (dd, J = 8.2, 1.2 Hz, 1H), 3.87-3.85 (m, 4H), 3.68 (d, J = 6.8 Hz, 1H), 3.20 (s, 3H), 2.56-2.33 (m, 4H), 1.40 (d, J = 6.8 Hz, 3H). |
| 296 | 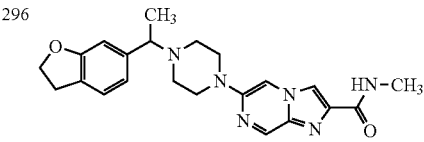 | Racemic | ¹H NMR (400 MHz, DMSO-d₆): δ 8.94 (s, 1H), 8.70 (s, 1H), 8.56 (d, J = 4.4 Hz, 1H), 8.29 (s, 1H), 7.16 (d, J = 7.2 Hz, 1H), 6.79 (d, J = 7.6 Hz, 1H), 6.74 (s, 1H), 4.51 (t, J = 8.8 Hz, 2H), 3.38-3.37 (m, 1H), 3.31-3.30 (m, 4H), 3.14 (t, J = 8.80 Hz, 2H), 2.81 (d, J = 4.40 Hz, 3H), 2.59-2.56 (m, 2H), 2.51-2.50 (m, 2H), 1.30 (d, J = 6.40 Hz, 3H). |
| 297 | 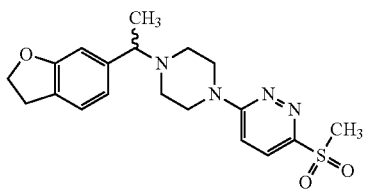 [SMILES: CC(c1ccc2c(c1)OCC2)N1CCN(c2ccc(S(C)(=O)=O)nn2)CC1] | Chiral HPLC SFC Method A: 1st eluting compound | ¹H NMR (400 MHz, DMSO-d₆): δ 7.83 (dd, J = 9.6, 1.6 Hz, 1H), 7.38 (d, J = 9.6 Hz, 1H), 7.16 (d, J = 7.20 Hz, 1H), 6.75 (d, J = 8.0 Hz, 1H), 6.78 (s, 1H), 4.51 (t, J = 8.80 Hz, 2H), 3.74-3.72 (m, 4H), 3.41-3.38 (m, 1H), 3.30 (s, 3H), 3.14 (t, J = 8.80 Hz, 2H), 2.45-2.41 (m, 4H), 1.30 (d, J = 6.80 Hz, 3H). |
| 298 | 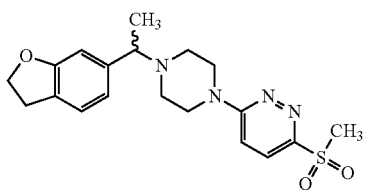 [SMILES: CC(c1ccc2c(c1)OCC2)N1CCN(c2ccc(S(C)(=O)=O)nn2)CC1] | Chiral HPLC SFC Method A: 2nd eluting compound | ¹H NMR (400 MHz, DMSO-d₆): δ 7.84 (dd, J = 9.6, 1.6 Hz, 1H), 7.38 (d, J = 9.6 Hz, 1H), 7.16 (d, J = 7.2 Hz, 1H), 6.75 (d, J = 8.0 Hz, 1H), 6.73 (s, 1H), 4.51 (t, J = 8.8 Hz, 2H), 3.72-3.69 (m, 4H), 3.51-3.47 (m, 1H), 3.30 (s, 3H), 3.14 (t, J = 8.8 Hz, 2H), 2.45-2.41 (m, 4H), 1.310 (d, J = 6.8 Hz, 3H). |
| 299 | 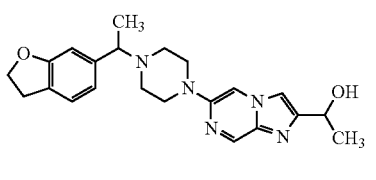 [SMILES: CC(O)c1cn2cc(N3CCN(C(C)c4ccc5c(c4)OCC5)CC3)ncc2n1] | Racemic | ¹H NMR (400 MHz, DMSO-d₆): δ 8.80 (s, 1H), 7.61 (d, J = 5.2 Hz, 2H), 7.18-7.16 (m, 1H), 6.79 (d, J = 7.6 Hz, 1H), 6.75 (s, 1H), 5.46-5.44 (m, 1H), 5.12 (t, J = 6.4 Hz, 1H), 4.54-4.51 (m, 2H), 3.39-3.37 (m, 1H), 3.35-3.20 (m, 4H), 3.15 (t, J = 8.40 Hz, 2H), 2.59-2.56 (m, 4H), 1.58 (d, J = 6.40 Hz, 3H), 1.30 (d, J = 6.80 Hz, 3H). |
| 300 | 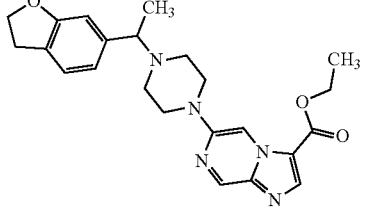 | Racemic | ¹H NMR (400 MHz, DMSO-d₆): δ 8.92 (s, 1H), 8.44 (d, J = 1.6 Hz, 1H), 7.84 (s, 1H), 7.16 (d, J = 7.6 Hz, 1H), 6.78 (d, J = 7.6 Hz, 1H), 6.73 (s, 1H), 4.51 (t, J = 8.0 Hz, 2H), 4.32-4.30 (m, 2H), 3.38-3.32 (m, 1H), 3.26 (br s, 4H), 3.17-3.12 (m, 2H), 2.57-2.55 (m, 2H), 2.46-2.32 (m, 2H), 1.33-1.23 (m, 6H). |
| 301 | 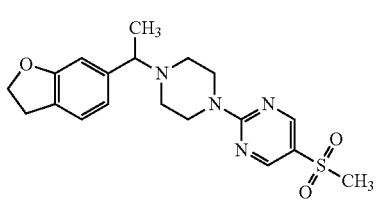 [SMILES: CC(c1ccc2c(c1)OCC2)N1CCN(c2ncc(S(C)(=O)=O)cn2)CC1] | Racemic | ¹H NMR (400 MHz, DMSO-d₆): δ 8.68 (s, 2H), 7.16 (d, J = 7.6 Hz, 1H), 6.76 (d, J = 7.6 Hz, 1H), 6.73 (s, 1H), 4.51 (t, J = 8.8 Hz, 2H), 3.85-3.84 (m, 4H), 3.38-3.35 (m, 1H), 3.21 (s, 3H), 3.14 (t, J = 8.8 Hz, 2H), 2.39-2.35 (m, 4H), 1.29 (d, J = 6.80 Hz, 3H). |

TABLE 2-continued

| Ex | Structure | Configuration specification | 1H NMR |
|---|---|---|---|
| 302 | 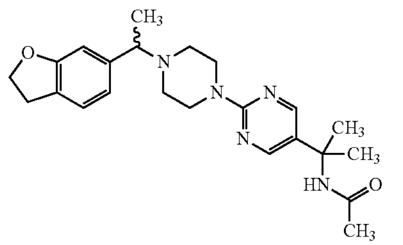 [SMILES: CC(=O)NC(C)(C)c1cnc(N2CCN(C(C)c3ccc4c(c3)OCC4)CC2)nc1] | Chiral HPLC SFC Method B: 1st eluting compound | ¹H NMR (400 MHz, DMSO-d₆): δ 8.27 (s, 2H), 8.05 (s, 1H), 7.15 (d, J = 5.6 Hz, 1H), 6.77 (d, J = 6.8 Hz, 1H), 6.73 (s, 1H), 4.51 (t, J = 8.4 Hz, 2H), 3.65 (s, 4H), 3.17-3.11 (m, 2H), 2.50-2.42 (m, 2H), 2.35-2.33 (m, 2H), 1.79 (s, 3H), 1.49 (s, 6H), 1.28 (d, J = 6.40 Hz, 3H). |
| 303 | 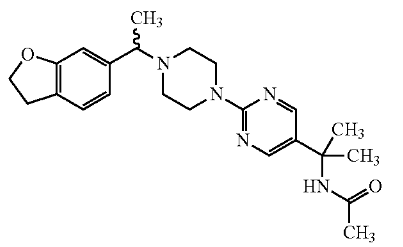 [SMILES: CC(=O)NC(C)(C)c1cnc(N2CCN(C(C)c3ccc4c(c3)OCC4)CC2)nc1] | Chiral HPLC SFC Method B: 2nd eluting compound | ¹H NMR (400 MHz, DMSO-d₆): δ 8.27 (s, 2H), 8.02 (s, 1H), 7.15 (d, J = 7.2 Hz, 1H), 6.78-6.73 (m, 2H), 4.51 (t, J = 8.8 Hz, 2H), 3.82-3.52 (m, 4H), 3.16-3.14 (m, 2H), 2.49-2.29 (m, 4H), 1.80 (d, J = 4.0 Hz, 3H), 1.50 (s, 6H), 1.28 (d, J = 5.60 Hz, 3H). |
| 304 | 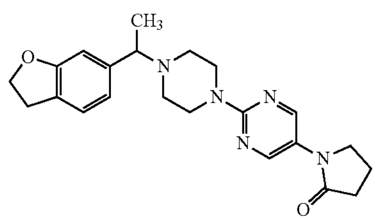 [SMILES: CC(c1ccc2c(c1)OCC2)N1CCN(c2ncc(N3CCCC3=O)cn2)CC1] | Racemic | ¹H NMR (400 MHz, DMSO-d₆): δ 8.57 (s, 2H), 7.14 (d, J = 7.6 Hz, 1H), 6.75 (d, J = 7.6 Hz, 1H), 6.71 (s, 1H), 4.50 (t, J = 8.4 Hz, 2H), 3.74 (t, J = 7.2 Hz, 2H), 3.66 (t, J = 4.8 Hz, 4H), 3.35-3.32 (m, 1H), 3.13 (t, J = 8.8 Hz, 2H), 2.46-2.42 (m, 4H), 2.40-2.33 (m, 2H), 2.06 (t, J = 7.6 Hz, 2H), 1.27 (d, J = 6.4 Hz, 3H). |
| 305 | 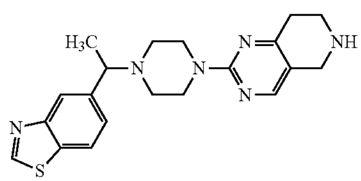 [SMILES: CC(c1ccc2scnc2c1)N1CCN(c2ncc3c(n2)CCNC3)CC1] | Racemic | ¹H NMR (400 MHz, DMSO-d₆): δ 9.39 (s, 1H), 8.13 (s, 1H), 8.09 (d, J = 6.4 Hz, 1H), 8.01 (s, 1H), 7.49 (d, J = 10.8 Hz, 1H), 3.83 (s, 2H), 3.68-3.66 (m, 5H), 3.11 (t, J = 7.2 Hz, 2H), 2.65-2.63 (m, 2H), 2.39-2.37 (m, 4H), 1.40 (d, J = 8.80 Hz, 3H). |
| 306 | 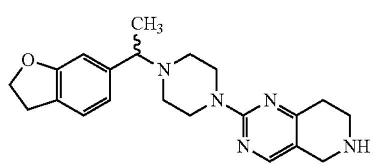 [SMILES: CC(c1ccc2c(c1)OCC2)N1CCN(c2ncc3c(n2)CCNC3)CC1] | Chiral HPLC Method D: 1st eluting compound | ¹H NMR (400 MHz, DMSO-d₆): δ 8.02 (s, 1H), 7.14 (d, J = 7.2 Hz, 1H), 6.75 (dd, J = 7.6, 1.2 Hz, 1H), 6.71 (s, 1H), 4.50 (t, J = 8.8 Hz, 2H), 3.67-3.65 (m, 5H), 3.18-3.17 (m, 2H), 2.95 (t, J = 6.0 Hz, 2H), 2.56-2.54 (m, 2H), 2.51-2.48 (m, 4H), 2.33-2.32 (m, 2H), 1.27 (d, J = 6.8 Hz, 3H). |
| 307 | 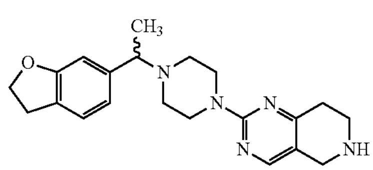 [SMILES: CC(c1ccc2c(c1)OCC2)N1CCN(c2ncc3c(n2)CCNC3)CC1] | Chiral HPLC Method D: 2nd eluting compound | ¹H NMR (400 MHz, DMSO-d₆): δ 8.01 (s, 1H), 7.14 (d, J = 7.6 Hz, 1H), 6.75 (dd, J = 7.6, 1.2 Hz, 1H), 6.71 (s, 1H), 4.50 (t, J = 8.8 Hz, 2H), 3.66-3.64 (m, 5H), 3.13 (t, J = 8.8 Hz, 2H), 2.94 (t, J = 6.0 Hz, 2H), 2.55-2.54 (m, 2H), 2.42-2.40 (m, 4H), 2.35-2.33 (m, 2H), 1.27 (d, J = 6.4 Hz, 3H). |
| 308 | 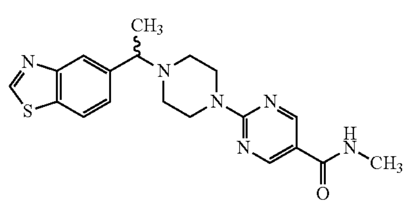 [SMILES: CNC(=O)c1cnc(N2CCN(C(C)c3ccc4scnc4c3)CC2)nc1] | Chiral HPLC SFC Method C: 1st eluting compound | ¹H NMR (400 MHz, DMSO-d₆): δ 9.39 (s, 1H), 8.72 (s, 2H), 8.39-8.22 (m, 1H), 8.13 (d, J = 8.4 Hz, 1H), 8.03 (s, 1H), 7.51 (d, J = 8.0 Hz, 1H), 3.85-3.76 (m, 4H), 3.72-3.63 (m, 1H), 2.75 (d, J = 3.6 Hz, 3H), 2.51-2.36 (m, 4H), 1.41 (d, J = 6.4 Hz, 3H). |

TABLE 2-continued

| Ex | Structure | Configuration specification | 1H NMR |
|---|---|---|---|
| 309 | 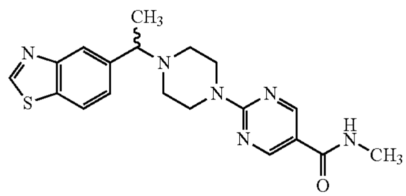 [SMILES: CNC(=O)c1cnc(N2CCN(C(C)c3ccc4scnc4c3)CC2)nc1] | Chiral HPLC SFC Method C: 2nd eluting compound | ¹H NMR (400 MHz, DMSO-d₆): δ 9.39 (s, 1H), 8.71 (s, 2H), 8.38-8.22 (m, 1H), 8.12 (d, J = 8.4 Hz, 1H), 8.03 (s, 1H), 7.51 (d, J = 7.2 Hz, 1H), 3.82-3.79 (m, 4H), 3.72-3.62 (m, 1H), 2.74 (d, J = 4.4 Hz, 3H), 2.51-2.37 (m, 4H), 1.41 (d, J = 6.4 Hz, 3H). |
| 310 | 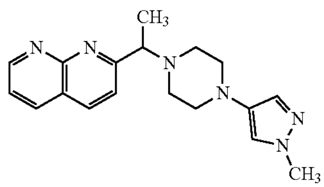 [SMILES: CC(c1ccc2cccnc2n1)N1CCN(c2cnn(C)c2)CC1] | Racemic | ¹H NMR (400 MHz, CDCl₃): δ 9.13-9.12 (m, 1H), 8.22-8.18 (m, 2H), 7.82 (d, J = 8.4 Hz, 1H), 7.52-7.49 (m, 1H), 7.20 (s, 1H), 6.93 (s, 1H), 4.01-3.96 (m, 1H), 3.84 (s, 3H), 3.05-2.87 (m, 4H), 2.87-2.75 (m, 2H), 2.69-2.59 (m, 2H), 1.56 (d, J = 6.8 Hz, 3H). |
| 311 | 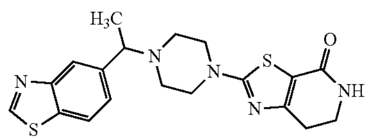 [SMILES: CC(c1ccc2scnc2c1)N1CCN(c2nc3c(s2)C(=O)NCC3)CC1] | Racemic | ¹H NMR (400 MHz, DMSO-d₆): δ 9.39 (s, 1H), 8.13 (d, J = 8.4 Hz, 1H), 8.03 (s, 1H), 7.50 (d, J = 8.4 Hz, 1H), 7.31 (s, 1H), 3.74-3.72 (m, 1H), 3.49-3.48 (m, 4H), 3.36 (t, J = 6.8 Hz, 2H), 2.69 (t, J = 6.8 Hz, 2H), 2.59-2.58 (m, 2H), 2.46-2.44 (m, 2H), 1.41 (d, J = 6.40 Hz, 3H). |
| 312 | 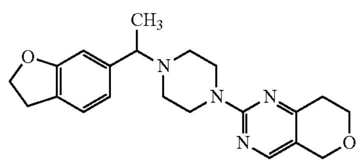 [SMILES: CC(c1ccc2c(c1)OCC2)N1CCN(c2ncc3c(n2)CCOC3)CC1] | Racemic | ¹H NMR (400 MHz, DMSO-d₆): δ 8.05 (s, 1H), 7.14 (d, J = 7.6 Hz, 1H), 6.75 (d, J = 7.6 Hz, 1H), 6.71 (s, 1H), 4.53-4.47 (m, 4H), 3.88 (t, J = 5.6 Hz, 2H), 3.65 (t, J = 9.2 Hz, 4H), 3.17-3.11 (m, 3H), 2.67-2.63 (m, 2H), 2.42-2.39 (m, 2H), 1.23-1.23 (m, 3H). |
| 313 | 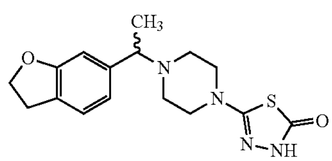 [SMILES: CC(c1ccc2c(c1)OCC2)N1CCN(c2n[nH]c(=O)s2)CC1] | Chiral HPLC Method R: 2nd eluting compound | ¹H NMR: (400 MHz, DMSO-d₆): δ 11.71 (s, 1H), 7.15 (d, J = 7.2 Hz, 1H), 6.75 (d, J = 7.6 Hz, 1H), 6.70 (s, 1H), 4.51 (t, J = 8.4 Hz, 2H), 3.45-3.30 (m, 1H), 3.17-3.12 (m, 6H), 2.47-2.34 (m, 4H), 1.26 (d, J = 6.8 Hz, 3H), |
| 314 | 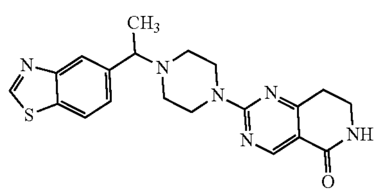 [SMILES: CC(c1ccc2scnc2c1)N1CCN(c2ncc3c(n2)CCNC3=O)CC1] | Racemic | ¹H NMR (400 MHz, DMSO-d₆): δ 9.39 (d, J = 6.8 Hz, 1H), 8.58 (d, J = 6.8 Hz, 1H), 8.12 (d, J = 10.8 Hz, 1H), 8.03 (s, 1H), 7.80-7.65 (m, 1H), 7.51-7.49 (m, 1H), 3.90-3.78 (m, 4H), 3.73-3.63 (m, 1H), 3.40-3.35 (m, 2H), 2.80-2.73 (m, 2H), 2.30-2.13 (m, 4H), 1.41 (d, J = 8.80 Hz, 3H). |
| 315 | 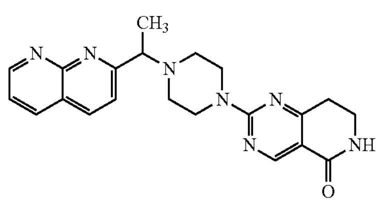 [SMILES: CC(c1ccc2cccnc2n1)N1CCN(c2ncc3c(n2)CCNC3=O)CC1] | Racemic | ¹H NMR (400 MHz, DMSO-d₆): δ 9.05 (s, 1H), 8.58 (s, 1H), 8.45 (d, J = 8.0 Hz, 2H), 7.81 (d, J = 8.4 Hz, 1H), 7.69 (s, 1H), 7.67-7.52 (m, 1H), 3.99-3.73 (m, 1H), 3.43-3.36 (m, 6H), 2.80-2.77 (m, 2H), 2.67-2.57 (m, 2H), 2.44-2.38 (m, 2H), 1.45 (d, J = 5.6 Hz, 3H). |
| 316 | 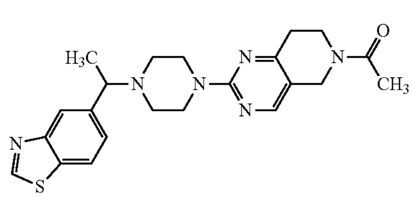 [SMILES: CC(=O)N1CCc2nc(N3CCN(C(C)c4ccc5scnc5c4)CC3)ncc2C1] | Racemic | ¹H NMR (400 MHz, DMSO-d₆): δ 9.39 (s, 1H), 8.18 (s, 1H), 8.13 (d, J = 2.4 Hz, 1H), 8.02 (s, 1H), 7.50 (d, J = 8.4 Hz, 1H), 4.48-4.43 (m, 2H), 4.12-4.12 (m, 1H), 3.69-3.68 (m, 6H), 3.19-3.18 (m, 2H), 2.73-2.72 (m, 1H), 2.68-2.67 (m, 1H), 2.45-2.34 (m, 2H), 2.08 (s, 3H), 1.40 (d, J = 4.40 Hz, 3H). |

TABLE 2-continued

| Ex | Structure | Configuration specification | 1H NMR |
|---|---|---|---|
| 317 | 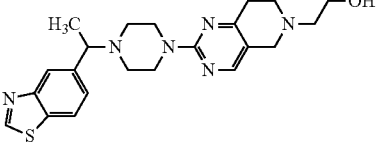 | Racemic | $^1$H NMR (400 MHz, DMSO-d$_6$): δ 9.39 (s, 1H), 8.12 (d, J = 8.4 Hz, 1H), 8.05 (s, 1H), 8.02 (s, 1H), 7.50 (d, J = 8.4 Hz, 1H), 4.49 (br s, 1H), 3.67-3.63 (m, 5H), 3.58-3.56 (m, 2H), 3.44-3.44 (m, 2H), 2.72-2.67 (m, 4H), 2.51-2.51 (m, 2H), 2.39-2.37 (m, 4H), 1.40 (d, J = 6.40 Hz, 3H). |
| 318 | 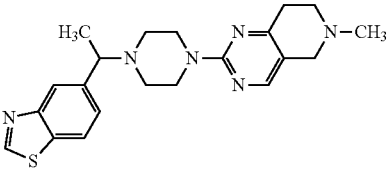 [SMILES: CC(c1ccc2scnc2c1)N1CCN(c2ncc3c(n2)CCN(C)C3)CC1] | Racemic | $^1$H NMR (400 MHz, DMSO-d$_6$): δ 9.39 (s, 1H), 8.12 (d, J = 8.4 Hz, 1H), 8.04-8.02 (m, 2H), 7.50 (d, J = 8.4 Hz, 1H), 3.67-3.64 (m, 5H), 3.31 (s, 2H), 2.68-2.66 (m, 2H), 2.59-2.58 (m, 2H), 2.38-2.32 (m, 4H), 2.32 (s, 3H), 1.40 (d, J = 6.8 Hz, 3H). |
| 319 | 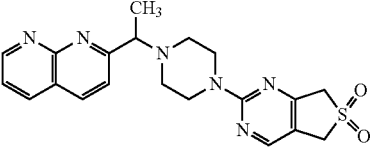 [SMILES: CC(c1ccc2cccnc2n1)N1CCN(c2ncc3c(n2)CS(=O)(=O)C3)CC1] | Racemic | $^1$H NMR (400 MHz, DMSO-d$_6$): δ 9.05 (d, J = 3.2 Hz, 1H), 8.44 (d, J = 8.0 Hz, 2H), 8.32 (s, 1H), 7.80 (d, J = 8.4 Hz, 1H), 7.63-7.61 (m, 1H), 4.43 (s, 2H), 4.38 (s, 2H), 3.88 (d, J = 6.4 Hz, 1H), 3.80-3.70 (m, 4H), 2.69-2.45 (m, 4H), 1.44 (d, J = 6.40 Hz, 3H). |
| 320 | 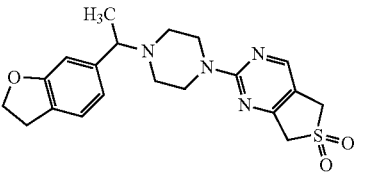 [SMILES: CC(c1ccc2c(c1)OCC2)N1CCN(c2ncc3c(n2)CS(=O)(=O)C3)CC1] | Racemic | $^1$H NMR (400 MHz, DMSO-d$_6$): δ 8.31 (s, 1H), 7.14 (d, J = 7.2 Hz, 1H), 6.75 (d, J = 7.2 Hz, 1H), 6.71 (s, 1H), 4.50 (t, J = 8.4 Hz, 2H), 4.43 (s, 2H), 4.38 (s, 2H), 3.60-3.72 (m, 4H), 3.17-3.10 (m, 3H), 2.45-2.33 (m, 4H), 1.27 (d, J = 6.8 Hz, 3H). |
| 321 | 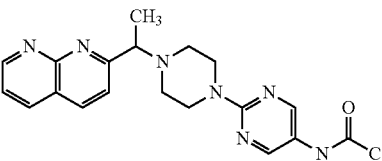 | Racemic | $^1$H NMR (400 MHz, DMSO-d$_6$): δ 9.83 (s, 1H), 9.06-9.04 (m, 1H), 8.50-8.41 (m, 4H), 7.81 (d, J = 8.8 Hz, 1H), 7.68-7.56 (m, 1H), 3.91-3.85 (m, 1H), 3.75-3.62 (m, 4H), 2.62-2.58 (m, 2H), 2.47-2.43 (m, 2H), 2.01 (s, 3H), 1.23 (d, J = 10.8 Hz, 3H). |
| 322 | 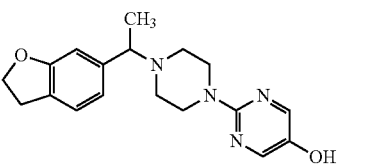 [SMILES: CC(c1ccc2c(c1)OCC2)N1CCN(c2ncc(O)cn2)CC1] | Racemic | $^1$H NMR (400 MHz, DMSO-d$_6$): δ 9.22-9.20 (m, 1H), 8.01-7.99 (m, 2H), 7.15 (d, J = 7.6 Hz, 1H), 6.77 (d, J = 7.6 Hz, 1H), 6.72 (s, 1H), 4.51 (t, J = 8.4 Hz, 2H), 3.60-3.45 (m, 4H), 3.31-3.28 (m, 1H), 3.14 (t, J = 8.4 Hz, 2H), 2.51-2.42 (m, 2H), 2.38-2.30 (m, 2H), 1.28 (d, J = 6.4 Hz, 3H). |
| 323 | 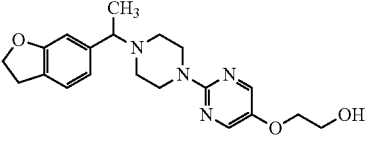 [SMILES: CC(c1ccc2c(c1)OCC2)N1CCN(c2ncc(OCCO)cn2)CC1] | Racemic | $^1$H NMR (400 MHz, DMSO-d$_6$): δ 8.18 (s, 2H), 7.14 (d, J = 7.6 Hz, 1H), 6.75 (d, J = 7.6 Hz, 1H), 6.71 (s, 1H), 4.86 (t, J = 5.6 Hz, 1H), 4.51-4.49 (m, 2H), 3.98-3.93 (m, 2H), 3.69-3.62 (m, 2H), 3.61-3.53 (m, 4H), 3.17-3.11 (m, 2H), 2.46-2.39 (m, 2H), 2.38-2.30 (m, 2H), 1.27 (d, J = 6.8 Hz, 3H). |
| 324 | 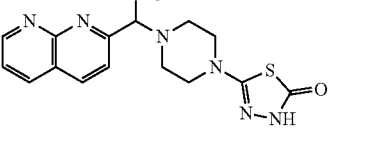 | Racemic | $^1$H NMR: (400 MHz, DMSO-d$_6$): δ 11.73 (s, 1H), 9.04 (d, J = 2.8 Hz, 1H), 8.44 (d, J = 8.4 Hz, 2H), 7.76 (d, J = 8.4 Hz, 1H), 7.61 (t, J = 3.6 Hz, 1H), 3.91-3.89 (m, 1H), 3.19-3.16 (m, 4H), 2.62-2.60 (m, 2H), 2.50-2.46 (m, 2H), 1.43 (d, J = 6.4 Hz, 3H). |
| 325 | 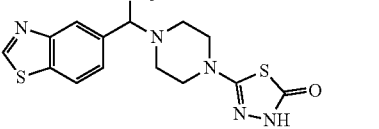 | Racemic | $^1$H NMR (400 MHz, DMSO-d$_6$): δ 11.71 (s, 1H), 9.04 (d, J = 8.4 Hz, 1H), 8.47-8.47 (m, 2H), 8.01 (s, 1H), 7.48 (d, J = 8.4 Hz, 1H), 3.69 (q, J = 6.4 Hz, 1H), 3.24-3.12 (m, 4H), 2.68-2.64 (m, 2H), 2.43-2.40 (m, 2H), 1.39 (d, J = 6.8 Hz, 3H). |

TABLE 2-continued

| Ex | Structure | Configuration specification | 1H NMR |
|---|---|---|---|
| 326 | 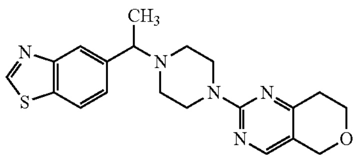 [SMILES: CC(c1ccc2scnc2c1)N1CCN(c2ncc3c(n2)CCOC3)CC1] | Racemic | $^1$H NMR (400 MHz, DMSO-d$_6$) : δ 9.39 (s, 1H), 8.12 (d, J = 8.0 Hz, 1H), 8.06 (s, 1H), 8.02 (s, 1H), 7.50 (d, J = 8.0 Hz, 1H), 4.54 (s, 2H), 3.89 (t, J = 5.6 Hz, 2H), 3.70-3.60 (m, 5H), 2.71-2.60 (m, 2H), 2.50-2.30 (m, 4H), 1.41 (d, J = 6.8 Hz, 3H). |
| 327 | 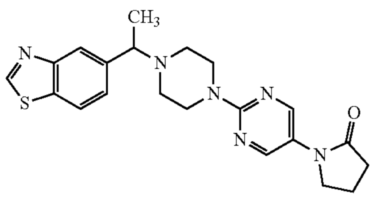 [SMILES: CC(c1ccc2scnc2c1)N1CCN(c2ncc(N3CCCC3=O)cn2)CC1] | Racemic | $^1$H NMR (400 MHz, DMSO-d$_6$) : δ 9.39 (s, 1H), 8.59-8.57 (m, 2H), 8.12 (d, J = 8.0 Hz, 1H), 8.03 (s, 1H), 7.51 (d, J = 8.4 Hz, 1H), 3.79-3.52 (m, 7H), 2.45-2.36 (m, 6H), 2.07 (t, J = 7.6 Hz, 2H), 1.41 (d, J = 6.4 Hz, 3H). |
| 328 | 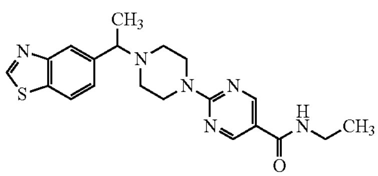 [SMILES: CCNC(=O)c1cnc(N2CCN(C(C)c3ccc4scnc4c3)CC2)nc1] | Racemic | $^1$H NMR (400 MHz, DMSO-d$_6$): δ 9.39 (s, 1H), 8.72 (s, 2H), 8.30 (t, J = 5.2 Hz, 1H), 8.12 (d, J = 8.4 Hz, 1H), 8.03 (s, 1H), 7.50 (d, J = 8.4 Hz, 1H), 3.82-3.78 (m, 4H), 3.67-3.63 (m, 1H), 3.28-3.21 (m, 4H), 2.46-2.36 (m, 2H), 1.41 (d, J = 6.8 Hz, 3H), 1.10 (t, J = 7.2 Hz, 3H). |
| 329 | 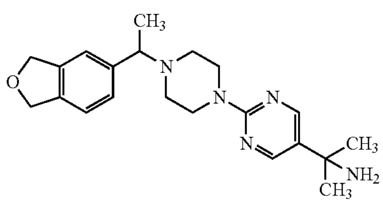 [SMILES: CC(c1ccc2c(c1)COC2)N1CCN(c2ncc(C(C)(C)N)cn2)CC1] | Racemic | $^1$H NMR (400 MHz, DMSO-d$_6$): δ 8.46 (s, 2H), 7.15 (d, J = 7.6 Hz, 1H), 6.75 (d, J = 7.6 Hz, 1H), 6.71 (s, 1H), 4.50 (t, J = 8.4 Hz, 1H), 3.66-3.62 (m, 4H), 3.12 (t, J = 8.4 Hz, 2H), 2.42-2.44 (m, 2H), 2.37-2.28 (m, 2H), 1.32 (s, 6H), 1.28 (t, J = 6.4 Hz, 3H). |
| 330 | 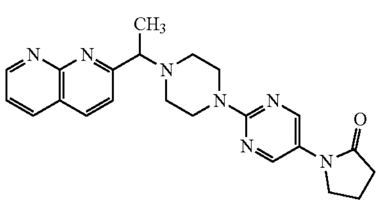 [SMILES: CC(c1ccc2cccnc2n1)N1CCN(c2ncc(N3CCCC3=O)cn2)CC1] | Racemic | $^1$H NMR (400 MHz, DMSO-d6): δ 9.06 (s, 1H), 8.59 (s, 2H), 8.46 (d, J = 8.0 Hz, 2H), 7.81 (d, J = 8.4 Hz, 1H), 7.62 (dd, J = 7.4, 4.3 Hz, 1H), 3.41-3.35 (m, 1H), 3.78-3.62 (m, 6H), 2.62-2.58 (m, 2H), 2.45-2.38 (m, 4H), 2.10-2.00 (m, 2H), 1.45 (d, J = 5.6 Hz, 3H). |
| 331 | 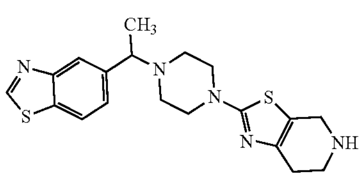 [SMILES: CC(c1ccc2scnc2c1)N1CCN(c2nc3c(s2)CNCC3)CC1] | Racemic | $^1$H NMR (400 MHz, DMSO-d$_6$): δ 9.38 (s, 1H), 8.11 (d, J = 8.4 Hz, 1H), 8.01 (s, 1H), 7.48 (d, J = 7.6 Hz, 1H), 4.01-4.09 (m, 1H), 3.71-3.63 (m, 3H), 3.32-3.29 (m, 4H), 3.17 (s, 1H), 2.94 (t, J = 5.6 Hz, 2H), 2.44-2.42 (m, 4H), 1.39 (d, J = 6.4 Hz, 3H). |
| 332 | 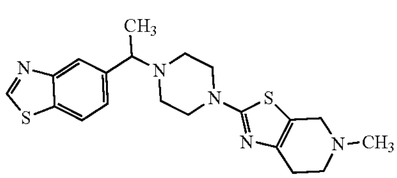 [SMILES: CC(c1ccc2scnc2c1)N1CCN(c2nc3c(s2)CN(C)CC3)CC1] | Racemic | $^1$H NMR (400 MHz, DMSO-d$_6$): δ 9.38 (s, 1H), 8.11 (d, J = 8.0 Hz, 1H), 8.01 (s, 1H), 7.49 (d, J = 8.0 Hz, 1H), 3.69-3.66 (m, 1H), 3.39-3.36 (m, 2H), 3.32-3.25 (m, 5H), 3.17 (s, 1H), 2.61 (t, J = 5.2 Hz, 2H), 2.59-2.41 (m, 4H), 2.31 (s, 3H), 1.39 (d, J = 6.8 Hz, 3H). |
| 333 | 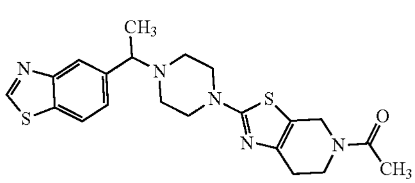 [SMILES: CC(=O)N1CCc2nc(N3CCN(C(C)c4ccc5scnc5c4)CC3)sc2C1] | Racemic | $^1$H NMR (400 MHz, DMSO-d$_6$): δ 9.38 (s, 1H), 8.12 (d, J = 8.0 Hz, 1H), 8.01 (s, 1H), 7.49 (d, J = 8.0 Hz, 1H), 4.48-4.45 (m, 2H), 3.70-3.64 (m, 3H), 3.36-3.33 (m, 4H), 2.55-2.60 (m, 2H), 2.49-2.39 (m, 4H), 2.07-2.03 (m, 3H), 1.40 (d, J = 6.4 Hz, 3H). |

TABLE 2-continued

| Ex | Structure | Configuration specification | 1H NMR |
|---|---|---|---|
| 334 | 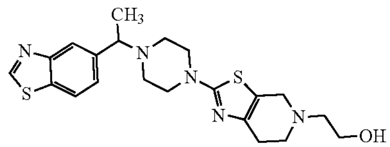 [SMILES: CC(c1ccc2scnc2c1)N1CCN(c2nc3c(s2)CN(CCO)CC3)CC1] | Racemic | ¹H NMR (400 MHz, DMSO-$d_6$): δ 9.38 (s, 1H), 8.11 (d, J = 8.4 Hz, 1H), 8.01 (s, 1H), 7.48 (d, J = 8.4 Hz, 1H), 4.51-4.39 (m, 1H), 3.69-3.66 (m, 1H), 3.54-3.48 (m, 4H), 3.32-3.28 (m, 4H), 2.73-2.70 (m, 2H), 2.59-2.52 (m, 6H), 2.46-2.40 (m, 2H), 1.39 (d, J = 6.4 Hz, 3H). |
| 335 | 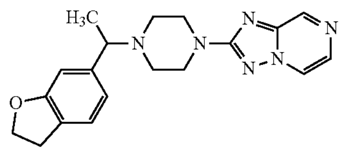 [SMILES: CC(c1ccc2c(c1)OCC2)N1CCN(c2nc3cnccn3n2)CC1] | Racemic | ¹H NMR (400 MHz, DMSO-$d_6$): δ 8.93 (s, 1H), 8.78 (d, J = 4.4 Hz, 1H), 8.04 (d, J = 4.4 Hz, 1H), 7.15 (d, J = 7.6 Hz, 1H), 6.74 (d, J = 13.6 Hz, 1H), 6.77 (s, 1H), 4.50 (t, J = 8.8 Hz, 2H), 3.51 (t, J = 4.8 Hz, 4H), 3.38-3.35 (m, 1H), 3.13 (t, J = 8.8 Hz, 2H), 2.61-2.49 (m, 2H), 2.44-2.40 (m, 2H), 1.28 (d, J = 6.8 Hz, 3H). |
| 336 | 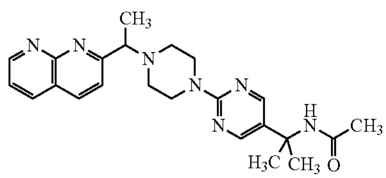 [SMILES: CC(=O)NC(C)(C)c1cnc(N2CCN(C(C)c3ccc4cccnc4n3)CC2)nc1] | Racemic | ¹H NMR (400 MHz, DMSO-$d_6$): δ 9.05-9.05 (m, 1H), 8.44 (d, J = 8.4 Hz, 2H), 8.26 (s, 2H), 8.02 (s, 1H), 7.81 (d, J = 8.4 Hz, 1H), 7.63-7.61 (m, 1H), 3.87-3.86 (m, 1H), 3.71-3.69 (m, 4H), 2.60-2.59 (m, 2H), 2.47-2.46 (m, 2H), 1.78 (s, 3H), 1.49 (s, 6H), 1.44 (d, J = 6.4 Hz, 3H). |
| 337 | 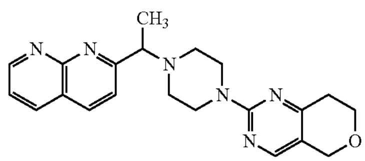 [SMILES: CC(c1ccc2cccnc2n1)N1CCN(c2ncc3c(n2)CCOC3)CC1] | Racemic | ¹HNMR (400 MHz, DMSO-$d_6$): δ 9.04 (t, J = 2.4 Hz, 1H), 8.44 (d, J = 8.4 Hz, 2H), 8.06 (s, 1H), 7.80 (d, J = 12.0 Hz, 1H), 7.63-7.62 (m, 1H), 4.53 (s, 2H), 3.90-3.88 (m, 3H), 3.71-3.69 (m, 4H), 2.69-2.66 (m, 2H), 2.59-2.58 (m, 2H), 2.46-2.45 (m, 2H), 1.43 (d, J = 6.4 Hz, 3H). |
| 338 | 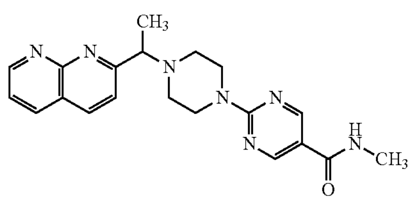 [SMILES: CNC(=O)c1cnc(N2CCN(C(C)c3ccc4cccnc4n3)CC2)nc1] | Racemic | ¹H NMR (400 MHz, DMSO-$d_6$): δ 9.05 (d, J = 2.0 Hz, 1H), 8.72 (s, 2H), 8.45 (d, J = 8.0 Hz, 2H), 8.29-8.27 (m, 1H), 7.80 (d, J = 8.4 Hz, 1H), 7.62-7.61 (m, 1H), 3.82-3.73 (m, 5H), 2.74-2.73 (m, 3H), 2.67-2.49 (m, 4H), 1.45 (d, J = 5.6 Hz, 3H). |
| 339 | 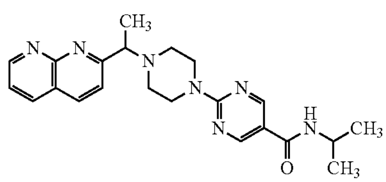 [SMILES: CC(C)NC(=O)c1cnc(N2CCN(C(C)c3ccc4cccnc4n3)CC2)nc1] | Racemic | ¹H NMR (400 MHz, DMSO-$d_6$): δ 9.05-9.04 (m, 1H), 8.72 (s, 2H), 8.45 (d, J = 8.8 Hz, 2H), 8.04 (d, J = 7.6 Hz, 1H), 7.80 (d, J = 8.4 Hz, 1H), 7.63-7.60 (m, 1H), 4.05-4.01 (m, 1H), 3.90-3.87 (m, 1H), 3.82-3.79 (m, 4H), 2.67-2.58 (m, 2H), 2.49-2.32 (m, 2H), 1.44 (d, J = 6.8 Hz, 3H), 1.13 (d, J = 6.4 Hz, 6H). |
| 340 | 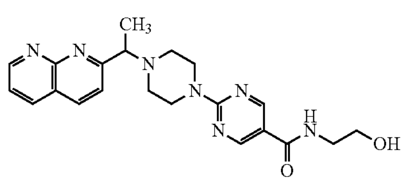 [SMILES: CC(c1ccc2cccnc2n1)N1CCN(c2ncc(C(=O)NCCO)cn2)CC1] | Racemic | ¹H NMR (400 MHz, DMSO-$d_6$): δ 9.05-9.01 (m, 1H), 8.74 (s, 2H), 8.45 (d, J = 8.4 Hz, 2H), 8.32-8.30 (m, 1H), 7.81 (d, J = 8.4 Hz, 1H), 7.63-7.60 (m, 1H), 4.71 (t, J = 5.2 Hz, 1H), 3.90-3.87 (m, 1H), 3.82-3.79 (m, 4H), 3.50-3.45 (m, 2H), 3.32-3.26 (m, 2H), 2.62-2.58 (m, 2H), 2.50-2.45 (m, 2H), 1.44 (d, J = 6.8 Hz, 3H). |
| 341 | 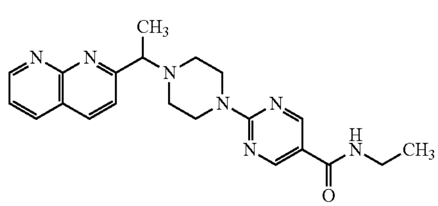 [SMILES: CCNC(=O)c1cnc(N2CCN(C(C)c3ccc4cccnc4n3)CC2)nc1] | Racemic | ¹H NMR (400 MHz, DMSO-$d_6$): δ 9.05-9.01 (m, 1H), 8.72 (s, 2H), 8.45 (d, J = 8.4 Hz, 2H), 8.32-8.30 (m, 1H), 7.81 (d, J = 8.4 Hz, 1H), 7.63-7.60 (m, 1H), 3.90-3.89 (m, 1H), 3.82-3.79 (m, 4H), 3.26-3.22 (m, 2H), 2.66-2.58 (m, 2H), 2.45-2.32 (m, 2H), 1.44 (d, J = 6.8 Hz, 3H), 1.09 (t, J = 7.2 Hz, 3H). |

TABLE 2-continued

| Ex | Structure | Configuration specification | 1H NMR |
|---|---|---|---|
| 342 | 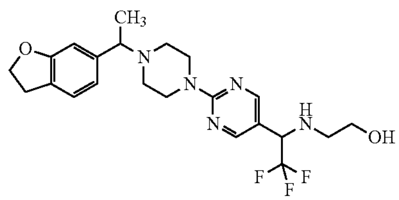 [SMILES: CC(c1ccc2c(c1)OCC2)N1CCN(c2ncc(C(NCCO)C(F)(F)F)cn2)CC1] | Racemic | ¹H NMR (400 MHz, DMSO-d₆): δ 8.38 (s, 2H), 7.14 (d, J = 6.0 Hz, 1H), 6.77-6.72 (m, 2H), 6.51-6.49 (m, 1H), 4.50-4.50 (m, 4H), 4.36-4.34 (m, 1H), 3.70-3.69 (m, 5H), 3.42-3.40 (m, 2H), 3.31-3.10 (m, 2H), 2.33-2.31 (m, 4H), 1.25 (d, J = 13.2 Hz, 3H). |
| 343 | 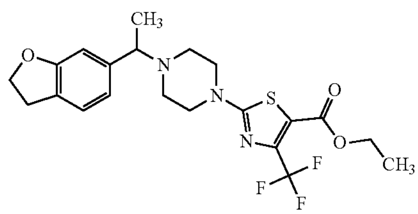 [SMILES: CCOC(=O)c1sc(N2CCN(C(C)c3ccc4c(c3)OCC4)CC2)nc1C(F)(F)F] | Racemic | ¹H NMR (400 MHz, DMSO-d₆): δ 7.16 (d, J = 7.6 Hz, 1H), 6.76 (d, J = 7.6 Hz, 1H), 6.72 (s, 1H), 4.51 (t, J = 8.8 Hz, 2H), 4.26-4.24 (m, 2H), 3.51-3.45 (m, 4H), 3.44-3.42 (m, 1H), 3.14 (t, J = 8.4 Hz, 2H), 2.45-2.44 (m, 4H), 1.28 (d, J = 6.8 Hz, 3H), 1.24 (t, J = 7.2 Hz, 3H). |
| 344 | 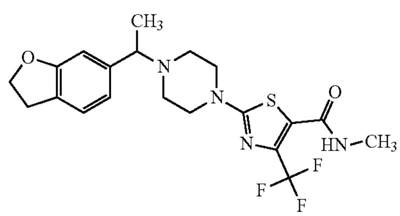 [SMILES: CNC(=O)c1sc(N2CCN(C(C)c3ccc4c(c3)OCC4)CC2)nc1C(F)(F)F] | Racemic | ¹H NMR (400 MHz, DMSO-d₆): δ 8.38 (d, J = 4.0 Hz, 1H), 7.17-7.15 (m, 1H), 6.77 (d, J = 7.6 Hz, 1H), 6.72 (s, 1H), 4.51 (t, J = 9.2 Hz, 2H), 3.42-3.40 (m, 5H), 3.14 (t, J = 8.4 Hz, 2H), 2.70-2.68 (m, 3H), 2.43-2.40 (m, 4H), 1.29 (d, J = 6.8 Hz, 3H). |
| 345 | 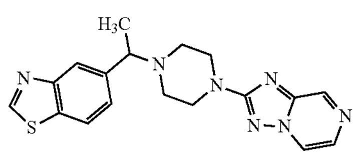 [SMILES: CC(c1ccc2scnc2c1)N1CCN(c2nc3cnccn3n2)CC1] | Racemic | ¹H NMR (400 MHz, DMSO-d₆): δ 9.39 (s, 1H), 8.94 (s, 1H), 8.79 (d, J = 4.4 Hz, 1H), 8.13 (d, J = 8.4 Hz, 1H), 8.05 (d, J = 4.8 Hz, 2H), 7.52 (d, J = 8.0 Hz, 1H), 3.72-3.68 (m, 1H), 3.56-3.54 (m, 4H), 2.59-2.56 (m, 4H), 1.42 (d, J = 6.4 Hz, 3H). |
| 346 | 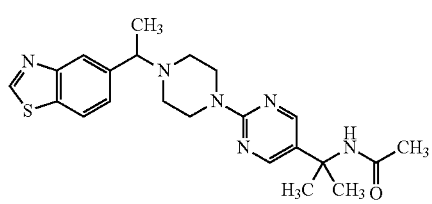 [SMILES: CC(=O)NC(C)(C)c1cnc(N2CCN(C(C)c3ccc4scnc4c3)CC2)nc1] | Racemic | ¹H NMR (400 MHz, DMSO-d₆): δ 9.38 (s, 1H), 8.25 (s, 2H), 8.11 (d, J = 8.0 Hz, 1H), 8.02-7.95 (m, 2H), 7.50 (d, J = 8.4 Hz, 1H), 3.67-3.64 (m, 5H), 2.50-2.32 (m, 4H), 1.78 (s, 3H), 1.48 (s, 6H), 1.40 (d, J = 6.0 Hz, 3H). |
| 347 | 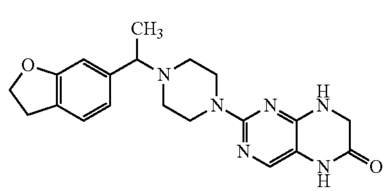 [SMILES: CC(c1ccc2c(c1)OCC2)N1CCN(c2ncc3c(n2)NCC(=O)N3)CC1] | Racemic | 1H NMR (400 MHz, DMSO-d₆): δ 10.12 (s, 1H), 7.40 (s, 1H), 7.31 (s, 1H), 7.14 (d, J = 7.2 Hz, 1H), 6.75 (d, J = 7.2 Hz, 1H), 6.70 (s, 1H), 4.51 (t, J = 8.8 Hz, 2H), 3.90 (s, 2H), 3.52-3.49 (m, 5H), 3.15 (t, J = 8.0 Hz, 2H), 2.36-2.30 (m, 4H), 1.25 (d, J = 5.20 Hz, 3H). |
| 348 | 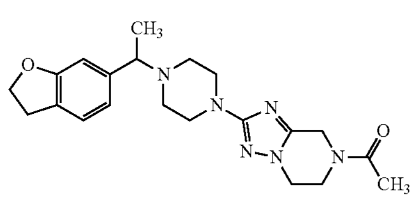 [SMILES: CC(=O)N1CCn2nc(N3CCN(C(C)c4ccc5c(c4)OCC5)CC3)nc2C1] | Racemic | ¹H NMR (400 MHz, DMSO-d₆): δ 7.15 (d, J = 7.6 Hz, 1H), 6.75 (d, J = 7.2 Hz, 1H), 6.70 (s, 1H), 4.68-4.58 (m, 2H), 4.51 (t, J = 8.8 Hz, 2H), 4.04-4.01 (m, 1H), 3.93-3.91 (m, 2H), 3.34-3.31 (m, 2H), 3.24-3.21 (m, 4H), 3.14 (t, J = 8.8 Hz, 2H), 2.44-2.41 (m, 2H), 2.37-2.33 (m, 2H), 2.13-2.09 (m, 3H), 1.27 (d, J = 6.4 Hz, 3H). |
| 349 | 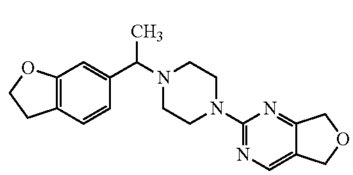 [SMILES: CC(c1ccc2c(c1)OCC2)N1CCN(c2ncc3c(n2)COC3)CC1] | Racemic | 1H NMR (400 MHz, DMSO-d₆): δ 8.92 (s, 1H), 7.15 (d, J = 7.6 Hz, 1H), 6.77-6.72 (m, 2H), 4.93 (s, 2H), 4.74 (s, 2H), 4.50 (t, J = 8.4 Hz, 2H), 3.71-3.68 (m, 4H), 3.17-3.11 (m, 3H), 2.46-2.40 (m, 2H), 2.37-2.31 (m, 2H), 1.28 (d, J = 6.80 Hz, 3H). |

TABLE 2-continued

| Ex | Structure | Configuration specification | 1H NMR |
|---|---|---|---|
| 350 | 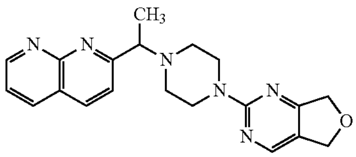 [SMILES: CC(c1ccc2cccnc2n1)N1CCN(c2ncc3c(n2)COC3)CC1] | Racemic | 1H NMR (400 MHz, DMSO-$d_6$): δ 9.05-9.04 (m, 1H), 8.44 (d, J = 8.4 Hz, 2H), 8.29 (s, 1H), 7.80 (d, J = 8.4 Hz, 1H), 7.63-7.60 (m, 1H), 4.92 (s, 2H), 4.73 (s, 2H), 3.88-3.86 (m, 1H), 3.74-3.72 (m, 4H), 2.60-2.56 (m, 2H), 2.46-2.43 (m, 2H), 1.43 (d, J = 6.40 Hz, 3H). |
| 351 | 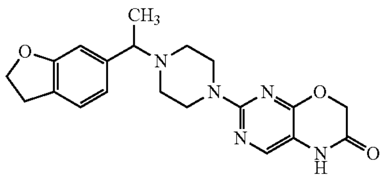 [SMILES: CC(c1ccc2c(c1)OCC2)N1CCN(c2ncc3c(n2)OCC(=O)N3)CC1] | Racemic | $^1$H NMR (400 MHz, DMSO-$d_6$): δ 10.57 (s, 1H), 7.79 (s, 1H), 7.15 (d, J = 7.6 Hz, 1H), 6.75 (d, J = 7.6 Hz, 1H), 6.71 (s, 1H), 4.76 (s, 2H), 4.51 (t, J = 8.8 Hz, 2H), 3.59-3.53 (m, 4H), 3.34-3.32 (m, 1H), 3.13 (t, J = 8.4 Hz, 2H), 2.42-2.39 (m, 2H), 2.33-2.30 (m, 2H), 1.27 (d, J = 6.80 Hz, 3H). |
| 352 | 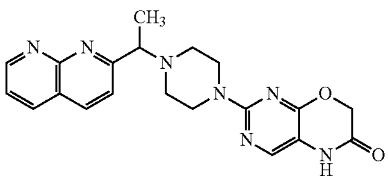 [SMILES: CC(c1ccc2cccnc2n1)N1CCN(c2ncc3c(n2)OCC(=O)N3)CC1] | Racemic | $^1$H NMR (400 MHz, DMSO-$d_6$): δ 10.56 (s, 1H), 9.05 (d, J = 2.0 Hz, 1H), 8.47-8.45 (m, 2H), 7.82-7.78 (m, 2H), 7.63-7.59 (m, 1H), 4.75 (s, 2H), 3.87-3.85 (m, 1H), 3.71-3.61 (m, 4H), 2.50-2.48 (m, 2H), 2.47-2.43 (m, 2H), 1.43 (d, J = 6.4 Hz, 3H). |
| 353 | 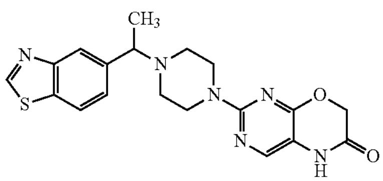 [SMILES: CC(c1ccc2scnc2c1)N1CCN(c2ncc3c(n2)OCC(=O)N3)CC1] | Racemic | $^1$H NMR (400 MHz, DMSO-$d_6$): δ 10.57 (s, 1H), 9.39 (s, 1H), 8.12 (d, J = 8.4 Hz, 1H), 8.01 (s, 1H), 7.78 (s, 1H), 7.49 (d, J = 8.0 Hz, 1H), 4.76 (s, 2H), 3.64-3.58 (m, 5H), 2.51-2.47 (m, 2H), 2.38-2.34 (m, 2H), 1.40 (d, J = 6.40 Hz, 3H). |
| 354 | 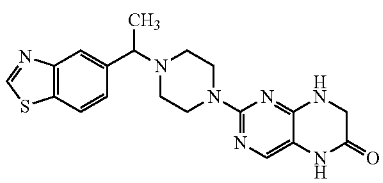 [SMILES: CC(c1ccc2scnc2c1)N1CCN(c2ncc3c(n2)NCC(=O)N3)CC1] | Racemic | $^1$H NMR (400 MHz, DMSO-$d_6$): δ 10.14 (s, 1H), 9.39 (s, 1H), 8.12 (d, J = 8.4 Hz, 1H), 8.01 (s, 1H), 7.49 (d, J = 8.0 Hz, 1H), 7.40 (s, 1H), 7.33 (s, 1H), 3.89 (s, 2H), 3.61 (d, J = 6.8 Hz, 1H), 3.59-3.55 (m, 4H), 2.45-2.40 (m, 4H), 1.39 (d, J = 6.8 Hz, 3H). |
| 355 | 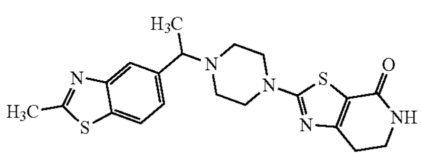 [SMILES: Cc1nc2cc(C(C)N3CCN(c4nc5c(s4)C(=O)NCC5)CC3)ccc2s1] | Racemic | $^1$H NMR (400 MHz, DMSO-$d_6$): δ 7.98 (d, J = 8.4 Hz, 1H), 7.85 (s, 1H), 7.39 (d, J = 8.0 Hz, 1H), 7.32 (s, 1H), 3.68-3.66 (m, 1H), 3.56-3.42 (m, 4H), 2.79 (s, 3H), 2.71-2.67 (m, 2H), 2.61-2.53 (m, 2H), 2.48-2.42 (m, 4H), 1.39 (d, J = 6.8 Hz, 3H). |
| 356 | 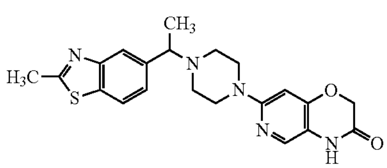 [SMILES: Cc1nc2cc(C(C)N3CCN(c4cc5c(cn4)NC(=O)CO5)CC3)ccc2s1] | Racemic | $^1$H NMR (400 MHz, DMSO-$d_6$) : δ 10.59 (s, 1H), 7.97 (d, J = 8.4 Hz, 1H), 7.84 (s, 1H), 7.65 (s, 1H), 7.38 (d, J = 8.4 Hz, 1H), 6.40 (s, 1H), 4.60 (s, 2H), 3.60-3.55 (m, 1H), 3.40-3.35 (m, 4H), 3.34 (s, 3H), 2.41-2.34 (m, 4H), 1.38 (d, J = 6.8 Hz, 3H). |
| 357 | 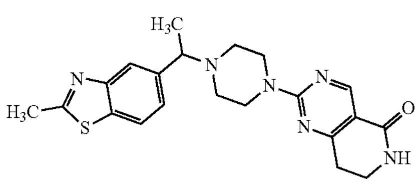 [SMILES: Cc1nc2cc(C(C)N3CCN(c4ncc5c(n4)CCNC5=O)CC3)ccc2s1] | Racemic | $^1$H NMR (400 MHz, DMSO-$d_6$): δ 8.58 (s, 1H), 7.97 (d, J = 8.4 Hz, 1H), 7.85 (s, 1H), 7.71 (s, 1H), 7.39 (d, J = 8.4 Hz, 1H), 3.92-3.75 (m, 4H), 3.64-3.60 (m, 1H), 3.42-3.35 (m, 2H), 2.79 (s, 3H), 2.79-2.75 (m, 2H), 2.49-2.35 (m, 4H), 1.39 (d, J = 6.4 Hz, 3H). |

TABLE 2-continued

| Ex | Structure | Configuration specification | 1H NMR |
|---|---|---|---|
| 358 | 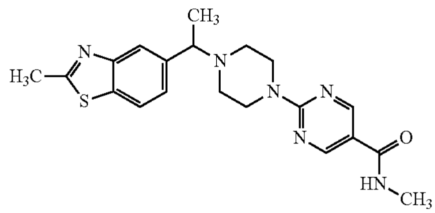 | Racemic | ¹H NMR (400 MHz, DMSO-$d_6$): δ 8.72 (s, 2H), 8.29 (d, J = 4.4 Hz, 1H), 7.97 (d, J = 8.0 Hz, 1H), 7.85 (s, 1H), 7.39 (dd, J = 8.4, 1.2 Hz, 1H), 3.80 (t, J = 4.8 Hz, 4H), 3.64-3.60 (m, 1H), 2.79 (s, 3H), 2.76-2.74 (m, 3H), 2.49-2.47 (m, 2H), 2.42-2.37 (m, 2H), 1.39 (d, J = 6.8 Hz, 3H). |
| 359 | 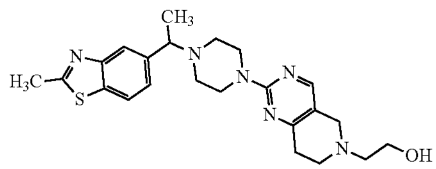 [SMILES: Cc1nc2cc(C(C)N3CCN(c4ncc5c(n4)CCN(CCO)C5)CC3)ccc2s1] | Racemic | ¹H NMR (400 MHz, DMSO-$d_6$): δ 8.19 (s, 1H), 7.97 (d, J = 8.4 Hz, 1H), 7.84 (s, 1H), 7.39 (d, J = 8.0 Hz, 1H), 5.31-5.30 (m, 1H), 4.49 (t, J = 5.2 Hz, 2H), 3.89-3.76 (m, 2H), 3.70-3.66 (m, 2H), 3.66-3.55 (m, 3H), 3.42-3.40 (m, 4H), 3.35-3.31 (m, 2H), 2.79 (s, 3H), 2.68-2.68 (m, 2H), 2.51-2.51 (m, 2H), 1.40 (d, J = 5.2 Hz, 3H). |
| 360 | 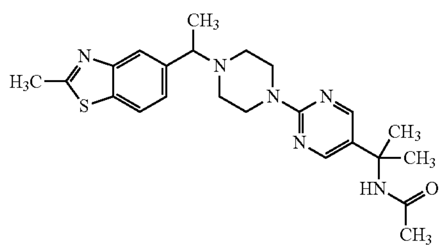 [SMILES: CC(=O)NC(C)(C)c1cnc(N2CCN(C(C)c3ccc4sc(C)nc4c3)CC2)nc1] | Racemic | ¹H NMR (400 MHz, DMSO-$d_6$): δ 8.26 (s, 2H), 8.04 (s, 1H), 7.97 (d, J = 8.4 Hz, 1H), 7.85 (s, 1H), 7.40 (dd, J = 8.4, 1.2 Hz, 1H), 3.67 (t, J = 4.4 Hz, 4H), 3.62-3.57 (m, 1H), 2.79 (s, 3H), 2.49-2.47 (m, 2H), 2.40-2.34 (m, 2H), 1.79 (s, 3H), 1.49 (s, 6H), 1.39 (d, J = 6.8 Hz, 3H). |
| 361 | 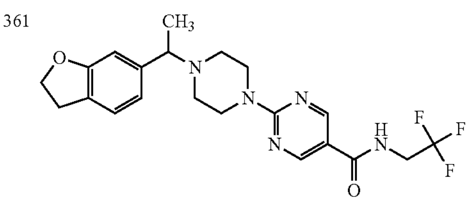 | Racemic | ¹H NMR (400 MHz, DMSO-$d_6$): δ 8.92 (t, J = 1.6 Hz, 1H), 8.78 (s, 2H), 7.15 (d, J = 7.6 Hz, 1H), 6.77-6.72 (m, 2H), 4.50 (t, J = 8.0 Hz, 2H), 4.09-4.05 (m, 2H), 3.80 (t, J = 4.8 Hz, 4H), 3.36 (t, J = 8.0 Hz, 1H), 3.13 (t, J = 8.8 Hz, 2H), 2.53-2.47 (m, 2H), 2.46-2.33 (m, 2H), 1.28 (d, J = 6.40 Hz, 3H). |
| 362 | 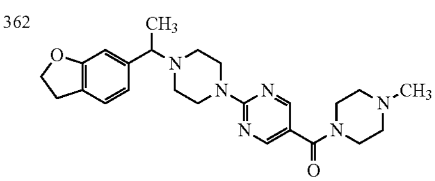 | Racemic | ¹H NMR (400 MHz, DMSO-$d_6$): δ 8.40 (s, 2H), 7.14 (d, J = 7.6 Hz, 1H), 6.77-6.72 (m, 2H), 4.50 (t, J = 6.8 Hz, 2H), 3.76-3.74 (m, 4H), 3.49-3.46 (m, 4H), 3.15-3.12 (m, 2H), 2.50-2.44 (m, 2H), 2.38-2.30 (m, 7H), 2.25-2.10 (m, 3H), 1.28 (d, J = 6.4 Hz, 3H). |
| 363 | 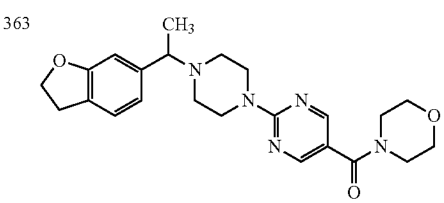 | Racemic | ¹H NMR (400 MHz, DMSO-$d_6$): δ 8.43 (s, 2H), 7.15 (d, J = 7.6 Hz, 1H), 6.76 (d, J = 8.8 Hz, 1H), 6.73 (s, 1H), 4.50 (t, J = 8.8 Hz, 2H), 3.76 (t, J = 10.0 Hz, 4H), 3.59 (d, J = 8.0 Hz, 4H), 3.54-3.45 (m, 4H), 3.42-3.38 (m, 1H), 3.18-3.11 (m, 2H), 2.52-2.50 (m, 2H), 2.38-2.33 (m, 2H), 1.28 (s, 3H). |
| 364 | 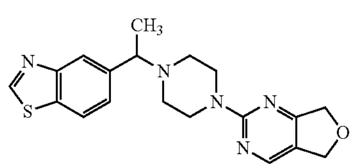 [SMILES: CC(c1ccc2scnc2c1)N1CCN(c2ncc3c(n2)COC3)CC1] | Racemic | ¹H NMR (400 MHz, DMSO-$d_6$): δ 9.39 (s, 1H), 8.29 (s, 1H), 8.12 (d, J = 8.4 Hz, 1H), 8.03 (s, 1H), 7.51 (d, J = 8.4 Hz, 1H), 4.92 (s, 2H), 4.73 (s, 2H), 3.74-3.60 (m, 5H), 2.45-2.51 (m, 2H), 2.41-2.38 (m, 2H), 1.41 (d, J = 6.8 Hz, 3H). |

TABLE 2-continued

| Ex | Structure | Configuration specification | 1H NMR |
|---|---|---|---|
| 365 | 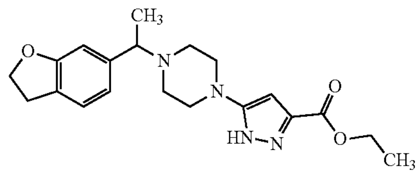 [SMILES: CCOC(=O)c1cc(N2CCN(C(C)c3ccc4c(c3)OCC4)CC2)[nH]n1] | Racemic | ¹H NMR (400 MHz, DMSO-d₆): δ 12.97-12.71 (m, 1H), 7.15 (d, J = 7.6 Hz, 1H), 6.76 (d, J = 7.6 Hz, 1H), 6.71 (s, 1H), 6.23-5.89 (m, 1H), 4.50 (t, J = 6.8 Hz, 2H), 4.29-4.21 (m, 2H), 3.15 (t, J = 6.8 Hz, 2H), 3.33-3.32 (m, 1H), 3.11-3.07 (m, 4H), 2.50-2.39 (m, 4H), 1.29-1.26 (m, 6H). |
| 366 | 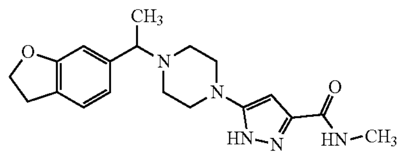 [SMILES: CNC(=O)c1cc(N2CCN(C(C)c3ccc4c(c3)OCC4)CC2)[nH]n1] | Racemic | ¹H NMR (400 MHz, DMSO-d₆): δ 12.49-12.37 (m, 1H), 8.24-8.23 (m, 1H), 7.15 (d, J = 7.6 Hz, 1H), 6.76 (d, J = 7.6 Hz, 1H), 6.71 (s, 1H), 6.17-5.79 (m, 1H), 4.50 (t, J = 8.8 Hz, 2H), 3.32-3.30 (m, 1H), 3.17-3.10 (m, 2H), 3.10-3.00 (m, 4H), 2.75-2.65 (m, 3H), 2.50-2.45 (m, 2H), 2.42-2.35 (m, 2H), 1.27 (d, J = 6.4 Hz, 3H). |
| 367 | 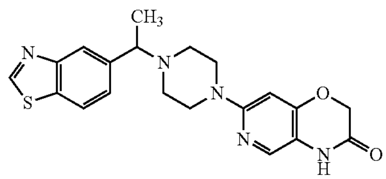 [SMILES: CC(c1ccc2scnc2c1)N1CCN(c2cc3c(cn2)NC(=O)CO3)CC1] | Racemic | ¹H NMR (400 MHz, DMSO-d₆): δ 10.57 (s, 1H), 9.38 (s, 1H), 8.11 (dd, J = 8.0, 3.6 Hz, 1H), 8.01 (s, 1H), 7.64 (d, J = 3.2 Hz, 1H), 7.49 (d, J = 6.4 Hz, 1H), 6.39 (s, 1H), 4.59 (s, 2H), 3.67-3.60 (m, 1H), 3.40-3.30 (m, 4H), 2.70-2.67 (m, 1H), 2.40-2.35 (m, 2H), 2.20-2.10 (m, 1H), 1.39 (d, J = 2.8 Hz, 3H). |
| 368 | 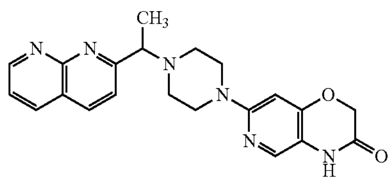 [SMILES: CC(c1ccc2cccnc2n1)N1CCN(c2cc3c(cn2)NC(=O)CO3)CC1] | Racemic | ¹H NMR (400 MHz, DMSO-d₆): δ 10.59 (s, 1H), 9.06 (d, J = 4.0 Hz, 1H), 8.45 (t, J = 5.2 Hz, 2H), 7.79 (d, J = 8.4 Hz, 1H), 7.65 (s, 1H), 7.62 (dd, J = 8.0, 4.4 Hz, 1H), 6.41 (s, 1H), 4.60 (s, 2H), 3.85 (q, J = 6.8 Hz, 1H), 3.40-3.30 (m, 4H), 2.65-2.57 (m, 2H), 2.50-2.40 (m, 2H), 1.44 (d, J = 6.8 Hz, 3H). |
| 369 | 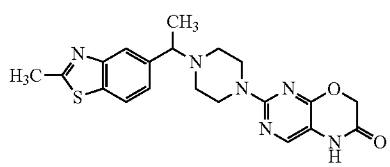 [SMILES: Cc1nc2cc(C(C)N3CCN(c4ncc5c(n4)OCC(=O)N5)CC3)ccc2s1] | Racemic | ¹H NMR (400 MHz, DMSO-d₆): δ 10.56 (s, 1H), 7.96 (d, J = 8.0 Hz, 1H), 7.83 (d, J = 1.2 Hz, 1H), 7.78 (s, 1H), 7.38 (dd, J = 8.4, 1.6 Hz, 1H), 4.75 (s, 2H), 3.59-3.57 (m, 5H), 2.79 (s, 3H), 2.52-2.49 (m, 2H), 2.34-2.31 (m, 2H), 1.37 (d, J = 6.80 Hz, 3H). |
| 370 | 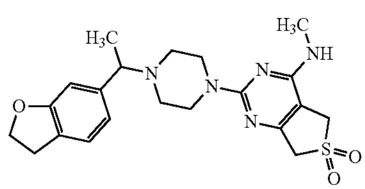 [SMILES: CNc1nc(N2CCN(C(C)c3ccc4c(c3)OCC4)CC2)nc2c1CS(=O)(=O)C2] | Racemic | ¹H NMR (400 MHz, DMSO-d₆): δ 7.14 (d, J = 7.6 Hz, 1H), 6.93-6.90 (m, 1H), 6.74 (d, J = 7.6 Hz, 1H), 6.70 (s, 1H), 4.49 (t, J = 8.8 Hz, 2H), 4.19 (s, 2H), 4.06 (s, 2H), 3.64 (br s, 4H), 3.38-3.33 (m, 1H), 3.12 (t, J = 8.8 Hz, 2H), 2.79 (d, J = 4.4 Hz, 3H), 2.33-2.30 (m, 4H), 1.27 (d, J = 6.40 Hz, 3H).-1H missing. |
| 371 | 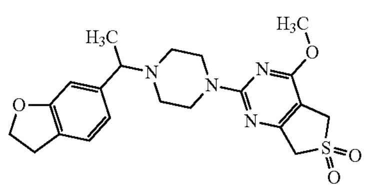 [SMILES: COc1nc(N2CCN(C(C)c3ccc4c(c3)OCC4)CC2)nc2c1CS(=O)(=O)C2] | Racemic | ¹H NMR (400 MHz, DMSO-d₆): δ 7.15 (d, J = 7.6 Hz, 1H), 6.77-6.72 (m, 2H), 4.50 (t, J = 8.4 Hz, 2H), 4.36 (s, 2H), 4.20 (s, 2H), 3.88 (s, 3H), 3.71 (br s, 4H), 3.38-3.34 (m, 1H), 3.13 (t, J = 8.0 Hz, 2H), 2.36-2.33 (m, 4H), 1.28 (d, J = 6.80 Hz, 3H). |
| 372 | 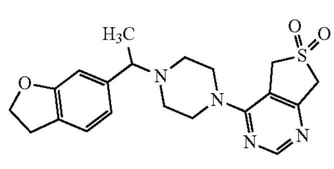 [SMILES: CC(c1ccc2c(c1)OCC2)N1CCN(c2ncnc3c2CS(=O)(=O)C3)CC1] | Racemic | ¹H NMR (400 MHz, DMSO-d₆): δ 8.46 (s, 1H), 7.16 (d, J = 7.2 Hz, 1H), 6.77-6.72 (m, 2H), 4.60 (s, 2H), 4.51 (t, J = 8.8 Hz, 2H), 4.42 (s, 2H), 3.58 (br s, 4H), 3.38 (t, J = 6.4 Hz, 1H), 3.18-3.12 (m, 2H), 2.40-2.34 (m, 4H), 1.28 (d, J = 6.80 Hz, 3H). |

TABLE 2-continued

| Ex | Structure | Configuration specification | 1H NMR |
|---|---|---|---|
| 373 | 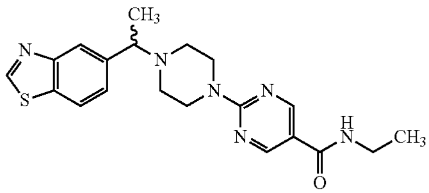 [SMILES: CCNC(=O)c1cnc(N2CCN(C(C)c3ccc4scnc4c3)CC2)nc1] | Chiral HPLC SFC Method C: 1st eluting compound | ¹H NMR (400 MHz, DMSO-d₆): δ 9.39 (s, 1H), 8.72 (s, 2H), 8.38-8.27 (m, 1H), 8.12 (d, J = 8.4 Hz, 1H), 8.03 (s, 1H), 7.51 (d, J = 8.4 Hz, 1H), 3.88-3.75 (m, 4H), 3.73-3.63 (m, 1H), 3.28-3.19 (m, 2H), 2.67-2.53 (m, 2H), 2.45-2.39 (m, 2H), 1.41 (d, J = 6.80 Hz, 3H), 1.10 (t, J = 7.20 Hz, 3H). |
| 374 | 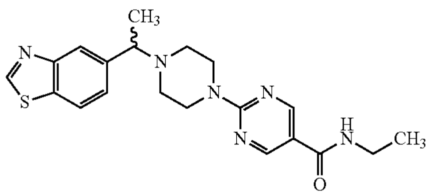 [SMILES: CCNC(=O)c1cnc(N2CCN(C(C)c3ccc4scnc4c3)CC2)nc1] | Chiral HPLC SFC Method C: 2nd eluting compound | ¹H NMR (400 MHz, DMSO-d₆): δ 9.39 (s, 1H), 8.72 (s, 2H), 8.31 (t, J = 5.2 Hz, 1H), 8.12 (d, J = 8.0 Hz, 1H), 8.03 (s, 1H), 7.51 (d, J = 8.4 Hz, 1H), 3.89-3.76 (m, 4H), 3.75-3.60 (m, 1H), 3.30-3.21 (m, 2H), 2.67-2.52 (m, 2H), 2.47-2.37 (m, 2H), 1.41 (d, J = 6.40 Hz, 3H), 1.10 (t, J = 7.20 Hz, 3H). |
| 375 | 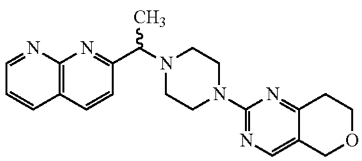 [SMILES: CC(c1ccc2cccnc2n1)N1CCN(c2ncc3c(n2)CCOC3)CC1] | Chiral HPLC SFC Method E: 1st eluting compound | ¹H NMR (400 MHz, DMSO-d₆): δ 9.06 (t, J = 2.4 Hz, 1H), 8.44 (d, J = 8.4 Hz, 2H), 8.07 (s, 1H), 7.80 (d, J = 12.0 Hz, 1H), 7.63 (s, 1H), 4.54 (s, 2H), 3.90-3.88 (m, 3H), 3.71-3.69 (m, 4H), 2.67-2.65 (m, 2H), 2.59-2.58 (m, 4H), 1.44 (d, J = 6.4 Hz, 3H). |
| 376 | 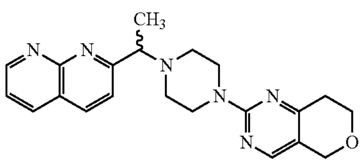 [SMILES: CC(c1ccc2cccnc2n1)N1CCN(c2ncc3c(n2)CCOC3)CC1] | Chiral HPLC SFC Method E: 2nd eluting compound | ¹H NMR (400 MHz, DMSO-d₆): δ 9.04 (t, J = 2.4 Hz, 1H), 8.44 (d, J = 8.4 Hz, 2H), 8.06 (s, 1H), 7.80 (d, J = 12.0 Hz, 1H), 7.63-7.62 (m, 1H), 4.53 (s, 2H), 3.90-3.88 (m, 3H), 3.71-3.69 (m, 4H), 2.69-2.66 (m, 2H), 2.59-2.58 (m, 2H), 2.46-2.45 (m, 2H), 1.43 (d, J = 6.4 Hz, 3H). |
| 377 | 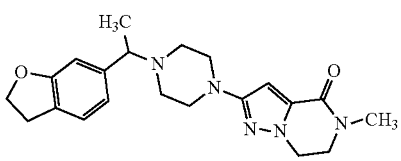 [SMILES: CC(c1ccc2c(c1)OCC2)N1CCN(c2cc3n(n2)CCN(C)C3=O)CC1] | Racemic | ¹H NMR (400 MHz, DMSO-d₆): δ 7.14 (d, J = 7.6 Hz, 1H), 6.75 (d, J = 7.6 Hz, 1H), 6.70 (s, 1H), 6.13 (s, 1H), 4.50 (t, J = 8.8 Hz, 2H), 4.13 (t, J = 6.0 Hz, 2H), 3.69 (t, J = 5.6 Hz, 2H), 3.32-0.00 (m, 1H), 3.13 (t, J = 8.8 Hz, 2H), 3.10-3.00 (m, 4H), 2.95 (s, 3H), 2.46-2.33 (m, 4H), 1.26 (d, J = 6.80 Hz, 3H). |
| 378 | 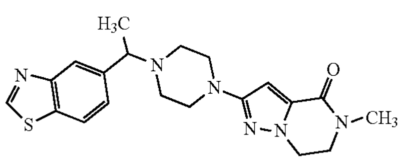 [SMILES: CC(c1ccc2scnc2c1)N1CCN(c2cc3n(n2)CCN(C)C3=O)CC1] | Racemic | ¹H NMR (400 MHz, DMSO-d₆): δ 9.38 (s, 1H), 8.30 (d, J = 5.6 Hz, 1H), 8.11 (d, J = 7.2 Hz, 1H), 7.49 (d, J = 6.4 Hz, 1H), 6.13 (s, 1H), 4.15-4.12 (m, 2H), 3.71-3.68 (m, 2H), 3.63-3.62 (m, 1H), 3.10-3.05 (m, 4H), 2.95 (s, 3H), 2.6-2.5 (m, 2H), 2.44-2.42 (m, 2H), 1.40-1.39 (m, 3H). |
| 379 | 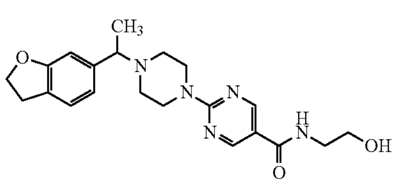 [SMILES: CC(c1ccc2c(c1)OCC2)N1CCN(c2ncc(C(=O)NCCO)cn2)CC1] | Racemic | ¹H NMR (400 MHz, DMSO-d₆): δ 8.74 (d, J = 2.0 Hz, 2H), 8.33 (t, J = 4.8 Hz, 1H), 7.15 (d, J = 7.20 Hz, 1H), 6.76 (d, J = 7.60 Hz, 1H), 6.72 (s, 1H), 4.73-4.72 (m, 1H), 4.53-4.49 (m, 2H), 3.79-3.78 (m, 4H), 3.49-3.48 (m, 2H), 3.38-3.36 (m, 1H), 3.31-3.28 (m, 2H), 3.16-3.11 (m, 2H), 2.46-2.44 (m, 2H), 2.37-2.33 (m, 2H), 1.29-1.28 (m, 3H). |
| 380 | 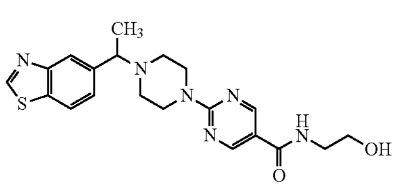 [SMILES: CC(c1ccc2scnc2c1)N1CCN(c2ncc(C(=O)NCCO)cn2)CC1] | Racemic | ¹H NMR (400 MHz, DMSO-d₆): δ 9.37 (s, 1H), 8.72 (s, 2H), 8.31 (t, J = 8.4 Hz, 1H), 8.11 (d, J = 8.4 Hz, 1H), 8.02 (s, 1H), 7.50 (d, J = 8.0 Hz, 1H), 4.70 (t, 1H, J = 5.6 Hz), 3.79-3.78 (m, 4H), 3.49-3.45 (m, 3H), 3.28-3.25 (m, 2H), 2.50-2.36 (m, 4H), 1.40 (d, J = 6.8 Hz, 3H). |

TABLE 2-continued

| Ex | Structure | Configuration specification | 1H NMR |
|---|---|---|---|
| 381 | 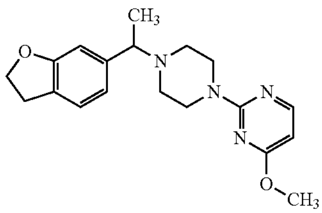 [SMILES: COc1ccnc(N2CCN(C(C)c3ccc4c(c3)OCC4)CC2)n1] | Racemic | ¹H NMR (400 MHz, DMSO-d₆): δ 8.05 (d, J = 5.6 Hz, 1H), 7.15 (d, J = 7.6 Hz, 1H), 6.76 (dd, J = 7.6, 1.2 Hz, 1H), 6.72 (s, 1H), 6.03 (d, J = 5.6 Hz, 1H), 4.50 (t, J = 8.4 Hz, 2H), 3.80 (s, 3H), 3.68 (t, J = 4.8 Hz, 4H), 3.37-3.35 (m, 1H), 3.13 (t, J = 8.4 Hz, 2H), 2.43-2.39 (m, 2H), 2.36-2.32 (m, 2H), 1.28 (d, J = 6.8 Hz, 3H). |
| 382 | 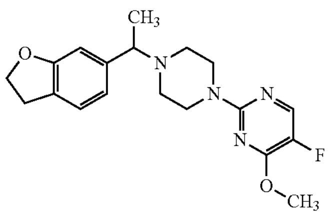 [SMILES: COc1nc(N2CCN(C(C)c3ccc4c(c3)OCC4)CC2)ncc1F] | Racemic | ¹H NMR (400 MHz, DMSO-d₆): δ 8.14 (d, J = 3.2 Hz, 1H), 7.15 (d, J = 7.2 Hz, 1H), 6.76 (d, J = 7.6 Hz, 1H), 6.72 (s, 1H), 4.51 (t, J = 8.8 Hz, 2H), 3.91 (s, 3H), 3.62-3.65 (m, 4H), 3.14 (t, J = 8.8 Hz, 2H), 2.45-2.25 (m, 4H), 1.28 (d, J = 6.4 Hz, 3H). |
| 383 | 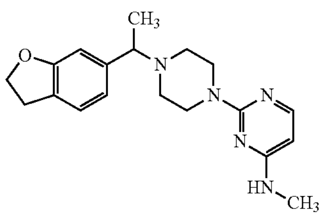 | Racemic | ¹H NMR (400 MHz, DMSO-d₆): δ 7.66 (s, 1H), 7.15 (d, J = 7.6 Hz, 1H), 6.87 (s, 1H), 6.75 (d, J = 7.6 Hz, 1H), 6.71 (s, 1H), 5.70 (d, J = 6.0 Hz, 1H), 4.51 (t, J = 8.8 Hz, 2H), 3.62-3.52 (m, 4H), 3.34 (s, 1H), 3.14 (t, J = 8.4 Hz, 2H), 2.73-2.68 (m, 3H), 2.38-2.30 (m, 4H), 1.28 (d, J = 6.4 Hz, 3H). |
| 384 | 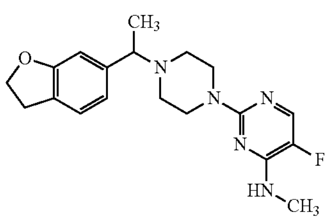 [SMILES: CNc1nc(N2CCN(C(C)c3ccc4c(c3)OCC4)CC2)ncc1F] | Racemic | ¹H NMR (400 MHz, DMSO-d₆): δ 7.71 (t, J = 1.6 Hz, 1H), 7.20 (d, J = 4.0 Hz, 1H), 7.15 (d, J = 7.6 Hz, 1H), 6.75 (d, J = 7.2 Hz, 1H), 6.71 (s, 1H), 4.51 (t, J = 8.8 Hz, 2H), 3.62-3.34 (m, 4H), 3.32 (s, 1H), 3.14 (t, J = 8.8 Hz, 2H), 2.79 (d, J = 4.4 Hz, 3H), 2.33-2.29 (m, 4H), 1.28 (d, J = 6.8 Hz, 3H). |
| 385 | 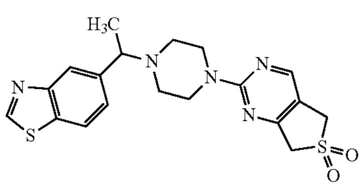 [SMILES: CC(c1ccc2scnc2c1)N1CCN(c2ncc3c(n2)CS(=O)(=O)C3)CC1] | Racemic | ¹H NMR (400 MHz, DMSO-d₆): δ 9.08-8.98 (m, 1H), 8.21 (s, 1H), 8.11 (s, 1H), 8.05-7.85 (m, 1H), 7.61-7.45 (m, 1H), 4.27 (s, 2H), 4.20 (s, 2H), 3.92-3.40 (m, 5H), 2.69-2.38 (m, 4H), 1.44 (d, J = 7.2 Hz, 3H). |
| 386 | 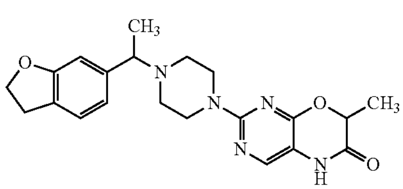 [SMILES: CC1Oc2nc(N3CCN(C(C)c4ccc5c(c4)OCC5)CC3)ncc2NC1=O] | Racemic | ¹H NMR (400 MHz, DMSO-d₆): δ 10.53 (s, 1H), 7.81 (s, 1H), 7.15 (d, J = 7.60 Hz, 1H), 6.76 (d, J = 7.20 Hz, 1H), 6.71 (s, 1H), 4.93 (dd, J = 13.80, 7.20 Hz, 1H), 4.51 (t, J = 8.80 Hz, 2H), 3.57 (t, J = 4.80 Hz, 4H), 3.29 (s, 1H), 3.14 (t, J = 8.40 Hz, 2H), 2.44-2.40 (m, 2H), 2.34-2.30 (m, 2H), 1.46 (d, J = 7.20 Hz, 3H), 1.26 (t, J = 8.00 Hz, 3H). |
| 387 | 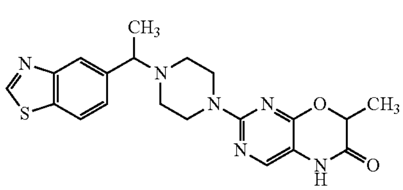 | Racemic | ¹H NMR (400 MHz, DMSO-d₆): δ 10.53 (s, 1H), 9.39 (s, 1H), 8.12 (d, J = 8.4 Hz, 1H), 8.02 (s, 1H), 7.80 (s, 1H), 7.50 (d, J = 8.4 Hz, 1H), 4.93 (dd, J = 13.6, 6.8 Hz, 1H), 3.64-3.60 (m, 5H), 2.51-2.47 (m, 2H), 2.38-2.34 (m, 2H), 1.45 (d, J = 6.8 Hz, 3H), 1.40 (d, J = 6.8 Hz, 3H). |

TABLE 2-continued

| Ex | Structure | Configuration specification | 1H NMR |
|---|---|---|---|
| 388 | 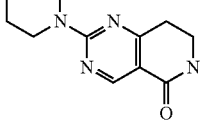 | Chiral HPLC SFC Method F: 1st eluting compound | ¹H NMR (400 MHz, DMSO-d₆): δ 8.58 (s, 1H), 7.97 (d, J = 8.0 Hz, 1H), 7.85 (s, 1H), 7.69 (s, 1H), 7.39 (d, J = 8.4 Hz, 1H), 3.82-3.81 (m, 4H), 3.63-3.62 (m, 1H), 3.37-3.36 (m, 2H), 2.79 (s, 3H), 2.79-2.75 (m, 2H), 2.44-2.41 (m, 2H), 2.42-2.41 (m, 2H), 1.39 (d, J = 6.4 Hz, 3H). |
| 389 | 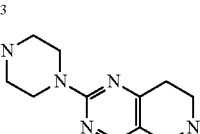 | Chiral HPLC SFC Method F: 2nd eluting compound | ¹H NMR (400 MHz, DMSO-d₆): δ 8.58 (s, 1H), 7.97 (d, J = 8.0 Hz, 1H), 7.85 (s, 1H), 7.69 (s, 1H), 7.39 (d, J = 8.4 Hz, 1H), 3.82-3.80 (m, 4H), 3.63-3.62 (m, 1H), 3.38-3.36 (m, 2H), 2.79 (s, 3H), 2.79-2.77 (m, 2H), 2.48-2.46 (m, 2H), 2.41-2.39 (m, 2H), 1.39 (d, J = 6.4 Hz, 3H). |
| 390 | 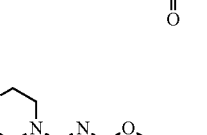 | Chiral HPLC SFC Method F: 2nd eluting compound | ¹H NMR (400 MHz, DMSO-d₆): δ 10.89-10.39 (m, 1H), 7.97 (d, J = 8.4 Hz, 1H), 7.83 (s, 1H), 7.77 (s, 1H), 7.38 (d, J = 8.0 Hz, 1H), 4.74 (s, 2H), 3.67-3.52 (m, 5H), 2.79 (s, 3H), 2.47-2.40 (m, 2H), 2.40-2.34 (m, 2H), 1.38 (d, J = 6.8 Hz, 3H). |
| 391 | 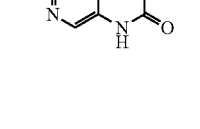 | Racemic | ¹H NMR (400 MHz, DMSO-d₆): δ 8.11 (s, 1H), 7.15 (d, J = 7.2 Hz, 1H), 6.76 (d, J = 7.2 Hz, 1H), 6.72 (s, 1H), 4.51 (t, J = 8.8 Hz, 2H), 4.31 (s, 2H), 3.75-3.65 (m, 4H), 3.40-3.30 (m, 2H), 3.60-3.50 (m, 1H), 3.20-3.10 (m, 4H), 2.30-2.20 (m, 4H), 1.28 (d, J = 6.4 Hz, 3H). |
| 392 | 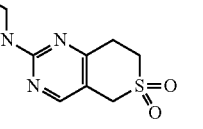 | Racemic | ¹H NMR (400 MHz, DMSO-d₆): δ 9.93 (s, 1H), 8.13-8.11 (m, 2H), 8.02 (s, 1H), 7.50 (d, J = 8.4 Hz, 1H), 4.30-4.25 (m, 2H), 3.70-3.60 (m, 4H), 3.60-3.55 (m, 1H), 3.40-3.35 (m, 2H), 3.20-3.10 (m, 2H), 2.40-2.37 (m, 4H), 1.40 (d, J = 6.40 Hz, 3H). |
| 393 | 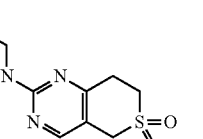 | Racemic | ¹H NMR (400 MHz, DMSO-d₆): δ 12.03 (s, 1H), 8.73 (s, 1H), 7.77-7.65 (m, 2H), 7.40 (d, J = 8.4 Hz, 1H), 3.67-3.55 (m, 1H), 3.34-3.24 (m, 4H), 2.52-2.46 (m, 4H), 2.09 (s, 3H), 1.38 (d, J = 4.0 Hz, 3H). |
| 394 | 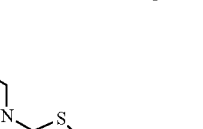 | Racemic | ¹H NMR (400 MHz, DMSO-d₆): δ 8.71 (s, 1H), 8.58 (s, 1H), 7.76-7.69 (m, 3H), 7.41 (dd, J = 8.0, 1.6 Hz, 1H), 3.82-3.72 (m, 4H), 3.64 (t, J = 6.8 Hz, 1H), 3.38-3.33 (m, 2H), 2.78 (t, J = 6.4 Hz, 2H), 2.41-2.37 (m, 4H), 1.38 (d, J = 6.8 Hz, 3H). |
| 395 | 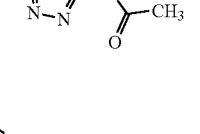 | Racemic | ¹H NMR (400 MHz, DMSO-d₆): δ 12.03 (s, 1H), 8.73 (s, 1H), 7.73 (d, J = 8.4 Hz, 2H), 7.43 (d, J = 8.4 Hz, 1H), 3.68-3.63 (m, 1H), 3.37-3.36 (m, 4H), 2.50-2.40 (m, 4H), 2.10 (s, 3H), 1.38 (d, J = 6.8 Hz, 3H). |

TABLE 2-continued

| Ex | Structure | Configuration specification | 1H NMR |
|---|---|---|---|
| 396 | 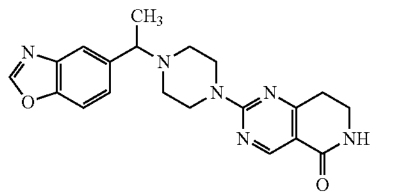 [SMILES: CC(c1ccc2ocnc2c1)N1CCN(c2ncc3c(n2)CCNC3=O)CC1] | Racemic | ¹H NMR (400 MHz, DMSO-d₆) : δ 8.73 (s, 1H), 8.59 (s, 1H), 7.74 (s, 1H), 7.71 (d, J = 4.4 Hz, 2H), 7.44 (d, J = 8.4 Hz, 1H), 3.88-3.80 (m, 4H), 3.66-3.61 (m, 1H), 3.40-3.30 (m, 2H), 2.78 (t, J = 6.4 Hz, 2H), 2.40-2.30 (m, 4H), 1.39 (d, J = 6.80 Hz, 3H). |
| 397 | 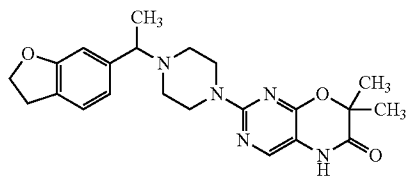 [SMILES: CC(c1ccc2c(c1)OCC2)N1CCN(c2ncc3c(n2)OC(C)(C)C(=O)N3)CC1] | Racemic | ¹H NMR (400 MHz, DMSO-d₆): δ 10.50 (s, 1H), 7.81 (s, 1H), 7.15 (d, J = 8.0 Hz, 1H), 6.76 (d, J = 8.4 Hz, 1H), 6.72 (s, 1H), 4.51 (t, J = 8.8 Hz, 2H), 3.56 (d, J = 4.4 Hz, 4H), 3.14 (t, J = 8.4 Hz, 2H), 2.65-2.55 (m, 3H), 2.50-2.48 (m, 2H), 1.46 (s, 6H), 1.27 (d, J = 6.4 Hz, 3H). |
| 398 | 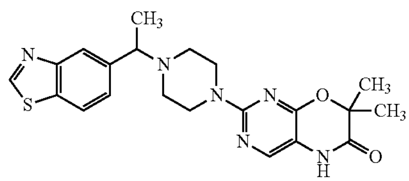 [SMILES: CC(c1ccc2scnc2c1)N1CCN(c2ncc3c(n2)OC(C)(C)C(=O)N3)CC1] | Racemic | ¹H NMR (400 MHz, DMSO-d₆): δ 10.50 (s, 1H), 9.39 (s, 1H), 8.12 (d, J = 8.4 Hz, 1H), 8.02 (s, 1H), 7.81 (s, 1H), 7.50 (d, J = 7.2 Hz, 1H), 3.64-3.58 (m, 5H), 2.50-2.42 (m, 2H), 2.40-2.30 (m, 2H), 1.46 (s, 6H), 1.40 (d, J = 6.8 Hz, 3H). |
| 399 | 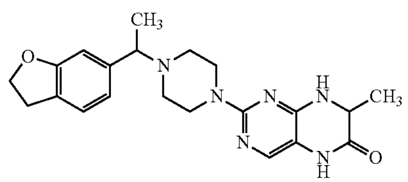 | Racemic | ¹H NMR (400 MHz, DMSO-d₆): δ 10.08 (s, 1H), 7.42 (d, J = 4.0 Hz, 2H), 7.14 (d, J = 7.2 Hz, 1H), 6.74 (d, J = 7.6 Hz, 1H), 6.69 (s, 1H), 4.50 (t, J = 8.8 Hz, 2H), 4.02-4.00 (m, 1H), 3.54-3.51 (m, 5H), 3.13 (t, J = 8.8 Hz, 2H), 2.36-2.32 (m, 4H), 1.30-1.28 (m, 6H). |
| 400 | 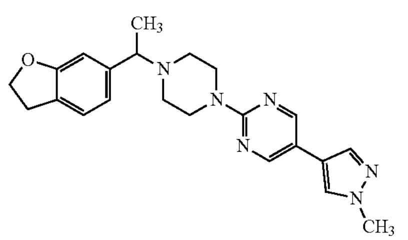 [SMILES: CC(c1ccc2c(c1)OCC2)N1CCN(c2ncc(-c3cnn(C)c3)cn2)CC1] | Racemic | ¹H NMR (400 MHz, DMSO-d₆): δ 8.55 (s, 2H), 8.04 (d, J = 2.4 Hz, 1H), 7.78 (d, J = 2.4 Hz, 1H), 7.14 (d, J = 7.6 Hz, 1H), 6.76 (d, J = 7.6 Hz, 1H), 6.72 (s, 1H), 4.50 (dt, J = 8.8, 2.4 Hz, 2H), 3.84 (d, J = 2.8 Hz, 3H), 3.70-3.65 (m, 4H), 3.38-3.30 (m, 1H), 3.13 (t, J = 8.8 Hz, 2H), 2.50-2.40 (m, 2H), 2.39-2.30 (m, 2H), 1.28 (d, J = 8.8 Hz, 3H). |
| 401 | 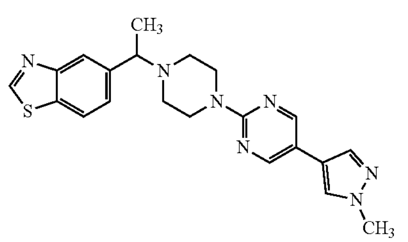 [SMILES: CC(c1ccc2scnc2c1)N1CCN(c2ncc(-c3cnn(C)c3)cn2)CC1] | Racemic | ¹H NMR (400 MHz, DMSO-d₆): δ 9.395 (s, 1H), 8.57 (s, 2H), 8.13 (d, J = 8.4 Hz, 1H), 8.04 (d, J = 8.4 Hz, 2H), 7.80 (s, 1H), 7.52 (d, J = 7.2 Hz, 1H), 3.85 (s, 3H), 3.75-3.70 (m, 4H), 3.68-3.63 (m, 1H), 2.45-2.40 (m, 4H), 1.42 (d, J = 6.8 Hz, 3H). |
| 402 | 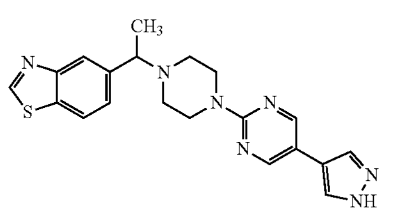 [SMILES: CC(c1ccc2scnc2c1)N1CCN(c2ncc(-c3cn[nH]c3)cn2)CC1] | Racemic | ¹H NMR (400 MHz, DMSO-d₆): δ 12.94 (s, 1H), 9.38 (s, 1H), 8.59 (s, 2H), 8.11 (d, J = 8.0 Hz, 2H), 8.02 (s, 1H), 7.85 (s, 1H), 7.50 (d, J = 8.0 Hz, 1H), 3.71-3.63 (m, 5H), 2.51-2.49 (m, 2H), 2.42-2.39 (m, 2H), 1.45 (d, J = 2.4 Hz, 3H). |

TABLE 2-continued

| Ex | Structure | Configuration specification | 1H NMR |
|---|---|---|---|
| 403 | 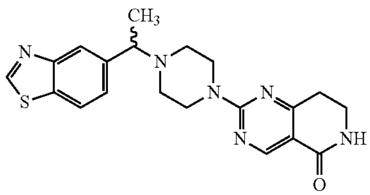 [SMILES: CC(c1ccc2scnc2c1)N1CCN(c2ncc3c(n2)CCNC3=O)CC1] | Chiral HPLC SFC Method G: 1st eluting compound | ¹H NMR (400 MHz, DMSO-d₆): δ 9.38 (s, 1H), 8.57 (s, 1H), 8.12 (d, J = 8.4 Hz, 1H), 8.02 (s, 1H), 7.68 (s, 1H), 7.50 (d, J = 8.4 Hz, 1H), 3.83-3.81 (m, 4H), 3.67-3.66 (m, 1H), 3.35-3.33 (m, 2H), 2.77 (t, J = 5.2 Hz, 2H), 2.46-2.40 (m, 4H), 1.40 (d, J = 5.2 Hz, 3H). |
| 404 | 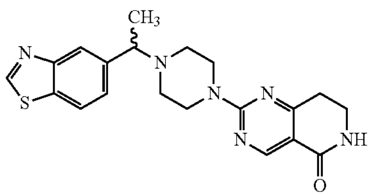 [SMILES: CC(c1ccc2scnc2c1)N1CCN(c2ncc3c(n2)CCNC3=O)CC1] | Chiral HPLC SFC Method G: 2nd eluting compound | ¹H NMR (400 MHz, DMSO-d₆): δ 9.39 (s, 1H), 8.58 (s, 1H), 8.12 (d, J = 8.0 Hz, 1H), 8.03 (s, 1H), 7.68 (s, 1H), 7.50 (d, J = 8.0 Hz, 1H), 3.83-3.81 (m, 4H), 3.68-3.67 (m, 1H), 3.35 (t, J = 6.8 Hz, 2H), 2.78 (t, J = 6.8 Hz, 2H), 2.47-2.40 (m, 4H), 1.41 (d, J = 6.40 Hz, 3H). |
| 405 | 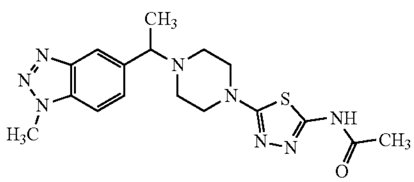 [SMILES: CC(=O)Nc1nnc(N2CCN(C(C)c3ccc4c(c3)nnn4C)CC2)s1] | Racemic | ¹H NMR (400 MHz, DMSO-d₆): δ 7.92 (s, 1H), 7.81 (d, J = 8.8 Hz, 1H), 7.59 (d, J = 8.4 Hz, 1H), 4.30 (s, 3H), 3.71-3.69 (m, 1H), 3.37-3.35 (m, 4H), 2.56-2.53 (m, 2H), 2.46-2.43 (m, 2H), 2.10 (s, 3H), 1.40 (d, J = 6.8 Hz, 3H). |
| 406 | 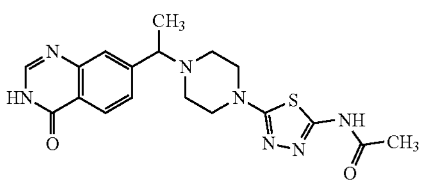 [SMILES: CC(=O)Nc1nnc(N2CCN(C(C)c3ccc4c(=O)[nH]cnc4c3)CC2)s1] | Racemic | ¹H NMR (400 MHz, DMSO-d₆): δ 12.05 (s, 1H), 12.04 (s, 1H), 8.10 (d, J = 6.4 Hz, 2H), 7.60 (s, 1H), 7.53 (d, J = 8.0 Hz, 1H), 3.66 (t, J = 6.4 Hz, 1H), 3.38-3.34 (m, 4H), 2.68-2.57 (m, 2H), 2.47-2.44 (m, 2H), 2.10 (s, 3H), 1.37 (d, J = 6.4 Hz, 3H). |
| 407 | 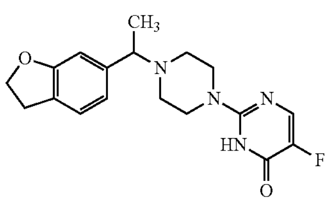 [SMILES: CC(c1ccc2c(c1)OCC2)N1CCN(c2ncc(F)c(=O)[nH]2)CC1] | Racemic | ¹H NMR (400 MHz, DMSO-d₆): δ 7.42-7.37 (m, 1H), 7.13 (d, J = 7.2 Hz, 1H), 6.74 (d, J = 7.20 Hz, 1H), 6.69 (s, 1H), 4.50 (t, J = 8.4 Hz, 2H), 3.45-3.39 (m, 4H), 3.29-3.27 (m, 1H), 3.16-3.11 (m, 2H), 2.41-2.30 (m, 4H), 1.25 (d, J = 6.40 Hz, 3H). |
| 408 | 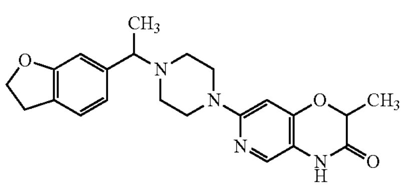 [SMILES: CC1Oc2cc(N3CCN(C(C)c4ccc5c(c4)OCC5)CC3)ncc2NC1=O] | Racemic | ¹H NMR (400 MHz, DMSO-d₆): δ 10.51 (s, 1H), 7.64 (s, 1H), 7.14 (d, J = 7.6 Hz, 1H), 6.75 (d, J = 7.6 Hz, 1H), 6.70 (s, 1H), 6.40 (s, 1H), 4.729 (t, J = 6.8 H, 1H), 4.50 (t, J = 8.8 Hz, 2H), 3.32-3.19 (m, 5H), 3.13 (t, J = 8.8 Hz, 2H), 2.45-2.33 (m, 4H), 1.39 (s, 3H), 1.27 (d, J = 6.8 Hz, 3H). |
| 409 | 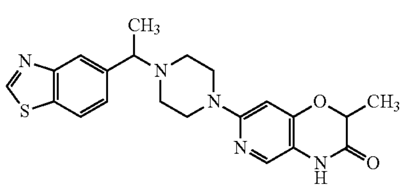 [SMILES: CC1Oc2cc(N3CCN(C(C)c4ccc5scnc5c4)CC3)ncc2NC1=O] | Racemic | ¹H NMR (400 MHz, DMSO-d₆): δ 10.53 (s, 1H), 9.39 (s, 1H), 8.12 (d, J = 8.0 Hz, 1H), 8.02 (s, 1H), 7.66 (s, 1H), 7.50 (d, J = 8.4 Hz, 1H), 6.42 (s, 1H), 4.75-4.70 (m, 1H), 3.65-3.60 (m, 1H), 3.36-3.34 (m, 4H), 2.41-2.39 (m, 4H), 1.41 (d, J = 6.0 Hz, 3H), 1.40 (s, 3H). |
| 410 | 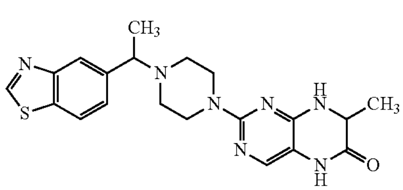 | Racemic | ¹H NMR (400 MHz, DMSO-d₆): δ 10.06 (s, 1H), 9.37 (s, 1H), 8.10 (d, J = 8.4 Hz, 1H), 8.00 (s, 1H), 7.48 (d, J = 8.4 Hz, 1H), 7.45-7.40 (m, 2H), 4.02-4.00 (m, 1H), 3.61-3.59 (m, 5H), 2.46-2.44 (m, 2H), 2.35-2.33 (m, 2H), 1.38 (d, J = 6.8 Hz, 3H), 1.28 (d, J = 6.8 Hz, 3H). |

TABLE 2-continued

| Ex | Structure | Configuration specification | 1H NMR |
|---|---|---|---|
| 411 | 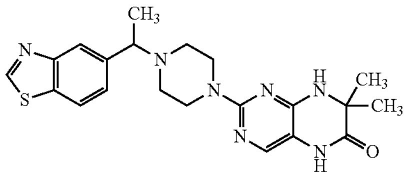 [SMILES: CC(c1ccc2scnc2c1)N1CCN(c2ncc3c(n2)NC(C)(C)C(=O)N3)CC1] | Racemic | ¹H NMR (400 MHz, DMSO-d₆): δ 10.05 (s, 1H), 9.39 (s, 1H), 8.12 (d, J = 8.4 Hz, 1H), 8.02 (s, 1H), 7.50 (d, J = 8.0 Hz, 1H), 7.46-7.42 (m, 2H), 3.62-3.60 (m, 5H), 2.47-2.46 (m, 2H), 2.36-2.35 (m, 2H), 1.39 (d, J = 6.8 Hz, 3H), 1.30 (s, 6H). |
| 412 | 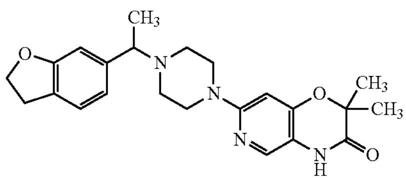 [SMILES: CC(c1ccc2c(c1)OCC2)N1CCN(c2cc3c(cn2)NC(=O)C(C)(C)O3)CC1] | Racemic | ¹H NMR (400 MHz, DMSO-d₆) : δ 10.50 (s, 1H), 7.66 (s, 1H), 7.15 (d, J = 7.6 Hz, 1H), 6.76 (d, J = 7.2 Hz, 1H), 6.72 (s, 1H), 6.39 (s, 1H), 4.51 (t, J = 8.4 Hz, 2H), 3.40-3.30 (m, 5H), 3.14 (t, J = 8.4 Hz, 2H), 2.49-2.40 (m, 2H), 2.38-2.30 (m, 2H), 1.41 (s, 6H), 1.28 (d, J = 6.4 Hz, 3H). |
| 413 | 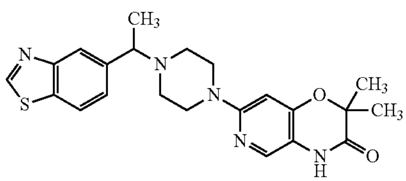 [SMILES: CC(c1ccc2scnc2c1)N1CCN(c2cc3c(cn2)NC(=O)C(C)(C)O3)CC1] | Racemic | ¹H NMR (400 MHz, DMSO-d₆) : δ 10.48 (s, 1H), 9.38 (s, 1H), 8.11 (d, J = 8.4 Hz, 1H), 8.01 (s, 1H), 7.64 (s, 1H), 7.49 (d, J = 8.0 Hz, 1H), 6.38 (s, 1H), 3.63-3.58 (m, 1H), 3.40-3.30 (m, 4H), 2.39-2.33 (m, 4H), 1.39-1.35 (m, 9H). |
| 414 | 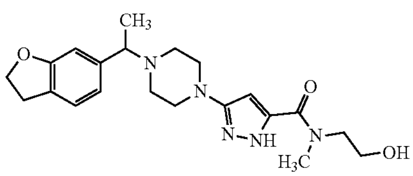 [SMILES: CC(c1ccc2c(c1)OCC2)N1CCN(c2cc(C(=O)N(C)CCO)[nH]n2)CC1] | Racemic | ¹H NMR (400 MHz, DMSO-d₆): δ 12.39 (s, 1H), 7.15 (d, J = 7.6 Hz, 1H), 6.76 (d, J = 7.2 Hz, 1H), 6.71 (s, 1H), 5.90 (s, 1H), 4.93 (s, 1H), 4.51 (t, J = 8.4 Hz, 2H), 3.57-3.10 (m, 5H), 3.26-2.96 (m, 9H), 2.51-2.39 (m, 4H), 1.27 (d, J = 6.0 Hz, 3H). |
| 415 | 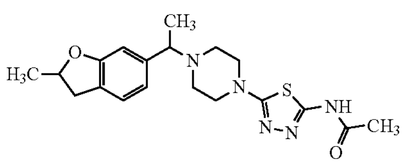 [SMILES: CC(=O)Nc1nnc(N2CCN(C(C)c3ccc4c(c3)OC(C)C4)CC2)s1] | Racemic | ¹H NMR (400 MHz, CDCl₃): δ 7.12 (d, J = 7.6 Hz, 1H), 6.75 (d, J = 7.2 Hz, 1H), 6.68 (s, 1H), 4.89 (d, J = 5.6 Hz, 1H), 3.34-3.31 (m, 4H), 3.24 (s, 1H), 2.78-2.76 (m, 2H), 2.51-2.43 (m, 4H), 2.10 (s, 3H), 1.39 (d, J = 4.0 Hz, 3H), 1.28 (d, J = 6.0 Hz, 3H). |
| 416 | 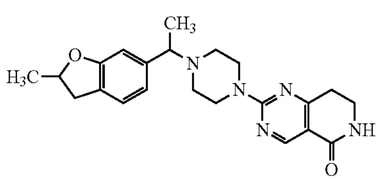 [SMILES: CC1Cc2ccc(C(C)N3CCN(c4ncc5c(n4)CCNC5=O)CC3)cc2O1] | Racemic | ¹H NMR (400 MHz, DMSO-d₆): δ 8.58 (s, 1H), 7.69 (s, 1H), 7.11 (d, J = 7.6 Hz, 1H), 6.75 (d, J = 7.2 Hz, 1H), 6.68 (s, 1H), 4.89-4.87 (m, 1H), 3.80-3.79 (m, 4H), 3.38-3.24 (m, 5H), 2.80-2.67 (m, 4H), 2.46-2.43 (m, 1H), 2.37-2.33 (m, 1H), 1.39-1.37 (m, 3H), 1.28 (d, J = 6.8 Hz, 3H). |
| 417 | 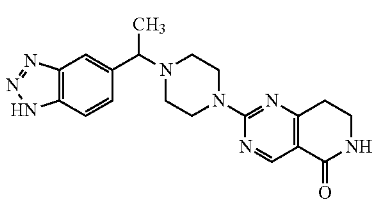 [SMILES: CC(c1ccc2[nH]nnc2c1)N1CCN(c2ncc3c(n2)CCNC3=O)CC1] | Racemic | ¹H NMR (400 MHz, DMSO-d₆): δ 8.57 (s, 1H), 7.87 (d, J = 8.8 Hz, 1H), 7.77 (s, 1H), 7.69 (s, 1H), 7.46 (d, J = 8.4 Hz, 1H), 3.80-3.78 (m, 4H), 3.65 (t, J = 6.4 Hz, 1H), 3.37-3.34 (m, 3H), 2.77 (t, J = 6.8 Hz, 2H), 2.52-2.49 (m, 2H), 2.40-2.37 (m, 2H), 1.38 (d, J = 6.4 Hz, 3H). |
| 418 | 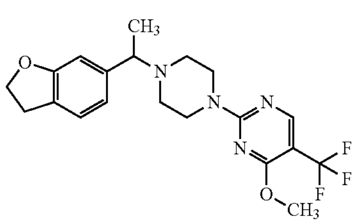 [SMILES: COc1nc(N2CCN(C(C)c3ccc4c(c3)OCC4)CC2)ncc1C(F)(F)F] | Racemic | ¹H NMR (400 MHz, DMSO-d₆): δ 8.24 (s, 1H), 7.15 (d, J = 6.8 Hz, 1H), 6.81 (s, 2H), 4.59 (t, J = 8.80 Hz, 2H), 3.95 (s, 3H), 3.86-3.76 (m, 4H), 3.51-3.40 (m, 1H), 3.21 (t, J = 8.00 Hz, 2H), 2.58-2.51 (m, 4H), 1.31-1.26 (m, 3H). |

TABLE 2-continued

| Ex | Structure | Configuration specification | 1H NMR |
|---|---|---|---|
| 419 | 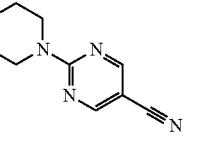 | Racemic | $^1$H NMR (400 MHz, DMSO-d$_6$): δ 8.73 (s, 2H), 7.15 (d, J = 7.2 Hz, 1H), 6.76 (d, J = 7.2 Hz, 1H), 6.73 (s, 1H), 4.51 (t, J = 8.8 Hz, 2H), 3.82-3.80 (m, 4H), 3.39-3.37 (m, 1H), 3.14 (t, J = 8.8 Hz, 2H), 2.40-2.34 (m, 4H), 1.29 (d, J = 6.8 Hz, 3H). |
| 420 | 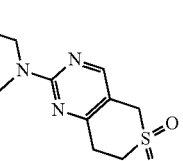 | Chiral HPLC SFC Method F: 1st eluting compound | $^1$H NMR (400 MHz, DMSO-d$_6$): δ 9.39 (s, 1H), 8.13-8.10 (m, 2H), 8.02 (s, 1H), 7.50 (d, J = 8.4 Hz, 1H), 4.31-4.30 (m, 2H), 3.80-3.71 (m, 4H), 3.64 (q, J = 5.6 Hz 1H), 3.48-3.45 (m, 2H), 3.15-3.12 (m, 2H), 2.40-2.37 (m, 4H), 1.40 (d, J = 5.6 Hz, 3H). |
| 421 | 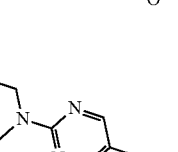 | Chiral HPLC SFC Method F: 2nd eluting compound | $^1$H NMR (400 MHz, DMSO-d$_6$): δ 9.39 (s, 1H), 8.13-8.10 (m, 2H), 8.02 (s, 1H), 7.50 (d, J = 8.4 Hz, 1H), 4.31-4.30 (m, 2H), 3.80-3.71 (m, 4H), 3.65 (q, J = 5.6 Hz 1H), 3.48-3.45 (m, 2H), 3.15-3.12 (m, 2H), 2.40-2.37 (m, 4H), 1.40 (d, J = 5.6 Hz, 3H). |
| 422 | 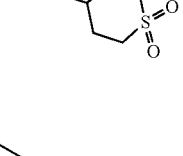 | Racemic | $^1$H NMR (400 MHz, DMSO-d$_6$): δ 12.35 (s, 1H), 7.15 (d, J = 7.2 Hz, 1H), 6.76 (d J = 7.1 Hz, 1H), 6.71 (ms, 1H), 6.00 (s, 1H), 4.51 (t, J = 8.8 Hz, 2H), 3.35-3.3 (m, 1H), 3.19-3.14 (m, 5H), 3.12-2.95 (m, 6H), 2.41-2.33 (m, 4H), 1.55 (d, J = 6.0 Hz, 3H). |
| 423 | 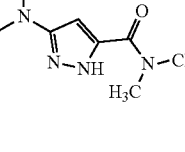 | Racemic | $^1$H NMR (400 MHz, DMSO-d$_6$): δ 8.45 (s, 1H), 7.16 (d, J = 7.2 Hz, 1H), 6.74 (d, J = 7.6 Hz, 1H), 6.71 (s, 1H), 4.60 (s, 1H), 4.50 (t, J = 8.6 Hz, 2H), 4.42 (s, 2H), 3.58-3.56 (m, 4H), 3.34-3.33 (m, 2H), 3.13 (t, J = 8.0 Hz, 2H), 2.40 (t, J = 39.2 Hz, 4H), 1.28 (d, J = 6.8 Hz, 3H). |
| 424 | 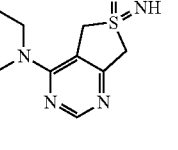 | S-enantiomer | $^1$H NMR (400 MHz, DMSO-d$_6$): δ 8.71 (s, 2H), 7.14 (d, J = 7.2 Hz, 1H), 6.75 (d, J = 7.6 Hz, 1H), 6.71 (s, 1H), 4.48 (t, J = 6.8 Hz, 2H), 3.81-3.79 (m, 4H), 3.36 (q, J = 6.8 Hz, 1H), 3.13 (t, J = 8.4 Hz, 2H), 2.45-2.39 (m, 4H), 1.28 (d, J = 6.4 Hz, 3H). |
| 425 | 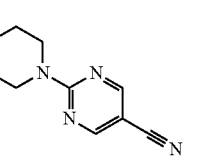 | Racemic | $^1$H NMR (400 MHz, DMSO-d$_6$): δ 12.48-12.44 (m, 1H), 8.24-7.77 (m, 1H), 7.15 (d, J = 7.6 Hz, 1H), 6.76 (d, J = 8.0 Hz, 1H), 6.71 (s, 1H), 6.24-5.81 (m, 1H), 4.74-4.72 (q, J = 6.8 Hz, 1H), 4.51 (t, J = 8.4 Hz, 2H), 3.48-3.45 (m, 2H), 3.34-3.30 (m, 1H), 3.18-3.14 (m, 4H), 3.10-3.04 (m, 4H), 2.50-2.34 (m, 4H), 1.28 (d, J = 6.8 Hz, 3H). |
| 426 | 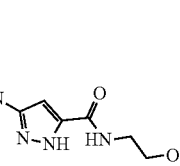 | Racemic | $^1$H NMR (400 MHz, DMSO-d$_6$): δ 7.15 (d, J = 7.6 Hz, 1H), 6.76 (d, J = 1.2 Hz, 1H), 6.71 (s, 1H), 4.51 (t, J = 8.8 Hz, 2H), 4.22 (t, J = 4.8 Hz, 2H), 3.72 (t, J = 4.8 Hz, 2H), 3.39-3.34 (m, 1H), 3.16-3.09 (m, 6H), 2.96 (s, 3H), 2.51-2.33 (m, 4H), 1.28 (d, J = 6.80 Hz, 3H). |

TABLE 2-continued

| Ex | Structure | Configuration specification | 1H NMR |
|---|---|---|---|
| 427 | 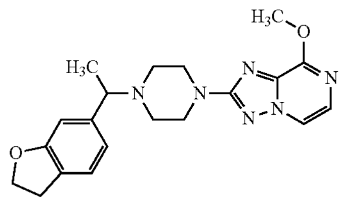 [SMILES: COc1nccn2nc(N3CCN(C(C)c4ccc5c(c4)OCC5)CC3)nc12] | Racemic | $^1$H NMR (400 MHz, DMSO-d$_6$): 8.38 (d, J = 4.4 Hz, 1H), 7.55 (d, J = 4.4 Hz, 1H), 7.16 (d, J = 7.2 Hz, 1H), 6.77 (d, J = 7.2 Hz, 1H), 6.73 (s, 1H), 4.51 (t, J = 8.8 Hz, 2H), 4.03 (s, 3H), 3.47-3.38 (m, 4H), 3.36-3.34 (m, 1H), 3.16 (t, J = 8.4 Hz, 2H), 2.43-2.34 (m, 4H), 1.29 (d, J = 6.8 Hz, 3H). |
| 428 | 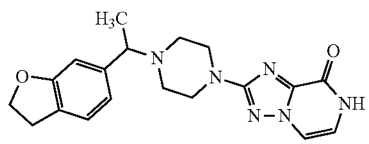 [SMILES: CC(c1ccc2c(c1)OCC2)N1CCN(c2nc3c(=O)[nH]ccn3n2)CC1] | Racemic | $^1$HNMR (400 MHz, DMSO-d6): δ 11.70 (s, 1H), 7.62 (d, J = 5.6 Hz, 1H), 7.15 (d, J = 7.6 Hz, 1H), 6.95 (d, J = 5.6 Hz, 1H), 6.76 (d, J = 8.4 Hz, 1H), 6.72 (s, 1H), 4.50 (t, J = 8.4 Hz, 2H), 3.48-4.34 (m, 4H), 3.13 (t, J = 8.8 Hz, 2H), 2.49-2.33 (m, 4H), 1.28 (d, J = 6.8 Hz, 3H). |
| 429 | 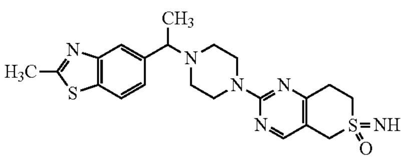 [SMILES: Cc1nc2cc(C(C)N3CCN(c4ncc5c(n4)CCS(=N)(=O)C5)CC3)ccc2s1] | Racemic | $^1$H NMR (400 MHz, DMSO-d$_6$): δ 8.07 (s, 1H), 7.96 (d, J = 8.4 Hz, 1H), 7.83 (s, 1H), 7.38 (dd, J = 8.6, 1.6 Hz, 1H), 4.22-4.10 (m, 2H), 3.90 (s, 1H), 3.71-3.69 (m, 4H), 3.60 (q, J = 6.8 Hz, 1H), 3.40-3.25 (m, 2H), 3.06 (t, J = 6.8 Hz, 2H), 2.79 (s, 3H), 2.45-2.33 (m, 4H), 1.38 (d, J = 6.8 Hz, 3H). |
| 430 | 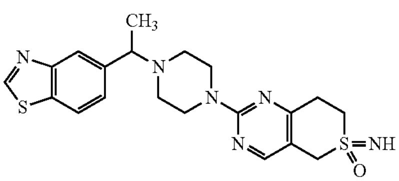 [SMILES: CC(c1ccc2scnc2c1)N1CCN(c2ncc3c(n2)CCS(=N)(=O)C3)CC1] | Racemic | $^1$H NMR (400 MHz, DMSO-d$_6$): δ 9.38 (s, 1H), 8.11 (d, J = 8.4 Hz, 1H), 8.07 (s, 1H), 8.02 (d, J = 8.4 Hz, 1H), 7.51-7.48 (dd, J = 8.4, 1.6 Hz, 1H), 4.18-4.08 (m, 2H), 3.90 (s, 1H), 3.72-3.64 (m, 5H), 3.36-3.29 (m, 2H), 3.06 (t, J = 6.4 Hz, 2H), 2.52-2.39 (m, 4H), 1.39 (d, J = 6.80 Hz, 3H). |
| 431 | 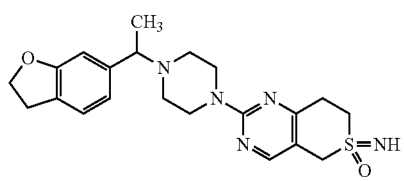 [SMILES: CC(c1ccc2c(c1)OCC2)N1CCN(c2ncc3c(n2)CCS(=N)(=O)C3)CC1] | Racemic | $^1$H NMR (400 MHz, DMSO-d$_6$): δ 8.08 (s, 1H), 7.14 (d, J = 7.6 Hz, 1H), 6.75 (d, J = 7.6 Hz, 1H), 6.71 (s, 1H), 4.50 (t, J = 8.8 Hz, 2H), 4.22-4.10 (m, 2H), 3.91 (s, 1H), 3.69-3.67 (m, 4H), 3.40-3.30 (m, 2H), 3.18-3.05 (m, 5H), 2.50-2.31 (m, 4H), 1.27 (d, J = 6.4 Hz, 3H). |
| 432 | 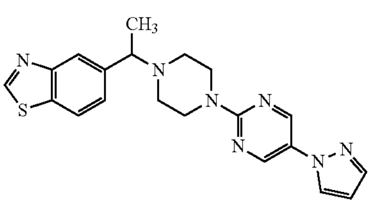 [SMILES: CC(c1ccc2scnc2c1)N1CCN(c2ncc(-n3cccn3)cn2)CC1] | Racemic | $^1$H NMR (400 MHz, DMSO-d$_6$): δ 9.40 (s, 1H), 8.77 (s, 2H), 8.33 (s, 1H), 8.13 (d, J = 7.2 Hz, 1H), 8.04 (s, 1H), 7.74 (s, 1H), 7.52 (d, J = 6.8 Hz, 1H), 6.54 (s, 1H), 3.37-3.67 (m, 5H), 2.68-2.34 (m, 4H), 1.43 (d, J = 4.8 Hz, 3H). |
| 433 | 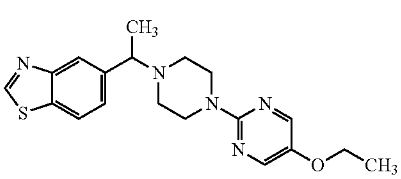 [SMILES: CCOc1cnc(N2CCN(C(C)c3ccc4scnc4c3)CC2)nc1] | Racemic | $^1$H NMR (400 MHz, DMSO-d$_6$): δ 9.38 (s, 1H), 8.16 (s, 2H), 8.12 (d, J = 8.4 Hz, 1H), 8.02 (s, 1H), 7.50 (d, J = 8.4 Hz, 1H), 4.00 (q, J = 6.8 Hz, 2H), 3.64-3.62 (m, 5H), 2.45-2.39 (m, 4H), 1.40 (d, J = 6.8 Hz, 3H), 1.28 (t, J = 6.8 Hz, 3H). |
| 434 | 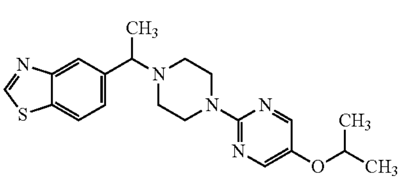 [SMILES: CC(C)Oc1cnc(N2CCN(C(C)c3ccc4scnc4c3)CC2)nc1] | Racemic | $^1$H NMR (400 MHz, DMSO-d$_6$): δ 9.38 (s, 1H), 8.15 (s, 2H), 8.12 (d, J = 8.4 Hz, 1H), 8.02 (s, 1H), 7.50 (d, J = 8.4 Hz, 1H), 4.44-4.43 (m, 1H), 3.63-3.61 (m, 5H), 2.45-2.39 (m, 4H), 1.40 (d, J = 6.8 Hz, 3H), 1.21 (d, J = 6.0 Hz, 6H). |

TABLE 2-continued

| Ex | Structure | Configuration specification | 1H NMR |
|----|-----------|------------------------------|--------|
| 435 | 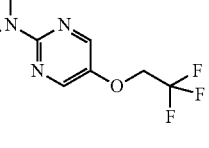 | Racemic | $^1$H NMR (400 MHz, DMSO-d$_6$): δ 9.38 (s, 1H), 8.27 (s, 2H), 8.12 (d, J = 8.4 Hz, 1H), 8.02 (s, 1H), 7.50 (dd, J = 8.4, 1.6 Hz, 1H), 4.73 (q, J = 8.8 Hz, 2H), 3.65-3.64 (m, 5H), 2.45-2.39 (m, 4H), 1.40 (d, J = 6.8 Hz, 3H). |
| 436 | 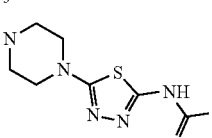 | Racemic | $^1$H NMR (400 MHz, DMSO-d$_6$): δ 12.00 (s, 1H), 7.09 (d, J = 7.6 Hz, 1H), 6.73 (d, J = 7.6 Hz, 1H), 6.63 (s, 1H), 3.37-3.33 (m, 4H), 2.96 (s, 2H), 2.50-2.35 (m, 4H), 2.09 (s, 3H), 1.40 (s, 3H), 1.39(s, 3H), 1.27 (d, J = 6.4 Hz, 3H). |
| 437 | 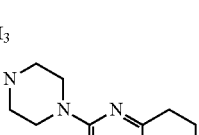 | Racemic | $^1$H NMR (400 MHz, DMSO-d$_6$): δ 8.58 (s, 1H), 7.70 (s, 1H), 7.10 (d, J = 7.6 Hz, 1H), 6.74 (d, J = 7.2 Hz, 1H), 6.65 (s, 1H), 3.80-3.79 (s, 4H), 3.37-3.36 (d, J = 4.0 Hz, 1H), 2.96 (s, 2H), 2.37-2.34 (m, 4H), 1.40 (d, J = 2.8 Hz, 6H), 1.28 (d, J = 6.8 Hz, 3H). |
| 438 | 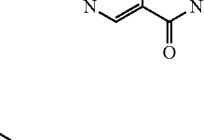 | Chiral HPLC SFC Method 1: 1st eluting compound | $^1$H NMR (400 MHz, DMSO-d$_6$): δ 7.14 (d, J = 7.2 Hz, 1H), 6.73 (d, J = 8.0 Hz, 1H), 6.70 (s, 1H), 6.46 (s, 2H), 4.52-4.48 (m, 2H), 3.37-3.365 (m, 1H), 3.19-3.11 (m, 6H), 2.45-2.36 (m, 4H), 1.25 (d, J = 6.8 Hz, 3H). |
| 439 | 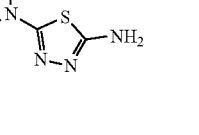 | Racemic | $^1$H NMR (400 MHz, DMSO-d$_6$): δ 12.03 (s, 1H), 7.61-7.59 (m, 2H), 7.32 (d, J = 9.6 Hz, 1H), 3.62-3.60 (m, 1H), 3.47-3.35 (m, 4H), 2.6 (s, 3H), 2.45-2.41 (m, 4H), 2.10 (s, 3H), 1.37 (d, J = 6.8 Hz, 3H). |
| 440 | 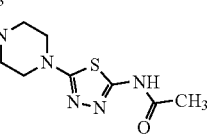 | Racemic | $^1$H NMR (400 MHz, DMSO-d$_6$): δ 8.57 (s, 1H), 7.70 (s, 1H), 7.60-7.58 (m, 2H), 7.32 (d, J = 8.0 Hz, 1H), 3.88-3.75 (m, 4H), 3.60 (q, J = 6.8 Hz, 1H), 3.43-3.33 (m, 2H), 2.78 (t, J = 6.8 Hz, 2H), 2.60 (s, 3H), 2.38-2.22 (m, 4H), 1.37 (d, J = 6.8 Hz, 3H). |
| 441 | 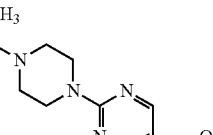 | Racemic | $^1$H NMR (400 MHz, DMSO-d$_6$): δ 8.67 (s, 2H), 7.59-7.57 (m, 2H), 7.31 (dd, J = 8.6, 0.8 Hz, 1H), 3.84 (t, J = 5.2 Hz, 4H), 3.61-3.59 (m, 1H), 3.20 (s, 3H), 2.59 (s, 3H), 2.50-2.48 (m, 2H), 2.41-2.37 (m, 2H), 1.36 (d, J = 6.8 Hz, 3H). |
| 442 | 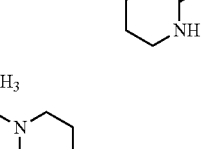 | Racemic | $^1$H NMR (400 MHz, DMSO-d$_6$): δ 8.10 (s, 1H), 7.60-7.58 (m, 2H), 7.31 (d, J = 8.4 Hz, 1H), 4.30 (s, 2H), 3.75-3.66 (m, 4H), 3.58-3.56 (m, 1H), 3.47 (t, J = 6.0 Hz, 2H), 3.14 (t, J = 6.8 Hz, 2H), 2.60 (s, 3H), 2.44-2.29 (m, 4H), 1.37 (d, J = 6.4 Hz, 3H). |

TABLE 2-continued

| Ex | Structure | Configuration specification | 1H NMR |
|---|---|---|---|
| 443 | 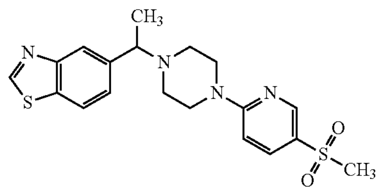 [SMILES: CC(c1ccc2scnc2c1)N1CCN(c2ccc(S(C)(=O)=O)cn2)CC1] | Racemic | $^1$H NMR (400 MHz, DMSO-d$_6$): δ 9.39 (s, 1H), 8.47 (d, J = 2.4 Hz, 1H), 8.13 (d, J = 6.4 Hz, 1H), 8.03 (s, 1H), 7.86 (d, J = 6.8 Hz, 1H), 7.50 (d, J = 8.0 Hz, 1H), 6.92 (d, J = 9.6 Hz, 1H), 3.75-3.67 (m, 5H), 3.14 (s, 3H), 2.55-2.51 (m, 2H), 2.44-2.41 (m, 2H), 1.41 (d, J = 6.4 Hz, 3H). |
| 444 | 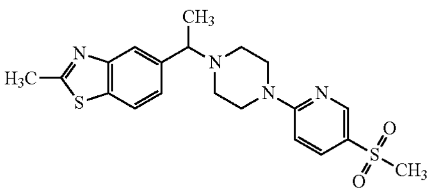 | Racemic | $^1$H NMR (400 MHz, DMSO-d$_6$): δ 8.47 (d, J = 1.6 Hz, 1H), 7.97 (d, J = 8.4 Hz, 1H), 7.87-7.85 (m, 2H), 7.39 (d, J = 7.2 Hz, 1H), 6.91 (d, J = 9.2 Hz, 1H), 3.67-3.61 (m, 5H), 3.13 (s, 3H), 2.79 (s, 3H), 2.55-2.55 (m, 2H), 2.45-2.43 (m, 2H), 1.39 (d, J = 6.4 Hz, 3H). |
| 445 | 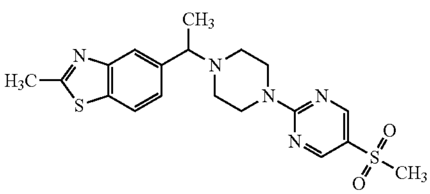 | Racemic | $^1$H NMR (400 MHz, DMSO-d$_6$): δ 8.69-8.67 (m, 2H), 7.97 (d, J = 8.4 Hz, 1H), 7.85 (s, 1H), 7.39 (d, J = 8.0 Hz, 1H), 3.92-3.86 (m, 4H), 3.64-3.63 (m, 1H), 3.21 (s, 3H), 2.80 (s, 3H), 2.43-2.40 (m, 4H), 1.39 (d, J = 6.8 Hz, 3H). |
| 446 | 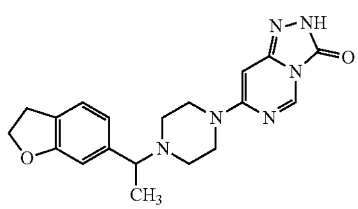 [SMILES: CC(c1ccc2c(c1)OCC2)N1CCN(c2cc3n[nH]c(=O)n3cn2)CC1] | Racemic | $^1$H NMR (400 MHz, DMSO-d$_6$): δ 8.84 (s, 1H), 7.16 (d, J = 7.6 Hz, 1H), 6.77 (d, J = 7.6 Hz, 1H), 6.73 (s, 1H), 6.33 (s, 1H), 4.51 (t, J = 8.8 Hz, 1H), 3.54-3.51 (m, 4H), 3.42-3.20 (m, 1H), 3.14 (t, J = 8.8 Hz, 2H), 2.40-2.30 (m, 4H), 1.29 (d, J = 6.8 Hz, 3H). |
| 447 | 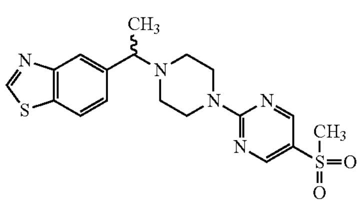 [SMILES: CC(c1ccc2scnc2c1)N1CCN(c2ncc(S(C)(=O)=O)cn2)CC1] | Chiral HPLC SFC Method G: 1st eluting compound | $^1$H NMR (400 MHz, DMSO-d$_6$): δ 9.39 (s, 1H), 8.67 (s, 2H), 8.11 (d, J = 8.4 Hz, 1H), 8.02 (s, 1H), 7.50 (dd, J = 8.4, 1.6 Hz 1H), 3.87-3.85 (m, 4H), 3.68 (q, d, J = 6.8 Hz, 1H), 3.20 (s, 3H), 2.56-2.41 (m, 4H), 1.42 (d, J = 6.8 Hz, 3H). |
| 448 | 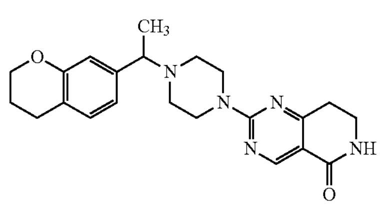 [SMILES: CC(c1ccc2c(c1)OCCC2)N1CCN(c2ncc3c(n2)CCNC3=O)CC1] | Racemic | $^1$H NMR (400 MHz, DMSO-d$_6$): δ 9.76 (s, 1H), 8.67 (s, 1H), 7.16 d, J = 7.6 Hz, 1H), 6.93 (d, J = 7.6 Hz, 2H), 4.80-4.70 (m, 2H), 4.40-4.38 (m, 1H), 4.15 (t, J = 4.4 Hz, 3H), 3.75 (m, 1H), 2.85-2.75 (m, 10H), 1.92 (t, J = 5.6 Hz, 2H), 1.61 (d, J = 6.8 Hz, 3H). |
| 449 | 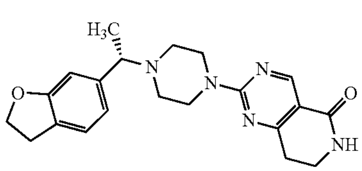 [SMILES: C[C@@H](c1ccc2c(c1)OCC2)N1CCN(c2ncc3c(n2)CCNC3=O)CC1] | S-enantiomer | $^1$H NMR (400 MHz, DMSO-d$_6$): δ 8.58 (s, 1H), 7.69 (s, 1H), 7.15 (d, J = 7.6 Hz, 1H), 6.76 (d, J = 7.6 Hz, 1H), 6.72 (s, 1H), 4.50 (t, J = 8.8 Hz, 2H), 3.81-3.76 (m, 4H), 3.38-3.37 (m, 3H), 3.13 (t, J = 8.8 Hz, 2H), 2.78 (t, J = 6.4 Hz, 2H), 2.42-2.38 (m, 4H), 1.28 (d, J = 6.80 Hz, 3H). |

TABLE 2-continued

| Ex | Structure | Configuration specification | 1H NMR |
|---|---|---|---|
| 450 | 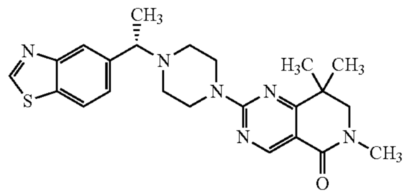 [SMILES: C[C@@H](c1ccc2scnc2c1)N1CCN(c2ncc3c(n2)C(C)(C)CN(C)C3=O)CC1] | S-enantiomer | ¹H NMR (400 MHz, DMSO-d₆): δ 9.38 (s, 1H), 8.60 (s, 1H), 8.12 (d, J = 8.4 Hz, 1H), 8.02 (s, 1H), 7.50 (d, J = 8.4 Hz, 1H), 3.84-3.71 (m, 4H), 3.68 (d, J = 7.2 Hz, 1H), 3.32 (d, J = 4.4 Hz, 2H), 2.96 (s, 3H), 2.46-2.33 (m, 2H), 1.41 (d, J = 6.8 Hz, 3H), 1.19 (s, 6H). |
| 451 | 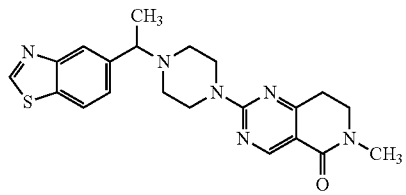 [SMILES: CC(c1ccc2scnc2c1)N1CCN(c2ncc3c(n2)CCN(C)C3=O)CC1] | Racemic | ¹H NMR (400 MHz, DMSO-d₆): δ 9.38 (s, 1H), 8.58 (s, 1H), 8.12 (d, J = 8.0 Hz, 1H), 8.02 (s, 1H), 7.50 (d, J = 8.0 Hz, 1H), 3.88-3.77 (m, 4H), 3.64-3.63 (m, 1H), 3.55-3.44 (m, 2H), 2.94 (s, 3H), 2.87-2.84 (m, 2H), 2.45-2.42 (m, 2H), 1.40 (d, J = 6.8 Hz, 3H). |
| 452 | 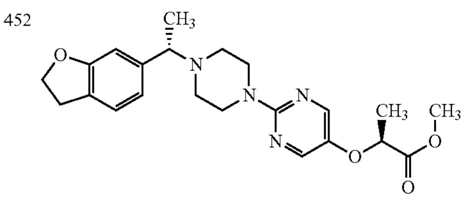 | S-enantiomer | ¹H NMR (400 MHz, DMSO-d₆): δ 8.16 (s, 2H), 7.14 (d, J = 7.6 Hz, 1H), 6.76 (d, J = 7.6 Hz, 1H), 6.71 (s, 1H), 4.90 (q, J = 7.2 Hz 1H), 4.50 (t, J = 8.8 Hz, 2H), 3.67 (s, 3H), 3.59 (t, J = 4.8 Hz, 3H), 3.13 (t, J = 8.4 Hz, 2H), 2.46-2.42 (m, 2H), 2.36-2.32 (m, 2H), 1.47 (d, J = 6.80 Hz, 3H), 1.28 (t, J = 6.4 Hz, 3H). |
| 453 | 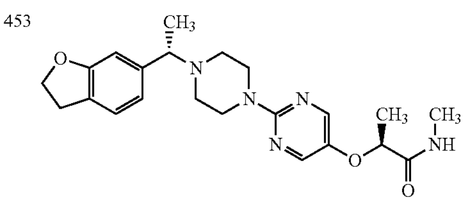 | S-enantiomer | ¹H NMR (400 MHz, DMSO-d₆): δ 8.26 (s, 2H), 8.04 (q, J = 4.4 Hz, 1H), 7.15 (d, J = 7.6 Hz, 3H), 6.75 (d, J = 7.6 Hz, 1H), 6.71 (s, 1H), 4.58 (q, J = 6.8 Hz, 1H), 4.50 (t, J = 8.8 Hz, 2H), 3.60-3.58 (m, 4H), 3.14 (t, J = 8.8 Hz, 2H) 2.60 (d, J = 8.8 Hz, 3H), 2.45-2.33 (m, 2H), 1.38 (d, J = 6.8 Hz, 3H), 1.28 (t, J = 8.0 Hz, 3H). |
| 454 | 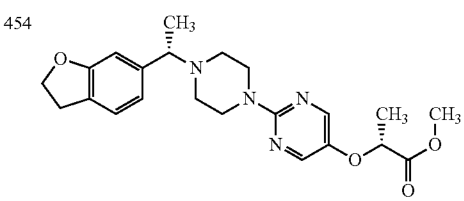 | S-enantiomer | ¹H NMR (400 MHz, DMSO-d₆): δ 8.17 (s, 2H), 7.15 (d, J = 7.2 Hz, 1H), 6.76 (d, J = 7.6 Hz, 1H), 6.72 (s, 1H), 4.91 (d, J = 6.8 Hz, 1H), 4.51 (t, J = 8.8 Hz, 2H), 3.67 (s, 3H), 3.61-3.58 (m, 4H), 3.33-3.29 (m, 1H), 3.14 (t, J = 8.4 Hz, 2H), 2.46-2.42 (m, 4H), 1.48 (d, J = 6.8 Hz, 3H), 1.26 (t, J = 6.8 Hz, 3H),. |
| 455 | 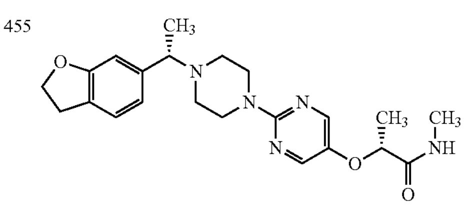 | S-enantiomer | ¹H NMR (400 MHz, DMSO-d₆): δ 8.15 (s, 2H), 8.05 (s, 1H), 7.15 (d, J = 7.2 Hz, 1H), 6.76 (d, J = 7.2 Hz, 1H), 6.72 (s, 1H), 4.58 (q, J = 6.4 Hz, 1H), 4.51 (t, J = 8.8 Hz, 2H), 3.59-3.57 (m, 4H), 3.18-3.11 (m, 3H), 2.67-2.59 (m, 3H), 2.35-2.34 (m, 4H), 1.38 (d, J = 6.4 Hz, 3H), 1.28 (d, J = 6.4 Hz, 3H). |
| 456 | 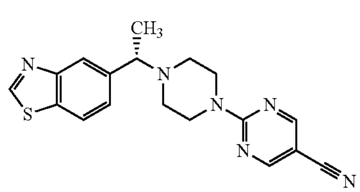 [SMILES: C[C@@H](c1ccc2scnc2c1)N1CCN(c2ncc(C#N)cn2)CC1] | S-enantiomer | ¹H NMR (400 MHz, DMSO-d₆): δ 9.39 (s, 1H), 8.72 (s, 2H), 8.12 (d, J = 8.0 Hz, 1H), 8.02 (s, 1H), 7.50 (dd, J = 8.2, 1.2 Hz, 2H), 3.83 (t, J = 4.8 Hz, 4H), 3.65 (q, J = 6.8 Hz, 1H), 2.46-2.42 (m, 4H), 1.41 (d, J = 6.8 Hz, 3H). |

TABLE 2-continued

| Ex | Structure | Configuration specification | 1H NMR |
|---|---|---|---|
| 457 | 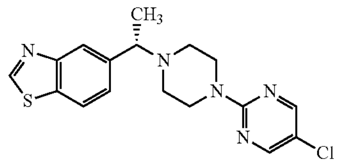 [SMILES: C[C@@H](c1ccc2scnc2c1)N1CCN(c2ncc(Cl)cn2)CC1] | S-enantiomer | $^1$H NMR (400 MHz, DMSO-d$_6$): δ 9.38 (s, 1H), 8.39 (s, 2H), 8.11 (d, J = 8.8 Hz, 1H), 8.02 (s, 1H), 7.50 (d, J = 8.2 Hz, 1H), 3.70-3.66 (m, J = 4.8 Hz, 5H), 2.50-2.33 (m, 4H), 1.40 (d, J = 6.4 Hz, 3H). |
| 458 | 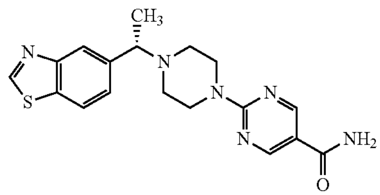 [SMILES: C[C@@H](c1ccc2scnc2c1)N1CCN(c2ncc(C(N)=O)cn2)CC1] | S-enantiomer | $^1$H NMR (400 MHz, DMSO-d$_6$): δ 9.39 (s, 1H), 8.75-8.74 (m, 2H), 8.12 (d, J = 8.4 Hz, 1H), 8.03 (d, J = 1.2 Hz, 1H), 7.82 (s, 1H), 7.50 (dd, J = 8.4, 1.2 Hz, 1H), 7.26 (s, 1H), 3.81 (t, J = 4.8 Hz, 4H), 3.67 (q, J = 6.4 Hz, 1H), 2.56-2.39 (m, 4H), 1.41 (d, J = 6.8 Hz, 3H). |
| 459 | 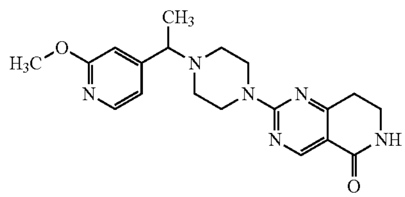 [SMILES: COc1cc(C(C)N2CCN(c3ncc4c(n3)CCNC4=O)CC2)ccn1] | Racemic | $^1$H NMR (400 MHz, DMSO-d$_6$): δ 8.58 (s, 1H), 8.11 (d, J = 5.2 Hz, 1H), 7.70 (s, 1H), 6.97 (d, J = 4.0 Hz, 1H), 6.75 (s, 1H), 3.83-3.50 (m, 7H), 3.48 (q, J = 5.8 Hz, 1H), 3.38-3.28 (m, 2H), 2.80-2.77 (m, 2H), 2.51-2.45 (m, 2H), 2.39-2.33 (m, 2H), 1.29 (d, J = 6.8 Hz, 3H). |
| 460 | 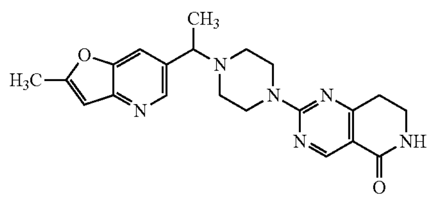 [SMILES: Cc1cc2ncc(C(C)N3CCN(c4ncc5c(n4)CCNC5=O)CC3)cc2o1] | Racemic | $^1$H NMR (400 MHz, DMSO-d$_6$): δ 8.57 (s, 1H), 8.40 (s, 1H), 7.84 (s, 1H), 7.70 (s, 1H), 6.74 (s, 1H), 3.81-3.79 (m, 4H), 3.71-3.69 (m, 1H), 3.38-3.36 (m, 2H), 2.78 (t, J = 6.4 Hz, 2H), 2.51 (s, 3H), 2.51-2.46 (m, 4H), 1.40 (d, J = 6.80 Hz, 3H). |
| 461 | 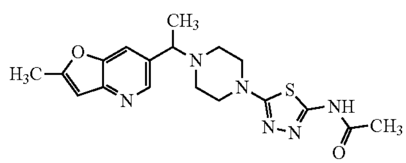 [SMILES: CC(=O)Nc1nnc(N2CCN(C(C)c3cnc4cc(C)oc4c3)CC2)s1] | Racemic | $^1$H NMR (400 MHz, DMSO-d$_6$): δ 8.40 (s, 1H), 7.84 (s, 1H), 6.75 (s, 1H), 3.72-3.51 (m, 1H), 3.36 (t, J = 4.8 Hz, 4H), 2.51 (s, 3H), 2.47-2.42 (m, 4H), 2.12 (s, 3H), 1.40 (d, J = 6.8 Hz, 3H). |
| 462 | 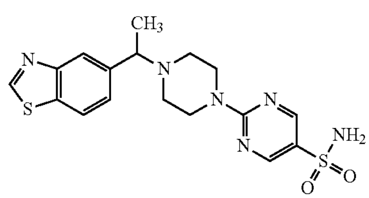 [SMILES: CC(c1ccc2scnc2c1)N1CCN(c2ncc(S(N)(=O)=O)cn2)CC1] | Racemic | $^1$H NMR (400 MHz, DMSO-d$_6$): δ 9.39 (s, 1H), 8.61 (s, 2H), 8.12 (d, J = 8.4 Hz, 1H), 8.03 (s, 1H), 7.50 (d, J = 8.4 Hz, 1H), 7.32 (s, 2H), 3.83-3.81 (m, 4H), 3.68-3.66 (m, 1H), 2.55-2.38 (m, 4H), 1.40 (d, J = 6.8 Hz, 3H). |
| 463 | 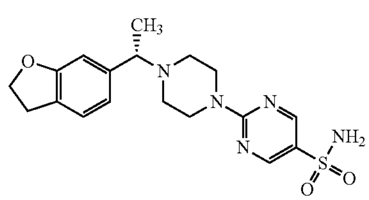 [SMILES: C[C@@H](c1ccc2c(c1)OCC2)N1CCN(c2ncc(S(N)(=O)=O)cn2)CC1] | S-enantiomer | $^1$H NMR (400 MHz, DMSO-d$_6$): δ 8.62 (s, 2H), 7.33 (s, 2H), 7.15 (d, J = 7.6 Hz, 1H), 6.77-6.72 (m, 2H), 4.50 (t, J = 8.8 Hz, 2H), 3.80-3.80 (m, 4H), 3.38-3.36 (m, 1H), 3.13 (t, J = 8.4 Hz, 2H), 2.46-2.35 (m, 4H), 1.28 (d, J = 6.8 Hz, 3H). |
| 464 | 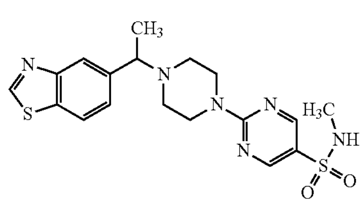 [SMILES: CNS(=O)(=O)c1cnc(N2CCN(C(C)c3ccc4scnc4c3)CC2)nc1] | Racemic | $^1$H NMR (400 MHz, DMSO-d$_6$): δ 9.38 (s,1H), 8.57 (s, 2H), 8.12 (dd, J = 8.2, 1.2 Hz, 1H), 8.03 (s, 1H), 7.50 (d, J = 8.4 Hz, 1H), 7.37-7.36 (m, 1H), 3.85-3.82 (m, 4H), 3.68 (q, J = 6.4 Hz, 1H), 2.56 (s, 3H), 2.45-2.41 (m, 4H), 1.41 (d, J = 6.4 Hz, 3H). |

TABLE 2-continued

| Ex | Structure | Configuration specification | 1H NMR |
|---|---|---|---|
| 465 | 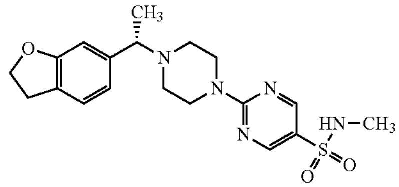 [SMILES: CNS(=O)(=O)c1cnc(N2CCN([C@@H](C)c3ccc4c(c3)OCC4)CC2)nc1] | S-enantiomer | ¹H NMR (400 MHz, DMSO-d₆): δ 8.58 (s, 2H), 7.36 (d, J = 5.2 Hz, 1H), 7.15 (d, J = 7.6 Hz, 1H), 6.76 (d, J = 7.6 Hz, 1H), 6.72 (s, 1H), 4.50 (t, J = 8.8 Hz, 2H), 3.82-3.79 (m, 4H), 3.52-3.32 (m, 1H), 3.13 (t, J = 8.8 Hz, 2H), 2.48-2.37 (m, 7H), 1.28 (d, J = 6.4 Hz, 3H). |
| 466 | 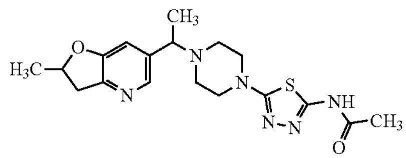 [SMILES: CC(=O)Nc1nnc(N2CCN(C(C)c3cnc4c(c3)OC(C)C4)CC2)s1] | Racemic | ¹H NMR (400 MHz, CDCl₃): δ 7.98 (s, 1H), 7.19 (s, 1H), 5.07-5.05 (m, 1H), 3.70-3.65 (m, 4H), 3.49-3.43 (m, 1H), 3.30-3.18 (m, 1H), 2.99-2.93 (m, 1H), 2.77-2.74 (m, 4H), 2.34 (s, 3H), 1.55 (d, J = 3.6 Hz, 3H), 1.27 (d, J = 5.20 Hz, 3H). |
| 467 | 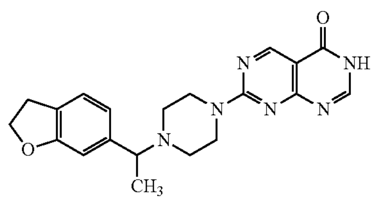 [SMILES: CC(c1ccc2c(c1)OCC2)N1CCN(c2ncc3c(=O)[nH]cnc3n2)CC1] | Racemic | ¹H NMR (400 MHz, DMSO-d₆): δ 12.30 (s, 1H), 8.99 (s, 1H), 8.24 (s, 1H), 7.15 (d, J = 7.2 Hz, 1H), 6.77 (d, J = 7.6 Hz, 1H), 6.73 (s, 1H), 4.51 (t, J = 8.8 Hz, 2H), 3.85-3.84 (m, 4H), 3.38 (q, J = 6.8 Hz, 1H), 3.14 (t, J = 8.4 Hz, 2H), 2.50-2.34 (m, 4H), 1.29 (d, J = 6.4 Hz, 3H). |
| 468 | 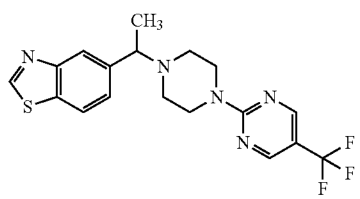 [SMILES: CC(c1ccc2scnc2c1)N1CCN(c2ncc(C(F)(F)F)cn2)CC1] | Racemic | ¹H NMR (400 MHz, DMSO-d₆): δ 9.41 (s, 1H), 8.52 (s, 2H), 8.12 (d, J = 8.0 Hz, 1H), 8.03 (s, 1H), 7.51 (d, J = 8.4 Hz, 1H), 6.94 (m, 1H), 3.80-3.79 (m, 4H), 3.66 (q, J = 6.4 Hz, 1H), 2.43-2.39 (m, 4H), 1.41 (d, J = 6.4 Hz, 3H). |
| 469 | 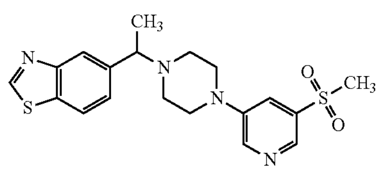 [SMILES: CC(c1ccc2scnc2c1)N1CCN(c2cncc(S(C)(=O)=O)c2)CC1] | Racemic | ¹H NMR (400 MHz, DMSO-d₆): δ 9.41 (d, J = 6.0 Hz, 1H), 8.58 (d, J = 2.8 Hz, 1H), 8.39 (d, J = 2.0 Hz, 1H), 8.14-8.12 (m, 1H), 8.05 (s, 1H), 7.62 (s, 1H), 7.52 (d, J = 8.4 Hz, 1H), 3.69 (q, J = 6.8 Hz, 1H), 3.35-3.30 (m, 4H), 2.67-2.61 (m, 4H), 1.43 (s, 3H). |
| 470 | 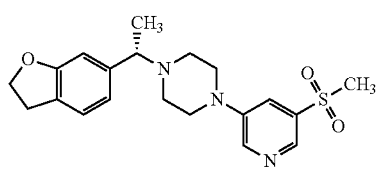 [SMILES: C[C@@H](c1ccc2c(c1)OCC2)N1CCN(c2cncc(S(C)(=O)=O)c2)CC1] | S-enantiomer | ¹H NMR (400 MHz, DMSO-d₆): δ 8.58 (d, J = 2.8 Hz, 1H), 8.39 (d, J = 1.6 Hz, 1H), 7.62-7.60 (m, 1H), 7.16 (d, J = 7.6 Hz, 1H), 6.78 (d, J = 7.6 Hz, 1H), 6.74 (s, 1H), 4.51 (t, J = 8.8 Hz, 2H), 3.39-3.37 (m, 1H), 3.33-3.29 (m, 7H), 3.14 (t, J = 8.4 Hz, 2H), 2.57-2.55 (m, 2H), 2.50-2.44 (m, 2H), 1.30 (d, J = 6.8 Hz, 3H). |
| 471 | 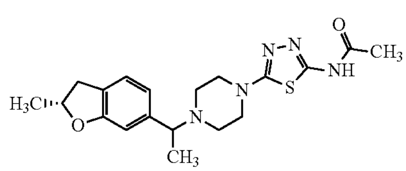 [SMILES: CC(=O)Nc1nnc(N2CCN(C(C)c3ccc4c(c3)O[C@H](C)C4)CC2)s1] | Racemic | ¹H NMR (400 MHz, DMSO-d₆): δ 12.02 (s, 1H), 7.11 (d, J = 7.2 Hz, 1H), 6.74 (d, J = 7.2 Hz, 1H), 6.67 (s, 1H), 4.89 (t, J = 6.0 Hz, 1H), 3.38-3.24 (m, 6H), 2.74 (q, J = 7.6 Hz, 1H), 2.43-2.40 (m, 4H), 2.10 (s, 3H), 1.38 (t, J = 2.0 Hz, 3H), 1.26 (t, J = 6.8 Hz, 3H). |
| 472 | 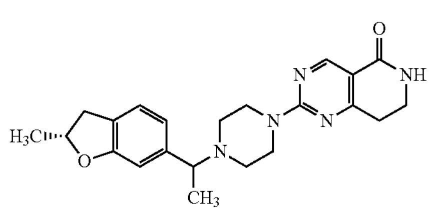 [SMILES: CC(c1ccc2c(c1)O[C@H](C)C2)N1CCN(c2ncc3c(n2)CCNC3=O)CC1] | Racemic | ¹H NMR (400 MHz, DMSO-d₆): δ 8.58 (d, J = 2.8 Hz, 1H), 7.70 (s, 1H), 7.11 (d, J = 7.6 Hz, 1H), 6.74 (d, J = 7.6 Hz, 1H), 6.68 (s, 1H), 4.88 (q, J = 8.0 Hz, 1H), 3.80-3.79 (m, 4H), 3.38-3.23 (m, 4H), 2.80-2.71 (m, 3H), 2.51-2.37 (m, 4H), 1.38 (t, J = 2.8 Hz, 3H), 1.27 (d, J = 6.4 Hz, 3H). |

TABLE 2-continued

| Ex | Structure | Configuration specification | 1H NMR |
|---|---|---|---|
| 473 | 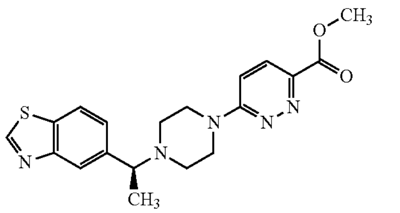 [SMILES: COC(=O)c1ccc(N2CCN([C@@H](C)c3ccc4scnc4c3)CC2)nn1] | S-enantiomer | ¹H NMR (400 MHz, DMSO-d$_6$): δ 9.40 (s, 1H), 8.12 (d, J = 8.4 Hz, 1H), 8.04 (s, 1H), 7.82 (d, J = 9.2 Hz, 1H), 7.51 (t, J = 7.6 Hz, 1H), 7.24 (d, J = 10 Hz, 1H) ,3.86 (s, 3H), 3.75-3.72 (m, 4H), 3.70-3.68 (m, 1H), 2.61-2.55 (m, 2H), 2.48-2.45 (m, 2H), 1.42 (d, J = 6.8 Hz, 3H) |
| 474 | 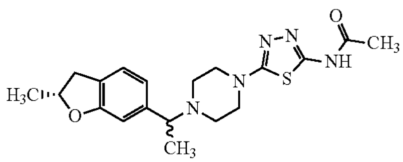 [SMILES: CC(=O)Nc1nnc(N2CCN(C(C)c3ccc4c(c3)O[C@H](C)C4)CC2)s1] | Chiral HPLC SFC Method F: 1st eluting compound | ¹H NMR (400 MHz, DMSO-d$_6$): δ 12.03 (s, 1H), 7.12 (d, J = 7.6 Hz, 1H), 6.75 (d, J = 7.6 Hz, 1H), 6.68 (s, 1H), 4.89 (q, J = 6.4 Hz, 1H), 3.40-3.24 (m, 5H), 2.77-2.68 (m, 1H), 2.44-2.39 (m, 7H), 2.10 (s, 3H), 1.39 (d, J = 6.0 Hz, 3H), 1.27 (t, J = 6.40 Hz, 3H). |
| 475 | 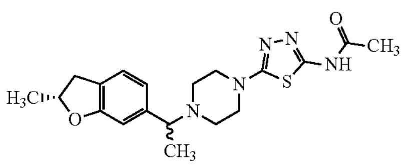 [SMILES: CC(=O)Nc1nnc(N2CCN(C(C)c3ccc4c(c3)O[C@H](C)C4)CC2)s1] | Chiral HPLC SFC Method F: 2nd eluting compound | ¹H NMR (400 MHz, DMSO-d$_6$): δ 12.03 (s, 1H), 7.12 (d, J = 7.2 Hz, 1H), 6.75 (d, J = 7.6 Hz, 1H), 6.68 (s, 1H), 4.90 (q, J = 8.0 Hz, 1H), 3.40-3.24 (m, 5H), 2.77-2.68 (m, 1H), 2.42-2.34 (m, 4H), 2.09 (s, 3H), 1.38 (d, J = 6.0 Hz, 3H), 1.27 (t, J = 6.8 Hz, 3H). |
| 476 | 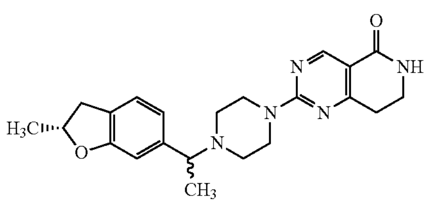 [SMILES: CC(c1ccc2c(c1)O[C@H](C)C2)N1CCN(c2ncc3c(n2)CCNC3=O)CC1] | Chiral HPLC SFC Method F: 1st eluting compound | ¹H NMR (400 MHz, DMSO-d$_6$): δ 8.58 (s, 1H), 7.69 (s, 1H), 7.11 (d, J = 7.6 Hz, 1H), 6.74 (d, J = 7.6 Hz, 1H), 6.68 (d, J = Hz, 1H), 4.89 (q, J = 7.2 Hz, 1H), 3.80-3.78 (m, 4H), 3.37-3.33 (m, 3H), 2.80-2.77 (m, 3H), 2.37-2.34 (m, 4H), 1.37 (d, J = 6.4 Hz, 3H), 1.28 (d, J = 6.40 Hz, 3H). |
| 477 | 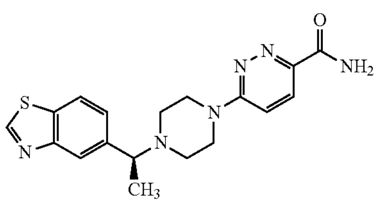 [SMILES: C[C@@H](c1ccc2scnc2c1)N1CCN(c2ccc(C(N)=O)nn2)CC1] | S-enantiomer | ¹H NMR (400 MHz, DMSO-d$_6$): δ 9.39 (s, 1H), 8.14-8.12 (m, 2H), 8.04 (s, 1H), 7.81 (d, J = 9.6 Hz, 1H), 7.52-7.50 (m, 2H), 7.28 (d, J = 9.6 Hz, 1H), 3.70-3.3.68 (m, 5H), 2.51-2.50 (m, 4H), 1.41 (d, J = 6.8 Hz, 3H). |
| 478 | 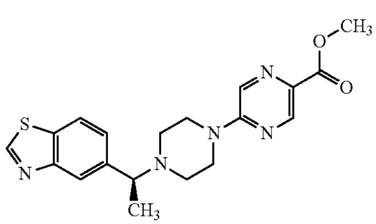 [SMILES: COC(=O)c1cnc(N2CCN([C@@H](C)c3ccc4scnc4c3)CC2)cn1] | S-enantiomer | ¹H NMR (400 MHz, DMSO-d$_6$): δ 9.38 (s, 1H), 8.62 (s, 1H), 8.32 (s, 1H), 8.12 (d, J = 8.0 Hz, 1H), 8.03 (s, 1H), 8.51 (d, J = 8.0 Hz, 1H), 3.80 (s, 3H), 3.73-3.3.68 (m, 5H), 2.57-2.43 (m, 4H), 1.41 (d, J = 6.8 Hz, 3H). |

Example B01: Human O-GlcNAcase enzyme inhibition assay

5 μl of the appropriate concentration of a solution of inhibitor in McIlvaine's Buffer (pH 6.5) in 2% DMSO (for a dose response curve calculation) is added into each well of a 384-well plate (Greiner, 781900). Then, 20 nM of His-Tagged hOGA and 10 μM of FL-GlcNAc (Fluorescein mono-beta-D-(2-deoxy-2-N-acetyl) glucopyranoside; Marker Gene Technologies Inc, M1485) were added to the 384-well plate for a final volume of 20 μl. After incubation for 60 min at room temperature, the reaction was terminated by the addition of 10 μL of stop buffer (200 mM glycine, pH 10.75). The level of fluorescence ($\lambda_{exc}$ 485 nm; $\lambda_{emm}$ 520 nm) was read on a PHERAstar machine. The amount of fluorescence measured was plotted against the concentration of inhibitor to produce a sigmoidal dose response curve to calculate an $IC_{50}$. All individual data was corrected by subtraction of the background (Thiamet 3 uM=100% inhibition) whilst 0.5% DMSO was considered as the control value (no inhibition).

Example B02: Pharmacodynamic Model: Total Protein O-GlcNAcylation Immunoassay (RL2 mAb, Meso Scale Electrochemiluminescence (ECL) Assay)

The test compound was administered orally to C57BL/6J mice. At defined time intervals after compound administration, typically a time ranging between 2 and 48 hours, preferably between 4 and 24 hours, mice were sacrificed by decapitation for blood collection and forebrain dissection. Right brain hemispheres were placed in 2 ml Precellys tubes, snap frozen in dry ice and stored at −80° C. Left hemispheres were placed in 2 ml Eppendorf tubes, snap frozen in dry ice and stored at −80° C. until further processing. Blood samples were collected in Sarstedt tubes containing 35 IU of Heparin and kept at 4° C. After centrifugation for 10 min at 3800×g, 4° C., 50 μL of plasma from each sample was transferred to a 1.5 ml Eppendorf tube and stored at −80° C.

For the preparation of soluble brain protein for the immunoassay the hemispheres were homogenized in ice-cold Cytobuster reagent (71009—Merck Millipore) buffer with protease inhibitor cocktail. After centrifugation for 15 min at 17000×g at 4° C. the supernatants were transferred into polycarbonate tubes (1 ml). The supernatants were cleared by centrifugation for 1 h. at 100000×g, 4° C., and the protein concentrations were determined by using the BCA kit (23227—Pierce, Rockford, Ill.) according to the manufacturer's instructions.

Total protein O-GlcNAcylation immunoassay:

Samples were randomised and 120 μg/ml (25 μl/well) of soluble brain protein was directly coated on a Multi-array 96-well high bind plate (L15XB-3 High bind—Meso Scale Discovery) overnight at 4° C. After washing (3× with PBS-T buffer), the plate was blocked with MSD blocker A solution for 1 h. at room temperature (RT) under agitation. After washing (3× with PBS-T buffer), the plate was incubated with 0.1 μg/ml of a mouse monoclonal antibody directed against O-GlcNAc moieties (RL2; MA1-072—Thermo Scientific) for 1 h. at RT under agitation. For the ECL assay, after washing (3× with PBS-T buffer), 1 μg/ml of a SULFO-TAG™ labeled anti-mouse secondary antibody (Meso Scale Discovery) was added and the plate was incubated for 1 h. at RT under agitation and protected from light. After washing (3× with PBS-T buffer), 150 μl/well of 1× Read Buffer T was added to the plates before reading on a Sector Imager 6000 (Meso Scale Discovery).

Example B03: Pharmaceutical Preparations (A) Injection vials: A solution of 100 g of an active ingredient according to the invention and 5 g of disodium hydrogen phosphate in 3 l of bi-distilled water was adjusted to pH 6.5 using 2 N hydrochloric acid, sterile filtered, transferred into injection vials, lyophilized under sterile conditions and sealed under sterile conditions. Each injection vial contained 5 mg of active ingredient.

(B) Suppositories: A mixture of 20 g of an active ingredient according to the invention was melted with 100 g of soy lecithin and 1400 g of cocoa butter, poured into moulds and allowed to cool. Each suppository contained 20 mg of active ingredient.

(C) Solution: A solution was prepared from 1 g of an active ingredient according to the invention, 9.38 g of $NaH_2PO_4.2H_2O$, 28.48 g of $Na_2HPO_4.12H_2O$ and 0.1 g of benzalkonium chloride in 940 ml of bi-distilled water. The pH was adjusted to 6.8, and the solution was made up to 1 l and sterilized by irradiation. This solution could be used in the form of eye drops.

(D) Ointment: 500 mg of an active ingredient according to the invention were mixed with 99.5 g of Vaseline under aseptic conditions.

(E) Tablets: A mixture of 1 kg of an active ingredient according to the invention, 4 kg of lactose, 1.2 kg of potato starch, 0.2 kg of talc and 0.1 kg of magnesium stearate was pressed to give tablets in a conventional manner in such a way that each tablet contained 10 mg of active ingredient.

(F) Coated tablets: Tablets were pressed analogously to EXAMPLE E and subsequently coated in a conventional manner with a coating of sucrose, potato starch, talc, tragacanth and dye.

(G) Capsules: 2 kg of an active ingredient according to the invention were introduced into hard gelatin capsules in a conventional manner in such a way that each capsule contained 20 mg of the active ingredient.

(H) Ampoules: A solution of 1 kg of an active ingredient according to the invention in 60 l of bi-distilled water was sterile filtered, transferred into ampoules, lyophilized under sterile conditions and sealed under sterile conditions. Each ampoule contained 10 mg of active ingredient.

(I) Inhalation spray: 14 g of an active ingredient according to the invention were dissolved in 10 l of isotonic NaCl solution, and the solution was transferred into commercially available spray containers with a pump mechanism. The solution could be sprayed into the mouth or nose. One spray shot (about 0.1 ml) corresponded to a dose of about 0.14 mg.

The invention claimed is:

1. A compound of formula (I)

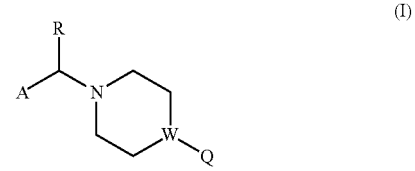

wherein

R is straight chain or branched alkyl having 1 to 6 carbon atoms, wherein 1 to 5 hydrogen atoms may be replaced by Hal or OH;

W is CH or N;

A is:

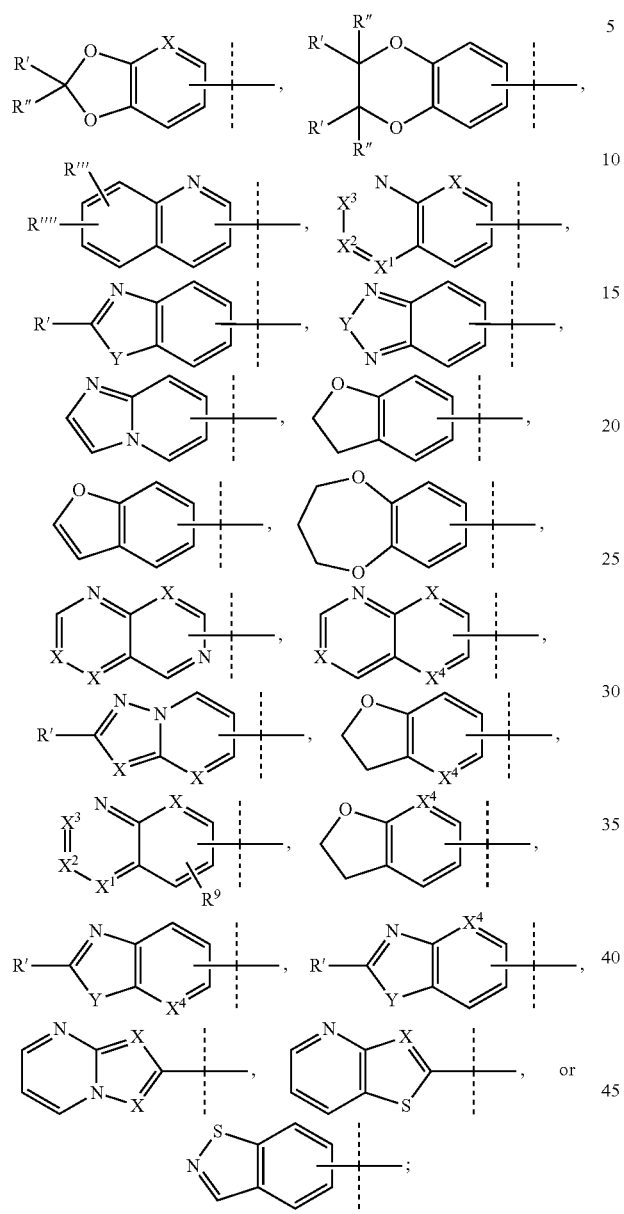

X is N or CR''';
X$^1$, X$^2$ is N or CR''';
X$^3$ is N or CR'''';
X$^4$ is N or CR$^9$;
R$^9$ is Hal, NR$^3$R$^4$, CHR$^3$R$^4$, OR$^3$, CN, or straight chain or branched alkyl having 1 to 12 carbon atoms, wherein 1 to 3 CH$_2$-groups may be replaced by a group selected from O, NR$_3$, S, SO, SO$_2$, S(O)(NH), CO, COO, OCO, CONR$^3$, and NR$^3$CO; and wherein 1 to 5 hydrogen atoms may be replaced by Hal, NR$^3$R$^4$ or NO$_2$;
Y is O, S, SO, or SO$_2$;
R', R'' are, independently, H, Hal, or straight chain or branched alkyl having 1 to 12 carbon atoms;
R''', R'''' are, independently, H, Hal, NR$^3$R$^4$, CHR$^3$R$^4$, OR$^3$, CN, or straight chain or branched alkyl having 1 to 12 carbon atoms, wherein 1 to 3 CH$_2$-groups may be replaced by a group selected from O, NR$_3$, S, SO, SO$_2$, S(O)(NH), CO, COO, OCO, CONR$^3$, and NR$^3$CO; and wherein 1 to 5 hydrogen atoms may be replaced by Hal, NR$^3$R$^4$, or NO$_2$;
R''''' is H, Hal, NR$^3$R$^4$, CHR$^3$R$^4$, CN, or straight chain or branched alkyl having 1 to 12 carbon atoms, wherein 1 to 3 CH$_2$-groups may be replaced by a group selected from O, NR$_3$, S, SO, SO$_2$, S(O)(NH), CO, COO, OCO, CONR$^3$, and NR$^3$CO; and wherein 1 to 5 hydrogen atoms may be replaced by Hal, NR$^3$R$^4$, or NO$_2$;
R$^3$, R$^4$ are, independently, H or a straight chain or branched alkyl group having 1 to 12 carbon atoms;

Q is:

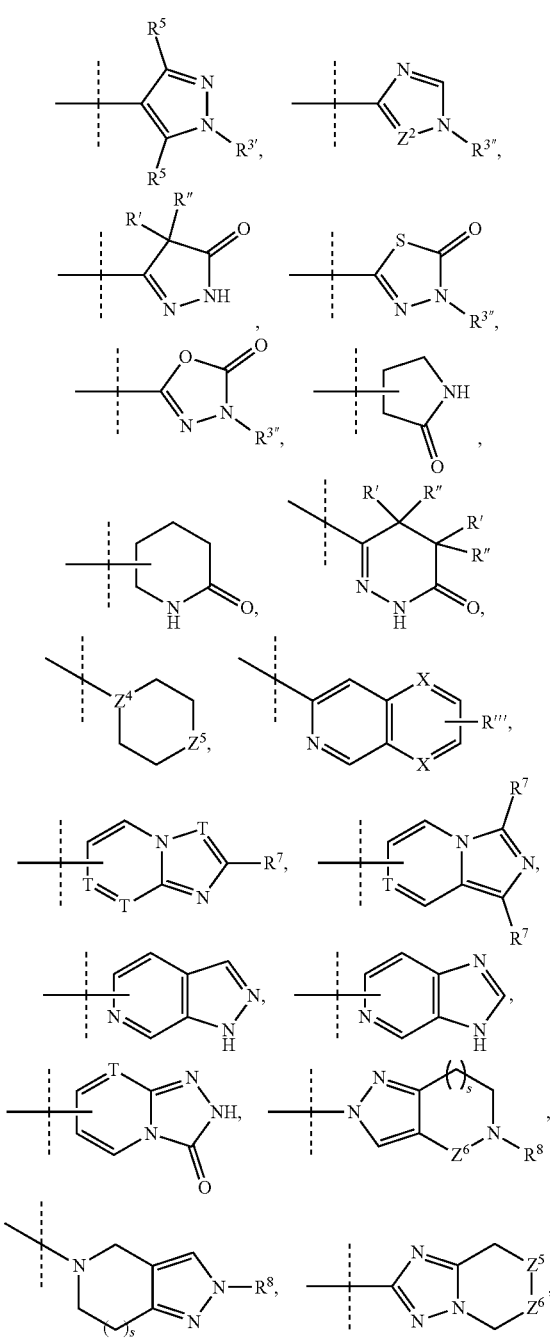

-continued

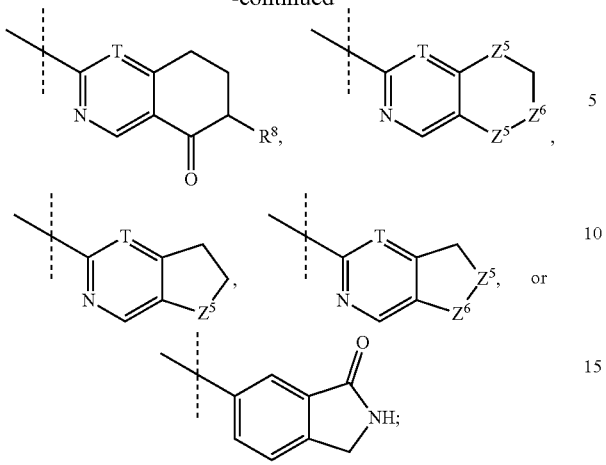

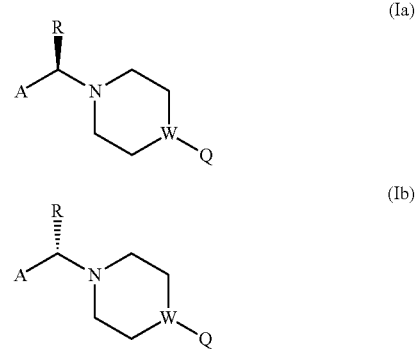

$Z^2$ is $CR^5$, $CR^6$, or N;
$Z^4$ is N, CH, CON, or COCH;
$Z^5$ is S, O, $NR^8$, $SO_2$, or $CHR^5$;
$Z^6$ is $CH_2$ or CO;
s is 0 or 1;
T is N, CH, or $CR^7$;
$R^{3'}$ is H or a straight chain or branched alkyl group having 1 to 12 carbon atoms, wherein 1 to 3 $CH_2$-groups may be replaced by a group selected from $SO_2$, CO, and O; and wherein 1 to 5 hydrogen atoms may be replaced by Hal;
$R^{3''}$ is a straight chain or branched alkyl group having 1 to 12 carbon atoms, wherein 1 to 3 $CH_2$-groups are replaced by a group selected from $SO_2$, CO, and O; and wherein 1 to 5 hydrogen atoms may be replaced by Hal;
$R^5$, $R^6$, $R^7$ are, independently, H, Hal, $NR^3R^4$, $NO_2$, Ar, Het, Cyc, straight chain or branched alkyl having 1 to 12 carbon atoms, wherein 1 to 3 $CH_2$-groups may be replaced by a group selected from O, $NR_3$, S, SO, $SO_2$, S(O)(NH), CO, COO, OCO, $CONR^3$, and $NR^3CO$; and wherein 1 to 5 hydrogen atoms may be replaced by Hal, $NR^3R^4$, $NO_2$, $OR^3$, Het, Ar, or Cyc;
$R^8$ is H, methyl, or straight chain or branched alkyl having 2 to 12 carbon atoms, wherein 1 to 3 $CH_2$-groups may be replaced by a group selected from O, $NR^3$, S, SO, $SO_2$, CO, COO, OCO, $CONR^3$, and $NR^3CO$; and wherein 1 to 5 hydrogen atoms may be replaced by Hal, $NR^3R^4$, or $NO_2$;
Hal is F, Cl, Br, or I;
Het is a saturated, unsaturated, or aromatic ring, being monocyclic or bicyclic or fused-bicyclic and having 3- to 8- members and containing 1 to 4 heteroatoms selected from N, O, and S, which may be substituted by 1 to 3 substituents selected from $R^5$, Hal, and $OR^3$;
Ar is a 6-membered carbocyclic aromatic ring or a fused or non-fused bicyclic aromatic ring system, which is optionally substituted by 1 to 3 substituents independently selected from $R^5$, $OR^3$, and Hal;
Cyc is a saturated or an unsaturated carbocyclic ring having from 3 to 8 carbon atoms which is optionally substituted by 1 to 3 substituents independently selected from $R^5$, Hal, and OH;
or a solvate, salt, tautomer, enantiomer, racemate, stereoisomer, or any mixture thereof in any ratio.

2. A compound of formula Ia or Ib:

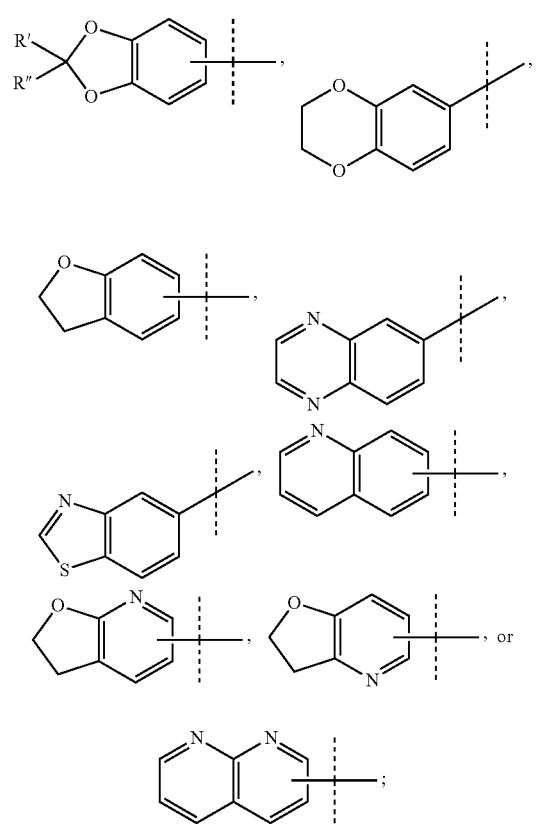

wherein A, R, W, and Q have the meaning given in claim 1.

3. A mixture comprising compounds Ia and Ib according to claim 2, in equal or unequal amounts, wherein:
the A groups in (Ia) and (Ib) are identical; the R groups in (Ia) and (Ib) are identical; the W groups in (Ia) and (Ib) are identical; and the Q groups in (Ia) and (Ib) are identical.

4. The compound according to claim 1, wherein R is methyl and/or W is N.

5. The compound according to claim 1, wherein A is:

wherein R' and R" have the meaning given in claim 1.

6. The compound according to claim 1, wherein Q is:

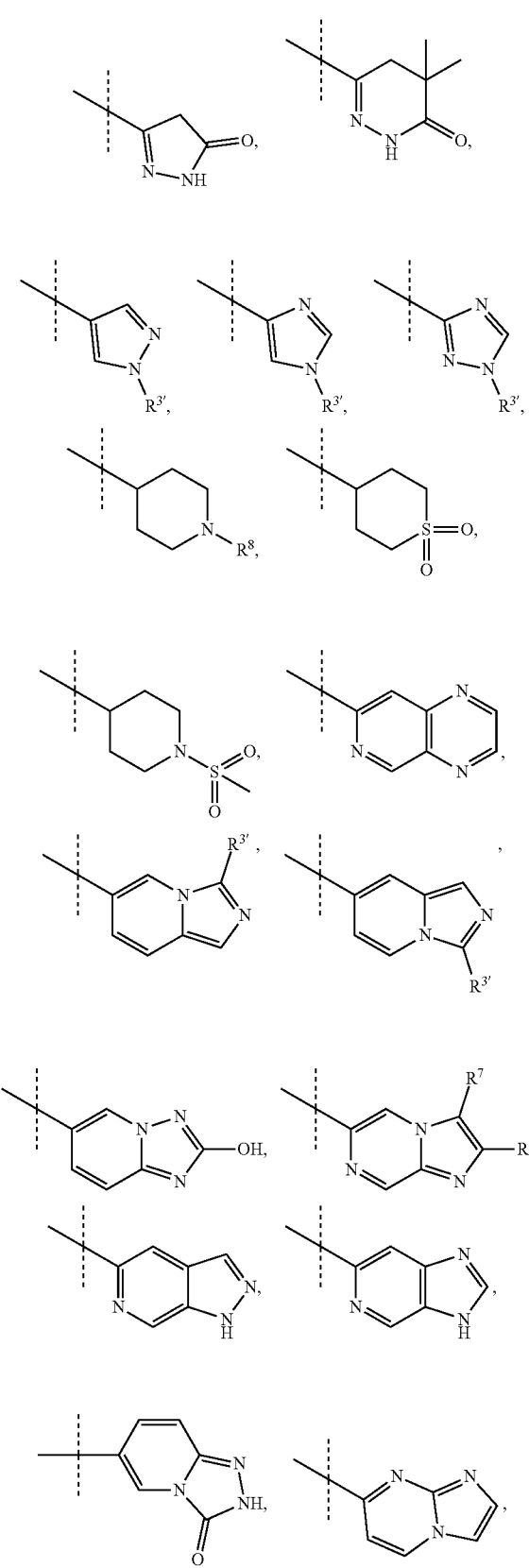
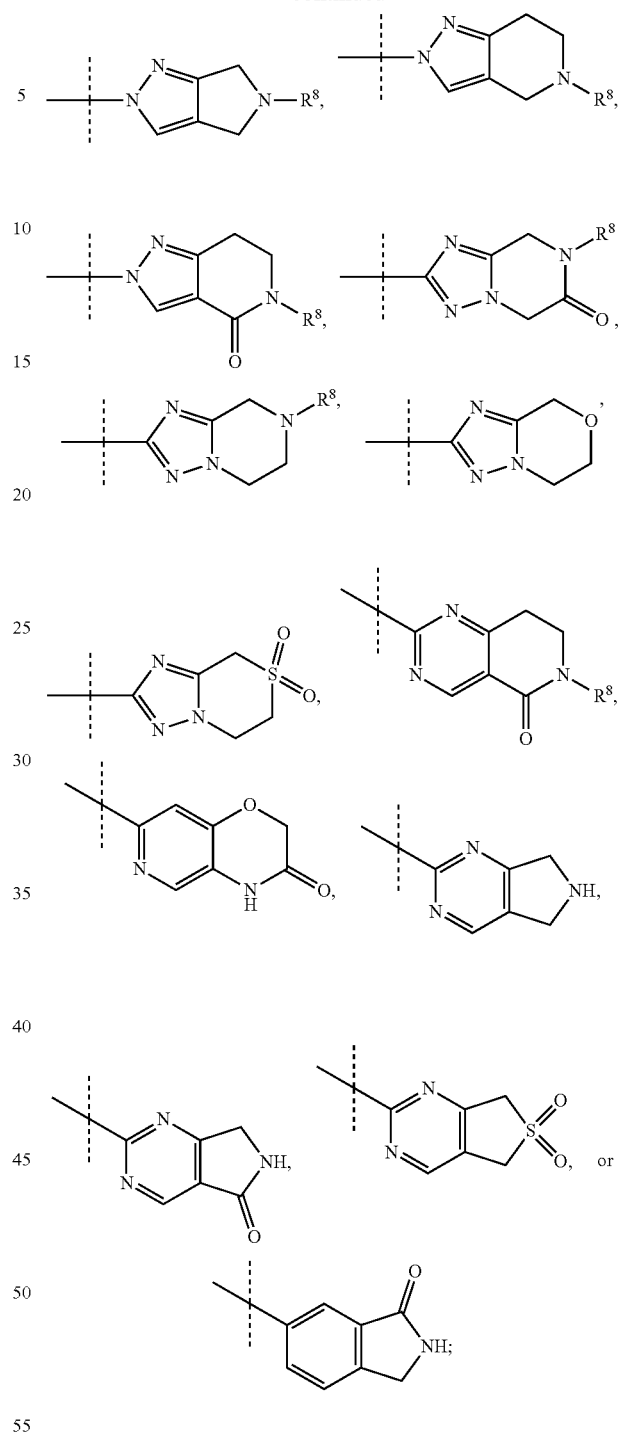

wherein $R^{3'}$, $R^7$ and $R^8$ have the meaning given in claim 1.

7. The compound according to claim 1, wherein $R^5$, $R^6$, and $R^7$ are, independently H, Hal, $NR_3R_4$, $NH_2$, $N(CH_3)_2$, phenyl, 2-, 3- or 4-hydroxy or methoxyphenyl, alkyl, $CF_3$, alkoxy, hydroxyalkylene, alkoxyalkylene, COOH, COOalkyl, CONHalkyl, $CONH_2$, $CON(CH_3)_2$, NHCOalkyl, NHalkyl, CO—N-morpholinyl, $CON(CH_3)CH_2CH_2N(CH_3)_2$, CO-1-piperidinyl, CO-4-hydroxy-1-piperidinyl, CO-1-piperazinyl, CO-4-methyl-1-piperazinyl, $CH_2$—N-morpholinyl, $CH_2N(H)COCH_3$, $CH_2N(CH_3)COCH_3$, substituted Cyc or Het, or unsubstituted Cyc or Het.

8. The compound according to claim 1, wherein the compound is selected from the group consisting of:

| No | Structure | Configuration specification |
|---|---|---|
| 1 | 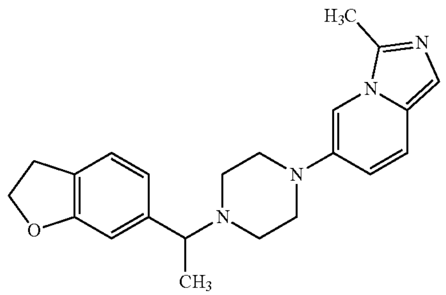 [SMILES: Cc1ncc2ccc(N3CCN(C(C)c4ccc5c(c4)OCC5)CC3)cn12] | racemic |
| 2 | 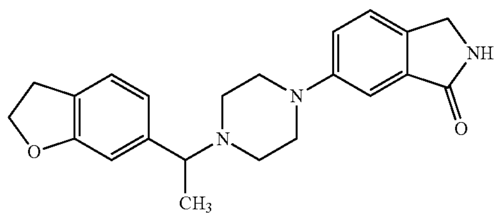 [SMILES: CC(c1ccc2c(c1)OCC2)N1CCN(c2ccc3c(c2)C(=O)NC3)CC1] | racemic |
| 3 | 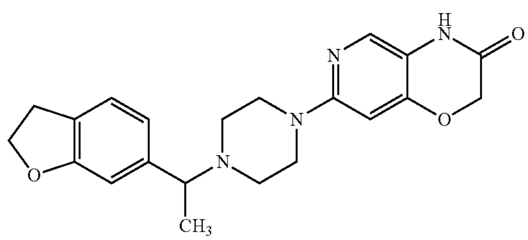 [SMILES: CC(c1ccc2c(c1)OCC2)N1CCN(c2cc3c(cn2)NC(=O)CO3)CC1] | racemic |
| 4 | 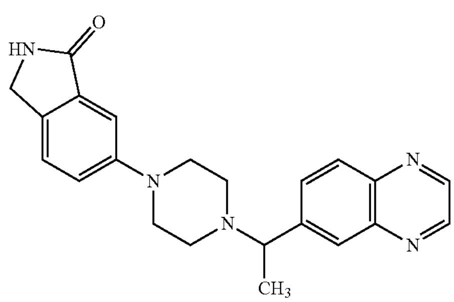 | racemic |
| 135 | 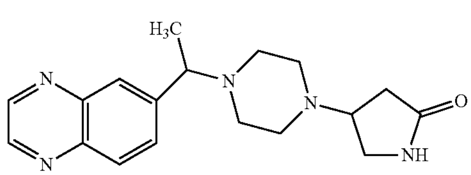 [SMILES: CC(c1ccc2nccnc2c1)N1CCN(C2CNC(=O)C2)CC1] | |
| 136 | 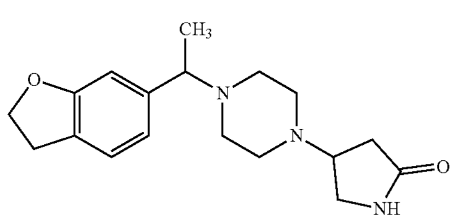 [SMILES: CC(c1ccc2c(c1)OCC2)N1CCN(C2CNC(=O)C2)CC1] | |

| No | Structure | Configuration specification |
|---|---|---|
| 137 | 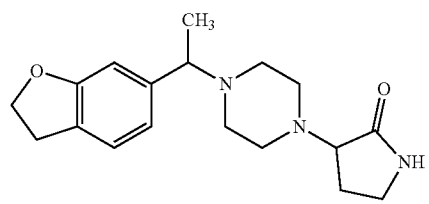 [SMILES: CC(c1ccc2c(c1)OCC2)N1CCN(C2CCNC2=O)CC1] | |
| 138 | 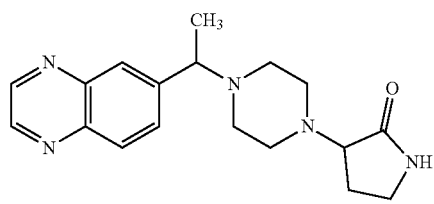 [SMILES: CC(c1ccc2nccnc2c1)N1CCN(C2CCNC2=O)CC1] | |
| 139 | 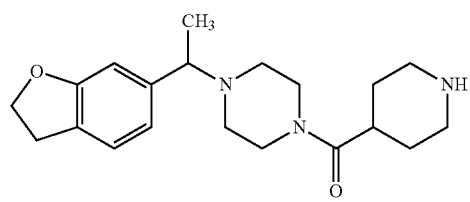 [SMILES: CC(c1ccc2c(c1)OCC2)N1CCN(C(=O)C2CCNCC2)CC1] | |
| 140 | 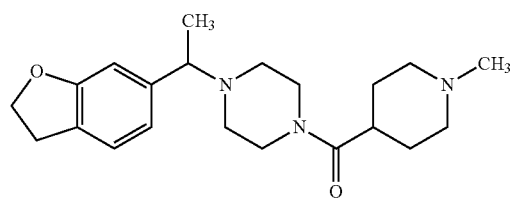 | |
| 141 | 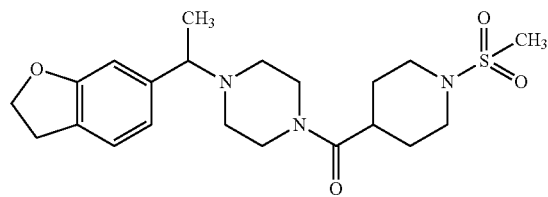 | |
| 142 | 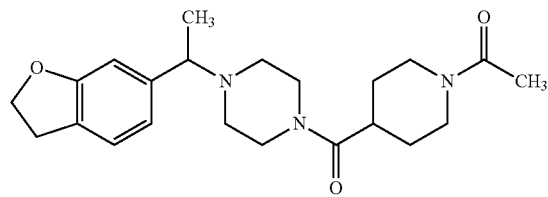 | |
| 143 | 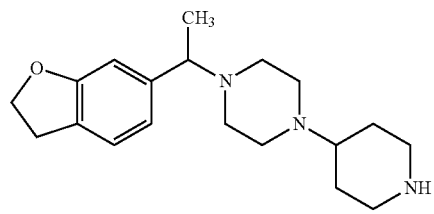 | |

| No | Structure | Configuration specification |
|---|---|---|
| 144 | 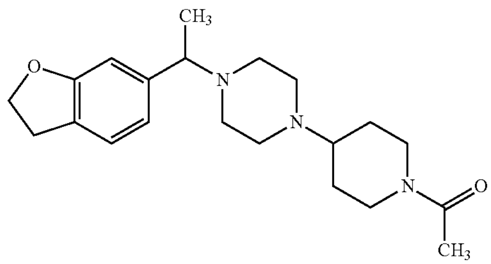 [SMILES: CC(=O)N1CCC(N2CCN(C(C)c3ccc4c(c3)OCC4)CC2)CC1] | |
| 145 | 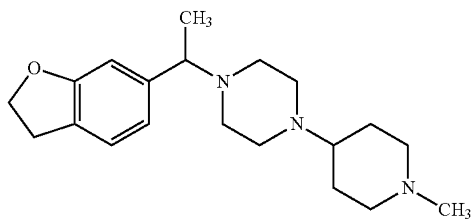 [SMILES: CC(c1ccc2c(c1)OCC2)N1CCN(C2CCN(C)CC2)CC1] | |
| 146 | 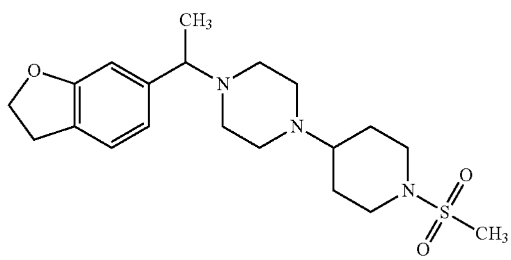 [SMILES: CC(c1ccc2c(c1)OCC2)N1CCN(C2CCN(S(C)(=O)=O)CC2)CC1] | |
| 147 | 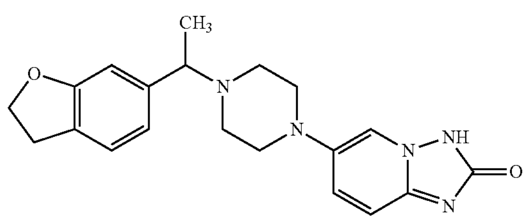 [SMILES: CC(c1ccc2c(c1)OCC2)N1CCN(c2ccc3nc(=O)[nH]n3c2)CC1] | |
| 148 | 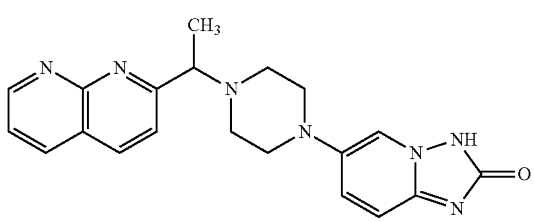 [SMILES: CC(c1ccc2cccnc2n1)N1CCN(c2ccc3nc(=O)[nH]n3c2)CC1] | |
| 149 | 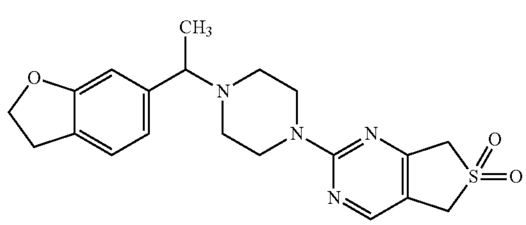 | |

-continued

| No | Structure | Configuration specification |
|---|---|---|
| 150 | 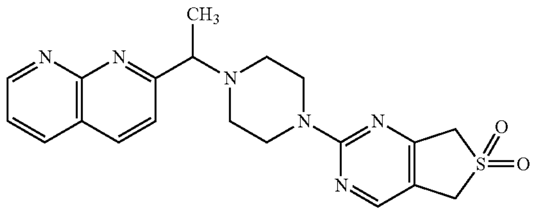 [SMILES: CC(c1ccc2cccnc2n1)N1CCN(c2ncc3c(n2)CS(=O)(=O)C3)CC1] | |
| 151 | 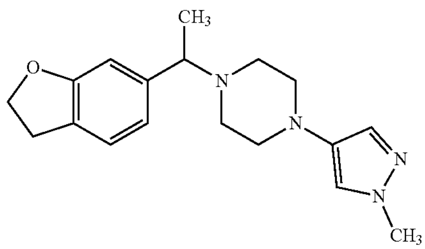 [SMILES: CC(c1ccc2c(c1)OCC2)N1CCN(c2cnn(C)c2)CC1] | |
| 152 | 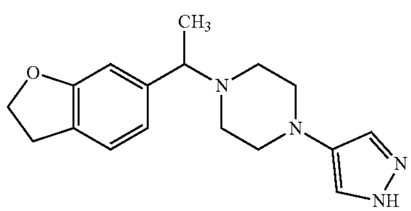 [SMILES: CC(c1ccc2c(c1)OCC2)N1CCN(c2cn[nH]c2)CC1] | |
| 153 | 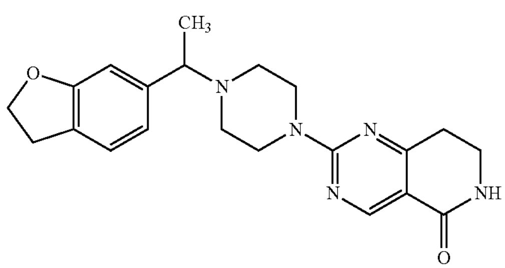 | |
| 154 | 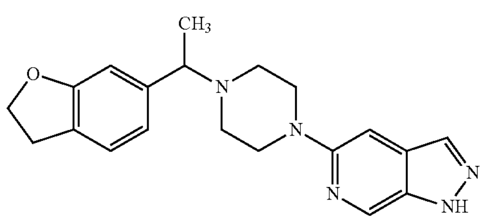 [SMILES: CC(c1ccc2c(c1)OCC2)N1CCN(c2cc3cn[nH]c3cn2)CC1] | |
| 155 | 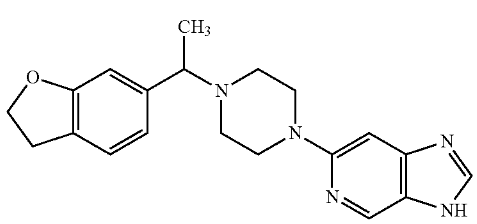 [SMILES: CC(c1ccc2c(c1)OCC2)N1CCN(c2cc3nc[nH]c3cn2)CC1] | |

-continued

| No | Structure | Configuration specification |
|---|---|---|
| 156 | 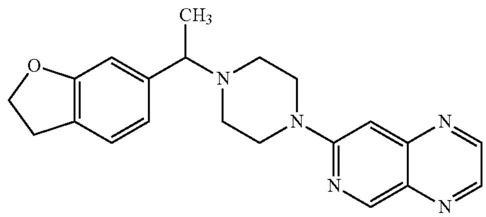 [SMILES: CC(c1ccc2c(c1)OCC2)N1CCN(c2cc3nccnc3cn2)CC1] | |
| 157 | 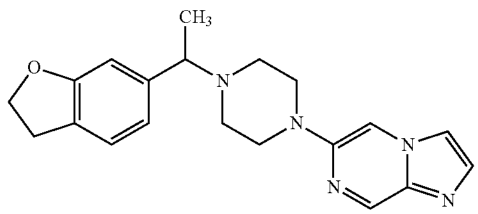 [SMILES: CC(c1ccc2c(c1)OCC2)N1CCN(c2cn3ccnc3cn2)CC1] | |
| 158 | 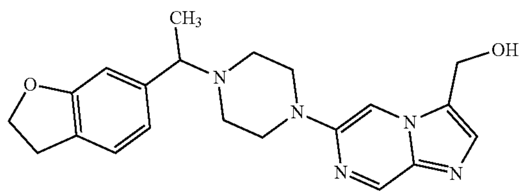 [SMILES: CC(c1ccc2c(c1)OCC2)N1CCN(c2cn3c(CO)cnc3cn2)CC1] | |
| 159 | 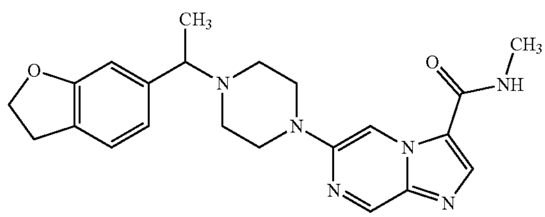 [SMILES: CNC(=O)c1cnc2cnc(N3CCN(C(C)c4ccc5c(c4)OCC5)CC3)cn12] | |
| 160 | 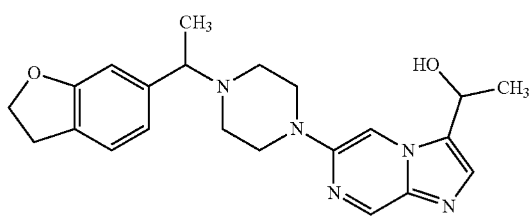 | |
| 161 | 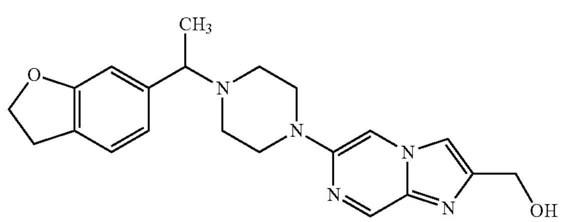 | |
| 162 | 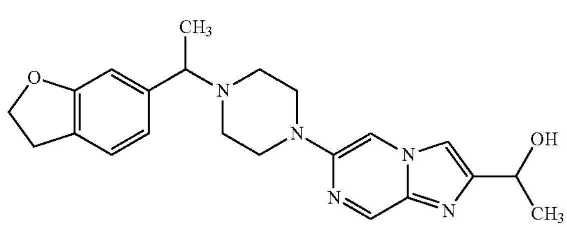 [SMILES: CC(O)c1cn2cc(N3CCN(C(C)c4ccc5c(c4)OCC5)CC3)ncc2n1] | |

-continued

| No | Structure | Configuration specification |
|---|---|---|
| 163 | 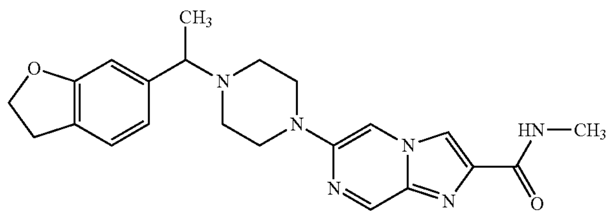 | |
| 164 | 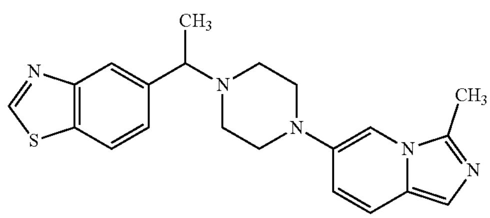 | |
| 165 | 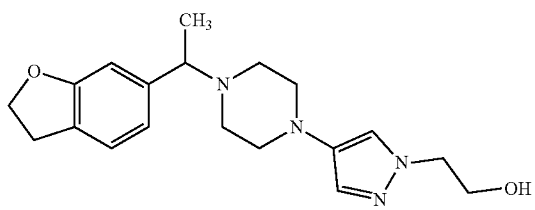 [SMILES: CC(c1ccc2c(c1)OCC2)N1CCN(c2cnn(CCO)c2)CC1] | |
| 166 | 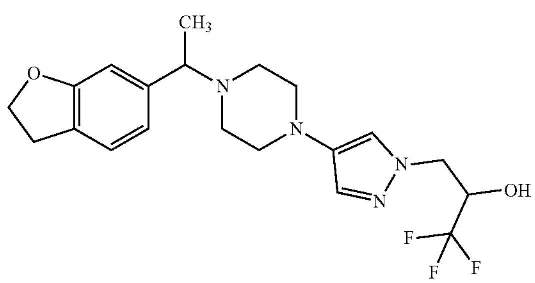 [SMILES: CC(c1ccc2c(c1)OCC2)N1CCN(c2cnn(CC(O)C(F)(F)F)c2)CC1] | |
| 167 | 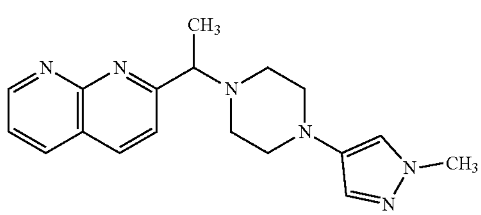 [SMILES: CC(c1ccc2cccnc2n1)N1CCN(c2cnn(C)c2)CC1] | |
| 168 | 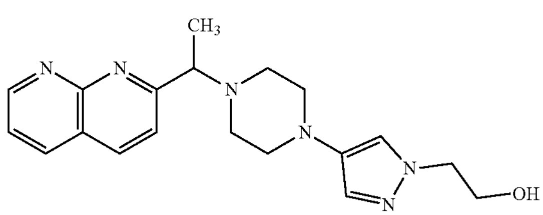 [SMILES: CC(c1ccc2cccnc2n1)N1CCN(c2cnn(CCO)c2)CC1] | |

-continued
| No | Structure | Configuration specification |
|---|---|---|
| 169 | 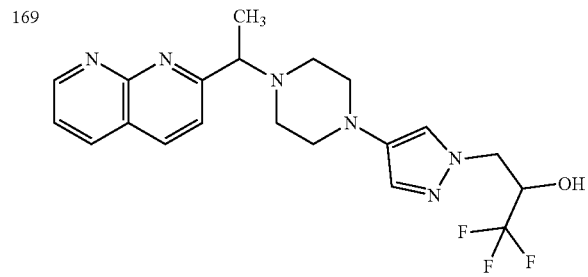 | |
| 170 | 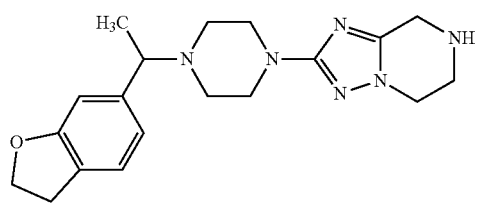 [SMILES: CC(c1ccc2c(c1)OCC2)N1CCN(c2nc3n(n2)CCNC3)CC1] | |
| 171 | 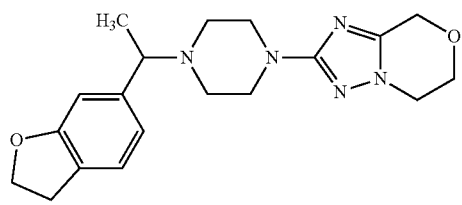 [SMILES: CC(c1ccc2c(c1)OCC2)N1CCN(c2nc3n(n2)CCOC3)CC1] | |
| 172 | 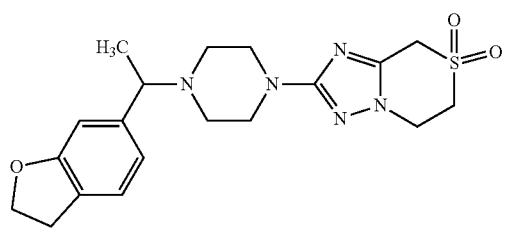 | |
| 173 | 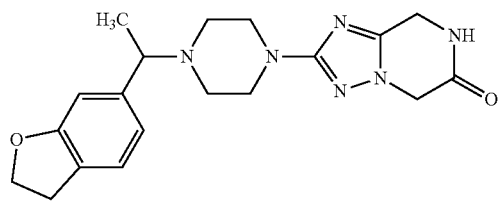 [SMILES: CC(c1ccc2c(c1)OCC2)N1CCN(c2nc3n(n2)CC(=O)NC3)CC1] | |
| 174 | 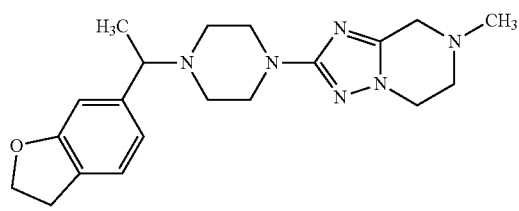 [SMILES: CC(c1ccc2c(c1)OCC2)N1CCN(c2nc3n(n2)CCN(C)C3)CC1] | |

| No | Structure | Configuration specification |
|---|---|---|
| 175 | 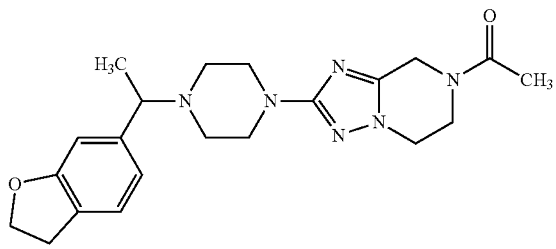 | |
| 176 | 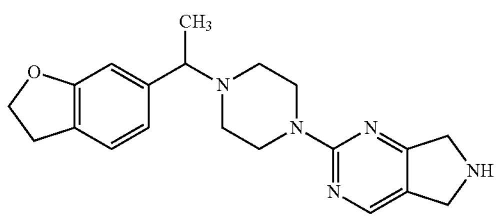 | |
| 177 | 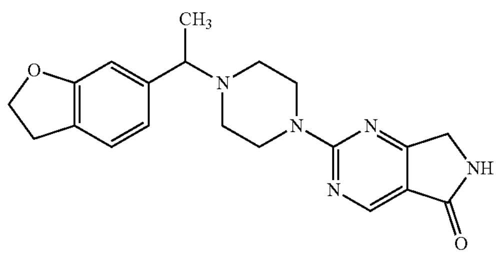 | |
| 178 | 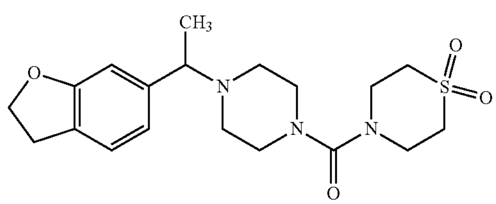 [SMILES: CC(c1ccc2c(c1)OCC2)N1CCN(C(=O)N2CCS(=O)(=O)CC2)CC1] | |
| 179 | 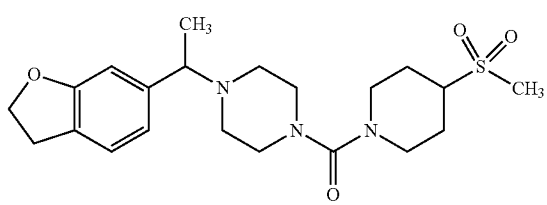 [SMILES: CC(c1ccc2c(c1)OCC2)N1CCN(C(=O)N2CCC(S(C)(=O)=O)CC2)CC1] | |
| 180 | 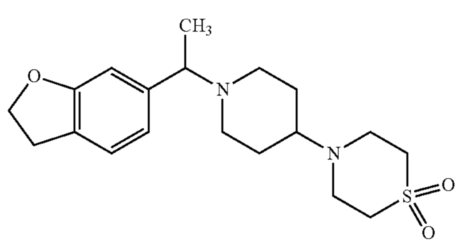 | |

-continued

| No | Structure | Configuration specification |
|---|---|---|
| 181 | 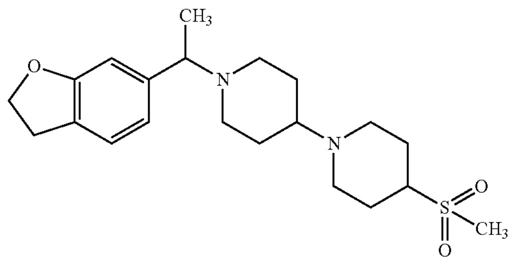 [SMILES: CC(c1ccc2c(c1)OCC2)N1CCC(N2CCC(S(C)(=O)=O)CC2)CC1] | |
| 182 | 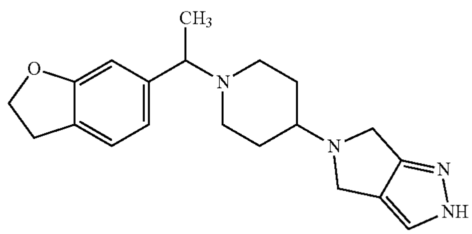 | |
| 183 | 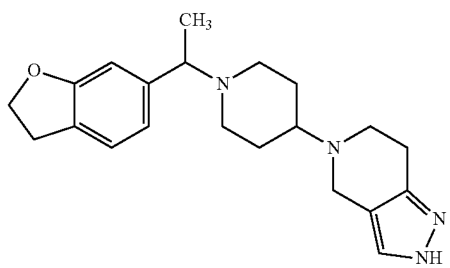 [SMILES: CC(c1ccc2c(c1)OCC2)N1CCC(N2CCc3n[nH]cc3C2)CC1] | |
| 214 | 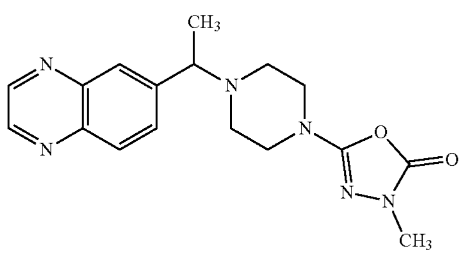 | |
| 215 | 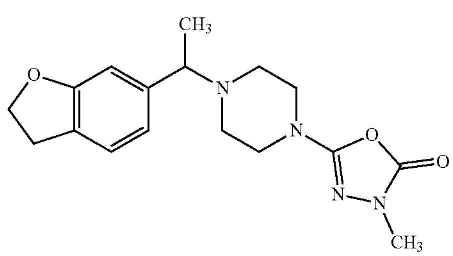 [SMILES: CC(c1ccc2c(c1)OCC2)N1CCN(c2nn(C)c(=O)s2)CC1] | |
| 216 | 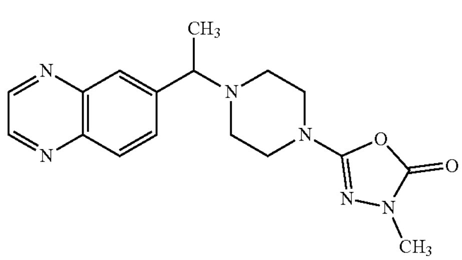 | |

-continued

| No | Structure | Configuration specification |
|---|---|---|
| 217 | 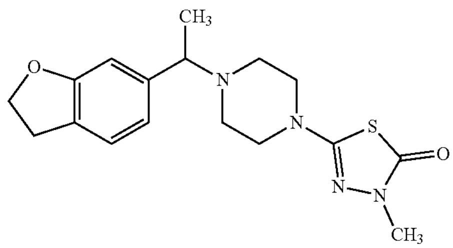 | |
| 231 | 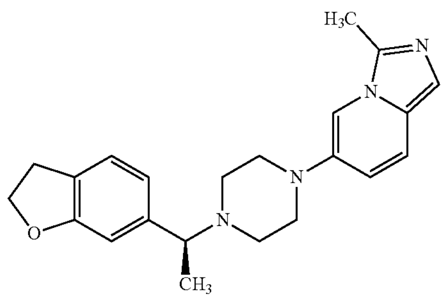 [SMILES: Cc1ncc2ccc(N3CCN([C@@H](C)c4ccc5c(c4)OCC5)CC3)cn12] | S-enantiomer |
| 232 | 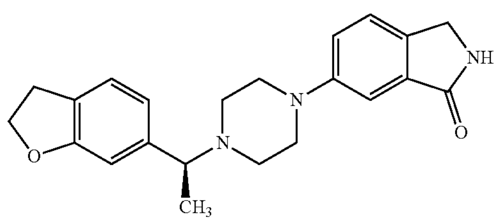 | S-enantiomer |
| 233 | 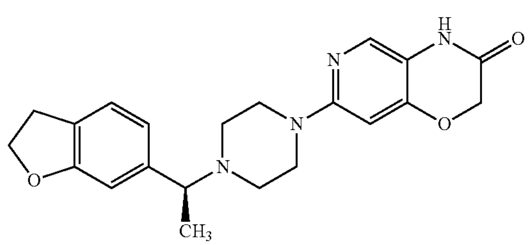 [SMILES: C[C@@H](c1ccc2c(c1)OCC2)N1CCN(c2cc3c(cn2)NC(=O)CO3)CC1] | S-enantiomer |
| 234 | 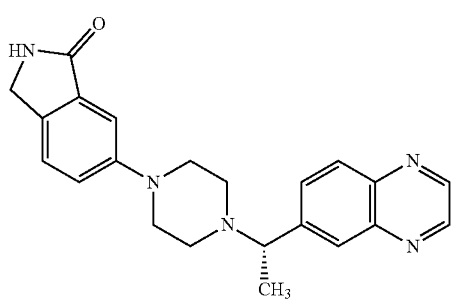 | S-enantiomer |
| 235 | 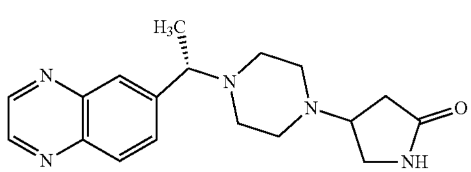 [SMILES: C[C@@H](c1ccc2nccnc2c1)N1CCN(C2CNC(=O)C2)CC1] | S-enantiomer |

-continued

| No | Structure | Configuration specification |
|---|---|---|
| 236 | 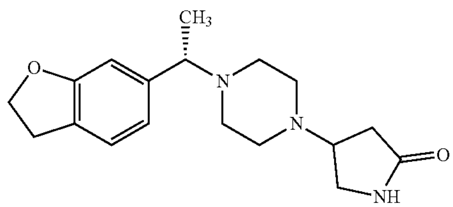 [SMILES: C[C@@H](c1ccc2c(c1)OCC2)N1CCN(C2CNC(=O)C2)CC1] | S-enantiomer |
| 237 | 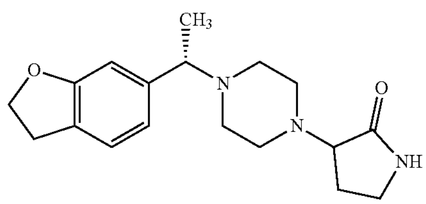 [SMILES: C[C@@H](c1ccc2c(c1)OCC2)N1CCN(C2CCNC2=O)CC1] | S-enantiomer |
| 238 | 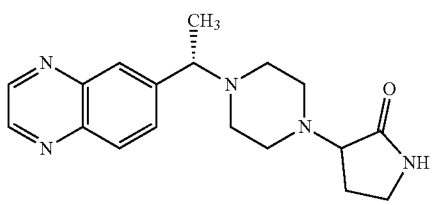 | S-enantiomer |
| 239 | 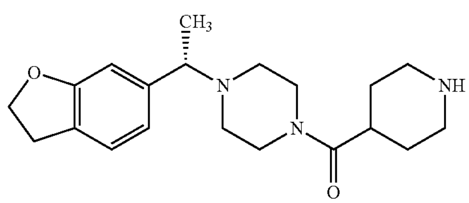 | S-enantiomer |
| 240 | 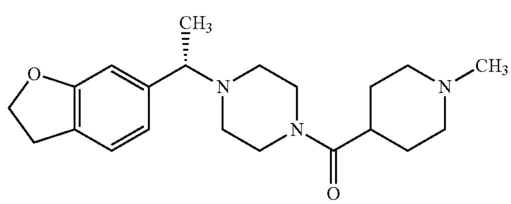 [SMILES: C[C@@H](c1ccc2c(c1)OCC2)N1CCN(C(=O)C2CCN(C)CC2)CC1] | S-enantiomer |
| 241 | 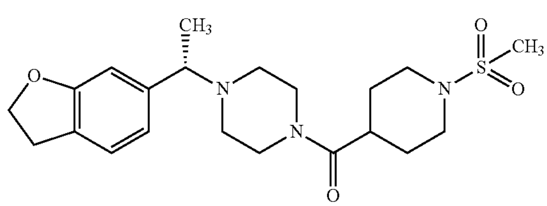 [SMILES: C[C@@H](c1ccc2c(c1)OCC2)N1CCN(C(=O)C2CCN(S(C)(=O)=O)CC2)CC1] | S-enantiomer |
| 242 | 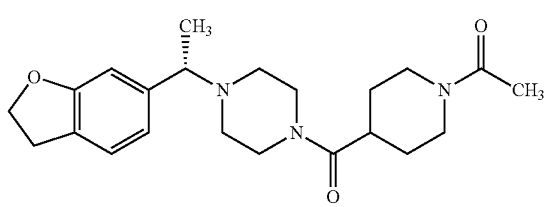 [SMILES: CC(=O)N1CCC(C(=O)N2CCN([C@@H](C)c3ccc4c(c3)OCC4)CC2)CC1] | S-enantiomer |

-continued

| No | Structure | Configuration specification |
|---|---|---|
| 243 | 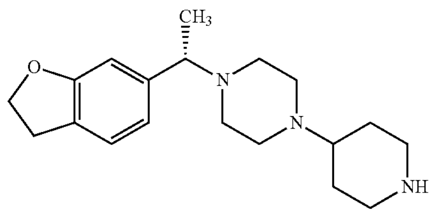 [SMILES: C[C@@H](c1ccc2c(c1)OCC2)N1CCN(C2CCNCC2)CC1] | S-enantiomer |
| 244 | 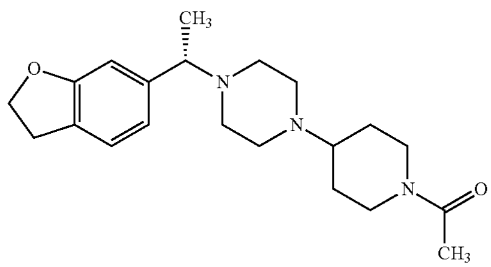 | S-enantiomer |
| 245 | 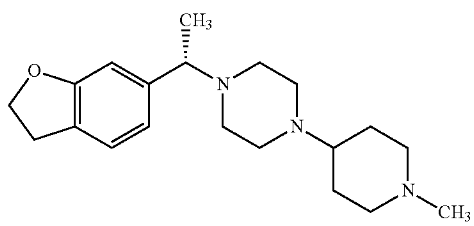 | S-enantiomer |
| 246 | 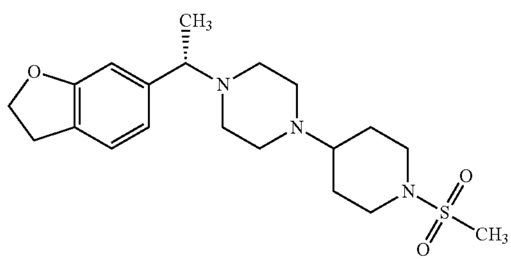 [SMILES: C[C@@H](c1ccc2c(c1)OCC2)N1CCN(C2CCN(S(C)(=O)=O)CC2)CC1] | S-enantiomer |
| 247 | 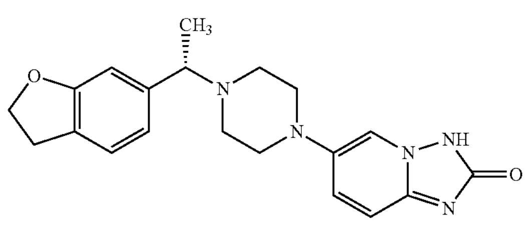 [SMILES: C[C@@H](c1ccc2c(c1)OCC2)N1CCN(c2ccc3nc(=O)[nH]n3c2)CC1] | S-enantiomer |
| 248 | 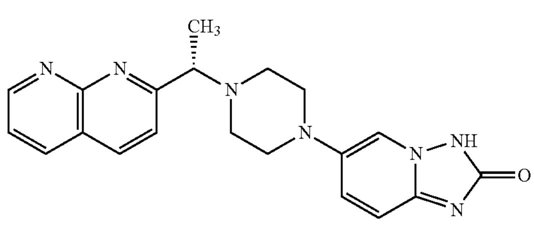 [SMILES: C[C@@H](c1ccc2cccnc2n1)N1CCN(c2ccc3nc(=O)[nH]n3c2)CC1] | S-enantiomer |

-continued

| No | Structure | Configuration specification |
|---|---|---|
| 249 | 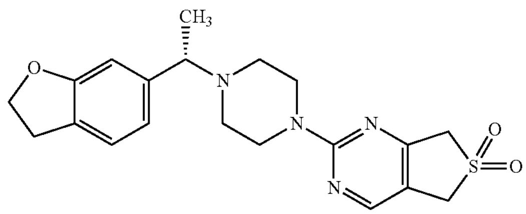 | S-enantiomer |
| 250 | 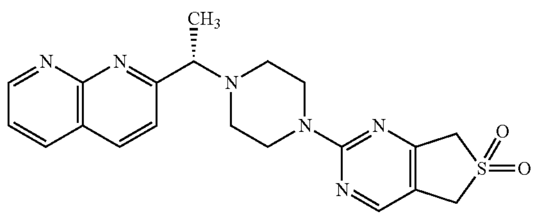 [SMILES: C[C@@H](c1ccc2cccnc2n1)N1CCN(c2ncc3c(n2)CS(=O)(=O)C3)CC1] | S-enantiomer |
| 251 | 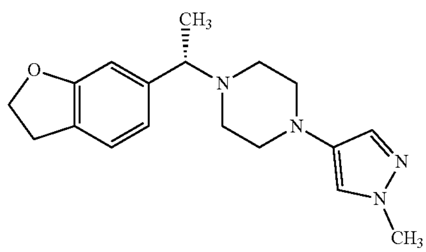 | S-enantiomer |
| 252 | 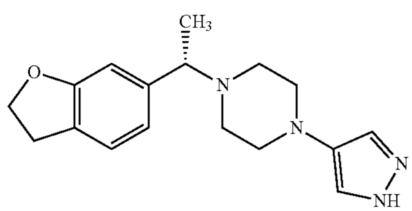 [SMILES: C[C@@H](c1ccc2c(c1)OCC2)N1CCN(c2cn[nH]c2)CC1] | S-enantiomer |
| 253 | 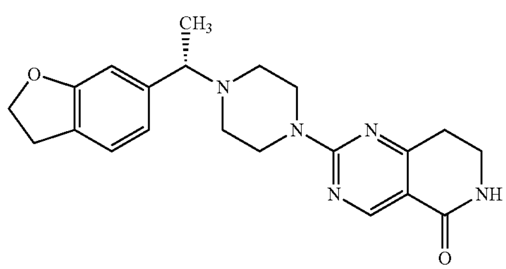 [SMILES: C[C@@H](c1ccc2c(c1)OCC2)N1CCN(c2ncc3c(n2)CCNC3=O)CC1] | S-enantiomer |
| 254 | 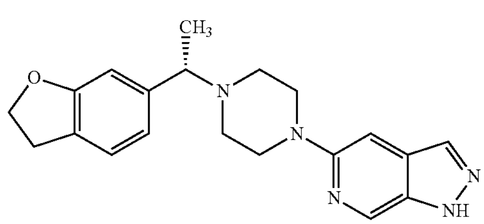 | S-enantiomer |

-continued

| No | Structure | Configuration specification |
|---|---|---|
| 255 | 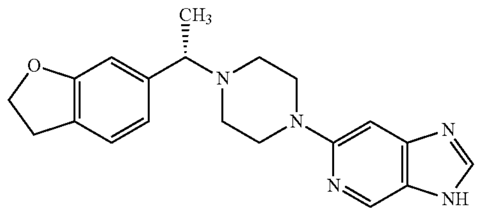 | S-enantiomer |
| 256 | 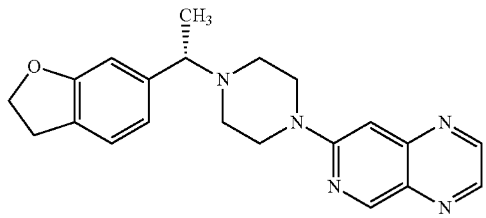 [SMILES: C[C@@H](c1ccc2c(c1)OCC2)N1CCN(c2cc3nccnc3cn2)CC1] | S-enantiomer |
| 257 | 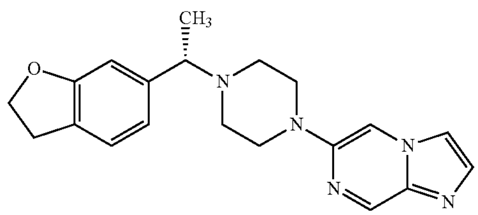 [SMILES: C[C@@H](c1ccc2c(c1)OCC2)N1CCN(c2cn3ccnc3cn2)CC1] | S-enantiomer |
| 258 | 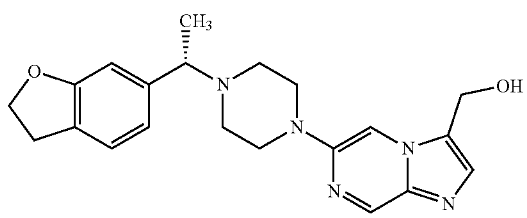 [SMILES: C[C@@H](c1ccc2c(c1)OCC2)N1CCN(c2cn3c(CO)cnc3cn2)CC1] | S-enantiomer |
| 259 | 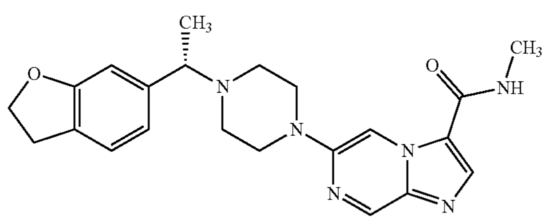 [SMILES: CNC(=O)c1cnc2cnc(N3CCN([C@@H](C)c4ccc5c(c4)OCC5)CC3)cn12] | S-enantiomer |
| 260 | 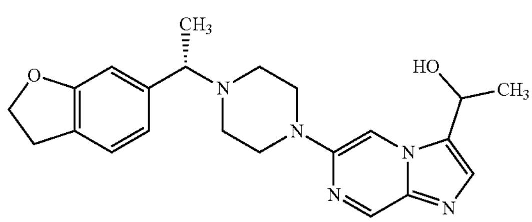 [SMILES: CC(O)c1cnc2cnc(N3CCN([C@@H](C)c4ccc5c(c4)OCC5)CC3)cn12] | S-enantiomer |
| 261 | 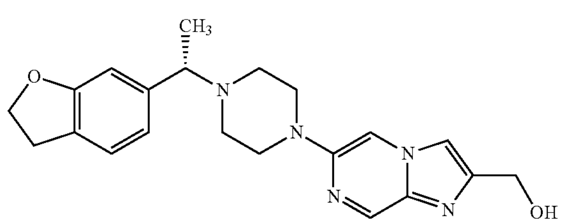 [SMILES: C[C@@H](c1ccc2c(c1)OCC2)N1CCN(c2cn3cc(CO)nc3cn2)CC1] | S-enantiomer |

-continued

| No | Structure | Configuration specification |
|---|---|---|
| 262 | 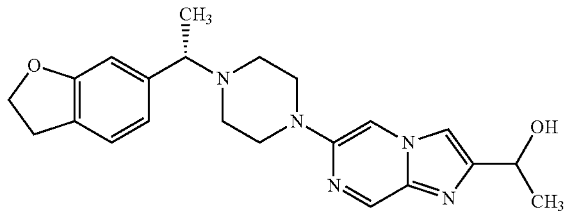 | S-enantiomer |
| 263 | 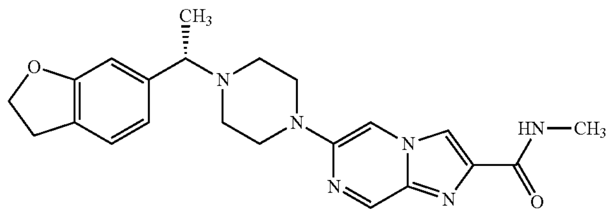 | S-enantiomer |
| 264 | 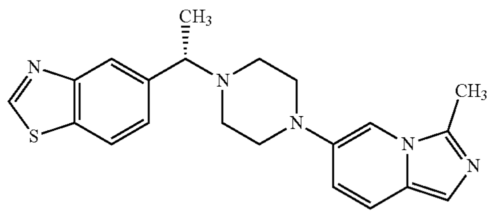 [SMILES: Cc1ncc2ccc(N3CCN([C@@H](C)c4ccc5scnc5c4)CC3)cn12] | S-enantiomer |
| 265 | 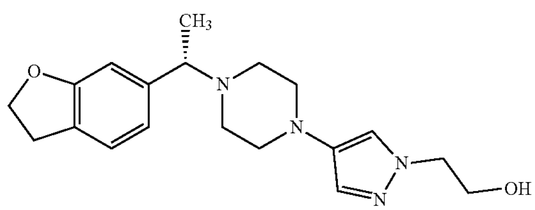 [SMILES: C[C@@H](c1ccc2c(c1)OCC2)N1CCN(c2cnn(CCO)c2)CC1] | S-enantiomer |
| 266 | 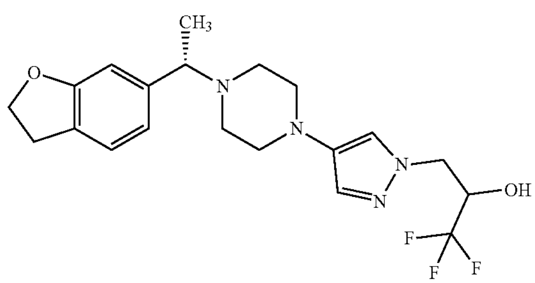 [SMILES: C[C@@H](c1ccc2c(c1)OCC2)N1CCN(c2cnn(CC(O)C(F)(F)F)c2)CC1] | S-enantiomer |
| 267 | 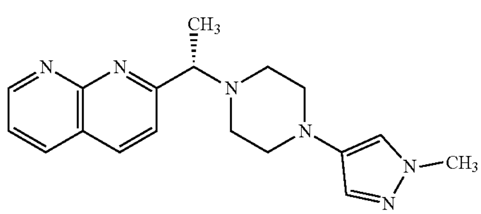 [SMILES: C[C@@H](c1ccc2cccnc2n1)N1CCN(c2cnn(C)c2)CC1] | S-enantiomer |
| 268 | 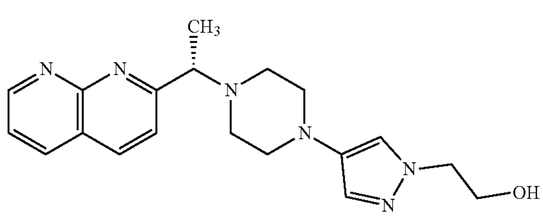 | S-enantiomer |

-continued
| No | Structure | Configuration specification |
|---|---|---|
| 269 | 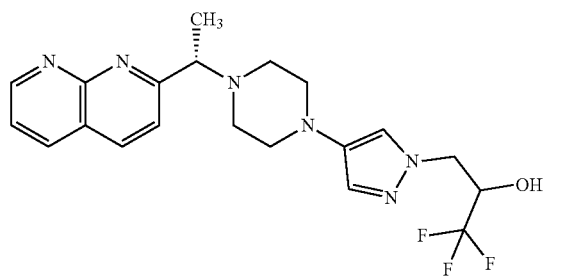 [SMILES: C[C@@H](c1ccc2cccnc2n1)N1CCN(c2cnn(CC(O)C(F)(F)F)c2)CC1] | S-enantiomer |
| 270 | 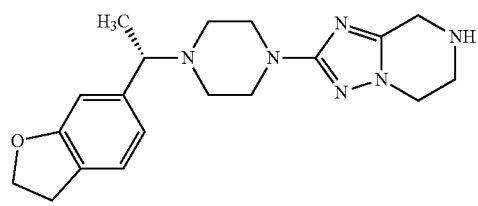 | S-enantiomer |
| 271 | 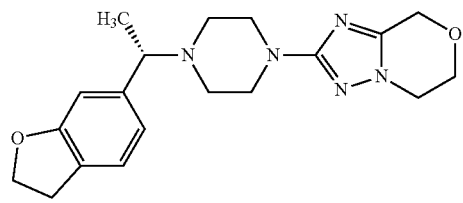 | S-enantiomer |
| 272 | 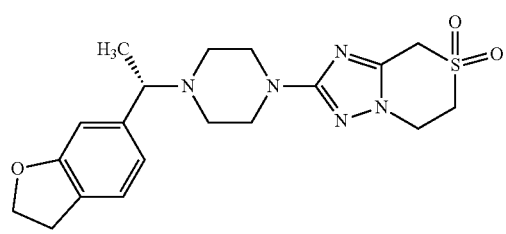 [SMILES: C[C@@H](c1ccc2c(c1)OCC2)N1CCN(c2nc3n(n2)CCS(=O)(=O)C3)CC1] | S-enantiomer |
| 273 | 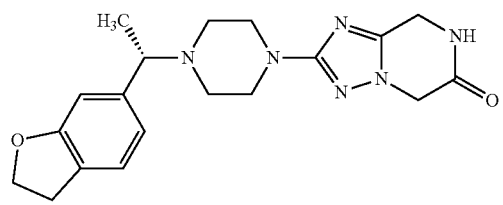 [SMILES: C[C@@H](c1ccc2c(c1)OCC2)N1CCN(c2nc3n(n2)CC(=O)NC3)CC1] | S-enantiomer |
| 274 | 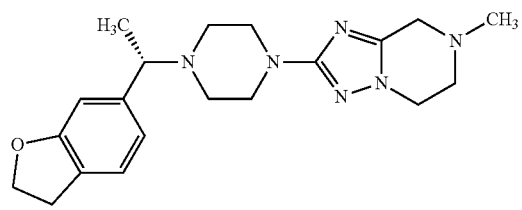 | S-enantiomer |

-continued

| No | Structure | Configuration specification |
|---|---|---|
| 275 | 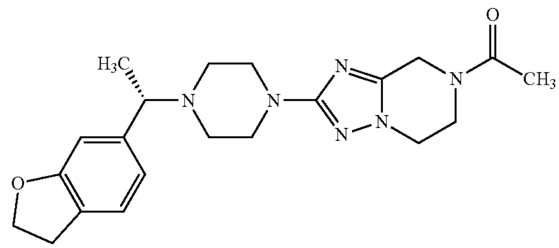 | S-enantiomer |
| 276 | 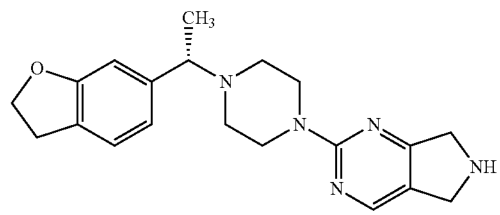 [SMILES: C[C@@H](c1ccc2c(c1)OCC2)N1CCN(c2ncc3c(n2)CNC3)CC1] | S-enantiomer |
| 277 | 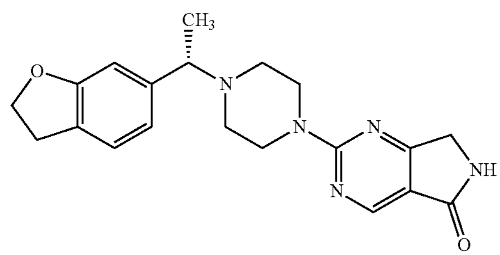 [SMILES: C[C@@H](c1ccc2c(c1)OCC2)N1CCN(c2ncc3c(n2)CNC3=O)CC1] | S-enantiomer |
| 278 | 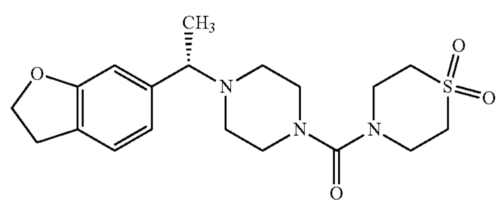 [SMILES: C[C@@H](c1ccc2c(c1)OCC2)N1CCN(C(=O)N2CCS(=O)(=O)CC2)CC1] | S-enantiomer |
| 279 | 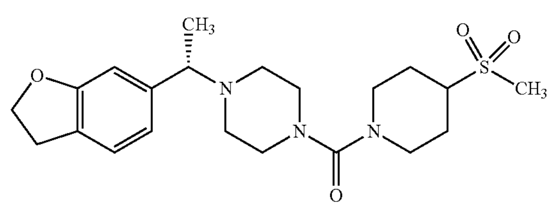 [SMILES: C[C@@H](c1ccc2c(c1)OCC2)N1CCN(C(=O)N2CCC(S(C)(=O)=O)CC2)CC1] | S-enantiomer |
| 280 | 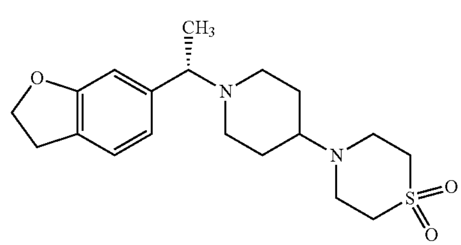 [SMILES: C[C@@H](c1ccc2c(c1)OCC2)N1CCC(N2CCS(=O)(=O)CC2)CC1] | S-enantiomer |

-continued

| No | Structure | Configuration specification |
|---|---|---|
| 281 | 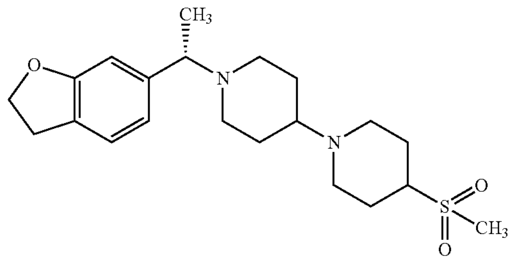 | S-enantiomer |
| 282 | 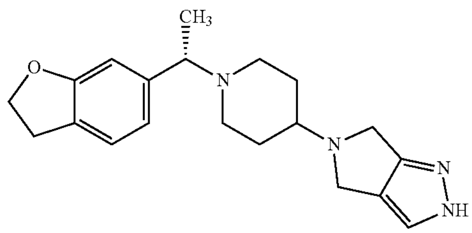 [SMILES: C[C@@H](c1ccc2c(c1)OCC2)N1CCC(N2Cc3c[nH]nc3C2)CC1] | S-enantiomer |
| 283 | 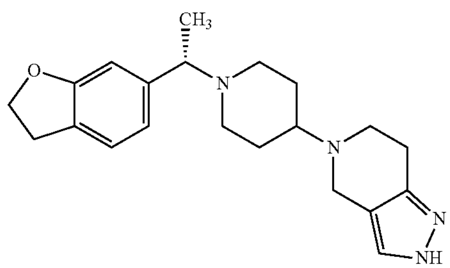 [SMILES: C[C@@H](c1ccc2c(c1)OCC2)N1CCC(N2CCc3n[nH]cc3C2)CC1] | S-enantiomer |
| 284 | 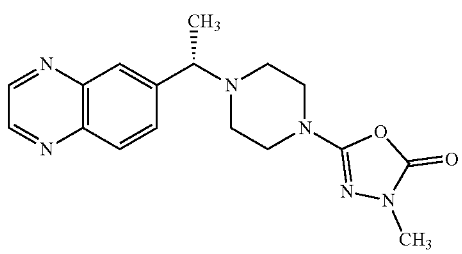 | S-enantiomer |
| 285 | 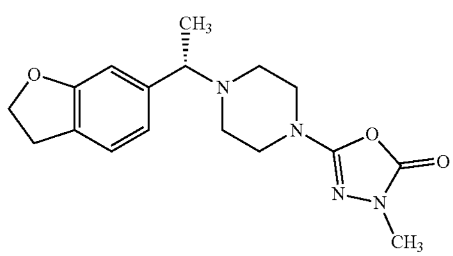 | S-enantiomer |
| 286 | 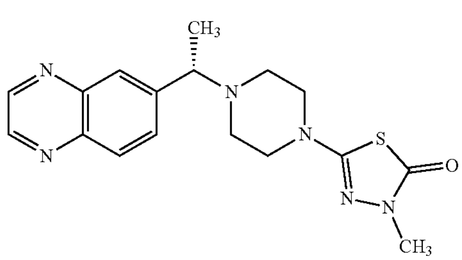 | S-enantiomer |

| No | Structure | Configuration specification |
|---|---|---|
| 287 | | S-enantiomer | or a solvate, salt, tautomer, enantiomer, racemate, or stereoisomer thereof, including mixtures thereof in any ratio.

9. A method for inhibiting a glycosidase, comprising contacting a system expressing the glycosidase with a compound of claim 1 under in-vitro conditions such that the glycosidase is inhibited.

10. A pharmaceutical composition comprising as active ingredient a compound according to claim 1 together with pharmaceutically tolerable adjuvants and/or excipients.

11. The pharmaceutical composition of claim 10, further comprising one or more additional active ingredients.

* * * * *

UNITED STATES PATENT AND TRADEMARK OFFICE
CERTIFICATE OF CORRECTION

Page 1 of 3

PATENT NO. : 11,612,599 B2
APPLICATION NO. : 16/078159
DATED : March 28, 2023
INVENTOR(S) : Anna Quattropani et al.

It is certified that error appears in the above-identified patent and that said Letters Patent is hereby corrected as shown below:

In the Specification

At Column 6, Line 32, compound structures:

"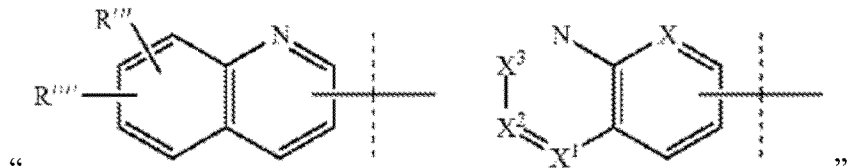"

Should read:

"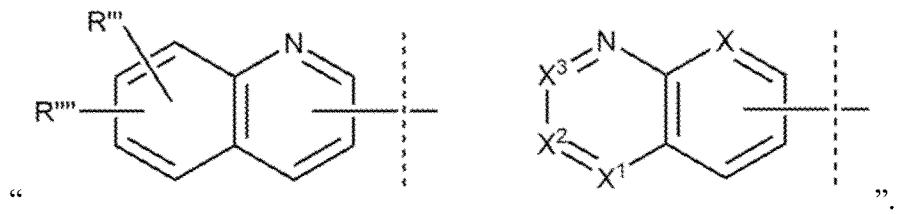".

At Column 6, Line 57, compound structures:

"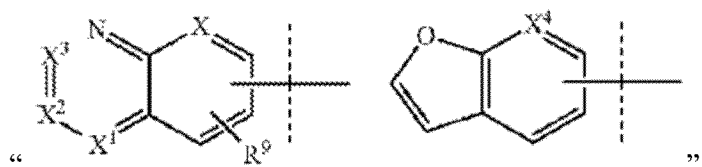"

Should read:

"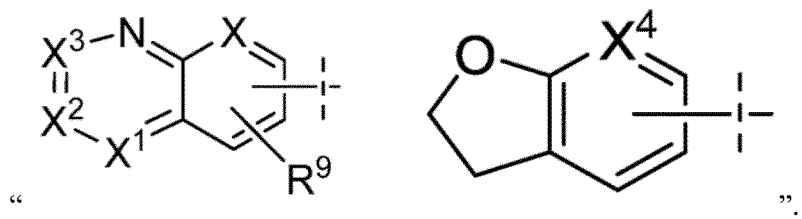".

Signed and Sealed this
Thirteenth Day of June, 2023

Katherine Kelly Vidal
*Director of the United States Patent and Trademark Office*

CERTIFICATE OF CORRECTION (continued)
U.S. Pat. No. 11,612,599 B2

In the Claims

At Column 279, Claim number 1, Line 12, compound structures:

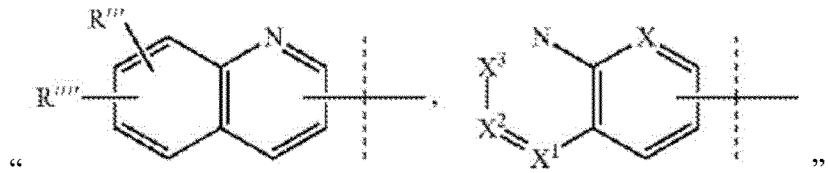

"                ,                "

Should read:

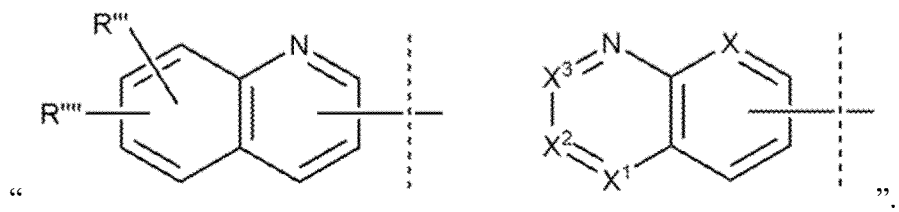

"                ,                ".

At Column 279, Claim number 1, Line 36, compound structures:

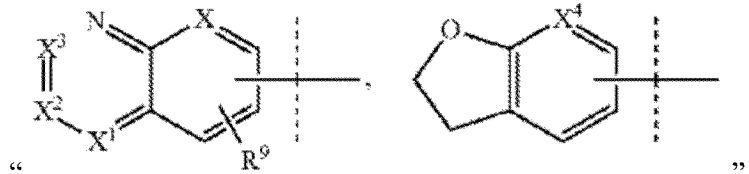

"                ,                "

Should read:

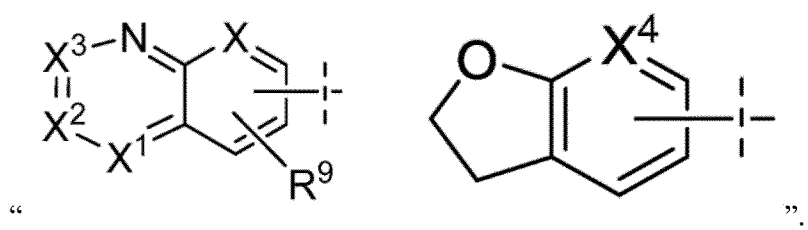

"                ,                ".

At Column 279, Claim number 1, Line 44, compound structures:

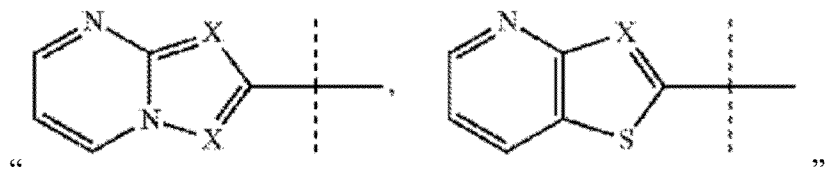

"                ,                "

Should read:

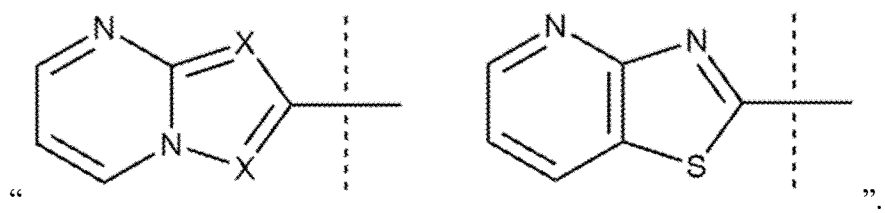

"                ,                ".

CERTIFICATE OF CORRECTION (continued)
U.S. Pat. No. 11,612,599 B2

At Column 279, Claim number 1, Line number 59:
"from O, NR₃, S, SO, SO₂, S(O)(NH), CO, COO, OCO,"
Should read:
"from O, NR$^3$, S, SO, SO$_2$, S(O)(NH), CO, COO, OCO,".

At Column 281, Claim number 1, Line number 5, compound structures:

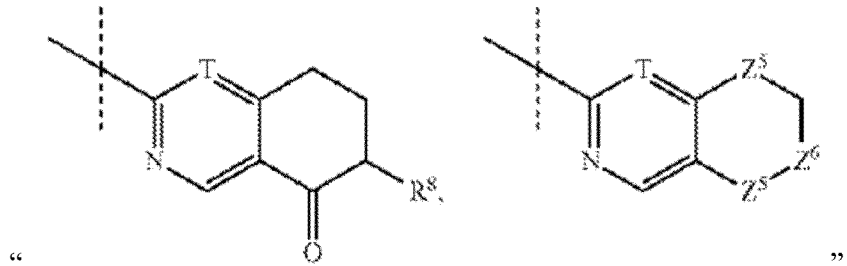

"   "

Should read:

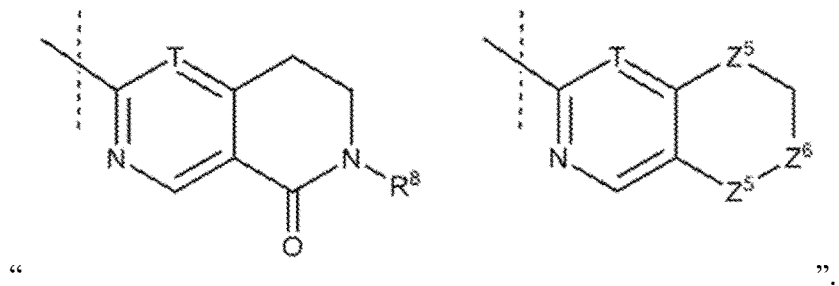

"   ".

At Column 281, Claim number 1, Line number 41:
"replaced by a group selected from O, NR₃, S, SO, SO₂,"
Should read:
"replaced by a group selected from O, NR$^3$, S, SO, SO$_2$,".